United States Patent
Chen et al.

(10) Patent No.: US 10,689,367 B2
(45) Date of Patent: Jun. 23, 2020

(54) TRIAZOLE PYRIDYL COMPOUNDS AS AGONISTS OF THE APJ RECEPTOR

(71) Applicant: AMGEN INC., Thousand Oaks, CA (US)

(72) Inventors: Yinhong Chen, Hayward, CA (US); Alan C. Cheng, San Francisco, CA (US); Mikkel V. Debenedetto, Waltham, MA (US); Paul John Dransfield, Arlington, MA (US); James S. Harvey, Arlington, MA (US); Jonathan Houze, Cambridge, MA (US); Aarif Yusuf Khakoo, Woodside, CA (US); Su-Jen Lai, Cambridge, MA (US); Zhihua Ma, Lexington, MA (US); Vatee Pattaropong, Bedford, MA (US); Gayathri Swaminath, Brisbane, CA (US); Charles Kreiman, Hopkinton, MA (US); David C. Moebius, Westwood, MA (US); Ankit Sharma, Quincy, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/347,970

(22) PCT Filed: Nov. 3, 2017

(86) PCT No.: PCT/US2017/059839
§ 371 (c)(1),
(2) Date: May 7, 2019

(87) PCT Pub. No.: WO2018/093580
PCT Pub. Date: May 24, 2018

(65) Prior Publication Data
US 2019/0300507 A1    Oct. 3, 2019

Related U.S. Application Data

(60) Provisional application No. 62/423,031, filed on Nov. 16, 2016.

(51) Int. Cl.
| | | |
|---|---|---|
| *C07D 401/14* | (2006.01) | |
| *C07D 405/14* | (2006.01) | |
| *C07D 413/14* | (2006.01) | |
| *A61P 9/04* | (2006.01) | |
| *C07D 417/14* | (2006.01) | |
| *A61K 45/06* | (2006.01) | |
| *C07D 401/12* | (2006.01) | |

(52) U.S. Cl.
CPC .............. *C07D 401/14* (2013.01); *A61P 9/04* (2018.01); *C07D 401/12* (2013.01); *C07D 405/14* (2013.01); *C07D 413/14* (2013.01); *C07D 417/14* (2013.01); *A61K 45/06* (2013.01)

(58) Field of Classification Search
CPC .. C07D 401/14; C07D 405/14; C07D 413/14; C07D 417/14; A61P 9/04; A61K 45/06
USPC .................................................... 548/264.8
See application file for complete search history.

(56) References Cited

U.S. PATENT DOCUMENTS

| | | |
|---|---|---|
| 4,844,730 A | 7/1989 | Moriya et al. |
| 4,941,912 A | 7/1990 | Kirsten et al. |
| 5,302,718 A | 4/1994 | Agback et al. |
| 5,328,803 A | 7/1994 | Fujikura et al. |
| 5,411,839 A | 5/1995 | Harder et al. |
| 5,451,588 A | 9/1995 | Baker et al. |
| 5,510,362 A | 4/1996 | Matassa et al. |
| 5,563,026 A | 10/1996 | Singer |
| 5,910,504 A | 6/1999 | Hutchinson |

(Continued)

FOREIGN PATENT DOCUMENTS

| | | |
|---|---|---|
| AU | 199886243 B2 | 4/1999 |
| AU | 2012200157 A1 | 9/2012 |

(Continued)

OTHER PUBLICATIONS

Brame; Hypertension. 2015, 65, 834-840. DOI: 10.1161/HYPERTENSIONHA.114.05099 (Year: 2015).*
Modzelewska-Banachiewicz; Pharmazie 1999, 54, 588-589. Abstract from STN CAPLUS Database, Accession No. 1999: 516211, 1 page. (Year: 1999).*
Neamati; Antiviral Chemistry & Chemotherapy 1997, 8, 485-495. DOI: 10.1177/095632029700800602 (Year: 1997).*
Okawa; J. Med. Chem. 2017, 60, 6942-6990. DOI: 10.1021/acs.jmedchem.7b00443 (Year: 2017).*

(Continued)

*Primary Examiner* — Daniel R Carcanague
(74) *Attorney, Agent, or Firm* — Bernard P. Friedrichsen

(57) ABSTRACT

Compounds of Formula I and Formula II, pharmaceutically acceptable salt thereof, stereoisomers of any of the foregoing, or mixtures thereof are agonists of the APJ Receptor and may have use in treating cardiovascular and other conditions. Compounds of Formula I and Formula II have the structures where the definitions of the variables are provided herein.

I

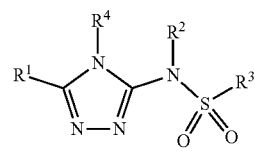

II

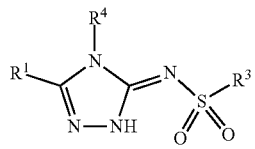

30 Claims, 3 Drawing Sheets

(56) References Cited

U.S. PATENT DOCUMENTS

| | | | |
|---|---|---|---|
| 6,069,141 A | 5/2000 | Barbachyn et al. |
| 6,194,090 B1 | 2/2001 | Okada |
| 6,555,693 B2 | 4/2003 | Ge et al. |
| 6,586,423 B2 | 7/2003 | Bilodeau et al. |
| 6,727,364 B2 | 4/2004 | Tullis et al. |
| 6,787,555 B2 | 9/2004 | Tullis et al. |
| 6,790,846 B2 | 9/2004 | Clark et al. |
| 7,084,145 B2 | 8/2006 | Armour et al. |
| 7,084,164 B2 | 8/2006 | Tobe et al. |
| 7,169,797 B2 | 1/2007 | Xin et al. |
| 7,297,168 B2 | 11/2007 | Murphy et al. |
| 7,361,669 B2 | 4/2008 | Scarborough et al. |
| 7,371,757 B2 | 5/2008 | Morningstar et al. |
| 7,615,569 B2 | 11/2009 | Fulp et al. |
| 7,635,751 B2 | 12/2009 | Kitada et al. |
| 7,638,541 B2 | 12/2009 | Chen et al. |
| 7,718,683 B2 | 5/2010 | Charvat et al. |
| 7,776,897 B2 | 8/2010 | Murakami et al. |
| 7,820,665 B2 | 10/2010 | Booker et al. |
| 8,034,834 B2 | 10/2011 | Du et al. |
| 8,053,456 B2 | 11/2011 | Sun et al. |
| 8,063,083 B2 | 11/2011 | Foley |
| 8,076,486 B2 | 12/2011 | Goutopoulos et al. |
| 8,101,618 B2 | 1/2012 | Kawamoto et al. |
| 8,252,822 B2 | 8/2012 | An et al. |
| 8,299,107 B2 | 10/2012 | Chimmanamada et al. |
| 8,318,790 B2 | 11/2012 | Ying et al. |
| 8,399,464 B2 | 3/2013 | Kuramochi et al. |
| 8,415,377 B2 | 4/2013 | Sun et al. |
| 8,426,602 B2 | 4/2013 | Meibom et al. |
| 8,431,604 B2 | 4/2013 | Netz et al. |
| 8,445,518 B2 | 5/2013 | Charvat et al. |
| 8,466,170 B2 | 6/2013 | Klein |
| 8,492,427 B2 | 7/2013 | Gancia et al. |
| 8,563,741 B2 | 10/2013 | Qian et al. |
| 8,648,104 B2 | 2/2014 | Du et al. |
| 8,673,848 B2 | 3/2014 | Zecri et al. |
| 8,742,133 B2 | 6/2014 | Ying et al. |
| 8,778,977 B2 | 7/2014 | Lind et al. |
| 8,835,464 B2 | 9/2014 | Sun et al. |
| 8,883,827 B2 | 11/2014 | Holsworth et al. |
| 9,156,796 B2 | 10/2015 | Hachtel et al. |
| 9,573,936 B2 | 2/2017 | Chen et al. |
| 9,656,997 B2 | 5/2017 | Chen et al. |
| 9,656,998 B2 | 5/2017 | Chen et al. |
| 9,745,286 B2 | 8/2017 | Chen et al. |
| 9,751,864 B2 | 9/2017 | Chen et al. |
| 9,845,310 B2 | 12/2017 | Chen et al. |
| 9,868,721 B2 | 1/2018 | Chen et al. |
| 9,988,369 B2 | 6/2018 | Chen et al. |
| 10,058,550 B2 | 8/2018 | Chen et al. |
| 10,100,059 B2 | 10/2018 | Runyon et al. |
| 10,150,760 B2 | 12/2018 | Chen et al. |
| 10,221,162 B2 | 3/2019 | Chen et al. |
| 10,344,016 B2* | 7/2019 | Dransfield ............ C07D 413/04 |
| 2002/0107245 A1 | 8/2002 | Wagle et al. |
| 2003/0158238 A1* | 8/2003 | Hale ................... C07D 231/12 514/359 |
| 2004/0167188 A1 | 8/2004 | Xin et al. |
| 2005/0075275 A1 | 4/2005 | Albrecht et al. |
| 2005/0165015 A1 | 7/2005 | Ncube et al. |
| 2005/0170431 A1 | 8/2005 | Ibrahim et al. |
| 2005/0288347 A1 | 12/2005 | Hodge et al. |
| 2006/0100235 A1* | 5/2006 | Andersen ............ A61K 31/4196 514/303 |
| 2006/0156480 A1 | 7/2006 | Lim |
| 2006/0281749 A1 | 12/2006 | Wagle et al. |
| 2008/0153869 A1 | 6/2008 | Bressi et al. |
| 2008/0249131 A1 | 10/2008 | Girardet et al. |
| 2009/0318438 A1 | 12/2009 | Chen et al. |
| 2010/0130472 A1 | 5/2010 | Young et al. |
| 2010/0249185 A1 | 9/2010 | Du et al. |
| 2010/0280032 A1 | 11/2010 | Zhou et al. |
| 2011/0046125 A1 | 2/2011 | Ying |
| 2011/0158940 A1 | 6/2011 | Byrd et al. |
| 2011/0190257 A1 | 8/2011 | Heald et al. |
| 2011/0207788 A1 | 8/2011 | Amberg et al. |
| 2011/0265691 A1 | 11/2011 | Orth et al. |
| 2012/0094837 A1 | 4/2012 | Muhlthau et al. |
| 2012/0208828 A1 | 8/2012 | Holsworth et al. |
| 2012/0238576 A1 | 9/2012 | Tao et al. |
| 2013/0034536 A1 | 2/2013 | Gedulin |
| 2013/0040950 A1 | 2/2013 | Short et al. |
| 2013/0059807 A1 | 3/2013 | Gedulin et al. |
| 2013/0059845 A1 | 3/2013 | Song et al. |
| 2013/0108573 A1 | 5/2013 | Gedulin et al. |
| 2013/0109671 A1 | 5/2013 | Gedulin et al. |
| 2013/0150385 A1 | 6/2013 | Blackman et al. |
| 2013/0156755 A1 | 6/2013 | Blackman et al. |
| 2013/0266636 A1 | 10/2013 | Cheresh et al. |
| 2013/0303505 A1 | 11/2013 | Bollu et al. |
| 2014/0005181 A1 | 1/2014 | Smith et al. |
| 2014/0031374 A1* | 1/2014 | Holsworth ........... C07D 401/12 514/256 |
| 2016/0058705 A1 | 3/2016 | Rajadas et al. |
| 2016/0060349 A1 | 3/2016 | Van Schravendijk et al. |
| 2016/0340336 A1 | 11/2016 | Chen et al. |
| 2016/0355507 A1 | 12/2016 | Johnson et al. |
| 2017/0035744 A1 | 2/2017 | Chen et al. |
| 2017/0037026 A1 | 2/2017 | Chen et al. |
| 2017/0042871 A1 | 2/2017 | Chen et al. |
| 2017/0042872 A1 | 2/2017 | Chen et al. |
| 2017/0042897 A1 | 2/2017 | Chen et al. |
| 2017/0044131 A1 | 2/2017 | Chen et al. |
| 2017/0281625 A1 | 10/2017 | Chen et al. |
| 2017/0320860 A1 | 11/2017 | Chen et al. |
| 2017/0355734 A1 | 12/2017 | Llorens-Cortes et al. |
| 2018/0118698 A1 | 5/2018 | Smith et al. |
| 2018/0282289 A1* | 10/2018 | Ikeda ..................... A61P 9/10 |
| 2019/0100510 A1 | 4/2019 | Dransfield et al. |
| 2019/0275008 A1* | 9/2019 | Brown .................. A61K 31/506 |
| 2019/0284173 A1* | 9/2019 | Chen .................... A61P 9/04 |
| 2019/0290647 A1* | 9/2019 | Chen .................... C07D 405/14 |
| 2019/0290648 A1* | 9/2019 | Chen .................... C07D 405/14 |

FOREIGN PATENT DOCUMENTS

| | | | |
|---|---|---|---|
| DE | 3928605 A1 | 3/1991 | |
| DE | 4035141 A1 | 5/1992 | |
| EP | 0121082 B1 | 10/1984 | |
| EP | 0330959 A2 | 2/1989 | |
| EP | 0359505 A1 * | 3/1990 | ........... C07D 401/06 |
| EP | 0409332 A2 | 1/1991 | |
| EP | 0484750 A1 | 10/1991 | |
| JP | 2003-5356 A | 8/2003 | |
| JP | 2003-321456 A | 11/2003 | |
| JP | 2005-170939 A | 6/2005 | |
| WO | 91/11909 A1 | 8/1991 | |
| WO | 99/46371 A1 | 9/1999 | |
| WO | 01/87855 A1 | 11/2001 | |
| WO | 2005/039569 A1 | 7/2005 | |
| WO | 2006/026488 A1 | 3/2006 | |
| WO | 2006/055760 A1 | 5/2006 | |
| WO | 2006/080533 A1 | 8/2006 | |
| WO | 2006/095783 A1 | 9/2006 | |
| WO | 2006/100588 A1 | 9/2006 | |
| WO | 2006/109817 A1 | 10/2006 | |
| WO | 2007/007688 A1 | 1/2007 | |
| WO | 2007/139952 A2 | 12/2007 | |
| WO | 2007/139967 A2 | 12/2007 | |
| WO | 2008/008375 A2 | 1/2008 | |
| WO | 2008/021364 A2 | 2/2008 | |
| WO | 2008/103352 A1 | 8/2008 | |
| WO | 2009/075890 A2 | 6/2009 | |
| WO | 2009/115503 A1 | 9/2009 | |
| WO | 2010/017545 A2 | 2/2010 | |
| WO | 2011/146801 A1 | 11/2011 | |
| WO | 2012/076898 A1 | 6/2012 | |
| WO | 2012/116247 A1 | 8/2012 | |
| WO | 2013/067162 A1 | 5/2013 | |
| WO | 2013/067165 A1 | 5/2013 | |
| WO | 2013/074594 A1 | 5/2013 | |
| WO | 2013/106437 A1 | 7/2013 | |
| WO | 2013/106614 A1 | 7/2013 | |

(56) References Cited

FOREIGN PATENT DOCUMENTS

| WO | 2013/111110 | A2 | 8/2013 | | |
|---|---|---|---|---|---|
| WO | 2013/148857 | A1 | 10/2013 | | |
| WO | 2013/184755 | A2 | 12/2013 | | |
| WO | 2014/044738 | A1 | 3/2014 | | |
| WO | 2014/099984 | A1 | 6/2014 | | |
| WO | 2014/150326 | A1 | 9/2014 | | |
| WO | 2014/194270 | A1 | 12/2014 | | |
| WO | 2015/140296 | A2 | 9/2015 | | |
| WO | 2015/163818 | A1 | 10/2015 | | |
| WO | 2015/184011 | A2 | 12/2015 | | |
| WO | 2015/188073 | A1 | 12/2015 | | |
| WO | 2016/151018 | A1 | 9/2016 | | |
| WO | WO-2016187308 | A1 | * 11/2016 | ........... | C07C 311/13 |
| WO | 2016/196771 | A1 | 12/2016 | | |
| WO | 2017/066402 | | 4/2017 | | |
| WO | 2017/091513 | A1 | 6/2017 | | |
| WO | 2017/096130 | A1 | 6/2017 | | |
| WO | 2017/100558 | A1 | 6/2017 | | |
| WO | 2017/106396 | A1 | 6/2017 | | |
| WO | 2017/165640 | A1 | 9/2017 | | |
| WO | 2017/174758 | A1 | 10/2017 | | |
| WO | WO-2017192485 | A1 | * 11/2017 | ........... | A61K 31/437 |
| WO | 2017/218617 | A1 | 12/2017 | | |
| WO | 2017/218633 | A1 | 12/2017 | | |
| WO | 2018/071622 | A1 | 4/2018 | | |
| WO | 2018/074526 | A1 | 4/2018 | | |
| WO | 2018/093576 | A1 | 5/2018 | | |
| WO | 2018/093577 | A1 | 5/2018 | | |
| WO | 2018/093579 | A1 | 5/2018 | | |
| WO | 2018/097944 | A1 | 5/2018 | | |
| WO | 2018/097945 | A1 | 5/2018 | | |
| WO | WO-2019089335 | A1 | * 5/2019 | ................ | A61P 9/00 |
| WO | WO-2019169193 | A1 | * 9/2019 | ........... | C07D 401/14 |

OTHER PUBLICATIONS

Read; Biochemical Pharmacology 2016, 116, 63-72. DOI: 10.1016/j.bcp.2016.07.018 (Year: 2016).*

SciFinder Structure Search with Substances Performed May 20, 2016.

SciFinder Structure Search with References Performed May 20, 2016.

SciFinder Structure Search Sulfonamide Tail with Substance Performed May 12, 2016.

Berry, M. F. et al., "Apelin Has In Vivo Inotropic Effects on Normal and Failing Hearts," Circulation 110, pp. II187-II193, (2004).

Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett.6b00038; lccn:2009200243; oclcnum:455500725; serissn:1948-5875; itc:84452717; itcp:10547084 (2016).

Chun, H. et al., "Apelin Signaling Antagonizes ANG II Effects in Mouse Models of Atherosclerosis," J. Clin. Invest. 118(10), pp. 3343-3354 (2008).

Japp, A. G. et al., "Acute Cardiovascular Effects of Apelin in Humans," Circulation 121, pp. 1818-1827 (2010).

Modzelewska-Banachiewicz et al., "Synthesis and Biological Action of 3-4-Disubstituted 5-Arylsulphonylamino-1,2,4-triazoles," Pharmazie 54, pp. 588-589 (1999).

Pauli, A. et al., "Toddler: an Embryonic Signal That Promotes Cell Movement via Apelin Receptors," Science 343, pp. 1248636-0-1248636-8 (2014).

Siddiquee, K. et al., "The Apelin receptor Inhibits the Angiotensin II Type 1 Receptor Via Allosteric Trans-Inhibition," Br. J. Pharmacol. 168, pp. 1104-1117 (2013).

Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).

Tatemoto, K. et al., "Isolation and Characterization of a Novel Endogenous Peptide Ligand for the Human APJ Receptor," Bioch. Biophys. Res. Comm., 251, pp. 471-476 (1998).

Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).

Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).

Barnes, G. et al., "Translational Promise of the Apelin-APJ System," Heart 96(13), pp. 1011-1016 (2010).

Kawamata, Y. et al., "Molecular Properties of Apelin: Tissue Distribution and Receptor Binding," Biochemica et Biophysica Acta 1538(2-3), pp. 162-171 (2001).

Nishizawa, N. et al., "High Potency Analog of Apelin, A Ligand of Orphan GPCT APJ," T Shiori (ed.) Petptide Science 2000: Proceedings of the 37$^{th}$ Japanese Peptide Symposium, pp. 151-154 (2000).

Medhurst, A. D. et al., "Pharmacological and Immunohistochemical Characteization of the APJ Receptor and its Endogenous Ligand Apelin," J. Neurochem. 84(5), pp. 1162-1172 (2003).

Hamada, J. et al., "Evaluation of Novel Cyclic Analogoues of Apelin," Int. J. Mol. Med. 22, pp. 547-552 (2008).

Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).

Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).

Thomas, J.B. et al., "Identification of N-[5-{[(4-Methylphenyesulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).

Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett 25, pp. 2060-2064 (2015).

Thompson, M. E. "α,N-Alkanesulfonamide Dianions: Formation and Chemoselective C-Alkylation," J. Org. Chem. 49, pp. 1700-1703 (1984).

Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).

Singh, O. M. et al., "A Facile One-Pot Synthetic Method for 1,2,4-Triazoles and 1,3-Disubstituted Thioureas," J. Chem. Res. pp. 483-485 (2006).

Carlsen, P.J.J. et al., "Synthesis of Unsymmetrically Substituted 4H-1,2,4-Triazoles," J. Heterocyclic Chem. 31, pp. 805-807 (1994).

Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).

Hassan, A. A. et al., "Thiosemicarbazides in Heterocyclization," J. Heterocyclic Chem. 48, pp. 495-516 (2011).

Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).

Ivanova, N. V. et al., "A Convenient Synthesis of 4,5-Disubstituted 1,2,4-Triazoles Functionalized in Position 3," Synthesis 1, pp. 156-160 (2005).

Modzelewska-Banaschiewicz, B et al., "Antiviral Activity of the Products of Cyclization of Dimethyl 2-[1-arylamino-1-arylmethylideine)hydrazono]succinate," Eur. J. Med. Chem. 36, pp. 93-99 (2001).

SciFinder Structure Search with Substances Performed Sep. 1, 2016.

SciFinder Structure Search with References Performed Sep. 1, 2016.

Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).

(56) References Cited

OTHER PUBLICATIONS

Johnson, M. G. et al., "Convenient Route to Secondary Sulfinates: Application to the Stereospecific Synthesis of α-C-Chiral Sulfonamides," Organic Letters 16(23), pp. 6248-6251 (2014).
Enders, D. et al., "Asymmetric Synthesis of α-Substituted N-Methylsulfonamides," Helvetica Chimica Acta, 85, pp. 3657-3677 (2002).
Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).
Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).
Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).
International Search Report for analogous PCT Application No. PCT/US2017/059839, dated Apr. 1, 2018.
Written Opinion for analogous PCT Application No. PCT/US2017/059839, dated Apr. 1, 2018.

\* cited by examiner

TRIAZOLE PYRIDYL COMPOUNDS AS AGONISTS OF THE APJ RECEPTOR

CROSS REFERENCES TO RELATED APPLICATIONS

This application claims the benefit of U.S. Provisional Application No. 62/423,031, filed on Nov. 16, 2016, which is hereby incorporated by reference in its entirety and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77—also referred to as Apelin-36) and a smaller 13 residue polypeptide (Apelin 65-77—also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at subnanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin 13. Nishizawa et al., in: T. Shioiri (ed.), Peptide Science 2000: Proceedings of the 37$^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule, but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMedChem 7:318-325, 2012. Additionally, PCT/US2013/075773 describes a group of modifications, including substitution of non-canonical amino acids and changes at the N- and C-terminal of the apelin molecule that can affect, inter alia, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336, WO 2016/187308, WO 2015/184011, and WO 2015/188073.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

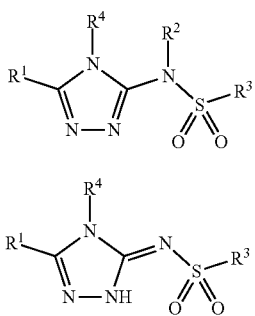

or a pharmaceutically acceptable salt thereof, a tautomer thereof, a pharmaceutically acceptable salt of the tautomer, a stereoisomer of any of the foregoing, or a mixture thereof, wherein:

$R^1$ is a pyridyl group that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$$NH_2$, —S(=O)$_2$NH($C_1$-$C_6$ alkyl), or —S(=O)$_2$N($C_1$-$C_6$ alkyl)$_2$;

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula —(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl $R^4$ group is unsubstituted or is substituted with 1, 2, 3, or 4 $R^{4a}$ substituents, wherein the $C_5$-$C_{10}$ polycyclic cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl $R^{4a}$ group is unsubstituted or is substituted with 1 or 2 $R^{4aa}$ substituents, and further wherein two $R^{4a}$ substituents on the same carbon atom of the $C_3$-$C_8$ cycloalkyl $R^4$ group may join together with the carbon atom to which they are attached to form a 3 to 6-membered heterocyclyl group containing 1 or 2 heteroatoms selected from N, O, or S which is unsubstituted or is substituted with 1 or 2 $R^{4aa}$ substituents;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—(C$_1$-C$_6$ alkyl), —C(=O)NH$_2$, —C(=O)NH(C$_1$-C$_6$ alkyl), or —C(=O)N(C$_1$-C$_6$ alkyl)$_2$;

R$^{4c}$ in each instance is selected from —F, —Cl, —Br, —I, —CN, —OH, oxo, —O—(C$_1$-C$_6$ alkyl), —O—(C$_1$-C$_6$ haloalkyl), —O—(C$_1$-C$_6$ perhaloalkyl), —S—(C$_1$-C$_6$ alkyl), —S—(C$_1$-C$_6$ haloalkyl), —S—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)NH(C$_3$-C$_6$ cycloalkyl), —C(=O)N(C$_1$-C$_6$ alkyl)(C$_3$-C$_6$ cycloalkyl), —C(=O)N(C$_3$-C$_6$ cycloalkyl)$_2$, —S(=O)—(C$_1$-C$_6$ alkyl), —S(=O)$_2$—(C$_1$-C$_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl R$^{4c}$ group, the 3 to 6 membered heterocyclyl R$^{4c}$ group, the phenyl R$^{4c}$ group, or the a 5 or 6 membered heteroaryl R$^{4c}$ ring are unsubstituted or are substituted with 1 or 2 R$^{4aa}$ substituents; and further wherein the 3 to 6 membered cycloalkyl R$^{4c}$ group and the 3 to 6 membered heterocyclyl R$^{4c}$ group may optionally be additionally substituted with an oxo substituent; and R$^{4aa}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —(C$_1$-C$_6$ alkyl)-OH, —(C$_1$-C$_6$ alkyl)-O—(C$_1$-C$_6$ alkyl), —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), or —C(=O)N(C$_1$-C$_6$ alkyl)$_2$.

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy.

Other objects, features and advantages of the invention will become apparent to those skilled in the art from the following description and claims.

DETAILED DESCRIPTION OF THE INVENTION

Figure 1:
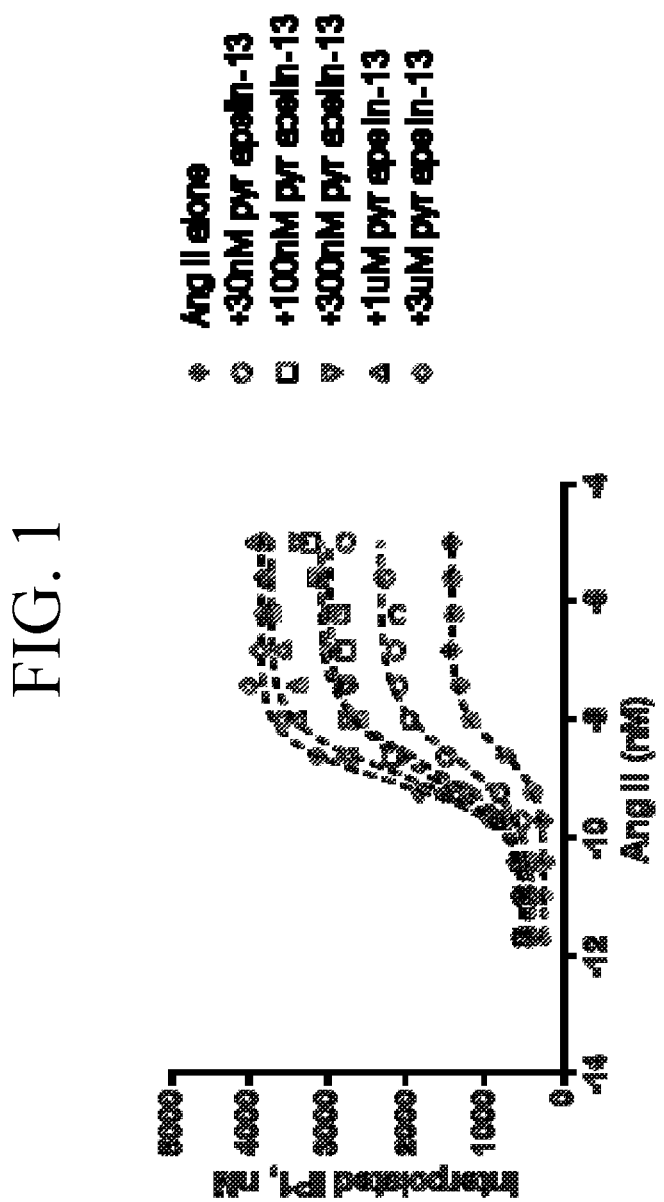
FIG. 1 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where $R^2$ is H. These forms are illustrated below as Tautomer A and Tautomer B:

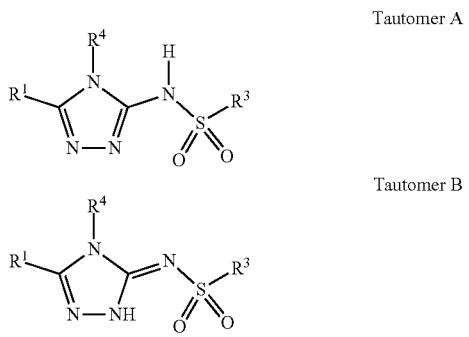

Tautomer A

Tautomer B

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

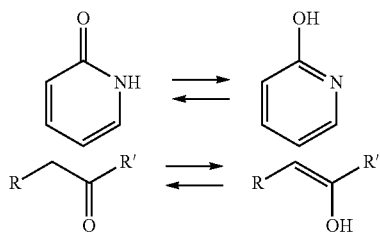

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as $(C_1-C_4)$alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 (14C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a $(C_1-C_6)$alkyl group and an alkyl group having 1 to 4 carbon atoms may be referred to as a $(C_1-C_4)$alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—$(C_1-C_6$ alkyl)-OH will be recognized as a group where an —O atom is bonded to a $C_1-C_6$ alkyl group and one of the H atoms bonded to a C atom of the $C_1-C_6$ alkyl group is replaced with a bond to the O atom of an —OH group. As another example, a group —O—$(C_1-C_6$ alkyl)-O—$(C_1-C_6$ alkyl) will be recognized as a group where an —O atom is bonded to a first $C_1-C_6$ alkyl group and one of the H atoms bonded to a C atom of the first $C_1-C_6$ alkyl group is replaced with a bond to a second O atom that is bonded to a second $C_1-C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a —($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a ($C_3$-$C_8$)cycloalkyl, a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_8$)cycloalkyl, a ($C_3$-$C_7$)cycloalkyl, a ($C_3$-$C_6$)cycloalkyl, or a ($C_4$-$C_7$)cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups using alternative language. Cycloalkyl groups may be monocyclic or polycyclic. For the purposes of this application, the term "polycyclic" when used with respect to cycloalkyl will include bicyclic cycloalkyl groups such as, but not limited to, norbornane, bicyclo[1.1.1]pentane, and bicyclo[3.1.0]hexane, and cycloalkyl groups with more ring systems such as, but not limited to, cubane and adamantane. The term "polycyclic" when used with respect to cycloalkyl will also include spirocyclic ring systems such as, but not limited to, spiro[2.2]pentane, spiro[2.3]hexane, spiro[3.3]heptane, and spiro[3.4]octane.

"Heterocyclyl" refers to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

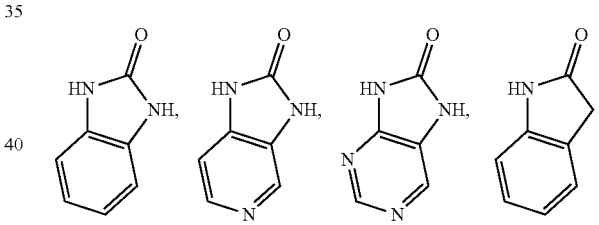

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H- pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (═O) or oxide (—O⁻) substituents, such as piperidinyl N-oxide, morpholinyl-N-oxide, 1-oxo-1-thiomorpholinyl, pyridinoyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize. this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

EMBODIMENTS

The embodiments listed below are presented in numbered form for convenience and in ease and clarity of reference in referring back to multiple embodiments.

In a first embodiment, the invention provides a compound of Formula I or Formula II:

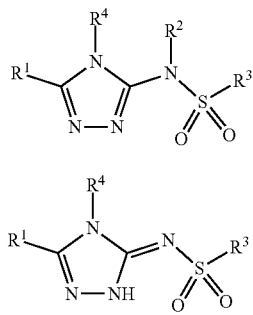

or a pharmaceutically acceptable salt thereof, a tautomer thereof, a pharmaceutically acceptable salt of the tautomer, a stereoisomer of any of the foregoing, or a mixture thereof, wherein:

$R^1$ is a pyridyl group that is unsubstituted or is substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$NH$_2$, —S(=O)$_2$NH($C_1$-$C_6$ alkyl), or —S(=O)$_2$N($C_1$-$C_6$ alkyl)$_2$;

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —NH$_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl $R^4$ group is unsubstituted or is substituted with 1, 2, 3, or 4 $R^{4a}$ substituents, wherein the $C_5$-$C_{10}$ polycyclic cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl $R^{4a}$ group is unsubstituted or is substituted with 1 or 2 $R^{4aa}$ substituents, and further wherein two $R^{4a}$ substituents on the same carbon atom of the $C_3$-$C_8$ cycloalkyl $R^4$ group may join together with the carbon atom to which they are attached to form a 3 to 6-membered heterocyclyl group containing 1 or 2 heteroatoms selected from N, O, or S which is unsubstituted or is substituted with 1 or 2 $R^{4aa}$ substituents;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), or —C(=O)N($C_1$-$C_6$ alkyl)$_2$;

$R^{4c}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), or —C(=O)N($C_1$-$C_6$ alkyl)$_2$.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

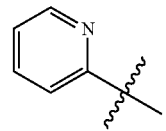 [SMILES: *c1ccccn1]

wherein the pyridyl is unsubstituted or is substituted with 1 or 2 $R^{1a}$ substituents, and the symbol ⌇, when drawn across a bond, indicates the point of attachment to the rest of the molecule.

3. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

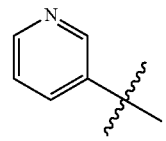 [SMILES: *c1cccnc1]

wherein the pyridyl is unsubstituted or is substituted with 1 or 2 $R^{1a}$ substituents, and the symbol ⌇, when drawn across a bond, indicates the point of attachment to the rest of the molecule.

4. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

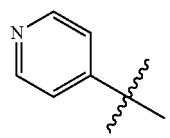 [SMILES: *c1ccncc1]

wherein the pyridyl is unsubstituted or is substituted with 1 or 2 $R^{1a}$ substituents, and the symbol ⌇, when drawn across a bond, indicates the point of attachment to the rest of the molecule.

5. The compound of any one of embodiments 1-4 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted pyridyl.

6. The compound of any one of embodiments 1-4 or the pharmaceutically acceptable salt thereof, the tautomer thereof, the pharmaceutically acceptable salt of the tautomer, the stereoisomer of any of the foregoing, or the mixture thereof, wherein $R^{1a}$ in each instance is independently selected from —$C_1$-$C_6$ alkyl, —O—($C_1$-$C_6$ alkyl), or —O—($C_1$-$C_6$ alkyl)-O—($C_1$-$C_6$ alkyl).

7. The compound of any one of embodiments 1-4 or the pharmaceutically acceptable salt thereof, the tautomer thereof, the pharmaceutically acceptable salt of the tautomer, the stereoisomer of any of the foregoing, or the mixture thereof, wherein $R^{1a}$ in each instance is independently selected from —$CH_3$, —$OCH_3$, or —$OCH_2CH_2OCH_3$.

8. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

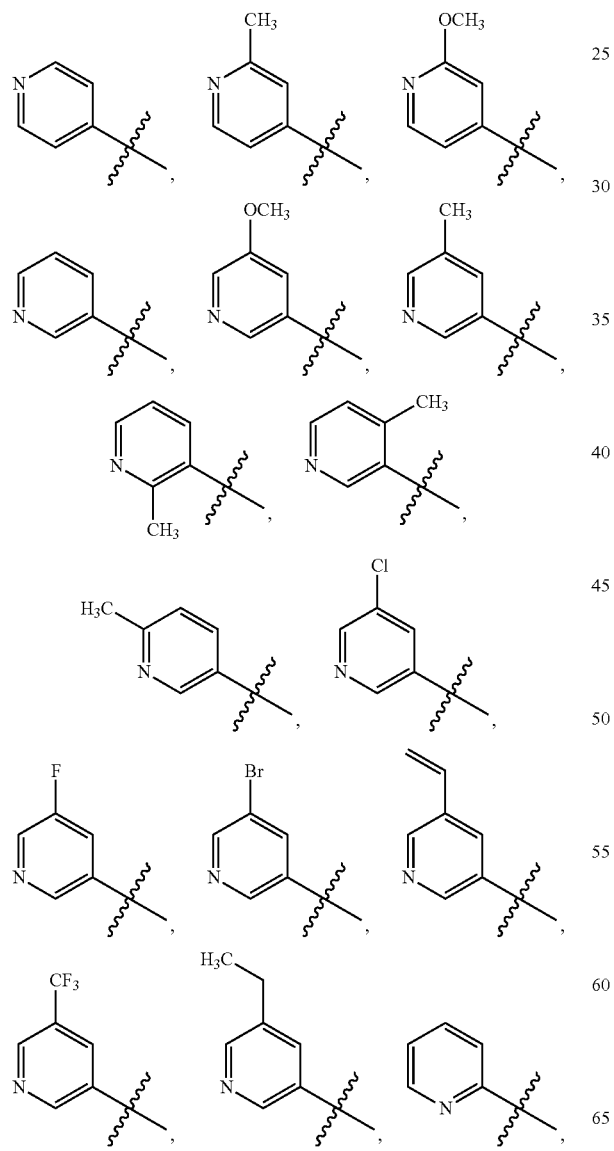

-continued

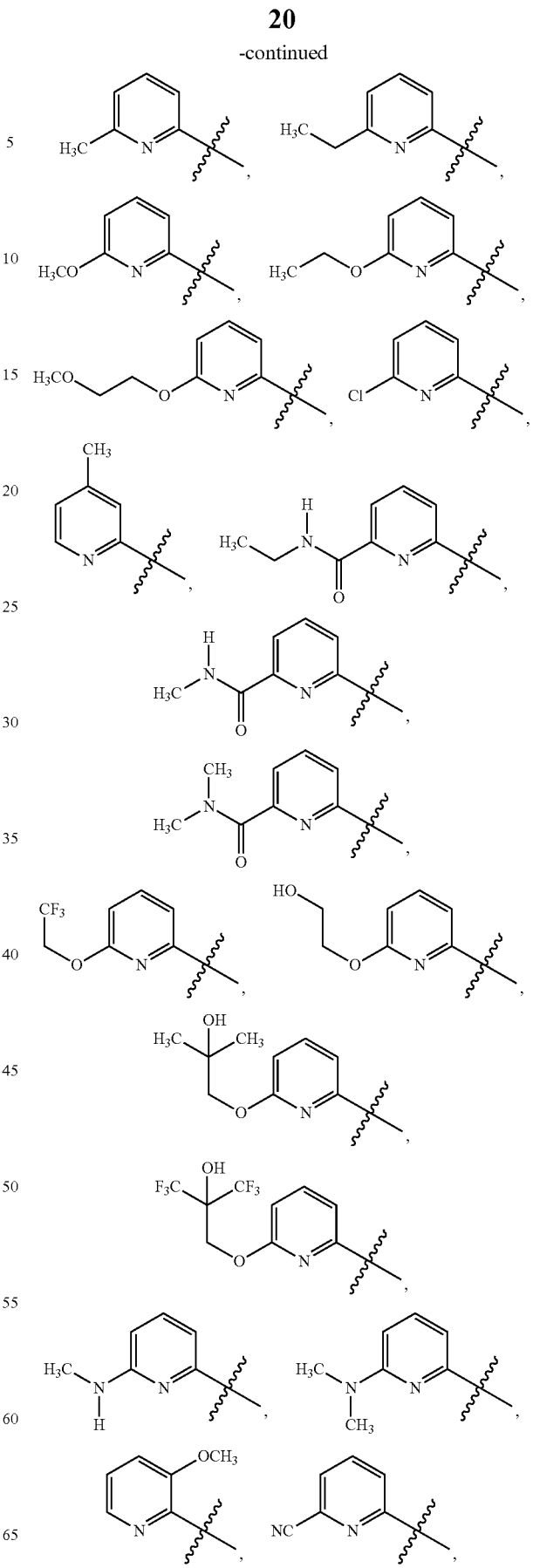

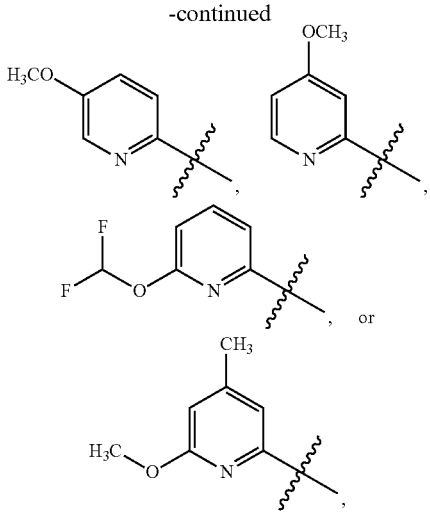

wherein the symbol ∼∼∼, when drawn across a bond, indicates the point of attachment to the rest of the molecule.

9. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

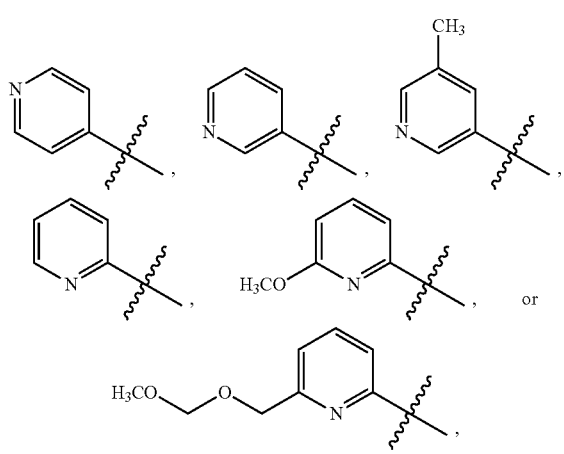

wherein the symbol ∼∼∼, when drawn across a bond, indicates the point of attachment to the rest of the molecule.

10. The compound of embodiment 9 or the pharmaceutically acceptable salt thereof, the tautomer thereof, the pharmaceutically acceptable salt of the tautomer, the stereoisomer of any of the foregoing, or the mixture thereof, wherein $R^1$ is selected from

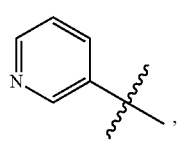 [SMILES: *c1cccnc1]

wherein the symbol ∼∼∼, when drawn across a bond, indicates the point of attachment to the rest of the molecule.

11. The compound of embodiment 9 or the pharmaceutically acceptable salt thereof, the tautomer thereof, the pharmaceutically acceptable salt of the tautomer, the stereoisomer of any of the foregoing, or the mixture thereof, wherein $R^1$ is selected from

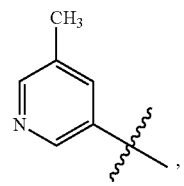 [SMILES: *c1cncc(C)c1]

wherein the symbol ∼∼∼, when drawn across a bond, indicates the point of attachment to the rest of the molecule.

12. The compound of embodiment 9 or the pharmaceutically acceptable salt thereof, the tautomer thereof, the pharmaceutically acceptable salt of the tautomer, the stereoisomer of any of the foregoing, or the mixture thereof, wherein $R^1$ is selected from

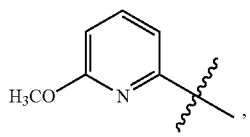

wherein the symbol ∼∼∼, when drawn across a bond, indicates the point of attachment to the rest of the molecule.

13. The compound of embodiment 9 or the pharmaceutically acceptable salt thereof, the tautomer thereof, the pharmaceutically acceptable salt of the tautomer, the stereoisomer of any of the foregoing, or the mixture thereof, wherein $R^1$ is selected from

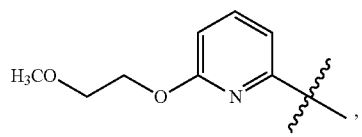 [SMILES: *c1cccc(OCCOC)n1]

wherein the symbol ∼∼∼, when drawn across a bond, indicates the point of attachment to the rest of the molecule.

14. The compound of any one of embodiments 1-13 or the pharmaceutically acceptable salt thereof, the tautomer thereof, the pharmaceutically acceptable salt of the tautomer, the stereoisomer of any of the foregoing, or the mixture thereof, wherein $R^2$ is selected from —H or —CH$_3$.

15. The compound of any one of embodiments 1-14 or the pharmaceutically acceptable salt thereof, the tautomer thereof, the pharmaceutically acceptable salt of the tautomer, the stereoisomer of any of the foregoing, or the mixture thereof, wherein $R^2$ is —H.

16. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic $C_3$-$C_5$ cycloalkyl group and is unsubstituted or is substituted with 1, 2, or 3 $R^{4a}$ substituents.

17. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein $R^4$ is a $C_5$-$C_{10}$ polycyclic cycloalkyl $R^4$ group and is unsubstituted or is substituted with 1 or 2 $R^{4b}$ substituents.

18. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein $R^4$ is a straight or branched chain $C_1$-$C_6$ alkyl $R^4$ group and is unsubstituted or is substituted with 1, 2, or 3 $R^{4c}$ substituents.

19. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein $R^4$ is selected from

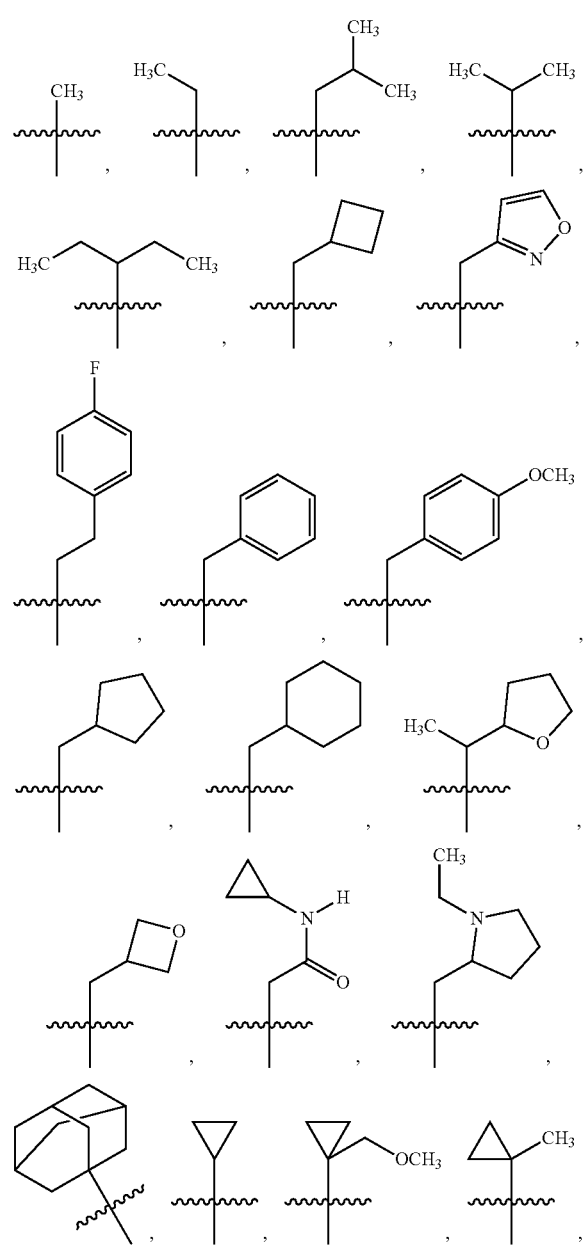

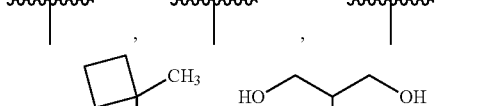
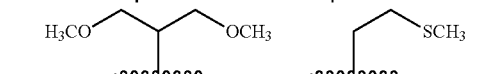
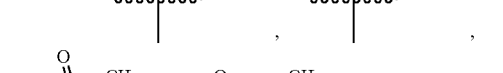
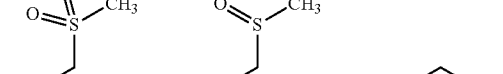
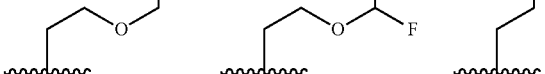
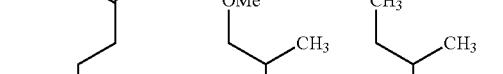
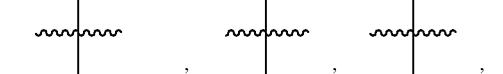
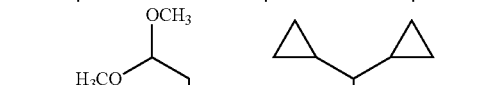
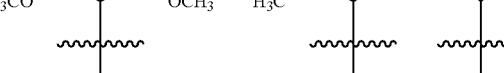
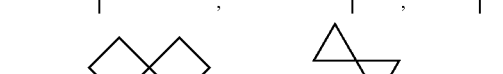

wherein the symbol ⁓, when drawn across a bond, indicates the point of attachment to the rest of the molecule.

20. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof wherein $R^4$ is selected from

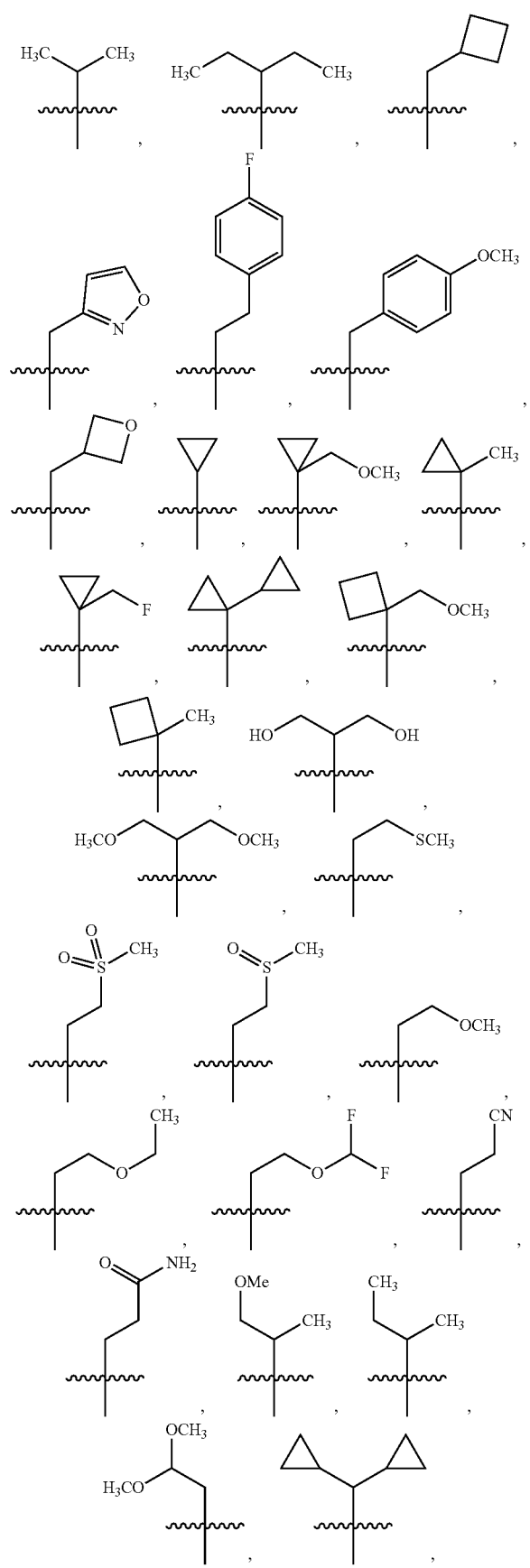

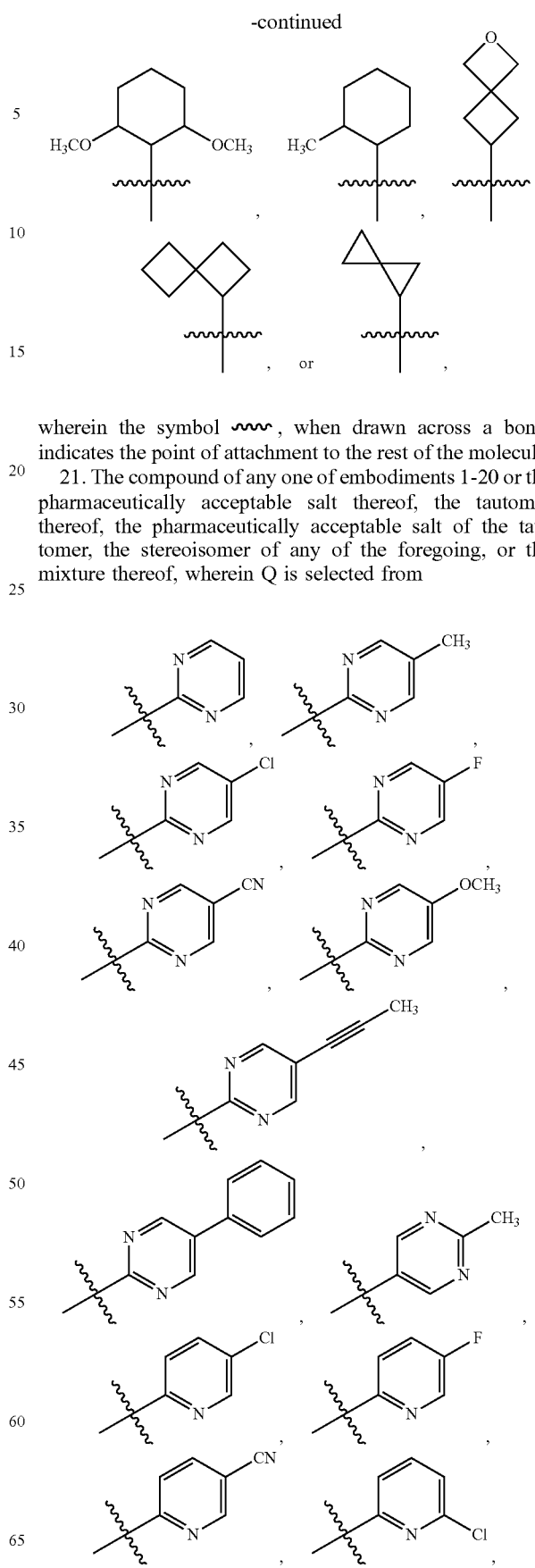

wherein the symbol ⌇, when drawn across a bond, indicates the point of attachment to the rest of the molecule.

21. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof, wherein Q is selected from -continued

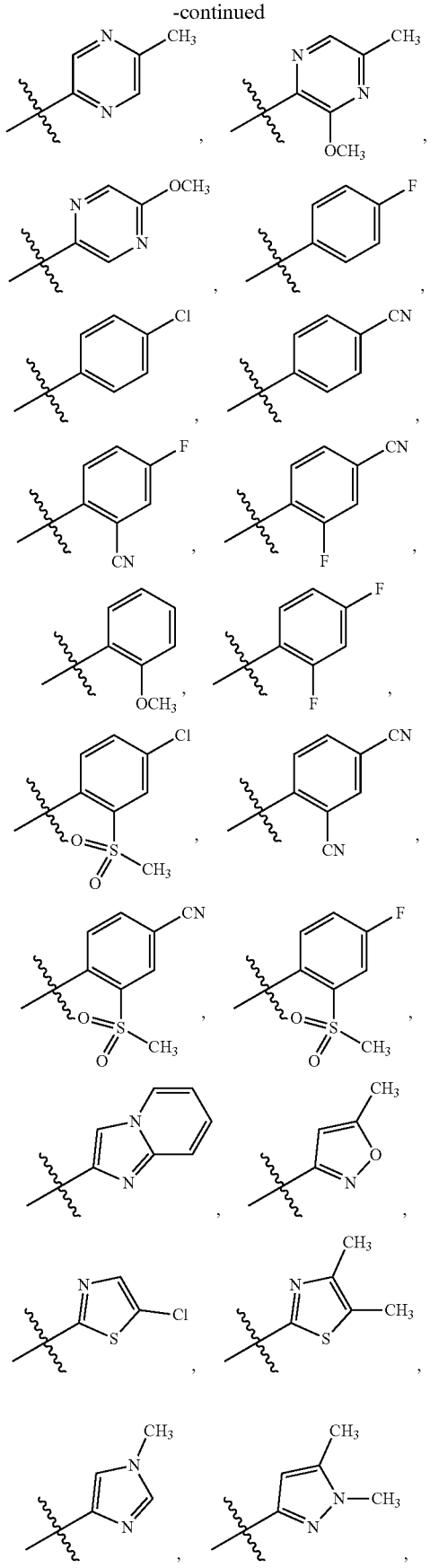

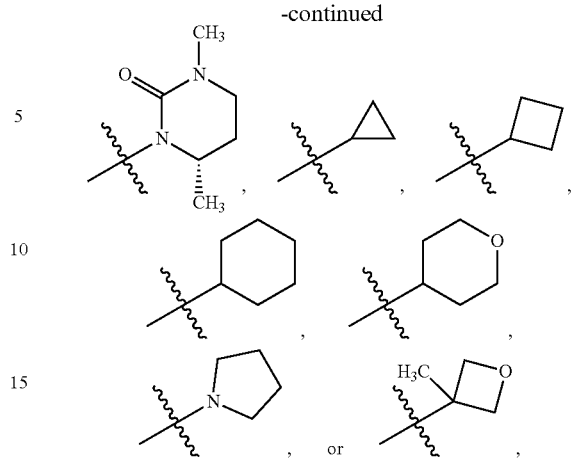

wherein the symbol ⌇, when drawn across a bond, indicates the point of attachment to the rest of the molecule.

22. The compound of any one of embodiments 1-20 or the pharmaceutically acceptable salt thereof, the tautomer thereof, the pharmaceutically acceptable salt of the tautomer, the stereoisomer of any of the foregoing, or the mixture thereof wherein Q is selected from

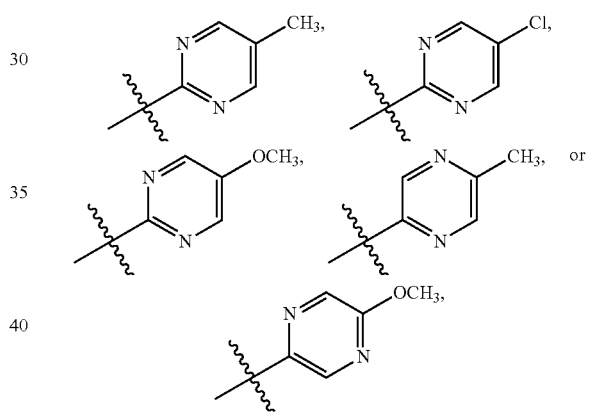

wherein the symbol ⌇, when drawn across a bond, indicates the point of attachment to the rest of the molecule.

23. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is

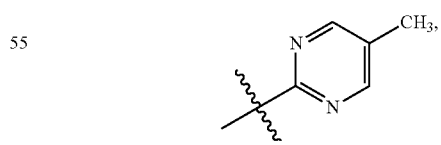

wherein the symbol ⌇, when drawn across a bond, indicates the point of attachment to the rest of the molecule.

24. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is

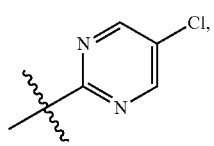 [SMILES: *c1ncc(Cl)cn1]

wherein the symbol ⌇, when drawn across a bond, indicates the point of attachment to the rest of the molecule.

25. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is

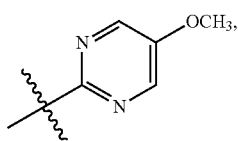 [SMILES: *c1ncc(OC)cn1]

wherein the symbol ⌇, when drawn across a bond, indicates the point of attachment to the rest of the molecule.

26. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is

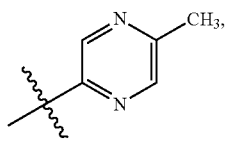 [SMILES: *c1cnc(C)cn1]

wherein the symbol ⌇, when drawn across a bond, indicates the point of attachment to the rest of the molecule.

27. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is

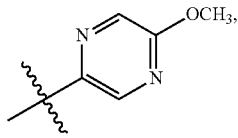 [SMILES: *c1cnc(OC)cn1]

wherein the symbol ⌇, when drawn across a bond, indicates the point of attachment to the rest of the molecule.

28. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

29. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl, pyrazinyl, or pyridyl group and Q is unsubstituted or is substituted with 1 or 2 $R^Q$ substituents.

30. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl or pyrazinyl group and Q is unsubstituted or is substituted with 1 or 2 $R^Q$ substituents.

31. The compound of any one of embodiments 1-30 or the pharmaceutically acceptable salt thereof, the tautomer thereof, the pharmaceutically acceptable salt of the tautomer, the stereoisomer of any of the foregoing, or the mixture thereof, wherein one of $R^{3b}$ and $R^{3c}$ is —H and the other is —H or —$CH_3$.

32. The compound of any one of embodiments 1-30 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents.

33. The compound of embodiment 32 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula

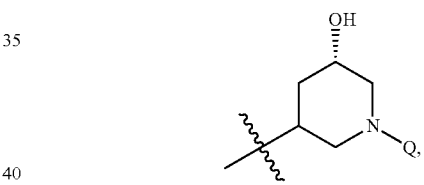

wherein the symbol ⌇, when drawn across a bond, indicates the point of attachment to the rest of the molecule.

34. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein $R^{3a}$ is —OH.

35. The compound of any one of embodiments 1-30 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —($CR^3R^{3e}$)—($CR^{3f}R^{3g}$)-Q.

36. The compound of any one of embodiments 1-30 or the pharmaceutically acceptable salt thereof, the tautomer thereof, the pharmaceutically acceptable salt of the tautomer, the stereoisomer of any of the foregoing, or the mixture thereof, wherein $R^3$ has the formula

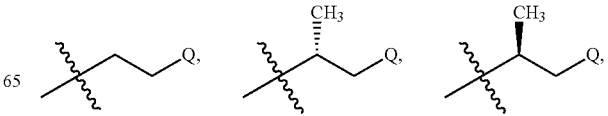

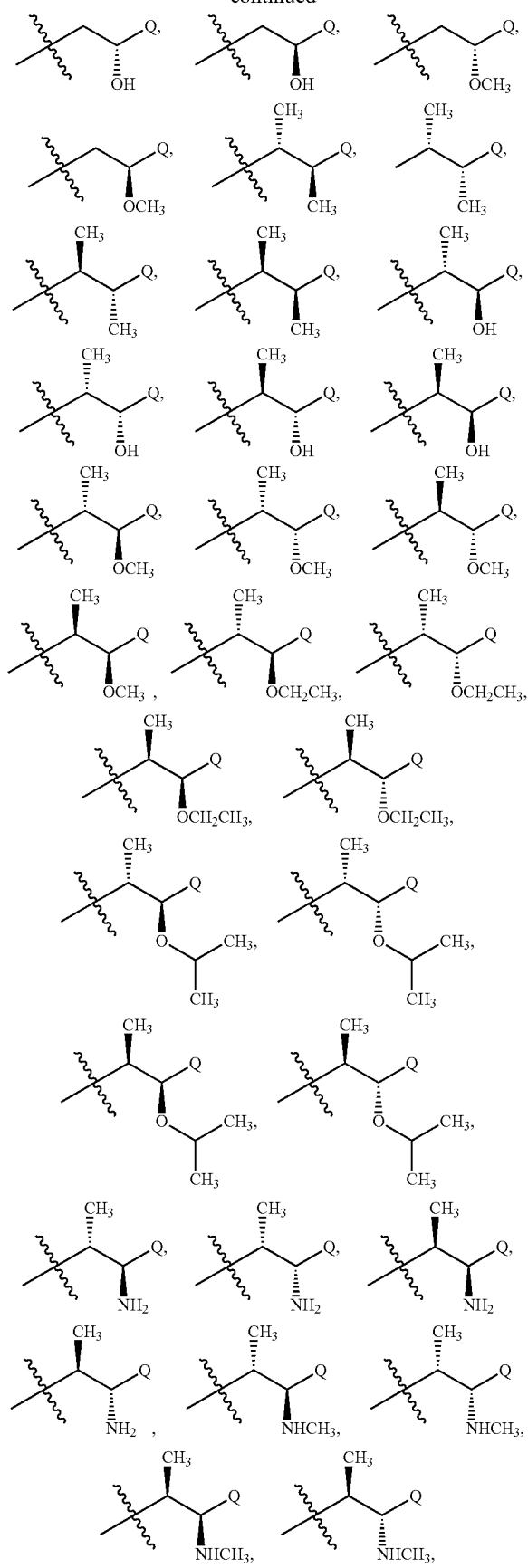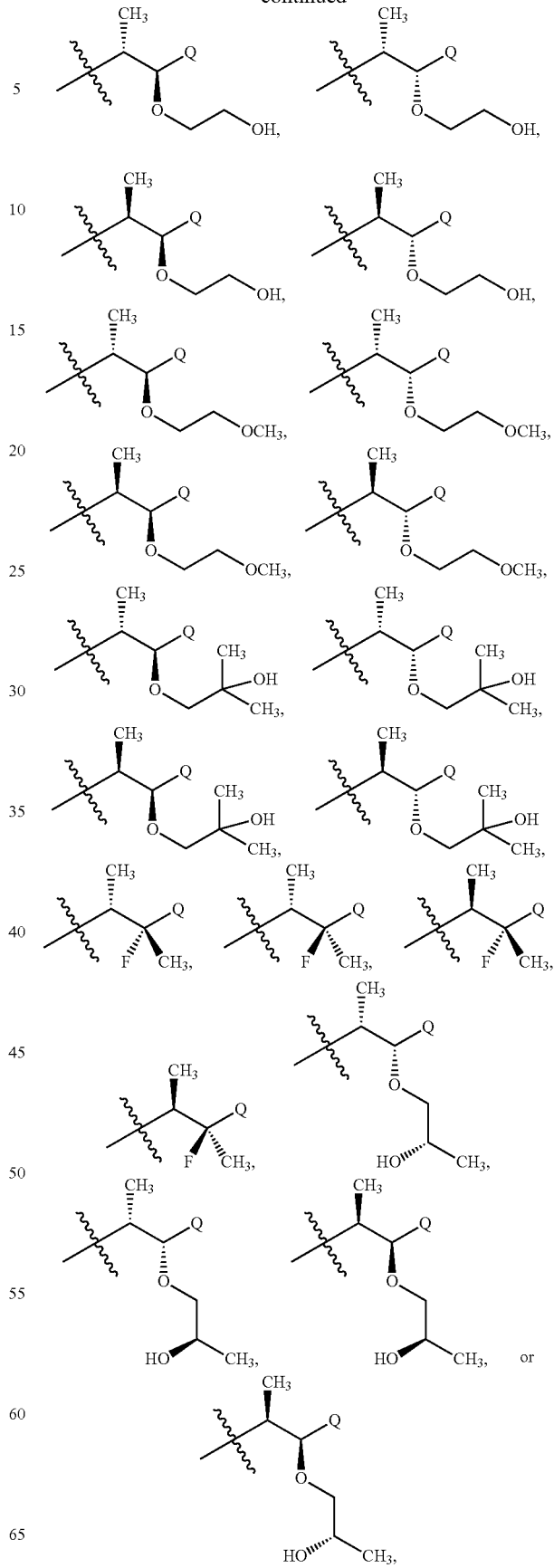

wherein the symbol ∿, when drawn across a bond, indicates the point of attachment to the rest of the molecule.

37. The compound of any one of embodiments 1-30 or the pharmaceutically acceptable salt thereof, the tautomer thereof, the pharmaceutically acceptable salt of the tautomer, the stereoisomer of any of the foregoing, or the mixture thereof, wherein $R^3$ has the formula

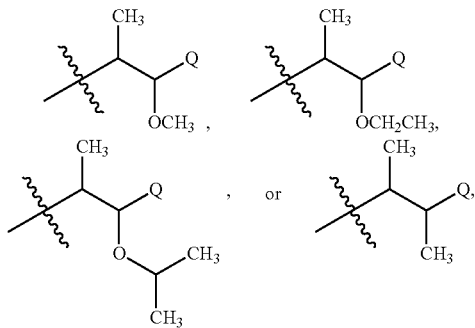

wherein the symbol ∿, when drawn across a bond, indicates the point of attachment to the rest of the molecule.

38. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

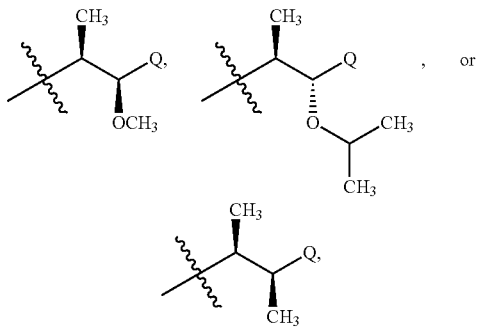

wherein the symbol ∿, when drawn across a bond, indicates the point of attachment to the rest of the molecule.

39. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

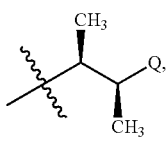

wherein the symbol ∿, when drawn across a bond, indicates the point of attachment to the rest of the molecule.

40. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

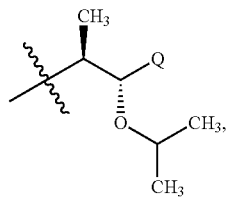

wherein the symbol ∿, when drawn across a bond, indicates the point of attachment to the rest of the molecule.

41. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

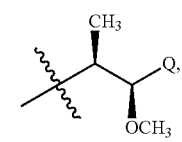

wherein the symbol ∿, when drawn across a bond, indicates the point of attachment to the rest of the molecule.

42. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

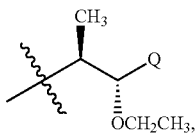

wherein the symbol ∿, when drawn across a bond, indicates the point of attachment to the rest of the molecule.

43. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

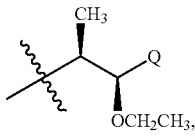

wherein the symbol ∿, when drawn across a bond, indicates the point of attachment to the rest of the molecule.

44. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ has the formula

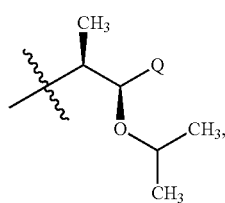

wherein the symbol ⌇, when drawn across a bond, indicates the point of attachment to the rest of the molecule.

45. The compound of embodiment 1, wherein the compound has the formula IA

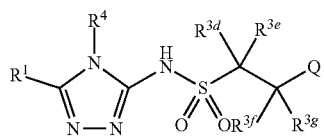

IA or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 1;

$R^{3d}$ and $R^{3e}$ are independently selected from —H or —$C_1$-$C_3$ alkyl;

$R^{3f}$ and $R^{3g}$ are independently selected from —H, —$C_1$-$C_6$ alkyl, or —O—($C_1$-$C_6$ alkyl);

$R^4$ is as defined in embodiment 1;

Q is a monocyclic heteroaryl group with 6 ring members containing 1 or 2 N heteroatoms, wherein the monocyclic heteroaryl Q groups are unsubstituted or are substituted with 1 or 2 $R^Q$ substituent; and $R^Q$ is independently selected from —F, —Cl, —Br, —CN, —O—$C_1$-$C_6$ alkyl or —$C_1$-$C_6$ alkyl.

46. The compound of embodiment 45 or the pharmaceutically acceptable salt thereof, the tautomer thereof, the pharmaceutically acceptable salt of the tautomer, the stereoisomer of any of the foregoing, or the mixture thereof, wherein:

$R^{3d}$ and $R^{3e}$ are independently selected from —H or —$CH_3$;

$R^{3f}$ and $R^{3g}$ are independently selected from —H, —$CH_3$, —$OCH_3$, or —$OCH(CH_3)_2$;

Q is a pyrimidinyl, a pyridinyl, or a pyrazinyl any of which are unsubstituted or are substituted with 1 or 2 $R^Q$ substituent; and $R^Q$ is independently selected from —F, —Cl, —Br, —CN, —$CH_3$, or —$OCH_3$.

47. The compound of embodiment 45 or embodiment 46 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted pyridyl group or is a pyridyl that is substituted with 1 $R^{1a}$ substituent.

48. The compound of embodiment 47 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl substituted with 1 $R^{1a}$ substituent selected from —$C_1$-$C_6$ alkyl, —O—($C_1$-$C_6$ alkyl), or —O—($C_1$-$C_6$ alkyl)-O—($C_1$-$C_6$ alkyl).

49. The compound of embodiment 47 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl substituted with 1 $R^{1a}$ substituent selected from —$CH_3$, —$OCH_3$, or —$OCH_2CH_2OCH_3$.

50. The compound of embodiment 47 or the pharmaceutically acceptable salt thereof, the tautomer thereof, the pharmaceutically acceptable salt of the tautomer, the stereoisomer of any of the foregoing, or the mixture thereof, wherein the $R^1$ is an unsubstituted pyridyl.

51. The compound of embodiment 45 or embodiment 46 or the pharmaceutically acceptable salt thereof, the tautomer thereof, the pharmaceutically acceptable salt of the tautomer, the stereoisomer of any of the foregoing, or the mixture thereof, wherein $R^1$ is selected from

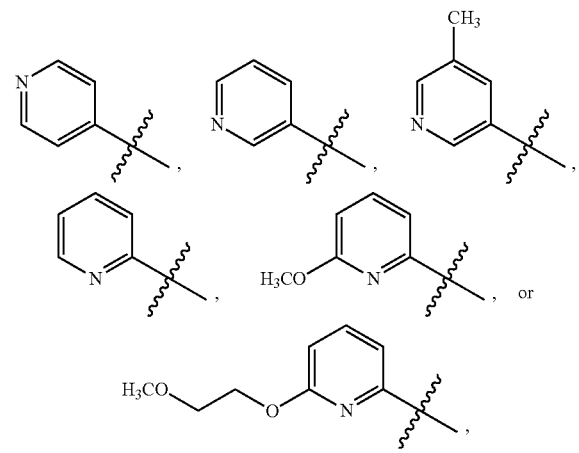

wherein the symbol ⌇, when drawn across a bond, indicates the point of attachment to the rest of the molecule.

52. The compound of any one of embodiments 45-51 or the pharmaceutically acceptable salt thereof, the tautomer thereof, the pharmaceutically acceptable salt of the tautomer, the stereoisomer of any of the foregoing, or the mixture thereof, wherein $R^3$ is selected from

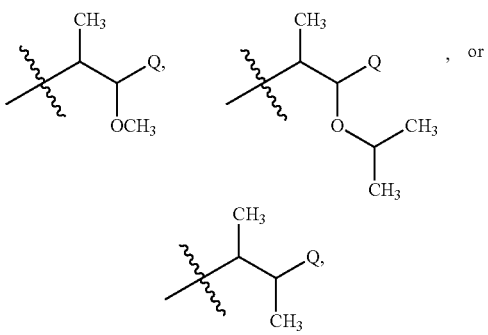

wherein the symbol ⌇, when drawn across a bond, indicates the point of attachment to the rest of the molecule.

53. The compound of any one of embodiments 45-51 or the pharmaceutically acceptable salt thereof, the tautomer thereof, the pharmaceutically acceptable salt of the tautomer, the stereoisomer of any of the foregoing, or the mixture thereof, wherein R³ is selected from

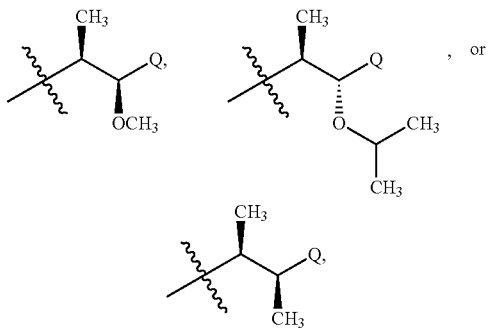

wherein the symbol ∿, when drawn across a bond, indicates the point of attachment to the rest of the molecule.

54. The compound of embodiment 1, wherein the compound is selected from
(2S,3R)—N-(4-((1r,2R,6S)-2,6-dimethoxycyclohexyl)-5-(5-methyl-3-pyridinyl)-4H-1,2,4-triazol-3-yl)-3-(5-methyl-2-pyrimidinyl)-2-butanesulfonamide;
(2S,3R)-3-(5-chloro-2-pyrimidinyl)-N-(5-(6-methoxy-2-pyridinyl)-4-(3-oxetanylmethyl)-4H-1,2,4-triazol-3-yl)-2-butanesulfonamide;
(1R,2S)-1-(5-chloro-2-pyrimidinyl)-1-methoxy-N-(4-(2-methoxyethyl)-5-(6-methoxy-2-pyridinyl)-4H-1,2,4-triazol-3-yl)-2-propanesulfonamide;
(1R,2S)-1-(5-chloro-2-pyrimidinyl)-1-methoxy-N-(4-(1-(methoxymethyl)cyclopropyl)-5-(6-methoxy-2-pyridinyl)-4H-1,2,4-triazol-3-yl)-2-propanesulfonamide;
(1R,2S)-1-(5-chloro-2-pyrimidinyl)-N-(4-(2-hydroxy-1-(hydroxymethyl)ethyl)-5-(6-methoxy-2-pyridinyl)-4H-1,2,4-triazol-3-yl)-1-methoxy-2-propanesulfonamide;
(1R,2S)-1-(5-chloro-2-pyrimidinyl)-1-methoxy-N-(4-(2-methoxy-1-(methoxymethyl)ethyl)-5-(6-methoxy-2-pyridinyl)-4H-1,2,4-triazol-3-yl)-2-propanesulfonamide;
(1R,2S)-1-(5-chloro-2-pyrimidinyl)-1-methoxy-N-(5-(6-methoxy-2-pyridinyl)-4-(2-oxaspiro[3.3]hept-6-yl)-4H-1,2,4-triazol-3-yl)-2-propanesulfonamide;
(1R,2S)—N-(4-(1,3-dimethoxy-2-propanyl)-5-(2-pyridinyl)-4H-1,2,4-triazol-3-yl)-1-methoxy-1-(5-methyl-2-pyrimidinyl)-2-propanesulfonamide;
(1S,2S)—N-(4-(1,3-dimethoxy-2-propanyl)-5-(5-methyl-3-pyridinyl)-4H-1,2,4-triazol-3-yl)-1-(5-methyl-2-pyrimidinyl)-1-(2-propanyloxy)-2-propanesulfonamide;
(1R,2S)-1-(5-chloro-2-pyrimidinyl)-1-methoxy-N-(5-(6-methoxy-2-pyridinyl)-4-(3-pentanyl)-4H-1,2,4-triazol-3-yl)-2-propanesulfonamide;
(1R,2S)-1-(5-chloro-2-pyrimidinyl)-1-methoxy-N-(5-(6-methoxy-2-pyridinyl)-4-(2-propanyl)-4H-1,2,4-triazol-3-yl)-2-propanesulfonamide;
(1S,2S)-1-(5-chloro-2-pyrimidinyl)-N-(4-(2-methoxyethyl)-5-(5-methyl-3-pyridinyl)-4H-1,2,4-triazol-3-yl)-1-(2-propanyloxy)-2-propanesulfonamide;
(1S,2S)-1-(5-chloro-2-pyrimidinyl)-N-(4-(1,3-dimethoxy-2-propanyl)-5-(5-methyl-3-pyridinyl)-4H-1,2,4-triazol-3-yl)-1-(2-propanyloxy)-2-propanesulfonamide;
(1R,2S)-1-(5-chloro-2-pyrimidinyl)-N-(4-(1,3-dimethoxy-2-propanyl)-5-(2-pyridinyl)-4H-1,2,4-triazol-3-yl)-1-methoxy-2-propanesulfonamide;
(1R,2S)-1-(5-chloro-2-pyrimidinyl)-N-(4-(1,3-dimethoxy-2-propanyl)-5-(5-methyl-3-pyridinyl)-4H-1,2,4-triazol-3-yl)-1-methoxy-2-propanesulfonamide;
(1R,2S)-1-(5-chloro-2-pyrimidinyl)-N-(4-(1,3-dimethoxy-2-propanyl)-5-(3-pyridinyl)-4H-1,2,4-triazol-3-yl)-1-methoxy-2-propanesulfonamide;
(2S,3R)—N-(4-(1,3-dimethoxy-2-propanyl)-5-(3-pyridinyl)-4H-1,2,4-triazol-3-yl)-3-(5-methyl-2-pyrazinyl)-2-butanesulfonamide;
(2S,3R)-3-(5-chloro-2-pyrimidinyl)-N-(4-(2-methoxyethyl)-5-(3-pyridinyl)-4H-1,2,4-triazol-3-yl)-2-butanesulfonamide;
(2S,3R)-3-(5-chloro-2-pyrimidinyl)-N-(4-(1,3-dimethoxy-2-propanyl)-5-(3-pyridinyl)-4H-1,2,4-triazol-3-yl)-2-butanesulfonamide;
(2S,3R)—N-(4-(2-methoxyethyl)-5-(6-methoxy-2-pyridinyl)-4H-1,2,4-triazol-3-yl)-3-(5-methoxy-2-pyrimidinyl)-2-butanesulfonamide;
(2S,3R)—N-(4-(2-methoxyethyl)-5-(2-pyridinyl)-4H-1,2,4-triazol-3-yl)-3-(5-methoxy-2-pyrimidinyl)-2-butanesulfonamide;
(1R,2S)-1-(5-chloro-2-pyrimidinyl)-N-(4-(2-ethoxyethyl)-5-(6-methoxy-2-pyridinyl)-4H-1,2,4-triazol-3-yl)-1-methoxy-2-propanesulfonamide;
(1S,2S)-1-(5-chloro-2-pyrimidinyl)-N-(4-(2-methoxyethyl)-5-(2-pyridinyl)-4H-1,2,4-triazol-3-yl)-1-(2-propanyloxy)-2-propanesulfonamide;
(1S,2S)-1-(5-chloro-2-pyrimidinyl)-N-(4-(2-methoxyethyl)-5-(6-methoxy-2-pyridinyl)-4H-1,2,4-triazol-3-yl)-1-(2-propanyloxy)-2-propanesulfonamide;
(1R,2S)-1-(5-chloro-2-pyrimidinyl)-N-(4-(dicyclopropylmethyl)-5-(6-methoxy-2-pyridinyl)-4H-1,2,4-triazol-3-yl)-1-methoxy-2-propanesulfonamide;
(1R,2S)-1-(5-chloro-2-pyrimidinyl)-1-methoxy-N-(5-(6-methoxy-2-pyridinyl)-4-(2-(methylsulfanyl)ethyl)-4H-1,2,4-triazol-3-yl)-2-propanesulfonamide;
(1R,2S)-1-(5-chloro-2-pyrimidinyl)-N-(4-(1,3-dimethoxy-2-propanyl)-5-(6-(2-methoxyethoxy)-2-pyridinyl)-4H-1,2,4-triazol-3-yl)-1-methoxy-2-propanesulfonamide;
(1R,2S)-1-(5-chloro-2-pyrimidinyl)-N-(4-(2-(difluoromethoxy)ethyl)-5-(6-methoxy-2-pyridinyl)-4H-1,2,4-triazol-3-yl)-1-methoxy-2-propanesulfonamide;
(1R,2S)-1-(5-chloro-2-pyrimidinyl)-N-(4-(2-cyanoethyl)-5-(6-methoxy-2-pyridinyl)-4H-1,2,4-triazol-3-yl)-1-methoxy-2-propanesulfonamide;
3-(3-(((((1R,2S)-1-(5-chloro-2-pyrimidinyl)-1-methoxy-2-propanyl)sulfonyl)amino)-5-(6-methoxy-2-pyridinyl)-4H-1,2,4-triazol-4-yl)propanamide;
(1R,2S)-1-(5-chloro-2-pyrimidinyl)-N-(4-(dicyclopropylmethyl)-5-(2-pyridinyl)-4H-1,2,4-triazol-3-yl)-1-methoxy-2-propanesulfonamide;
(1R,2S)-1-(5-chloro-2-pyrimidinyl)-1-methoxy-N-(4-(3-pentanyl)-5-(2-pyridinyl)-4H-1,2,4-triazol-3-yl)-2-propanesulfonamide;
(1R,2S)-1-(5-chloro-2-pyrimidinyl)-1-methoxy-N-(4-((2S)-1-methoxy-2-propanyl)-5-(6-methoxy-2-pyridinyl)-4H-1,2,4-triazol-3-yl)-2-propanesulfonamide;
(1R,2S)-1-(5-chloro-2-pyrimidinyl)-1-methoxy-N-(4-((2R)-1-methoxy-2-propanyl)-5-(6-methoxy-2-pyridinyl)-4H-1,2,4-triazol-3-yl)-2-propanesulfonamide;
(1R,2S)-1-(5-chloro-2-pyrimidinyl)-1-methoxy-N-(4-(1-(methoxymethyl)cyclobutyl)-5-(6-methoxy-2-pyridinyl)-4H-1,2,4-triazol-3-yl)-2-propanesulfonamide;
(1R,2S)-1-(5-chloro-2-pyrimidinyl)-1-methoxy-N-(4-(1-(methoxymethyl)cyclobutyl)-5-(2-pyridinyl)-4H-1,2,4-triazol-3-yl)-2-propanesulfonamide;
(2S,3R)-3-(5-chloro-2-pyrimidinyl)-N-(4-((2R)-1-methoxy-2-propanyl)-5-(3-pyridinyl)-4H-1,2,4-triazol-3-yl)-2-butanesulfonamide;

(2S,3R)-3-(5-chloro-2-pyrimidinyl)-N-(4-((2S)-1-methoxy-2-propanyl)-5-(3-pyridinyl)-4H-1,2,4-triazol-3-yl)-2-butanesulfonamide;

(1R,2S)—N-(4-((2R)-2-butanyl)-5-(6-methoxy-2-pyridinyl)-4H-1,2,4-triazol-3-yl)-1-(5-chloro-2-pyrimidinyl)-1-methoxy-2-propanesulfonamide;

(1R,2S)—N-(4-((2S)-2-butanyl)-5-(6-methoxy-2-pyridinyl)-4H-1,2,4-triazol-3-yl)-1-(5-chloro-2-pyrimidinyl)-1-methoxy-2-propanesulfonamide;

(1R,2S)-1-(5-chloro-2-pyrimidinyl)-1-methoxy-N-(5-(6-methoxy-2-pyridinyl)-4-((1R)-spiro[3.3]heptan-1-yl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S)-spiro[3.3]heptan-1-yl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-(2-(methylsulfonyl)ethyl)-4H-1,2,4-triazol-3-yl)-2-propanesulfonamide;

(1S,2S)—N-(4-(1-methylcyclopropyl)-5-(5-methyl-3-pyridinyl)-4H-1,2,4-triazol-3-yl)-1-(1-methylethoxy)-1-(5-methyl-2-pyrimidinyl)-2-propanesulfonamide;

(1R,2S)-1-(5-chloro-2-pyrimidinyl)-1-methoxy-N-(4-(1-methylcyclobutyl)-5-(6-methyl-2-pyridinyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(3-pyridinyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(2-pyridinyl)-4H-1,2,4-triazol-3-yl)-2-propanesulfonamide;

(1S,2S)—N-(4-(1-(methoxymethyl)cyclopropyl)-5-(3-pyridinyl)-4H-1,2,4-triazol-3-yl)-1-(5-methyl-2-pyrimidinyl)-1-(2-propanyloxy)-2-propanesulfonamide;

(1S,2S)—N-(4-(1-(methoxymethyl)cyclopropyl)-5-(5-methyl-3-pyridinyl)-4H-1,2,4-triazol-3-yl)-1-(5-methyl-2-pyrimidinyl)-1-(2-propanyloxy)-2-propanesulfonamide;

(1S,2S)—N-(4-(1-(methoxymethyl)cyclopropyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(1S,2S)—N-(4-(1-(methoxymethyl)cyclopropyl)-5-(2-pyridinyl)-4H-1,2,4-triazol-3-yl)-1-(5-methyl-2-pyrimidinyl)-1-(2-propanyloxy)-2-propanesulfonamide;

(2S,3R)—N-(4-(1-(methoxymethyl)cyclopropyl)-5-(3-pyridinyl)-4H-1,2,4-triazol-3-yl)-3-(5-methyl-2-pyrazinyl)-2-butanesulfonamide;

(1R,2S)-1-methoxy-N-(4-(1-(methoxymethyl)cyclopropyl)-5-(2-pyridinyl)-4H-1,2,4-triazol-3-yl)-1-(5-methyl-2-pyrimidinyl)-2-propanesulfonamide;

(2S,3R)-3-(5-chloro-2-pyrimidinyl)-N-(4-(1-(methoxymethyl)cyclopropyl)-5-(3-pyridinyl)-4H-1,2,4-triazol-3-yl)-2-butanesulfonamide;

(1R,2S)-1-(5-chloro-2-pyrimidinyl)-N-(4-cyclopropyl-5-(6-methoxy-2-pyridinyl)-4H-1,2,4-triazol-3-yl)-1-methoxy-2-propanesulfonamide;

(1S,2S)-1-(5-chloro-2-pyrimidinyl)-N-(4-cyclopropyl-5-(6-methoxy-2-pyridinyl)-4H-1,2,4-triazol-3-yl)-1-(2-propanyloxy)-2-propanesulfonamide;

(1R,2S)-1-(5-chloro-2-pyrimidinyl)-N-(4-(cyclobutylmethyl)-5-(6-methoxy-2-pyridinyl)-4H-1,2,4-triazol-3-yl)-1-methoxy-2-propanesulfonamide;

(1R,2S)-1-(5-chloro-2-pyrimidinyl)-N-(4-(2-(4-fluorophenyl)ethyl)-5-(6-methoxy-2-pyridinyl)-4H-1,2,4-triazol-3-yl)-1-methoxy-2-propanesulfonamide;

(1R,2S)-1-(5-chloro-2-pyrimidinyl)-1-methoxy-N-(5-(6-methoxy-2-pyridinyl)-4-((1R,2R)-2-methylcyclohexyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R,2S)-2-methylcyclohexyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S,2R)-2-methylcyclohexyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S,2S)-2-methylcyclohexyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-(1,2-oxazol-3-ylmethyl)-4H-1,2,4-triazol-3-yl)-2-propanesulfonamide;

(1R,2S)-1-(5-chloro-2-pyrimidinyl)-N-(4-(2,2-dimethoxyethyl)-5-(6-methoxy-2-pyridinyl)-4H-1,2,4-triazol-3-yl)-1-methoxy-2-propanesulfonamide;

(1R,2S)-1-(5-chloro-2-pyrimidinyl)-1-methoxy-N-(4-(2-propanyl)-5-(2-pyridinyl)-4H-1,2,4-triazol-3-yl)-2-propanesulfonamide;

(1R,2S)-1-(5-chloro-2-pyrimidinyl)-1-methoxy-N-(4-(2-propanyl)-5-(3-pyridinyl)-4H-1,2,4-triazol-3-yl)-2-propanesulfonamide;

(1R,2S)-1-(5-chloro-2-pyrimidinyl)-1-methoxy-N-(4-(2-propanyl)-5-(4-pyridinyl)-4H-1,2,4-triazol-3-yl)-2-propanesulfonamide;

(1R,2S)-1-(5-chloro-2-pyrimidinyl)-1-methoxy-N-(4-(4-methoxybenzyl)-5-(6-methoxy-2-pyridinyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R)-spiro[2.2]pentan-1-yl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S)-spiro[2.2]pentan-1-yl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-(2-((S)-methylsulfinyl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-(2-((R)-methylsulfinyl)ethyl)-4H-1,2,4-triazol-3-yl)-2-propanesulfonamide;

(1R,2S)-1-(5-chloro-2-pyrimidinyl)-1-methoxy-N-(4-(1-methylcyclopropyl)-5-(2-pyridinyl)-4H-1,2,4-triazol-3-yl)-2-propanesulfonamide;

(2S,3R)—N-(4-(1,3-dimethoxy-2-propanyl)-5-(6-methoxy-2-pyridinyl)-4H-1,2,4-triazol-3-yl)-3-(5-methyl-2-pyrimidinyl)-2-butanesulfonamide;

(2S,3R)—N-(4-(1,3-dimethoxy-2-propanyl)-5-(6-methoxy-2-pyridinyl)-4H-1,2,4-triazol-3-yl)-3-(5-methoxy-2-pyrimidinyl)-2-butanesulfonamide;

(1R,2S)—N-(4-(1,3-dimethoxy-2-propanyl)-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-(1,3-dimethoxy-2-propanyl)-5-(6-methoxy-2-pyridinyl)-4H-1,2,4-triazol-3-yl)-1-methoxy-1-(5-methoxy-2-pyrazinyl)-2-propanesulfonamide;

(2S,3R)—N-(4-(1,3-dimethoxy-2-propanyl)-5-(6-methoxy-2-pyridinyl)-4H-1,2,4-triazol-3-yl)-3-(5-methyl-2-pyrazinyl)-2-butanesulfonamide;

(1R,2S)—N-(4-(1,3-dimethoxy-2-propanyl)-5-(6-methoxy-2-pyridinyl)-4H-1,2,4-triazol-3-yl)-1-methoxy-1-(5-methyl-2-pyrazinyl)-2-propanesulfonamide;

(1S,2S)—N-(4-(1,3-dimethoxy-2-propanyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(1S,2S)—N-(4-(1,3-dimethoxy-2-propanyl)-5-(6-methoxy-2-pyridinyl)-4H-1,2,4-triazol-3-yl)-1-(5-methyl-2-pyrazinyl)-1-(2-propanyloxy)-2-propanesulfonamide;

(1R,2S)-1-(5-chloro-2-pyrimidinyl)-N-(4-(1-(fluoromethyl)cyclopropyl)-5-(6-methoxy-2-pyridinyl)-4H-1,2,4-triazol-3-yl)-1-methoxy-2-propanesulfonamide;

(1R,2S)—N-(4-([1,1'-bi(cyclopropyl)]-1-yl)-5-(6-methoxy-2-pyridinyl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-(2-pyridinyl)-4H-1,2,4-triazol-3-yl)-1-(5-chloro-2-pyrimidinyl)-1-methoxy-2-propanesulfonamide;

(1R,2S)—N-(4-([1,1'-bi(cyclopropyl)]-1-yl)-5-(6-methoxy-2-pyridinyl)-4H-1,2,4-triazol-3-yl)-1-methoxy-1-(5-methyl-2-pyrazinyl)-2-propanesulfonamide;

(1R,2S)—N-(4-([1,1'-bi(cyclopropyl)]-1-yl)-5-(2-pyridinyl)-4H-1,2,4-triazol-3-yl)-1-methoxy-1-(5-methyl-2-pyrazinyl)-2-propanesulfonamide;

(1R,2S)-1-(5-chloro-2-pyrimidinyl)-1-methoxy-N-(4-(3-pentanyl)-5-(3-pyridinyl)-4H-1,2,4-triazol-3-yl)-2-propanesulfonamide;

(1R,2S)-1-(5-chloro-2-pyrimidinyl)-N-(4-(dicyclopropylmethyl)-5-(3-pyridinyl)-4H-1,2,4-triazol-3-yl)-1-methoxy-2-propanesulfonamide;

(1S,2S)-1-(5-chloro-2-pyrimidinyl)-N-(4-(1,3-dimethoxy-2-propanyl)-5-(2-pyridinyl)-4H-1,2,4-triazol-3-yl)-1-(2-propanyloxy)-2-propanesulfonamide;

(2S,3R)—N-(4-cyclopropyl-5-(6-methoxy-2-pyridinyl)-4H-1,2,4-triazol-3-yl)-3-(5-methyl-2-pyrimidinyl)-2-butanesulfonamide;

(2S,3R)—N-(4-cyclopropyl-5-(6-methoxy-2-pyridinyl)-4H-1,2,4-triazol-3-yl)-3-(5-methoxy-2-pyrazinyl)-2-butanesulfonamide;

(2S,3R)—N-(4-cyclopropyl-5-(6-methoxy-2-pyridinyl)-4H-1,2,4-triazol-3-yl)-3-(5-methoxy-2-pyrimidinyl)-2-butanesulfonamide;

(1R,2S)—N-(4-cyclopropyl-5-(6-methoxy-2-pyridinyl)-4H-1,2,4-triazol-3-yl)-1-methoxy-1-(5-methyl-2-pyrimidinyl)-2-propanesulfonamide;

(1R,2S)—N-(4-cyclopropyl-5-(6-methoxy-2-pyridinyl)-4H-1,2,4-triazol-3-yl)-1-methoxy-1-(5-methoxy-2-pyrazinyl)-2-propanesulfonamide;

(1R,2S)—N-(4-cyclopropyl-5-(6-methoxy-2-pyridinyl)-4H-1,2,4-triazol-3-yl)-1-methoxy-1-(5-methyl-2-pyrazinyl)-2-propanesulfonamide;

(1S,2S)—N-(4-cyclopropyl-5-(6-methoxy-2-pyridinyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-1-methoxy-N-(4-((2R)-1-methoxy-2-propanyl)-5-(2-pyridinyl)-4H-1,2,4-triazol-3-yl)-2-propanesulfonamide;

(1R,2S)-1-(5-chloro-2-pyrimidinyl)-1-methoxy-N-(4-((2R)-1-methoxy-2-propanyl)-5-(3-pyridinyl)-4H-1,2,4-triazol-3-yl)-2-propanesulfonamide;

(1R,2S)-1-(5-chloro-2-pyrimidinyl)-1-methoxy-N-(4-((2R)-1-methoxy-2-propanyl)-5-(5-methyl-3-pyridinyl)-4H-1,2,4-triazol-3-yl)-2-propanesulfonamide;

(1S,2S)-1-(5-chloro-2-pyrimidinyl)-N-(4-cyclopropyl-5-(2-pyridinyl)-4H-1,2,4-triazol-3-yl)-1-(2-propanyloxy)-2-propanesulfonamide;

(1S,2S)-1-(5-chloro-2-pyrimidinyl)-N-(4-cyclopropyl-5-(3-pyridinyl)-4H-1,2,4-triazol-3-yl)-1-(2-propanyloxy)-2-propanesulfonamide;

(1S,2S)-1-(5-chloro-2-pyrimidinyl)-N-(4-cyclopropyl-5-(5-methyl-3-pyridinyl)-4H-1,2,4-triazol-3-yl)-1-(2-propanyloxy)-2-propanesulfonamide;

(1R,2S)-1-(5-chloro-2-pyrimidinyl)-1-methoxy-N-(4-methyl-5-(2-pyridinyl)-4H-1,2,4-triazol-3-yl)-2-propanesulfonamide;

(1R,2S)-1-(5-chloro-2-pyrimidinyl)-N-(4-ethyl-5-(2-pyridinyl)-4H-1,2,4-triazol-3-yl)-1-methoxy-2-propanesulfonamide; or (1R,2S)-1-(5-chloro-2-pyrimidinyl)-1-methoxy-N-(4-(2-methoxyethyl)-5-(2-pyridinyl)-4H-1,2,4-triazol-3-yl)-2-propanesulfonamide, or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds listed above or the pharmaceutically acceptable salt thereof, or the mixture thereof. In still other such embodiments, the embodiment provides any of the compounds listed above or the pharmaceutically acceptable salt thereof, or the stereoisomer thereof or the mixture thereof.

55. The compound of embodiment 1, wherein the compound is selected from (1R,2S)—N-(4-benzyl-5-(6-methoxypyridin-2-yl)-4H-1,2,4-triazol-3-yl)-1-(5-chloropyrimidin-2-yl)-1-methoxypropane-2-sulfonamide;

(1R,2S)-1-(5-chloropyrimidin-2-yl)-N-(4-isobutyl-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-(cyclopentylmethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-(cyclohexylmethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-1-methoxy-N-(5-(6-methoxypyridin-2-yl)-4-((1S)-1-(tetrahydrofuran-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((1R)-1-(tetrahydrofuran-2-yl)ethyl)-4H-1,2,4-triazol-3-yl)propane-2-sulfonamide;

2-(3-((1S,2R)-2-(5-chloropyrimidin-2-yl)-2-methoxy-1-methylethylsulfonamido)-5-(6-methoxypyridin-2-yl)-4H-1,2,4-triazol-4-yl)-N-cyclopropylacetamide;

(1R,2S)-1-(5-chloropyrimidin-2-yl)-N-(4-(((S)-1-ethylpyrrolidin-2-yl)methyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-(((R)-1-ethylpyrrolidin-2-yl)methyl)-5-(6-methoxypyridin-2-yl)-4H-1,2,4-triazol-3-yl)-1-methoxypropane-2-sulfonamide; or (1R,2S)—N-(4-(adamantan-1-yl)-5-(6-methoxypyridin-2-yl)-4H-1,2,4-triazol-3-yl)-1-(5-chloropyrimidin-2-yl)-1-methoxypropane-2-sulfonamide, or or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds listed above or the pharmaceutically acceptable salt thereof, or the mixture thereof. In still other such embodiments, the embodiment provides any of the compounds listed above or the pharmaceutically acceptable salt thereof, or the stereoisomer thereof or the mixture thereof.

56. The compound of embodiment 1, wherein the compound is selected from (1R,2S)-1-(5-chloro-2-pyrimidinyl)-1-methoxy-N-(4-(2-propanyl)-5-(3-pyridinyl)-4H-1,2,4-triazol-3-yl)-2-propanesulfonamide;

(1R,2S)-1-(5-chloro-2-pyrimidinyl)-1-methoxy-N-(4-(2-propanyl)-5-(4-pyridinyl)-4H-1,2,4-triazol-3-yl)-2-propanesulfonamide;

(1R,2S)-1-(5-chloro-2-pyrimidinyl)-1-methoxy-N-(4-(2-propanyl)-5-(2-pyridinyl)-4H-1,2,4-triazol-3-yl)-2-propanesulfonamide;

(1R,2S)-1-(5-chloropyrimidin-2-yl)-1-methoxy-N-(5-(6-methoxypyridin-2-yl)-4-(oxetan-2-ylmethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-((S)-4-methylmorpholin-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-((R)-4-methylmorpholin-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-((S)-4-methylmorpholin-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-((R)-4-methylmorpholin-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((S)-oxetan-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((R)-oxetan-2-yl)methyl)-4H-1,2,4-triazol-3-yl)propane-2-sulfonamide;

(1R,2S)—N-(4-((R)-1-((R)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide;

(1R,2S)—N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide;

(1R,2S)—N-(4-((S)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide;

(1R,2S)—N-(4-((S)-1-((R)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide;

(2S,3R)—N-(4-((R)-1-((R)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide;

(2S,3R)—N-(4-((R)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide;

(2S,3R)—N-(4-((S)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide;

(2S,3R)—N-(4-((S)-1-((R)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide;

(1S,2S)—N-(4-((R)-1-((R)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide;

(1S,2S)—N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide;

(1S,2S)—N-(4-((S)-1-((S)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide;

(1S,2S)—N-(4-((S)-1-((R)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide;

1R,2S)-1-(5-chloropyrimidin-2-yl)-N-(4-(cyclopropyl-2,2,3,3-d4)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-cyclopropyl-5-(5-methylpyridin-3-yl)-4H-1,2,4-triazol-3-yl)-1-methoxypropane-2-sulfonamide;

(1R,2S)-1-(5-chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide;

(1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide;

(2S,3R)-3-(5-chloro-2-pyrimidinyl)-N-(5-(6-methoxy-2-pyridinyl)-4-((1R)-spiro[2.2]pentan-1-yl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-spiro[2.2]pentan-1-yl)-4H-1,2,4-triazol-3-yl)-2-butanesulfonamide;

(1R,2S)-1-methoxy-N-(5-(6-methoxypyridin-2-yl)-4-((R)-spiro[2.2]pentan-1-yl)-4H-1,2,4-triazol-3-yl)-1-(5-methoxypyrimidin-2-yl)propane-2-sulfonamide;

(1R,2S)-1-methoxy-N-(5-(6-methoxypyridin-2-yl)-4-((S)-spiro[2.2]pentan-1-yl)-4H-1,2,4-triazol-3-yl)-1-(5-methoxypyrimidin-2-yl)propane-2-sulfonamide;

(1R,2S)-1-(5-chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide;

(1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide;

(1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide;

(1R,2S)-1-methoxy-1-(5-methoxypyrazin-2-yl)-N-(5-(6-methoxypyridin-2-yl)-4-((S)-spiro[2.2]pentan-1-yl)-4H-1,2,4-triazol-3-yl)propane-2-sulfonamide;

(1R,2S)-1-methoxy-1-(5-methoxypyrazin-2-yl)-N-(5-(6-methoxypyridin-2-yl)-4-((R)-spiro[2.2]pentan-1-yl)-4H-1,2,4-triazol-3-yl)propane-2-sulfonamide;

(1R,2S)-1-(5-chloropyrimidin-2-yl)-N-(4-(dispiro[2.0.24.13]heptan-7-yl)-5-(6-methoxypyridin-2-yl)-4H-1,2,4-triazol-3-yl)-1-methoxypropane-2-sulfonamide;

(1S,2S)—N-(4-(cyclopropyl-2,2,3,3-d4)-5-(6-methoxypyridin-2-yl)-4H-1,2,4-triazol-3-yl)-1-isopropoxy-1-(5-methylpyrimidin-2-yl)propane-2-sulfonamide;

(1R,2S)-1-(5-chloropyrimidin-2-yl)-N-(4-((1R,2S)-2-fluorocyclopropyl)-5-(6-methoxypyridin-2-yl)-4H-1,2,4-triazol-3-yl)-1-methoxypropane-2-sulfonamide;

(1R,2S)-1-(5-chloropyrimidin-2-yl)-1-methoxy-N-(4-(4-methoxybenzyl)-5-(6-methoxypyridin-2-yl)-4H-1,2,4-triazol-3-yl)propane-2-sulfonamide;

(1S,2S)—N-(4-(1,3-dimethoxy-2-propanyl)-5-(6-methoxy-2-pyridinyl)-4H-1,2,4-triazol-3-yl)-1-(5-fluoro-2-pyrimidinyl)-1-(2-propanyloxy)-2-propanesulfonamide;

(1S,2S)—N-(4-(1,3-dimethoxy-2-propanyl)-5-(6-methoxy-2-pyridinyl)-4H-1,2,4-triazol-3-yl)-1-(5-methoxy-2-pyrimidinyl)-1-(2-propanyloxy)-2-propanesulfonamide;

(2S,3R)-3-(5-chloro-2-pyrimidinyl)-N-(4-((2S)-1-methoxy-2-propanyl)-5-(6-methoxy-2-pyridinyl)-4H-1,2,4-triazol-3-yl)-2-butanesulfonamide;

(2S,3R)-3-(5-chloro-2-pyrimidinyl)-N-(4-((2S)-1-methoxy-2-propanyl)-5-(2-pyridinyl)-4H-1,2,4-triazol-3-yl)-2-butanesulfonamide;

(2S,3R)-3-(5-chloro-2-pyrimidinyl)-N-(4-((2S)-1-methoxy-2-propanyl)-5-(5-methyl-3-pyridinyl)-4H-1,2,4-triazol-3-yl)-2-butanesulfonamide;

(1S,2S)-1-(5-chloro-2-pyrimidinyl)-N-(5-(6-methoxy-2-pyridinyl)-4-(2-propanyl)-4H-1,2,4-triazol-3-yl)-1-(2-propanyloxy)-2-propanesulfonamide;

(1S,2S)-1-(5-chloro-2-pyrimidinyl)-N-(4-((2R)-1-methoxy-2-propanyl)-5-(6-methoxy-2-pyridinyl)-4H-1,2,4-triazol-3-yl)-1-(2-propanyloxy)-2-propanesulfonamide;

(1S,2S)-1-(5-chloro-2-pyrimidinyl)-N-(4-((2S)-1-methoxy-2-propanyl)-5-(6-methoxy-2-pyridinyl)-4H-1,2,4-triazol-3-yl)-1-(2-propanyloxy)-2-propanesulfonamide;

(1R,2S)-1-(5-chloro-2-pyrimidinyl)-1-methoxy-N-(4-(cis-3-methoxycyclobutyl)-5-(6-methoxy-2-pyridinyl)-4H-1,2,4-triazol-3-yl)-2-propanesulfonamide;

(1R,2S)-1-(5-chloro-2-pyrimidinyl)-1-methoxy-N-(4-(trans-3-methoxycyclobutyl)-5-(6-methoxy-2-pyridinyl)-4H-1,2,4-triazol-3-yl)-2-propanesulfonamide;

(1R,2S)-1-(5-chloro-2-pyrimidinyl)-N-(4-cyclobutyl-5-(6-methoxy-2-pyridinyl)-4H-1,2,4-triazol-3-yl)-1-methoxy-2-propanesulfonamide;

(1R,2S)-1-(5-chloro-2-pyrimidinyl)-N-(4-cyclopentyl-5-(6-methoxy-2-pyridinyl)-4H-1,2,4-triazol-3-yl)-1-methoxy-2-propanesulfonamide;

(1R,2S)-1-(5-chloro-2-pyrimidinyl)-N-(4-cyclohexyl-5-(6-methoxy-2-pyridinyl)-4H-1,2,4-triazol-3-yl)-1-methoxy-2-propanesulfonamide;

(1R,2S)-1-(5-chloro-2-pyrimidinyl)-N-(4-((1r,2R,6S)-2,6-dimethoxycyclohexyl)-5-(6-methoxy-2-pyridinyl)-4H-1,2,4-triazol-3-yl)-1-methoxy-2-propanesulfonamide;

(1R,2S)-1-(5-chloropyrimidin-2-yl)-N-(4-(isoxazol-4-ylmethyl)-5-(6-methoxypyridin-2-yl)-4H-1,2,4-triazol-3-yl)-1-methoxypropane-2-sulfonamide;

(2S,3R)-3-(5-chloropyrimidin-2-yl)-N-(4-(isoxazol-4-ylmethyl)-5-(6-methoxypyridin-2-yl)-4H-1,2,4-triazol-3-yl)butane-2-sulfonamide;

(1R,2S)—N-(4-(isoxazol-4-ylmethyl)-5-(6-methoxypyridin-2-yl)-4H-1,2,4-triazol-3-yl)-1-methoxy-1-(5-methyl-pyrazin-2-yl)propane-2-sulfonamide;

(1R,2S)-1-(5-chloropyrimidin-2-yl)-1-methoxy-N-(5-(6-methoxypyridin-2-yl)-4-((3-methylisoxazol-5-yl)methyl)-4H-1,2,4-triazol-3-yl)propane-2-sulfonamide;

(2S,3R)-3-(5-chloropyrimidin-2-yl)-N-(5-(6-methoxypyridin-2-yl)-4-((3-methylisoxazol-5-yl)methyl)-4H-1,2,4-triazol-3-yl)butane-2-sulfonamide;

(1R,2S)-1-methoxy-N-(5-(6-methoxypyridin-2-yl)-4-((3-methylisoxazol-5-yl)methyl)-4H-1,2,4-triazol-3-yl)-1-(5-methylpyrazin-2-yl)propane-2-sulfonamide;

(1R,2S)-1-(5-chloro-2-pyrimidinyl)-N-(4-((3-ethyl-5-methyl-1,2-oxazol-4-yl)methyl)-5-(6-methoxy-2-pyridinyl)-4H-1,2,4-triazol-3-yl)-1-methoxy-2-propane sulfonamide;

(2S,3R)-3-(5-chloro-2-pyrimidinyl)-N-(4-((3-ethyl-5-methyl-1,2-oxazol-4-yl)methyl)-5-(6-methoxy-2-pyridinyl)-4H-1,2,4-triazol-3-yl)-2-butanesulfonamide;

(1S,2S)—N-(4-((3-ethyl-5-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propane sulfonamide;

(1R,2S)—N-(4-((3-ethyl-5-methylisoxazol-4-yl)methyl)-5-(6-methoxypyridin-2-yl)-4H-1,2,4-triazol-3-yl)-1-methoxy-1-(5-methylpyrazin-2-yl)propane-2-sulfonamide;

(2S,3R)-3-(5-chloropyrimidin-2-yl)-N-(4-((3-ethylisoxazol-5-yl)methyl)-5-(6-methoxypyridin-2-yl)-4H-1,2,4-triazol-3-yl)butane-2-sulfonamide;

(1R,2S)-1-(5-chloro-2-pyrimidinyl)-1-methoxy-N-(4-((3-methoxy-1,2-oxazol-5-yl)methyl)-5-(6-methoxy-2-pyridinyl)-4H-1,2,4-triazol-3-yl)-2-propanesulfonamide;

(2S,3R)-3-(5-chloro-2-pyrimidinyl)-N-(4-((3-methoxy-1,2-oxazol-5-yl)methyl)-5-(6-methoxy-2-pyridinyl)-4H-1,2,4-triazol-3-yl)-2-butanesulfonamide;

(1R,2S)-1-methoxy-N-(4-((3-methoxy-1,2-oxazol-5-yl)methyl)-5-(6-methoxy-2-pyridinyl)-4H-1,2,4-triazol-3-yl)-1-(5-methyl-2-pyrazinyl)-2-propanesulfonamide;

(1R,2S)-1-(5-chloro-2-pyrimidinyl)-1-methoxy-N-(5-(6-methoxy-2-pyridinyl)-4-((1R)-1-(1,2-oxazol-5-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S)-1-(1,2-oxazol-5-yl)ethyl)-4H-1,2,4-triazol-3-yl)-2-propanesulfonamide;

(2S,3R)-3-(5-chloro-2-pyrimidinyl)-N-(5-(6-methoxy-2-pyridinyl)-4-((1R)-1-(1,2-oxazol-5-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-1-(1,2-oxazol-5-yl)ethyl)-4H-1,2,4-triazol-3-yl)-2-butanesulfonamide;

2-((1S,2S)-2-(((5-(6-methoxy-2-pyridinyl)-4-((1R)-1-(1,2-oxazol-5-yl)ethyl)-4H-1,2,4-triazol-3-yl)methyl)sulfonyl)-1-(2-propanyloxy)propyl)-5-methylpyrimidine;

2-((1S,2S)-2-(((5-(6-methoxy-2-pyridinyl)-4-((1S)-1-(1,2-oxazol-5-yl)ethyl)-4H-1,2,4-triazol-3-yl)methyl)sulfonyl)-1-(2-propanyloxy)propyl)-5-methylpyrimidine;

(1R,2S)-1-methoxy-N-(5-(6-methoxy-2-pyridinyl)-4-((3-(trifluoromethyl)-1,2-oxazol-5-yl)methyl)-4H-1,2,4-triazol-3-yl)-1-(5-methyl-2-pyrazinyl)-2-propanesulfonamide;

(2S,3R)-3-(5-chloro-2-pyrimidinyl)-N-(5-(6-methoxy-2-pyridinyl)-4-((3-(trifluoromethyl)-1,2-oxazol-5-yl)methyl)-4H-1,2,4-triazol-3-yl)-2-butanesulfonamide;

(1R,2S)-1-(5-chloro-2-pyrimidinyl)-1-methoxy-N-(5-(6-methoxy-2-pyridinyl)-4-((3-(trifluoromethyl)-1,2-oxazol-5-yl)methyl)-4H-1,2,4-triazol-3-yl)-2-propanesulfonamide;

(1R,2S)-1-methoxy-N-(5-(6-methoxy-2-pyridinyl)-4-(1,2-oxazol-5-ylmethyl)-4H-1,2,4-triazol-3-yl)-1-(5-methyl-2-pyrazinyl)-2-propanesulfonamide;

(2S,3R)-3-(5-chloro-2-pyrimidinyl)-N-(5-(6-methoxy-2-pyridinyl)-4-(1,2-oxazol-5-ylmethyl)-4H-1,2,4-triazol-3-yl)-2-butanesulfonamide;

(1R,2S)—N-(4-((1R)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide;

(1R,2S)—N-(4-((1S)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide;

(1S,2S)—N-(4-((1R)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(1S,2S)—N-(4-((1S)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(2S,3R)-3-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-2-butanesulfonamide;

(2S,3R)-3-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-2-butanesulfonamide;

(1R,2S)-1-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide;

(1R,2S)-1-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide;

(1S,2S)—N-(5-(6-methoxy-2-pyridinyl)-4-((1S)-1-(1,2-oxazol-5-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1R)-1-(1,2-oxazol-5-yl)ethyl)-4H-1,2,4-triazol-3-yl)-1-(5-methyl-2-pyrimidinyl)-1-(2-propanyloxy)-2-propanesulfonamide;

(1S,2S)—N-(4-((R)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(1S,2S)—N-(4-((S)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide;

(2S,3R)-3-(5-chloro-2-pyrimidinyl)-N-(5-(6-methoxy-2-pyridinyl)-4-((1R)-1-(3-methyl-1,2-oxazol-4-yl)propyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-1-(3-methyl-1,2-oxazol-4-yl)propyl)-4H-1,2,4-triazol-3-yl)-2-butanesulfonamide;

(2S,3R)-3-(5-chloro-2-pyrimidinyl)-N-(4-((S)-cyclopropyl(3-methyl-1,2-oxazol-4-yl)methyl)-5-(6-methoxy-2-pyridinyl)-4H-1,2,4-triazol-3-yl)-2-butanesulfonamide;

(2S,3R)-3-(5-chloro-2-pyrimidinyl)-N-(4-((R)-cyclopropyl(3-methyl-1,2-oxazol-4-yl)methyl)-5-(6-methoxy-2-pyridinyl)-4H-1,2,4-triazol-3-yl)-2-butanesulfonamide;

(1S,2S)—N-(5-(6-methoxy-2-pyridinyl)-4-((1S)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1R)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-1-methoxy-N-(5-(6-methoxy-2-pyridinyl)-4-((1S)-1-(1-methyl-H-1,2,4-triazol-3-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R)-1-(1-methyl-1H-1,2,4-triazol-3-yl)ethyl)-4H-1,2,4-triazol-3-yl)-2-propanesulfonamide;

(2S,3R)-3-(5-chloro-2-pyrimidinyl)-N-(5-(6-methoxy-2-pyridinyl)-4-((1S)-1-(1-methyl-1H-1,2,4-triazol-3-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1R)-1-(1-methyl-1H-1,2,4-triazol-3-yl)ethyl)-4H-1,2,4-triazol-3-yl)-2-butanesulfonamide;

(1S,2S)—N-(5-(6-methoxy-2-pyridinyl)-4-((1S)-1-(3-methyl-1,2,4-oxadiazol-5-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1R)-1-(3-methyl-1,2,4-oxadiazol-5-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1S)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1R)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-1-methoxy-N-(5-(6-methoxy-2-pyridinyl)-4-((1S)-1-(5-methyl-1,2,4-oxadiazol-3-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R)-1-(5-methyl-1,2,4-oxadiazol-3-yl)ethyl)-4H-1,2,4-triazol-3-yl)-2-propanesulfonamide;

(2S,3R)-3-(5-chloro-2-pyrimidinyl)-N-(5-(6-methoxy-2-pyridinyl)-4-((1R)-1-(5-methyl-1,2,4-oxadiazol-3-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-1-(5-methyl-1,2,4-oxadiazol-3-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1R)-1-(3-methyl-1,2,4-oxadiazol-5-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-1-(3-methyl-1,2,4-oxadiazol-5-yl)ethyl)-4H-1,2,4-triazol-3-yl)-2-butanesulfonamide;

(1R,2S)-1-(5-chloro-2-pyrimidinyl)-1-methoxy-N-(5-(6-methoxy-2-pyridinyl)-4-((1S)-1-(1-methyl-H-1,2,4-triazol-5-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R)-1-(1-methyl-1H-1,2,4-triazol-5-yl)ethyl)-4H-1,2,4-triazol-3-yl)-2-propanesulfonamide;

(2S,3R)-3-(5-chloro-2-pyrimidinyl)-N-(5-(6-methoxy-2-pyridinyl)-4-((1R)-1-(1-methyl-1H-1,2,4-triazol-5-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1S)-1-(1-methyl-1H-1,2,4-triazol-5-yl)ethyl)-4H-1,2,4-triazol-3-yl)-2-butanesulfonamide;

(1S,2S)—N-(5-(6-methoxy-2-pyridinyl)-4-((1R)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propanesulfonamide;

(1S,2S)—N-(5-(6-methoxy-2-pyridinyl)-4-((1S)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propane sulfonamide;

(1R,2S)-1-(5-chloro-2-pyrimidinyl)-1-methoxy-N-(5-(6-methoxy-2-pyridinyl)-4-((1S)-1-(5-methyl-1,3-oxazol-2-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1R)-1-(5-methyl-1,3-oxazol-2-yl)ethyl)-4H-1,2,4-triazol-3-yl)-2-propanesulfonamide;

(2S,3R)-3-(5-chloro-2-pyrimidinyl)-N-(5-(6-methoxy-2-pyridinyl)-4-((1S)-1-(5-methyl-1,3-oxazol-2-yl)ethyl)-4H-1,2,4-triazol-3-yl)-2-butanesulfonamide;

(2S,3R)-3-(5-chloro-2-pyrimidinyl)-N-(5-(6-methoxy-2-pyridinyl)-4-((1R)-1-(5-methyl-1,3-oxazol-2-yl)ethyl)-4H-1,2,4-triazol-3-yl)-2-butanesulfonamide;

(1S,2S)—N-(5-(6-methoxy-2-pyridinyl)-4-((1R)-1-(5-methyl-1,2,4-oxadiazol-3-yl)ethyl)-4H-1,2,4-triazol-3-yl)-1-(5-methyl-2-pyrimidinyl)-1-(2-propanyloxy)-2-propane sulfonamide;

(1S,2S)—N-(5-(6-methoxy-2-pyridinyl)-4-((1S)-1-(5-methyl-1,2,4-oxadiazol-3-yl)ethyl)-4H-1,2,4-triazol-3-yl)-1-(5-methyl-2-pyrimidinyl)-1-(2-propanyloxy)-2-propane sulfonamide;

(2S,3R)-3-(5-chloropyrimidin-2-yl)-N-(4-(isoxazol-3-ylmethyl)-5-(6-methoxypyridin-2-yl)-4H-1,2,4-triazol-3-yl)butane-2-sulfonamide;

(1S,2S)-1-isopropoxy-N-(4-(isoxazol-3-ylmethyl)-5-(6-methoxypyridin-2-yl)-4H-1,2,4-triazol-3-yl)-1-(5-methylpyrimidin-2-yl)propane-2-sulfonamide;

(1R,2S)-1-(5-chloropyrimidin-2-yl)-N-(4-(isoxazol-3-ylmethyl)-5-(5-methylpyridin-3-yl)-4H-1,2,4-triazol-3-yl)-1-methoxypropane-2-sulfonamide;

(1R,2S)—N-(4-(bicyclo[1.1.1]pentan-1-yl)-5-(6-methoxypyridin-2-yl)-4H-1,2,4-triazol-3-yl)-1-(5-chloropyrimidin-2-yl)-1-methoxypropane-2-sulfonamide;

(1R,2S)-1-(5-chloro-2-pyrimidinyl)-1-methoxy-N-(5-(6-methoxy-2-pyridinyl)-4-((1R)-1-(1,2-oxazol-3-yl)ethyl)-4H-1,2,4-triazol-3-yl)-2-propanesulfonamide;

(1R,2S)-1-(5-chloro-2-pyrimidinyl)-1-methoxy-N-(5-(6-methoxy-2-pyridinyl)-4-((1S)-1-(1,2-oxazol-3-yl)ethyl)-4H-1,2,4-triazol-3-yl)-2-propanesulfonamide;

(1R,2S)-1-(5-chloropyrimidin-2-yl)-N-(4-(isoxazol-5-ylmethyl)-5-(6-methoxypyridin-2-yl)-4H-1,2,4-triazol-3-yl)-1-methoxypropane-2-sulfonamide;

(2S,3R)-3-(5-chloropyrimidin-2-yl)-N-(4-((R)-1-(isoxazol-3-yl)ethyl)-5-(6-methoxypyridin-2-yl)-4H-1,2,4-triazol-3-yl)butane-2-sulfonamide;

(2S,3R)-3-(5-chloropyrimidin-2-yl)-N-(4-((S)-1-(isoxazol-3-yl)ethyl)-5-(6-methoxypyridin-2-yl)-4H-1,2,4-triazol-3-yl)butane-2-sulfonamide;

(1S,2S)-1-isopropoxy-N-(4-((R)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide;

(1S,2S)-1-isopropoxy-N-(4-((S)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide;

(1R,2S)-1-(5-chloropyrimidin-2-yl)-1-methoxy-N-(5-(6-methoxypyridin-2-yl)-4-((5-methylisoxazol-3-yl)methyl)-4H-1,2,4-triazol-3-yl)propane-2-sulfonamide;

(2S,3R)-3-(5-chloropyrimidin-2-yl)-N-(5-(6-methoxypyridin-2-yl)-4-((5-methylisoxazol-3-yl)methyl)-4H-1,2,4-triazol-3-yl)butane-2-sulfonamide;

(1S,2S)-1-isopropoxy-N-(5-(6-methoxypyridin-2-yl)-4-((R)-1-((S)-tetrahydrofuran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((R)-1-((R)-tetrahydrofuran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((S)-1-((S)-tetrahydrofuran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((S)-1-((R)-tetrahydrofuran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-(((R)-tetrahydrofuran-2-yl)methyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-(((S)-tetrahydrofuran-2-yl)methyl)-4H-1,2,4-triazol-3-yl)-1-(5-methylpyrimidin-2-yl)propane-2-sulfonamide;

(1R,2S)-1-(5-chloropyrimidin-2-yl)-1-methoxy-N-(5-(6-methoxypyridin-2-yl)-4-(((R)-tetrahydrofuran-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((S)-tetrahydrofuran-2-yl)methyl)-4H-1,2,4-triazol-3-yl)propane-2-sulfonamide;

(2S,3R)-3-(5-chloropyrimidin-2-yl)-N-(5-(6-methoxypyridin-2-yl)-4-(((R)-tetrahydrofuran-2-yl)methyl)-4H-1,2,4-triazol-3-yl)butane-2-sulfonamide;

(2S,3R)-3-(5-chloropyrimidin-2-yl)-N-(5-(6-methoxypyridin-2-yl)-4-(((S)-tetrahydrofuran-2-yl)methyl)-4H-1,2,4-triazol-3-yl)butane-2-sulfonamide;

(1R,2S)-1-(5-chloropyrimidin-2-yl)-1-methoxy-N-(5-(6-methoxypyridin-2-yl)-4-(2-(pyridin-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(2-(pyridin-3-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((R)-tetrahydrofuran-3-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((S)-tetrahydrofuran-3-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((R)-tetrahydro-2H-pyran-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((S)-tetrahydro-2H-pyran-2-yl)methyl)-4H-1,2,4-triazol-3-yl)propane-2-sulfonamide;

(1R,2S)-1-(5-chloropyrimidin-2-yl)-N-(4-(((R)-5,5-dimethyltetrahydrofuran-2-yl)methyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-(((S)-5,5-dimethyltetrahydrofuran-2-yl)methyl)-5-(6-methoxypyridin-2-yl)-4H-1,2,4-triazol-3-yl)-1-methoxypropane-2-sulfonamide;

(2S,3R)—N-(4-(isoxazol-3-ylmethyl)-5-(6-methoxypyridin-2-yl)-4H-1,2,4-triazol-3-yl)-3-(5-methylpyrimidin-2-yl)butane-2-sulfonamide;

(1R,2S)-1-(5-chloropyrimidin-2-yl)-N-(4-((3-ethylisoxazol-5-yl)methyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((3-ethylisoxazol-5-yl)methyl)-5-(5-methylpyridin-3-yl)-4H-1,2,4-triazol-3-yl)-1-methoxypropane-2-sulfonamide;

(1S,2S)—N-(4-((3-ethylisoxazol-5-yl)methyl)-5-(6-methoxypyridin-2-yl)-4H-1,2,4-triazol-3-yl)-1-isopropoxy-1-(5-methylpyrimidin-2-yl)propane-2-sulfonamide;

(2S,3R)—N-(4-((R)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide;

(2S,3R)—N-(4-((S)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide;

(2S,3R)-3-(5-chloropyrimidin-2-yl)-N-(5-(6-methoxypyridin-2-yl)-4-((R)-1-(1-methyl-1H-pyrazol-4-yl)ethyl)-4H-1,2,4-triazol-3-yl)butane-2-sulfonamide;

(2S,3R)-3-(5-chloropyrimidin-2-yl)-N-(5-(6-methoxypyridin-2-yl)-4-((S)-1-(1-methyl-1H-pyrazol-4-yl)ethyl)-4H-1,2,4-triazol-3-yl)butane-2-sulfonamide;

(1R,2S)-1-(5-chloropyrimidin-2-yl)-1-methoxy-N-(5-(5-methylpyridin-3-yl)-4-(((R)-tetrahydro-2H-pyran-2-yl)methyl)-4H-1,2,4-triazol-3-yl)propane-2-sulfonamide;

(1R,2S)-1-(5-chloropyrimidin-2-yl)-1-methoxy-N-(5-(5-methylpyridin-3-yl)-4-(((S)-tetrahydro-2H-pyran-2-yl)methyl)-4H-1,2,4-triazol-3-yl)propane-2-sulfonamide;

(1S,2S)-1-isopropoxy-N-(5-(6-methoxypyridin-2-yl)-4-(((R)-tetrahydro-2H-pyran-2-yl)methyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-(((S)-tetrahydro-2H-pyran-2-yl)methyl)-4H-1,2,4-triazol-3-yl)-1-(5-methylpyrimidin-2-yl)propane-2-sulfonamide;

(1R,2S)-1-(5-chloropyrimidin-2-yl)-1-methoxy-N-(5-(6-methoxypyridin-2-yl)-4-((tetrahydro-2H-pyran-4-yl)methyl)-4H-1,2,4-triazol-3-yl)propane-2-sulfonamide;

(1R,2S)—N-(4-(((R)-1,4-dioxan-2-yl)methyl)-5-(6-methoxypyridin-2-yl)-4H-1,2,4-triazol-3-yl)-1-(5-chloropyrimidin-2-yl)-1-methoxypropane-2-sulfonamide;

(1R,2S)—N-(4-(((S)-1,4-dioxan-2-yl)methyl)-5-(6-methoxypyridin-2-yl)-4H-1,2,4-triazol-3-yl)-1-(5-chloropyrimidin-2-yl)-1-methoxypropane-2-sulfonamide;

(1R,2S)-1-(5-chloropyrimidin-2-yl)-1-methoxy-N-(5-(6-methoxypyridin-2-yl)-4-(((2R,6R)-6-methyltetrahydro-2H-pyran-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((2S,6S)-6-methyltetrahydro-2H-pyran-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((2R,6S)-6-methyltetrahydro-2H-pyran-2-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((2S,6R)-6-methyltetrahydro-2H-pyran-2-yl)methyl)-4H-1,2,4-triazol-3-yl)propane-2-sulfonamide;

(1R,2S)-1-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-1-methoxy-N-(5-(6-methoxypyridin-2-yl)-4-(((R)-tetrahydro-2H-pyran-3-yl)methyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-(((S)-tetrahydro-2H-pyran-3-yl)methyl)-4H-1,2,4-triazol-3-yl)propane-2-sulfonamide;

(2S,3R)-3-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)butane-2-sulfonamide;

(2S,3R)-3-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)butane-2-sulfonamide;

(1S,2S)—N-(4-((R)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide;

(1S,2S)—N-(4-((S)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide;

(1R,2S)-1-(5-chloropyrimidin-2-yl)-1-methoxy-N-(5-(6-methoxypyridin-2-yl)-4-((S)-1-((R)-tetrahydro-2H-pyran-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-((S)-tetrahydro-2H-pyran-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-((R)-tetrahydro-2H-pyran-2-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-((S)-tetrahydro-2H-pyran-2-yl)ethyl)-4H-1,2,4-triazol-3-yl)propane-2-sulfonamide;

(1S,2S)-1-isopropoxy-N-(5-(6-methoxypyridin-2-yl)-4-((S)-1-((R)-tetrahydro-2H-pyran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((R)-1-((S)-tetrahydro-2H-pyran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((R)-1-((R)-tetrahydro-2H-pyran-2-yl)ethyl)-4H-1,2,4-triazol-3-yl)-1-(5-methylpyrimidin-2-yl)propane-2-sulfonamide;

(1S,2S)-1-isopropoxy-N-(5-(6-methoxypyridin-2-yl)-4-((S)-1-((S)-tetrahydro-2H-pyran-2-yl)ethyl)-4H-1,2,4-triazol-3-yl)-1-(5-methylpyrimidin-2-yl)propane-2-sulfonamide;

(1R,2S)-1-methoxy-N-(5-(6-methoxy-2-pyridinyl)-4-((1R)-1-((2S)-tetrahydro-2H-pyran-2-yl)propyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-((1R)-1-((2R)-tetrahydro-2H-pyran-2-yl)propyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-((1S)-1-((2S)-tetrahydro-2H-pyran-2-yl)propyl)-4H-1,2,4-triazol-3-yl)-1-(5-methyl-2-pyrimidinyl)-2-propanesulfonamide;

(1R,2S)-1-methoxy-N-(5-(6-methoxy-2-pyridinyl)-4-((1S)-1-((2R)-tetrahydro-2H-pyran-2-yl)propyl)-4H-1,2,4-triazol-3-yl)-1-(5-methyl-2-pyrimidinyl)-2-propanesulfonamide;

(1R,2S)-1-methoxy-N-(5-(6-methoxypyridin-2-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(6-methoxypyridin-2-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(6-methoxypyridin-2-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(6-methoxypyridin-2-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(5-methylpyridin-3-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(5-methylpyridin-3-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(5-methylpyridin-3-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide;

(1R,2S)-1-methoxy-N-(5-(5-methylpyridin-3-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide;

(1R,2S)-1-(5-chloropyrimidin-2-yl)-1-methoxy-N-(5-(6-methoxypyridin-2-yl)-4-((R)-1-(pyrimidin-5-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-(pyrimidin-5-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-(1-methyl-1H-pyrazol-4-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-(1-methyl-1H-pyrazol-4-yl)ethyl)-4H-1,2,4-triazol-3-yl)propane-2-sulfonamide;

(1R,2S)-1-(5-chloropyrimidin-2-yl)-N-(4-((R)-1-(3,5-difluorophenyl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((S)-1-(3,5-difluorophenyl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((R)-1-(3,5-difluorophenyl)propyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((S)-1-(3,5-difluorophenyl)propyl)-5-(6-methoxypyridin-2-yl)-4H-1,2,4-triazol-3-yl)-1-methoxypropane-2-sulfonamide;

(1R,2S)-1-(5-chloropyrimidin-2-yl)-1-methoxy-N-(5-(6-methoxypyridin-2-yl)-4-((S)-1-(thiazol-4-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-(thiazol-4-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((R)-1-(thiazol-5-yl)ethyl)-4H-1,2,4-triazol-3-yl)propane-2-sulfonamide;

(1R,2S)-1-(5-chloropyrimidin-2-yl)-1-methoxy-N-(5-(6-methoxypyridin-2-yl)-4-((S)-1-(thiazol-5-yl)ethyl)-4H-1,2,4-triazol-3-yl)propane-2-sulfonamide;

(1R,2S)-1-(5-chloropyrimidin-2-yl)-N-(4-((R)-1-(5-fluoropyridin-3-yl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-N-(4-((S)-1-(5-fluoropyridin-3-yl)ethyl)-5-(6-methoxypyridin-2-yl)-4H-1,2,4-triazol-3-yl)-1-methoxypropane-2-sulfonamide;

(1R,2S)-1-(5-chloropyrimidin-2-yl)-1-methoxy-N-(5-(6-methoxypyridin-2-yl)-4-((R)-1-(pyridin-3-yl)ethyl)-4H-1,2,4-triazol-3-yl)propane-2-sulfonamide; or (1R,2S)-1-(5-chloropyrimidin-2-yl)-1-methoxy-N-(5-(6-methoxypyridin-2-yl)-4-((S)-1-(pyridin-3-yl)ethyl)-4H-1,2,4-triazol-3-yl)propane-2-sulfonamide; or or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds listed above or the pharmaceutically acceptable salt thereof, or the mixture thereof. In still other such embodiments, the embodiment provides any of the compounds listed above or the pharmaceutically acceptable salt thereof, or the stereoisomer thereof or the mixture thereof.

57. In another embodiment, the invention provides a pharmaceutical composition, comprising the compound of any one of embodiments 1-56 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

58. A pharmaceutical composition, comprising the compound of any one of embodiments 1-56 or the pharmaceutically acceptable salt thereof and at least one pharmaceutically acceptable excipient.

59. A pharmaceutical composition, comprising the compound of any one of embodiments 1-56 and at least one pharmaceutically acceptable excipient.

60. A pharmaceutical composition, comprising the pharmaceutically acceptable salt of the compound of any one of embodiments 1-56 and at least one pharmaceutically acceptable excipient.

61. The pharmaceutical composition of embodiment 57, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

62. The pharmaceutical composition of embodiment 57, further comprising a therapeutic agent selected from an angiotensin converting enzyme (ACE) inhibitor or an angiotensin-receptor blocker (ARB).

63. In another embodiment, the invention provides a method of treating a cardiovascular condition, the method comprising: administering to a subject an effective amount of the compound of any one of embodiments 1-56 or the pharmaceutically acceptable salt thereof, the stereoisomer of any of the foregoing, or the mixture thereof, or the pharmaceutical composition of any one of embodiments 57-63.

64. The method of embodiment 63, wherein the cardiovascular condition is heart failure.

65. The method of embodiment 63, wherein the cardiovascular condition is heart failure with reduced ejection fraction.

66. The method of embodiment 63, wherein the cardiovascular condition is heart failure with preserved ejection fraction.

67. The method of embodiment 63, wherein the cardiovascular condition is chronic systolic heart failure or chronic diastolic heart failure.

68. The method of embodiment 63, wherein the cardiovascular condition is acute heart failure.

69. The method of embodiment 63, wherein the cardiovascular condition is hypertension.

70. In another embodiment, the invention provides a method of improving cardiac contractility in a subject suffering from a cardiovascular condition, the method comprising: administering to the subject an effective amount of the compound of any one of embodiments 1-56 or the pharmaceutically acceptable salt thereof, the stereoisomer of any of the foregoing, or the mixture thereof, or the pharmaceutical composition of any one of embodiments 57-63, wherein cardiac contractility is improved in the subject after administration.

71. In another embodiment, the invention provides a method of increasing ejection fraction in a subject suffering from a cardiovascular condition, the method comprising: administering to the subject an effective amount of the compound of any one of embodiments 1-56 or the pharmaceutically acceptable salt thereof, the stereoisomer of any of the foregoing, or the mixture thereof, or the pharmaceutical composition of any one of embodiments 57-63, wherein the ejection fraction is increased in the subject after administration.

72. In another embodiment, the invention provides a method of treating a condition in a subject where it is desired to activate the APJ Receptor, the method comprising: administering to the subject an effective amount of the compound of any one of embodiments 1-56 or the pharmaceutically acceptable salt thereof, the stereoisomer of any of the foregoing, or the mixture thereof or the pharmaceutical composition of any one of embodiments 57-63.

73. The method of embodiment 72, wherein the condition is obesity or diabetes.

74. The method of embodiment 72, wherein the condition is diabetic nephropathy or chronic kidney disease.

75. The method of any one of embodiments 63-74, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

76. The method of any one of embodiments 63-74, wherein the method includes administering at least one additional therapeutic agent to the subject, wherein the additional therapeutic agent is selected from an angiotensin converting enzyme (ACE) inhibitor or an angiotensin-receptor blocker (ARB).

77. In another embodiment, the invention provides a compound of any one of embodiments 1-56 or the pharmaceutically acceptable salt thereof, the stereoisomer of any of the foregoing, or the mixture thereof, or the pharmaceutical composition of any one of embodiments 57-63 for use in treating a cardiovascular condition.

78. The compound of embodiment 77, wherein the cardiovascular condition is heart failure.

79. The compound of embodiment 77, wherein the cardiovascular condition is heart failure with reduced ejection fraction.

80. The compound of embodiment 77, wherein the cardiovascular condition is heart failure with preserved ejection fraction.

81. The compound of embodiment 77, wherein the cardiovascular condition is chronic systolic heart failure or chronic diastolic heart failure.

82. The compound of embodiment 77, wherein the cardiovascular condition is acute heart failure.

83. The compound of embodiment 77, wherein the cardiovascular condition is hypertension.

84. In another embodiment, the invention provides a compound of any one of embodiments 1-56 or the pharmaceutically acceptable salt thereof, the stereoisomer of any of the foregoing, or the mixture thereof, or the pharmaceutical composition of any one of embodiments 57-63 for use in activating the APJ Receptor or for treating a condition where it is desirable to activate the APJ Receptor.

85. The compound of embodiment 84, wherein the condition is obesity or diabetes.

86. The compound of embodiment 84, wherein the condition is diabetic nephropathy or chronic kidney disease.

87. In another embodiment, the invention provides a use of the compound of any one of embodiments 1-56 or the pharmaceutically acceptable salt thereof, the stereoisomer of any of the foregoing, or the mixture thereof in the preparation of a medicament for treating a cardiovascular condition.

88. The use of embodiment 87, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

89. The use of embodiment 87, further comprising a therapeutic agent selected from an angiotensin converting enzyme (ACE) inhibitor or an angiotensin-receptor blocker (ARB).

90. The use of the compound of embodiment 87, wherein the cardiovascular condition is heart failure.

91. The use of the compound of embodiment 87, wherein the cardiovascular condition is heart failure with reduced ejection fraction.

92. The use of the compound of embodiment 87, wherein the cardiovascular condition is heart failure with preserved ejection fraction.

93. The use of the compound of embodiment 87, wherein the cardiovascular condition is chronic systolic heart failure or chronic diastolic heart failure.

94. The use of the compound of embodiment 87, wherein the cardiovascular condition is acute heart failure.

95. The use of the compound of embodiment 87, wherein the cardiovascular condition is hypertension.

96. In another embodiment, the invention provides a use of the compound of any one of embodiments 1-56 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

97. The use of embodiment 96, wherein the condition is obesity or diabetes.

98. The use of embodiment 96, wherein the condition is diabetic nephropathy or chronic kidney disease.

99. In another embodiment, the invention provides a treatment regimen for a cardiovascular disease, the regimen comprising: the compound of any one of embodiments 1-56 or the pharmaceutically acceptable salt thereof, the stereoisomer of any of the foregoing, or the mixture thereof.

100. The treatment regimen of embodiment 99, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

101. The treatment regimen of embodiment 99, wherein the regimen further comprises a therapeutic agent selected from an angiotensin converting enzyme (ACE) inhibitor or an angiotensin-receptor blocker (ARB).

102. In another embodiment, the invention provides a kit, the kit comprising: the compound of any one of embodiments 1-56 or the pharmaceutically acceptable salt thereof, the stereoisomer of any of the foregoing, or the mixture thereof.

103. The kit of embodiment 102, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

104. The kit of embodiment 102, wherein the kit further comprises a therapeutic agent selected from an angiotensin converting enzyme (ACE) inhibitor or an angiotensin-receptor blocker (ARB).

105. In another embodiment, the invention provides a compound of Formula V, a salt thereof, a tautomer thereof, or a salt of the tautomer:

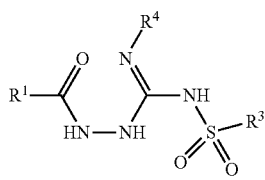

wherein:

R[1] is a pyridyl group that is unsubstituted or is substituted with 1, 2, or 3 R[1a] substituents;

R[1a] in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2NH_2$, —S(=O)$_2$NH($C_1$-$C_6$ alkyl), or —S(=O)$_2$N($C_1$-$C_6$ alkyl)$_2$;

R[3] is selected from an unsubstituted $C_1$-$C_{10}$ alkyl, a $C_1$-$C_{10}$ alkyl substituted with 1, 2, or 3 R[3a] substituents, a group of formula —(CR[3b]R[3c])-Q, a group of formula —NH—(CR[3b]R[3c])-Q, a group of formula —(CR[3b]R[3c])—C(=O)-Q, a group of formula —(CR[3d]R[3e])—(CR[3f]R[3g])-Q a group of formula —(CR[3b]=CR[3c])-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 R[3h] substituents;

R[3a] in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

R[3b] and R[3c] are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

R[3d] and R[3e] are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

R[3f] and R[3g] are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

R[3h] in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 R[Q] substituent;

R[Q] in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo R[Q] substituent;

R[4] is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl R[4] group is unsubstituted or is substituted with 1, 2, 3, or 4 R[4a] substituents, wherein the $C_5$-$C_{10}$ polycyclic cycloalkyl R[4] group is unsubstituted or is substituted with 1, 2, 3, or 4 R[4b] substituents, and further wherein the straight or branched chain $C_1$-$C_6$ alkyl R[4] group is unsubstituted or is substituted with 1, 2, or 3 R[4c] substituents;

R[4a] in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl R[4a] group is unsubstituted or is substituted with 1 or 2 R[4aa] substituents, and further wherein two R[4a] substituents on the same carbon atom of the $C_3$-$C_8$ cycloalkyl R[4] group may join together with the carbon atom to which they are attached to form a 3 to 6-membered heterocyclyl group containing 1 or 2 heteroatoms selected from N, O, or S which is unsubstituted or is substituted with 1 or 2 R[4aa] substituents;

R[4b] in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

R[4c] in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH(C$_1$-C$_6$ alkyl), —C(=O)N(C$_1$-C$_6$ alkyl)$_2$, —C(=O)NH(C$_3$-C$_6$ cycloalkyl), —C(=O)N(C$_1$-C$_6$ alkyl)(C$_3$-C$_6$ cycloalkyl), —C(=O)N(C$_3$-C$_6$ cycloalkyl)$_2$, —S(=O)—(C$_1$-C$_6$ alkyl), —S(=O)$_2$—(C$_1$-C$_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl R$^{4c}$ group, the 3 to 6 membered heterocyclyl R$^{4c}$ group, the phenyl R$^{4c}$ group, or the a 5 or 6 membered heteroaryl R$^{4c}$ ring are unsubstituted or are substituted with 1 or 2 R$^{4aa}$ substituents; and further wherein the 3 to 6 membered cycloalkyl R$^{4c}$ group and the 3 to 6 membered heterocyclyl R$^{4c}$ group may optionally be additionally substituted with an oxo substituent; and R$^{4aa}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —(C$_1$-C$_6$ alkyl)-OH, —(C$_1$-C$_6$ alkyl)-O—(C$_1$-C$_6$ alkyl), —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), or —C(=O)N(C$_1$-C$_6$ alkyl)$_2$.

106. The compound of embodiment 105, the salt thereof, the tautomer thereof, or the salt of the tautomer, wherein the compound has any of the R$^1$, R$^{1a}$, R$^{1a'}$, R$^{1b'}$ R$^3$, R$^{3a}$, R$^{3b}$, R$^{3c}$, R$^{3d}$, R$^{3e}$, R$^{3f}$, R$^{3g}$, R$^{3h}$, R$^4$, R$^{4a}$, R$^{4b}$, Q, or R$^Q$, values or combinations of values of any one of embodiments 2-53.

107. In another embodiment, the invention provides a method for preparing a compound of Formula VI, a salt thereof, a tautomer thereof, or a salt of the tautomer:

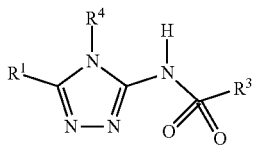

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

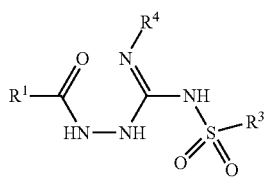

V wherein:
R$^1$ is a pyridyl group that is unsubstituted or is substituted with 1, 2, or 3 R$^{1a}$ substituents;
R$^{1a}$ in each instance is independently selected from —F, —Cl, —Br, —I, —C$_1$-C$_6$ alkyl, —C$_1$-C$_6$ haloalkyl, —C$_1$-C$_6$ perhaloalkyl, —(C$_1$-C$_6$ alkyl)-OH, —(C$_1$-C$_6$ haloalkyl)-OH, —(C$_1$-C$_6$ perhaloalkyl)-OH, —(C$_1$-C$_6$ alkyl)-O—(C$_1$-C$_6$ alkyl), —CN, —OH, —O—(C$_1$-C$_6$ alkyl), —O—(C$_1$-C$_6$ haloalkyl), —O—(C$_1$-C$_6$ perhaloalkyl), —C$_2$-C$_6$ alkenyl, —O—(C$_1$-C$_6$ alkyl)-OH, —O—(C$_1$-C$_6$ alkyl)-O—(C$_1$-C$_6$ alkyl), —O—(C$_1$-C$_6$ haloalkyl)-OH, —O—(C$_1$-C$_6$ haloalkyl)-O—(C$_1$-C$_6$ alkyl), —O—(C$_1$-C$_6$ perhaloalkyl)-OH, —O—(C$_1$-C$_6$ perhaloalkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), —S(=O)$_2$NH$_2$, —S(=O)$_2$NH(C$_1$-C$_6$ alkyl), or —S(=O)$_2$N(C$_1$-C$_6$ alkyl)$_2$;

R$^3$ is selected from an unsubstituted C$_1$-C$_{10}$ alkyl, a C$_1$-C$_{10}$ alkyl substituted with 1, 2, or 3 R$^{3a}$ substituents, a group of formula —(CR$^{3b}$R$^{3c}$)-Q, a group of formula —NH—(CR$^{3b}$R$^{3c}$)-Q, a group of formula —(CR$^{3b}$R$^{3c}$)—C(=O)-Q, a group of formula —(CR$^{3d}$R$^{3e}$)—(CR$^{3f}$R$^{3g}$)-Q, a group of formula —(CR$^{3b}$=CR$^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 R$^{3h}$ substituents;

R$^{3a}$ in each instance is independently selected from —F, —Cl, —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —C$_2$-C$_6$ alkenyl, —C$_2$-C$_6$ alkynyl, —NH$_2$, —NH(C$_1$-C$_6$ alkyl), or —N(C$_1$-C$_6$ alkyl)$_2$;

R$^{3b}$ and R$^{3c}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3f}$ and R$^{3g}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3h}$ in each instance is independently selected from —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), —N(C$_1$-C$_6$ alkyl)$_2$, or oxo;

Q is a monocyclic or bicyclic C$_6$-C$_{10}$ aryl group, a monocyclic or bicyclic heteroaryl group with 5 to 10 ring members containing 1, 2, or 3 heteroatoms selected from N, O, or S, a C$_3$-C$_8$ cycloalkyl group, or a 3 to 7 membered heterocyclyl group containing 1, 2, or 3 heteroatoms selected from N, O, or S, wherein the C$_6$-C$_{10}$ aryl group, the heteroaryl group, the cycloalkyl group, and the heterocyclyl group are unsubstituted or are substituted with 1, 2, 3, or 4 R$^Q$ substituent;

R$^Q$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —C$_2$-C$_6$ alkenyl, —C$_2$-C$_6$ alkynyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —C(=O)—(C$_1$-C$_6$ alkyl), —C(=O)

OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl $R^4$ group is unsubstituted or is substituted with 1, 2, 3, or 4 $R^{4a}$ substituents, wherein the $C_5$-$C_{10}$ polycyclic cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl $R^{4a}$ group is unsubstituted or is substituted with 1 or 2 $R^{4aa}$ substituents, and further wherein two $R^{4a}$ substituents on the same carbon atom of the $C_3$-$C_8$ cycloalkyl $R^4$ group may join together with the carbon atom to which they are attached to form a 3 to 6-membered heterocyclyl group containing 1 or 2 heteroatoms selected from N, O, or S which is unsubstituted or is substituted with 1 or 2 $R^{4aa}$ substituents;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^{4c}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

108. The method of embodiment 107, wherein $R^1$, $R^{1a}$, $R^{1a'}$, $R^{1b'}$, $R^3$, $R^{3a}$, $R^{3b}$, $R^{3c}$, $R^{3d}$, $R^{3e}$, $R^{3f}$, $R^{3g}$, $R^3$, $R^4$, $R^{4a}$, $R^{4b}$, Q, or $R^Q$, have any of the values or combination of values of any one of embodiments 2-53.

109. The method of embodiment 107 or embodiment 108, wherein cyclizing further comprises heating the compound of Formula V, the salt thereof, the tautomer thereof, or the salt of the tautomer in the presence of the acid or the base.

110. The method of embodiment 109, wherein heating the compound of Formula V, the salt thereof, the tautomer thereof, or the salt of the tautomer comprises heating the compound to a temperature of from 50° C. to 100° C.

111. The method of embodiment 109, wherein heating the compound of Formula V, the salt thereof, the tautomer thereof, or the salt of the tautomer comprises heating the compound to a temperature of from 60° C. to 85° C.

112. The method of any one of embodiments 107-111, wherein the cyclizing of the compound of Formula V, the salt thereof, the tautomer thereof, or the salt of the tautomer is performed in the presence of the base.

113. The method of any one of embodiments 107-111, wherein the base is a metal hydroxide.

114. The method of embodiment 111, wherein the metal hydroxide is selected from NaOH or LiOH.

115. The method of any one of embodiments 112-114, wherein the cyclizing is carried out in an alcohol solvent.

116. The method of embodiment 115, wherein the alcohol is isopropanol.

117. The method of any one of embodiments 107-111, wherein cyclizing further comprises heating the compound of Formula V, the salt thereof, the tautomer thereof, or the salt of the tautomer in the presence of the acid.

118. The method of embodiment 117, wherein the acid is selected from a sulfonic acid, a carboxylic acid, polyphosphoric acid, phosphoric acid, sulfuric acid, or hydrochloric acid.

119. The method of embodiment 118, wherein the sulfonic acid is methanesulfonic acid.

120. The method of embodiment 118, wherein the acid is trifluoroacetic acid, acetic acid, or trichloroacetic acid.

121. The method of any one of embodiments 117-120, wherein the cyclizing is carried out in a cyclic ether, an acyclic ether, N,N-dimethylformamide, or acetonitrile.

122. The method of embodiment 121, wherein the cyclizing is carried out in a cyclic ether.

123. The method of embodiment 122, wherein the cyclic ether is selected from tetrahydrofuran, tetrahydropyran, or 1,4-dioxane.

124. The method of embodiment 122, wherein the cyclic ether is 1,4-dioxane.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet where the effective amount of the active ingredient ranges from 5 mg to 60 mg, from 6 mg to 58 mg, from 10 mg to 40 mg, from 15 mg to 30 mg, from 16 mg to 25 mg, or from 17 mg to 20 mg. In some such compositions, the amount of active ingredient is 17 mg.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non- DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1H$ NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a L Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^1$, $R^3$, and Q groups taught in WO 2016/187308 and U.S. Pat. Appl. Pub. No. US 2016/0340336.

The following Abbreviations are used to refer to various reagents and solvents:
ACN Acetonitrile
AcOH Acetic Acid
d day or days
DCM Dichloromethane
DEA: Diethylamine
(DHQD)$_2$PHAL 1,4-Bis[(S)-[2R,4S,5R)-5-ethyl-1-azabicyclo[2.2.2]octan-2-yl]-(6-methoxyquinolin-4-yl)methoxy]phthalazine
DMF N,N-Dimethylformamide
DMSO Dimethylsulfoxide
EtOAc Ethyl Acetate
EtOH Ethanol
EtOTf Ethyl trifluoromethanesulfonate
h hour or hours
IPA Isopropanol
min minute or minutes
MeOH Methanol
MeOTf Methyl trifluoromethanesulfonate
RT Room temperature
SFC Supercritical fluid chromatography
t-BuOH t-Butyl alcohol
TBSOTf t-Butyldimethylsilyl trifluoromethanesulfonate
TBS t-Butyldimethylsilane
TEA Triethylamine
TFA Trifluoroacetic acid
THF Tetrahydrofuran
TLC Thin Layer Chromatography
TMSCl Chlorotrimethylsilane Example 1.0. Preparation of (2S,3R)—N-(4-((1r,2R,6S)-2,6-dimethoxycyclohexyl)-5-(5-methyl-3-pyridinyl)-4H-1,2,4-triazol-3-yl)-3-(5-methyl-2-pyrimidinyl)-2-butanesulfonamide

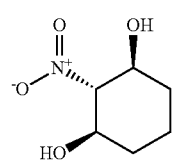

(1R,2r,3S)-2-Nitrocyclohexane-1,3-diol, Example 1.1

A 500 mL round bottom flask was charged with glutaric dialdehyde (12.5 g, 50 mL, 25% aqueous solution, 125 mmol) and diluted with nitromethane (27.6 mL, 512 mmol) and a 1:1 solution of MeOH (69.3 mL) and water (69.3 mL). The solution was cooled to 0° C. and sodium carbonate (48.4 g, 457 mmol) in water (69.3 mL) was added. The resulting mixture was warmed to RT and stirred for 4 h. Carefully, AcOH (32.3 mL, 570 mmol) was added and the solution was concentrated in vacuo to remove all organics (bath temp 30-35° C.). Next, the water solution was partitioned with diethyl ether (5×200 mL), and the ether layer was dried over sodium sulfate, filtered and concentrated in vacuo. The material was then recrystallized with EtOAc to obtain the desired product ((1R,2r,3S)-2-nitrocyclohexane-1,3-diol (7.5 g, 37.3%)).

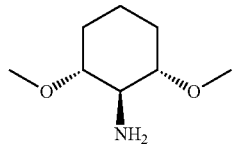

(1R,2r,6S)-2,6-Dimethoxycyclohexanamine, Example 1.2

Silver(I) oxide (6.15 mL, 192 mmol) was added to a DMF (96 mL) solution containing iodomethane (30.0 mL, 479 mmol) and (1R,2r,3S)-2-nitrocyclohexane-1,3-diol (7.72 g, 47.9 mmol). The resulting mixture was stirred overnight at RT. The reaction was then filtered and the filtrate was partitioned with EtOAc/water, washed with brine, dried over sodium sulfate and concentrated in vacuo. Next, the residue was dissolved in EtOH and Raney 2400 nickel (0.316 mL, 47.9 mmol) was added. The reaction was shaken in a Parr hydrogenator at 50 psi overnight. The reaction was then carefully filtered and concentrated in vacuo.

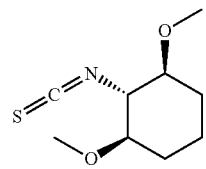

(1R,2R,3S)-2-Isothiocyanato-1,3-dimethoxycyclohexane, Example 1.3

1,1"-Thiocarbonyldi-2(1H)-pyridone (0.802 g, 3.45 mmol) was added to a DCM (15.70 mL) solution containing (1r,2R,6S)-2,6-dimethoxycyclohexanamine (0.5 g, 3.14 mmol). The resulting mixture was stirred overnight at RT. The reaction was concentrated and purified on silica eluting with a hexane/EtOAc gradient (0-100%). The desired fractions were pooled and concentrated to yield the title compound (0.45 g, 71%).

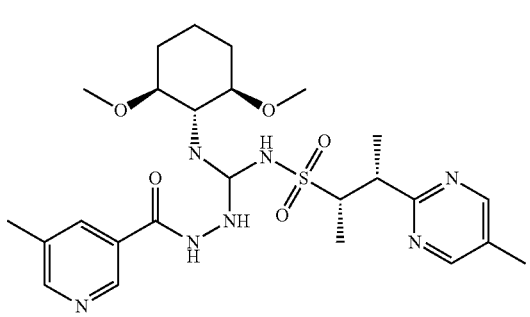

(Z)—N'-((1r,2R,6S)-2,6-Dimethoxycyclohexyl)-2-(5-methylnicotinoyl)-N-(((2S,3R)-3-(5-methylpyrimidin-2-yl)butan-2-yl)sulfonyl)hydrazinecarboximidamide, Example 1.4

A 40 mL pressure release vial was charged with (2S,3R)-3-(5-methylpyrimidin-2-yl)butane-2-sulfonamide (150 mg, 0.654 mmol, Example 27.0) and (1R,2r,3S)-2-isothiocyanato-1,3-dimethoxycyclohexane (133 mg, 0.661 mmol, Example 1.3). The mixture was dissolved in ACN (6542 µL, Sigma-Aldrich) and cesium carbonate (79 µL, 0.981 mmol, Sigma-Aldrich) was added in one portion at RT. After 21 h, LCMS showed complete consumption of the sulfonamide to a peak containing a mass consistent with the desired thiourea intermediate. To the resulting thick white slurry was added 5-methylnicotinohydrazide (99 mg, 0.654 mmol, Bellen Chemistry Co., LTD) and silver nitrate (51.1 µL, 1.308 mmol). The white slurry immediately turned brown and after several min black. After 30 min, LCMS showed complete consumption of the thiourea to a peak containing the mass of the desired product. The reaction mixture was loaded directly onto a Biotage column. ACN was used to rinse the remaining contents of vial onto the column. The column was dried and the material was purified by flash chromatography: Biotage SNAP Ultra 25 g–CV=45 mL, eluting with EtOAc:EtOH 3:1 (v/v) in heptanes 0% (3 CV), 10-100% (10 CV), 100% (5 CV) to provide Example 1.4 (217 mg, 0.396 mmol, 60.6% yield) as an amorphous white solid. LCMS-ESI (pos.) m/z: 548.2 (M+H)+.

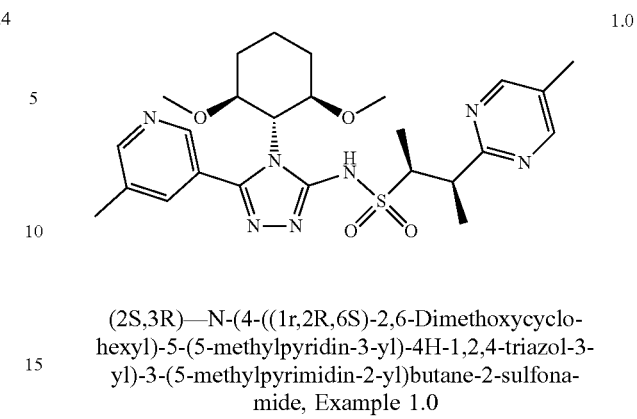

(2S,3R)—N-(4-((1r,2R,6S)-2,6-Dimethoxycyclohexyl)-5-(5-methylpyridin-3-yl)-4H-1,2,4-triazol-3-yl)-3-(5-methylpyrimidin-2-yl)butane-2-sulfonamide, Example 1.0

A 40 mL pressure release vial was charged with Example 1.4 and partially dissolved in IPA (1826 µL) and water (913 µL). To that solution was added sodium hydroxide 1.0 N (822 µL, 0.822 mmol). The vial was sealed and placed into a reaction block preheated to 80° C. After 20 h, a ~1:1 ratio of product to starting material persisted. An additional 1.5 equivalents of sodium hydroxide 1.0 N (822 µL, 0.822 mmol) was added to the RT solution. The reaction was placed back into the heating block and after 20 h, LCMS showed a ~4:1 ratio of product to starting material. The RT solution was neutralized to a pH of 7 using HCl 1.0 N solution (1643 µL, 1.643 mmol). The mixture was poured directly onto a Biotage column and the silica was dried. Once dry, the material was purified by flash chromatography: 50 g Biotage SNAP Ultra-CV=85 mL, eluting with EtOAc:EtOH 3:1 (v/v) in heptanes 0% (3 CV), 0-50% (3 CV), 50% (6 CV) to provide Example 1.0 (78.5 mg, 27% yield) an amorphous white foam. 1H NMR (500 MHz, DMSO-$d_6$) δ 13.21 (1H, s) 8.60-8.63 (4H, m) 7.86 (1H, s) 4.17-4.26 (2H, m) 3.80-3.90 (1H, m) 3.65-3.74 (1H, m) 3.55 (1H, t, J=10.15 Hz) 3.18 (3H, s) 3.16 (3H, s) 2.37-2.39 (3H, m) 2.25 (3H, s) 2.17 (2H, br d, J=12.26 Hz) 1.65-1.74 (1H, m) 1.40 (3H, d, J=7.07 Hz) 1.27 (3H, d, J=7.01 Hz) 1.08-1.18 (1H, m) 0.94-1.04 (2H, m).

The compounds in the following table were synthesized following the procedure in Example 1.0 using the known starting material as described.

TABLE 1

| Example | Reagents | Structure, Name and Data |
|---|---|---|
| 2.0 | (2S,3R)-3-(5-chloropyrimidin-2-yl)butane-2-sulfonamide (Example 27.4), 6-methoxypicolinohydrazide (commercially available from Sigma Aldrich), and 3-(isothiocyanatomethyl)oxetane (Example 28.0). | (2S,3R)-3-(5-chloro-2-pyrimidinyl)-N-(5-(6-methoxy-2-pyridinyl)-4-(3-oxetanylmethyl)-4H-1,2,4-triazol-3-yl)-2-butanesulfonamide. <br> 1H NMR (400 MHz, CDCl$_3$) δ 8.63 (s, 2 H) 7.85 (dd, J = 7.46, 0.62 Hz, 1 H) 7.64-7.73 (m, 1 H) 6.79 (dd, J = 8.29, 0.62 Hz, 1 H) 5.16 (qd, J = 7.07, 4.09 Hz, 1 H) 4.75 (dd, J = 13.68, 5.60 Hz, 1 H) 4.43 (dd, J = 7.46 Hz, 1 H) 4.14 (dd, J = 13.01, 3.06 Hz, 1 H) 3.89-4.01 (m, 4H) 13.79, 3.72-3.88 (m, 3 H) 2.47-2.59 (m, 1 H) 2.22 (t, J = 4.98 Hz, 1 H) 1.54 (d, J = 2.59 Hz, 3 H) 1.52 (d, J = 2.59 Hz, 3 H). <br> LCMS ESI (pos.) m/z: 494.2 (M + H)+. |

TABLE 1-continued

| Example | Reagents | Structure, Name and Data |
|---|---|---|
| 3.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-methoxyethyl isothiocyanate, (commercially available from Sigma-Aldrich). | 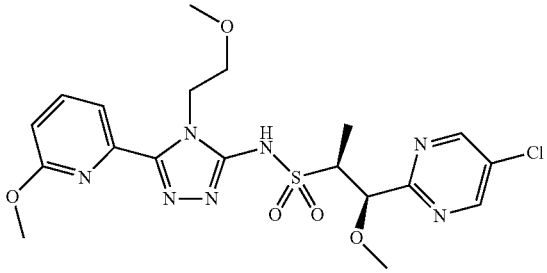 [SMILES: COCCn1c(NS(=O)(=O)[C@@H](C)[C@H](OC)c2ncc(Cl)cn2)nnc1-c1cccc(OC)n1]<br>(1R,2S)-1-(5-chloro-2-pyrimidinyl)-1-methoxy-N-(4-(2-methoxyethyl)-5-(6-methoxy-2-pyridinyl)-4H-1,2,4-triazol-3-yl)-2-propanesulfonamide.\<br>$^1$H NMR (400 MHz, CDCl$_3$) δ 11.20 (br s, 1 H) 8.72 (s, 2 H) 7.68-7.75 (m, 1 H) 7.60-7.67 (m, 1 H) 6.85-6.92 (m, 1 H) 5.08 (d, J = 4.46 Hz, 1 H) 4.58-4.72 (m, 2 H) 3.96 (s, 3 H) 3.77 (qd, J = 7.01, 4.46 Hz, 1 H) 3.65-3.73 (m, 2 H) 3.33 (s, 3 H) 3.24 (s, 3 H) 1.45 (d, J = 7.05 Hz, 3 H). LCMS ESI (pos.) m/z: 498.2 (M + H)$^+$. |
| 4.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanato-1-(methoxymethyl)cyclopropane (Example 72.0). | 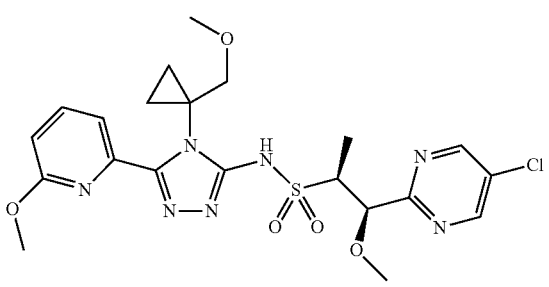 [SMILES: COCC1(n2c(NS(=O)(=O)[C@@H](C)[C@H](OC)c3ncc(Cl)cn3)nnc2-c2cccc(OC)n2)CC1]<br>(1R,2S)-1-(5-chloro-2-pyrimidinyl)-1-methoxy-N-(4-(1-methoxymethyl)cyclopropyl)5-(6-methoxy-2-pyridinyl)-4H-1,2,4-triazol-3-yl)-2-propanesulfonamide.<br>$^1$H NMR (400 MHz, CDCl$_3$) δ 11.08 (br s, 1 H) 8.73 (s, 2 H) 7.70 (dd, J = 8.34, 7.41 Hz, 1 H) 7.53 (d, J = 7.36 Hz, 1 H) 6.90 (dd, J = 8.40, 0.62 Hz, 1 H) 5.13 (d, J = 4.04 Hz, 1 H) 3.99 (s, 2 H) 3.97 (s, 3 H) 3.76 (qd, J = 7.00, 3.99 Hz, 1 H) 3.36 (s, 3 H) 3.36 (s, 3 H) 1.47 (d, J = 7.05 Hz, 3 H) 0.9 1.36 (m, 4 H). LCMS ESI (pos.)m/z: 524.0 (M + H)$^+$. |
| 5.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 5-isothiocyanato-2,2-dimethyl-1,3-dioxane (Example 28.1). Example 5.0 was prepared by acidic (10 eq. of 1 molar hydrochloric acid in dioxane, 0.15 molar) deprotection of the product obtained from reacting the reagents described above | 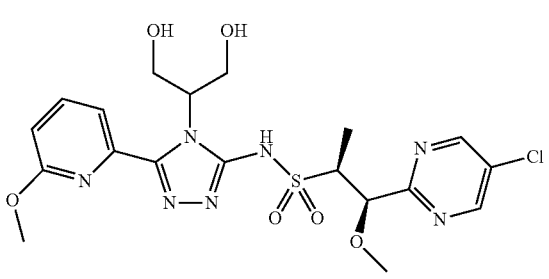 [SMILES: COc1cccc(-c2nnc(NS(=O)(=O)[C@@H](C)[C@H](OC)c3ncc(Cl)cn3)n2C(CO)CO)n1]<br>(1R,2S)-1-(5-chloro-2-pyrimidinyl)-N-(4-(2-hydroxy-1-(hydroxymethyl)ethyl)-5-(6-methoxy-2-pyridinyl)-4H-1,2,4-triazol-3-yl)-1-methoxy-2-propanesulfonamide.<br>$^1$H NMR (400 MHz, CDCl$_3$) δ 11.66-12.17 (br s, 1 H) 8.74 (s, 2 H) 7.67-7.79 (m, 1 H) 7.56 (d, J = 7.26 Hz, 1 H) 6.90 (d, J = 8.29 Hz, 1 H) 5.45-5.59 (m, 1 H) 5.13 (d, J = 3.32 Hz, 1 H) 4.44 (br dd, J = 12.70, 5.23 Hz, 2 H) 4.22-4.38 (m, 2 H) 4.12 (td, J = 11.53, 4.30 Hz, 2 H) 3.95 (s, 3 H) 3.66 (qd, J = 7.03, 3.27 Hz, 1 H) 3.33 (s. 3 H) 1.40 (d, J = 7.15 Hz, 3 H). LCMS ESI (pos.)m/z: 514.1 (M + H)$^+$. |

TABLE 1-continued

| Example | Reagents | Structure, Name and Data |
|---|---|---|
| 6.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1,3-dimethoxypropane (Example 72.0). | 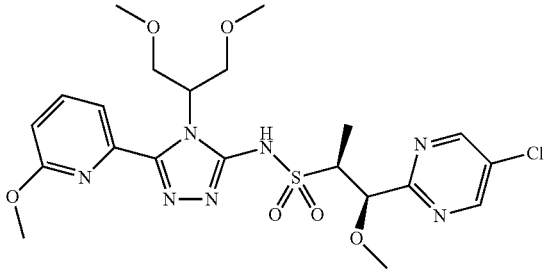<br>(1R,2S)-1-(5-chloro-2-pyrimidinyl)-1-methoxy-N-(4-(2-methoxy-1-(methoxymethyl)ethyl)-5-(6-methoxy-2-pyridinyl)-4H-1,2,4-triazol-3-yl)-2-propanesulfonamide.<br>$^1$H NMR (400 MHz, CDCl$_3$) δ 1.45 (d, J = 7.05 Hz, 3 H) 3.28 (s, 3H) 3.30 (s, 3H) 23.39 (s, 3 H) 3.73-3.84 (m, 3 H) 3.98 (s, 3 H) 4.21 (ddd, J = 11.38, 9.77, 7.98 Hz, 2 H) 5.08 (d, J = 4.35 Hz, 1 H) 5.77 (br t, J = 6.43 Hz, 1 H) 6.89 (dd, J = 8.34, 0.67 Hz, 1 H) 7.55 (dd, J = 7.36, 0.73 Hz, 1 H) 7.72 (dd, J = 8.34, 7.41 Hz, 1 H) 8.77 (s, 2 H).<br>LCMS ESI (pos.)m/z: 514.1 (M + H)$^+$. |
| 7.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 6-isothiocyanato-2-oxaspiro[3.3]heptane (Example 28.2). | 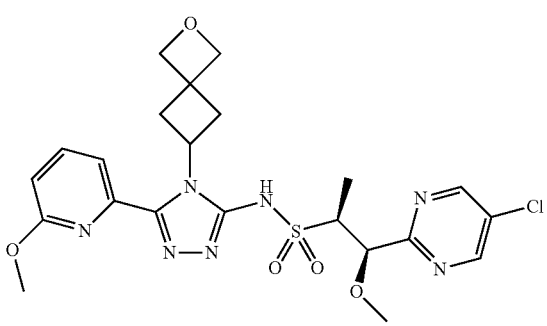 [SMILES: COc1cccc(-c2nnc(NS(=O)(=O)[C@@H](C)[C@H](OC)c3ncc(Cl)cn3)n2C2CC3(COC3)C2)n1]<br>(1R,2S)-1-(5-chloro-2-pyrimidinyl)-1-methoxy-N-(5-(6-methoxy-2-pyridinyl)-4-(2-oxaspiro[3.3]hept-6-yl)-4H-1,2,4-triazol-3-yl)-2-propanesulfonamide.<br>$^1$H NMR (400 MHz, CDCl$_3$) δ 8.76 (s, 2H) 7.77 (t, J = 7.88 Hz, 1 H) 7.52 (d, J = 7.36 Hz, 1 H) 6.94 (d, J = 8.40 Hz, 1 H) 5.54 (quin, J = 8.73 Hz, 1 H) 5.02 (d, J = 4.15 Hz, 1 H) 4.73 (d, J = 9.95 Hz, 4 H) 3.99 (s, 3 H) 3.64-3.76 (m, 1 H) 3.44 (br dd, J = 12.54, 9.12 Hz, 2 H) 3.30 (s, 3 H) 2.56-2.72 (m, 2 H) 1.44 (d, J= 6.95 Hz. 3 H).<br>LCMS ESI (pos.)m/z: 536.0 (M + H)$^+$. |
| 8.0 | (1R,2S)-1-(5-methylpyrimidin-2-yl)-1-methoxypropane-2-sulfonamide (Example 29.0), picolinohydrazide (commercially available from TCI America), and 2-isothiocyanato-1,3-dimethoxypropane (Example 71.0). | 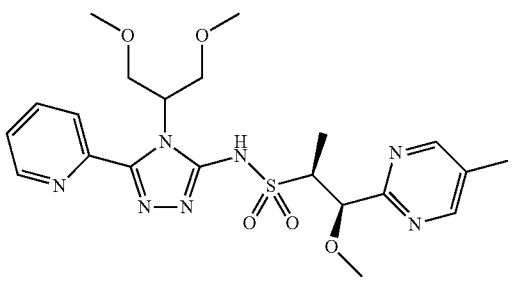 [SMILES: COCC(COC)n1c(NS(=O)(=O)[C@@H](C)[C@H](OC)c2ncc(C)cn2)nnc1-c1ccccn1]<br>(1R,2S)-N-(4-(1,3-dimethoxy-2-propanyl)-5-(2-pyridinyl)-4H-1,2,4-triazol-3-yl)-1-methoxy-1-(5-methyl-2-pyrimidinyl)-2-propanesulfonamide.<br>$^1$H NMR (400 MHz, CDCl$_3$) δ 11.31 (s, 1 H) 8.66-8.73 (m, 1 H) 8.61 (s, 2 H) 7.99 (dt, J = 7.93, 1.01 Hz, 1 H) 7.84 (td, J = 7.83, 1.76 Hz, 1 H) 7.41 (ddd, J = 7.59, 4.85, 1.14 Hz, 1 H) 5.80-5.95 (m, 1 H) 5.06 (d, J = 4.15 Hz, 1 H) 4.21 (td, J = 10.18, 8.24 Hz, 2 H) 3.70-3.90 (m, 3 H) 3.37 (s, 3 H) 3.31 (s, 3 H) 3.28 (s, 3 H) 2.33 (s, 3 H) 1.46 (d, J = 7.05 Hz, 3 H).<br>LCMS ESI (pos.) m/z: 492.0 (M + H)$^+$. |

TABLE 1-continued

| Example | Reagents | Structure, Name and Data |
|---|---|---|
| 9.0 | (1S,2S)-1-isopropoxy-1-(5-methylpyrimidin-2-yl)propane-2-sulfonamide (Example 31.0), 5-methylnicotinohydrazide (commercially available from Bellen), and 2-isothiocyanato-1,3-dimethoxypropane (Example 71.0). | 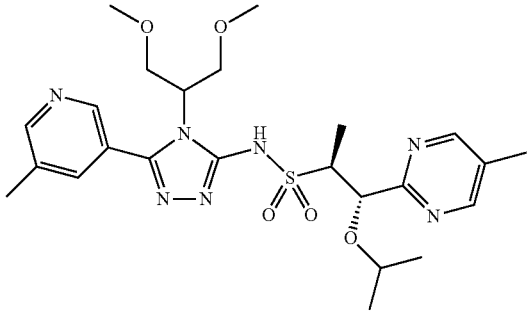<br>(1S,2S)-N-(4-(1,3-dimethoxy-2-propanyl)-5-(5-methyl-3-pyridinyl)-4H-1,2,4-triazol-3-yl)-1-(5-methyl-2-pyridinyl)-1-(2-propanyloxy)-2-propanesulfonamide.<br>$^1$H NMR (400 MHz, CDCl$_3$) δ 13.24 (s, 1 H) 8.77 (d, J = 1.76 Hz, 1 H) 8.65 (s, 2 H) 8.61 (d, J = 1.56 Hz, 1 H) 7.87 (S, 1 H) 4.89 (d, J = 3.42 Hz, 1 H) 4.37 (td, J = 8.84, 4.41 Hz, 1 H) 4.25-4.34 (m, 1 H) 4.21 (t, J = 9.23 Hz, 1 H) 3.80 (qd, J = 7.01, 3.42 Hz, 1 H) 3.50-3.63 (m, 3 H) 3.35 (s, 3 H) 3.28 (s, 3 H) 2.45 (s, 3 H) 2.35 (s, 3 H) 1.64 (d, J = 7.05 Hz, 3 H) 1.10 (d, J = 5.91 Hz, 3 H) 0.96 (d, J = 6.12 Hz, 3 H). LCMS ESI (pos.) m/z: 534.2 (M + H)$^+$. |
| 10.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanatopentane (commercially available from Oakwood Products, Inc.). | 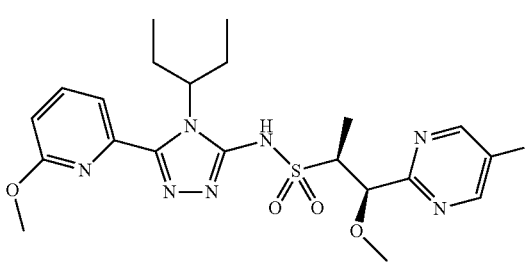<br>(1R,2S)-1-(5-chloro-2-pyrimidinyl)-1-methoxy-N-(5-(6-methoxy-2-pyridinyl)-4-(3-pentanyl)-4H-1,2,4-triazol-3-yl)-2-propanesulfonamide.<br>$^1$H NMR (400 MHz, CDCl$_3$) δ 11.11 (s, 1 H) 8.74 (s, 2 H) 7.72 (dd, J = 8.29, 7.36 Hz, 1 H) 7.50 (d, J = 7.26 Hz, 1 H) 6.90 (dd, J = 8.34, 0.78 Hz, 1 H) 5.08 (d, J = 4.46 Hz, 1 H) 4.94-5.06 (m, 1 H) 3.96 (s, 3 H) 3.70-3.80 (m, 1 H) 3.40 (s, 3 H) 2.25-2.48 (m, 2 H) 1.79-1.97 (m, 2 H) 1.45 (d, J = 7.05 Hz, 3 H) 0.89 (t, J = 7.46 Hz, 3 H) 0.85 (t, J = 7.41 Hz, 3 H). LCMS ESI (pos.) m/z: 510.2 (M + H)$^+$. |
| 11.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 3-isothiocyanatopentane (commercially available from Sigma Aldrich). | 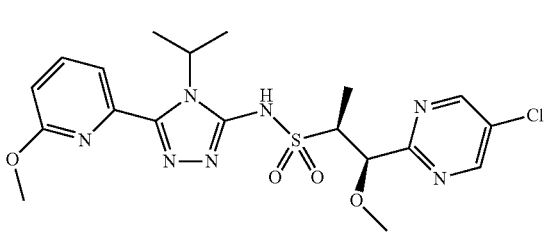 [SMILES: COc1cccc(-c2nnc(NS(=O)(=O)[C@@H](C)[C@H](OC)c3ncc(Cl)cn3)n2C(C)C)n1]<br>(1R,2S)-1-(5-chloro-2-pyrimidinyl)-1-methoxy-N-(5-(6-methoxy-2-pyridinyl)-4-(2-propanyl)-4H-1,2,4-triazol-3-yl)-2-propanesulfonamide.<br>$^1$H NMR (400 MHz, CDCl$_3$) δ 11.10 (br s, 1 H) 8.74 (s, 2 H) 7.73 (dd, J = 8.34, 7.31 Hz, 1 H) 7.49 (dd, J = 7.36, 0.73 Hz, 1 H) 6.91 (dd, J = 8.40, 0.73 Hz, 1 H) 5.33 (m, 1 H) 5.11 (d, J = 4.15 Hz, 1 H) 3.96 (s, 3 H) 3.76 (qd, J = 7.01. 4.25 Hz, 1 H) 3.38 (s, 3 H) 1.67 (d, J = 2.59 Hz, 3 H) 1.65 (d, J = 2.59 Hz, 3 H) 1.47 (d, J = 7.05 Hz, 3 H). LCMS ESI (pos.) m/z: 482.2 (M + H)$^+$. |

TABLE 1-continued

| Example | Reagents | Structure, Name and Data |
|---|---|---|
| 12.0 | (1S,2S)-1-(5-chloropyrimidin-2-yl)-1-isopropoxypropane-2-sulfonamide (Example 31.01), 5-methylnicotinohydrazide (commercially available from Bellen), and 2-methoxyethyl isothiocyanate (commercially available from Sigma-Aldrich). | 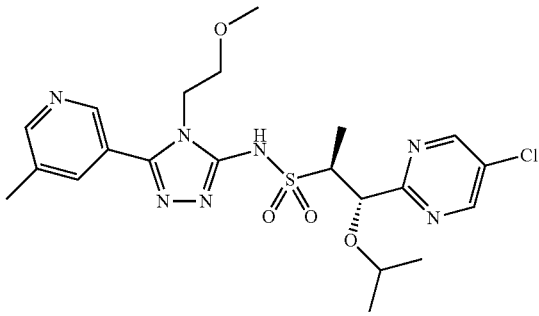 [SMILES: COCCn1c(NS(=O)(=O)[C@@H](C)[C@@H](OC(C)C)c2ncc(Cl)cn2)nnc1-c1cncc(C)c1]<br>(1S,2S)-1-(5-chloro-2-pyrimidinyl)-N-(4-(2-methoxyethyl)-5-(5-methyl-3-pyridinyl)-4H-1,2,4-triazol-3-yl)-1-(2-propanyloxy)-2-propanesulfonamiide.<br>$^1$H NMR (400 MHz, CDCl$_3$) δ 12.13 (s, 1 H) 8.86 (d, J = 1.56 Hz, 1 H) 8.76 (s, 2 H) 8.63 (d, J = 1.45 Hz, 1 H) 7.96 (d, J = 0.62 Hz, 1 H) 4.92 (d, J = 3.94 Hz, 1 H) 3.94-4.11 (m, 2 H) 3.81-3.91 (m, 2 H) 3.72 (qd, J = 5.22, 3.42 Hz, 1 H) 3.56 (m, 1 H) 3.32 (s, 3 H) 2.46 (s, 3 H) 1.59 (d, J = 7.05 Hz, 3 H) 1.10 (d, J = 6.01 Hz, 3 H) 0.94 (d, J = 6.12 Hz, 3 H).<br>LCMS ESI (pos.) m/z: 510.2 (M + H)$^+$. |
| 13.0 | (1S,2S)-1-(5-chloropyrimidin-2-yl)-1-isopropoxypropane-2-sulfonamide (Example 31.01), 5-methylnicotinohydrazide (commercially available from Bellen), and 2-isothiocyanato-1,3-dimethoxypropane (Example 71.0). | 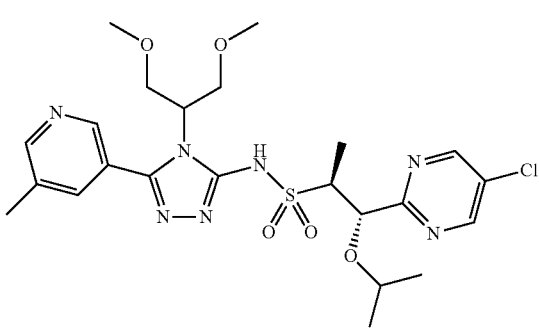 [SMILES: COCC(COC)n1c(NS(=O)(=O)[C@@H](C)[C@@H](OC(C)C)c2ncc(Cl)cn2)nnc1-c1cncc(C)c1]<br>(1S,2S)-1-(5-chloro-2-pyrimidinyl)-N-(4-(1,3-dimethoxy-2-propanyl)-5-(5-methyl-3-pyridinyl)-4H-1,2,4-triazol-3-yl)-1-(2-propanyloxy)-2-propanesulfonamide.<br>$^1$H NMR (500 MHz, DMSO-d$_6$) δ 13.01 (br s, 1 H) 8.96 (s, 2 H) 8.56-8.70 (m, 2 H) 7.86 (br s, 1 H) 4.93 (br d, J = 6.62 Hz, 1 H) 4.33 (dt, J = 8.60, 4.33 Hz, 1 H) 4.07 (br d, J = 8.82 Hz, 2 H) 3.42-3.68 (m, 4 H) 3.21 (s, 3 H) 3.19 (s, 3 H) 2.39 (s, 3 H) 1.16 (br d, J = 7.01 Hz, 3 H) 1.03-1.12 (m, 3 H) 0.86 (br d, J = 6.10 Hz, 3 H).<br>LCMS ESI (pos.) m/z: 554.2 (M + H)$^+$. |
| 14.0 | (1R,2S)-1-(5-chloropyrimidin-2-yl)-1-methoxypropane-2-sulfonamide (Example 29.3), picolinohydrazide (commercially available from TCI America), and 2-isothiocyanato-1,3-dimethoxypropane (Example 71.0). | 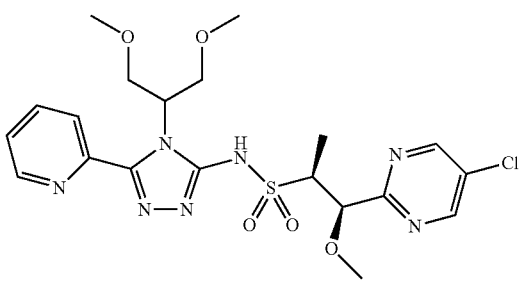 [SMILES: COCC(COC)n1c(NS(=O)(=O)[C@@H](C)[C@H](OC)c2ncc(Cl)cn2)nnc1-c1ccccn1]<br>(1R,2S)-1-(5-chloro-2-pyrimidinyl)-N-(4-(1,3-dimethoxy-2-propanyl)-5-(2-pyridinyl)-4H-1,2,4-triazol-3-yl)-1-methoxy-2-propanesulfonamiide.<br>$^1$H NMR (500 MHz, DMSO-d$_6$) δ 13.20 (br s, 1 H) 8.95 (s, 2 H) 8.74 (br d, J = 4.54 Hz, 1 H) 7.98-8.06 (m, 1 H) 7.90-7.98 (m, 1 H) 7.54-7.64 (m, 1 H) 5.59-5.93 (m, 1 H) 4.96 (br d, J = 3.89 Hz, 1 H) 4.06 (dt, J = 18.10, 9.12 Hz, 2 H) 3.61-3.71 (m, 2 H) 3.47-3.57 (m, 1 H) 3.31 (s, 3H) 3.18 (s, 3 H) 3.18 (s, 3 H) 1.29 (br d, J = 7.01 Hz, 3 H).<br>LCMS ESI (pos.) m/z: 512.2 (M + H)$^+$. |

TABLE 1-continued

| Example | Reagents | Structure, Name and Data |
|---|---|---|
| 15.0 | (1R,2S)-1-(5-chloropyrimidin-2-yl)-1-methoxypropane-2-sulfonamide (Example 29.3), 5-methylnicotinohydrazide (commercially available from Bellen), and 2-isothiocyanato-1,3-dimethoxypropane (Example 71.0). | 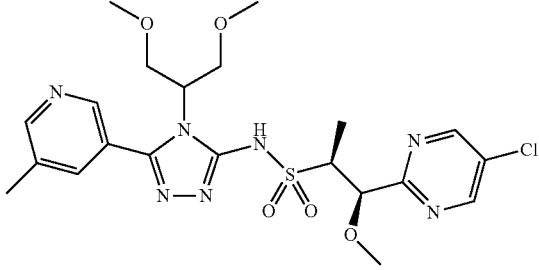 [SMILES: COCC(COC)n1c(NS(=O)(=O)[C@@H](C)[C@H](OC)c2ncc(Cl)cn2)nnc1-c1cncc(C)c1] (1R,2S)-1-(5-chloro-2-pyrimidinyl)-N-(4-(1,3-dimethoxy-2-propanyl)-5-(5-methyl-3-pyridinyl)-4H-1,2,4-triazol-3-yl)-1-methoxy-2-propanesulfonamiide. $^1$H NMR (500 MHz, DMSO-$d_6$) δ 13.18 (br s, 1 H) 8.96 (s, 2 H) 8.62 (br d, J = 16.09 Hz, 2 H) 7.87 (br s, 1 H) 4.98 (br d, J = 3.63 Hz, 1 H) 4.34 (br dd, J = 9.02, 4.48 Hz, 1 H) 4.07 (q, J = 9.86 Hz, 2 H) 3.46-3.58 (m, 3 H) 3.21 (s, 3 H) 3.20 (s, 3 H) 3.19 (s, 3 H) 2.39 (s, 3 H) 1.30 (br d, J = 7.01 Hz, 3 H). LCMS ESI (pos.) m/z: 526.2 (M + H)$^+$. |
| 16.0 | (1R,2S)-1-(5-chloropyrimidin-2-yl)-1-methoxypropane-2-sulfonamide (Example 29.3), nicotinohydrazide (commercially available from Acros), and 2-isothiocyanato-1,3-dimethoxypropane (Example 71.0). | 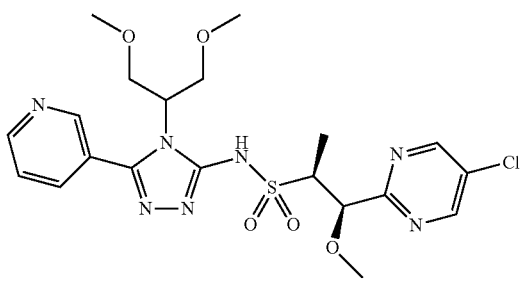 [SMILES: COCC(COC)n1c(NS(=O)(=O)[C@@H](C)[C@H](OC)c2ncc(Cl)cn2)nnc1-c1cccnc1] (1R,2S)-1-(5-chloro-2-pyrimidinyl)-N-(4-(1,3-dimethoxy-2-propanyl)-5-(methyl-3-pyridinyl)-4H-1,2,4-triazol-3-yl)-1-methoxy-2-propanesulfonamiide. $^1$H NMR (500 MHz, DMSO-$d_6$) δ 13.20 (br s, 1 H) 8.96 (s, 2 H) 8.80 (b rs, 2 H) 8.06 (br d, J = 7.91 Hz, 1 H) 7.63 (br dd, J = 7.59, 5.00 Hz, 1 H) 4.98 (br d, J = 3.63 Hz, 1 H) 4.32 (dt, J = 8.82, 4.41 Hz, 1 H) 3.99-4.16 (m, 2 H) 3.46-3.57 (m, 3 H) 3.14-3.24 (m, 9 H) 1.30 (br d, J = 7.01 Hz, 3 H). LCMS ESI (pos.) m/z: 512.2 (M + H)$^+$. |
| 17.0 | (2S,3R)-3-(5-methylpyrazin-2-yl)butane-2-sulfonamide (Example 27.2), nicotinohydrazide (commercially available from Acros), and 2-isothiocyanato-1,3-dimethoxypropane (Example 71.0). | 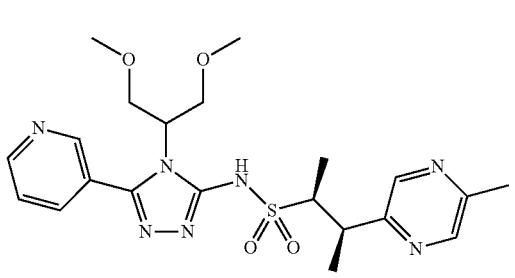 [SMILES: COCC(COC)n1c(NS(=O)(=O)[C@@H](C)[C@H](C)c2cnc(C)cn2)nnc1-c1cccnc1] (2S,3R)-N-(4-(1,3-dimethoxy-2-propanyl)-5-(3-pyridinyl)-4H-1,2,4-triazol-3-yl)-3-(5-methyl-2-pyrazinyl)-2-butanesulfonamide. $^1$H NMR (400 MHz, CDCl$_3$) δ 11.38 (br s, 1 H) 8.94 (d, J = 1.55 Hz, 1 H) 8.79 (dd, J = 4.92, 1.61 Hz, 1 H) 8.45 (d, J = 1.24 Hz, 1 H) 8.39 (s, 1 H) 8.07 (dt, J = 7.98, 1.92 Hz, 1 H) 7.47 (dd, J = 7.41, 4.92 Hz, 1 H) 4.31-4.42 (m, 1 H) 4.09-4.20 (m, 2 H) 3.77-3.88 (m, 1 H) 3.69 (qd, J = 6.98. 4.77 Hz, 1 H) 3.46-3.55 (m, 2 H) 3.26 (s, 3 H) 3.26 (s, 3 H) 2.55 (s, 3 H) 1.48 (d, J = 7.05 Hz, 3 H) 1.42 (d, J = 6.95 Hz, 3 H). LCMS ESI (pos.) m/z: 476.2 (M + H)$^+$. |

TABLE 1-continued

| Example | Reagents | Structure, Name and Data |
|---|---|---|
| 18.0 | (2S,3R)-3-(5-chloropyrimidin-2-yl)butane-2-sulfonamide (Example 27.4), nicotinohydrazide (commercially available from Acros), and 2-methoxyethyl isothiocyanate (commercially available from Sigma-Aldrich). | 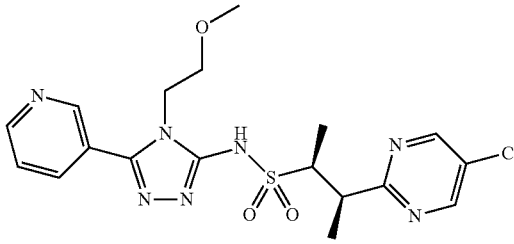<br>(2R,3S)-3-(5-chloro-2-pyrimidinyl)-N-(4-(2-methoxyethyl)-5-(3-pyridinyl)-4H-1,2,4-triazol-3-yl)-2-butanesulfonamide.<br>$^1$H NMR (400 MHz, CDCl$_3$) δ 11.32 (br s, 1 H) 9.07 (d, J = 1.56 Hz, 1 H) 8.82 (dd, J = 4.82, 1.30 Hz, 1 H) 8.65 (s, 2 H) 8.23 (dt, J = 7.96, 1.72 Hz, 1 H) 7.52 (dd, J = 7.83, 4.92 Hz, 1 H) 3.96-4.04 (m, 2 H) 3.93 (quin, J = 6.87 Hz, 1 H) 3.81 (quin, J = 6.87 Hz, 1 H) 3.69-3.77 (m, 2 H) 3.30 (s, 3 H) 1.49 (d, J = 7.05 Hz, 3 H) 1.46 (d, J = 7.05 Hz, 3 H). LCMS ESI (pos.) m/z: 452.2 (M + H)$^+$. |
| 19.0 | (2S,3R)-3-(5-chloropyrimidin-2-yl)butane-2-sulfonamide (Example 27.4), nicotinohydrazide (commercially available from Acros), and 2-methoxyethyl isothiocyanate (commercially available from Sigma-Aldrich). | 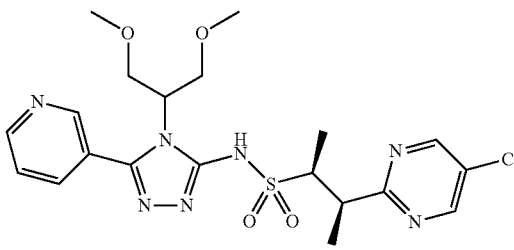<br>(2S,3R)-3-(5-chloro-2-pyrimidinyl)-N-(4-(1,3dimethoxy-2-propanyl)-5-(3-pyridinyl)-4H-1,2,4-triazol-3-yl)-2-butanesulfonamide.<br>$^1$H NMR (500 MHz, DMSO-d$_6$) δ 13.20 (br s, 1 H) 8.88 (s, 2 H) 8.77-8.86 (m, 2 H) 8.06 (br d, J = 7.79 Hz, 1 H) 7.63 (br dd, J = 7.59, 4.74 Hz, 1 H) 4.29-4.40 (m, 1 H) 4.01 (br d, J = 4.80 Hz, 2 H) 3.65-3.84 (m, 2 H) 3.47-3.56 (m, 2 H) 3.16 (s, 3 H) 3.16 (s, 3 H) 1.38 (br d, J = 7.01 Hz, 3 H) 1.22-1.32 (m, 3 H). LCMS ESI (pos.) m/z: 496.2 (M + H)$^+$. |
| 20.0 | (2S,3R)-3-(5-methoxypyrimidin-2-yl)butane-2-sulfonamide (Example 27.6), 6-methoxypicolinohydrazide (commercially available from Sigma Aldrich), and 2-methoxyethyl isothiocyanate (commercially available from Sigma-Aldrich). | 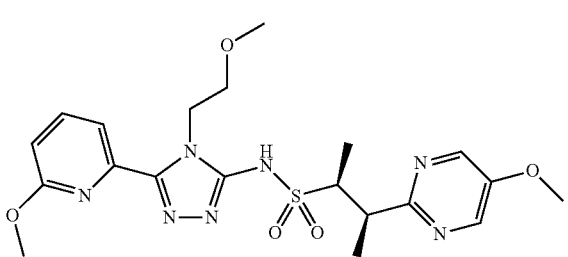 [SMILES: COCCn1c(NS(=O)(=O)[C@@H](C)[C@H](C)c2ncc(OC)cn2)nnc1-c1cccc(OC)n1]<br>(2S,3R)-N-(4-(2-methoxyethyl)-5-(6-methoxy-2-pyridinyl)-4H-1,2,4-triazol-3-yl)-3-(5-methoxy-2-pyrimidinyl)-2-butanesulfonamide.<br>$^1$H NMR (500 MHz, DMSO-d$_6$) δ 1.26 (br d, J = 6.75 Hz, 3 H) 1.32 (br d, J = 6.75 Hz, 3 H) 3.10 (s, 3 H) 3.17 (br d, J = 4.93 Hz, 1 H) 3.52-3.62 (m, 2 H) 3.65-3.79 (m, 2 H) 3.82 (s, 3 H) 3.91 (s, 3 H) 4.25-4.37 (m, 1 H) 4.37-4.49 (m, 1 H) 7.01 (br d, J = 8.30 Hz, 1 H) 7.62 (br d, J = 7.40 Hz, 1 H) 7.89 (br t, J = 7.91 Hz, 1 H) 8.43 (s, 2 H) 13.18 (s, 1 H). LCMS ESI (pos.) m/z: 478.2 (M + H)$^+$. |
| 21.0 | (2S,3R)-3-(5-methoxypyrimidin-2-yl)butane-2-sulfonamide (Example 27.6), picolinohydrazide (commercially available from TCI America), and 2-methoxyethyl isothiocyanate (commercially available from Sigma-Aldrich). | 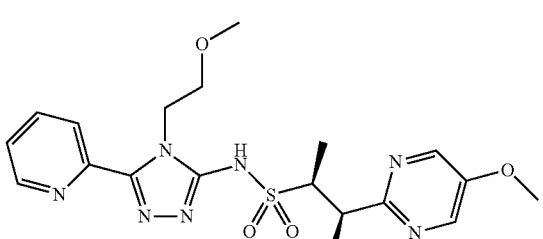<br>(2S,3R)-N-(4-(2-methoxyethyl)-5-(2-pyridinyl)-4H-1,2,4-triazol-3-yl)-3-(5-methoxy-2-pyrimidinyl)-2-butanesulfonamide.<br>$^1$H NMR (500 MHz, DMSO-d$_6$) δ 13.20 (br s, 1 H) 8.72 (br d, J = 4.54 |

TABLE 1-continued

| Example | Reagents | Structure, Name and Data |
|---|---|---|
| | | Hz, 1 H) 8.43 (s, 2 H) 7.94-8.07 (m, 2 H) 7.53-7.64 (m, 1 H) 4.36-4.49 (m, 1 H) 4.25-4.36 (m, 1 H) 3.83 (s, 3 H) 3.66-3.79 (m, 2 H) 3.50 (br t, J = 5.25 Hz, 2 H) 3.05 (s, 3 H) 1.32 (br d, J = 6.75 Hz, 3 H) 1.22-1.29 (m, 3 H). LCMS ESI (pos.) m/z: 448.2 (M + H)+. |
| 22.0 | (1R,2S)-1-(5-chloropyrimidin-2-yl)-1-methoxypropane-2-sulfonamide (Example 29.3), 6-methoxypicolinohydrazide (commercially available from Sigma-Aldrich), and 2-ethoxyethyl isothiocyanate (commercially available from Enamine). | 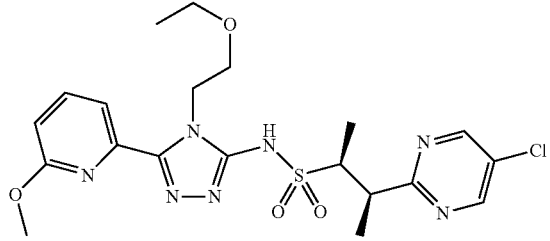 (1R,2S)-1-(5-chloro-2-pyrimidinyl)-N-(4-(2-ethoxyethyl)-5-(6-methoxy-2-pyridinyl)-4H-1,2,4-triazol-3-yl)-1-methoxy-2-propanesulfonamide. $^1$H NMR (500 MHz, DMSO-$d_6$) δ 13.22 (br s, 1 H) 8.91 (s, 1 H) 7.89 (br t, J = 7.85 Hz, 1 H) 7.60 (br d, J = 7.40 Hz, 1 H) 7.01 (br d, J = 8.30 Hz, 1 H) 4.86 (br d, J = 4.67 Hz, 1 H) 4.30-4.49 (m, 2 H) 3.93 (s, 3 H) 3.60 (br s, 3 H) 3.06-3.40 (m, 5 H) 1.32 (br d, J = 6.88 Hz, 3 H) 0.88 (br t, J = 6.94 Hz, 3 H). LCMS ESI (pos.) m/z: 512.2 (M + H)+. |
| 23.0 | (1S,2S)-1-(5-chloropyrimidin-2-yl)-1-isopropoxypropane-2-sulfonamide (Example 31.01), picolinohydrazide (commercially available from TCI America), and 2-methoxyethyl isothiocyanate (commercially available from Sigma-Aldrich). | 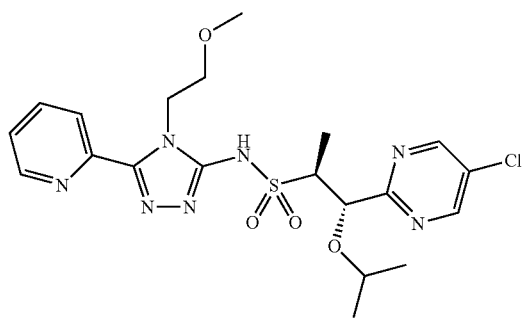 [SMILES: COCCn1c(NS(=O)(=O)[C@@H](C)[C@@H](OC(C)C)c2ncc(Cl)cn2)nnc1-c1ccccn1] (1S,2S)-1-(5-chloro-2-pyrimidinyl)-N-(4-(2-methoxyethyl)-5-(2-pyridinyl)-4H-1,2,4-triazol-3-yl)-1-(2-propanyloxy)-2-propanesulfonamide. $^1$H NMR (400 MHz, CDCl$_3$) δ 11.86 (br s, 1 H) 8.73 (s, 2 H) 8.63-8.70 (m, 1 H) 8.00 (d, J = 7.98 Hz, 1 H) 7.83 (td, J = 7.80. 1.71 Hz, 1 H) 7.40 (ddd, J = 7.57, 4.87, 1.04 Hz, 1 H) 4.94 (d, J = 4.15 Hz, 1 H) 4.67-4.78 (m, 1 H) 4.60 (dt, J = 13.63, 5.73 Hz, 1 H) 3.85 (qd, J = 7.01. 4.35 Hz, 1 H) 3.59-3.72 (m, 2 H) 3.54 (spt, J = 6.08 Hz, 1 H) 3.20 (s, 3 H) 1.54 (d, J = 7.05 Hz, 3 H) 1.08 (d, J = 6.01 Hz, 3 H) 0.92 (d, J = 6.12 Hz, 3 H). LCMS ESI (pos.) m/z: 496.2 (M + H)+. |
| 24.0 | (1S,2S)-1-(5-chloropyrimidin-2-yl)-1-isopropoxypropane-2-sulfonamide (Example 31.01), 6-methoxypicolinohydrazide (commercially available from Sigma-Aldrich), and 2-methoxyethyl isothiocyanate (commercially available from Sigma-Aldrich). | 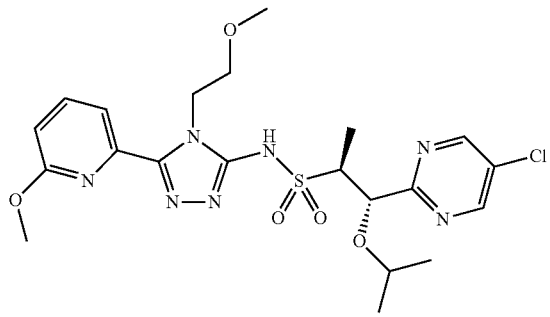 (1S,2S)-1-(5-chloro-2-pyrimidinyl)-N-(4-(2-methoxyethyl)-5-(6-methoxy-2-pyridinyl)-4H-1,2,4-triazol-3-yl)-1-methoxy-2-propanesulfonamide. $^1$H NMR (400 MHz, CDCl$_3$) δ 11.81 (br s, 1 H) 8.73 (s, 2 H) 7.67-7.74 (m, 1 H) 7.62 (dd, J = 7.36, 0.73 Hz, 1 H) 6.87 (dd, J = 8.24, 0.67 Hz, 1 H) 4.94 (d, J = 4.35 Hz, 1 H) 4.64-4.74 (m, 1 H) 4.54-4.64 (m, 1 H) 3.96 (s, 3 H) 3.86 (qd, J = 7.01. 4.35 Hz, 1 H) 3.61-3.75 (m, 2 H) 3.54 (m, 1 H) 3.24 (s, 3 H) 1.54 (d, J = 7.05 Hz, 3 H) 1.09 (d, J = 6.01 Hz. 3 H) 0.92 (d, J = 6.12 Hz, 3 H). LCMS ESI (pos.) m/z: 512.2 (M + H)+. |

TABLE 1-continued

| Example | Reagents | Structure, Name and Data |
|---|---|---|
| 25.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (isothiocyanatomethylene)dicyclopropane (commercially available from Frontier Scientific Services Inc.). | 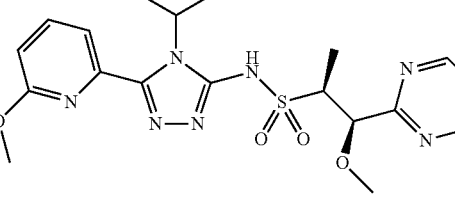<br>(1R,2S)-1-(5-chloro-2-pyrimidinyl)-N-(4-(dicyclopropylmethyl)-5-(6-methoxy-2-pyridinyl)-4H-1,2,4-triazol-3-yl)-1-methoxy-2-propanesulfonamide.<br>$^1$H NMR (400 MHz, CDCl$_3$) δ 0.04-0.26 (m, 2 H) 0.32 (br s, 2 H) S, 2 H) 0.42 (br s, 2 H) 0.74 (br s, 2 H) 1.45 (d, J = 6.95 Hz, 3 H) 2.22 (br s, 2 H) 3.36 (s, 3 H) 3.69-3.85 (m, 4 H) 3.98 (br d, J = 5.08 Hz, 1 H) 5.10 (br d, J = 3.52 Hz, 1 H) 6.86 (d, J = 8.29 Hz, 1 H) 7.58 (br s, 1 H) 7.70 (dd, J = 8.24, 7.52 Hz, 1 H) 8.73 (s, 2 H) 11.17 (br s, 1 H).<br>LCMS ESI (pos.) m/z: 534.2 (M + H)$^+$. |
| 26.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (2-isothiocyanatoethyl)(methyl)sulfane (commercially available from Enamine). | 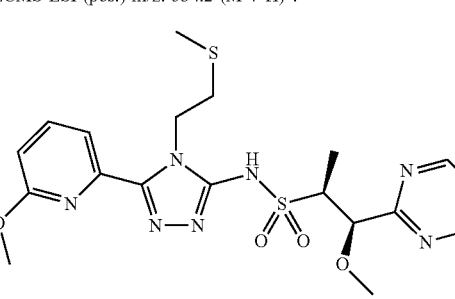<br>(1R,2S)-1-(5-chloro-2-pyrimidinyl)-1-methoxy-N-(5-(6-methoxy-2-pyridinyl)-4-(2-(methylsulfanyl)ethyl)-4H-1,2,4-triazol-3-yl)-2-propanesulfonamide.<br>$^1$H NMR (400 MHz, CDCl$_3$) δ 8.77 (s, 2 H) 7.63-7.80 (m, 2 H) 6.86-6.97 (m, 1 H) 5.08-5.20 (m, 1 H) 4.61-4.72 (m, 1 H) 4.04 (d, J = 3.11 Hz, 1 H) 3.99 (s, 3 H) 3.74-3.86 (m, 1 H) 3.35 (s, 3 H) 2.90-2.99 (m, 1 H) 2.78 (br d, J = 3.63 Hz, 1 H) 2.15 (s, 3 H) 1.49 (d, J = 6.95 Hz, 3 H).<br>LCMS ESI (pos.) m/z: 514.1 (M + H)$^+$. |

Example 27.0: Preparation of (2S,3R)-3-(5-methyl-pyrimidin-2-yl)butane-2-sulfonamide

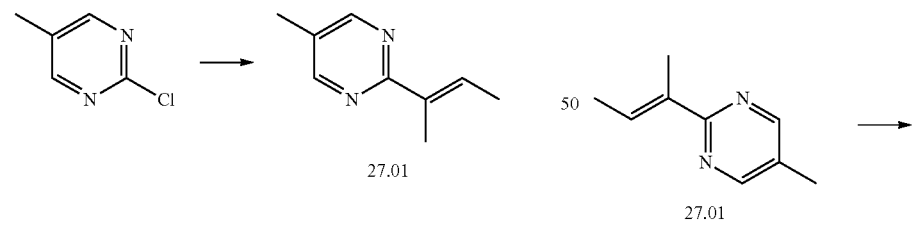

(E)-2-(But-2-en-2-yl)-5-methylpyrimidine, Example 27.01

2-Chloro-5-methyl-pyrimidine (18 mL, 151 mmol), potassium (Z)-but-2-en-2-yltrifluoroborate (commercially available from Sigma Aldrich, 31 g, 191 mmol), tricyclohexylphosphine (8.5 g, 30.2 mmol) and Pd$_2$(dba)$_3$ (13.82 g, 15.09 mmol) were added to a flask, which was then degassed and backfilled with nitrogen. To the flask was added 1,4-dioxane (252 mL) and aqueous potassium phosphate tribasic (37.5 mL, 453 mmol). The resulting reaction was heated at 100° C. for 16 h. The reaction was then cooled to RT. The residue was filtered through a plug of silica gel and then loaded onto silica gel (0-20% EtOAc in heptanes) to afford (E)-2-(but-2-en-2-yl)-5-methylpyrimidine 27.01 (19 g, 125 mmol, 83% yield).

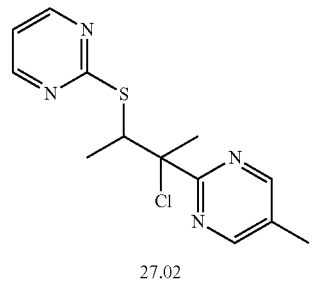

2-(2-Chloro-3-(pyrimidin-2-ylthio)butan-2-yl)-5-methylpyrimidine, Example 27.02

To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at RT. To the cloudy reaction mixture was added (E)-2-(but-2-en-2-yl)-5-methylpyrimidine 27.01 (20 g, 132 mmol) dropwise, and the mixture was stirred for a further 2 h. The reaction mixture was then concentrated in vacuo. Aqueous sodium bicarbonate solution was added to the mixture to neutralize the reaction mixture. The reaction was extracted with EtOAc and concentrated in vacuo. The residue was purified on silica gel with 0-25% EtOAc in hexanes to give the desired product 2-(2-chloro-3-(pyrimidin-2-ylthio)butan-2-yl)-5-methylpyrimidine 27.02 (30 g, 76% yield).

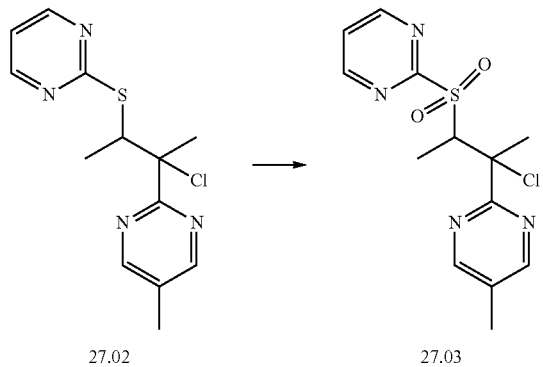 [SMILES: Cc1cnc(C(C)(Cl)C(C)Sc2ncccn2)nc1 ; Cc1cnc(C(C)(Cl)C(C)S(=O)(=O)c2ncccn2)nc1]

2-(2-Chloro-3-(pyrimidin-2-ylsulfonyl)butan-2-yl)-5-methylpyrimidine, Example 27.03

To a solution of 2-(2-chloro-3-(pyrimidin-2-ylthio)butan-2-yl)-5-methylpyrimidine 27.02 (30 g, 100 mmol) in DCM (201 mL) was added meta-chloroperoxybenzoic acid (45.0 g, 201 mmol). The reaction was stirred at RT for 1 d. The reaction was concentrated in vacuo and an aqueous sodium bicarbonate solution and a sodium thiosulfate solution were added. The mixture was extracted with EtOAc and concentrated in vacuo to give the desired product 2-(2-chloro-3-(pyrimidin-2-ylsulfonyl)butan-2-yl)-5-methylpyrimidine 27.03 (33.2 g, 100 mmol, 100% yield).

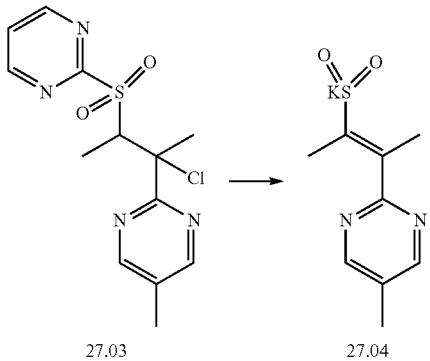

Potassium (E)-3-(5-methylpyrimidin-2-yl)but-2-ene-2-sulfinate, Example 27.04

To a solution of 2-(2-chloro-3-(pyrimidin-2-ylsulfonyl)butan-2-yl)-5-methylpyrimidine 27.03 (33 g, 100 mmol) in MeOH (249 mL) was added potassium carbonate (27.6 g, 200 mmol). The reaction was stirred at RT for 16 h. The reaction was concentrated in vacuo to give the desired product potassium (E)-3-(5-methylpyrimidin-2-yl)but-2-ene-2-sulfinate 27.04 (21.57 g, 100% yield), which was used without further purification.

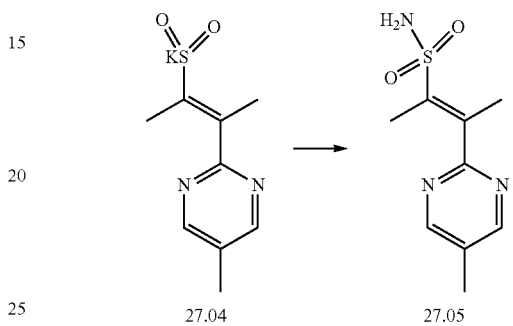

(E)-3-(5-Methylpyrimidin-2-yl)but-2-ene-2-sulfonamide, Example 27.05

To a solution of potassium (E)-3-(5-methylpyrimidin-2-yl)but-2-ene-2-sulfinate (Example 27.04, 21.57 g, 85 mmol) in water (424 mL, 85 mmol) was added potassium acetate (5.30 mL, 85 mmol), followed by amidoperoxymonosulfuric acid (19.18 g, 170 mmol). The reaction was stirred at RT for 24 h. The reaction was extracted with EtOAc and concentrated in vacuo. The product thus obtained was purified on silica gel eluting with 0-50% EtOAc in hexanes to give the desired product (E)-3-(5-methylpyrimidin-2-yl)but-2-ene-2-sulfonamide 27.05 (12 g, 61% yield).

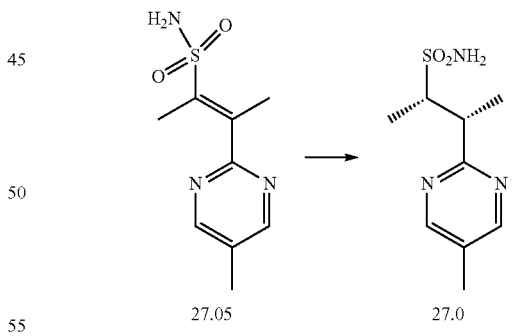

(2S,3R)-3-(5-Methylpyrimidin-2-yl)butane-2-sulfonamide, Example 27.0

A 900 mL pressure reactor was charged under nitrogen flow with (E)-3-(5-methylpyrimidin-2-yl)but-2-ene-2-sulfonamide, Example 27.05 (40.00 g, 0.176 mol, 1 equiv), zinc trifluoromethane sulfonate (12.79 g, 0.0352 mol, 0.2 equiv, Aldrich), bis(1,5-cyclooctadiene)rhodium(I) tetrafluoroborate (1.43 g, 0.00352 mol, 0.02 equiv, Strem Chemicals, Inc.), (S)-1-[(R)-2-(di-1-naphthylphosphino)ferrocenyl]- ethyl-di-tert.-butylphosphine (2.60 g, 0.00405 mol, 0.023 equiv, Solvias) and MeOH (520 mL). The mixture was purged with nitrogen and then with hydrogen and the media was stirred under 3-4 bars of hydrogen for 20 h. The reaction was monitored by HPLC and showed a complete conversion. The reactor was purged with nitrogen and the resulting suspension was concentrated at 35° C. under vacuum to give the initial material as an orange solid. The initial material was mixed with EtOH (742 mL) and the resulting suspension was stirred at 20-25° C. for 40 min. The solid was filtered, washed with EtOH (2×97 mL) and dried at 40° C. under vacuum to give the title compound as a white powder (85% yield, 99% ee). $^1$H NMR (400 MHz, DMSO-d$_6$) δ 8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). LCMS (ESI, positive ion) m/z; 230.1 (M+H)$^+$.

The compounds in the following table were synthesized following the procedure in Example 27.0 using the known starting material as described.

TABLE 2

| Example | Reagents | Structure, Name and Data |
|---|---|---|
| 27.1 | 2-chloro-5-fluoro-pyrimidine. | 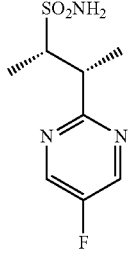<br>(2S,3R)-3-(5-fluoropyrimidin-2-yl)butane-2-sulfonamide.<br>LCMS ESI (pos.) m/z: 234.2 (M + H)$^+$. |
| 27.2 | 2-bromo-5-methylpyrazine. The title compound was the first isomer to elute under the following SFC conditions: Run on Thar 200 SFC with 250 × 30 mm AD-H column with 20 mL/min MeOH (+20 mM NH$_3$) + 80 g/min CO$_2$, 20% co-solvent at 100 g/min. Temperature. = 29° C., Outlet pressure = 100 bar, Wavelength = 271 mm Injected 1.0 mL of 550 mg of the enantiomerically enriched product dissolved in 20 mL MeOH:DCM, 15:5; c = 27.5 mg/mL and 27.5 mg per injection. Cycle time 5.0 min, run time 13 min. | 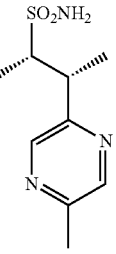<br>(2S,3R)-3-(5-methylpyrazin-2-yl)butane-2-sulfonamide.<br>$^1$H NMR (400 MHz, DMSO-d$_6$) δ 8.46 (d, J = 6.5 Hz, 2H), 6.84 (s, 2H), 3.63 (qd, J = 7.0, 4.3 Hz, 1H), 3.44 (qd, J = 7.0, 4.3 Hz, 1H), 2.47 (s, 3H), 1.31 (d, J = 7.0 Hz, 3H), 1.23 (d, J = 7.0 Hz, 3H). LCMS ESI (pos.) m/z: 230.0 (M + H)$^+$. |
| 27.3 | 2-bromo-5-methylpyrazine. The title compound is the enantiomer of Example 27.2. Example 27.3 is the second isomer to elute from the AD-H column on subjecting the enantiomerically enriched product to the SFC conditions described in Example 27.2. | 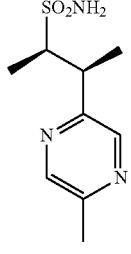<br>(2R,3S)-3-(5-methylpyrazin-2-yl)butane-2-sulfonamide.<br>LCMS-ESI (pos.) m/z: 230.0 (M + H)$^+$. |

TABLE 2-continued

| Example | Reagents | Structure, Name and Data |
|---|---|---|
| 27.4 | 2-chloro-5-chloro-pyrimidine. Recrystallization: Example 27.4 (38 g, 90% ee) was dissolved in IPA (400 mL) at 70° C. | (2S,3R)-3-(5-chloropyrimidin-2-yl)butane-2-sulfonamide.<br>$^1$H NMR (400 MHz, DMSO-$d_6$) δ 8.93-8.85 (m, 2H), 6.86 (d, J = 4.0 Hz, 2H), 3.73-3.59 (m, 2H), 1.31 (dt, J = 7.3, 2.4 Hz, 3H), 1.25-1.19 (m, 3H). LCMS (ESI + ve ion) m/z: 250.2 (M + H)$^+$. |
| 27.5 | 2-bromo-5-methoxypyrazine. | (2S,3R)-3-(5-methoxypyrazin-2-yl)butane-2-sulfonamide.<br>$^1$H NMR (400 MHz, DMSO-$d_6$) δ 8.26 (d, J = 1.4 Hz, 1H), 8.12 (d, J = 1.4 Hz, 1H), 6.84 (s, 2H), 3.90 (d, J = 1.5 Hz, 3H), 3.62 (dd, J = 7.1, 4.3 Hz, 1H), 3.42-3.38 (m, 1H), 1.32 (d, J = 1.5 Hz, 3H), 1.23-1.21 (m, 3H). LCMS ESI (pos.) m/z: 246.2 (M + H)$^+$. |
| 27.6 | 2-chloro-5-methoxypyrimidine. | (2S,3R)-3-(5-methoxypyrimidin-2-yl)butane-2-sulfonamide.<br>LCMS (ESI + ve ion) m/z: 246.2 (M + H)$^+$. |

Example 28.0. Preparation of 3-(isothiocyanatomethyl)oxetane

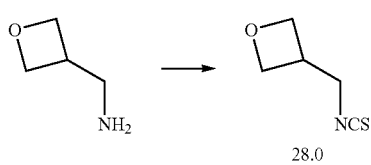

3-(Isothiocyanatomethyl)oxetane, Example 28.0

To a dry 200 mL round-bottom flask was added di(2-pyridyl) thionocarbonate (2.67 g, 11.48 mmol) in then added dropwise via a addition funnel over 20 min at RT. The reaction mixture was stirred at RT for 19 h. Next, the reaction mixture was concentrated in vacuo. The initial material was absorbed onto a plug of silica gel and purified by chromatography through a Redi-Sep pre-packed silica gel column (24 g), eluting with a gradient of 0% to 50% EtOAc in heptanes, to provide the title compound, Example 28.0, (1.48 g, 100% yield) as an orange oil. $^1$H NMR (400 MHz, CDCl$_3$) δ 3.25-3.35 (m, 1H) 3.83 (d, J=6.74 Hz, 2H) 4.45 (t, J=6.06 Hz, 2H) 4.82-4.87 (m, 2H). LCMS ESI (pos.) m/z: (M+H)$^+$=130.0.

The compounds set forth in the following table were synthesized following the procedure in Example 28.0 using the known starting material as described.

TABLE 3

| Example | Reagents | Structure, Name and Data |
|---|---|---|
| 28.1 | 2,2-dimethyl-1,3-dioxan-5-amine (commercially available from ChemBridge). | 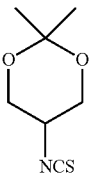<br>5-isothiocyanato-2,2-dimethyl-1,3-dioxane. $^1$H NMR (400 MHz, CDCl$_3$) δ 1.43 (s, 3 H) 1.47 (s, 3 H) 3.55 (tt, J = 5.07, 3.43 Hz, 1 H) 3.87 (dd, J = 12.13, 5.08 Hz, 2 H) 4.08 (dd, J = 12.02, 3.42 Hz, 2 H). LCMS-ESI (pos.) m/z: 174.2 (M + H)$^+$. |
| 28.2 | 2-oxaspiro[3.3]heptane-6-amine hydrochloride (commercially available from Synthonix) and Hunig's base (commercially available from Sigma-Aldrich). | 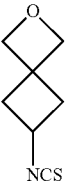<br>6-isothiocyanato-2-oxaspiro[3.3]heptanes. $^1$H NMR (400 MHz, CDCl$_3$) δ 2.38-2.47 (m, 2 H) 2.69-2.77 (m, 2 H) 3.92 (quin, J = 7.62 Hz, 1 H) 4.64 (d, J = 2.38 Hz, 4 H). LCMS-ESI (pos.) m/z: 156.0 (M + H)$^+$. |
| 28.3 | 3,5-difluoropyridin-4-amine (commercially available from Enamine). | 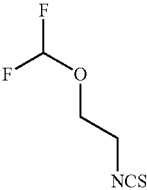<br>1-(difluoromethoxy)-2-isothiocyanatoethane. $^1$H NMR (400 MHz, CD$_3$CN) δ 3.81 (t, J = 5.03 Hz, 2 H) 4.05 (t, J = 5.03 Hz, 2 H) 6.44 (t, J = 75.67 Hz, 1 H). |
| 28.4 | 3-aminopropanenitrile hydrochloride (commercially available from Enamine) and Hunig's base (commercially available from Sigma-Aldrich). | 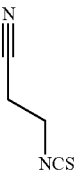<br>3-isothiocyanatopropanenitrile. $^1$H NMR (400 MHz, CD$_3$CN) δ 2.81 (t, J = 6.22 Hz, 2 H) 3.84 (t, J = 6.22 Hz, 2 H). LCMS-ESI (pos.) m/z: 113.2 (M + H)$^+$. |

TABLE 3-continued

| Example | Reagents | Structure, Name and Data |
|---|---|---|
| 28.5 | 1-(methoxymethyl)cyclobutanamine hydrochloride (commercially available from Enamine) and Hunig's base (commercially available from Sigma-Aldrich). | 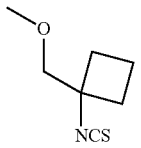<br>1-isothiocyanato-1-(methoxymethyl)cyclobutane.<br>$^1$H NMR (400 MHz, CD$_3$CN) δ 1.73-1.97 (m, 2 H) 2.18-2.26 (m, 2 H) 2.31-2.40 (m, 2 H) 3.40 (s, 3 H) 3.52 (s, 2 H). |
| 28.6 | spiro[3.3]1heptan-1-amine (commercially available from Frontier Scientific Services Inc.) and Hunig's base (commercially available from Sigma-Aldrich). | 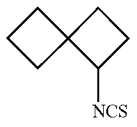<br>1-isothiocyanatospiro[3.3]heptanes.<br>$^1$H NMR (400 MHz, CD$_3$CN) δ 0.82-0.91 (m, 1 H) 1.24-1.34 (m, 1 H) 1.76-2.06 (m, 5 H) 2.17-2.26 (m, 1 H) 2.33-2.41 (m, 1 H) 3.85-3.90 (m, 1 H). |
| 28.7 | spiro[2.2]pentan-1-amine hydrochloride (commercially available from Enamine) and Hunig's base (commercially available from Sigma-Aldrich). | <br>1-isothiocyanatospiro[2.2]pentane.<br>$^1$H NMR (400 MHz, CD$_3$CN) δ 1.26-1.45 (m, 2 H) 0.96-1.08 (m, 2 H) 0.89-0.96 (m, 1 H). LCMS-ESI (pos.) m/z: 148.0 (M + Na)$^+$. |
| 28.8 | 1-(fluoromethyl)cyclopropanamine hydrochloride (commercially available from Wuxi AppTec.) and Hunig's base (commercially available from Sigma-Aldrich). | 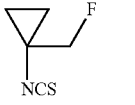<br>1-(fluoromethyl)-1-isothiocyanatocyclopropane.<br>$^1$H NMR (400 MHz, CDCl$_3$) δ 4.46 (d, J = 49.13 Hz, 1 H) 1.19-1.26 (m, 2 H) 1.02 (td, J = 6.74, 0.62 Hz, 2 H). |
| 28.9 | (R)-1-methoxy-2-propanamine, hydrochloride (commercially available from Combi-Blocks Inc.) and Hunig's base (commercially available from Sigma-Aldrich). | 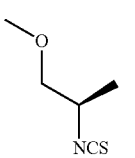<br>(R)-2-isothiocyanato-1-methoxypropane.<br>$^1$H NMR (400 MHz, CD$_3$CN) δ 4.03 (quind, J = 6.71, 6.71, 6.71, 6.71, 4.35 Hz, 1 H) 3.40-3.50 (m, 2 H) 3.37 (s, 3 H) 1.30 (d, J = 6.74 Hz, 3 H). |

TABLE 3-continued

| Example | Reagents | Structure, Name and Data |
|---|---|---|
| 28.10 | (S)-1-methoxy-2-propanamine, (commercially available from Sigma-Aldrich). | 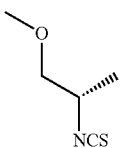<br>(S)-2-isothiocyanato-1-methoxypropane.<br>$^1$H NMR (400 MHz, CDCl$_3$) δ 1.33 (d, J = 6.74 Hz, 3 H) 3.42-3.46 (m, 5 H) 3.93 (sxt, J = 6.30 Hz, 1 H). |
| 28.11 | tetrahydro-4-methyl-2H-pyran-4-amine hydrochloride (commercially available from Synthonix Inc.) and Hunig's base (commercially available from Sigma-Aldrich). | 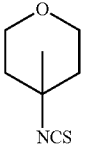<br>4-isothiocyanato-4-methyltetrahydro-2H-pyran.<br>$^1$H NMR (400 MHz, CDCl$_3$) δ .45 (s, 3 H) 1.66-1.81 (m, 4 H) 3.67 (td, J = 11.64, 2.64 Hz, 2 H) 3.81-3.87 (m, 2 H). |
| 28.12 | [1,1'-bi(cyclopropan)]-1-amine hydrochloride (commercially available from Enamine). | 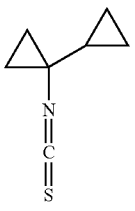<br>1-isothiocyanato-1,1'-bi(cyclopropane). $^1$H NMR (400 MHz, CD$_3$CN) δ 0.77-1.06 (m, 4 H) 1.22-1.40 (m, 4 H) 3.21 (dd, J = 6.63, 3.11 Hz, 1 H). LCMS-ESI (pos.) m/z: 148.0 (M + Na)$^+$. |

Example 29.0. Preparation of (1R,2S)-1-methoxy-1-(5-methylpyrimidin-2-yl)propane-2-sulfonamide

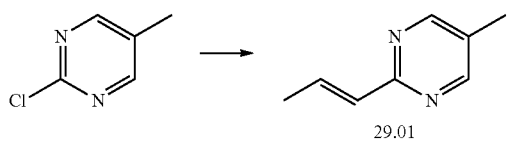

(E)-5-Methyl-2-(prop-1-en-1-yl)pyrimidine, Example 29.01

To a 500 mL round bottom flask was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with N$_2$ (5×) and then 1,4-dioxane (200 mL) and water (20 mL) were added. The resulting yellow suspension was bubbled with Ar for 15 min and then 1,1-bis[(di-t-butyl-p-methylaminophenyl]palladium(II) chloride (Amphos, commercially available from Strem, 2.64 g, 3.73 mmol) was added, a reflux condenser was attached, and the reaction was warmed to 90° C. in an oil bath and stirred under N$_2$ for 16.5 h. The reaction was then cooled to RT. The reaction was diluted with water (250 mL), and extracted with EtOAc (2×250 mL). The organic layers were combined, dried (MgSO$_4$), and concentrated. The residue was purified by flash chromatography on silica gel eluting with 0-20% EtOAc/hexanes) to afford (E)-5-methyl-2-(prop-1-en-1-yl)pyrimidine 29.01 (12.96 g, 97 mmol, 100% yield) as a yellow/orange oily solid. $^1$H NMR (300 MHz, CDCl$_3$) δ 8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). LCMS-ESI (pos.) m/z: 135.2 (M+H)$^+$.

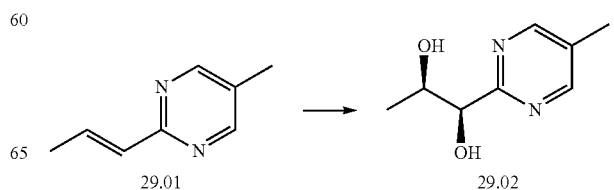

(1R,2R)-1-(5-Methylpyrimidin-2-yl)propane-1,2-diol, Example 29.02

Racemic conditions. To a solution of (E)-5-methyl-2-(prop-1-en-1-yl)pyrimidine, 29.01 (5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.111 mmol). The resulting reaction mixture was stirred at RT under $N_2$ for 21.5 h. LCMS showed complete conversion to a product corresponding to the mass of the desired product ($(M+H)^+$=169). The reaction was passed through a Varian Chem-Elut cartridge to remove water and concentrated in vacuo. Water was still present, and the residue was dissolved in DCM, dried ($MgSO_4$), and concentrated. The residue was purified by flash chromatography (120 g $SiO_2$, 0-10% MeOH/DCM) to give the racemic syn-diol (1S,2S)-1-(5-methylpyrimidin-2-yl)propane-1,2-diol and (2R,2R)-1-(5-methylpyrimidin-2-yl)propane-1,2-diol (5.85 g, 34.8 mmol, 81% yield) as a light yellow solid. $^1$H NMR (300 MHz, $CDCl_3$) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). LCMS-ESI (pos.) m/z: 169.2 (M+H). Chiral conditions. A batch of AD-mix-beta was prepared from: (26 mg, 0.07 mmol) $K_2OsO_2(OH)_4$; (16.4 g, 49.9 mmol) $K_3Fe(CN)_6$; (6.89 g, 49.9 mmol) $K_2CO_3$; and (125 mg, 0.16 mmol) $(DHQD)_2PHAL$. In a 50 mL round bottom flask was added t-BuOH (5 mL), water (5.00 mL), and 1.4 g of AD-mix-beta (prepared above) and methanesulfonamide (95 mg, 1.00 mmol). The mixture was stirred at RT until clear, and then cooled to 0° C. (E)-5-Methyl-2-(prop-1-en-1-yl)pyrimidine (intermediate 29.01 168 mg, 1 mmol) in t-BuOH (1 mL) was added, and the slurry was stirred at 0° C. for 2 h. LCMS (1.5 h) showed ~10% conversion. The reaction was allowed to warm slowly to RT as the ice bath melted and stirred an additional 22 h. LCMS showed ~90% conversion. The reaction was quenched with saturated aqueous sodium sulfite (10 mL), and extracted with EtOAc (2×20 mL). The combined organic layers were washed with 2 N NaOH (10 mL), dried ($MgSO_4$), and concentrated. The aqueous layer was extracted with DCM (2×50 mL), EtOAc (2×50 mL), and 10% IPA in $CHCl_3$ (2×50 mL). The combined organic layers were concentrated in vacuo and the residue purified by flash column chromatography (12 g $SiO_2$, 5-100% 3:1 EtOAc:EtOH/heptanes) to give (1R,2R)-1-(5-methylpyrimidin-2-yl)propane-1,2-diol (Example 29.02, 88.6 mg, 0.527 mmol, 52.7% yield) as a clear, colorless oil. Chiral Analysis: SFC Chiral Analysis showed the % ee to be 94.8% using an AS-H (100×2.1 mm, 3 um), 10% organic modifier (IPA with 20 mM ammonia), 90% carbon dioxide. F=1.0 mL/min, column temperature=RT, BRP=105 bar.

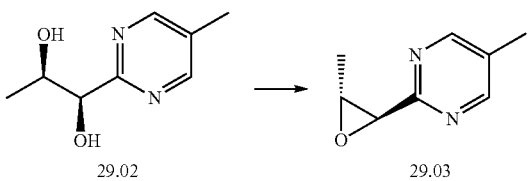

5-Methyl-2-((2R,3R)-3-methyloxiran-2-yl)pyrimidine, Example 29.03

To a solution of syn-diol (1R,2R)-1-(5-methylpyrimidin-2-yl)propane-1,2-diol 11.2 (1.46 g, 8.68 mmol) in DCM (25 mL) (cooled with a RT water bath) was added 1,1,1-trimethoxyethane (2.50 mL, 2.29 mmol). Chlorotrimethylsilane (2.50 mL, 19.7 mmol) was then added in 2 portions 5 min apart. The reaction had a small exotherm on the first portion of addition of TMSCl (23-28° C.). The reaction was stirred at RT under $N_2$ for 23 h. LCMS indicated incomplete conversion. Thus, an additional 1.25 equiv. of 1,1,1-trimethoxyethane (1.25 mL, 9.95 mmol) and chlorotrimethylsilane (1.25 mL, 9.85 mmol) were added, and the reaction was stirred for an additional d. The reaction was then concentrated in vacuo. The residue was dissolved in MeOH (20 mL), potassium carbonate (1.50 g, 10.85 mmol) was added and the reaction was stirred at RT for 4 h. LCMS (4 h) showed complete conversion to product corresponding to desired epoxide LCMS; ($(M+H)^+$=151). The reaction was filtered, the filter cake washed with DCM (5 mL), and the combined filtrates concentrated in vacuo. The residue was purified by flash column chromatography on silica gel eluting with 0-100% EtOAc/hexanes) to afford 5-methyl-2-((2R,3R)-3-methyloxiran-2-yl)pyrimidine 29.03 (1.00 g, 6.6 mmol, 77%) as a clear, light yellow oil. $^1$H NMR (300 MHz, $CDCl_3$) δ 8.54 (s, 2H), 3.81 (d, J=1.9 Hz, 1H), 3.32-3.53 (m, 1H), 2.31 (s, 3H), 1.50 (d, J=5.1 Hz, 3H). LCMS-ESI (pos.) m/z: 151.2 $(M+H)^+$.

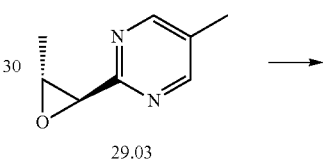

(1R,2S)-2-(Benzo[d]thiazol-2-ylthio)-1-(5-methylpyrimidin-2-yl)propan-1-ol, Example 29.04

To a solution of 5-methyl-2-((2R,3R)-3-methyloxiran-2-yl)pyrimidine 29.03 (250 mg, 1.33 mmol) in DCM (5 mL) was added benzo[d]thiazole-2-thiol (245 mg, 1.465 mmol), followed by tris(((trifluoromethyl)sulfonyl)oxy)ytterbium (83 mg, 0.133 mmol). The suspension was heated in a 35° C. heating block for 17 h and showed 100% conversion to the desired product. The reaction was cooled to RT, loaded on a plug of silica, and purified by flash chromatography (12 g $SiO_2$, 5-100% 3:1 EtOAc:EtOH/heptanes) to afford (1R,2S)-2-(benzo[d]thiazol-2-ylthio)-1-(5-methylpyrimidin-2-yl)propan-1-ol 29.04 (428 mg, 1.35 mmol, 100% yield) as a clear colorless oil. $^1$H NMR (300 MHz, $CDCl_3$) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). LCMS-ESI (pos.) m/z: 318.2 $(M+H)^+$.

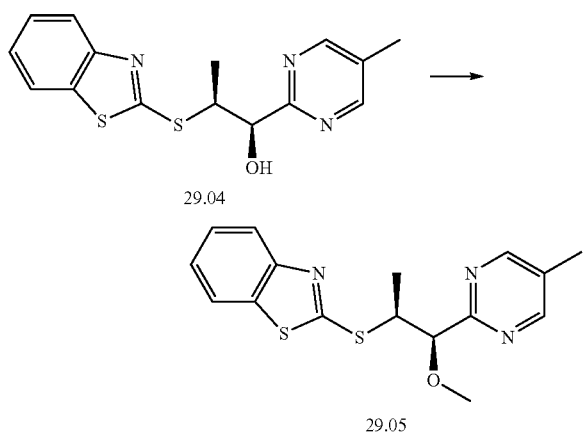

2-(((1R,2S)-1-Methoxy-1-(5-methylpyrimidin-2-yl)propan-2-yl)thio)benzo[d]thiazole, Example 29.05

To a 50 mL flask equipped with a magnetic stirrer was charged a (1R,2S)-2-(benzo[d]thiazol-2-ylthio)-1-(5-methylpyrimidin-2-yl)propan-1-ol 29.04 (350 mg, 1.103 mmol) in 2-methyltetrahydrofuran (1.1 mL). The reaction mixture was cooled to −78° C. and potassium bis(trimethylsilyl)amide (1M solution in THF, 1.32 μL, 1.32 mmol)) was added dropwise (total addition time: 2 min). The resulting mixture was stirred for 1 h and then MeOTf (374 μL, 3.31 mmol) was added dropwise. The reaction mixture was stirred at −78° C. for 15 min. LCMS showed complete conversion to the product. The reaction mixture was quenched by adding a saturated aqueous NH$_4$Cl solution (30 mL) at −78° C. The reaction was allowed to warm to RT and the aqueous layer was back extracted with EtOAc (3×75 mL). The combined organic layers were washed with brine, dried (Na$_2$SO$_4$), and concentrated. The material thus obtained was purified by chromatography through a Biotage 50 g ultra silica gel column, eluting with a gradient of 0-25% EtOAc in hexanes, to provide 2-(((1R,2S))-1-methoxy-1-(5-methylpyrimidin-2-yl)propan-2-yl)thio)benzo[d]thiazole 29.05 (0.32 g, 75% for two rims) as a light-yellow oil.

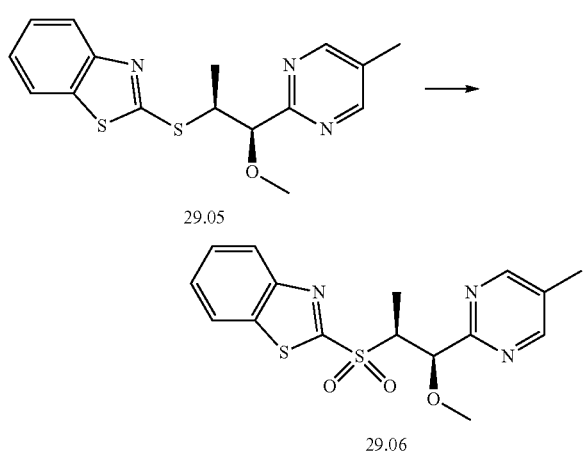

2-(((1R,2S)-1-Methoxy-1-(5-methylpyrimidin-2-yl)propan-2-yl)sulfonyl)benzo[d]thiazole, Example 29.06

A solution of Example 29.05 (313 mg, 0.94 mmol) in DCM (2.8 mL) at 0° C. was treated with 3-chloroperoxybenzoic acid, (77% max, 476 mg, 2.13 mmol). The reaction was stirred at 0° C. for 1 h before the ice bath was removed. LCMS showed desired product, sulfoxide, and the presumed sulfoxide/sulfone. The mixture was allowed to warm to ambient temperature and stirred for an additional 40 h. The reaction was quenched with saturated aqueous sodium bisulfite (6 mL), a saturated aqueous solution of sodium bicarbonate (5 mL), and was then stirred for 10 min. The reaction was extracted with EtOAc (2×20 mL) and the organic layers were combined, washed with a saturated aqueous NaHCO$_3$ solution (10 mL), brine (10 mL), dried (MgSO$_4$) and filtered. Iodide/starch strip indicator showed no peroxide present. The filtrates were concentrated to give a clear, colorless oil (360 mg). Purification of the residue by flash chromatography (40 g SiO$_2$, 0-100% 3:1 EtOAc:EtOH/heptanes) gave Example 29.06 (285 mg, 0.78 mmol, 83% yield, 77% purity) as a white foam. $^1$H NMR (300 MHz, CDCl$_3$) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). LCMS-ESI (pos.) m/z: 364.0 (M+H).

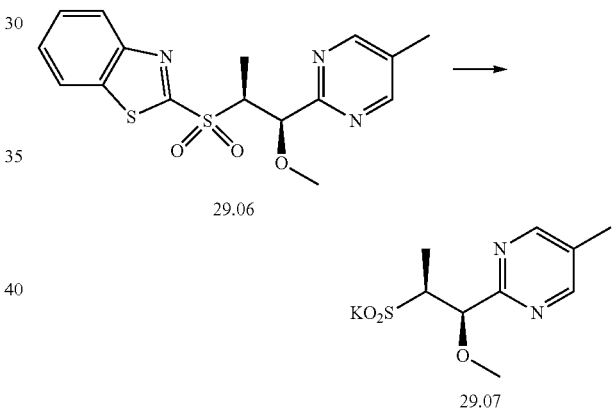

Potassium (1R,2S)-1-methoxy-1-(5-methylpyrimidin-2-yl)propane-2-sulfinate, Example 29.07

To a solution of Example 29.06 (268 mg, 0.74 mmol) in MeOH (1843 μL) was added potassium carbonate (204 mg, 1.48 mmol). The reaction was stirred at RT for 17 h. LCMS showed desired product formation as the sulfinic acid. LCMS ((M+H)$^+$=231.1). The reaction was concentrated in vacuo (yellow solid) and used directly in the following step. Note: Epimerization occurred in this reaction (~15%).

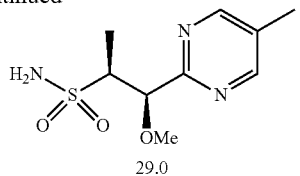

29.0

(1R,2S)-1-Methoxy-1-(5-methylpyrimidin-2-yl)propane-2-sulfonamide, Example 29.0

To a suspension of Example 29.07 (198 mg, 0.74 mmol) in water (3.7 mL) was added potassium acetate (72.4 mg, 0.74 mmol), followed by hydroxylamine-o-sulfonic acid, 97% (167 mg, 1.476 mmol). The reaction mixture was stirred at RT for 4.5 h. LCMS showed desired product formation plus a small peak that corresponded to the stereoisomer. The reaction mixture was extracted with EtOAc (2×) and the organic layers were combined, dried ($Na_2SO_4$), and concentrated in vacuo. The residue was loaded onto a silica gel column eluting with 0-30% (3:1 EtOAc:EtOH)/DCM to afford Example 29.0 (114 mg, 0.465 mmol, 63.0% yield) as a white solid. (contained ~15% other diastereomer). $^1$H NMR (300 MHz, $CDCl_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). LCMS-ESI (pos.) m/z: 246.1 (M+H)$^+$.

The compounds set forth in the following table were synthesized following the procedure in Example 29.0 using the known starting material as described.

TABLE 4

| Example | Reagents | Structure, Name and Data |
|---|---|---|
| 29.1 | 2-bromo-5-methyl pyrazine (commercially available from NOWA pharmaceuticals). | (1R,2S)-1-methoxy-1-(5-methylpyrazin-2-yl)propane-2-sulfonamide. LCMS-ESI (pos.) m/z: 246.2 (M + H)$^+$. |
| 29.2 | 2-chloro-5-fluoropyrimidine (commercially available from Oakwood). | (1R,2S)-1-(5-fluoropyrimidin-2-yl)-1-methoxypropane-2-sulfonamide. LCMS-ESI (pos.) m/z: 250.1 (M + H)$^+$. |
| 29.3 | 2,5-dichloropyrimidine (commercially available from Oakwood). | (1R,2S)-1-(5-chloropyrimidin-2-yl)-1-methoxypropane-2-sulfonamide. LCMS-ESI (pos.) m/z: 265.9 (M + H)$^+$. |
| 29.4 | 2-chloropyrimidine (commercially available from Acros Organics). | (1R,2S)-1-methoxy-1-(pyrimidin-2-yl)propane-2-sulfonamide. LCMS-ESI (pos.) m/z: 232.0 (M + H)$^+$. |

TABLE 4-continued

| Example | Reagents | Structure, Name and Data |
|---|---|---|
| 29.5 | 2-chloro-5-fluoropyrimidine (commercially available from Oakwood). EtOTf used in place of MeOTf in Example 29.5. | 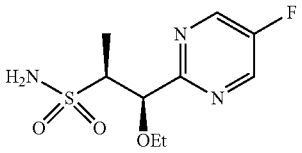<br>(1R,2S)-1-ethoxy-1-(5-fluoropyrimidin-2-yl)propane-2-sulfonamide.<br>LCMS-ESI (pos.) m/z: 264.0 (M + H)$^+$. |
| 29.6 | 2-chloro-5-fluoropyrimidine (commercially available from Oakwood). TBSOTf used in place of MeOTf in Example 29.5. | 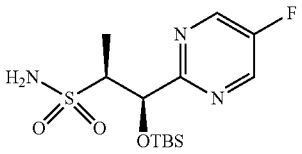<br>(1R,2S)-1-((tert-butyldimethylsilyl)oxy)-1-(5-fluoropyrimidin-2-yl)propane-2-sulfonamide.<br>LCMS-ESI (pos.) m/z: 350.1 (M + H)$^+$. |
| 29.7 | 2,5-dichloropyrimidine (commercially available from Oakwood), EtOTf used in place of MeOTf in Example 29.05. | 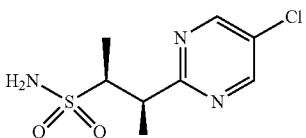<br>(1R,2S)-1-(5-chloropyrimidin-2-yl)-1-ethoxypropane-2-sulfonamide.<br>LCMS-ESI (pos.) m/z: 279.9. |
| 29.9 | 2-bromo-5-methoxypyrazine (Manchester). | 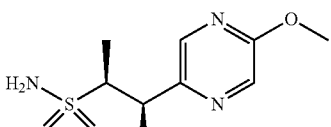<br>(1R,2S)-1-methoxy-1-(5-methoxypyrazin-2-yl)propane-2-sulfonamide.<br>LCMS-ESI (pos.) m/z: 262.2 (M + H)$^+$. |

Example 29.8. Preparation of Example (1R,2S)-1-methoxy-1-(5-methoxypyrimidin-2-yl)propane-2-sulfonamide

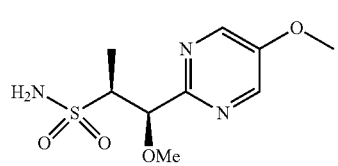

(1R,2S)-1-Methoxy-1-(5-methoxypyrimidin-2-yl)propane-2-sulfonamide, Example 29.8

The title compound was obtained as a by-product of the synthesis of (1R,2S)-1-methoxy-1-(5-fluoropyrimidin-2-yl)propane-2-sulfonamide (Example 29.2) during step 29.07 and isolated in the final step of the synthesis of Example 29.2 to give the title compound 29.8 (240 mg, 10.2% yield) as a white solid. $^1$H NMR (CDCl$_3$) δ 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (pos.) m/z: 284.1 (M+Na)$^+$.

Example 30.0. Preparation of N,N-bis(4-methoxybenzyl)ethanesulfonamide

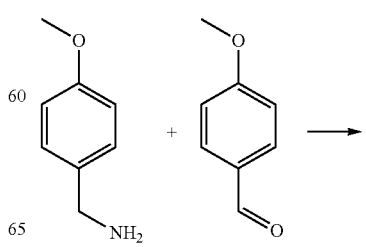

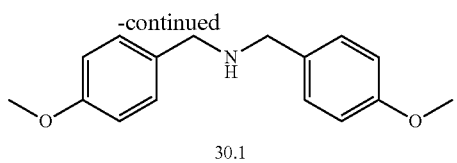

Bis(4-methoxybenzyl)amine, Example 30.1

4-Methoxybenzylamine (neat, 600 g, 4.37 mol, 1 eq) and 4-methoxybenzaldehyde (532 mL, 4.37 mol, 1 eq) were added to a 10 L round bottom flask at ambient temperature with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portion wise over ~2 h (Note: During the addition of NaBH$_4$, the internal temperature of the reaction rose to 42° C.) and further stirred at RT overnight. The reaction was quenched slowly with water (600 mL). The mixture was concentrated in vacuo at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give bis(4-methoxybenzyl) amine 30.1 (1112 g, 99% yield) as a semi-solid. The material was used directly in the next step without further purification. $^1$H-NMR (400 MHz, CDCl$_3$) δ 7.28 (t, J=7.12 Hz, 4H), 6.89 (d, J=8.60 Hz, 4H), 3.83 (m, 6H), 3.76 (s, 4H) (—NH proton not observed). LCMS-ESI (pos.) m/z: 258.4 (M+H)$^+$.

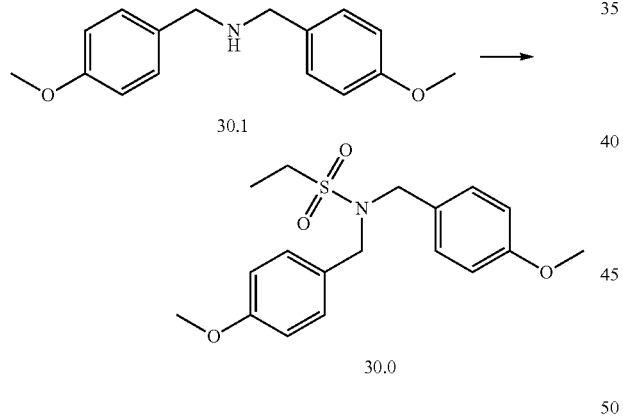

N,N-Bis(4-methoxybenzyl)ethanesulfonamide, Example 30.0

To a solution of bis(4-methoxybenzyl)amine 30.1 (900 g, 3.49 mol, 1 eq) in DCM (9 L) was added TEA (634 mL, 4.55 mol, 1.3 eq), followed by dropwise addition of ethanesulfonyl chloride (399 mL, 4.19 mol, 1.2 eq). (The internal temperature was kept between 5-10° C. during the addition of the ethane sulfonyl chloride). Once the addition was complete, the cooling bath was removed. After 1.5 h, TLC showed complete loss of starting material. The reaction was quenched by the addition of water (4 L) to the reaction mixture. The layers were separated and the aqueous layer was extracted with DCM (2×2 L). The combined organic layers were washed with brine (2×1 L), dried over Na$_2$SO$_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound 30.0 (1125 g, 3.22 mol, 92%) as a white solid. $^1$H-NMR (400 MHz, CDCl$_3$) δ 7.23 (dd, J=2.08, 6.62 Hz, 4H), 6.90 (dd, J=2.12, 6.60 Hz, 4H), 4.29 (s, 4H), 3.83 (m, 6H), 2.92 (q, J=7.40 Hz, 2H), 1.33 (t, J=7.40 Hz, 3H). GC-LCMS (ESI pos. ion) m/z: =372.2 (M+Na)+.

Example 31.0: Preparation of (1S,2S)-1-isopropoxy-1-(5-methylpyrimidin-2-yl)propane-2-sulfonamide

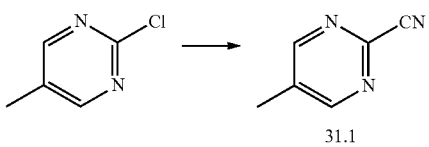

5-Methylpyrimidine-2-carbonitrile, Example 31.1

A solution of 2-chloro-5-methylpyrimidine (500 g, 3889 mmol, 1.0 equiv) in DMF (5 L) was degassed with N$_2$ for 20 min and dppf (108 g, 194 mmol, 0.05 equiv) and Pd$_2$(dba)$_3$ (178 g, 194 mmol, 0.05 equiv) were added to the reaction mixture. Zn(CN)$_2$ (685 g, 5834 mmol, 1.5 equiv) was added, and the reaction mixture was heated at 100° C. for 16h. The reaction was quenched with water (5 L) and stirred for 10 min. The reaction mixture was filtered through a Celite® brand filter aid pad. Filtrate was diluted with water (4 L) and extracted with EtOAc (2×4 L). The combined organic layers were washed with brine (4 L), dried over Na$_2$SO$_4$, filtered and concentrated under reduced pressure to give the initial product which was further purified by column chromatography using silica gel (60-120 mesh) and 0-10% EtOAc in hexanes to obtain Example 31.1 (330 g, 71%) as an off white solid. $^1$H NMR (400 MHz, DMSO-d$_6$) δ 8.89 (s, 2H), 2.39 (s, 3H).

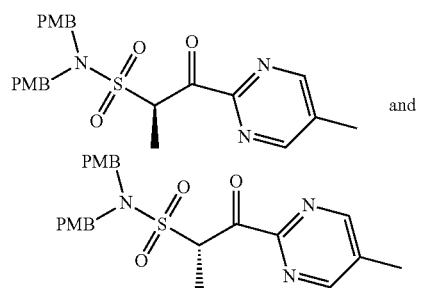

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 31.2

A solution of Example 30.0 (293 g, 839 mmol, 2.0 equiv) in THF (2 L) was added isopropylmagnesium chloride (420 mL, 839 mmol, 2.0 equiv, 2.0 M in diethyl ether) at 0° C.

The reaction mixture was stirred at RT for 3 h. To the reaction mixture was added 5-methylpyrimidine-2-carbonitrile (50 g, 420 mmol, 1.0 equiv) in THF (100 mL) at 0° C. The resulting mixture was stirred at RT for 2h. The reaction was quenched with 1.5 N HCl (500 mL) and water (2 L) and stirred for 10 min. The mixture was extracted with EtOAc (2×1 L) and the combined organic layers were washed with brine (500 mL), dried over Na$_2$SO$_4$ and filtered. The organic layer was concentrated under reduced pressure to give the initial compound which was purified by column chromatography using silica gel (100-200 mesh) and 0-50% EtOAc in hexanes as eluent providing Example 31.2 (60 g, 30% yield) as a brown liquid. $^1$H NMR (400 MHz, DMSO-d$_6$) δ 8.90 (s, 2H), 7.15-7.09 (m, 4H), 6.85-6.80 (m, 4H), 4.34-4.18 (m, 5H), 3.71 (m, 6H), 2.39 (s, 3H), 1.50 (d, J=6.9 Hz, 3H). LCMS-ESI (pos.) m/z: (M+H)+: 470.0.

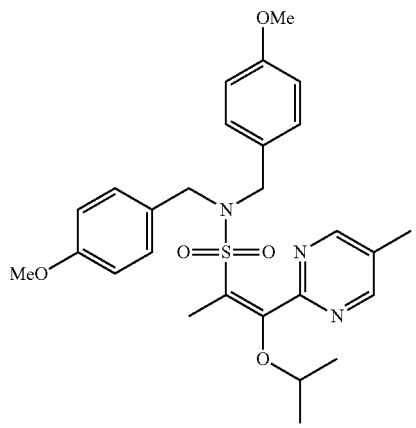

31.3

(E)-1-Isopropoxy-N,N-bis(4-methoxybenzyl)-1-(5-methylpyrimidin-2-yl)prop-1-ene-2-sulfonamide, Example 31.3

To a solution of Example 31.2 (120 g, 256 mmol, 1.0 equiv) in DMF (1.2 L) was added 2-iodopropane (129 mL, 1278 mmol, 5.0 equiv) and potassium carbonate (70.6 g, 511 mmol, 2.0 equiv). The reaction mixture was then stirred at 60° C. for 14 h. The reaction was quenched with water (1 L), stirred for 10 min and extracted with EtOAc (2×1 L). The combined organic layers were washed with brine (1 L), dried over Na$_2$aSO$_4$, filtered and concentrated under reduced pressure to give the initial material. The initial product was purified by column chromatography using silica gel (100-200 mesh) and 0-50% EtOAc in hexanes as eluent providing Example 31.3 (75 g, 57.4% yield) as an off white solid. $^1$H NMR (400 MHz, DMSO-d$_6$) δ 8.72 (s, 2H), 7.09 (d, J=8.3 Hz, 4H), 6.86 (d, J=8.3 Hz, 4H), 4.16 (s, 4H), 3.73 (s, 3H), 3.73 (s, 3H), 3.71-3.67 (m, 1H), 2.31 (s, 3H), 1.87 (s, 3H), 1.19-1.16 (m, 6H). LCMS-ESI (pos.) m/z: (M+H)$^+$: 512.1.

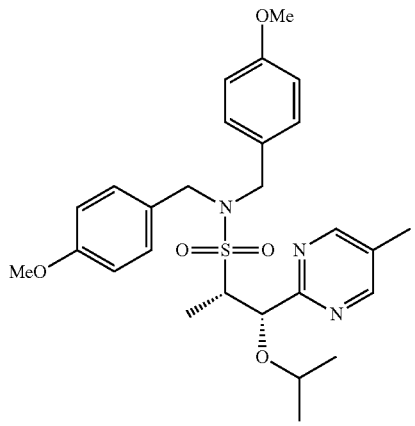

31.4

(1S,2R)-1-Isopropoxy-N,N-bis(4-methoxybenzyl)-1-(5-methylpyrimidin-2-yl)propane-2-sulfonamide, Example 31.4. To a solution of Example 31.3

(180 g, 352 mmol, 1.0 equiv) in MeOH (1800 mL) were added zinc triflate (256 g, 704 mmol, 2.0 equiv) and (S)—RuCl[(p-cymene(BINAP)]Cl (6.54 g, 7.04 mmol, 0.02 equiv). The resulting mixture was heated at 60° C. under H$_2$ pressure (60 psi) for 16 h. The reaction mixture was then concentrated in vacuo to obtain the initial product which was further purified by column chromatography using silica gel (60-120 mesh) and 0-50% EtOAc in DCM as eluent to obtain Example 31.4 (140 g, 77%, 92% ee) as an off white solid. $^1$H NMR (400 MHz, DMSO-d$_6$) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (m, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). LCMS-ESI (pos.) m/z: (M+H)+: 514.2.

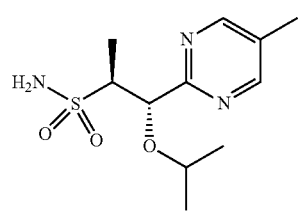

31.0

(1S,2S)-1-Isopropoxy-1-(5-methylpyrimidin-2-yl)propane-2-sulfonamide, Example 31.0

To a solution of Example 31.4 (140.0 g, 273 mmol, 1.0 equiv) in DCM (500 mL) was added TFA (250 mL) at 0° C., and the resulting reaction mixture was allowed to stir at RT for 16 h. The reaction mixture was then concentrated in vacuo to obtain the initial material which was dissolved in DCM (1 L) and washed with a saturated aqueous NaHCO$_3$ solution (1 L). The organic layer was dried over Na$_2$SO$_4$, filtered and concentrated under reduced pressure to obtain the initial material which was further purified by column chromatography using silica gel (60-120 mesh) and 0-2% MeOH in DCM to obtain Example 31.0 (72 g, 97% yield, 90% ee) as an off white solid. Example 31.0 (72 g, 90% ee) was suspended in IPA (500 mL) and heated to 70° C. until the mixture become homogeneous. Once the solution became homogeneous, the mixture was cooled to RT overnight. The white solid thus obtained was filtered, dried under vacuum to obtain Example 31.0 (30 g, >99%). The mother liquor was concentrated and the solid obtained was recrystallized again following the same procedure. $^1$H NMR (400 MHz, DMSO-d$_6$) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). LCMS-ESI (pos.) m/z: (M+H)+: 274.1.

The compounds in the following table were synthesized following the procedure in Example 31.0 using the known starting material as described.

TABLE 5

| Example | Reagents | Structure, Name and Data |
|---|---|---|
| 31.01 | 2-chloro-5-chloro-pyrimidine. | 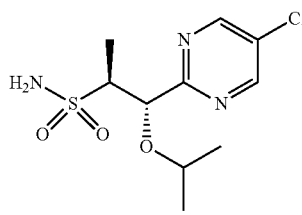<br>(1S,2S)-1-(5-chloropyrimidin-2-yl)-1-isopropoxypropane-2-sulfonamide.<br>LCMS ESI (pos.) m/z: 234.2 (M + H)+. |
| 31.02 | 2-chloro-5-methylpyrazine. | 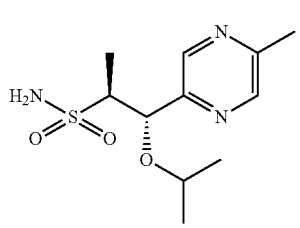<br>(1S,2S)-1-isopropoxy-1-(5-methylpyrazin-2-yl)propane-2-sulfonamide.<br>LCMS ESI (pos.) m/z: 274.1 (M + H)+. |

Example 32.0. Preparation of (2S,3R)-3-(5-chloropyridin-2-yl)butane-2-sulfonamide

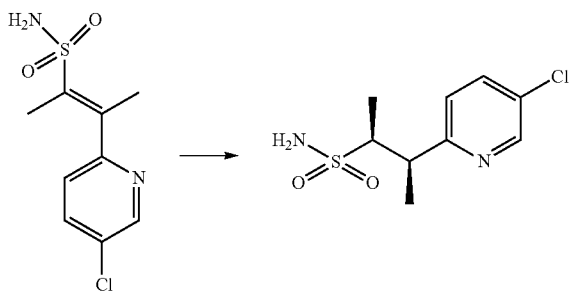

(2S,3R)-3-(5-Chloropyridin-2-yl)butane-2-sulfonamide, Example 32.0

To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1,5-cyclooctadiene)rhodium(I) tetrafluroborate (0.329 g, 0.811 mmol) and (S)-1-[(R)-2-(Di-1-naphthylphosphino)ferrocenyl]-ethyl-di-tert-butylphosphine (0.651 g, 1.013 mmol). The reaction mixture was degassed with argon and hydrogen three times followed by addition of hydrogen. The mixture was then stirred under hydrogen (50 Psi) in a 200 mL Mini-clave at RT for 16 h and then was heated at 65° C. for 16 h. The reaction was concentrated under reduced pressure providing the initial product which was purified by column chromatography (silica gel 60-120 mesh) using 40-45% of EtOAc in petroleum ether as an eluent to obtain the desired product Example 32.0 (9 g, 36.2 mmol, 89%) as a brownish solid in 82% ee. Recrystallization from i-PrOH yielded >97% ee material. 1H NMR (400 MHz, DMSO-d$_6$) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (pos.) m/z: 249.0 (M+H)+.

Example 33.0. Preparation of (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide

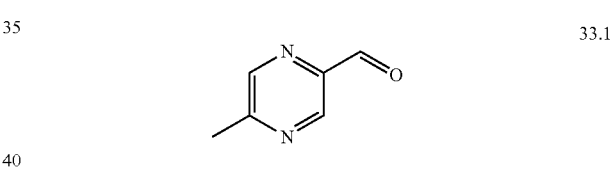

5-Methylpyrazine-2-carbaldehyde, Example 33.1

A solution of lithium aluminum hydride (164.0 mL, 0.164 mol, 1.0 M in THF, 0.5 equiv.) was added to a suspension of methyl 5-methylpyrazine-2-carboxylate (50 g, 0.328 mol, 1.0 equiv.) in anhydrous THF (750 mL) at −78° C. The internal temperature was kept below −72° C. during the addition of lithium aluminum hydride. On completion of addition, the reaction mixture was stirred at −78° C. for a further 20 min and then quenched with glacial AcOH (50.0 mL) at the same temperature. The resulting mixture was warmed to RT and the volatiles were removed by evaporation under vacuum. The residue was dissolved in hydrochloric acid (1.5 N, 500 mL) and extracted with DCM (2×2 L). The combined organic layers were washed with a saturated aqueous sodium hydrogen carbonate solution (2×500 mL), dried over anhydrous Na$_2$SO$_4$, and concentrated in vacuo to yield a brown oil. The initial product was purified by column chromatography (silica gel 60-120 mesh) eluting with a gradient of 10% EtOAc in petroleum ether to provide the title compound as a pale yellow liquid (21.3 g, 53%). TLC Info: (9.0/1.0 Petroleum ether/EtOAc). $^1$H NMR (400 MHz, CDCl$_3$) δ 10.14 (s, 1H), 9.07 (d, J=1.5 Hz, 1H), 8.63 (d, J=1.4 Hz, 1H), and 2.70 (s, 3H). LCMS-ESI (pos.) m/z: 123 (M+H)+.

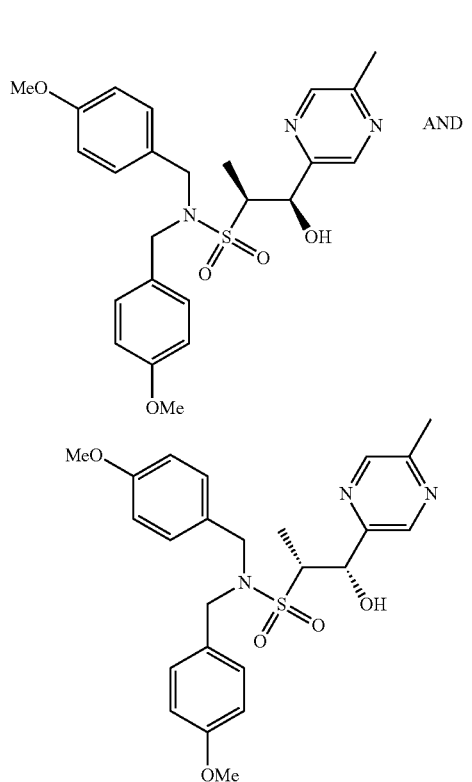

33.2

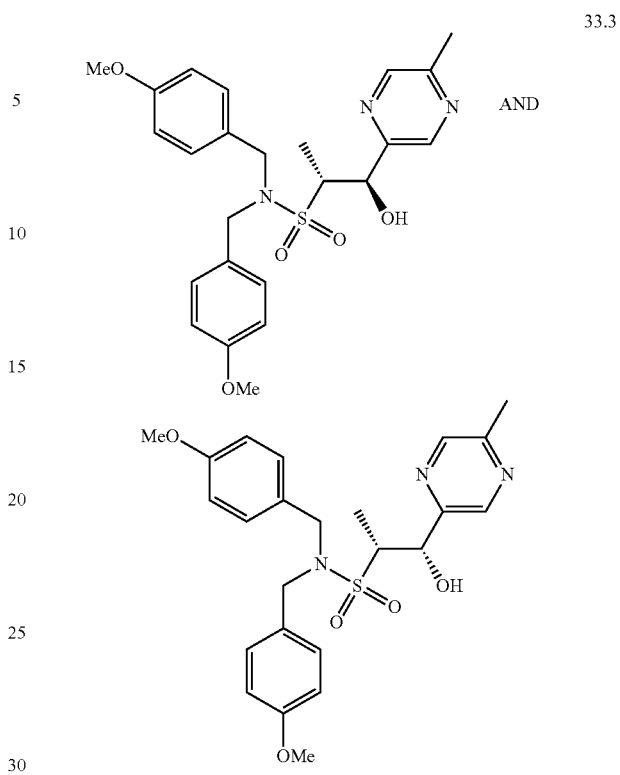

33.3

(1R,2S)-1-Hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide, Example 33.2

(1S,2S)-1-Hydroxy-N,N-bis(4-methoxybenzyl)-1-(5-methyl-pyrazin-2-yl)propane-2-sulfonamide and (1R,2R)-1-hydroxy-N,N-bis(4-methoxybenzyl)-1-(5-methyl-pyrazin-2-yl)propane-2-sulfonamide, Example 33.3

To a solution of N,N-bis(4-methoxybenzyl)ethanesulfonamide (Example 12.0, 73.13 g, 0.209 mol, 1.2 equiv.) in anhydrous THF (600 mL) at −78° C. was added n-butyl lithium (83.71 mL, 0.209 mol, 2.5 M solution in hexanes, 1.2 equiv.) via additional funnel slowly, and the resulting mixture was stirred for 10 min. A solution of 5-methylpyrazine-2-carbaldehyde (Example 33.1, 21.3 g, 0.174 mol, 1.0 equiv.) in anhydrous THF (150 mL) was then added, and the resulting mixture was stirred at the same temperature for 45 min and allowed to warm to RT for 2 h. The reaction mixture was quenched by addition of an aqueous ammonium chloride solution (200 mL) and extracted with EtOAc (2×2 L). The combined organic layers were washed with brine (2×500 mL). After drying over anhydrous $Na_2SO_4$, the filtrate was concentrated in vacuo, to afford an oil. The oil thus obtained was purified by flash column chromatography (silica gel, 230-400 mesh) to afford the two isomers. The faster moving isomer (32 g as white solid) was obtained from the column with a gradient of 10% to 30% EtOAc in petroleum ether. $^1$H NMR (400 MHz, DMSO-$d_6$) δ 8.61 (d, J=1.5 Hz, 1H), 8.51 (d, J=1.5 Hz, 1H), 7.22-7.11 (m, 4H), 6.90-6.80 (m, 4H), 6.10 (d, J=5.9 Hz, 1H), 5.29 (dd, J=5.9, 2.2 Hz, 1H), 4.36-4.16 (m, 4H), 3.73 (m, 6H), 3.70-3.66 (m, 1H) 2.50 (merged with solvent peak, 3H) and 1.10 (d, J=7.0 Hz, 3H). LCMS-ESI (pos.) m/z: 472.4 (M+H)$^+$.

Further elution of the mixture with a gradient of 30% to 35% EtOAc in petroleum ether yielded Example 33.3 (16 g, pale yellow gummy liquid). $^1$H NMR (400 MHz, CDCl$_3$) δ 8.62 (d, J=1.6 Hz, 1H), 8.44 (d, J=1.5 Hz, 1H), 7.25-7.12 (m, 4H), 6.93-6.82 (m, 4H), 5.17 (d, J=7.1 Hz, 1H), 4.47 (d, J=15.2 Hz, 3H), 4.14 (d, J=15.4 Hz, 2H), 3.82 (s, 3H), 3.82 (s, 3H), 3.66-3.61 (m, 1H), 2.60 (d, J=2.0 Hz, 3H), and 1.08 (dd, J=7.2, 2.1 Hz, 3H). LCMS (ESI positive ion) m/z: 472.4 (M+H)$^+$.

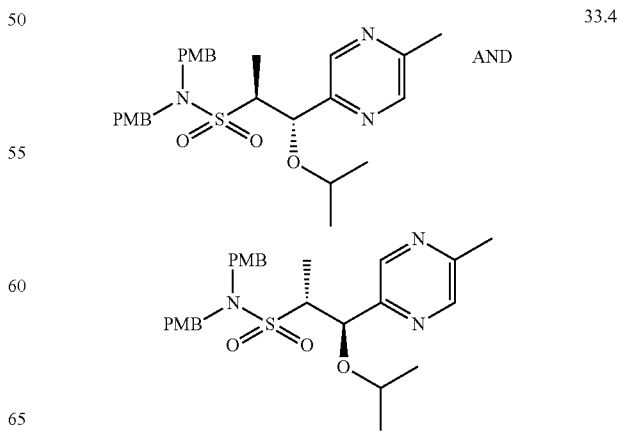

33.4

(1S,2S)-1-Isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide, Example 33.4

To a flask containing Example 33.3 (4.16 g, 8.81 mmol) and isopropyl iodide (12.3 mL, 123 mmol) in anhydrous toluene (35 mL) was added silver(I) oxide (4.17 g, 18.0 mmol) carefully in portions. Upon complete addition of silver oxide, the reaction was protected from light and heated to an internal temperature of 72° C. After 60 h, the mixture was cooled to RT and then filtered through a Chemglass disposable filter that was rinsed with EtOAc. The filtrate was concentrated in vacuo. The dark brown residue was loaded onto a silica gel column (10-55% EtOAc in heptanes). Fractions containing the product were combined and then concentrated under reduced pressure to afford Example 33.4 (1.52 g, 2.97 mmol, 34% yield) as a dark brown oil that was used without further purification. $^1$H NMR (400 MHz, DMSO-$d_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). LCMS-ESI (pos.), m/z: 514.0 (M+H)$^+$.

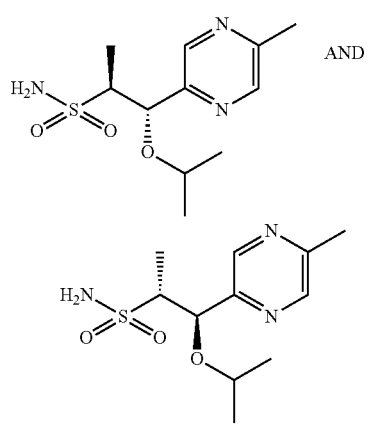

33.5 AND

(1R,2R)-1-Isopropoxy-1-(5-methylpyrazin-2-yl)propane-2-sulfonamide and (1S,2S)-1-isopropoxy-1-(5-methylpyrazin-2-yl)propane-2-sulfonamide, Example 33.5

Anisole (1.3 mL, 11.9 mmol) was added to a flask containing Example 33.4 (1.5 g, 3 mmol) and DCM (7.5 mL). The homogeneous solution was cooled in an ice-water bath. After 15 minutes, TFA (7.6 mL, 99 mmol) was added dropwise to the reaction solution. Upon complete addition of TFA, the reaction was allowed to warm to RT. After 20 h, the brownish reaction solution was concentrated in vacuo. The residue was loaded onto a silica gel column (15-85% EtOAc in heptanes). Fractions containing the product were concentrated under reduced pressure to afford Example 33.5 (714 mg, 2.6 mmol, 88% yield) as an off white solid. LCMS-ESI (pos.), m/z: 224.0 (M+H).

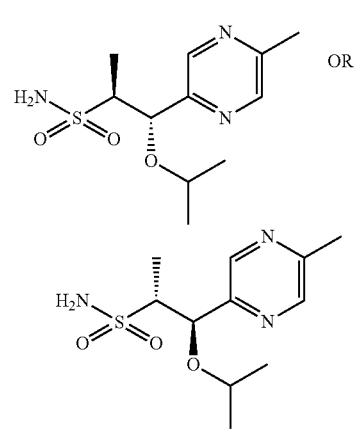

33.6

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide, Example 33.6

Example 33.5 (714 mg, 2.6 mmol) was purified by preparative SFC method: Column: IC (2×25 cm) Mobile Phase: 70:30 (A:B) A: Liquid CO$_2$, B: IPA to afford peak 1 as Example 33.6 (293 mg, 1.07 mmol, 36% yield). $^1$H NMR (400 MHz, DMSO-$d_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured CH$_3$ in DMSO peak). LCMS-ESI (pos.), m/z: 274.2 (M+H)$^+$.

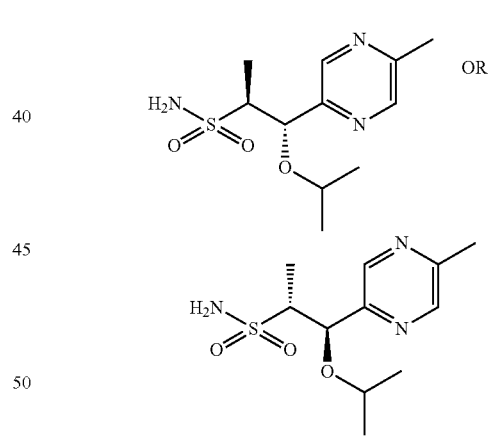

33.0

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide Example 33.0

Further elution under the conditions described in Example 33.6 delivered the second eluting peak as Example 33.0 (303 mg, 1.11 mmol, 37% yield). $^1$H NMR (400 MHz, DMSO-$d_6$) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured CH$_3$ in DMSO peak). LCMS-ESI (pos.), m/z: 274.2 (M+H)$^+$.

Example 34.0. Preparation of (1R,2S)-1-((tert-butyldimethylsilyl)oxy)-N,N-bis(4-methoxybenzyl)-1-(5-methylpyrimidin-2-yl)propane-2-sulfonamide

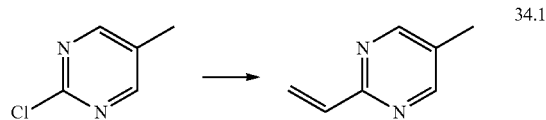

5-Methyl-2-vinylpyrimidine, Example 34.1

A 3 L 3-necked round bottom flask was fitted with a reflux condenser, a temperature controller and a septum and then charged with 2-chloro-5-methylpyrimidine (81 mL, 778 mmol), potassium vinyltrifluoroborate (156 g, 1167 mmol), triphenylphosphine (18.02 mL, 78 mmol), cesium carbonate (156 mL, 1945 mmol) and a large stir bar. Water (1.6 L) was added and the mixture was stirred for several min and then THF (244 mL) was added. Argon was bubbled through the mixture for 5 min and then palladium (II) chloride (1.72 g, 38.9 mmol) was added. The reaction was further sparged with argon for 5 min. The temperature was raised to 62° C. and stirring was continued to completion. The reaction was then cooled to RT and filtered through two Whatman GF/F filter cups, rinsing with ether. The mixture was transferred to a separatory funnel and the layers were separated. The aqueous layer was further extracted with diethyl ether (4×200 mL). The organic layers were combined and dried over anhydrous MgSO$_4$ and then filtered. The mixture was partially concentrated on the rotory evaporator at 20° C. and 115 torr for an extended period of time to give an orange liquid. The material was further purified by Kugelrohr distillation to provide the title compound (65.4 g, 70%) as a light yellow oil. $^1$H NMR (400 MHz, CDCl$_3$) δ 2.31 (s, 3H), 5.68 (d, J=10.56 Hz, 1H), 6.55 (d, J=17.22 Hz, 1H), 6.86 (dd, J=17.41, 10.56 Hz, 1H), 8.54 (s, 2H). LCMS-ESI (pos.) m/z: 121.1 (M+H)$^+$.

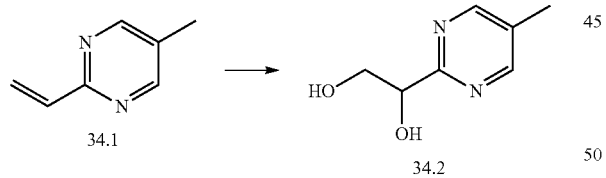

1-(5-Methylpyrimidin-2-yl)ethane-1,2-diol, Example 34.2

To a 2 L round-bottom flask was added 5-methyl-2-vinylpyrimidine (64.5 g, 537 mmol), osmium tetroxide (0.204 mL, 3.93 mmol), 1,4-dioxane (537 mL, 537 mmol), 4-methylmorpholine-N-oxide, 50% wt. in water (40 mL, 341 mmol) and 4-methylmorpholine-4-oxide (94 g, 805 mmol). The reaction mixture was stirred over 2 d. LCMS showed that the reaction was complete and the solvent was then removed in vacuo. The compound was purified by silica gel. The gradient was 100% heptanes for 3 CV's, then 0-100% EtOAc-EtOH(3:1) in heptanes for 6 CV's, then 100% EtOAc:EtOH(3:1) for 5 CV's. The desired compound was collected and concentrated in vacuo. The material was triturated with 40% EtOAc in hexanes to give a solid which was collected by filtration. The solid was washed with 20% EtOAc in hexanes several times and then dried to give the title compound (67.3 g). $^1$H NMR (400 MHz, CDCl$_3$) δ 8.59 (s, 2H), 4.81-4.98 (m, 1H), 3.88-4.19 (m, 2H), 2.36 (s, 3H).

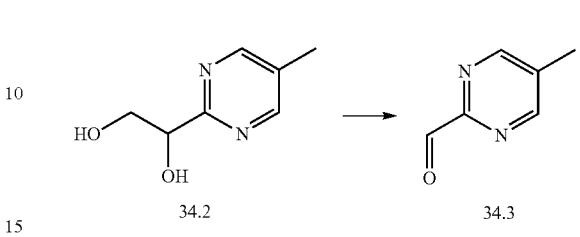

5-Methylpyrimidine-2-carbaldehyde, Example 34.3

A 5 L flask equipped with a mechanical stirrer was charged with 1-(5-methylpyrimidin-2-yl)ethane-1,2-diol (64.3 g, 417 mmol), 1,4-dioxane (1043 mL) and water (261 mL). The reaction was cooled in an ice-water bath. Sodium periodate (223 g, 1043 mmol) was added and the internal temperature was monitored until it returned to RT. The reaction was further stirred at RT for 2 hr and 20 min. DCM (2 L) was then added. The resulting solution was filtered through a plug of dried MgSO$_4$ (700 g). The plug was washed with DCM (7 L). The solvent was concentrated in vacuo and the aldehyde was azeotroped with toluene to deliver the title compound (44 g) as a white solid. LCMS-ESI (pos.) m/z: 122.8 (M+H)$^+$.

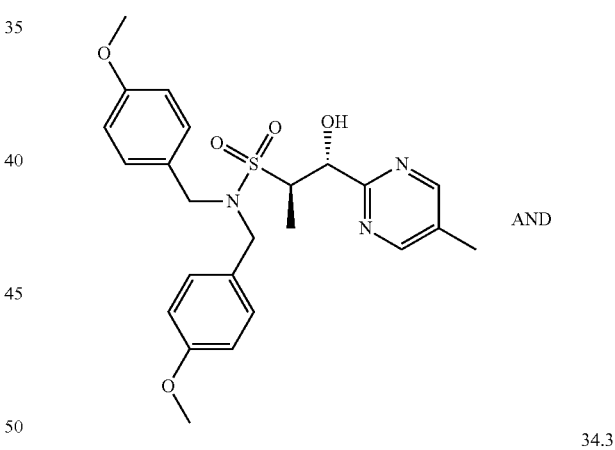

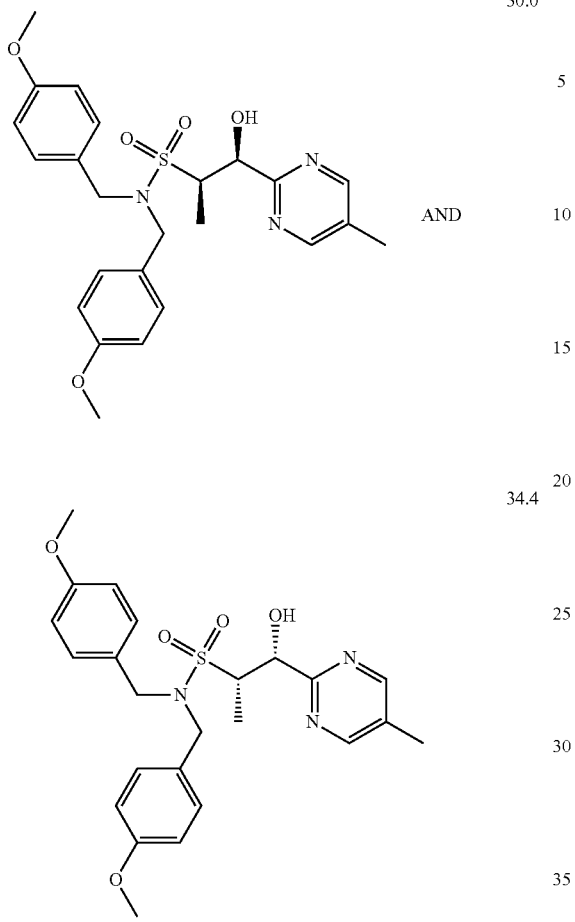

(1R,2S)-1-Hydroxy-N,N-bis(4-methoxybenzyl)-1-(5-methylpyrimidin-2-yl)propane-2-sulfonamide and (1S,2S)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide
Example 34.4

A 3 L flask was charged with N,N-bis(4-methoxybenzyl) ethanesulfonamide (Example 30.0, 151 g, 432 mmol) and anhydrous THF (1.2 L) under nitrogen and then equipped with a pre-dried addition funnel under nitrogen. The flask was cooled in a dry ice-acetone bath. n-Butyl-lithium (1.6 M, 270 mL, 432 mmol) was first cannulated into the additional funnel and then it was added slowly into the reaction flask and the mixture was stirred for 10 min. 5-Methylpyrimidine-2-carbaldehyde (34.3, 44 g, 360 mmol) in THF (300 mL) was then cannulated into the reaction. The reaction continued at −78° C. for 45 min and then was warmed to RT and stirring was continued for 2 h and 10 min. A saturated solution of ammonium chloride was added to quench the reaction and the mixture was extracted with EtOAc and concentrated in vacuo to give the product.

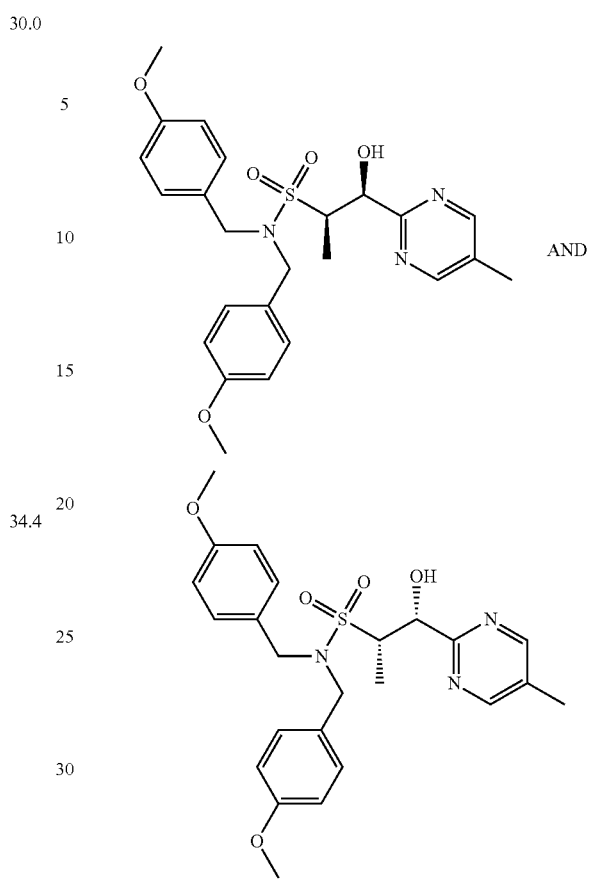

(1R,2S)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide,
Example 34.5

The mixture of diastereomers was separated and purified on silica gel eluting with 0-50% EtOAc gradient in DCM to give the title compound (56.4 g). LCMS-ESI (pos.) m/z: 472.1 (M+H)+.

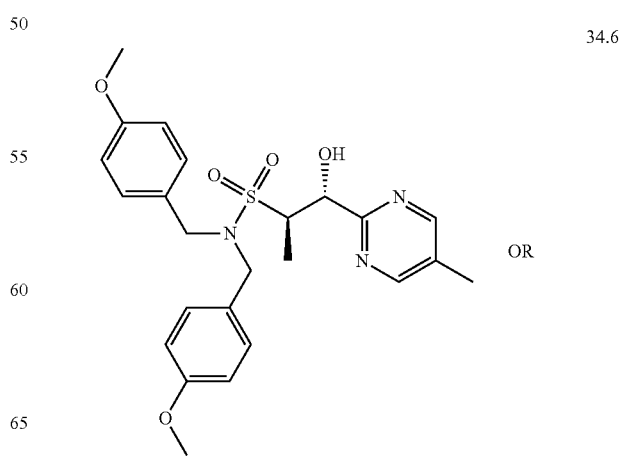

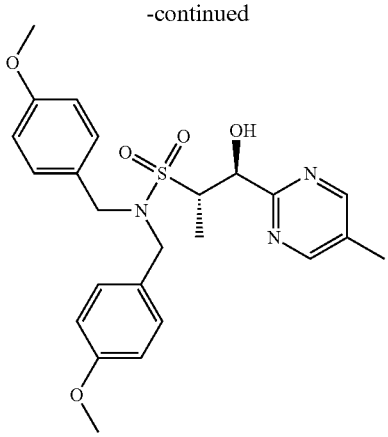

(1S,2S)-1-Hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide Example 34.6

Further elution under the conditions described in Example 34.5 delivered the title compound. LCMS-ESI (pos.) m/z: 472.1 (M+H)$^+$.

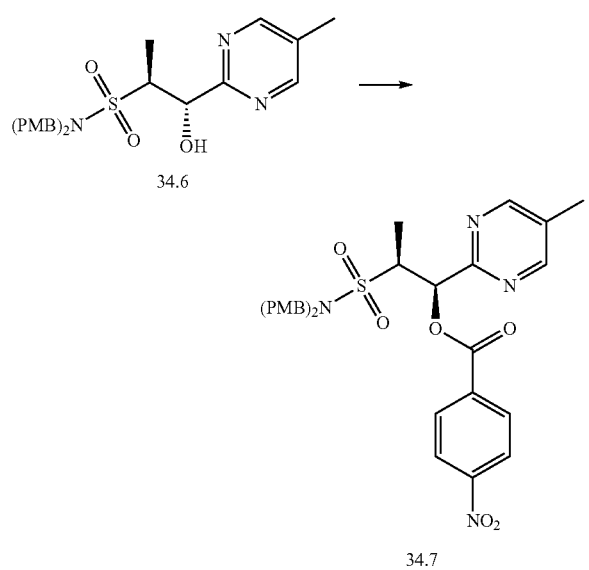

(1R,2S)-2-(N,N-Bis(4-methoxybenzyl)sulfamoyl)-1-(5-methylpyrimidin-2-yl)propyl 4-nitrobenzoate, Example 34.7

To a stirred solution of Example 34.6 (22.7 g, 48.1 mmol) in toluene (241 mL) was added 4-nitrobenzoic acid (12.07 g, 72.2 mmol) and triphenylphosphine (18.94 g, 72.2 mmol) followed by dropwise addition of (E)-diisopropyl diazene-1,2-dicarboxylate (14.22 mL, 72.2 mmol). The mixture was stirred at RT overnight. The reaction was then concentrated in vacuo and purified on silica gel eluting with 0-50% EtOAc/hexanes to give the desired compound (1R,2S)-2-(N,N-bis(4-methoxybenzyl)sulfamoyl)-1-(5-methylpyrimidin-2-yl)propyl 4-nitrobenzoate (29.9 g, 48.1 mmol, 100% yield). LCMS-ESI (pos.) m/z: 621.3 (M+H)$^+$.

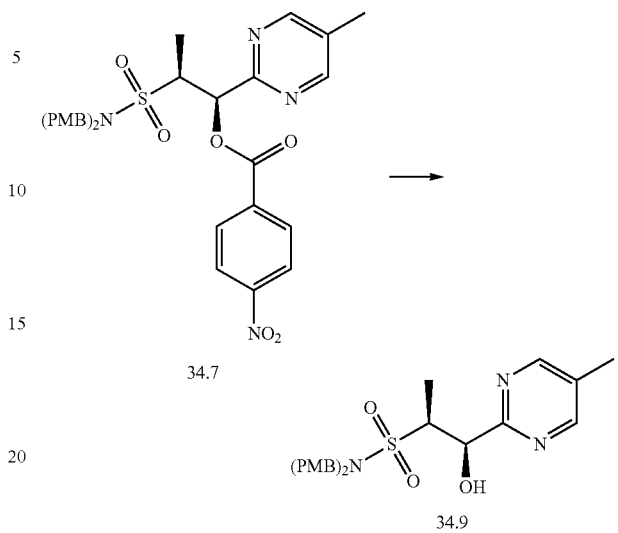

(1R,2S)-2-(N,N-Bis(4-methoxybenzyl)sulfamoyl)-1-(5-methylpyrimidin-2-yl)propyl 4-nitrobenzoate, Example 34.9

To a stirred solution of 34.7 (76 g, 122 mmol) in MeOH (612 mL) at 0° C. was added potassium carbonate (16.92 g, 122 mmol). The mixture was allowed to warm to RT over 1 h. The reaction was then concentrated in vacuo and purified on silica gel eluting with 0-40% EtOAc in hexanes to give (1R,2S)-1-hydroxy-N,N-bis(4-methoxybenzyl)-1-(5-methylpyrimidin-2-yl)propane-2-sulfonamide. LCMS-ESI (pos.) m/z: 472.0 (M+H)$^+$.

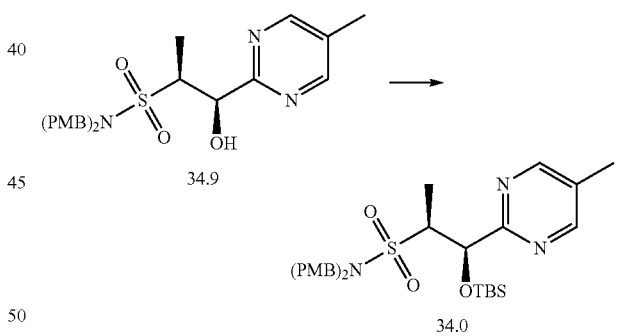

(1R,2S)-1-((tert-Butyldimethylsilyl)oxy)-N,N-bis(4-methoxybenzyl)-1-(5-methylpyrimidin-2-yl)propane-2-sulfonamide, Example 34.0

To a stirred solution of Example 34.9 (28 g, 59.4 mmol) in DCM (297 mL, 59.4 mmol) at 0° C. was added TBSOTf (15.00 mL, 65.3 mmol), followed by TEA (9.12 mL, 65.3 mmol). The mixture was allowed to warm to RT over 1 h. The reaction was then concentrated in vacuo and purified on silica gel eluting with 0-30% EtOAc in hexanes to give the desired compound (1R,2S)-1-((tert-butyldimethylsilyl)oxy)-N,N-bis(4-methoxybenzyl)-1-(5-methylpyrimidin-2-yl)propane-2-sulfonamide (15 g, 25.6 mmol, 43.1% yield). LCMS-ESI (pos.) m/z: 586.0 (M+H)$^+$.

Example 35.0. Preparation of (2R,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide

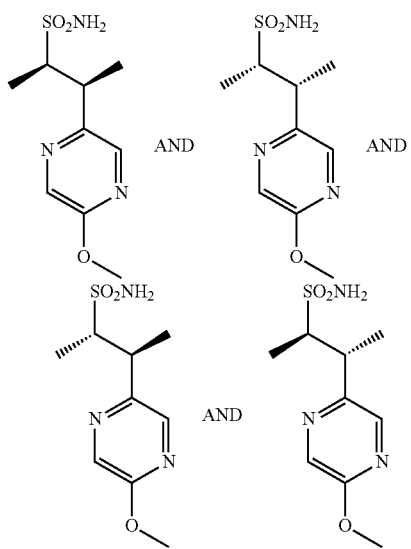

35.0

(2R,3R)-3-(5-Methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 35.0

Example 35.0 was synthesized following the procedure in Example 32.0 using 2-bromo-5-methoxypyrazine (commercially available from Ark Pharm, Inc.). LCMS-ESI (pos.) m/z: 246.2 (M+H)$^+$.

Example 36.0. Preparation of (2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide or (2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide

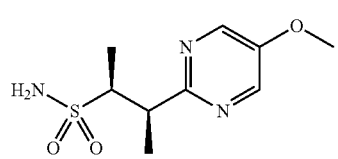

36.1

(2S,3R)-3-(5-Methoxypyrimidin-2-yl)butane-2-sulfonamide, Example 36.1

A round bottom flask was charged with (2S,3R)-3-(5-fluoropyrimidin-2-yl)butane-2-sulfonamide (575 mg, 2.47 mmol, Example 27.1), MeOH (7 mL), and potassium carbonate (679 mg, 4.91 mmol). The reaction was stirred at RT. After 48 h, the reaction was heated to 50° C. and stirred for 24 h. The temperature was then raised to 65° C. and the mixture was stirred for 48 h. LCMS-ESI showed the reaction was 75% complete. The reaction was allowed to cool to RT and filtered. The solids were rinsed with MeOH (2×5 mL). The filtrate was concentrated in vacuo and adsorbed onto a plug of silica gel and chromatographed through a RediSep® pre-packed silica gel column, eluting with 0-40% EtOAc:EtOH (3:1) in heptanes. The organic layer from several fractions were concentrated in vacuo to give a mixture of starting material and the title compound (56 mg, 0.23 mmol, 9% yield) as an off-white solid. The desired fractions were washed with a saturated aqueous solution of NaCl and extracted with CHCl$_3$:IPA (9:1, 3×15 mL). The combined organic layers were dried over MgSO$_4$ and concentrated in vacuo to give more title compound (114 mg). The material was carried forward without further purification. LCMS-ESI (pos.) m/z: 246.1 (M+H)$^+$.

Example 37.0. Preparation of (3R,5S)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide

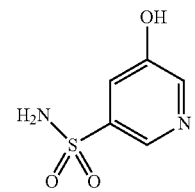

37.1

5-Hydroxypyridine-3-sulfonamide, Example 37.1

To a 100 mL round-bottom flask was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.16 mmol) and Pd$_2$(dba)$_3$ (commercially available from Sigma-Aldrich, 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was allowed to cool to RT. The reaction mixture was then diluted with 1.0 N HCl and washed with Et₂O. The aqueous phase was concentrated in vacuo to afford Example 37.1 (0.387 g, 2.22 mmol, 100% yield) as a white solid, which was directly used in the next step without further purification. LCMS-ESI (pos.), m/z: 175.1 (M+H)⁺.

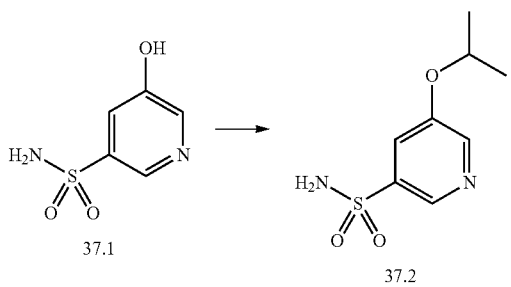

5-Isopropoxypyridine-3-sulfonamide, Example 37.2

To a suspension of 5-hydroxypyridine-3-sulfonamide, Example 37.1 (1.1 g, 6.32 mmol) in THF (16 mL) and IPA (16 mL) was added triphenylphosphine (1.99 g, 7.58 mmol). The mixture was bubbled with argon for 3 min before diisopropyl azodicarboxylate (1.49 mL, 7.58 mmol) was added dropwise at 0° C. under N₂ stream. The reaction was then stirred at 0° C. to RT for 15 h. The reaction mixture was concentrated in vacuo. The material thus obtained was absorbed onto a plug of silica gel and purified by chromatography through a RediSep-Sep pre-packed silica gel column (40 g), eluting with a gradient of 0% to 100% EtOAc in heptanes to provide the enriched product fractions which were combined and extracted with 1.0 N HCl. The desired product was enriched in acidic aqueous solution, which was then modified by a saturated aqueous NaHCO₃ to pH>8. The basic aqueous solution was then extracted with DCM. The organic extract was washed with brine and dried over Na₂SO₄. The solution was filtered and concentrated in vacuo to give Example 37.2 (0.95 g, 70% yield) as a white solid. LCMS-ESI (pos.), m/z: 217.2 (M+H)⁺.

37.3

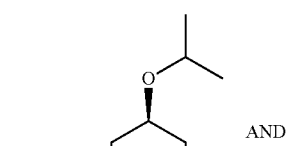 AND 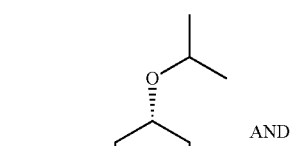 AND

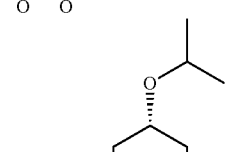 AND 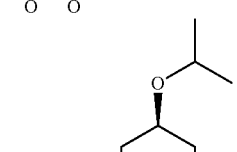

(3S,5R)-5-Isopropoxypiperidine-3-sulfonamide and
(3R,5R)-5-isopropoxypiperidine-3-sulfonamide and
(3S,5S)-5-isopropoxypiperidine-3-sulfonamide and
(3R,5S)-5-isopropoxypiperidine-3-sulfonamide,
Example 37.3

A solution of Example 37.2 (1.8 g, 8.32 mmol) in AcOH (41.6 mL) was bubbled with argon gas for 2 min before platinum (IV) oxide (1.89 g, 8.32 mmol) was added under argon stream. The mixture was stirred at RT under 45 psi of hydrogen gas for two days. Next, Celite® brand filter aid (5 g) was added to the reaction mixture. The mixture was stirred at RT for 10 min. The mixture was filtered and the solution was concentrated in vacuo to give the initial product mixture as a light yellow oil, which was used as such in the next step. LCMS-ESI (pos.), m/z: 223.3 (M+H)⁺.

37.4

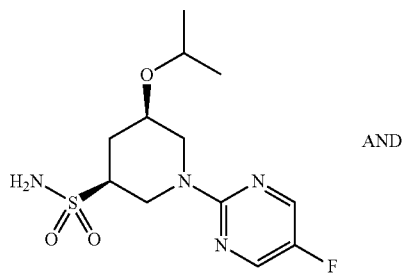 AND

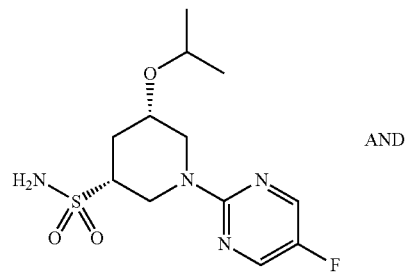 AND

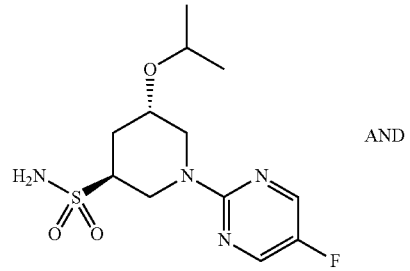 AND

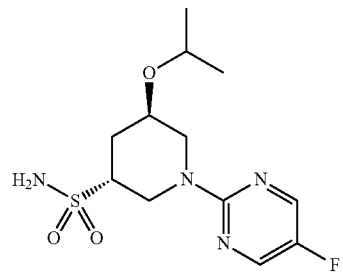

(3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 37.4

To a 40 mL vial (with pressure release septa) was added Example 37.3 (2.0 g, 4.96 mmol) and 2-chloro-5-fluoropyrimidine (3.29 g, 24.79 mmol). The reaction mixture was stirred at 90° C. for 21 h. LCMS indicated the reaction was complete. The reaction mixture was then concentrated in vacuo. The initial material was absorbed onto a plug of silica gel and purified by chromatography through a RediSep-Sep pre-packed silica gel column (40 g), eluting with a gradient of 0% to 100% EOAc in heptanes, to provide Example 37.4, as a mixture of diastereomers (0.5 g, 1.6 mmol, 32% yield) as off-white solid. LCMS-ESI (pos.), m/z: 319.2 (M+H)⁺.

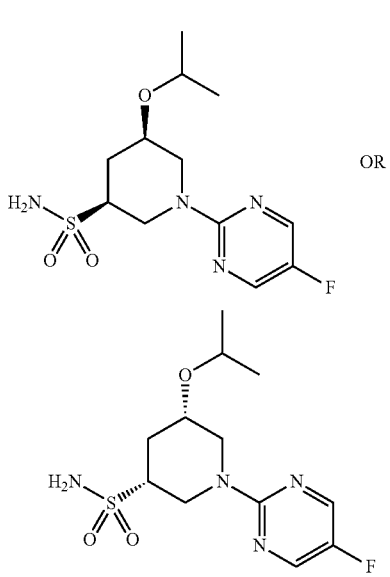

37.6

OR

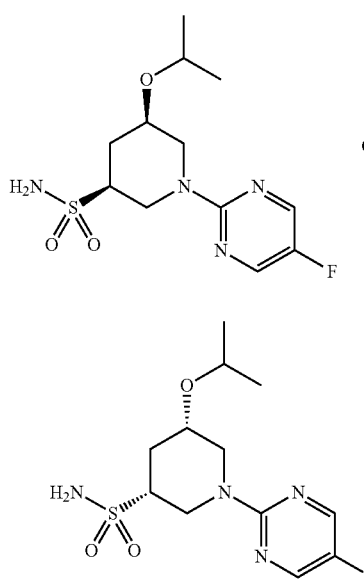

37.5

OR (3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 37.6

Further elution under the conditions described in Example 37.5 gave Example 37.6 as the third peak. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)⁺.

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 37.5

Example 37.4 was separated by SFC on Chiralpak AS-H column using 15% MeOH/CO₂. Example 37.5 and Example 37.6 are a pair of enantiomers. Example 37.5 was the second peak among 4 isomers (earlier peak vs. its opposite enantiomer) to elute on the AS-H column. ¹H NMR (400 MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)⁺.

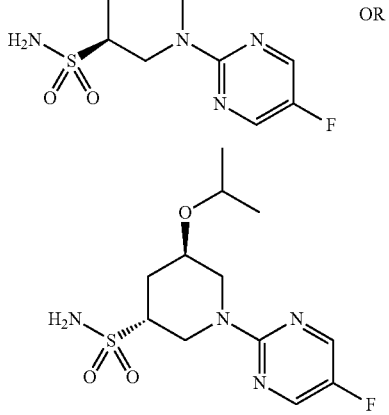

37.7

OR (3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 37.7

Examples 37.7 and 37.8 are a pair of enantiomers. Example 37.7 was the first peak among 4 isomers (earlier peak vs. its opposite enantiomer) to elute on the AS-H column under conditions described in Example 37.5. $^1$H NMR (400 MHz, CD$_3$OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)$^+$.

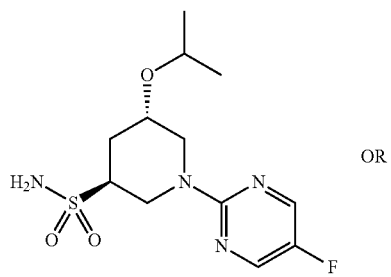

37.8

OR

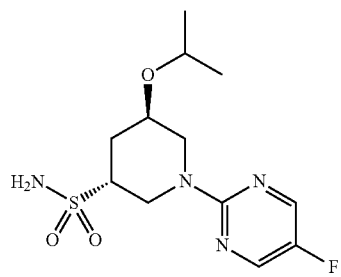

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 37.8

Further elution under the conditions described in Example 37.5 gave Example 37.8 as the fourth peak. $^1$H NMR (400 MHz, CD$_3$OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)$^+$.

Example 38.0. Preparation of (S)-tert-butyl 3-sulfamoylpiperidine-1-carboxylate and (R)-tert-butyl 3-sulfamoylpiperidine-1-carboxylate

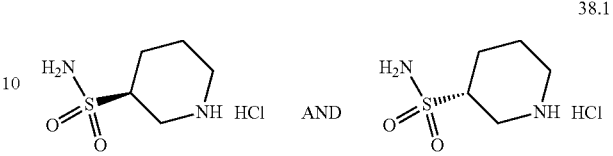

38.1

(S)-Piperidine-3-sulfonamide hydrochloride and (R)-piperidine-3-sulfonamide hydrochloride, Example 38.1

A solution of 4-chloropyridine-3-sulfonamide (5.0 g, 25.9 mmol) in AcOH (150 mL) was placed in a Parr bottle. The solution was bubbled with nitrogen gas for 5 min. To this solution was added a suspension of platinum (IV) oxide (5.9 g, 25.9 mmol) in AcOH (30 mL). The reaction was stirred under an atmosphere of hydrogen (50 psi) for 72 h. The reaction mixture was then filtered through a Celite® brand filter aid pad, and the pad was washed with MeOH (2×50 mL). The combined filtrate was concentrated under reduced pressure to provide initial Example 38.1 (6.0 g) as oil which was used in the next step without further purification. LCMS-ESI (pos.) m/z: 165 (M+H)$^+$.

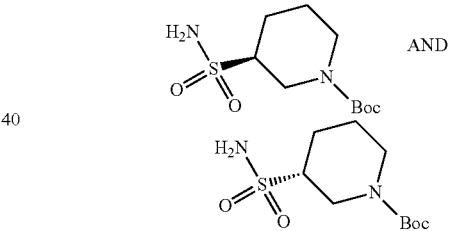

38.0

(S)-tert-Butyl 3-sulfamoylpiperidine-1-carboxylate and (R)-tert-butyl 3-sulfamoylpiperidine-1-carboxylate, Example 38.0

To a mixture of 38.1 (12.0 g, 59.8 mmol) and TEA (41.6 mL, 298.9 mmol) in DCM (215 mL) was added a solution of boc anhydride (15.7 mL, 71.8 mmol) in DCM (70 mL) at RT. The reaction mixture was stirred for 16 h at RT. The reaction mixture was washed with water (2×200 mL). The combined organic layers were washed with brine (100 mL), dried over sodium sulfate and evaporated under reduced pressure to obtain the product which was purified by column chromatography (silica: 100-200 mesh; elution: 0-30% EtOAc in DCM) to provide the title compound—(4.6 g, 34%, over two steps) as a white solid. $^1$H NMR (400 MHz, CD$_3$CN) δ 5.30 (s, 2H), 4.36 (d, J=11.8 Hz, 1H), 3.94 (d, J=13.3 Hz, 1H), 3.01-2.84 (m, 2H), 2.64-2.58 (s, 1H), 2.20 (d, J=13.3 Hz, 1H), 1.78 (d, J=13.5 Hz, 1H), 1.74-1.57 (m, 2H), 1.43 (s, 9H). LCMS-ESI (pos.) m/z: 263 (M−H)$^+$.

Example 39.0: Preparation of (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide

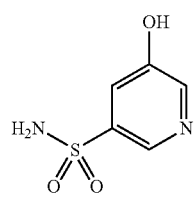

39.1

5-Hydroxypyridine-3-sulfonamide, Example 39.1

To a 100 mL round-bottom flask was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.16 mmol) and $Pd_2(dba)_3$ (commercially available from Sigma-Aldrich, 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under $N_2$ for 17 h. LCMS analysis indicated the reaction was complete. The reaction mixture was allowed to cool to RT. The reaction mixture was diluted with 1.0 N HCl and washed with $Et_2O$. The aqueous phase was concentrated in vacuo to afford the title compound 39.1 (0.387 g, 2.22 mmol, 100% yield) as a white solid, which was directly used in the next step without further purification. LCMS-ESI (pos.), m/z: 175.1 $(M+H)^+$.

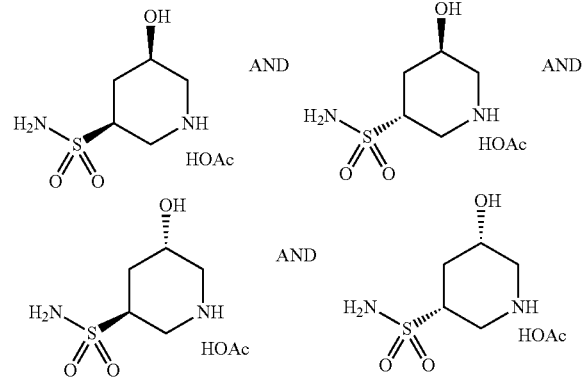

39.2

(3R,5R)-5-Hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 39.2

To a 1 L hydrogenation flask was added 39.1 (6.46 g, 37.1 mmol) and AcOH (250 mL, 4330 mmol). Water (20 mL) was added as co-solvent. The mixture was bubbled with $N_2$ for 2 min before platinum (iv) oxide hydrate (8.42 g, 37.1 mmol) was added under $N_2$ flow. The flask was set up on a Parr shaker, vacuumed and back-filled with $N_2$ two times, and then placed under vacuum and back-filled with hydrogen gas (tank). The reaction mixture was stirred at RT under 50 psi of hydrogen gas for 24 h. LCMS analysis indicated that the reaction was complete. Celite® brand filter agent (20 g) was added to the mixture with stirring. The solid was removed by filtration after 10 min of stirring. The filter cake was rinsed with MeOH. The combined organics were concentrated in vacuo to afford 39.2 (8.91 g, 100% yield) as a light-yellow oil, which was directly used in the next step without purification. LCMS-ESI (pos.), m/z: 181.1 $(M+H)^+$.

39.0

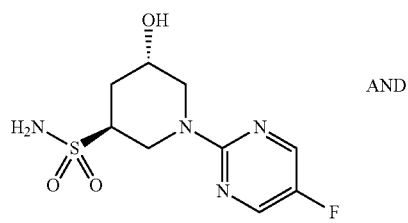

AND

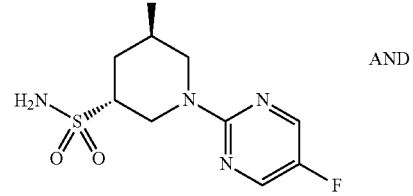

AND

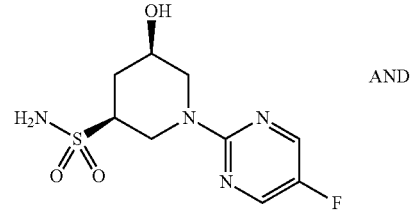

AND

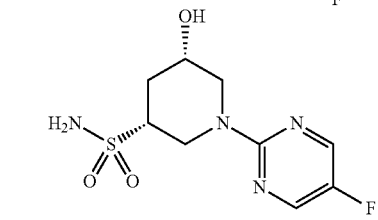

(3S,5S)-1-(5-Fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 39.0

To a 500 mL round-bottom flask was added 39.2 (8.91 g, 37.1 mmol) and Hunig's base (32.3 mL, 185 mmol) in DMF (80 mL). 2-Chloro-5-fluoropyrimidine (18.32 mL, 148 mmol) was then added with stirring. The reaction mixture was stirred at 120° C. for 18 h. LCMS analysis indicated the reaction was complete. The reaction mixture was allowed to cool to RT and then was diluted with water and extracted with DCM. The organic layers were washed with brine and dried over Na$_2$SO$_4$. The solution was filtered and concentrated in vacuo to give the initial material as an orange oil. The material thus obtained was purified by silica gel chromatography (a gradient of 0-100% EtOAc in DCM), to provide 39.0 (3.7 g, 10.93 mmol, 36% yield) as a light-yellow solid. LCMS-ESI (pos.), m/z: 277.0 (M+H)$^+$.

Example 40.3. Preparation of (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide

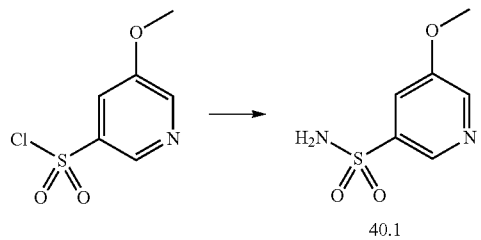

5-Methoxypyridine-3-sulfonamide, Example 40.1

A reaction mixture of 5-methoxypyridine-3-sulfonyl chloride (commercially available from Enamine, KIEV, Ukraine) (1.0 g, 4.82 mmol) and ammonia, (0.5 M solution in 1,4-dioxane, 96 mL, 48.2 mmol) was stirred at 0 to RT for 30 min. LCMS indicated the reaction was complete, and the reaction was filtered and the cake was rinsed with dioxane. The combined solution was concentrated in vacuo to give the title compound (0.91 g, 100% yield) as a light yellow foam which was used as such in the next step without purification. LCMS-ESI (pos.) m/z: 189.2 (M+H)$^+$.

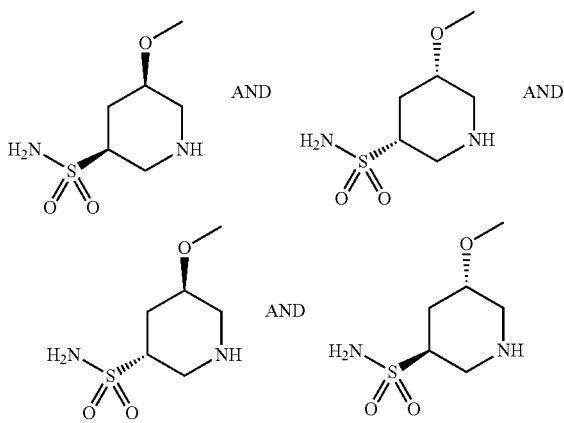

(3R,5R)-5-Methoxypiperidine-3-sulfonamide and (3R,5S)-5-methoxypiperidine-3-sulfonamide and (3S,5R)-5-methoxypiperidine-3-sulfonamide and (3S,5S)-5-methoxypiperidine-3-sulfonamide tetraacetate, Example 40.2

A solution of 5-methoxypyridine-3-sulfonamide (0.9 g, 4.78 mmol) in AcOH (31.9 mL) was bubbled with argon gas for 2 min before platinum (iv) oxide ((1.09 g, 4.78 mmol) was added under an argon stream. The resulting mixture was stirred at RT under 45 psi of hydrogen gas for 38 h. The mixture was filtered and the filtrate was concentrated in vacuo to give the title compound (1.22 g, 100% yield) as a light yellow foam, which was used as such for the next step. LCMS-ESI (pos.) m/z: 195.2 (M+H)$^+$.

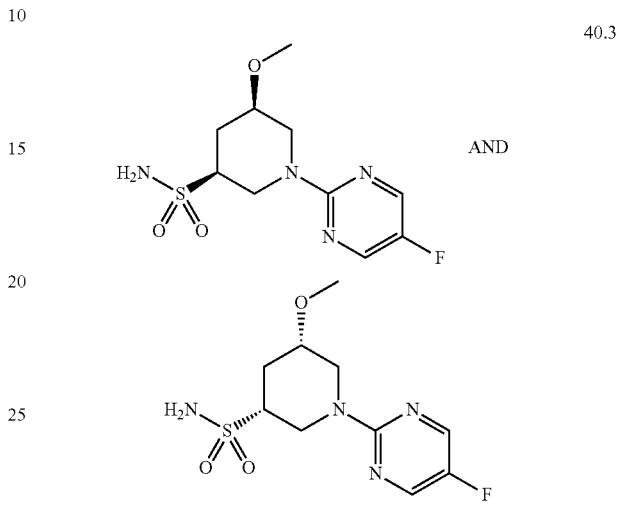

(3S,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide, Example 40.3

To a 40 mL vial (w/ pressure release septa) was added 5-methoxypiperidine-3-sulfonamide acetate, (40.2, 2.45 g, 9.62 mmol), N-ethyl-N-isopropylpropan-2-amine (16.75 mL, 96 mmol) and 2-chloro-5-fluoropyrimidine (6.37 g, 48.1 mmol) in DMSO (48 mL). The reaction mixture was stirred at 100° C. for 23 h. LCMS indicated formation of the desired product. The reaction mixture was diluted with water and extracted with DCM. The organic extract was washed with saturated aqueous NaCl, brine and dried over Na$_2$SO$_4$. The solution was filtered and concentrated in vacuo to give the initial material as an orange oil. The initial material was absorbed onto a plug of silica gel and purified by chromatography through a RediSep-Sep pre-packed silica gel column (40 g), eluting with a gradient of 0% to 100% ⅓ EtOH/EtOAc in heptanes to provide the title compound, 40.3 (0.51 g, 18% yield) as white solid, LCMS-ESI (pos.) m/z: 291.0 (M+H)$^+$.

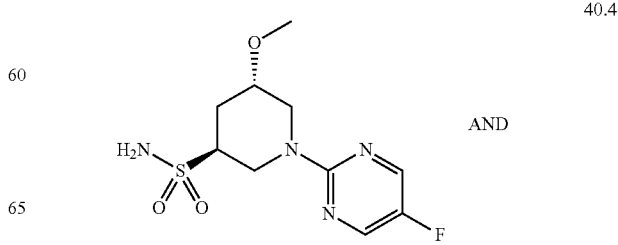

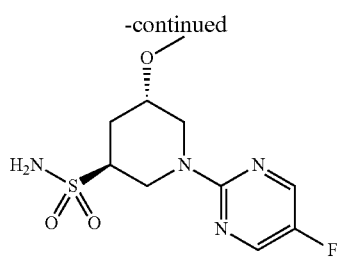

(3S,5S)-1-(5-Fluoropyrimidin-2-yl)-5-methoxypiperidine-3-sulfonamide and (3R,5R)-1-(5-fluoropyrimidin-2-yl)-5-methoxypiperidine-3-sulfonamide, Example 40.4

Further elution under the conditions described in Example 40.3 delivered 40.4 (0.24 g, 0.832 mmol, 8.65% yield) as a light yellow solid. LCMS-ESI (pos.) m/z: 291.0 (M+H)+.

40.5

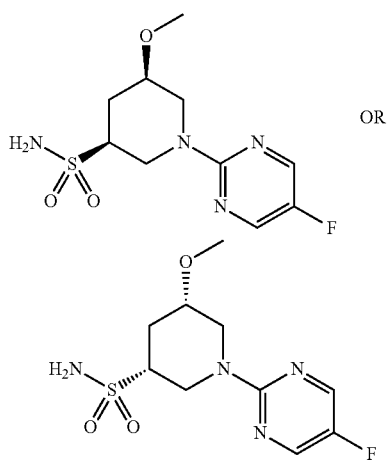

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 40.5

Example 40.5 was obtained by chiral separation of 40.3 on SFC: Chiralpak AD-H, 30% MeOH/CO₂, with 0.2% DEA. Example 40.5 was the earlier peak to elute on Chiralpak AD-H column. ¹H NMR (400 MHz, CD₃OD) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (pos.) m/z: 291.0 (M+H)+.

40.6

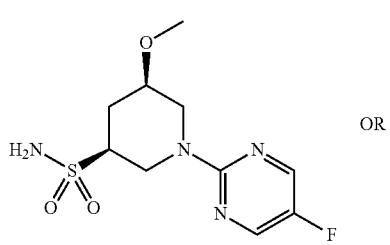

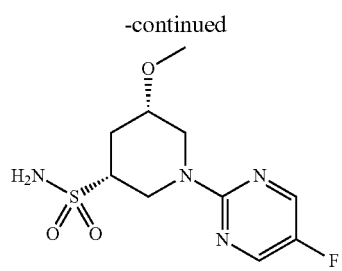

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 40.6

Further elution under the conditions described in Example 40.5 delivered Example 40.6. ¹H NMR (400 MHz, CD₃OD) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45 (s, 3H) 4.97 (ddt, 1H) 5.17 (ddt, 1H) 8.32 (s, 2H). LCMS-ESI (pos.) m/z: 291.0 (M+H)+.

40.7

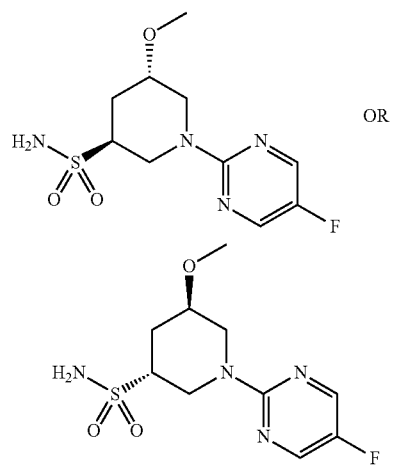

(3S,5S)-1-(5-Fluoropyrimidin-2-yl)-5-methoxypiperidine-3-sulfonamide or (3R,5R)-1-(5-fluoropyrimidin-2-yl)-5-methoxypiperidine-3-sulfonamide, Example 40.7

Example 40.7 was obtained by chiral separation of 40.4 on SFC: Chiralpak AD-H, 25% MeOH/CO₂, with 0.2% DEA. Example 40.7 was the earlier peak to elute on the Chiralpak AD-H column. ¹H NMR (400 MHz, CD₃OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H) LCMS-ESI (pos.) m/z: 291.0 (M+H)+.

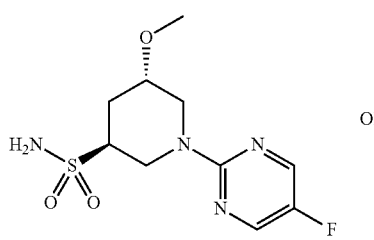

40.8

OR

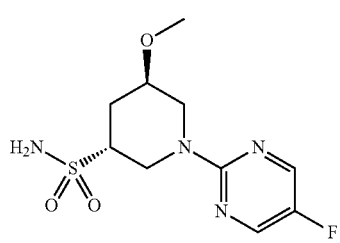

(3R,5R)-1-(5-Fluoropyrimidin-2-yl)-5-methoxypiperidine-3-sulfonamide or (3S,5S)-1-(5-fluoropyrimidin-2-yl)-5-methoxypiperidine-3-sulfonamide, Example 40.8

Further elution under the conditions described in Example 40.6 delivered Example 40.8. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 291.0 (M+H)$^+$.

Example 41.0. Preparation of Examples (1R,2S)-1-ethoxy-1-(5-methylpyrimidin-2-yl)propane-2-sulfonamide and (1S,2R)-1-ethoxy-1-(5-methylpyrimidin-2-yl)propane-2-sulfonamide

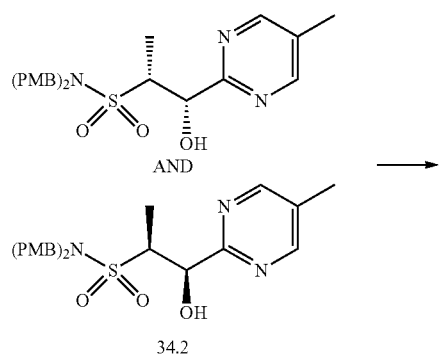

34.2

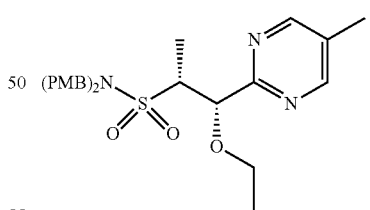

AND

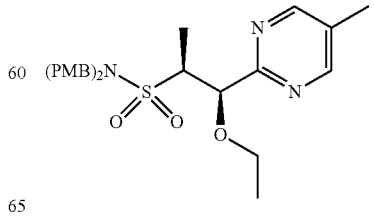

41.1

(1R,2S)-1-Ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 41.1

To a −78° C. solution of 34.2 (1.62 g, 3.4 mmol) in THF (70 mL) was added potassium bis(trimethylsilyl)amide (1.0 M solution in THF, 10.6 mL, 10.6 mmol) slowly via syringe. After 1.25 h, EtOTf (1.4 mL, 10.6 mmol) was added slowly via syringe. The resulting orange solution was stirred at −78° C. for 45 min and then was quenched with a 2:1 mixture of saturated aqueous ammonium chloride and water (75 mL). The resulting mixture was extracted with EtOAc (4×). The combined organic layers were dried over anhydrous sodium sulfate and concentrated in vacuo. The residue was purified by silica gel chromatography (eluent: 10-65% EtOAc in hexanes over a 40 min period) to provide 41.1 (1.02 g, 60% yield) as a light yellow oil. LCMS-ESI (pos.) m/z: 500.1 (M+H)$^+$.

145
-continued

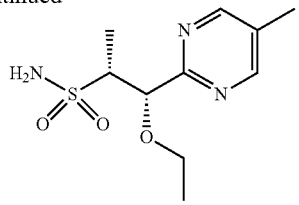

AND

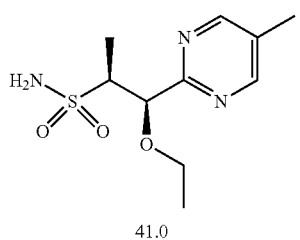

41.0

(1R,2S)-1-Ethoxy-1-(5-methylpyrimidin-2-yl)propane-2-sulfonamide and (1S,2R)-1-ethoxy-1-(5-methylpyrimidin-2-yl)propane-2-sulfonamide, Example 41.0

Example 41.1 (1.02 g, 2.0 mmol) was dissolved in TFA (14 mL), and anisole (466 μL, 4.3 mmol) was added via syringe. The resulting orange solution was stirred at RT for 16.5 h and then concentrated in vacuo. The residue was purified by silica gel chromatography (eluent: pure DCM grading to 4.5% MeOH in DCM) to provide the title compound Example 41.0 (495 mg, 93% yield) as a white solid. LCMS-ESI (pos.) m/z: 260.0 (M+H)$^+$.

The compounds set forth in the following table were synthesized following the procedure in Example 41.0 using the known starting material as described.

TABLE 6

| Example | Reagents | Structure, Name and Data |
|---|---|---|
| 41.2 | Material prepared in an analogous manner to that of Example 34.2 employing the cis olefin. | (1R,2R)-1-ethoxy-1-(5-methylpyrimidin-2-yl)propane-2-sulfonamide and (1S,2S)-1-ethoxy-1-(5-methylpyrimidin-2-yl)propane-2-sulfonamide. LCMS-ESI (pos.) m/z: 260.0 (M + H)$^+$. |
| 41.3 | 5-chloropicolinaldehyde (commercially available from Combi-Blocks) and MeOTf (commercially available from Combi-Blocks). | |

TABLE 6-continued

| Example | Reagents | Structure, Name and Data |
|---|---|---|
| | | 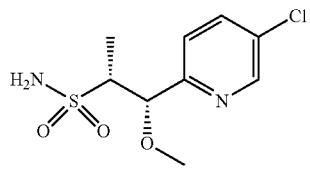<br>(1R,2S)-1-(5-chloropyridin-2-yl)-1-methoxypropane-2-sulfonamide and (1S,2R)-1-(5-chloropyridin-2-yl)-1-methoxypropane-2-sulfonamide.<br>LCMS-ESI (pos.) m/z: 265.0 (M + H)$^+$. |
| 41.4 | Example 41.3 was purified by preparative SFC using the following method: Column: Chiral Pak IC (250 × 4.6) mm 5 u, Mobile Phase: 0.1% DEA IN Hexanes:EtOH (80:20), Flow: 1.0 mL/min. to provide peak 1. | 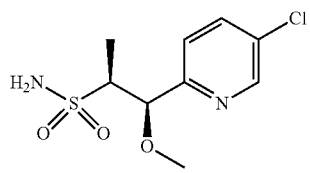<br>OR<br>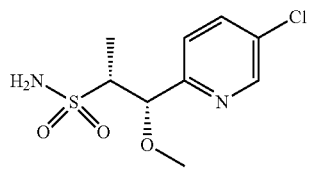<br>(1R,2S)-1-(5-chloropyridin-2-yl)-1-methoxypropane-2-sulfonamide or (1S,2R)-1-(5-chloropyridin-2-yl)-1-methoxypropane-2-sulfonamide.<br>$^1$H NMR (400 MHz, DMSO-d$_6$) δ 8.64 (d, J = 2.5 Hz, 1H), 7.99 (dt, J = 8.4, 2.3 Hz, 1H), 7.44 (d, J = 8.4 Hz, 1H), 6.81 (s, 2H), 4.89 (d, J = 2.5 Hz, 1H), 3.33 (m, 4H), 1.10 (dd, J = 7.0, 1.9 Hz, 3H). LCMS-ESI (pos.) m/z: 265.0 (M + H)$^+$. |

TABLE 6-continued

| Example | Reagents | Structure, Name and Data |
|---|---|---|
| 41.5 | Example 41.3 was purified by preparative SFC using the following method: Column: Chiral Pak IC (250 × 4.6) mm 5 u, Mobile Phase: 0.1% DEA IN Hexane:EtOH (80:20), Flow: 1.0 mL/min. to provide peak 2. | 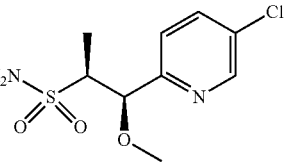<br>OR<br>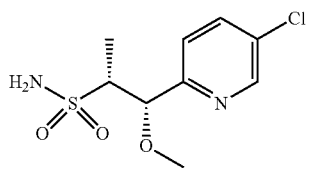<br>(1R,2S)-1-(5-chloropyridin-2-yl)-1-methoxypropane-2-sulfonamide or (1S,2R)-1-(5-chloropyridin-2-yl)-1-methoxypropane-2-sulfonamide<br>$^1$H NMR (400 MHz, DMSO-d$_6$) δ 8.64 (d, J = 2.4 Hz, 1H), 7.99 (dd, J = 8.3, 2.4 Hz, 1H), 7.44 (d, J = 8.4 Hz, 1H), 6.81 (s, 2H), 4.89 (d, J = 2.3 Hz, 1H), 3.33 (m, 4H), and 1.10 (d, J = 7.0 Hz, 3H). LCMS-ESI (pos.) m/z: 265.0 (M + H)$^+$. |

The compounds in the following table were synthesized following the procedure in Example 1.0 using the known starting material as described.

TABLE 7

| Example | Reagents | Structure, Name and Data |
|---|---|---|
| 42.0 | (1R,2S)-1-(5-chloropyrimidin-2-yl)-1-methoxypropane-2-sulfonamide (Example 29.3), 6-(2-methoxyethoxy)picolinohydrazide (commercially available from Frontier Scientific Services Inc.), and 2-isothiocyanato-1,3-dimethoxypropane (Example 71.0). | 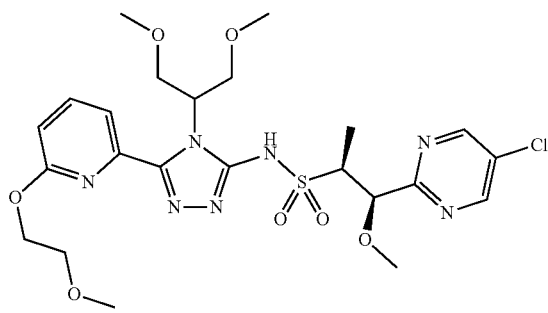<br>(1R,2S)-1-(5-chloro-2-pyrimidinyl)-N-(4-(1,3-dimethoxy-2-propanyl)-5-(6-(2-methoxyethoxy)-2-pyridinyl)-4H-1,2,4-triazol-3-yl)-1-methoxy-2-propanesulfonamide.<br>$^1$H NMR (400 MHz, CDCl$_3$) δ 1.45 (d, J = 7.05 Hz, 3 H) 3.27 (s, 3 H) 3.29 (s, 3 H) 3.39 (s, 3 H) 3.46 (s, 3 H) 3.72-3.81 (m, 5 H) 4.15-4.24 (m, 2 H) 4.50-4.54 (m, 2 H) 5.07 (d, J = 4.35 Hz, 1 H) 5.72 (br t, J = 6.95 Hz, 1 H) 6.95 (d, J = 8.19 Hz, 1 H) 7.55 (d, J = 7.15 Hz, 1 H) 7.72 (dd, J = 8.29, 7.46 Hz, 1 H) 8.75 (s, 2 H). LCMS ESI (pos.) m/z: 586.2 (M + H)$^+$. |

TABLE 7-continued

| Example | Reagents | Structure, Name and Data |
|---|---|---|
| 43.0 | (1R,2S)-1-(5-chloropyrimidin-2-yl)-1-methoxypropane-2-sulfonamide (Example 29.3) 6-methoxypicolinohydrazide (commercially available from Sigma Aldrich), and 1-(difluoromethoxy)-2-isothiocyanatoethane (Example 28.3). | 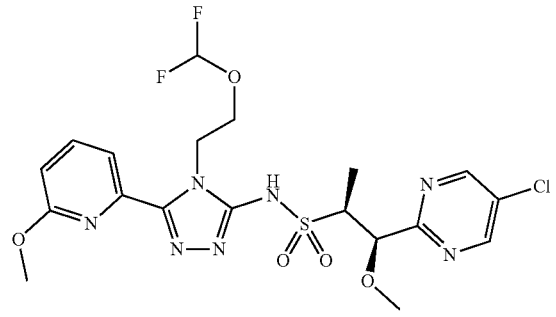<br>(1R,2S)-1-(5-chloro-2-pyrimidinyl)-N-(4-(2-(difluoromethoxy)ethyl)-5-(6-methoxy-2-pyridinyl)-4H-1,2,4-triazol-3-yl)-1-methoxy-2-propanesulfonamide.<br>$^1$H NMR (400 MHz, CDCl$_3$) δ 1.45 (d, J = 7.05 Hz, 3 H) 3.33 (s, 3 H) 3.73-3.80 (m, 1 H) 3.96 (s, 3 H) 4.18-4.28 (m, 2 H) 4.75-4.84 (m, 2 H) 5.07 (d, J = 4.35 Hz, 1 H) 6.12 (t, J = 73.29 Hz, 1 H) 6.90 (dd, J = 8.24, 0.88 Hz, 1 H) 7.65-7.75 (m, 2 H) 8.73 (s, 2 H). LCMS ESI (pos.) m/z: 534.0 (M + H)$^+$. |
| 44.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 3-isothiocyanatopropanenitrile (Example 28.4). | 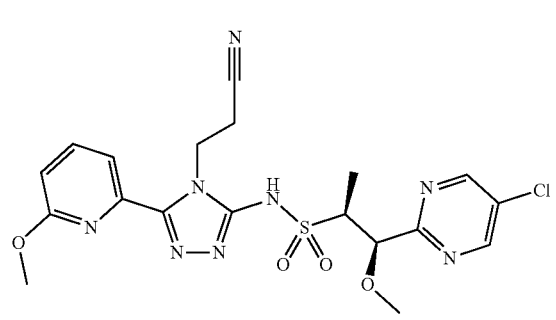<br>(1R,2S)-1-(5-chloro-2-pyrimidinyl)-N-(4-(2-cyanoethyl)-5-(6-methoxy-2-pyridinyl)-4H-1,2,4-triazol-3-yl)-1-methoxy-2-propanesulfonamide.<br>$^1$H NMR (400 MHz, CD$_3$OD) δ 1.40 (d, J = 6.95 Hz, 3 H) 3.15 (td, J = 7.07, 2.33 Hz, 2 H) 3.27 (s, 3 H) 3.68 (dd, J = 7.05, 3.94 Hz, 1 H) 4.04 (s, 3 H) 4.73-4.83 (m, 2 H) 5.08 (d, J = 3.94 Hz, 1 H) 6.96 (dd, J = 8.34, 0.78 Hz, 1 H) 7.73 (dd, J = 7.46, 0.73 Hz, 1 H) 7.83 (dd, J = 8.24, 7.52 Hz, 1 H) 8.83 (s, 2 H). LCMS ESI (pos.) m/z: 493.1 (M + H)$^+$. |

TABLE 7-continued

| Example | Reagents | Structure, Name and Data |
|---|---|---|
| 45.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 3-isothiocyanatopropanenitrile (Example 28.4) The title compound was obtained as a side-product in the experiment for preparation of Example 44.0. | 3-(3-(((((1R,2S)-1-(5-chloro-2-pyrimidinyl)-1-methoxy-2-propanyl)sulfonyl)amino)-5-(6-methoxy-2-pyridinyl)-4H-1,2,4-triazol-4-yl)propanamide.<br>$^1$H NMR (400 Hz, CD$_3$OD) δ 1.40 (d, J = 6.95 Hz, 3 H) 2.84 (dd, J = 9.23, 7.05 Hz, 2 H) 3.25 (s, 3 H) 3.64-3.72 (m, 1 H) 3.99 (s, 3 H) 4.60-4.83 (m, 2 H) 5.05 (d, J = 4.25 Hz, 1 H) 6.94 (dd, J = 8.40, 0.62 Hz, 1 H) 7.68 (d, J = 7.26 Hz, 1 H) 7.82 (dd, J = 8.34, 7.52 Hz, 1 H) 8.82 (s, 2 H). LCMS ESI (pos.) m/z: 511.1 (M + H)$^+$. |
| 46.0 | (1R,2S)-1-(5-chloropyrimidin-2-yl)-1-methoxypropane-2-sulfonamide (Example 29.3), picolinohydrazide (commercially available from TCI America), and (isothiocyanatomethylene)dicyclopropane (commercially available from Frontier Scientific Services Inc.). | (1R,2S)-1-(5-chloro-2-pyrimidinyl)-N-(4-(dicyclopropylmethyl)-5-(2-pyridinyl)-4H-1,2,4-triazol-3-yl)-1-methoxy-2-propanesulfonamide.<br>$^1$H NMR (400 MHz, CDCl$_3$) δ 0.25 (br s, 2 H) 0.37 (br s, 4 H) 0.70 (br s, 2 H) 1.44 (d, J = 6.95 Hz, 3 H) 1.77-2.06 (m, 1 H) 2.13-2.25 (m, 1 H) 3.38 (s, 3 H) 3.69-3.82 (m, 1 H) 3.99-4.11 (m, 1 H) 5.08 (br s, 1 H) 7.34-7.44 (m, 1 H) 7.83 (td, J = 7.80, 1.71 Hz, 1 H) 7.98 (d, J = 7.98 Hz, 1 H) 8.56 (br s, 1 H) 8.72 (s, 2H) 11.20 (br s, 1 H). LCMS ESI (pos.) m/z: 504.2 (M + H)$^+$. |
| 47.0 | (1R,2S)-1-(5-chloropyrimidin-2-yl)-1-methoxypropane-2-sulfonamide (Example 29.3), picolinohydrazide (commercially available from TCI America), and 3-isothiocyanatopentane (commercially available from Oakwood). | (1R,2S)-1-(5-chloro-2-pyrimidinyl)-1-methoxy-N-(4-(3-pentanyl)-5-(2-pyridinyl)-4H-1,2,4-triazol-3-yl)-2-propanesulfonamide.<br>$^1$H NMR (400 MHz, CDCl$_3$) δ 0.82 (t, J = 7.46 Hz, 3 H) 0.87 (t, J = 7.41 Hz, 3 H) 1.45 (d, J = 6.95 Hz, 3 H) 1.75-1.89 (m, 2 H) 2.36 (br dd, J = 13.42, 7.10 Hz, 2 H) 3.39 (s, 3 H) 3.74 (qd, J = 6.98, 4.46 Hz, 1 H) 5.06 (d, J = 4.46 Hz, 1 H) 5.12 (br s, 1 H) 7.42 (ddd, J = 7.59, 4.85, 1.24 Hz, 1 H) 7.84 (td, J = 7.77, 1.87 Hz, 1 H) 7.94 (d, J = 7.65 Hz, 1 H) 8.67-8.74 (m, 3 H) 11.17 (br s, 1H). LCMS ESI (pos.) m/z: 480.2 (M + H)$^+$. |

| Example | Reagents | Structure, Name and Data |
|---|---|---|
| 48.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1-methoxypropane (commercially available from Enamine). The title compound was the first diastereomer to elute from a Regis Whelk-O column, SFC with 25% IPA. | 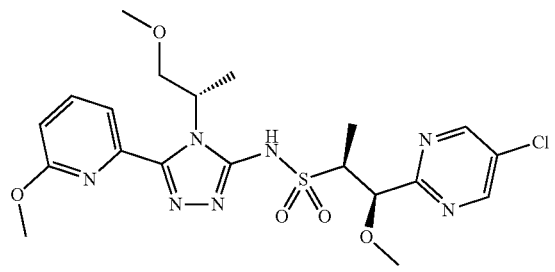<br>(1R,2S)-1-(5-chloro-2-pyrimidinyl)-1-methoxy-N-(4-((2S)-1-methoxy-2-propanyl)-5-(6-methoxy-2-pyridinyl)-4H-1,2,4-triazol-3-yl)-2-propanesulfonamide.<br>$^1$H NMR (400 MHz, CDCl$_3$) δ 1.45 (d, J = 7.05 Hz, 3 H) 1.67 (d, J = 7.05 Hz, 3 H) 3.24 (s, 3 H) 3.36 (s, 3 H) 3.55 (dd, J = 9.74, 5.60 Hz, 1 H) 3.71-3.79 (m, 1 H) 3.95 (s, 3 H) 4.28 (t, J = 9.38 Hz, 1 H) 5.10 (d, J = 4.15 Hz, 1 H) 5.39-5.49 (m, 1 H) 6.89 (d, J = 8.29 Hz, 1 H) 7.52 (d, J = 7.36 Hz, 1 H) 7.72 (dd, J = 8.29, 7.36 Hz, 1 H) 8.74 (s, 2 H). LCMS ESI (pos.) m/z: 512.2 (M + H)$^+$. |
| 49.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1-methoxypropane (commercially available from Enamine). The title compound was the second diastereomer to elute from Regis Whelk-O column, SFC with 25% IPA. | 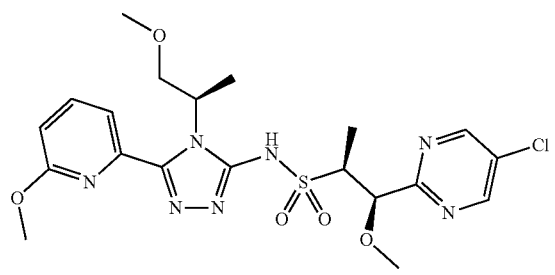<br>(1R,2S)-1-(5-chloro-2-pyrimidinyl)-1-methoxy-N-(4-((2R)-1-methoxy-2-propanyl)-5-(6-methoxy-2-pyridinyl)-4H-1,2,4-triazol-3-yl)-2-propanesulfonamide.<br>$^1$H NMR (400 MHz, CDCl$_3$) δ 1.46 (d, J = 7.05 Hz, 3 H) 1.65 (d, J = 7.05 Hz, 3 H) 3.25 (s, 3 H) 3.40 (s, 3 H) 3.58 (dd, J = 9.64, 5.70 Hz, 1 H) 3.71-3.82 (m, 1 H) 3.95 (s, 3 H) 4.23 (t, J = 9.28 Hz, 1 H) 5.08 (d, J = 4.46 Hz, 1 H) 5.39-5.49 (m, 1 H) 6.88 (d, J = 8.19 Hz, 1 H) 7.52 (d, J = 7.05 Hz, 1 H) 7.71 (dd, J = 8.29, 7.46 Hz, 1 H) 8.73 (s, 2 H). LCMS ESI (pos.) m/z: 512.2 (M + H)$^+$. |

TABLE 7-continued

| Example | Reagents | Structure, Name and Data |
|---|---|---|
| 50.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanato-1-(methoxymethyl)cyclobutane (Example 28.5). | 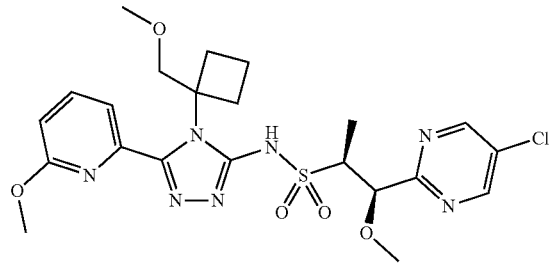<br>(1R,2S)-1-(5-chloro-2-pyrimidinyl)-1-methoxy-N-(4-(1-(methoxymethyl)cyclobutyl)-5-(6-methoxy-2-pyridinyl)-4H-1,2,4-triazol-3-yl)-2-propanesulfonamide.<br>$^1$H NMR (400 MHz, CDCl$_3$) δ 1.45 (d, J = 7.05 Hz, 3 H) 1.59-1.71 (m, 1 H) 1.71-1.87 (m, 2 H) 2.20-2.36 (m, 2 H) 2.39 (br s, 2 H) 3.39 (s, 3 H) 3.44 (s, 3 H) 3.73 (br dd, J = 6.95, 4.35 Hz, 1 H) 3.96-4.09 (m, 5 H) 5.08 (d, J = 4.35 Hz, 1 H) 6.87 (d, J = 8.40 Hz, 1 H) 7.39 (d, J = 6.74 Hz, 1 H) 7.67 (dd, J = 8.34, 7.31 Hz, 1 H) 8.74 (s, 2H) 11.03 (br s, 1 H). LCMS ESI (pos.) m/z: 538.0 (M + H)$^+$. |
| 51.0 | (1R,2S)-1-(5-chloropyrimidin-2-yl)-1-methoxypropane-2-sulfonamide (Example 29.3), picolinohydrazide (commercially available from TCI America), and 1-isothiocyanato-1-(methoxymethyl)cyclobutane (Example 28.5). | 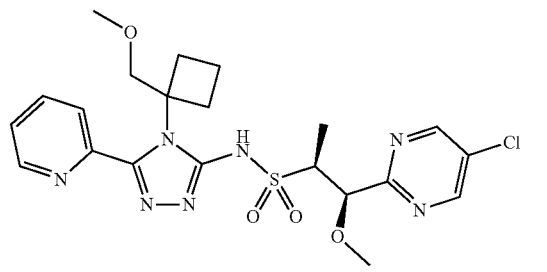<br>(1R,2S)-1-(5-chloro-2-pyrimidinyl)-1-methoxy-N-(4-(1-(methoxymethyl)cyclobutyl)-5-(2-pyridinyl)-4H-1,2,4-triazol-3-yl)-2-propanesulfonamide.<br>$^1$H NMR (400 MHz, CDCl$_3$) δ 1.45 (d, J = 7.05 Hz, 3 H) 1.62-1.84 (m, 2 H) 2.23 (br s, 2 H) 2.32 (br s, 2 H) 3.39 (s, 3 H) 3.47 (s, 3 H) 3.73 (br dd, J = 6.95, 4.56 Hz, 1 H) 4.04 (q, J = 9.71 Hz, 2 H) 5.07 (d, J = 4.46 Hz, 1 H) 7.43 (ddd, J = 7.59, 4.85, 1.14 Hz, 1 H) 7.82 (td, J = 7.77, 1.76 Hz, 1 H) 7.92 (d, J = 7.88 Hz, 1 H) 8.70-8.75 (m, 3 H) 11.03 (br s, 1 H). LCMS ESI (pos.) m/z: 508.0 (M + H)$^+$. |
| 52.0 | (2S,3R)-3-(5-chloropyrimidin-2-yl)butane-2-sulfonamide (Example 27.4), nicotinohydrazide (commercially available from Acros), and 2-isothiocyanato-1-methoxypropane (commercially available from Enamine). The title compound was the first diastereomer to elute from a Chiralpak AD-H column, SFC with 35% IPA. | 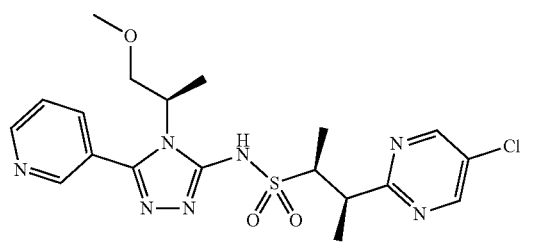<br>OR |

| Example | Reagents | Structure, Name and Data |
|---|---|---|
| | | 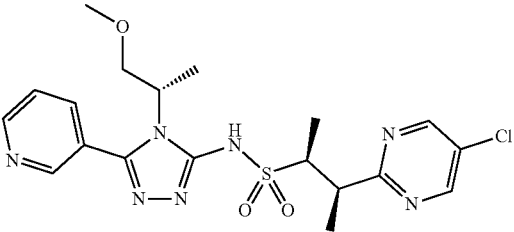 (2S,3R)-3-(5-chloro-2-pyrimidinyl)-N-(4-((2R)-1-methoxy-2-propanyl)-5-(3-pyridinyl)-4H-1,2,4-triazol-3-yl)-2-butanesulfonamide or (2S,3R)-3-(5-chloro-2-pyrimidinyl)-N-(4-((2S)-1-methoxy-2-propanyl)-5-(3-pyridinyl)-4H-1,2,4-triazol-3-yl)-2-butanesulfonamide. $^1$H NMR (400 MHz, CDCl$_3$) δ 1.47 (m, 6H) 1.52 (d, J = 6.95 Hz, 3 H) 3.31 (s, 3 H) 3.43 (dd, J = 9.64, 3.84 Hz, 1 H) 3.77-3.95 (m, 2 H) 4.20-4.37 (m, 2 H) 7.50 (dd, J = 7.77, 4.98 Hz, 1 H) 8.04 (dt, J = 7.96, 1.93 Hz, 1 H) 8.65 (s, 2 H) 8.81 (br d, J = 3.84 Hz, 1 H) 8.92 (s, 1 H) 11.29 (br s, 1 H). LCMS ESI (pos.) m/z: 466.0 (M + H)$^+$. |
| 53.0 | (2S,3R)-3-(5-chloropyrimidin-2-yl)butane-2-sulfonamide (Example 27.4), nicotinohydrazide (commercially available from Acros), and 2-isothiocyanato-1-methoxypropane (commercially available from Enamine). The title compound was the second diastereomer to elute from a Chiralpak AD-H column, SFC with 35% IPA. | 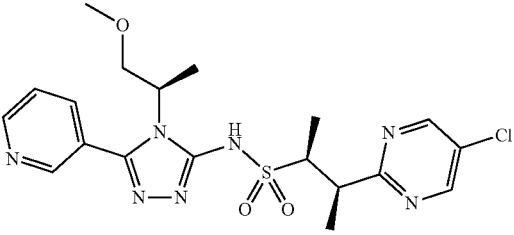 OR 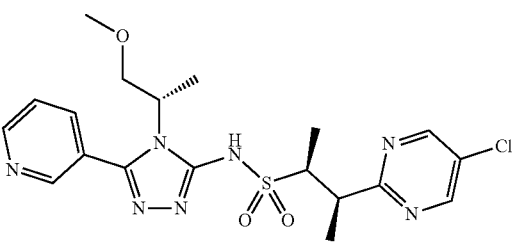 (2S,3R)-3-(5-chloro-2-pyrimidinyl)-N-(4-((2R)-1-methoxy-2-propanyl)-5-(3-pyridinyl)-4H-1,2,4-triazol-3-yl)-2-butanesulfonamide or (2S,3R)-3-(5-chloro-2-pyrimidinyl)-N-(4-((2S)-1-methoxy-2-propanyl)-5-(3-pyridinyl)-4H-1,2,4-triazol-3-yl)-2-butanesulfonamide. $^1$H NMR (400 MHz, CDCl$_3$) δ 1.48 (dd, J, 1.55 Hz, 3H) 1.48 (dd, J, 1.55 Hz, 3H) 1.52 (d, J = 6.84 Hz, 3 H) 3.33 (s, 3 H) 3.41-3.52 (m, 1 H) 3.73-3.96 (m, 2 H) 4.21-4.37 (m, 2 H) 7.53 (dd, J = 7.67, 5.18 Hz, 1 H) 8.08 (br d, J = 7.98 Hz, 1 H) 8.66 (s, 2 H) 8.82 (br d, J = 3.94 Hz, 1 H) 8.94 (br s, 1 H) 11.22 (br s, 1 H). LCMS ESI (pos.) ink: 466.0 (M + H)$^+$. |

TABLE 7-continued

| Example | Reagents | Structure, Name and Data |
|---|---|---|
| 54.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1-methoxypropane (commercially available from Enamine).<br>The title compound was the first diastereomer to elute from a Chiralpak AD-H column, SFC with 25% IPA. | OR<br><br>(1R,2S)-N-(4-((2R)-2-butanyl)-5-(6-methoxy-2-pyridinyl)-4H-1,2,4-triazol-3-yl)-1-(5-chloro-2-pyrimidinyl)-1-methoxy-2-propanesulfonamide or (1R,2S)-N-(4-((2S)-2-butanyl)-5-(6-methoxy-2-pyridinyl)-4H-1,2,4-triazol-3-yl)-1-(5-chloro-2-pyrimidinyl)-1-methoxy-2-propanesulfonamide.<br>$^1$H NMR (500 MHz, CDCl$_3$) δ 0.86 (t, J = 7.46 Hz, 3 H) 1.45 (d, J = 7.01 Hz, 3 H) 1.63 (d, J = 6.88 Hz, 3 H) 1.92 (dt, J = 14.11, 7.15 Hz, 1 H) 2.26-2.37 (m, 1 H) 3.39 (s, 3 H) 3.69-3.82 (m, 1 H) 3.95 (s, 3 H) 5.05-5.14 (m, 2 H) 6.90 (d, J = 8.43 Hz, 1 H) 7.49 (d, J = 7.27 Hz, 1 H) 7.72 (t, J = 7.85 Hz, 1 H) 8.74 (s, 2H) 11.07 (br s, 1 H). LCMS ESI (pos.) m/z: 496.1 (M + H)$^+$. |
| 55.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1-methoxypropane (commercially available from Enamine).<br>The title compound was the second diastereomer to elute from a Chiralpak AD-H column, SFC with 25% IPA. | OR |

TABLE 7-continued

| Example | Reagents | Structure, Name and Data |
|---|---|---|

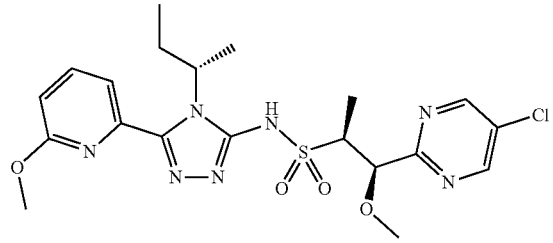

(1R,2S)-N-(4-((2R)-2-butanyl)-5-(6-methoxy-2-pyridinyl)-4H-1,2,4-triazol-3-yl)-1-(5-chloro-2-pyrimidinyl)-1-methoxy-2-propanesulfonamide or (1R,2S)-N-(4-((2S)-2-butanyl)-5-(6-methoxy-2-pyridinyl)-4H-1,2,4-triazol-3-yl)-1-(5-chloro-2-pyrimidinyl)-1-methoxy-2-propanesulfonamide.
$^1$H NMR (500 MHz, CDCl$_3$) δ 0.83 (t, J = 7.46 Hz, 3 H) 1.45 (d, J = 7.01 Hz, 3 H) 1.65 (d, J = 6.88 Hz, 3 H) 1.90 (dt, J = 14.08, 7.10 Hz, 1 H) 2.29-2.40 (m, 1 H) 3.37 (s, 3 H) 3.67-3.81 (m, 1 H) 3.95 (s, 3 H) 5.05-5.14 (m, 2 H) 6.90 (d, J = 8.30 Hz, 1 H) 7.49 (d, J = 7.27 Hz, 1 H) 7.72 (t, J = 7.85 Hz, 1 H) 8.73 (s, 2H) 11.12 (br s, 1 H). LCMS ESI (pos.) m/z: 496.1 (M + H)$^+$.

| 56.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatospiro[3.3]heptanes (Example 28.6). This was a mixture of two diastereomer with dr of 1/1. | 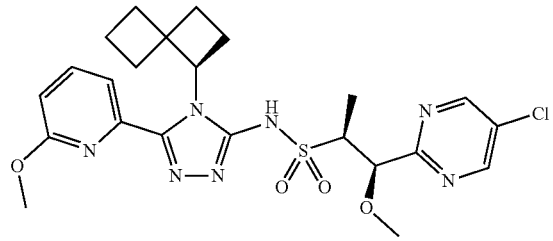<br><br>AND<br><br>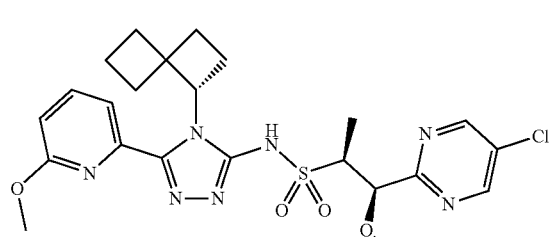<br><br>(1R,2S)-1-(5-chloro-2-pyrimidinyl)-1-methoxy-N-(5-(6-methoxy-2-pyridinyl)-4-((1R)-spiro[3.3]heptan-1-yl)-4H-1,2,4-triazol-3-yl)-2-propanesulfonamide and (1R,2S)-1-(5-chloro-2-pyrimidinyl)-1-methoxy-N-(5-(6-methoxy-2-pyridinyl)-4-((1S)-spiro[3.3]heptan-1-yl)-4H-1,2,4-triazol-3-yl)-2-propanesulfonamide. CMS ESI (pos.) m/z: 534.2 (M + H)$^+$. |

Example 57.0. Preparation of (1R,2S)-1-(5-chloro-2-pyrimidinyl)-1-methoxy-N-(5-(6-methoxy-2-pyridinyl)-4-(2-(methylsulfonyl)ethyl)-4H-1,2,4-triazol-3-yl)-2-propanesulfonamide 57.0

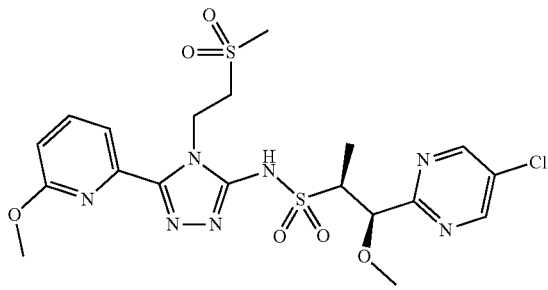

(1R,2S)-1-(5-Chloro-2-pyrimidinyl)-1-methoxy-N-(5-(6-methoxy-2-pyridinyl)-4-(2-(methylsulfonyl)ethyl)-4H-1,2,4-triazol-3-yl)-2-propanesulfonamide, Example 57.0

To a solution of (1R,2S)-1-(5-chloropyrimidin-2-yl)-1-methoxy-N-(5-(6-methoxypyridin-2-yl)-4-(2-(methylthio)ethyl)-4H-1,2,4-triazol-3-yl)propane-2-sulfonamide, Example 26.0 (220 mg, 0.428 mmol) in DCM (2853 μL) was added 3-chloroperoxybenzoic acid (288 mg, 1.284 mmol) portion-wise under an argon stream at 0° C. The reaction was stirred at 0 to RT for 3 h. The reaction mixture was diluted with water and extracted with DCM. The organic layer was concentrated in vacuo and absorbed onto a plug of silica gel and purified by chromatography through a Redi-Sep pre-packed silica gel column (12 g), eluting with a gradient of 10% to 100% of 33% EtOH/EtOAc in heptanes, to provide Example 57.0 (180 mg, 77% yield) as white glass. $^1$H NMR (400 MHz, CDCl$_3$) δ 1.44 (d, J=7.05 Hz, 3H) 3.06 (s, 3H) 3.26 (s, 3H) 3.64-3.73 (m, 3H) 4.02 (s, 3H) 4.89-5.02 (m, 2H) 5.09 (d, J=3.73 Hz, 1H) 6.91 (dd, J=8.09, 1.04 Hz, 1H) 7.66-7.75 (m, 2H) 8.72 (s, 2H) 11.36 (s, 1H). LCMS ESI (pos.) m/z: 546.0 (M+H)$^+$.

The compounds in the following table were synthesized following the procedure in Example 1.0 using the known starting material as described.

TABLE 8

| | | |
|---|---|---|
| 58.0 | (1S,2S)-1-isopropoxy-1-(5-methylpyrimidin-2-yl)propane-2-sulfonamide (Example 31.0), 1-isothiocyanato-1-methylcyclopropane (commercially available from Enamine), and 5-methylnicotinic acid hydrazide (commercially available from Bellen). | 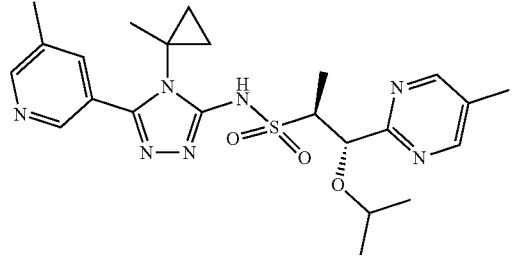<br>(1S,2S)-1-isopropoxy-N-(4-(1-methylcyclopropyl)-5-(5-methylpyridin-3-yl)-4H-1,2,4-triazol-3-yl)-1-(5-methylpyrimidin-2-yl)propane-2-sulfonamide.<br>$^1$H NMR (400 MHz, CD$_2$Cl$_2$) δ 12.47 (br. s., 1H), 8.76 (d, J = 1.9 Hz, 1H), 8.63 (d, J = 0.6 Hz, 2H), 8.60-8.57 (m, 1H), 7.83 (dt, J = 0.8, 2.2 Hz, 1H), 4.85 (d, J = 4.1 Hz, 1H), 3.73 (dq, J = 4.1, 7.0 Hz, 1H), 3.47 (m, 1H), 2.44 (d, J = 0.6 Hz, 3H), 2.33 (s, 3H), 1.73 (s, 3H), 1.53 (d, J = 7.0 Hz, 3H), 1.02 (d, J = 6.0 Hz, 3H), 0.96 (s, 2H), 0.87 (br. s., 2H), 0.79 (d, J = 6.2 Hz, 3H). LCMS ESI (pos.) m/z: 486.2 (M + H)$^+$. |

TABLE 8-continued

| | | |
|---|---|---|
| 59.0 | (1R,2S)-1-(5-chloropyrimidin-2-yl)-1-methoxypropane-2-sulfonamide (Example 29.3), 1-isothiocyanato-1-methylcyclobutane (commercially available from Ukrorgsyntez), and 6-methylpicolinohydrazide (commercially available from Enamine). | 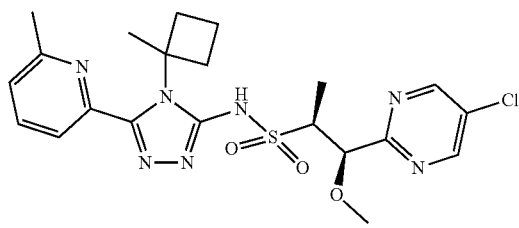 |

(1R,2S)-1-(5-chloropyrimidin-2-yl)-1-methoxy-N-(4-(1-methylcyclobutyl)-5-(6-methylpyridin-2-yl)-4H-1,2,4-triazol-3-yl)propane-2-sulfonamide
$^1$H NMR (400 MHz, CD$_2$Cl$_2$) δ 10.98 (br. s., 1H), 8.74-8.70 (m, 2H), 7.76-7.69 (m, 1H), 7.56 (td, J = 0.8, 7.7 Hz, 1H), 7.30-7.25 (m, 1H), 4.99 (d, J = 4.1 Hz, 1H), 3.66-3.57 (m, 1H), 3.28 (s, 3H), 2.58 (s, 3H), 2.31-2.11 (m, 4H), 1.98 (s, 3H), 1.86-1.74 (m, 1H), 1.70-1.60 (m, 1H), 1.41-1.34 (m, 3H). LCMS ESI (pos.) m/z: 492.2 (M + H)$^+$.

| | | |
|---|---|---|
| 60.0 | (1R,2S)-1-(5-chloropyrimidin-2-yl)-1-methoxypropane-2-sulfonamide (Example 29.3), nicotinohydrazide (commercially available from Acros), and 1-isothiocyanato-1-(methoxymethyl)cyclopropane (Example 72.0). | 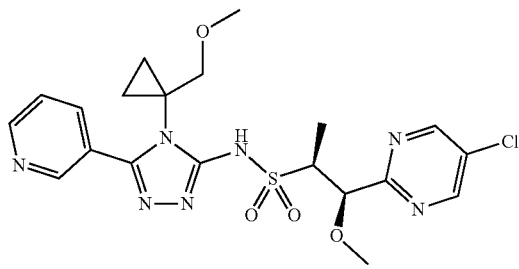 |

(1R,2S)-1-(5-chloro-2-pyrimidinyl)-1-methoxy-N-(4-(1-(methoxymethyl)cyclopropyl)-5-(3-pyridinyl)-4H-1,2,4-triazol-3-yl)-2-propanesulfonamide.
$^1$H NMR (500 MHz, DMSO-d$_6$) δ 1.00-1.23 (br s, 4 H) 1.32 (br d, J = 7.01 Hz, 3 H) 2.99-3.23 (m, 7 H) 3.40-3.53 (m, 1 H) 4.07 (br d, J = 4.28 Hz, 1 H) 5.01 (br d, J = 3.37 Hz, 1 H) 7.57 (br dd, J = 7.72, 4.87 Hz, 1 H) 8.42 (br d, J = 7.91 Hz, 1 H) 8.74 (br d, J = 3.50 Hz, 1 H) 8.96 (s, 2 H) 9.06 (s, 1 H) 13.13 (br s, 1 H). LCMS ESI (pos.) m/z: 494.2 (M + H)$^+$.

| | | |
|---|---|---|
| 61.0 | (1R,2S)-1-(5-chloropyrimidin-2-yl)-1-methoxypropane-2-sulfonamide (Example 29.3), picolinohydrazide (commercially available from TCI America), and 1-isothiocyanato-1-(methoxymethyl)cyclopropane (Example 72.0). | 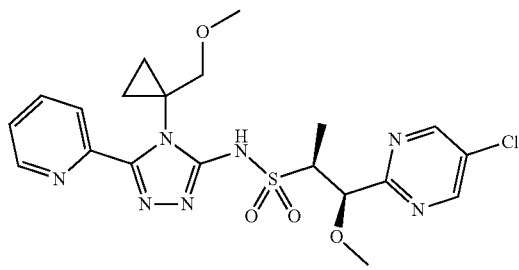 |

(1R,2S)-1-(5-chloro-2-pyrimidinyl)-1-methoxy-N-(4-(1-(methoxymethyl)cyclopropyl)-5-(2-pyridinyl)-4H-1,2,4-triazol-3-yl)-2-propanesulfonamide.
$^1$H NMR (400 MHz, CDCl$_3$) δ 1.09 (br s, 4 H) 1.47 (d, J = 7.05 Hz, 3 H) 3.36 (s, 3 H) 3.39 (s, 3 H) 3.70-3.82 (m, 1 H) 3.85 (br s, 1 H) 3.88-3.99 (m, 1 H) 5.12 (d, J = 4.15 Hz, 1 H) 7.43 (ddd, J = 7.64, 4.85, 1.09 Hz, 1 H) 7.84 (td, J = 7.83, 1.76 Hz, 1 H) 8.07 (d, J = 7.88 Hz, 1 H) 8.71-8.74 (m, 3 H) 11.10 (br s, 1 H). LCMS ESI (pos.) m/z: 494.2 (M + H)$^+$.

TABLE 8-continued

| | | |
|---|---|---|
| 62.0 | (1S,2S)-1-isopropoxy-1-(5-methylpyrimidin-2-yl)propane-2-sulfonamide (Example 31.0), nicotinohydrazide (commercially available from Acros), and 1-isothiocyanato-1-(methoxymethyl)cyclopropane (Example 72.0). | 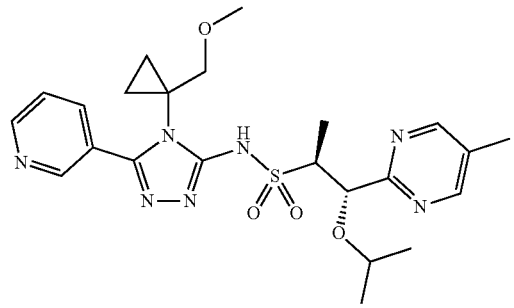<br>(1S,2S)-N-(4-(1-(methoxymethyl)cyclopropyl)-5-(3-pyridinyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 0.67 (br s, 4 H) 0.89-1.10 (m, 9 H) 2.28 (s, 3 H) 2.52-2.56 (m, 5 H) 3.52-3.64 (m, 1 H) 4.84 (br d, J = 7.66 Hz, 1 H) 7.58 (br dd, J = 7.79, 4.93 Hz, 1 H) 8.42 (br d, J = 7.92 Hz, 1 H) 8.68 (s, 2 H) 8.74 (br d, J = 3.50 Hz, 1 H) 9.06 (s, 1 H). LCMS ESI (pos.) m/z: 502.2 (M + H)$^+$. |
| 63.0 | (1S,2S)-1-isopropoxy-1-(5-methylpyrimidin-2-yl)propane-2-sulfonamide (Example 31.0), 5-methylnicotinohydrazide (commercially available from Bellen), and 1-isothiocyanato-1-(methoxymethyl)cyclopropane (Example 72.0). | 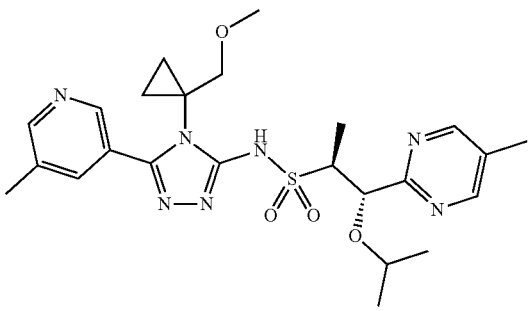<br>(1S,2S)-N-(4-(1-(methoxymethyl)cyclopropyl)-5-(5-methyl-3-pyridinyl)-4H-1,2,4-triazol-3-yl)-1-(5-methyl-2-pyrimidinyl)-1-(2-propanyloxy)-2-propanesulfonamide.<br>$^1$H NMR (400 MHz, CDCl$_3$) δ 0.80 (d, J = 6.12 Hz, 3 H) 0.97 (br s, 2 H) 0.99-1.11 (m, 5 H) 1.58 (d, J = 7.05 Hz, 3 H) 2.32 (s, 3 H) 2.41 (s, 3 H) 3.04 (br s, 1 H) 3.38 (s, 3 H) 3.41-3.56 (m, 1 H) 3.80 (qd, J = 7.00, 3.99 Hz, 1 H) 4.46 (br s, 1 H) 4.86 (d, J = 3.94 Hz, 1 H) 8.26 (br s, 1 H) 8.56 (d, J = 1.45 Hz, 1 H) 8.61 (s, 2 H) 9.10 (s, 1 H) 12.80 (br s, 1H). LCMS ESI (pos.) m/z: 516.2 (M + H)$^+$. |

TABLE 8-continued

| | | |
|---|---|---|
| 64.0 | (1S,2S)-1-isopropoxy-1-(5-methylpyrimidin-2-yl)propane-2-sulfonamide (Example 31.0), 6-methoxypicolinohydrazide (commercially available from Sigma Aldrich), and 1-isothiocyanato-1-(methoxymethyl)cyclopropane (Example 72.0), | 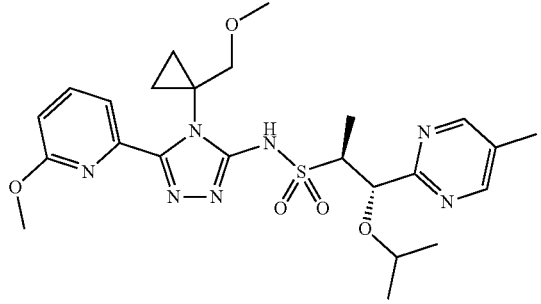<br>(1S,2S)-N-(4-(1-(methoxymethyl)cyclopropyl)-5-(6-methoxy-2-pyridinyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-d$_6$) δ 0.66 (br s, 4 H) 0.89 (br s, 1 H) 0.99 (br d, J = 5.84 Hz, 4 H) 1.04-1.12 (m, 4 H) 2.27 (s, 3 H) 2.52-2.57 (m, 2 H) 3.14-3.23 (m, 1 H) 3.52-3.70 (m, 1 H) 3.91 (s, 5 H) 4.07 (br d, J = 5.32 Hz, 1 H) 4.84 (br d, J = 7.79 Hz, 1 H) 7.01 (br d, J = 8.43 Hz, 1 H) 7.47 (br d, J = 7.27 Hz, 1 H) 7.88 (br t, J = 7.85 Hz, 1 H) 8.67 (s, 2 H) 12.91 (br s, 1 H). LCMS ESI (pos.) m/z: 532.2 (M + H)$^+$. |
| 65.0 | (1S,2S)-1-isopropoxy-1-(5-methylpyrimidin-2-yl)propane-2-sulfonamide (Example 31.0), picolinohydrazide (commercially available from TCI America), and 1-isothiocyanato-1-(methoxymethyl)cyclopropane (Example 72.0). | 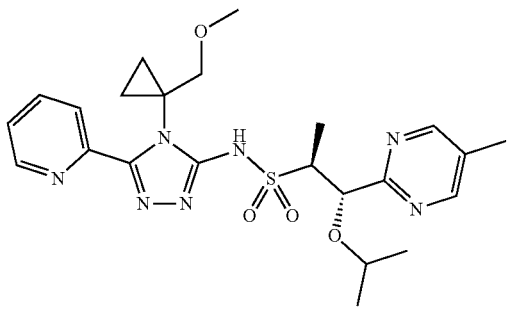<br>(1S,2S)-N-(4-(1-(methoxymethyl)cyclopropyl)-5-(2-pyridinyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-d$_6$) δ 0.68 (br s, 4 H) 0.78-0.96 (m, 2 H) 0.99 (br d, J = 5.97 Hz, 3 H) 1.04 (br d, J = 6.36 Hz, 4 H) 2.27 (s, 3 H) 2.52-2.56 (m, 5 H) 3.25 (br s, 2 H) 3.55-3.69 (m, 1 H) 3.83 (q, J = 10.12 Hz, 2 H) 4.85 (br d, J = 7.66 Hz, 1 H) 7.53-7.65 (m, 1 H) 7.88 (br d, J = 7.78 Hz, 1 H) 8.00 (br t, J = 7.72 Hz, 1 H) 8.67 (s, 2 H) 8.74 (br d, J = 4.15 Hz, 1 H). LCMS ESI (pos.) m/z: 502.2 (M + H)$^+$. |

TABLE 8-continued

| 66.0 | (2S,3R)-3-(5-methylpyrazin-2-yl)butane-2-sulfonamide (Example 27.2), picolinohydrazide (commercially available from TCI America), and 1-isothiocyanato-1-(methoxymethyl)cyclopropane (Example 72.0). | 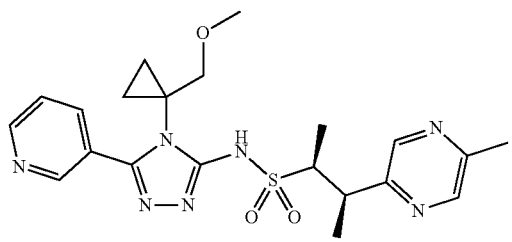<br>(2S,3R)-N-(4-(1-(methoxymethyl)cyclopropyl)-5-(3-pyridinyl)-4H-1,2,4-triazol-3-yl)-3-(5-methyl-2-pyrazinyl)-2-butanesulfonamide.<br>$^1$H NMR (400 MHz, CDCl$_3$) δ 11.43 (br s, 1 H) 9.23 (d, J = 1.55 Hz, 1 H) 8.76 (dd, J = 4.87, 1.66 Hz, 1 H) 8.49 (dt, J = 8.11, 1.90 Hz, 1 H) 8.45 (d, J = 1.35 Hz, 1 H) 8.38 (d, J = 0.73 Hz, 1 H) 7.42 (ddd, J = 8.01, 4.90, 0.78 Hz, 1 H) 4.00-4.80 (m, 1 H) 3.89 (qd, J = 7.08, 4.46 Hz, 1 H) 3.68 (qd, J = 6.98, 4.46 Hz, 1 H) 3.37 (s, 3 H) 2.73-3.17 (m, 1 H) 2.54 (s, 3 H) 2.11 (br d, J = 13.89 Hz, 1 H) 1.49 (d, J = 7.15 Hz, 3 H) 1.44 (d, J = 7.05 Hz, 3 H) 1.06 (br s, 2 H) 0.52-0.99 (m, 2 H). LCMS ESI (pos.) m/z: 234.2 (M + H)$^+$. |
| --- | --- | --- |
| 67.0 | (1R,2S)-1-methoxy-1-(5-methylpyrimidin-2-yl)propane-2-sulfonamide (Example 29.0), picolinohydrazide (commercially available from TCI America), and 1-isothiocyanato-1-(methoxymethyl)cyclopropane (Example 72.0). | 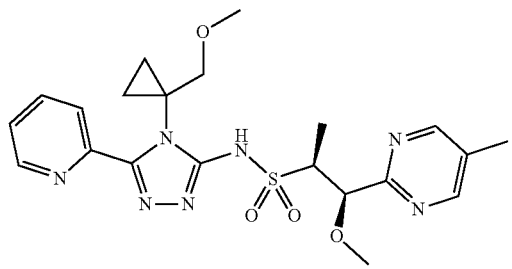<br>(1R,2S)-1-methoxy-N-(4-(1-(methoxymethyl)cyclopropyl)-5-(2-pyridinyl)-4H-1,2,4-triazol-3-yl)-1-(5-methyl-2-pyrimidinyl)-2-propanesulfonamide.<br>$^1$H NMR (400 MHz, CDCl$_3$) δ 0.94 (br s, 1 H) 1.08 (br d, J = 4.87 Hz, 2 H) 1.18 (br s, 1 H) 1.48 (d, J = 7.05 Hz, 3 H) 2.18 (br s, 1 H) 2.34 (s, 3 H) 3.30-3.38 (m, 3 H) 3.72-3.83 (m, 1 H) 3.86 (br s, 1 H) 3.92 (br s, 1 H) 5.10 (d, J = 4.04 Hz, 1 H) 7.43 (ddd, J = 7.67, 4.77, 1.14 Hz, 1 H) 7.85 (td, J = 7.83, 1.76 Hz, 1 H) 8.09 (d, J = 7.67 Hz, 1 H) 8.62 (s, 2 H) 8.74 (d, J = 4.96 Hz, 1 H). LCMS ESI (pos.) m/z: 474.0 (M + H)$^+$. |

TABLE 8-continued

| | | |
|---|---|---|
| 68.0 | (2S,3R)-3-(5-chloropyrimidin-2-yl)butane-2-sulfonamide (Example 27.4), picolinohydrazide (commercially available from TCI America), and 1-isothiocyanato-1-(methoxymethyl)cyclopropane (Example 72.0). | 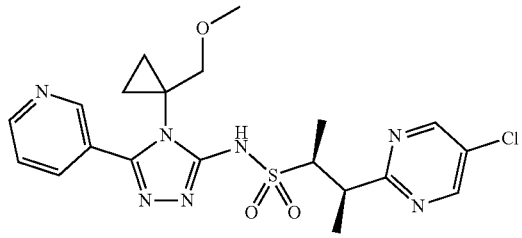<br>(2S,3R)-3-(5-chloro-2-pyrimidinyl)-N-(4-(1-(methoxymethyl)cyclopropyl)-5-(3-pyridinyl)-4H-1,2,4-triazol-3-yl)-2-butanesulfonamide.<br>$^1$H NMR (400 MHz, CDCl$_3$) δ 0.87 (br d, J = 7.36 Hz, 2 H) 1.09 (br s, 2 H) 1.47-1.49 (m, 6H) 3.38 (S, 3 H) 3.76-3.97 (m, 3 H) 4.38 (br s, 1 H) 7.49 (br dd, J = 7.67, 4.98 Hz, 1 H) 8.58 (br d, J = 7.98 Hz, 1 H) 8.64 (s, 2 H) 8.74-8.82 (m, 1 H) 9.30 (br s, 1 H) 11.31 (br s, 1 H). LCMS ESI (pos.) m/z: 478.2 (M + H)$^+$. |
| 69.0 | (1R,2S)-1-(5-chloropyrimidin-2-yl)-1-methoxypropane-2-sulfonamide (Example 29.3), 6-methoxypicolinohydrazide (commercially available from Sigma Aldrich), and isothiocyanatocyclopropane (commercially available from Lancaster). | 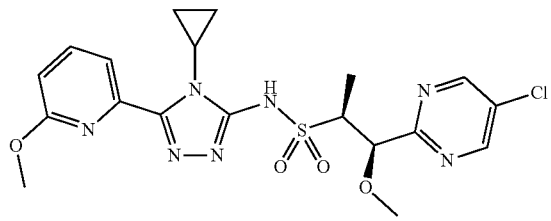<br>(1R,2S)-1-(5-chloro-2-pyrimidinyl)-N-(4-cyclopropyl-5-(6-methoxy-2-pyridinyl)-4H-1,2,4-triazol-3-yl)-1-methoxy-2-propanesulfonamide.<br>$^1$H NMR (400 MHz, CDCl$_3$) d 0.78-0.88 (m, 1 H) 0.88-1.06 (m, 3 H) 1.47 (d, J = 6.95 Hz, 3 H) 1.84 (br s, 1 H) 3.25-3.29 (m, 1 H) 3.32 (s, 3 H) 3.71-3.79 (m, 1 H) 3.96 (s, 3 H) 5.11 (d, J = 3.63 Hz, 1 H) 6.89 (d, J = 8.29 Hz, 1 H) 7.45 (d, J = 7.26 Hz, 1 H) 7.71 (t, J = 7.77 Hz, 1 H) 8.73 (s, 2 H) 11.06 (br s, 1H). LCMS ESI (pos.) m/z: 480.0 (M + H)$^+$. |
| 70.0 | (1S,2S)-1-(5-chloropyrimidin-2-yl)-1-isopropoxypropane-2-sulfonamide (Example 31.01), 6-methoxypicolinohydrazide (commercially available from Sigma Aldrich), and isothiocyanatocyclopropane (commercially available from Lancaster). | 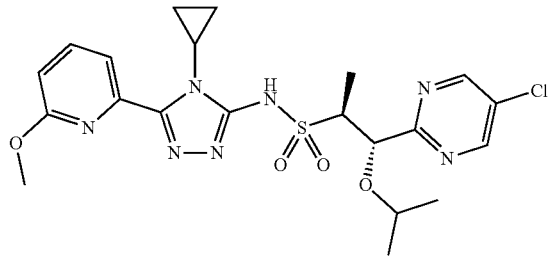<br>(1S,2S)-1-(5-chloro-2-pyrimidinyl)-N-(4-cyclopropyl-5-(6-methoxy-2-pyridinyl)-4H-1,2,4-triazol-3-yl)-1-(2-propanyloxy)-2-propanesulfonamide.<br>$^1$H NMR (400 MHz, CDCl$_3$) δ 0.79-0.89 (m, 5 H) 0.99-1.11 (m, 5 H) 1.54 (d, J = 7.05 Hz, 3 H) 3.26 (dq, J = 7.15, 3.59 Hz, 1 H) 3.52 (quin, J = 6.06 Hz, 1 H) 3.88 (qd, J = 7.05, 4.87 Hz, 2 H) 3.97 (s, 3 H) 4.94 (d, J = 4.66 Hz, 1 H) 6.85-6.95 (m, 1 H) 7.44 (d, J = 7.26 Hz, 1 H) 7.65-7.78 (m, 1 H) 8.73 (s, 2 H). LCMS ESI (pos.) m/z: 508.0 (M + H)$^+$. |

Example 71.0. Preparation of 2-isothiocyanato-1,3-dimethoxypropane

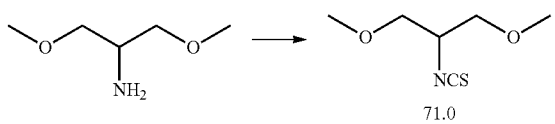

71.0

2-Isothiocyanato-1,3-dimethoxypropane, Example 71.0

To a dry 200 mL round-bottom flask was added di(2-pyridyl) thionocarbonate (5.34 g, 23.00 mmol) in DCM (73.0 mL). 2-Amino-1,3-dimethoxypropane in DCM (15 mL) was added dropwise via an addition funnel over 5 min. The reaction mixture was then stirred at RT for 3.5 h. The reaction mixture was concentrated in vacuo. The residual material was absorbed onto a plug of silica gel and purified by chromatography through a Redi-Sep pre-packed silica gel column (40 g), eluting with a gradient of 0% to 50% EtOAc in heptanes, to provide 2-isothiocyanato-1,3-dimethoxypropane (3.28 g, 20.34 mmol, 93% yield) as colorless oil. LCMS-ESI (pos.) m/z: 162.2 (M+H)$^+$.

The compounds set forth in the following table were synthesized following the procedure in Example 71.0 using the known starting material as described.

TABLE 9

| Example | Reagents | Structure, Name and Data |
|---|---|---|
| 72.0 | 1-(methoxymethyl)cyclopropanamine hydrochloride (J&W Pharm Lab) and N,N-diisopropylethylamine (commercially available from Sigma Aldrich). | 1-isothiocyanato-1-(methoxymethyl)cyclopropane. $^1$H NMR (400 MHz, CDCl$_3$) δ 3.47 (s, 2H), 3.43 (s, 3H), 1.06-1.16 (m, 2H), 0.81-0.94 (m, 2H). |

The compounds in the following table were synthesized following the procedure in Example 1.0 using the known starting material as described.

TABLE 10

| Example | Reagents | Structure, Name and Data |
|---|---|---|
| 73.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (isothiocyanatomethyl)cyclobutane (commercially available from Frontier Scientific Services Inc.). | (1R,2S)-1-(5-chloropyrimidin-2-yl)-N-(4-(cyclobutylmethyl)-5-(6-methoxypyridin-2-yl)-4H-1,2,4-triazol-3-yl)-1-methoxypropane-2-sulfonamide. $^1$H NMR (600 MHz, DMSO-d$_6$) δ 13.20 (br s, 1H), 8.91 (s, 2H), 7.89 (t, J = 7.86 Hz, 1H), 7.63 (d, J = 7.40 Hz, 1H), 7.02 (d, J = 8.39 Hz, 1H), 4.85 (d, J = 5.11 Hz, 1H), 4.36 (dd, J = 7.25, 13.43 Hz, 1H), 4.23 (dd, J = 7.63, 13.43 Hz, 1H), 3.93 (s, 3H), 3.63 (dd, J = 5.38, 6.83 Hz, 1H), 3.12-3.18 (m, 3H), 2.68 (td, J = 7.61, 15.30 Hz, 1H), 1.79-1.86 (m, 2H), 1.66-1.78 (m, 4H), 1.34 (d, J = 6.94 Hz, 3H). LCMS ESI (pos.) m/z: 508.20 (M + H)$^+$ |

TABLE 10-continued

| Example | Reagents | Structure, Name and Data |
|---|---|---|
| 74.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-fluoro-4-(2-isothiocyanatoethyl)benzene (commercially available from Frontier Scientific Services Inc.). | 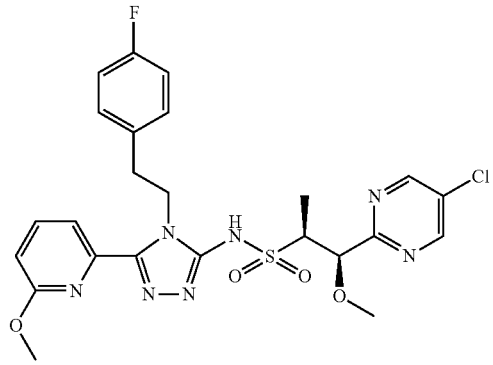<br><br>(1R,2S)-1-(5-chloropyrimidin-2-yl)-N-(4-(4-fluorophenethyl)-5-(6-methoxypyridin-2-yl)-4H-1,2,4-triazol-3-yl)-1-methoxypropane-2-sulfonamide.<br>$^1$H NMR (600 MHz, DMSO-$d_6$) δ 13.20 (s, 1H), 8.92 (s, 2H), 7.82 (dd, J = 7.48, 8.24 Hz, 1H), 7.38 (d, J = 7.32 Hz, 1H), 7.04 (t, J = 6.54 Hz, 2H), 6.94-6.98 (m, 3H), 4.90 (d, J = 4.58 Hz, 1H), 4.47-4.57 (m, 2H), 3.88 (s, 3H), 3.56 (dd, J = 4.65, 7.02 Hz, 1H), 3.15 (s, 3H), 2.96 (t, J = 7.29 Hz, 2H), 1.31 (d, J = 7.02 Hz, 3H). LCMS ESI (pos.) m/z: 562.20 (M + H)$^+$ |
| 75.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanato-2-methylcyclohexane (commercially available from Frontier Scientific Services Inc.). | 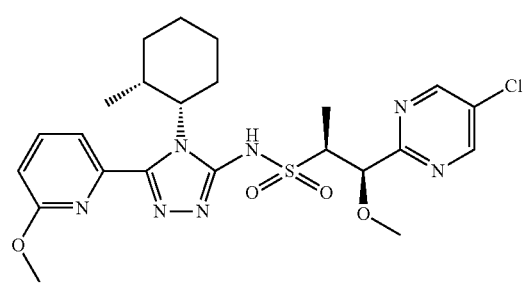<br>AND<br>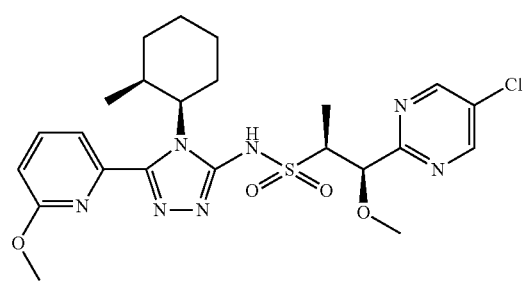<br>AND<br>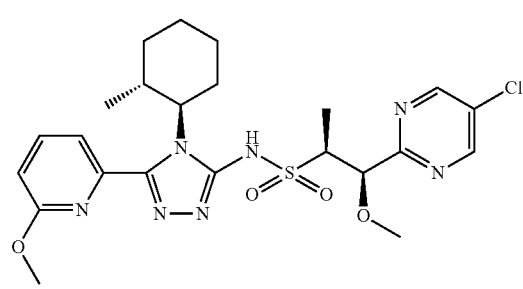<br>AND |

| Example | Reagents | Structure, Name and Data |
|---|---|---|
| | | 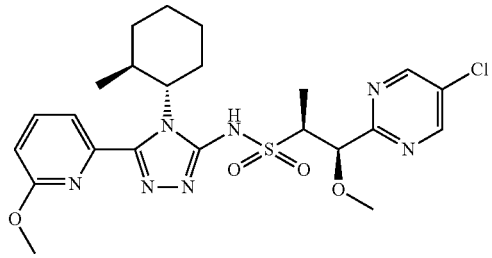
(1R,2S)-1-(5-chloropyrimidin-2-yl)-1-methoxy-N-(5-(6-methoxypyridin-2-yl)-4-((1S,2R)-2-methylcyclohexyl)-4H-1,2,4-triazol-3-yl)propane-2-sulfonamide and (1R,2S)-1-(5-chloropyrimidin-2-yl)-1-methoxy-N-(5-(6-methoxypyridin-2-yl)-4-((1R,2S)-2-methylcyclohexyl)-4H-1,2,4-triazol-3-yl)propane-2-sulfonamide and (1R,2S)-1-(5-chloropyrimidin-2-yl)-1-methoxy-N-(5-(6-methoxypyridin-2-yl)-4-((1R,2R)-2-methylcyclohexyl)-4H-1,2,4-triazol-3-yl)propane-2-sulfonamide and (1R,2S)-1-(5-chloropyrimidin-2-yl)-1-methoxy-N-(5-(6-methoxypyridin-2-yl)-4-((1S,2S)-2-methylcyclohexyl)-4H-1,2,4-triazol-3-yl)propane-2-sulfonamide.
LCMS ESI (pos.) m/z: 536.20 (M + H)⁺ |
| 76.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 3-(isothiocyanatomethyl)isoxazole (commercially available from Frontier Scientific Services Inc.). | (1R,2S)-1-(5-chloropyrimidin-2-yl)-N-(4-(isoxazol-3-ylmethyl)-5-(6-methoxypyridin-2-yl)-4H-1,2,4-triazol-3-yl)-1-methoxypropane-2-sulfonamide.
$^1$H NMR (600 MHz, DMSO-$d_6$) δ 13.35 (br s, 1H), 8.91 (s, 2H), 8.84 (d, J = 1.68 Hz, 1H), 7.85-7.89 (m, 1H), 7.67 (d, J = 7.40 Hz, 1H), 6.96 (d, J = 8.32 Hz, 1H), 6.55 (d, J = 1.75 Hz, 1H), 5.70 (d, J = 16.56 Hz, 1H), 5.58 (d, J = 16.48 Hz, 1H), 4.78 (d, J = 4.96 Hz, 1H), 3.70 (s, 3H), 3.57 (dd, J = 4.96, 6.94 Hz, 1H), 3.13 (s, 3H), 1.24 (d, J = 6.94 Hz, 3H). LCMS ESI (pos.) m/z: 521.20 (M + H)⁺ |

TABLE 10-continued

| Example | Reagents | Structure, Name and Data |
|---|---|---|
| 77.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-isothiocyanato-1,1-dimethoxyethane (commercially available from Frontier Scientific Services Inc.). | 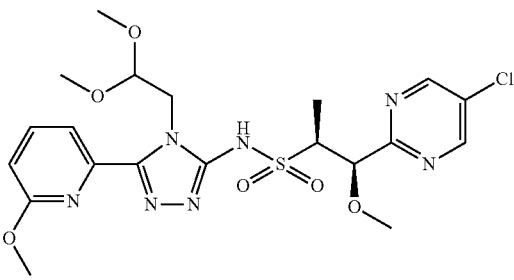(1R,2S)-1-(5-chloropyrimidin-2-yl)-N-(4-(2,2-dimethoxyethyl)-5-(6-methoxypyridin-2-yl)-4H-1,2,4-triazol-3-yl)-1-methoxypropane-2-sulfonamide.<br>$^1$H NMR (600 MHz, DMSO-d$_6$) δ 13.24 (br s, 1H), 8.91 (s, 2H), 7.90 (t, J = 7.78 Hz, 1H), 7.61 (d, J = 7.40 Hz, 1H), 7.01 (d, J = 8.32 Hz, 1H), 4.86 (d, J = 4.96 Hz, 1H), 4.62 (t, J = 5.53 Hz, 1H), 4.45 (dd, J = 5.15, 13.85 Hz, 1H), 4.39 (dd, J = 5.76, 13.85 Hz, 1H), 3.93 (s, 3H), 3.59-3.64 (m, 1H), 3.18 (s, 3H), 3.16 (s, 3H), 3.15 (s, 3H), 1.33 (d, J = 7.02 Hz, 3H). LCMS ESI (pos.) m/z: 528.20 (M + H)$^+$ |

Following the procedures described herein, the following compounds may be synthesized using the intermediates and conditions described in the following table.

TABLE 11

| Example | Reagents | Structure, Name and Data |
|---|---|---|
| 78.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (isothiocyanatomethyl)benzene (commercially available from Frontier Scientific Services Inc.). | 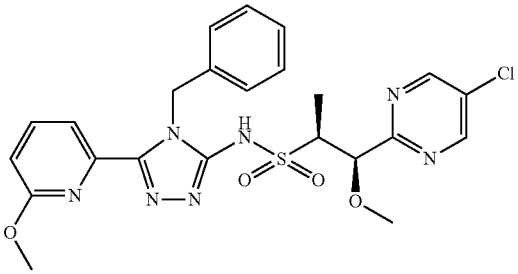(1R,2S)-N-(4-benzyl-5-(6-methoxypyridin-2-yl)-4H-1,2,4-triazol-3-yl)-1-(5-chloropyrimidin-2-yl)-1-methoxypropane-2-sulfonamide. |
| 79.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanato-2-methylpropane (commercially available from Frontier Scientific Services Inc.). | 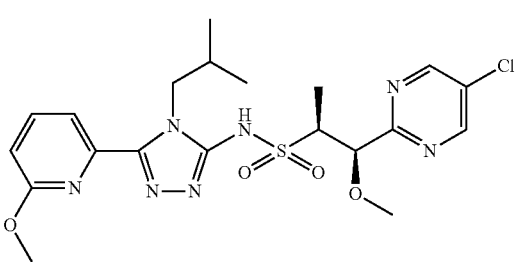(1R,2S)-1-(5-chloropyrimidin-2-yl)-N-(4-isobutyl-5-(6-methoxypyridin-2-yl)-4H-1,2,4-triazol-3-yl)-1-methoxypropane-2-sulfonamide. |

TABLE 11-continued

| Example | Reagents | Structure, Name and Data |
|---|---|---|
| 80.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (isothiocyanatomethyl)cyclopentane (commercially available from Frontier Scientific Services Inc.). | 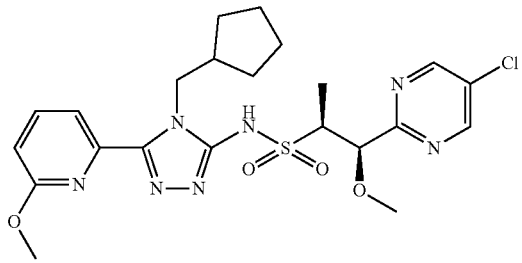<br><br>(1R,2S)-1-(5-chloropyrimidin-2-yl)-N-(4-(cyclopentylmethyl)-5-(6-methoxypyridin-2-yl)-4H-1,2,4-triazol-3-yl)-1-methoxypropane-2-sulfonamide. |
| 81.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (isothiocyanatomethyl)cyclohexane (commercially available from Frontier Scientific Services Inc.). | 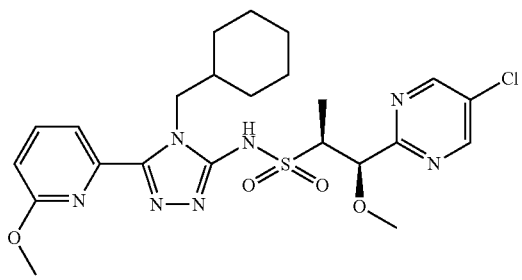<br><br>(1R,2S)-1-(5-chloropyrimidin-2-yl)-N-(4-(cyclohexylmethyl)-5-(6-methoxypyridin-2-yl)-4H-1,2,4-triazol-3-yl)-1-methoxypropane-2-sulfonamide. |
| 82.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 2-(1-isothiocyanatoethyl)tetrahydrofuran (commercially available from Frontier Scientific Services Inc.). | 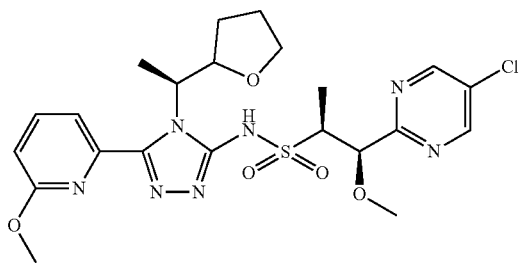<br><br>AND<br><br>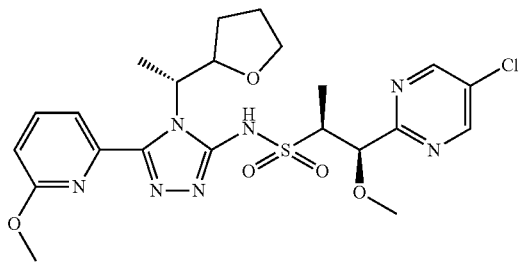<br><br>(1R,2S)-1-(5-chloropyrimidin-2-yl)-1-methoxy-N-(5-(6-methoxypyridin-2-yl)-4-((1S)-1-(tetrahydrofuran-2-yl)ethyl)-4H-1,2,4-triazol-3-yl)propane-2-sulfonamide and (1R,2S)-1-(5-chloropyrimidin-2-yl)-1-methoxy-N-(5-(6-methoxypyridin-2-yl)-4-((1R)-1-(tetrahydrofuran-2-yl)ethyl)-4H-1,2,4-triazol-3-yl)propane-2-sulfonamide. |

TABLE 11-continued

| Example | Reagents | Structure, Name and Data |
|---|---|---|
| 83.0 | (1R,2S)-1-(5-chloropyrimidin-2-yl)-1-methoxypropane-2-sulfonamide (Example 29.3), 6-methoxypicolinohydrazide (commercially available from Sigma Aldrich), and N-cyclopropyl-2-isothiocyanatoacetamide (commercially available from Frontier Scientific Services Inc.). | 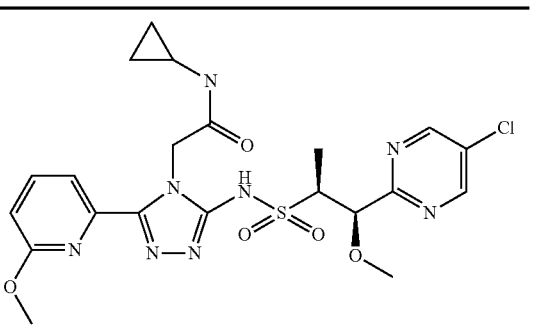<br>2-(3-((1S,2R)-2-(5-chloropyrimidin-2-yl)-2-methoxy-1-methylethylsulfonamido)-5-(6-methoxypyridin-2-yl)-4H-1,2,4-triazol-4-yl)-N-cyclopropylacetamide. |
| 84.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-ethyl-2-(isothiocyanatomethyl)pyrrolidine (commercially available from Frontier Scientific Services Inc.). | 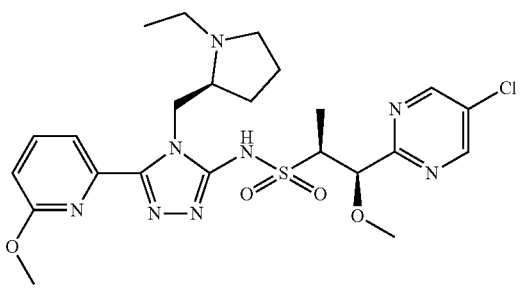<br>AND<br>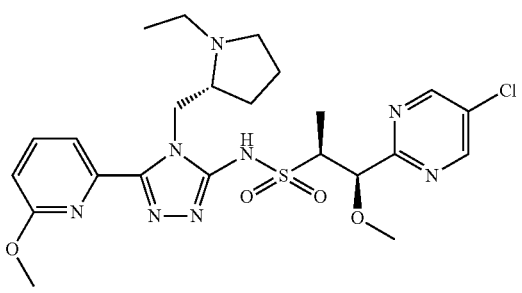<br>(1R,2S)-1-(5-chloropyrimidin-2-yl)-N-(4-(((S)-1-ethylpyrrolidin-2-yl)methyl)-5-(6-methoxypyridin-2-yl)-4H-1,2,4-triazol-3-yl)-1-methoxypropane-2-sulfonamide and (1R,2S)-1-(5-chloropyrimidin-2-yl)-N-(4-(((R)-1-ethylpyrrolidin-2-yl)methyl)-5-(6-methoxypyridin-2-yl)-4H-1,2,4-triazol-3-yl)-1-methoxypropane-2-sulfonamide. |
| 85.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatoadamantane (commercially available from Frontier Scientific Services Inc.). | 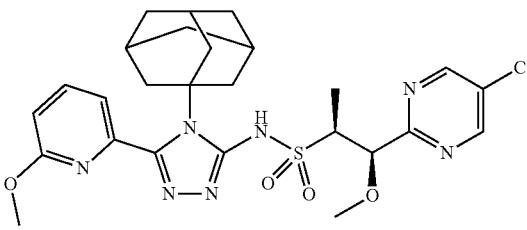<br>(1R,2S)-N-(4-(adamantan-1-yl)-5-(6-methoxypyridin-2-yl)-4H-1,2,4-triazol-3-yl)-1-(5-chloropyrimidin-2-yl)-1-methoxypropane-2-sulfonamide. |

The compounds set forth in the following table were synthesized following the procedure in Example 1.0 using the known starting material as described.

TABLE 12

| Example | Reagents | Structure, Name and Data |
|---|---|---|
| 86.0 | picolinohydrazide (commercially available from Sigma-Aldrich Inc.), 2-isothiocyanatopropane (commercially available from Sigma-Aldrich Inc.), and (1R,2S)-1-(5-chloropyrimidin-2-yl)-1-methoxypropane-2-sulfonamide (Example 29.3). | 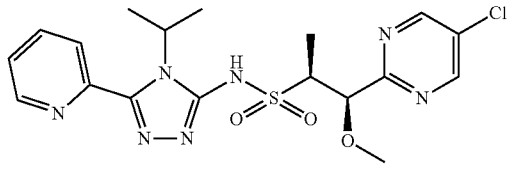<br>(1R,2S)-1-(5-chloropyrimidin-2-yl)-N-(4-isopropyl-5-(pyridin-2-yl)-4H-1,2,4-triazol-3-yl)-1-methoxypropane-2-sulfonamide.<br>$^1$H NMR (600 MHz, DMSO-$d_6$) δ 8.90-9.01 (m, 2 H) 8.72-8.79 (m, 1 H) 8.00-8.05 (m, 1 H) 7.90-7.94 (m, 1 H) 7.56-7.62 (m, 1 H) 5.12-5.18 (m, 1 H) 4.92-4.97 (m, 1 H) 3.54-3.60 (m, 1 H) 3.13-3.16 (m, 3 H) 1.47-1.49 (m, 6H) 1.29-1.32 (m, 3 H) LCMS-ESI (pos.) m/z: 452.2 (M + H)$^+$. |
| 87.0 | nicotinohydrazide (commercially available from Sigma-Aldrich), 2-isothiocyanatopropane (commercially available from Sigma-Aldrich), and (1R,2S)-1-(5-chloropyrimidin-2-yl)-1-methoxypropane-2-sulfonamide (Example 29.3). | 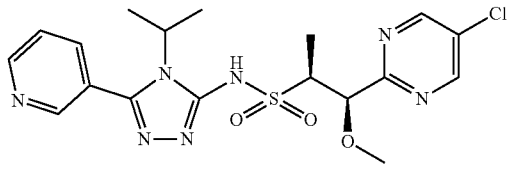<br>(1R,2S)-1-(5-chloropyrimidin-2-yl)-N-(4-isopropyl-5-(pyridin-3-yl)-4H-1,2,4-triazol-3-yl)-1-methoxypropane-2-sulfonamide.<br>$^1$H NMR (600 MHz, DMSO-$d_6$) δ 8.91-8.94 (m, 2H) 8.73-8.76 (m, 1 H) 8.70-8.73 (m, 1 H) 7.93-7.98 (m, 1 H) 7.56-7.60 (m, 1 H) 4.88-4.92 (m, 1 H) 4.15-4.23 (m, 1 H) 3.80-3.87 (m, 1 H) 3.20-3.22 (m, 3 H) 1.37-1.41 (m, 6H) 1.27-1.32 (m, 3 H). LCMS-ESI (pos.) m/z: 452.2 (M + H)$^+$. |
| 88.0 | isonicotinohydrazide (commercially available from Sigma-Aldrich), 2-isothiocyanatopropane (commercially available from Sigma-Aldrich), and (1R,2S)-1-(5-chloropyrimidin-2-yl)-1-methoxypropane-2-sulfonamide (Example 29.3). | 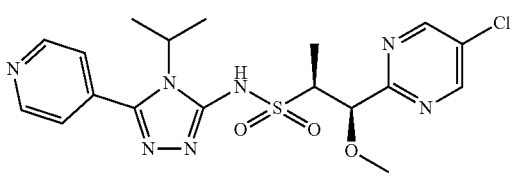<br>(1R,2S)-1-(5-chloropyrimidin-2-yl)-N-(4-isopropyl-5-(pyridin-4-yl)-4H-1,2,4-triazol-3-yl)-1-methoxypropane-2-sulfonamide.<br>$^1$H NMR (600 MHz, DMSO-$d_6$) δ 12.96-13.35 (m, 1 H) 8.94-8.99 (m, 2 H) 8.80-8.83 (m, 2 H) 7.61-7.65 (m, 2 H) 4.92-4.98 (m, 1 H) 4.23-4.32 (m, 1 H) 3.16-3.19 (m, 3 H) 1.43-1.47 (m, 6H) 1.30-1.33 (m, 3 H). LCMS-ESI (pos.) m/z: 452.2 (M + H)$^+$. |

| Example | Reagents | Structure, Name and Data |
|---|---|---|
| 89.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-(isothiocyanatomethyl)-4-methoxybenzene (commercially available from Frontier Scientific Services Inc.). | 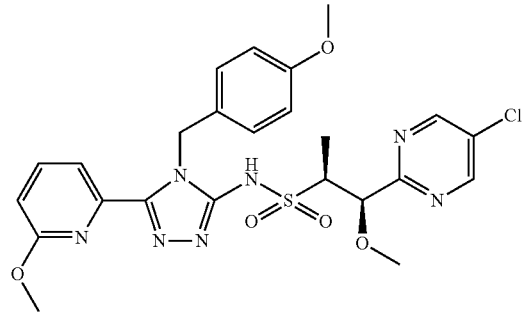<br><br>(1R,2S)-1-(5-chloropyrimidin-2-yl)-1-methoxy-N-(4-(4-methoxybenzyl)-5-(6-methoxypyridin-2-yl)-4H-1,2,4-triazol-3-yl)propane-2-sulfonamide.<br>$^1$H NMR (500 MHz, CDCl$_3$) δ 10.99 (br s, 1H), 8.71 (s, 2H), 7.71 (t, J = 7.81 Hz, 1H), 7.61 (d, J = 7.27 Hz, 1H), 7.14-7.19 (m, J = 8.56 Hz, 2H), 6.89 (d, J = 8.30 Hz, 1H), 6.71-6.78 (m, J = 8.69 Hz, 2H), 5.62-5.69 (m, 2H), 4.82 (d, J = 5.19 Hz, 1H), 3.83 (s, 3H), 3.73-3.77 (m, 1H), 3.73 (s, 3H), 3.27-3.38 (m, 3H), 1.33 (d, J = 7.01 Hz, 3H). LCMS-ESI (pos.) m/z: 560.0 (M + H)$^+$. |
| 90.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatospiro[2.2]pentane (Example 28.7).<br>The title compound was the first diastereomer to elute from Chiralpak AD-H column, SFC with 40% IPA. | 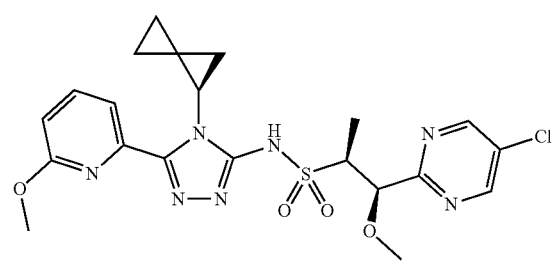<br><br>OR<br><br>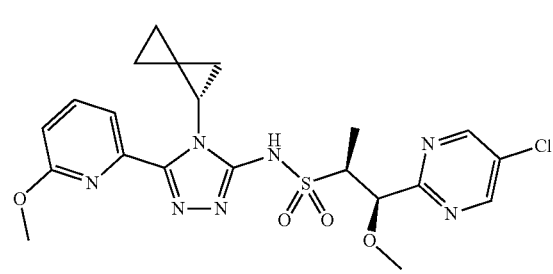<br><br>(1R,2S)-1-(5-chloro-2-pyrimidinyl)-1-methoxy-N-(5-(6-methoxy-2-pyridinyl)-4-((1R)-spiro[2.2]pentan-1-yl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-spiro[2.2]pentan-1-yl)-4H-1,2,4-triazol-3-yl)-2-propane sulfonamide.<br>$^1$H NMR (400 MHz, CD$_3$OD) δ 8.84 (s, 2 H) 7.84 (dd, J = 8.40, 7.36 Hz, 1 H) 7.49 (dd, J = 7.26, 0.62 Hz, 1 H) 6.97 (dd, J = 8.40, 0.62 Hz, 1 H) 5.09 (d, J = 3.94 Hz, 1 H) 3.99 (s, 3 H) 3.72 (dd, J = 6.74, 3.94 Hz, 1 H) 3.66 (qd, J = 7.03, 3.99 Hz, 1 H) 3.22 (s, 3 H) 1.49-1.59 (m, 2 H) 1.42 (d, J = 7.05 Hz, 3 H) 0.66-0.83 (m, 2 H) 0.62 (dt, J = 8.94, 4.70 Hz, 1 H) 0.29 (dt, J = 9.23, 4.72 Hz, 1 H). LCMS ESI (pos.) m/z: 506.0 (M + H)$^+$. |

TABLE 12-continued

| Example | Reagents | Structure, Name and Data |
|---|---|---|
| 91.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatospiro[2.2]pentane (Example 28.7). The title compound was the second diastereomer to elute from Chiralpak AD-H column, SFC with 40% IPA. | 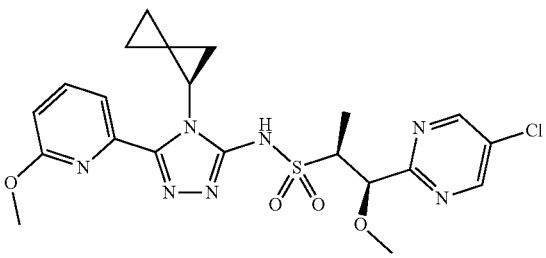<br>OR<br>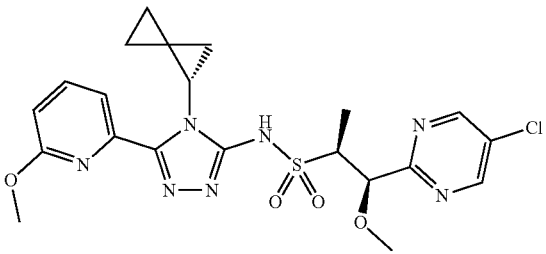<br>(1R,2S)-1-(5-chloro-2-pyrimidinyl)-1-methoxy-N-(5-(6-methoxy-2-pyridinyl)-4-((1R)-spiro[2.2]pentan-1-yl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-spiro[2.2]pentan-1-yl)-4H-1,2,4-triazol-3-yl)-2-propanesulfonamide. <sup>1</sup>H NMR (400 MHz, CD<sub>3</sub>OD) δ 8.84 (s, 2 H) 7.84 (dd, J = 8.40, 7.36 Hz, 1 H) 7.48 (d, J = 7.11 Hz, 1 H) 6.96 (d, J = 8.46 Hz, 1 H) 5.01 (d, J = 4.98 Hz, 1 H) 3.99 (s, 3 H) 3.64-3.81 (m, 2 H) 3.32 (s, 3 H) 1.49-1.55 (m, 1 H) 1.39-1.49 (m, 4 H) 0.67-0.78 (m, 2 H) 0.56-0.62 (m, 1 H) 0.22 (dt, J = 9.28, 4.79 Hz, 1 H). LCMS ESI (pos.) m/z: 506.0 (M + H)<sup>+</sup>. |
| 92.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatospiro[3.3]heptanes (Example 28.6). The title compound was the first diastereomer to elute from Chiralpak AS-H column, SFC with 30% IPA. | 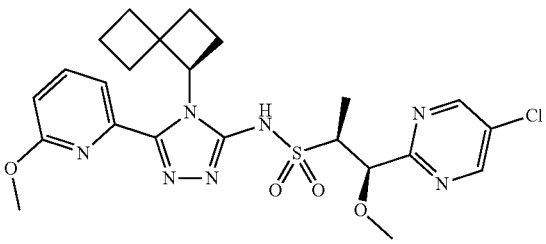<br>OR |

$^1$H NMR (400 MHz, CD$_3$OD) δ 8.84 (s, 2 H) 7.84 (dd, J = 8.40, 7.36 Hz, 1 H) 7.48 (d, J = 7.11 Hz, 1 H) 6.96 (d, J = 8.46 Hz, 1 H) 5.01 (d, J = 4.98 Hz, 1 H) 3.99 (s, 3 H) 3.64-3.81 (m, 2 H) 3.32 (s, 3 H) 1.49-1.55 (m, 1 H) 1.39-1.49 (m, 4 H) 0.67-0.78 (m, 2 H) 0.56-0.62 (m, 1 H) 0.22 (dt, J = 9.28, 4.79 Hz, 1 H). LCMS ESI (pos.) m/z: 506.0 (M + H)$^+$.

| Example | Reagents | Structure, Name and Data |
|---|---|---|
| | | 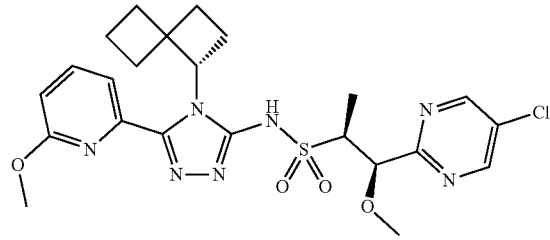<br>(1R,2S)-1-(5-chloro-2-pyrimidinyl)-1-methoxy-N-(5-(6-methoxy-2-pyridinyl)-4-((1R)-spiro[3.3]heptan-1-yl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-spiro[3.3]heptan-1-yl)-4H-1,2,4-triazol-3-yl)-2-propanesulfonamide.<br>$^1$H NMR (400 MHz, CDCl$_3$) δ 8.74 (s, 2 H) 7.73 (dd, J = 8.29, 7.46 Hz, 1 H) 7.50 (d, J = 6.84 Hz, 1 H) 6.91 (d, J = 8.40 Hz, 1 H) 5.50 (t, J = 9.12 Hz, 1 H) 5.07 (d, J = 4.77 Hz, 1 H) 3.97 (s, 3 H) 3.74-3.84 (m, 1 H) 3.44 (s, 3 H) 3.29-3.42 (m, 1 H) 1.70-2.33 (m, 8 H) 1.53-1.67 (m, 1 H) 1.50 (d, J = 7.05 Hz, 3 H). LCMS ESI (pos.) m/z: 534.0 (M + H)$^+$. |
| 93.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanatospiro[3.3]heptanes (Example 28.6).<br>The title compound was the second diastereomer to elute from Chiralpak AS-H column, SFC with 30% IPA. | 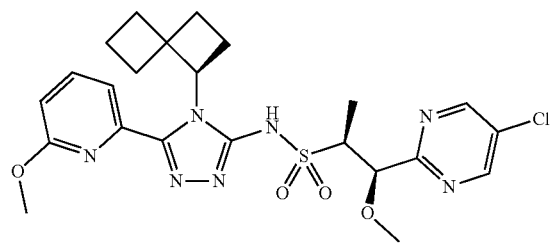<br>OR<br>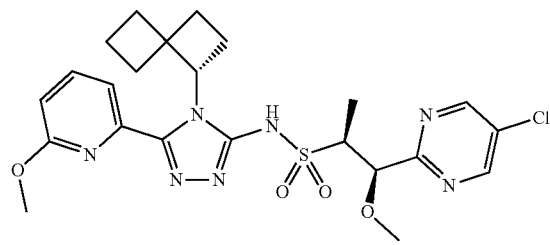<br>(1R,2S)-1-(5-chloro-2-pyrimidinyl)-1-methoxy-N-(5-(6-methoxy-2-pyridinyl)-4-((1R)-spiro[3.3]heptan-1-yl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-spiro[3.3]heptan-1-yl)-4H-1,2,4-triazol-3-yl)-2-propanesulfonamide.<br>$^1$H NMR (400 MHz, CDCl$_3$) δ 11.15 (br s, 1 H) 8.74 (s, 2 H) 7.73 (dd, J = 8.34, 7.41 Hz, 1 H) 7.51 (dd, J = 7.31, 0.67 Hz, 1 H) 6.91 (dd, J = 8.34, 0.67 Hz, 1 H) 5.56 (t, J = 9.07 Hz, 1 H) 5.08 (d, J = 4.46 Hz, 1 H) 3.97 (s, 3 H) 3.75 (qd, J = 7.05, 4.46 Hz, 1 H) 3.40-3.56 (m, 1 H) 3.37 (s, 3 H) 2.01-2.33 (m, 4 H) 1.71-1.90 (m, 4 H) 1.51-1.62 (m, 1 H) 1.48 (d, J = 7.05 Hz, 3 H). LCMS ESI (pos.) m/z: 534.0 (M + H)$^+$. |

TABLE 12-continued

| Example | Reagents | Structure, Name and Data |
|---|---|---|
| 94.0 | The title compound was the first diastereomer to elute from a Chiralpak AS-H column, SFC with 30% IPA by chiral separation of the mixture of two diastereomers which was prepared from Example 26.0 using the same procedure as described in Example 57.0 but with a reduced amount of oxidant (1 eq of mCPBA was used instead of 3 eq). | 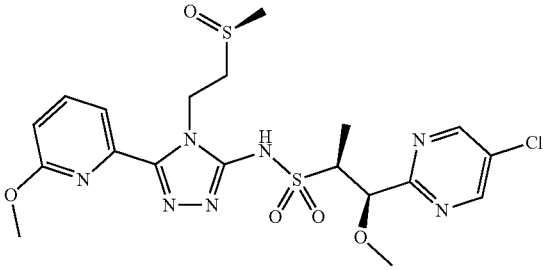<br><br>OR<br><br>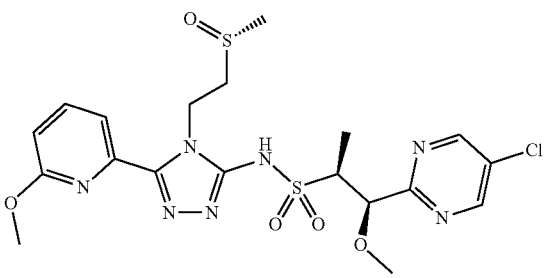<br><br>(1R,2S)-1-(5-chloro-2-pyrimidinyl)-1-methoxy-N-(5-(6-methoxy-2-pyridinyl)-4-(2-((S)-methylsulfinyl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-(2-((R)-methylsulfinyl)ethyl)-4H-1,2,4-triazol-3-yl)-2-propanesulfonamide.<br>$^1$H NMR (400 MHz, CD$_3$OD) δ 8.75 (s, 2 H) 7.71-7.79 (m, 1 H) 7.64-7.71 (m, 1 H) 6.92 (d, J = 8.19 Hz, 1 H) 4.83-5.16 (m, 3 H) 4.04 (s, 3 H) 3.76 (qd, J = 7.01, 4.04 Hz, 1 H) 3.17-3.42 (m, 5 H) 2.70 (s, 3 H) 1.45 (d, J = 7.05 Hz, 3 H). LCMS ESI (pos.) m/z: 530.0 (M + H)$^+$. |
| 95.0 | The title compound was the second diastereomer to elute from a Chiralpak AS-H column SFC with 30% IPA by chiral separation of the mixture of two diastereomers which was prepared as described in Example 94.0. | 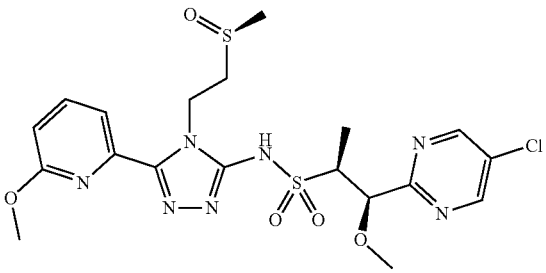<br><br>OR |

TABLE 12-continued

| Example | Reagents | Structure, Name and Data |
|---|---|---|
| | | 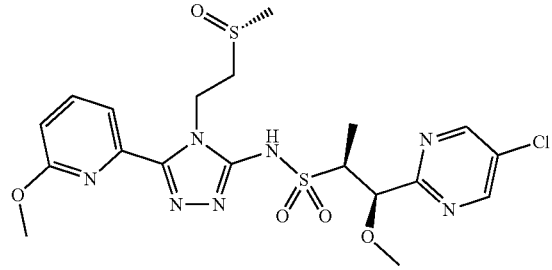<br>(1R,2S)-1-(5-chloro-2-pyrimidinyl)-1-methoxy-N-(5-(6-methoxy-2-pyridinyl)-4-(2-((S)-methylsulfinyl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-(2-((R)-methylsulfinyl)ethyl)-4H-1,2,4-triazol-3-yl)-2-propanesulfonamide.<br>$^1$H NMR (400 MHz, CDCl$_3$) δ 8.74 (s, 2 H) 7.70-7.76 (m, 1 H) 7.64-7.70 (m, 1 H) 6.91 (dd, J = 8.09, 0.73 Hz, 1 H) 5.01-5.15 (m, 2 H) 4.83-5.01 (m, 1 H) 4.04 (s, 3 H) 3.75 (qd, J = 7.01, 4.15 Hz, 1 H) 3.16-3.42 (m, 5 H) 2.70 (s, 3 H) 1.44 (d, J = 7.05 Hz, 3 H).<br>LCMS ESI (pos.) m/z: 530.0 (M + H)$^+$. |
| 97.0 | (1R,2S)-1-(5-chloropyrimidin-2-yl)-1-methoxypropane-2-sulfonamide (Example 29.3), picolinohydrazide (commercially available from TCI America), and 1-isothiocyanato-1-methylcyclopropane (commercially available from Enamine). | 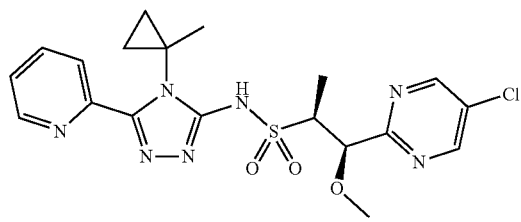<br>(1R,2S)-1-(5-chloro-2-pyrimidinyl)-1-methoxy-N-(4-(1-methylcyclopropyl)-5-(2-pyridinyl)-4H-1,2,4-triazol-3-yl)-2-propanesulfonamide.<br>$^1$H NMR (400 MHz, CDCl$_3$) δ 0.88 (m, 4 H) 1.48 (d, J = 6.95 Hz, 3 H) 1.78 (s, 3 H) 3.36 (s, 3H) 3.76 (qd, J = 7.00, 3.99 Hz, 1 H) 5.13 (d, J = 3.94 Hz, 1 H) 7.44 (q, J = 4.60 Hz, 1 H) 7.85 (d, J = 3.52 Hz, 2 H) 8.72-8.78 (m, 3 H) 11.01 (br s, 1 H). LCMS ESI (pos.) m/z: 464.0 (M + H)$^+$. |

TABLE 12-continued

| Example | Reagents | Structure, Name and Data |
|---|---|---|
| 98.0 | (2S,3R)-3-(5-methylpyrimidin-2-yl)butane-2-sulfonamide (Example 27.0), 6-methoxypicolinohydrazide (commercially available from Sigma Aldrich), and 2-isothiocyanato-1,3-dimethoxypropane (Example 71.0). | 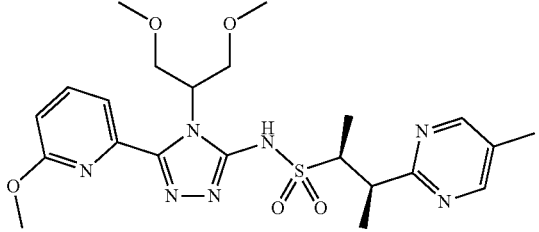<br>(2S,3R)-N-(4-(1,3-dimethoxy-2-propanyl)-5-(6-methoxy-2-pyridinyl)-4H-1,2,4-triazol-3-yl)-3-(5-methyl-2-pyrimidinyl)-2-butanesulfonamide.<br>$^1$H NMR (600 MHz, DMSO-$d_6$) δ 1.24 (d, J = 7.02 Hz, 3 H) 1.37 (d, J = 7.10 Hz, 3 H) 2.24 (s, 3 H) 3.14 (s, 3 H) 3.15 (s, 3 H) 3.65 (ddd, J = 9.90, 8.64, 5.80 Hz, 2 H) 3.73 (dd, J = 7.02, 3.81 Hz, 1 H) 3.78 (dd, J = 7.06, 3.78 Hz, 1 H) 3.92 (s, 3 H) 3.97-4.13 (m, 2 H) 5.68 (br s, 1H) 7.03 (dd, J = 8.39, 0.69 Hz, 1 H) 7.54 (d, J = 7.32 Hz, 1 H) 7.91 (dd, J = 8.39, 7.40 Hz, 1 H) 8.59 (d, J = 0.69 Hz, 2 H) 13.15 (s, 1 H). LCMS ESI (pos.) m/z: 506.2 (M + H)$^+$. |
| 99.0 | (2S,3R)-3-(5-methoxypyrimidin-2-yl)butane-2-sulfonamide (Example 27.6), 6-methoxypicolinohydrazide (commercially available from Sigma Aldrich), and 2-isothiocyanato-1,3-dimethoxypropane (Example 71.0). | 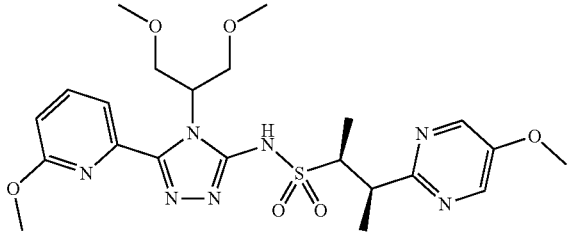<br>(2S,3R)-N-(4-(1,3-dimethoxy-2-propanyl)-5-(6-methoxy-2-pyridinyl)-4H-1,2,4-triazol-3-yl)-3-(5-methoxy-2-pyrimidinyl)-2-butanesulfonamide.<br>$^1$H NMR (600 MHz, DMSO-$d_6$) δ 1.23 (d, J = 7.02 Hz, 3 H) 1.37 (d, J = 7.10 Hz, 3 H) 3.14 (s, 3 H) 3.15 (s, 3 H) 3.60-3.72 (m, 3 H) 3.79 (dd, J = 7.13, 3.78 Hz, 1 H) 3.88 (s, 3 H) 3.92 (s, 3 H) 4.05 (q, J = 10.02 Hz, 2 H) 5.64 (br s, 1H) 7.03 (dd, J = 8.39, 0.69 Hz, 1 H) 7.54 (d, J = 7.40 Hz, 1 H) 7.91 (dd, J = 8.39, 7.40 Hz, 1 H) 8.49 (s, 2 H) 13.15 (s, 1 H). LCMS ESI (pos.) m/z: 522.2 (M + H)$^+$. |

TABLE 12-continued

| Example | Reagents | Structure, Name and Data |
|---|---|---|
| 100.0 | (1R,2S)-1-methoxy-1-(5-methylpyrimidin-2-yl)propane-2-sulfonamide (Example 29.0), 6-methoxypicolinohydrazide (commercially available from Sigma Aldrich), and 2-isothiocyanato-1,3-dimethoxypropane (Example 71.0). | 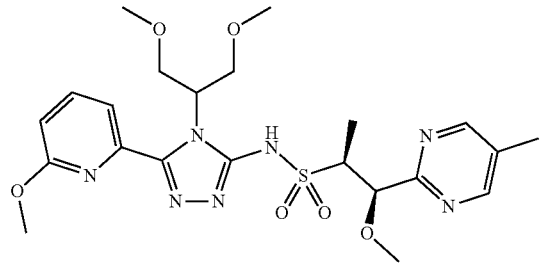<br>(1R,2S)-N-(4-(1,3-dimethoxy-2-propanyl)-5-(6-methoxy-2-pyridinyl)-4H-1,2,4-triazol-3-yl)-1-methoxy-1-(5-methyl-2-pyrimidinyl)-2-propanesulfonamide.<br>$^1$H NMR (600 MHz, DMSO-$d_6$) δ 1.28 (d, J = 7.02 Hz, 3 H) 2.27 (s, 3 H) 3.17-3.18 (m, 9 H) 3.35 (s, 3H) 3.50 (dd, J = 7.02, 3.43 Hz, 1 H) 3.67 (dd, J = 9.99, 5.72 Hz, 2 H) 3.93 (s, 3 H) 4.07 (s, 1 H) 4.11 (br s, 1 H) 4.96 (d, J = 3.43 Hz, 1 H) 5.38 (br s, 1H) 7.03 (dd, J = 8.35, 0.65 Hz, 1 H) 7.54 (d, J = 7.32 Hz, 1 H) 7.90 (dd, J = 8.32, 7.40 Hz, 1 H) 8.66 (d, J = 0.61 Hz, 2 H) 13.13 (s, 1 H). LCMS ESI (pos.) m/z: 522.2 (M + H)$^+$. |
| 101.0 | (1R,2S)-1-methoxy-1-(5-methoxypyrazin-2-yl)propane-2-sulfonamide (Example 29.9), 6-methoxypicolinohydrazide (commercially available from Sigma Aldrich), and 2-isothiocyanato-1,3-dimethoxypropane (Example 71.0). | 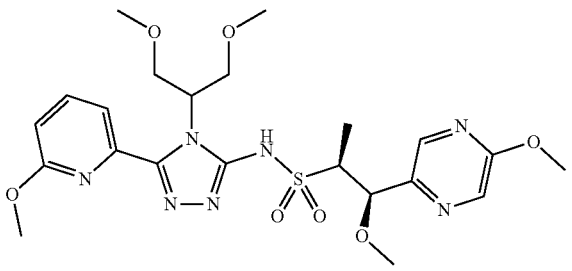<br>(1R,2S)-N-(4-(1,3-dimethoxy-2-propanyl)-5-(6-methoxy-2-pyridinyl)-4H-1,2,4-triazol-3-yl)-1-methoxy-1-(5-methoxy-2-pyrazinyl)-2-propanesulfonamide.<br>$^1$H NMR (600 MHz, DMSO-$d_6$) δ 1.24 (d, J = 7.02 Hz, 3 H) 3.17 (s, 3 H) 3.18 (s, 3 H) 3.23 (s, 3 H) 3.33-3.38 (m, 1 H) 3.67 (ddd, J = 9.96, 5.76, 2.59 Hz, 2 H) 3.92 (s, 3 H) 3.93 (s, 3 H) 4.04-4.12 (m, 2 H) 4.96 (d, J = 2.98 Hz, 1 H) 5.38 (br s, 1H) 7.03 (d, J = 8.22 Hz, 1 H) 7.54 (d, J = 7.40 Hz, 1 H) 7.91 (dd, J = 8.32, 7.40 Hz, 1 H) 8.17 (d, J = 0.84 Hz, 1 H) 8.31 (d, J = 1.30 Hz, 1 H) 13.15 (s, 1 H). LCMS ESI (pos.) m/z: 538.2 (M + H)$^+$. |

TABLE 12-continued

| Example | Reagents | Structure, Name and Data |
|---|---|---|
| 102.0 | (2S,3R)-3-(5-methylpyrazin-2-yl)butane-2-sulfonamide (Example 27.2), 6-methoxypicolinohydrazide (commercially available from Sigma Aldrich), and 2-isothiocyanato-1,3-dimethoxypropane (Example 71.0). | 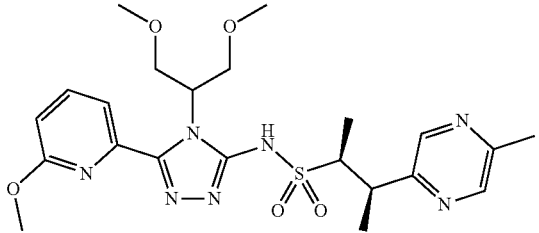<br>(2S,3R)-N-(4-(1,3-dimethoxy-2-propanyl)-5-(6-methoxy-2-pyridinyl)-4H-1,2,4-triazol-3-yl)-3-(5-methyl-2-pyrazinyl)-2-butanesulfonamide.<br>$^1$H NMR (600 MHz, DMSO-$d_6$) δ 1.26 (d, J = 7.02 Hz, 3 H) 1.36 (d, J = 7.10 Hz, 3 H) 2.45 (s, 3 H) 3.15 (s, 3 H) 3.15 (s, 3 H) 3.51 (dd, J = 7.02, 4.20 Hz, 1 H) 3.64 (dt, J = 10.09, 5.67 Hz, 2 H) 3.71 (dd, J = 7.02, 4.20 Hz, 1 H) 3.92 (s, 3 H) 4.04 (br t, J = 9.38 Hz, 2 H) 5.36 (br s, 1H) 7.03 (d, J = 8.39 Hz, 1 H) 7.54 (d, J = 7.32 Hz, N 1 H) 7.91 (t, J = 7.92 Hz, 1 H) 8.45 (d, J = 8.09 Hz, 2 H) 13.14 (s, 1 H). LCMS ESI (pos.) m/z: 506.2 (M + H)$^+$. |
| 103.0 | (1R,2S)-1-methoxy-1-(5-methylpyrazin-2-yl)propane-2-sulfonamide (Example 29.1), 6-methoxypicolinohydrazide (commercially available from Sigma Aldrich), and 2-isothiocyanato-1,3-dimethoxypropane (Example 71.0). | 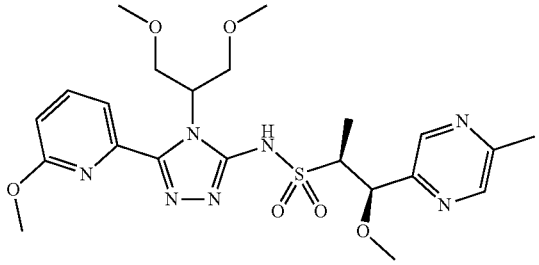<br>(1R,2S)-N-(4-(1,3-dimethoxy-2-propanyl)-5-(6-methoxy-2-pyridinyl)-4H-1,2,4-triazol-3-yl)-1-methoxy-1-(5-methyl-2-pyrazinyl)-2-propanesulfonamide.<br>$^1$H NMR (600 MHz, DMSO-$d_6$) δ 1.22 (d, J = 7.02 Hz, 3 H) 3.17 (s, 3 H) 3.18 (s, 3 H) 3.25 (s, 3 H) 3.39 (dd, J = 7.10, 2.90 Hz, 1 H) 3.67 (ddd, J = 9.94, 5.74, 2.94 Hz, 2 H) 3.93 (s, 3 H) 4.99 (d, J = 2.82 Hz, 1 H) 5.67 (br s, 1 H) 7.02 (d, J = 0.69 Hz, 1 H) 7.04 (d, J = 0.69 Hz, 1 H) 7.54 (d, J = 7.32 Hz, 1 H) 7.89-7.91 (m, 1 H) 8.51 (d, J = 1.30 Hz, 1 H) 8.54 (s, 1 H) 13.17 (s, 1 H). LCMS ESI (pos.) m/z: 522.2 (M + H)$^+$. |
| 104.0 | (1S,2S)-1-isopropoxy-1-(5-methylpyrimidin-2-yl)propane-2-sulfonamide (Example 31.0), 6-methoxypicolinohydrazide (commercially available from Sigma Aldrich), and 2-isothiocyanato-1,3-dimethoxypropane (Example 71.0). | 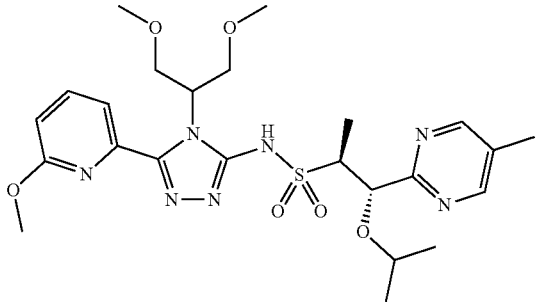 |

TABLE 12-continued

| Example | Reagents | Structure, Name and Data |
|---|---|---|
| | | (1S,2S)-N-(4-(1,3-dimethoxy-2-propanyl)-5-(6-methoxy-2-pyridinyl)-4H-1,2,4-triazol-3-yl)-1-(5-methyl-2-pyrimidinyl)-1-(2-propanyloxy)-2-propanesulfonamide.<br>$^1$H NMR (600 MHz, DMSO-$d_6$) δ 0.79 (d, J = 6.18 Hz, 3 H) 1.03 (d, J = 6.03 Hz, 3 H) 1.09 (d, J = 7.10 Hz, 3 H) 2.28 (s, 3 H) 3.19 (s, 3 H) 3.19 (s, 3 H) 3.67 (dd, J = 9.96, 5.68 Hz, 1 H) 3.71 (dd, J = 10.07, 5.87 Hz, 1 H) 3.92 (s, 3 H) 4.08-4.11 (m, 2 H) 4.85 (d, J = 7.17 Hz, 1 H) 7.02 (dd, J = 8.35, 0.65 Hz, 1 H) 7.53 (d, J = 7.40 Hz, 1 H) 7.91 (dd, J = 8.32, 7.40 Hz, 1 H) 8.67 (d, J = 0.69 Hz, 2 H) 13.09 (s, 1H). LCMS ESI (pos.) m/z: 550.2 (M + H)$^+$. |
| 105.0 | (1S,2S)-1-isopropoxy-1-(5-methylpyrazin-2-yl)propane-2-sulfonamide (Example 31.02), 6-methoxypicolinohydrazide (commercially available from Sigma Aldrich), and 2-isothiocyanato-1,3-dimethoxypropane (Example 71.0). | (1S,2S)-N-(4-(1,3-dimethoxy-2-propanyl)-5-(6-methoxy-2-pyridinyl)-4H-1,2,4-triazol-3-yl)-1-(5-methyl-2-pyrazinyl)-1-(2-propanyloxy)-2-propanesulfonamide.<br>$^1$H NMR (600 MHz, DMSO-$d_6$) δ 0.88 (d, J = 6.18 Hz, 3 H) 1.08 (d, J = 6.03 Hz, 3 H) 1.14 (d, J = 7.10 Hz, 3 H) 3.18 (s, 3 H) 3.18 (s, 3 H) 3.43 (quin, J = 6.08 Hz, 1 H) 3.56-3.61 (m, 1 H) 3.63-3.69 (m, 2 H) 3.92 (s, 3 H) 4.89 (d, J = 6.18 Hz, 1 H) 5.58 (br s, 1H) 7.03 (dd, J = 8.35, 0.65 Hz, 1 H) 7.52 (d, J = 7.40 Hz, 1 H) 7.91 (d, J = 0.99 Hz, 1 H) 8.48 (s, 1 H) 8.57 (d, J = 1.37 Hz, 1 H) 13.05 (s, 1 H). LCMS ESI (pos.) m/z: 550.2 (M + H)$^+$. |
| 106.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-(fluoromethyl)-1-isothiocyanatocyclopropane (Example 28.8). | (1R,2S)-1-(5-chloro-2-pyrimidinyl)-N-(4-(1-(fluoromethyl)cyclopropyl)-5-(6-methoxy-2-pyridinyl)-4H-1,2,4-triazol-3-yl)-1-methoxy-2-propanesulfonamide.<br>$^1$H NMR (600 MHz, DMSO-$d_6$) δ 1.18 (br s,4 H) 1.32 (d, J = 7.02 Hz, 3 H) 3.15 (s, 3 H) 3.47-3.60 (m, 1 H) 3.90 (s, 3 H) 4.86-4.97 (m, 3 H) 7.01 (d, J = 8.39 Hz, 1 H) 7.47 (d, J = 7.32 Hz, 1 H) 7.89 (dd, J = 8.24, 7.48 Hz, 1 H) 8.94 (s, 2 H) 13.06 (s, 1 H). LCMS ESI (pos.) m/z: 512.0 (M + H)$^+$. |

TABLE 12-continued

| Example | Reagents | Structure, Name and Data |
|---|---|---|
| 107.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-isothiocyanato-1,1'-bi(cyclopropane) (Example 28.12). | 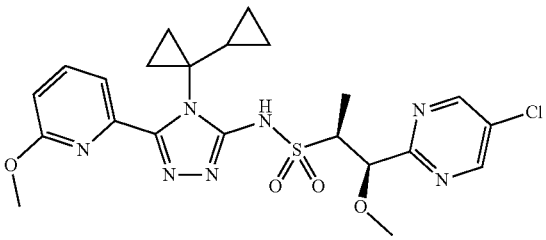<br>(1R,2S)-N-(4-([1,1'-bi(cyclopropyl)]-1-yl)-5-(6-methoxy-2-pyridinyl)-4H-1,2,4-triazol-3-yl)-1-(5-chloro-2-pyrimidinyl)-1-methoxy-2-propanesulfonamide.<br>$^1$H NMR (600 MHz, DMSO-$d_6$) δ 0.43 (br s, 2 H) 0.77 (br s, 4 H) 1.31 (d, J = 7.01 Hz, 3 H) 2.04-2.09 (m, 1 H) 3.09-3.23 (m, 2 H) 3.34 (s, 3 H) 3.48-3.53 (m, 1 H) 3.93 (s, 3 H) 4.95 (d, J = 4.20 Hz, 1 H) 7.03 (dd, J = 8.33, 0.70 Hz, 1 H) 7.46 (dd, J = 7.32, 0.78 Hz, 1 H) 7.89 (dd, J = 8.41, 7.32 Hz, 1 H) 8.96 (s, 2 H) 13.03 (s, 1 H). LCMS ESI (pos.) m/z: 520.2 (M + H)$^+$. |
| 108.0 | (1R,2S)-1-(5-chloropyrimidin-2-yl)-1-methoxypropane-2-sulfonamide (Example 29.3), picolinohydrazide (commercially available from TCI America), and 1-isothiocyanato-1,1'-bi(cyclopropane)(Example 28.12). | 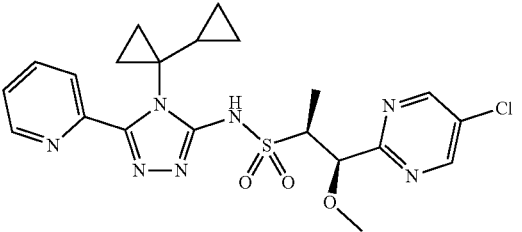<br>(1R,2S)-N-(4-([1,1'-bi(cyclopropyl)]-1-yl)-5-(2-pyridinyl)-4H-1,2,4-triazol-3-yl)-1-(5-chloro-2-pyrimidinyl)-1-methoxy-2-propanesulfonamide.<br>$^1$H NMR (600 MHz, DMSO-$d_6$) δ 0.42 (br d, J = 7.01 Hz, 2 H) 0.48-0.63 (m, 2 H) 0.72 (br s, 2 H) 0.80-0.95 (m, 1 H) 1.08-1.24 (m, 1 H) 1.31 (d, J = 7.01 Hz, 3 H) 2.00-2.05 (m, 1 H) 3.15 (s, 3 H) 3.46-3.53 (m, 1 H) 4.97 (d, J = 4.05 Hz, 1 H) 7.58 (dd, J = 7.40, 5.06 Hz, 1 H) 7.83 (d, J = 7.79 Hz, 1 H) 8.00 (t, J = 7.71 Hz, 1 H) 8.77 (br d, J = 4.36 Hz, 1 H) 8.96 (s, 2 H) 13.06 (s, 1 H). LCMS ESI (pos.) m/z: 490.2 (M + H)$^+$. |

TABLE 12-continued

| Example | Reagents | Structure, Name and Data |
|---|---|---|
| 109.0 | (1R,2S)-1-methoxy-1-(5-methylpyrazin-2-yl)propane-2-sulfonamide (Example 29.1), 6-methoxypicolinohydrazide (commercially available from Sigma Aldrich), and 1-isothiocyanato-1,1'-bi(cyclopropane)(Example 28.12). | 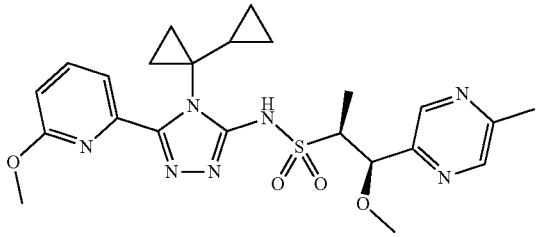<br>(1R,2S)-N-(4-([1,1'-bi(cyclopropyl)]-1-yl)-5-(6-methoxy-2-pyridinyl)-4H-1,2,4-triazol-3-yl)-1-methoxy-1-(5-methyl-2-pyrazinyl)-2-propanesulfonamide.<br>$^1$H NMR (600 MHz, DMSO-d$_6$) δ 0.42 (br s, 4 H) 0.77 (br s, 4 H) 1.22 (d, J = 7.01 Hz, 3 H) 2.04-2.09 (m, 1 H) 3.16 (d, J = 4.98 Hz, 1 H) 3.23 (br s, 3H) 3.37-3.42 (m, 4 H) 3.93 (s, 3 H) 5.00-5.02 (m, 1 H) 7.03 (d, J = 8.25 Hz, 1 H) 7.46 (d, J = 7.32 Hz, 1 H) 7.89 (t, J = 7.86 Hz, 1 H) 8.50 (br s, 1 H) 8.53 (s, 1 H) 13.06 (br s, 1 H)). LCMS ESI (pos.) m/z: 500.2 (M + H)$^+$. |
| 110.0 | (1R,2S)-1-methoxy-1-(5-methylpyrazin-2-yl)propane-2-sulfonamide (Example 29.1), picolinohydrazide (commercially available from TCI America), and 1-isothiocyanato-1,1'-bi(cyclopropane)(Example 28.12). | 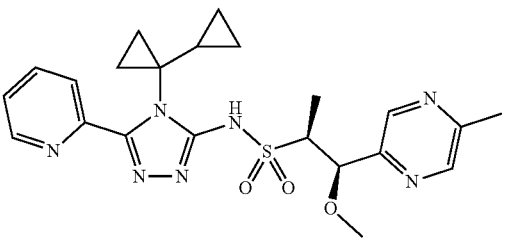<br>(1R,2S)-N-(4-([1,1'-bi(cyclopropyl)]-1-yl)-5-(2-pyridinyl)-4H-1,2,4-triazol-3-yl)-1-methoxy-1-(5-methyl-2-pyrazinyl)-2-propanesulfonamide.<br>$^1$H NMR (600 MHz, DMSO-d$_6$) δ 0.43 (br d, J = 7.01 Hz, 2 H) 0.53 (br s, 2 H) 0.73 (br s, 4 H) 1.23 (d, J = 7.01 Hz, 3 H) 2.01-2.06 (m, 1 H) 3.23 (br s, 3 H) 3.39-3.43 (m, 4 H) 5.02-5.04 (m, 1 H) 7.60 (t, J = 6.40 Hz, 1 H) 7.85 (d, J = 7.79 Hz, 1 H) 8.02 (t, J = 7.78 Hz, 1 H) 8.51 (s, 1 H) 8.55 (s, 1 H) 8.78 (br d, J = 4.36 Hz, 1 H) 13.11 (br s, 1 H). LCMS ESI (pos.) m/z: 470.2 (M + H)$^+$. |
| 111.0 | (1R,2S)-1-(5-chloropyrimidin-2-yl)-1-methoxypropane-2-sulfonamide (Example 29.3), nicotinohydrazide (commercially available from Sigma-Aldrich), and 3-isothiocyanatopentane, (commercially available from Oakwood). | 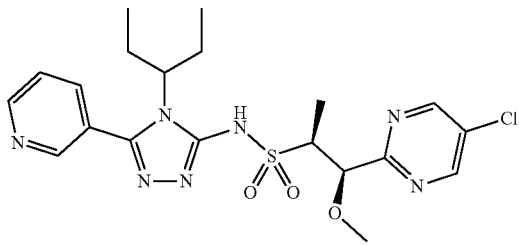<br>(1R,2S)-1-(5-chloro-2-pyrimidinyl)-1-methoxy-N-(4-(3-pentanyl)-5-(3-pyridinyl)-4H-1,2,4-triazol-3-yl)-2-propanesulfonamide.<br>$^1$H NMR (600 MHz, DMSO-d$_6$) δ 0.66-0.76 (m, 8 H) 1.26 (d, J = 7.01 Hz, 3 H) 2.00-2.19 (m, 2 H) 3.20 (s, 3 H) 3.57-3.64 (m, 1 H) 3.70 (br s, 1 H) 4.96 (d, J = 3.89 Hz, 1 H) 7.61 (dd, J = 7.71, 5.06 Hz, 1 H) 7.96 (br d, J = 7.94 Hz, 1 H) 8.67-8.72 (m, 1 H) 8.78 (d, J = 4.83 Hz, 1 H) 8.96 (s, 2 H). LCMS ESI (pos.) m/z: 480.2 (M + H)$^+$. |

TABLE 12-continued

| Example | Reagents | Structure, Name and Data |
|---|---|---|
| 112.0 | (1R,2S)-1-(5-chloropyrimidin-2-yl)-1-methoxypropane-2-sulfonamide (Example 29.3), nicotinohydrazide (commercially available from Sigma-Aldrich Inc.), and (isothiocyanatomethylene)dicyclopropane (commercially available from Frontier Scientific Services Inc.). | 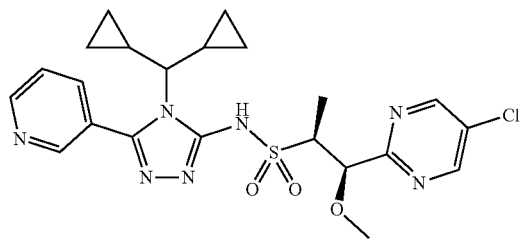<br>(1R,2S)-1-(5-chloro-2-pyrimidinyl)-N-(4-(dicyclopropylmethyl)-5-(3-pyridinyl)-4H-1,2,4-triazol-3-yl)-1-methoxy-2-propanesulfonamide.<br>$^1$H NMR (500 MHz, CDCl$_3$) δ 0.34 (br s, 3 H) 0.48 (br s, 3 H) 0.69 (br s, 3 H) 0.85 (br s, 1 H) 1.43 (br d, J = 6.88 Hz, 3 H) 2.06-2.29 (m, 1 H) 3.36 (s, 3H) 3.70-3.77 (m, 1 H) 5.09 (br d, J = 3.50 Hz, 1 H) 7.49 (dd, J = 7.72, 5.00 Hz, 1 H) 7.89 (br s, 1 H) 8.74 (s, 2 H) 8.82 (br d, J = 4.28 Hz, 2 H) 11.24 (br s, 1 H). LCMS ESI (pos.) m/z: 504.0 (M + H)$^+$. |
| 113.0 | (1S,2S)-1-(5-chloropyrimidin-2-yl)-1-isopropoxypropane-2-sulfonamide (Example 31.01), picolinohydrazide (commercially available from TCI America), and 2-isothiocyanato-1,3-dimethoxypropane (Example 71.0). | 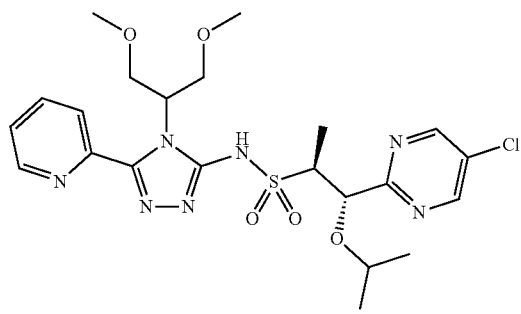<br>(1S,2S)-1-(5-chloro-2-pyrimidinyl)-N-(4-(1,3-dimethoxy-2-propanyl)-5-(2-pyridinyl)-4H-1,2,4-triazol-3-yl)-1-(2-propanyloxy)-2-propanesulfonamide.<br>$^1$H NMR (400 MHz, CDCl$_3$) δ 11.95 (br s, 1 H) 8.75 (s, 2 H) 8.71 (dt, J = 4.09, 0.75 Hz, 1 H) 7.98 (d, J = 7.98 Hz, 1 H) 7.84 (td, J = 7.77, 1.76 Hz, 1 H) 7.41 (ddd, J = 7.62, 4.87, 1.09 Hz, 1 H) 5.78-5.89 (m, 1 H) 4.93 (d, J = 4.04 Hz, 1 H) 4.22 (dd, J = 10.00, 8.45 Hz, 1 H) 4.16 (dd, J = 10.16, 7.98 Hz, 1 H) 3.72-3.90 (m, 3 H) 3.57 (spt, J = 6.08 Hz, 1 H) 3.32 (s, 3 H) 3.28 (s, 3 H) 1.57 (d, J = 7.05 Hz, 3 H) 1.11 (d, J = 6.01 Hz, 3 H) 0.96 (d, J = 6.22 Hz, 3 H). LCMS ESI (pos.) m/z: 540.0 (M + H)$^+$. |

TABLE 12-continued

| Example | Reagents | Structure, Name and Data |
|---|---|---|
| 114.0 | (2S,3R)-3-(5-methylpyrimidin-2-yl)butane-2-sulfonamide (Example 27.0), 6-methoxypicolinohydrazide (commercially available from Sigma Aldrich), and isothiocyanatocyclopropane (commercially available from Lancaster). | 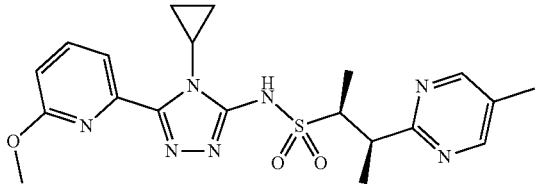<br>(2S,3R)-N-(4-cyclopropyl-5-(6-methoxy-2-pyridinyl)-4H-1,2,4-triazol-3-yl)-3-(5-methyl-2-pyrimidinyl)-2-butanesulfonamide.<br>$^1$H NMR (600 MHz, DMSO-$d_6$) δ 0.55-0.69 (m, 2 H) 0.83-0.94 (m, 2 H) 1.26 (d, J = 6.77 Hz, 3 H) 1.35 (d, J = 6.85 Hz, 3 H) 2.21 (s, 3 H) 3.12-3.19 (m, 1 H) 3.71-3.79 (m, 2 H) 3.91 (s, 3 H) 6.99 (d, J = 8.43 Hz, 1 H) 7.45 (d, J = 7.32 Hz, 1 H) 7.88 (dd, J = 8.37, 7.36 Hz, 1 H) 8.56 (s, 2 H) 13.00 (s, 1 H). LCMS ESI (pos.) m/z: 444.2 (M + H)$^+$. |
| 118.0 | (2S,3R)-3-(5-methoxypyrazin-2-yl)butane-2-sulfonamide (Example 27.5), 6-methoxypicolinohydrazide (commercially available from Sigma Aldrich), and isothiocyanatocyclopropane (commercially available from Lancaster). | 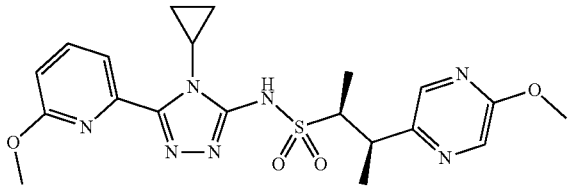<br>(2S,3R)-N-(4-cyclopropyl-5-(6-methoxy-2-pyridinyl)-4H-1,2,4-triazol-3-yl)-3-(5-methoxy-2-pyrazinyl)-2-butanesulfonamide.<br>$^1$H NMR (600 MHz, DMSO-$d_6$) δ 0.55-0.63 (m, 1 H) 0.63-0.72 (m, 1 H) 0.84-0.95 (m, 2 H) 1.28 (d, J = 7.01 Hz, 3 H) 1.34 (d, J = 7.16 Hz, 3 H) 3.15 (ddd, J = 7.24, 3.54, 3.39 Hz, 1 H) 3.42-3.53 (m, 1 H) 3.68 (dd, J = 7.08, 4.67 Hz, 1 H) 3.84 (s, 3 H) 3.91 (s, 3 H) 7.00 (dd, J = 8.37, 0.66 Hz, 1 H) 7.45 (dd, J = 7.32, 0.62 Hz, 1 H) 7.89 (dd, J = 8.37, 7.36 Hz, 1 H) 8.13 (d, J = 1.09 Hz, 1 H) 8.21 (d, J = 1.32 Hz, 1 H) 12.97 (s, 1 H). LCMS ESI (pos.) m/z: 460.2 (M + H)$^+$. |
| 119.0 | (2S,3R)-3-(5-methoxypyrimidin-2-yl)butane-2-sulfonamide (Example 27.6), 6-methoxypicolinohydrazide (commercially available from Sigma Aldrich), and isothiocyanatocyclopropane (commercially available from Lancaster). | 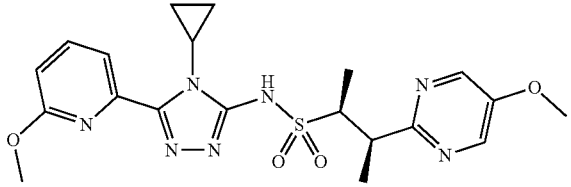<br>(2S,3R)-N-(4-cyclopropyl-5-(6-methoxy-2-pyridinyl)-4H-1,2,4-triazol-3-yl)-3-(5-methoxy-2-pyrimidinyl)-2-butanesulfonamide.<br>$^1$H NMR (600 MHz, DMSO-$d_6$) δ 0.57-0.63 (m, 1 H) 0.63-0.69 (m, 1 H) 0.85-0.94 (m, 2 H) 1.26 (d, J = 6.93 Hz, 3 H) 1.35 (d, J = 7.08 Hz, 3 H) 3.12-3.18 (m, 1 H) 3.71 (br dd, J = 6.97, 4.48 Hz, 1 H) 3.73-3.79 (m, 1 H) 3.84 (s, 3 H) 3.91 (s, 3 H) 6.99 (d, J = 8.41 Hz, 1 H) 7.45 (d, J = 7.32 Hz, 1 H) 7.88 (dd, J = 8.37, 7.36 Hz, 1 H) 8.46 (s, 2 H) 13.00 (br s, 1 H). LCMS ESI (pos.) m/z: 460.2 (M + H)$^+$. |

TABLE 12-continued

| Example | Reagents | Structure, Name and Data |
|---|---|---|
| 120.0 | (1R,2S)-1-methoxy-1-(5-methylpyrimidin-2-yl)propane-2-sulfonamide (Example 29.0), 6-methoxypicolinohydrazide (commercially available from Sigma Aldrich), and isothiocyanatocyclopropane (commercially available from Lancaster). | 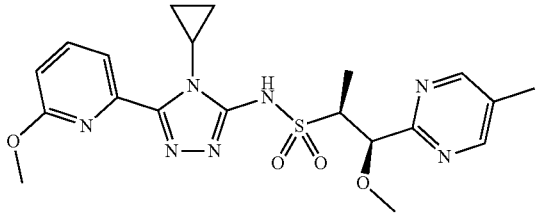<br>(1R,2S)-N-(4-cyclopropyl-5-(6-methoxy-2-pyridinyl)-4H-1,2,4-triazol-3-yl)-1-methoxy-1-(5-methyl-2-pyrimidinyl)-2-propanesulfonamide.<br>$^1$H NMR (600 MHz, DMSO-$d_6$) δ 0.62 (br d, J = 2.96 Hz, 1 H) 0.75 (br dd, J = 3.78, 1.60 Hz, 1 H) 0.88-0.96 (m, 2 H) 1.30 (d, J = 7.01 Hz, 3 H) 2.25 (s, 3 H) 3.08 (s, 3 H) 3.13-3.20 (m, 1 H) 3.54 (dd, J = 7.01, 3.97 Hz, 1 H) 3.92 (s, 3 H) 4.89 (d, J = 3.97 Hz, 1 H) 7.01 (dd, J = 8.41, 0.62 Hz, 1 H) 7.46 (d, J = 7.32 Hz, 1 H) 7.89 (dd, J = 8.33, 7.40 Hz, 1 H) 8.64 (s, 2 H) 13.02 (br s, 1 H). LCMS ESI (pos.) m/z: 460.2 (M + H)$^+$. |
| 121.0 | (1R,2S)-1-methoxy-1-(5-methoxypyrazin-2-yl)propane-2-sulfonamide (Example 29.9), 6-methoxypicolinohydrazide (commercially available from Sigma Aldrich), and isothiocyanatocyclopropane (commercially available from Lancaster). | 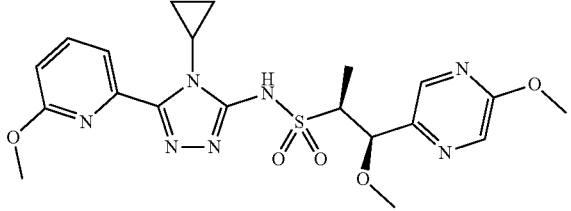<br>(1R,2S)-N-(4-cyclopropyl-5-(6-methoxy-2-pyridinyl)-4H-1,2,4-triazol-3-yl)-1-methoxy-1-(5-methoxy-2-pyrazinyl)-2-propanesulfonamide.<br>$^1$H NMR (600 MHz, DMSO-$d_6$) δ 0.61-0.68 (m, 1 H) 0.68-0.75 (m, 1 H) 0.88-0.96 (m, 2 H) 1.28 (d, J = 7.08 Hz, 3 H) 3.14-3.19 (m, 4 H) 3.35-3.46 (m, 1 H) 3.88 (s, 3 H) 3.92 (s, 3 H) 4.89 (d, J = 3.74 Hz, 1 H) 7.00 (d, J = 8.33 Hz, 1 H) 7.46 (dd, J = 7.32, 0.62 Hz, 1 H) 7.89 (dd, J = 8.33, 7.40 Hz, 1 H) 8.17 (d, J = 0.86 Hz, 1 H) 8.28 (d, J = 1.32 Hz, 1 H) 13.02 (br s, 1 H). LCMS ESI (pos.) m/z: 476.2 (M + H)$^+$. |
| 122.0 | (1R,2S)-1-methoxy-1-(5-methylpyrazin-2-yl)propane-2-sulfonamide (Example 29.1), 6-methoxypicolinohydrazide (commercially available from Sigma Aldrich), and isothiocyanatocyclopropane (commercially available from Lancaster). | 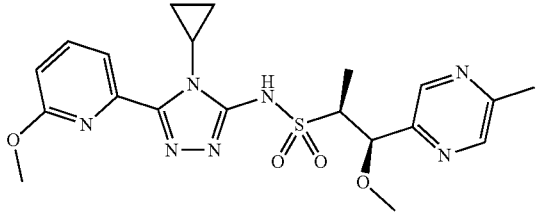<br>(1R,2S)-N-(4-cyclopropyl-5-(6-methoxy-2-pyridinyl)-4H-1,2,4-triazol-3-yl)-1-methoxy-1-(5-methyl-2-pyrazinyl)-2-propanesulfonamide.<br>$^1$H NMR (600 MHz, DMSO-$d_6$) δ 0.61-0.69 (m, 1 H) 0.69-0.76 (m, 1 H) 0.89-0.96 (m, 2 H) 1.25 (d, J = 7.01 Hz, 3 H) 2.48 (s, 3 H) 3.15-3.22 (m, 4 H) 3.36-3.46 (m, 1 H) 3.92 (s, 3 H) 4.94 (d, J = 3.43 Hz, 1 H) 7.00 (d, J = 8.36 Hz, 1 H) 7.46 (dd, J = 7.28, 0.66 Hz, 1 H) 7.89 (dd, J = 8.33, 7.32 Hz, 1 H) 8.51 (s, 2 H) 13.05 (br s, 1 H). LCMS ESI (pos.) m/z: 460.2 (M + H)$^+$. |

TABLE 12-continued

| Example | Reagents | Structure, Name and Data |
|---|---|---|
| 123.0 | (1S,2S)-1-isopropoxy-1-(5-methylpyrimidin-2-yl)propane-2-sulfonamide (Example 31.0), 6-methoxypicolinohydrazide (commercially available from Sigma Aldrich), and isothiocyanatocyclopropane (commercially available from Lancaster). | 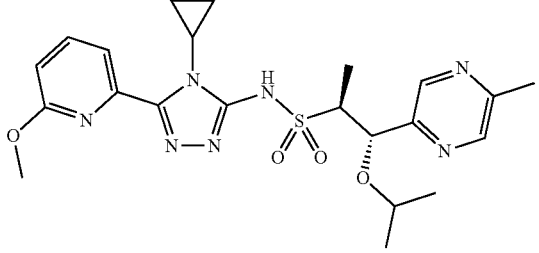<br>(1S,2S)-N-(4-cyclopropyl-5-(6-methoxy-2-pyridinyl)-4H-1,2,4-triazol-3-yl)-1-(5-methyl-2-pyrimidinyl)-1-(2-propanyloxy)-2-propanesulfonamide.<br>$^1$H NMR (600 MHz, DMSO-d$_6$) δ 0.46-0.54 (m, 1 H) 0.64 (d, J = 6.15 Hz, 3 H) 0.89-1.02 (m, 9 H) 2.27 (s, 3 H) 3.20-3.27 (m, 2 H) 3.54-3.62 (m, 1 H) 3.90 (s, 3 H) 4.81 (d, J = 8.02 Hz, 1 H) 7.00 (dd, J = 8.41, 0.62 Hz, 1 H) 7.44 (d, J = 7.32 Hz, 1 H) 7.89 (dd, J = 8.37, 7.36 Hz, 1 H) 8.67 (d, J = 0.62 Hz, 2 H) 12.92 (s, 1 H). LCMS ESI (pos.) m/z: 488.2 (M + H)$^+$. |
| 124.0 | (1R,2S)-1-(5-chloropyrimidin-2-yl)-1-methoxypropane-2-sulfonamide (Example 29.3), picolinohydrazide (commercially available from TCI America), and (R)-2-isothiocyanato-1-methoxypropane (Example 28.9). | 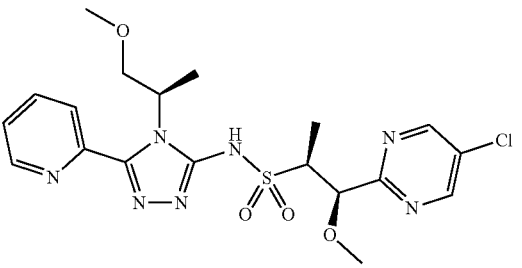<br>(1R,2S)-1-(5-chloro-2-pyrimidinyl)-1-methoxy-N-(4-((2R)-1-methoxy-2-propanyl)-5-(2-pyridinyl)-4H-1,2,4-triazol-3-yl)-2-propanesulfonamide.<br>$^1$H NMR (600 MHz, DMSO-d$_6$) δ 1.29 (d, J = 7.01 Hz, 3 H) 1.49 (d, J = 7.01 Hz, 3 H) 3.09 (s, 3 H) 3.16 (s, 3 H) 3.46 (dd, J = 9.96, 5.22 Hz, 1 H) 3.50 (qd, J = 6.93, 4.13 Hz, 1 H) 4.02 (br t, J = 9.69 Hz, 1 H) 4.96 (d, J = 4.05 Hz, 1 H) 5.31-5.42 (m, 1 H) 7.60 (ddd, J = 7.61, 4.85, 1.17 Hz, 1 H) 7.92 (dt, J = 7.88, 0.96 Hz, 1 H) 8.02 (td, J = 7.79, 1.71 Hz, 1 H) 8.75 (s, 1 H) 8.96 (s, 2 H) 13.19 (s, 1 H). LCMS ESI (pos.) m/z: 482.2 (M + H)$^+$. |

TABLE 12-continued

| Example | Reagents | Structure, Name and Data |
|---|---|---|
| 125.0 | (1R,2S)-1-(5-chloropyrimidin-2-yl)-1-methoxypropane-2-sulfonamide (Example 29.3), nicotinohydrazide (commercially available from Sigma-Aldrich Inc.), and (R)-2-isothiocyanato-1-methoxypropane (Example 28.9). | 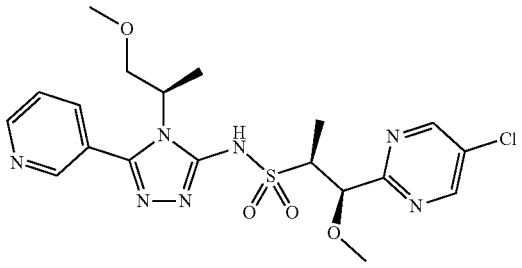<br>(1R,2S)-1-(5-chloro-2-pyrimidinyl)-1-methoxy-N-(4-((2R)-1-methoxy-2-propanyl)-5-(3-pyridinyl)-4H-1,2,4-triazol-3-yl)-2-propanesulfonamide.<br>$^1$H NMR (600 MHz, DMSO-d$_6$) δ 1.29 (d, J = 7.01 Hz, 3 H) 1.43 (d, J = 7.01 Hz, 3 H) 3.17 (s, 3 H) 3.18 (s, 3 H) 3.23-3.33 (m, 1 H) 3.45-3.56 (m, 1 H) 4.01 (br t, J = 9.77 Hz, 1 H) 4.14-4.27 (m, 1 H) 4.97 (d, J = 3.89 Hz, 1 H) 7.62 (dd, J = 7.78, 4.98 Hz, 1 H) 8.06 (br d, J = 7.94 Hz, 1 H) 8.79 (m, 2 H) 8.97 (s, 2 H) 13.17 (br s, 1 H). LCMS ESI (pos.) m/z: 482.2 (M + H)$^+$. |
| 126.0 | (1R,2S)-1-(5-chloropyrimidin-2-yl)-1-methoxypropane-2-sulfonamide (Example 29.3), 5-methylnicotinohydrazide (commercially available from Bellen), and (R)-2-isothiocyanato-1-methoxypropane (Example 28.9). | 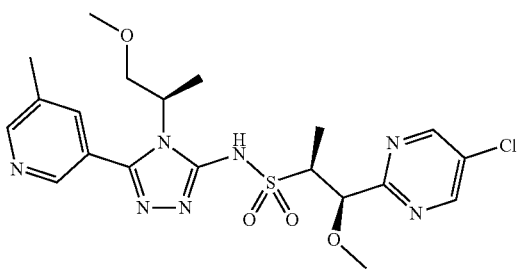<br>(1R,2S)-1-(5-chloro-2-pyrimidinyl)-1-methoxy-N-(4-((2R)-1-methoxy-2-propanyl)-5-(5-methyl-3-pyridinyl)-4H-1,2,4-triazol-3-yl)-2-propanesulfonamide.<br>$^1$H NMR (600 MHz, DMSO-d$_6$) δ 1.29 (d, J = 7.01 Hz, 3 H) 1.43 (d, J = 7.01 Hz, 3 H) 2.39 (s, 3 H) 3.17 (s, 3 H) 3.18 (s, 3 H) 3.37-3.42 (m, 1 H) 3.50 (br s, 1 H) 4.02 (br t, J = 9.77 Hz, 1 H) 4.21-4.29 (m, 1 H) 4.97 (d, J = 3.97 Hz, 1 H) 7.86 (s, 1 H) 8.58 (d, J = 1.56 Hz, 1 H) 8.63 (s, 1 H) 8.97 (s, 2 H) 13.15 (br s, 1 H). LCMS ESI (pos.) m/z: 496.2 (M + H)$^+$. |

TABLE 12-continued

| Example | Reagents | Structure, Name and Data |
|---|---|---|
| 127.0 | (1S,2S)-1-(5-chloropyrimidin-2-yl)-1-isopropoxypropane-2-sulfonamide (Example 31.01), picolinohydrazide (commercially available from TCI America), and isothiocyanatocyclopropane (commercially available from Lancaster). | 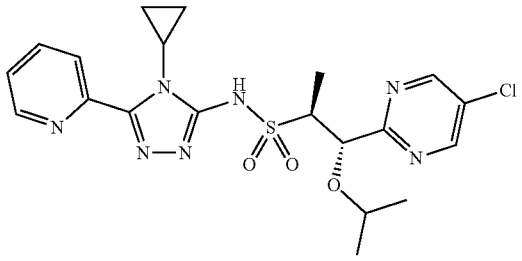<br>(1S,2S)-1-(5-chloro-2-pyrimidinyl)-N-(4-cyclopropyl-5-(2-pyridinyl)-4H-1,2,4-triazol-3-yl)-1-(2-propanyloxy)-2-propanesulfonamide.<br>$^1$H NMR (600 MHz, DMSO-d$_6$) δ 0.47-0.50 (m, 1H) 0.70 (d, J = 6.15 Hz, 3 H) 0.81-0.89 (m, 2 H) 0.93 (br s, 1 H) 1.00 (d, J = 6.07 Hz, 3 H) 1.09 (d, J = 7.16 Hz, 3 H) 3.14-3.17 (m, 1 H) 3.28-3.34 (m, 1 H) 3.60 (t, J = 7.24 Hz, 1 H) 4.90 (d, J = 7.32 Hz, 1 H) 7.59 (ddd, J = 7.63, 4.83, 1.17 Hz, 1 H) 7.84 (d, J = 8.01 Hz, 1 H) 8.01 (td, J = 7.77, 1.75 Hz, 1 H) 8.77 (s, 1 H) 8.96 (s, 2 H) 12.89 (s, 1 H). LCMS ESI (pos.) m/z: 478.2 (M + H)$^+$. |
| 128.0 | (1S,2S)-1-(5-chloropyrimidin-2-yl)-1-isopropoxypropane-2-sulfonamide (Example 31.01), nicotinohydrazide (commercially available from Sigma-Aldrich), and isothiocyanatocyclopropane (commercially available from Lancaster). | 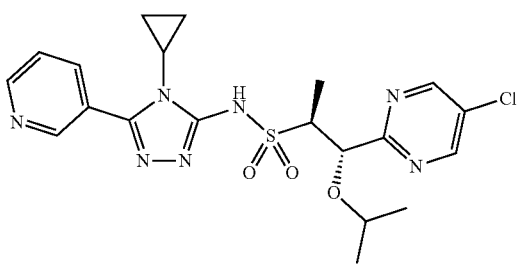<br>(1S,2S)-1-(5-chloro-2-pyrimidinyl)-N-(4-cyclopropyl-5-(3-pyridinyl)-4H-1,2,4-triazol-3-yl)-1-(2-propanyloxy)-2-propanesulfonamide.<br>$^1$H NMR (600 MHz, DMSO-d$_6$) δ 0.42-0.50 (m, 1 H) 0.70 (d, J = 6.07 Hz, 3 H) 0.78-0.86 (m, 1 H) 0.86-0.93 (m, 1 H) 0.97 (br s, 1 H) 1.02 (d, J = 5.99 Hz, 3 H) 1.10 (d, J = 7.16 Hz, 3 H) 3.25 (tt, J = 7.06, 3.68 Hz, 1 H) 3.33 (m, 1H) 3.56-3.68 (m, 1 H) 4.91 (d, J = 7.24 Hz, 1 H) 7.60 (ddd, J = 7.96, 4.85, 0.74 Hz, 1 H) 8.21 (dt, J = 8.16, 1.84 Hz, 1 H) 8.75 (dd, J = 4.87, 1.60 Hz, 1 H) 8.93-9.00 (m, 3 H), 12.90 (s, 1 H). LCMS ESI (pos.) m/z: 478.2 (M + H)$^+$. |

TABLE 12-continued

| Example | Reagents | Structure, Name and Data |
|---|---|---|
| 129.0 | (1S,2S)-1-(5-chloropyrimidin-2-yl)-1-isopropoxypropane-2-sulfonamide (Example 31.01), 5-methylnicotinohydrazide (commercially available from Bellen), and isothiocyanatocyclopropane (commercially available from Lancaster). | 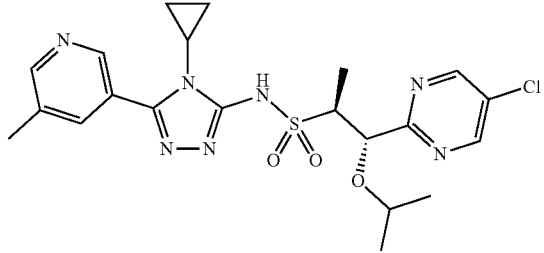<br>(1S,2 S)-1-(5-chloro-2-pyrimidinyl)-N-(4-cyclopropyl-5-(5-methyl-3-pyridinyl)-4H-1,2,4-triazol-3-yl)-1-(2-propanyloxy)-2-propanesulfonamide.<br>$^1$H NMR (600 MHz, DMSO-$d_6$) δ 12.89 (br s, 1 H) 8.96 (s, 2 H) 8.77 (d, J = 1.64 Hz, 1 H) 8.60 (d, J = 1.32 Hz, 1 H) 8.02 (d, J = 0.70 Hz, 1 H) 4.90 (d, J = 7.32 Hz, 1 H) 3.59 (quin, J = 7.16 Hz, 1 H) 3.34 (m, 1 H) 3.25 (tt, J = 7.02, 3.69 Hz, 1 H) 2.40 (s, 3 H) 1.10 (d, J = 7.16 Hz, 3 H) 1.01 (d, J = 6.07 Hz, 3 H) 0.96-1.00 (m, 1 H) 0.87-0.94 (m, 1 H) 0.80-0.87 (m, 1 H) 0.69 (d, J = 6.07 Hz, 3 H) 0.42-0.49 (m, 1 H). LCMS ESI (pos.) m/z: 512.2 (M + H)$^+$. |
| 130.0 | (1R,2S)-1-(5-chloropyrimidin-2-yl)-1-methoxypropane-2-sulfonamide (Example 29.3), picolinohydrazide (commercially available from TCI America), and methyl isothiocyanate, (commercially available from Acros Organics). | 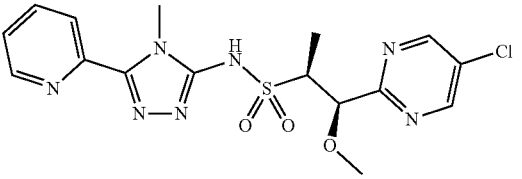<br>(1R,2S)-1-(5-chloropyrimidin-2-yl)-1-methoxy-N-(4-methyl-5-(pyridin-2-yl)-4H-1,2,4-triazol-3-yl)propane-2-sulfonamide.<br>$^1$H NMR (400 MHz, DMSO-$d_6$) δ 13.23 (br s, 1H), 8.88 (s, 2H), 8.73 (br d, J = 4.8 Hz, 1H), 8.00 (br s, 2H), 7.63-7.53 (m, 1H), 4.78 (d, J = 5.4 Hz, 1H), 3.71-3.58 (m, 1H), 3.53 (s, 3H), 3.13 (s, 3H), 1.35 (d, J = 6.8 Hz, 3H). LCMS-ESI (pos.) m/z: 424.0 (M + H)$^+$. |
| 131.0 | (1R,2S)-1-(5-chloropyrimidin-2-yl)-1-methoxypropane-2-sulfonamide (Example 29.3), picolinohydrazide (commercially available from TCI America), and ethyl isothiocyanate (commercially available from TCI America). | 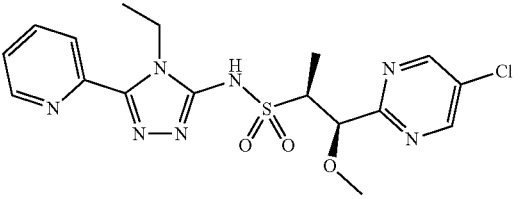<br>(1R,2S)-1-(5-chloropyrimidin-2-yl)-N-(4-ethyl-5-(pyridin-2-yl)-4H-1,2,4-triazol-3-yl)-1-methoxypropane-2-sulfonamide.<br>$^1$H NMR (400 MHz, DMSO-$d_6$) δ 13.24 (br s, 1H), 8.90 (s, 2H), 8.74 (d, J = 4.8 Hz, 1H), 8.01 (d, J = 3.7 Hz, 2H), 7.61-7.55 (m, 1H), 4.87 (d, J = 4.8 Hz, 1H), 4.26-4.09 (m, 2H), 3.65-3.53 (m, 1H), 3.11 (s, 3H), 1.32 (d, J = 7.0 Hz, 3H), 1.23 (t, J = 7.0 Hz, 3H). LCMS-ESI (pos.) m/z: 438.0 (M + H)$^+$. |

TABLE 12-continued

| Example | Reagents | Structure, Name and Data |
|---------|----------|--------------------------|
| 132.0 | (1R,2S)-1-(5-chloropyrimidin-2-yl)-1-methoxypropane-2-sulfonamide (Example 29.3), picolinohydrazide (commercially available from TCI America), and 2-methoxyethyl isothiocyanate (commercially available from Sigma Aldrich). | 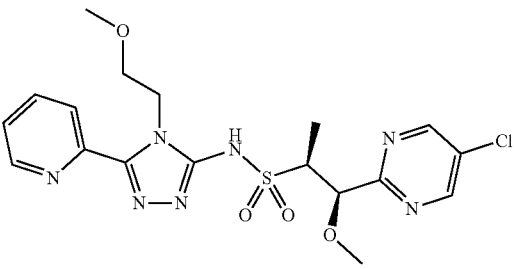<br>(1R,2S)-1-(5-chloropyrimidin-2-yl)-1-methoxy-N-(4-(2-methoxyethyl)-5-(pyridin-2-yl)-4H-1,2,4-triazol-3-yl)propane-2-sulfonamide.<br>$^1$H NMR (400 MHz, DMSO-$d_6$) δ 13.25 (br s, 1H), 8.91 (s, 2H), 8.73 (d, J = 4.4 Hz, 1H), 8.04-7.95 (m, 2H), 7.57 (t, J = 5.4 Hz, 1H), 4.88 (d, J = 4.6 Hz, 1H), 4.48-4.34 (m, 2H), 3.64-3.50 (m, 3H), 3.13 (s, 3H), 3.11-3.05 (m, 3H), 1.31 (d, J = 6.8 Hz, 3H). LCMS-ESI (pos.) m/z: 468.0 (M + H)$^+$. |

The compounds set forth in the following table were synthesized following the procedure in Example 41.0 using the known starting material as described.

TABLE 13

| Example | Reagents | Structure, Name and Data |
|---------|----------|--------------------------|
| 115.0 | 5-chloropicolinaldehyde (commercially available from Combi-Blocks) and MeOTf (commercially available from Combi-Blocks). | 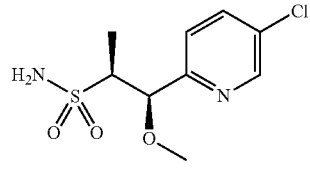<br>AND<br>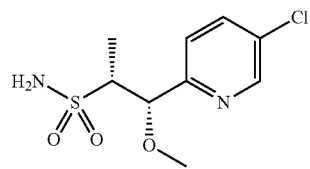<br>(1R,2S)-1-(5-chloropyridin-2-yl)-1-methoxypropane-2-sulfonamide and (1S,2R)-1-(5-chloropyridin-2-yl)-1-methoxypropane-2-sulfonamide.<br>LCMS-ESI (pos.) m/z: 265.0 (M + H)$^+$. |
| 116.0 | Example 115.0 was purified using the following preparative SFC method: Column: Chiral Pak IC (250 × 4.6) mm 5u, Mobile Phase: 0.1% DEA inHexanes:EtOH (80:20), Flow: 1.0 mL/min. to provide peak 1. | 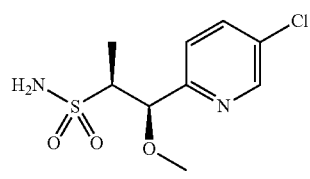<br>OR<br>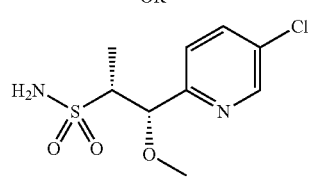 |

TABLE 13-continued

| Example | Reagents | Structure, Name and Data |
|---|---|---|
| | | (1R,2S)-1-(5-chloropyridin-2-yl)-1-methoxypropane-2-sulfonamide or (1S,2R)-1-(5-chloropyridin-2-yl)-1-methoxypropane-2-sulfonamide. $^1$H NMR (400 MHz, DMSO-d$_6$) δ 8.64 (d, J = 2.5 Hz, 1H), 7.99 (dt, J = 8.4, 2.3 Hz, 1H), 7.44 (d, J = 8.4 Hz, 1H), 6.81 (s, 2H), 4.89 (d, J = 2.5 Hz, 1H), 3.33 (m, 4H), 1.10 (dd, J = 7.0, 1.9 Hz, 3H). LCMS-ESI (pos.) m/z: 265.0 (M + H)$^+$. |
| 117.0 | Example 115.0 was purified using the following preparative SFC method: Column: CHIRAL PAK IC (250 × 4.6) mm 5u, Mobile Phase: 0.1% DEA in Hexane:EtOH (80:20), Flow: 1.0 mL/min. to provide peak 2. | 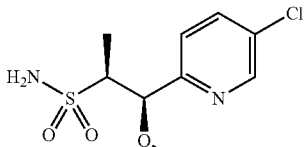 OR 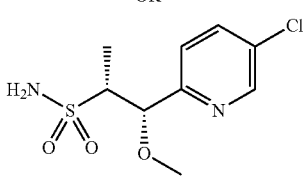 (1R,2S)-1-(5-chloropyridin-2-yl)-1-methoxypropane-2-sulfonamide or (1S,2R)-1-(5-chloropyridin-2-yl)-1-methoxypropane-2-sulfonamide. $^1$H NMR (400 MHz, DMSO-d$_6$) δ 8.64 (d, J = 2.4 Hz, 1H), 7.99 (dd, J = 8.3, 2.4 Hz, 1H), 7.44 (d, J = 8.4 Hz, 1H), 6.81 (s, 2H), 4.89 (d, J = 2.3 Hz, 1H), 3.33 (m, 4H), and 1.10 (d, J = 7.0 Hz, 3H). LCMS-ESI (pos.) m/z: 265.0 (M + H)$^+$. |

Example 133.0: Preparation of (1R,2S)-1-hydroxy-N,N-bis(4-methoxybenzyl)-1-(5-methylpyrimidin-2-yl)propane-2-sulfonamide 133.1

N-Methoxy-N,5-dimethylpyrimidine-2-carboxamide, Example 133.1

To a solution of 5-methylpyrimidine-2-carboxylic acid (1 g, 7.24 mmol) in DMF (72.4 mL) was added 5-methylpyrimidine-2-carboxylic acid (1 g, 7.24 mmol), N,O-dimethylhydroxylamine hydrochloride (0.777 g, 7.96 mmol). The mixture was cooled to 0° C. and 1-propanephosphonic acid cyclic anhydride, 50 wt. % solution in EtOAc (9.21 mL, 14.48 mmol) was added dropwise. The mixture was allowed to warm to 23° C. overnight. LCMS indicated complete conversion to product. The mixture was diluted with water, extracted with CHCl$_3$:IPA (3:1) and washed with brine, NaHCO$_3$. The mixture was dried over Na$_2$SO$_4$, concentrated in vacuo and purified by silica gel chromatography (0-100% heptanes:EtOAc) to yield N-methoxy-N,5-dimethylpyrimidine-2-carboxamide (0.7 g, 3.86 mmol, 53.4% yield). $^1$H NMR (500 MHz, CDCl$_3$) δ 8.61-8.69 (m, 2H) 3.61-3.79 (m, 3H) 3.27-3.47 (m, 3H) 2.34-2.45 (m, 3H). LCMS-ESI (pos.) m/z: 182.2 (M+H)$^+$.

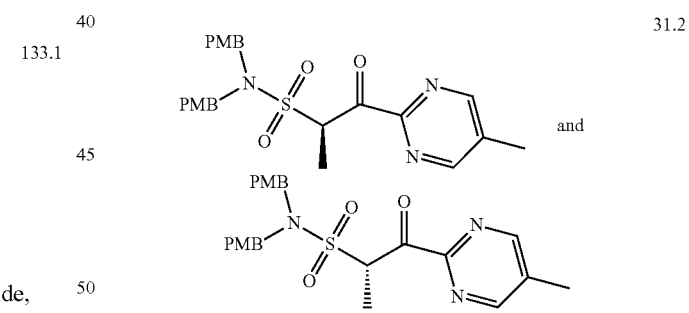

31.2 and (R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 31.2

A solution of N,N-bis(4-methoxybenzyl)ethanesulfonamide (azeotroped three times with toluene before use) (Example 30.0, 0.771 g, 2.208 mmol) was dissolved in THF (3.68 mL) and cooled to −78° C. using a dry ice acetone bath (internal reaction temperature/bath temperature not monitored). To this was added a solution of n-butyllithium (0.883 mL, 2.21 mmol, 2.5M in hexanes). The reaction turned pink immediately and then slowly faded to yellow upon stirring at −78° C. for 30 min. This solution was then added quickly to a solution of N-methoxy-N,5-dimethylpyrimidine-2-carboxamide (Example 133.1, 0.2 g, 1.104 mmol) in THF (0.5 mL) at RT. The reaction was stirred at RT for ~20 min after which LCMS indicated complete consumption of Weinreb amide and conversion to product. The reaction was quenched by addition to separation funnel that contained 1M HCl (~15 mL). The mixture was extracted with DCM, (aqueous layer was checked for product by LCMS) dried over $Na_2SO_4$ and concentrated in vacuo. The mixture was then purified by silica gel chromatography 0-100% EtOAc:heptanes to yield N,N-bis(4-methoxybenzyl)-1-(5-methylpyrimidin-2-yl)-1-oxopropane-2-sulfonamide (0.36 g, 0.767 mmol, 69.5% yield) $^1$H NMR (500 MHz, DMSO-$d_6$) δ 8.86-8.93 (m, 2H) 7.06-7.15 (m, 4H) 6.79-6.87 (m, 4H) 5.87-5.95 (m, 1H) 4.20-4.34 (m, 4H) 3.67-3.73 (m, 6H) 2.38-2.42 (m, 3H) 1.46-1.55 (m, 3H). LCMS-ESI (pos.) m/z: 470.0 (M+H)$^+$.

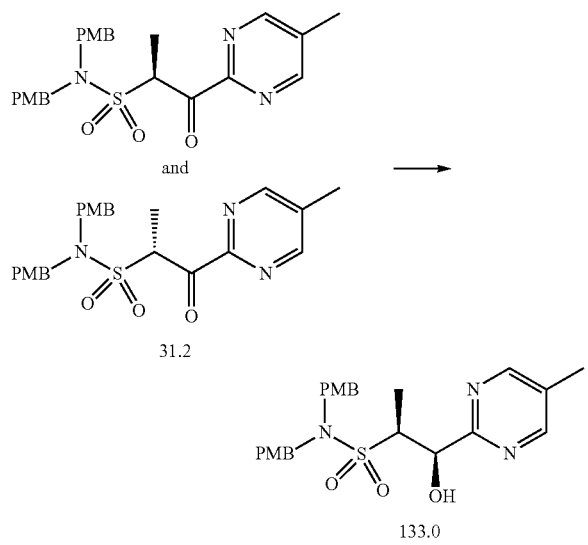

(1R,2S)-1-Hydroxy-N,N-bis(4-methoxybenzyl)-1-(5-methylpyrimidin-2-yl)propane-2-sulfonamide, Example 133.0. To a solution of Example 31.2

(1 g, 2.130 mmol) in DMF (22.18 mL) was added (N-((1S,2S)-1,2-diphenyl-2-((3-phenylpropyl)amino)ethyl)-4-methylphenylsulfonamido)ruthenium(II) chloride (9.91 mg, 0.016 mmol). The mixture was then degassed by placing under vacuum and backfilling with $N_2$ three times. To this was added a solution of HCOOH:$Et_3$N (5:2 v/v) (0.55 mL) and the reaction was stirred at RT for 12 h after which LCMS indicated complete conversion to product and 7:1 d.r. (syn:anti). The mixture was then washed with 5% LiCl (aq), extracted with DCM and then with $CHCl_3$:IPA (3:1). The aqueous layer was checked for product by LCMS. The organic layers were combined, dried over $Na_2SO_4$ and concentrated in vacuo. The mixture was loaded directly onto a silica gel column and purified using a gradient of 0-100% heptanes:EtOAc. DMF caused both syn and anti to co-elute. The factions were combined and concentrated in vacuo. The mixture was repurified using the same gradient to yield (1R,2S)-1-hydroxy-N,N-bis(4-methoxybenzyl)-1-(5-methylpyrimidin-2-yl)propane-2-sulfonamide (0.77 g, 1.633 mmol, 77% yield) as an off white solid. $^1$H NMR (500 MHz, DMSO-$d_6$) δ 8.85-8.93 (m, 2H) 7.08-7.15 (m, 4H) 6.78-6.86 (m, 4H) 5.86-5.96 (m, 1H) 4.20-4.35 (m, 4H) 3.68-3.75 (m, 6H) 3.28-3.34 (m, 2H) 2.37-2.42 (m, 3H) 1.47-1.54 (m, 3H). LCMS-ESI (pos.) m/z: 572.2 (M+H)$^+$.

The compounds set forth in the following table were synthesized following the procedure in Example 1.0 using the known starting material as described.

TABLE 14

| Example | Reagents | Structure, Name and Data |
|---|---|---|
| 134.0 | nicotinohydrazide (commercially available from Sigma-Aldrich Inc.), 2-isothiocyanatopropane (commercially available from Sigma-Aldrich Inc.), and (1R,2S)-1-(5-chloropyrimidin-2-yl)-1-methoxypropane-2-sulfonamide (Example 29.3). | (1R,2S)-1-(5-chloro-2-pyrimidinyl)-1-methoxy-N-(4-(2-propanyl)-5-(3-pyridinyl)-4H-1,2,4-triazol-3-yl)-2-propanesulfonamide. $^1$H NMR (600 MHz, DMSO-$d_6$) δ 8.90-8.97 (m, 1 H) 8.72-8.76 (m, 1 H) 8.69-8.72 (m, 1 H) 7.89-8.01 (m, 1 H) 7.58 (dd, J = 7.9, 4.9 Hz, 1 H) 4.86-4.93 (m, 1H) 4.18 (dt, J = 13.7, 6.9 Hz, 1 H) 3.83 (br s, 1 H) 3.20 (s, 3 H) 1.39 (m, 6 H) 1.25-1.32 (m, 3 H) LCMS-ESI (pos.) m/z: 452.2 (M + H)$^+$. |

TABLE 14-continued

| Example | Reagents | Structure, Name and Data |
|---|---|---|
| 135.0 | isonicotinohydrazide (commercially available from Oakwood), 2-isothiocyanatopropane (commercially available from Sigma-Aldrich Inc.), and (1R,2S)-1-(5-chloropyrimidin-2-yl)-1-methoxypropane-2-sulfonamide (Example 29.3). | 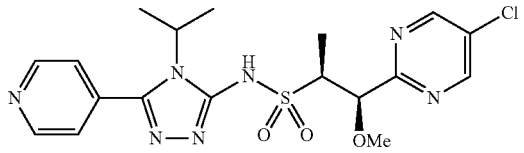 [SMILES: CO[C@H](c1ncc(Cl)cn1)[C@H](C)S(=O)(=O)Nc1nnc(-c2ccncc2)n1C(C)C]<br>(1R,2S)-1-(5-chloro-2-pyrimidinyl)-1-methoxy-N-(4-(2-propanyl)-5-(4-pyridinyl)-4H-1,2,4-triazol-3-yl)-2-propanesulfonamide.<br>$^1$H NMR (600 MHz, DMSO-$d_6$) δ 13.21 (br d, J = 4.2 Hz, 1 H) 8.91-9.05 (m, 2 H) 8.78-8.87 (m, 2 H) 7.56-7.70 (m, 2 H) 4.89-5.03 (m, 1 H) 4.22-4.35 (m, 1 H) 3.50-3.66 (m, 1 H) 3.17-3.20 (m, 3 H) 1.44-1.47 (m, 6 H) 1.31-1.33 (m, 3 H). LCMS-ESI (pos.) m/z: 452.2 (M + H)$^+$. |
| 136.0 | picolinohydrazide (commercially available from Sigma-Aldrich Inc.), 2-isothiocyanatopropane (commercially available from Sigma-Aldrich Inc.), and (1R,2S)-1-(5-chloropyrimidin-2-yl)-1-methoxypropane-2-sulfonamide | 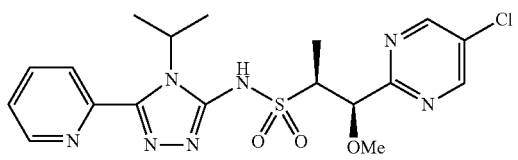 [SMILES: CO[C@H](c1ncc(Cl)cn1)[C@H](C)S(=O)(=O)Nc1nnc(-c2ccccn2)n1C(C)C]<br>(1R,2S)-1-(5-chloro-2-pyrimidinyl)-1-methoxy-N-(4-(2-propanyl)-5-(2-pyridinyl)-4H-1,2,4-triazol-3-yl)-2-propanesulfonamide.<br>$^1$H NMR (600 MHz, DMSO-d6) δ 8.91-8.99 (m, 2 H) 8.72-8.80 (m, 1 H) 7.98-8.07 (m, 1 H) 7.89-7.98 (m, 1 H) 7.53-7.62 (m, 1 H) 5.08-5.19 (m, 1 H) 4.91-4.99 (m, 1 H) 3.52-3.60 (m, 1 H) 3.13-3.16 (m, 3H) 1.44-1.51 (m, 6 H) 1.26-1.33 (m, 3 H) LCMS-ESI (pos.) m/z: 452.2 (M + H)$^+$. |
| 137.0 | 6-methoxypicolinohydrazide (commercially available from Sigma-Aldrich Inc.), 2-(isothiocyanatomethyl)oxetane (Example 137.1), and (1R,2S)-1-(5-chloropyrimidin-2-yl)-1-methoxypropane-2-sulfonamide (Example 29.3). | 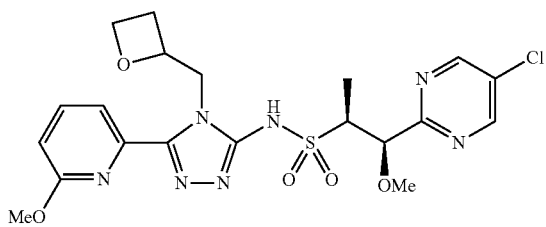 [SMILES: COc1cccc(-c2nnc(NS(=O)(=O)[C@@H](C)[C@H](OC)c3ncc(Cl)cn3)n2CC2CCO2)n1]<br>(1R,2S)-1-(5-chloropyrimidin-2-yl)-1-methoxy-N-(5-(6-methoxypyridin-2-yl)-4-(oxetan-2-ylmethyl)-4H-1,2,4-triazol-3-yl)propane-2-sulfonamide.<br>$^1$H NMR (500 MHz, DMSO-d6) δ 12.91-13.46 (m, 1 H) 8.83-8.97 (m, 2 H) 7.86-7.99 (m, 1 H) 7.58-7.69 (m, 1 H) 6.97-7.01 (m, 1 H) 4.92 (br d, J = 5.8 Hz, 1 H) 4.82-4.89 (m, 1 H) 4.67-4.82 (m, 1 H) 4.33-4.44 (m, 2 H) 4.20-4.29 (m, 1 H) 3.93 (d, J = 2.6 Hz, 3 H) 3.56-3.70 (m, 1 H) 3.29-3.34 (m, 2 H) 3.14-3.17 (m, 2 H) 2.60-2.71 (m, 1 H) 2.33-2.49 (m, 2 H) 1.28-1.36 (m, 3 H) LCMS-ESI (pos.) m/z: 510.2 (M + H)$^+$. |

TABLE 14-continued

| Example | Reagents | Structure, Name and Data |
|---|---|---|
| 138.0 | 6-methoxypicolinohydrazide (commercially available from Sigma-Aldrich Inc.), (R)-2-((R)-1-isothiocyanatoethyl)-4-methylmorpholine and (S)-2-((R)-1-isothiocyanatoethyl)-4-methylmorpholine and (R)-2-((S)-1-isothiocyanatoethyl)-4-methylmorpholine and (S)-2-((S)-1-isothiocyanatoethyl)-4-methylmorpholine (Example 138.1), and (1R,2S)-1-(5-chloropyrimidin-2-yl)-1-methoxypropane-2-sulfonamide (Example 29.3). The product was purified by chiral SFC: Chiralpak AD-H 2 × 25 cm, Mobile Phase: 25% EtOH, Flowrate: 80 mL/min, Pressure Drop: 90 bar, BPR: 100 bar, UV Detector Wavelength: 219 nm. This was the first peak to elute under these conditions. | (structures) OR (structures) OR (structures) OR (structures)<br><br>(1R,2S)-1-(5-chloropyrimidin-2-yl)-1-methoxy-N-(5-(6-methoxypyridin-2-yl)-4-((R)-1-((S)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((R)-4-methylmorpholin-2-yl)ethyl)-4H-1,2,4-triazol-3-yl)propane-2-sulfonamide.<br>$^1$H NMR (500 MHz, DMSO-d6) δ 13.03-13.32 (m, 1 H) 8.84-9.06 (m, 2 H) 7.83-8.04 (m, 1 H) 7.45-7.65 (m, 1 H) 6.92-7.12 (m, 1 H) 5.06-5.33 (m, 1 H) 4.99-5.06 (m, 1 H) 4.26-4.36 (m, 1 H) 4.04-4.12 (m, 2 H) 3.90-3.96 (m, 3 H) 3.77-3.84 (m, 1 H) 3.40-3.55 (m, 2 H) 3.16-3.19 (m, 3 H) 2.54-2.76 (m, 1 H) 2.07-2.15 (m, 3 H) 1.83-1.95 (m, 1 H) 1.52 (br d, J = 6.7 Hz, 3 H) 1.27-1.32 (m, 3 H). LCMS-ESI (pos.) m/z: 567.2 (M + H)$^+$. |

TABLE 14-continued

| Example | Reagents | Structure, Name and Data |
|---|---|---|
| 139.0 | 6-methoxypicolinohydrazide (commercially available from Sigma-Aldrich Inc.), (R)-2-((R)-1-isothiocyanatoethyl)-4-methylmorpholine and (S)-2-((R)-1-isothiocyanatoethyl)-4-methylmorpholine and (R)-2-((S)-1-isothiocyanatoethyl)-4-methylmorpholine and (S)-2-((S)-1-isothiocyanatoethyl)-4-methylmorpholine (Example 138.1), and (1R,2S)-1-(5-chloropyrimidin-2-yl)-1-methoxypropane-2-sulfonamide (Example 29.3). The product was purified by chiral SFC: Chiralpak AD-H 2 × 25 cm, Mobile Phase: 25% EtOH, Flowrate: 80 mL/min, Pressure Drop: 90 bar, BPR: 100 bar, UV Detector Wavelength: 219 nm. This was the second peak to elute under these conditions. | 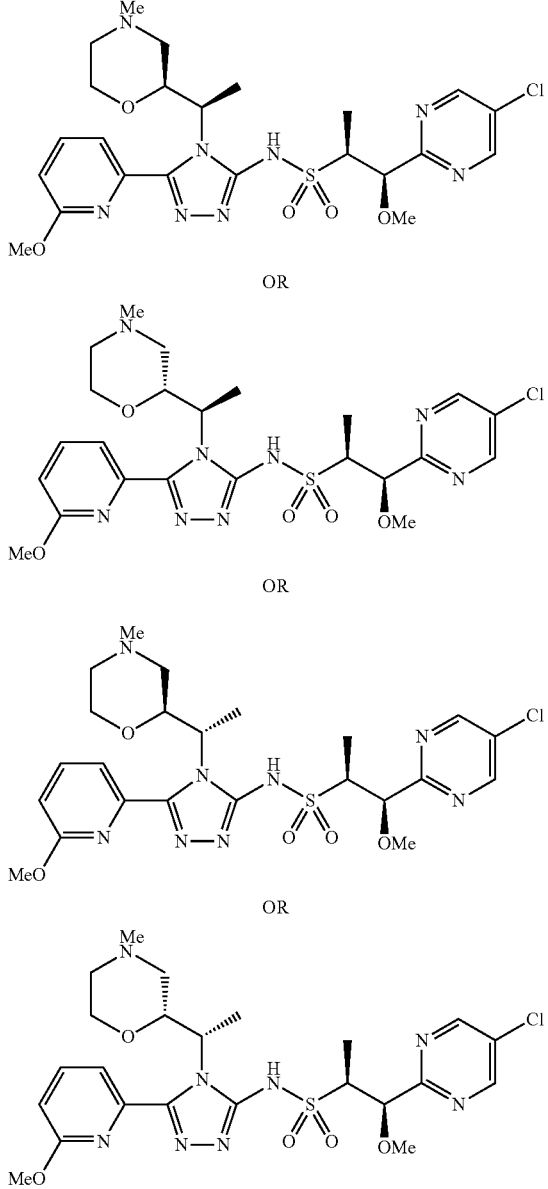 (1R,2S)-1-(5-chloropyrimidin-2-yl)-1-methoxy-N-(5-(6-methoxypyridin-2-yl)-4-((R)-1-((S)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-4-methylmorpholin-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((R)-4-methylmorpholin-2-yl)ethyl)-4H-1,2,4-triazol-3-yl)propane-2-sulfonamide. $^1$H NMR (500 MHz, DMSO-d6) δ 12.92-13.41 (m, 1 H) 8.83-9.09 (m, 2 H) 7.92 (t, J = 7.9 Hz, 1 H) 7.47-7.73 (m, 1 H) 7.05 (d, J = 8.3 Hz, 1 H) 5.05-5.32 (m, 1 H) 4.97 (d, J = 4.2 Hz, 1 H) 4.30 (br t, J = 8.8 Hz, 1 H) 3.91-3.97 (m, 3 H) 3.76-3.86 (m, |

| Example | Reagents | Structure, Name and Data |
|---|---|---|
| | | 1 H) 3.49-3.57 (m, 2 H) 3.17 (d, J = 5.2 Hz, 3 H) 2.53-2.58 (m, 1 H) 2.40-2.46 (m, 1 H) 2.03-2.10 (m, 3 H) 1.84-1.94 (m, 1 H) 1.73 (br s, 1 H) 1.53 (br d, J = 6.7 Hz, 3 H) 1.31 (d, J = 7.0 Hz, 3 H) LCMS-ESI (pos.) m/z: 567.2 (M + H)⁺. |
| 140.0 | 6-methoxypicolinohydrazide (commercially available from Sigma-Aldrich Inc.), 2-(isothiocyanatomethyl)oxetane (Example 137.1), and (1R,2S)-1-(5-chloropyrimidin-2-yl)-1-methoxypropane-2-sulfonamide (Example 29.3). The product was purified by chiral SFC: ChromegaChiral CC4 2 × 25 cm, Mobile Phase: 60% MeOH, Flowrate: 80 mL/min, Pressure Drop: 142 bar, BPR: 100 bar, UV Detector Wavelength: 220 nm. This was the first peak to elute under these conditions. | 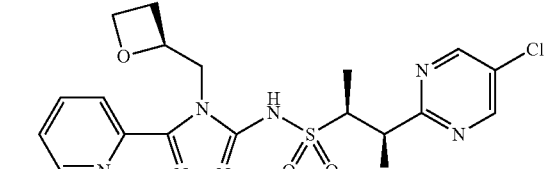<br>OR<br>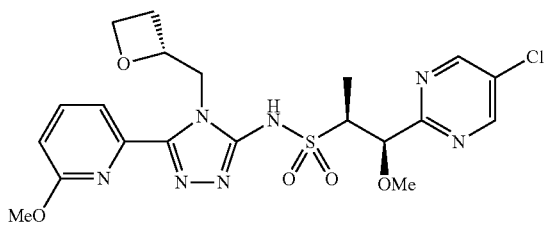<br>(1R,2S)-1-(5-chloropyrimidin-2-yl)-1-methoxy-N-(5-(6-methoxypyridin-2-yl)-4-(((S)-oxetan-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((R)-oxetan-2-yl)methyl)-4H-1,2,4-triazol-3-yl)propane-2-sulfonamide.<br>¹H NMR (500 MHz, DMSO-d6) δ 13.16-13.36 (m, 1 H) 8.80-8.99 (m, 2 H) 7.76-7.95 (m, 1 H) 7.50-7.68 (m, 1 H) 6.90-7.04 (m, 1 H) 4.91-4.98 (m, 1 H) 4.86-4.90 (m, 1 H) 4.71 (dd, J = 13.9, 6.4 Hz, 1 H) 4.51 (dd, J = 13.9, 4.7 Hz, 1 H) 4.32-4.43 (m, 1 H) 4.18-4.28 (m, 1 H) 3.93 (s, 3 H) 3.59 (br dd, J = 6.7, 5.2 Hz, 1 H) 3.12 (s, 3 H) 2.59-2.72 (m, 1 H) 2.37-2.46 (m, 1 H) 1.32 (d, J = 6.9 Hz, 3 H) LCMS-ESI (pos.) m/z: 510.2 (M + H)⁺. |
| 141.0 | 6-methoxypicolinohydrazide (commercially available from Sigma-Aldrich Inc.), 2-(isothiocyanatomethyl)oxetane (Example 137.1), and (1R,2S)-1-(5-chloropyrimidin-2-yl)-1-methoxypropane-2-sulfonamide (Example 29.3). The product was purified by chiral SFC: ChromegaChiral CC4 2 × 25 cm, Mobile Phase: 60% MeOH, Flowrate: 80 mL/min, Pressure Drop: 142 bar, BPR: 100 bar, UV Detector Wavelength: 220 nm. This was the second peak to elute under these conditions | 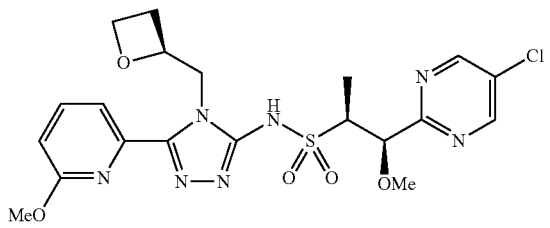<br>OR<br>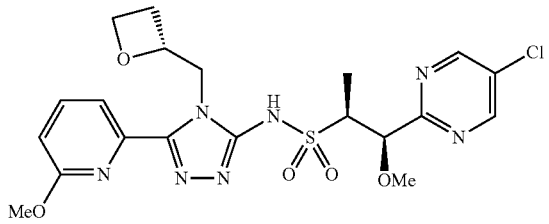<br>(1R,2S)-1-(5-chloropyrimidin-2-yl)-1-methoxy-N-(5-(6-methoxypyridin-2-yl)-4-(((S)-oxetan-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((R)-oxetan-2-yl)methyl)-4H-1,2,4-triazol-3-yl)propane-2-sulfonamide. ¹H NMR (500 MHz, DMSO-d6) δ |

| Example | Reagents | Structure, Name and Data |
|---|---|---|
| | | 13.04-13.45 (m, 1 H) 8.74-9.04 (m, 2 H) 7.76-7.96 (m, 1 H) 7.47-7.66 (m, 1 H) 6.88-7.16 (m, 1 H) 4.87-4.98 (m, 1 H) 4.82-4.87 (m, 1 H) 4.74-4.82 (m, 1 H) 4.34-4.44 (m, 2 H) 4.23 (dt, J = 9.0, 6.1 Hz, 1 H) 3.93 (s, 3 H) 3.58-3.69 (m, 1 H) 3.16-3.18 (m, 3 H) 2.55-2.66 (m, 1 H) 2.41-2.48 (m, 1 H) 1.33 (d, J = 7.0 Hz, 3 H). LCMS-ESI (pos.) m/z: 510.2 (M + H)+ |
| 142.0 | 6-methoxypicolinohydrazide (commercially available from Sigma-Aldrich Inc.), 1-(1,4-dioxan-2-yl)ethan-1-amine (Example 142.1), and (1R, 2S)-1-(5-chloropyrimidin-2-yl)-1-methoxypropane-2-sulfonamide (Example 29.3). The product was purified by chiral SFC: ChromegaChiral CC4 2 × 25 cm, Mobile Phase: 40% MeOH, Flowrate: 80 mL/min, Pressure Drop: 91 bar, BPR: 100 bar, UV Detector Wavelength: 222 nm. This was the first peak to elute under these conditions | (1R,2S)-N-(4-((R)-1-((R)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((S)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((S)-1-((R)-1,4-dioxan-2-yl)ethyl)-5-(6-methoxypyridin-2-yl)-4H-1,2,4-triazol-3-yl)-1-(5-chloropyrimidin-2-yl)-1- |

TABLE 14-continued

| Example | Reagents | Structure, Name and Data |
|---|---|---|
| | | methoxypropane-2-sulfonamide.<br>¹H NMR (500 MHz, DMSO-d6) δ 13.07-13.39 (m, 1 H) 8.85-9.16 (m, 2 H) 7.86-8.16 (m, 1 H) 7.55 (d, J = 7.3 Hz, 1 H) 7.06 (d, J = 8.4 Hz, 1 H) 5.07-5.34 (m, 1 H) 4.94-5.07 (m, 1 H) 4.32-4.52 (m, 1 H) 3.96 (s, 3 H) 3.78 (br d, J = 9.9 Hz, 1 H) 3.54-3.73 (m, 3 H) 3.41-3.53 (m, 1 H) 3.34-3.41 (m, 1 H) 3.27-3.30 (m, 1 H) 3.15 (s, 3 H) 1.51 (d, J = 6.7 Hz, 3 H) 1.30 (d, J = 7.0 Hz, 3 H) LCMS-ESI (pos.) m/z: 554.2 (M + H)⁺. |
| 143.0 | 6-methoxypicolinohydrazide (commercially available from Sigma-Aldrich Inc.), 1-(1,4-dioxan-2-yl)ethan-1-amine (Example 142.1), and (1R,2S)-1-(5-chloropyrimidin-2-yl)-1-methoxypropane-2-sulfonamide (Example 29.3).<br>The product was purified by chiral SFC: ChromegaChiral CC4 2 × 25 cm, Mobile Phase: 40% MeOH, Flowrate: 80 mL/min, Pressure Drop: 91 bar, BPR: 100 bar, UV Detector Wavelength: 222 nm.<br>This was the second peak to elute under these conditions | OR<br><br>OR<br><br>OR<br><br>(1R,2S)-N-(4-((R)-1-((R)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((S)-1-((S)-1,4-dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-((S)-1-((R)-1,4- |

| Example | Reagents | Structure, Name and Data |
|---|---|---|
| | | dioxan-2-yl)ethyl)-5-(6-methoxypyridin-2-yl)-4H-1,2,4-triazol-3-yl)-1-(5-chloropyrimidin-2-yl)-1-methoxypropane-2-sulfonamide.<br>$^1$H NMR (500 MHz, DMSO-$d_6$) δ 13.08-13.28 (m, 1 H) 8.79-9.05 (m, 2 H) 7.71-8.01 (m, 1 H) 7.55 (d, J = 7.3 Hz, 1 H) 7.06 (d, J = 8.4 Hz, 1 H) 5.04-5.32 (m, 1 H) 4.99 (d, J = 3.9 Hz, 1 H) 4.38 (br d, J = 2.1 Hz, 1 H) 3.95 (s, 3 H) 3.71-3.80 (m, 1 H) 3.44-3.66 (m, 4 H) 3.38 (br d, J = 2.3 Hz, 1 H) 3.26 (br t, J = 10.5 Hz, 1 H) 3.17 (s, 3 H) 1.51 (br d, J = 6.7 Hz, 3 H) 1.31 (d, J = 7.0 Hz, 3 H) LCMS-ESI (pos.) m/z: 554.2 (M + H)$^+$. |
| 144.0 | 6-methoxypicolinohydrazide (commercially available from Sigma-Aldrich Inc.), 1-(1,4-dioxan-2-yl)ethan-1-amine (Example 142.1), and (2S,3R)-3-(5-chloropyrimidin-2-yl)butane-2-sulfonamide (Example 27.4). The product was purified by chiral SFC: Chiralpak AD-H 2 × 25 cm, Mobile Phase: 35% MeOH, Flowrate: 80 mL/min, Pressure Drop: 110 bar, BPR: 100 bar, UV Detector Wavelength: 219 nm. This was the first peak to elute under these conditions | 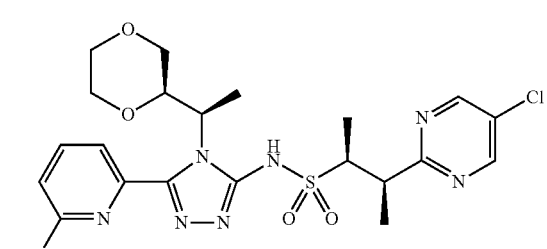<br>OR<br>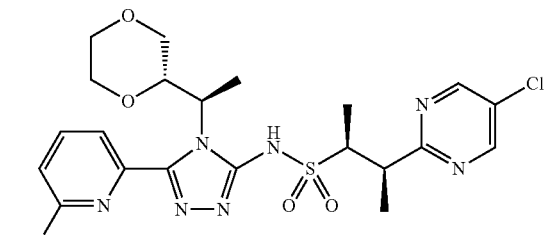<br>OR<br>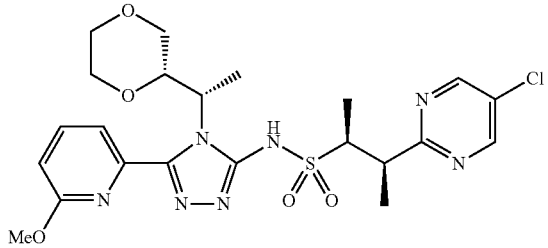<br>OR<br>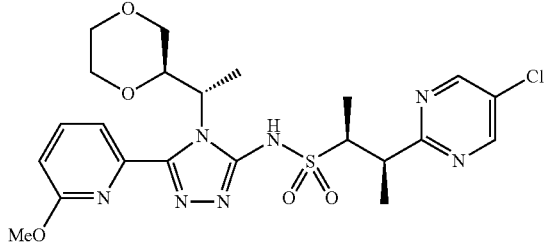<br>(2S,3R)-N-(4-((R)-1-((R)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((R)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((S)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or |

TABLE 14-continued

| Example | Reagents | Structure, Name and Data |
|---|---|---|
| | | (2S,3R)-N-(4-((S)-1-((R)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide. <br> $^1$H NMR (500 MHz, DMSO-d6) δ 13.11-13.45 (m, 1 H) 8.77-8.91 (m, 2 H) 7.80-8.03 (m, 1 H) 7.55 (d, J = 7.3 Hz, 1 H) 7.06 (s, 1 H) 5.00-5.32 (m, 1 H) 4.22-4.47 (m, 1 H) 3.94 (s, 3 H) 3.68-3.83 (m, 3 H) 3.52-3.65 (m, 2 H) 3.34-3.50 (m, 2 H) 3.20-3.28 (m, 1H) 1.48 (d, J = 6.9 Hz, 3 H) 1.38 (d, J = 7.1 Hz, 3 H) 1.29 (d, J = 6.9 Hz, 3 H). LCMS-ESI (pos.) m/z: 538.2 (M + H)$^+$. |
| 145.0 | 6-methoxypicolinohydrazide (commercially available from Sigma-Aldrich Inc.), 1-(1,4-dioxan-2-yl)ethan-1-amine (Example 142.1), and (2S,3R)-3-(5-chloropyrimidin-2-yl)butane-2-sulfonamide(Example 27.4). The product was purified by chiral SFC: Chiralpak AD-H 2 × 25 cm, Mobile Phase: 35% MeOH, Flowrate: 80 mL/min, Pressure Drop: 110 bar, BPR: 100 bar, UV Detector Wavelength: 219 mn. This was the first peak to elute under these conditions | OR <br><br> OR <br><br> OR <br><br> (2S,3R)-N-(4-((R)-1-((R)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((R)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((S)-1-((S)-1,4-dioxan-2-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((S)-1-((R)-1,4-dioxan-2-yl)ethyl)-5- |

TABLE 14-continued

| Example | Reagents | Structure, Name and Data |
|---|---|---|
| | | (6-methoxypyridin-2-yl)-4H-1,2,4-triazol-3-yl)-3-(5-chloropyrimidin-2-yl)butane-2-sulfonamide. $^1$H NMR (500 MHz, DMSO-d6) δ 13.11-13.37 (m, 1 H) 8.87 (s, 2 H) 7.92 (t, J = 7.9 Hz, 1 H) 7.55 (d, J = 7.3 Hz, 1 H) 7.06 (d, J = 8.2 Hz, 1 H) 5.07-5.32 (m, 1 H) 4.34 (br d, J = 1.6 Hz, 1 H) 3.91-3.97 (m, 3 H) 3.65-3.81 (m, 3 H) 3.46-3.65 (m, 3 H) 3.36 (br d, J = 2.3 Hz, 1 H) 3.26 (br t, J = 10.7 Hz, 1 H) 1.45-1.53 (m, 3 H) 1.33-1.42 (m, 3 H) 1.30 (d, J = 7.0 Hz, 3 H) LCMS-ESI (pos.) m/z: 538.2 (M + H)$^+$. |
| 146.0 | 6-methoxypicolinohydrazide (commercially available from Sigma-Aldrich Inc.), 1-(1,4-dioxan-2-yl)ethan-1-amine (Example 142.1), and (1S,2S)-1-(5-chloropyrimidin-2-yl)-1-isopropoxypropane-2-sulfonamide (Example 31.01). The product was purified by two chiral SFC purifications: Chiralpak IC 2 × 25 cm and Chiralpak IC 2 × 15 cm, Mobile Phase: 35% MeOH, Flowrate: 60 mL/min, Pressure Drop: 120 bar, BPR: 100 bar, UV Detector Wavelength: 219 nm. This was the first peak to elute under these conditions. | [Structure] OR [Structure] OR [Structure] OR [Structure] (1S,2S)-N-(4-((R)-1-((R)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide or (1S,2S)-N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide or (1S,2S)-N-(4- |

TABLE 14-continued

| Example | Reagents | Structure, Name and Data |
|---|---|---|
| | | ((S)-1-((S)-1,4-dioxan-2-yl)ethyl)-5-(6-methoxypyridin-2-yl)-4H-1,2,4-triazol-3-yl)-1-(5-chloropirimidin-2-yl)-1-isopropoxypropane-2-sulfonamide or (1S,2S)-N-(4-((S)-1-((R)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide.<br>$^1$H NMR (500 MHz, DMSO-d6) δ 12.81-13.02 (m, 1 H) 8.86-9.06 (m, 2 H) 7.80-8.10 (m, 1 H) 7.53 (d, J = 7.3 Hz, 1 H) 7.06 (d, J = 8.4 Hz, 1 H) 5.04-5.27 (m, 1 H) 4.87-5.04 (m, 1 H) 4.26-4.46 (m, 1 H) 3.91-3.98 (m, 3 H) 3.73-3.82 (m, 1 H) 3.53-3.67 (m, 4 H) 3.41 (s, 2 H) 3.27 (s, 1 H) 1.53 (br d, J = 6.7 Hz, 3 H) 1.21 (d, J = 7.1 Hz, 3 H) 1.04 (d, J = 6.0 Hz, 3 H) 0.81 (d, J = 6.1 Hz, 3 H) LCMS-ESI (pos.) m/z: 582.2 (M + H)$^{+-}$ |
| 147.0 | 6-methoxypicolinohydrazide (commercially available from Sigma-Aldrich Inc.), 1-(1,4-dioxan-2-yl)ethan-1-amine (Example 142.1), and (1S,2S)-1-(5-chloropyrimidin-2-yl)-1-isopropoxypropane-2-sulfonamide (Example 31.01).<br>The product was purified by two chiral SFC purications: Chiralpak IC 2 × 25 cm and Chiralpak IC 2 × 15 cm, Mobile Phase: 35% MeOH, Flowrate: 60 mL/min, Pressure Drop: 120 bar, BPR: 100 bar, UV Detector Wavelength: 219 nm.<br>This was the first peak to elute under these conditions | 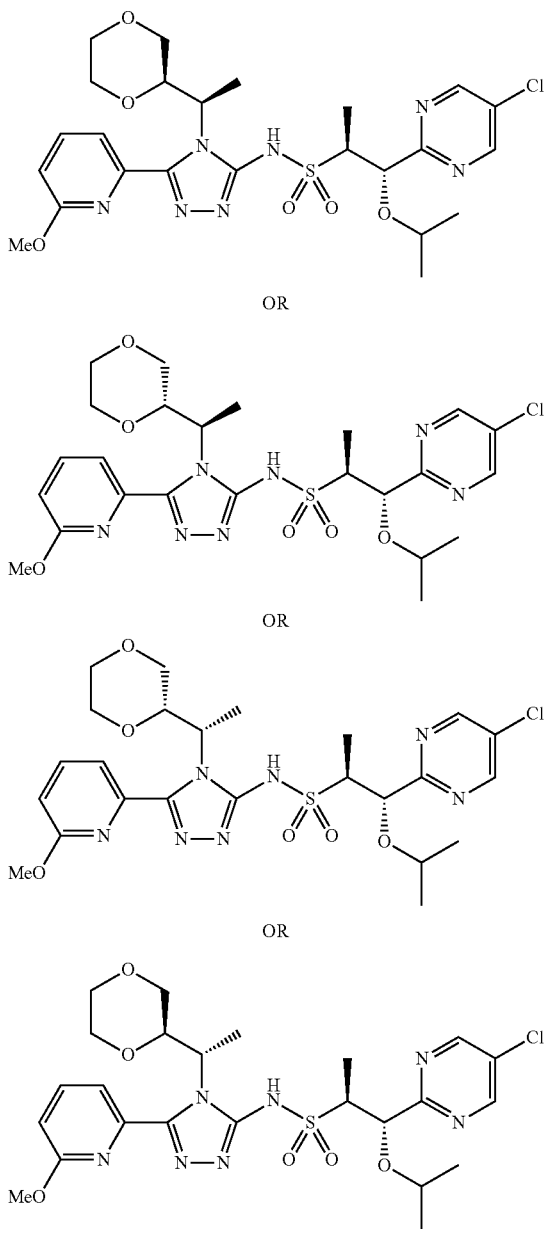<br><br>(1S,2S)-N-(4-((R)-1-((R)-1,4-dioxan-2-yl)ethyl)-5-(6-methoxypyridin-2-yl)-4H-1,2,4-triazol-3-yl)-1- |

TABLE 14-continued

| Example | Reagents | Structure, Name and Data |
|---|---|---|
| | | (5-chloropyrimidin-2-yl)-1-isopropoxypropane-2-sulfonamide or (1S,2S)-N-(4-((R)-1-((S)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide or (1S,2S)-N-(4-((S)-1-((S)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide or (1S,2S)-N-(4-((S)-1-((R)-1,4-dioxan-2-yl)ethyl)-5-(6-methoxypyridin-2-yl)-4H-1,2,4-triazol-3-yl)-1-(5-chloropyrimidin-2-yl)-1-isopropoxypropane-2-sulfonamide.<br>$^1$H NMR (500 MHz, DMSO-d$_6$) δ 12.88-13.11 (m, 1 H) 8.84-9.07 (m, 2 H) 7.93 (t, J = 7.8 Hz, 1 H) 7.54 (d, J = 7.4 Hz, 1 H) 7.06 (d, J = 8.4 Hz, 1 H) 5.02-5.27 (m, 1 H) 4.92-5.02 (m, 1 H) 4.31-4.47 (m, 1 H) 3.91-3.98 (m, 3 H) 3.73-3.81 (m, 1 H) 3.54-3.67 (m, 4 H) 3.50 (dt, J = 12.2, 6.0 Hz, 1 H) 3.35-3.43 (m, 1 H) 3.22-3.29 (m, 1 H) 1.47-1.54 (m, 3 H) 1.17-1.28 (m, 3 H) 1.06-1.10 (m, 3 H) 0.86 (d, J = 6.1 Hz, 3 H) LCMS-ESI (pos.) m/z: 582.2 (M + H)$^+$. |

The compounds set forth in the following table were synthesized following the procedure in Example 28.0 using the known starting material as described.

TABLE 15

| Example | Reagents | Structure, Name and Data |
|---|---|---|
| 137.1 | oxetan-2-ylmethanamine (commercially available from Synthonix) | 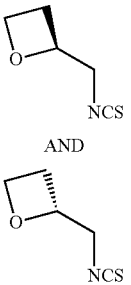<br>AND<br>(S)-2-(isothiocyanatomethyl)oxetane and (R)-2-(isothiocyanatomethyl)oxetane LCMS-ESI (pos.) m/z: 130.2 (M + H)$^+$. |
| 138.1 | 1-(4-methylmorpholin-2-yl)ethan-1-amine (commercially available from Enamine). | 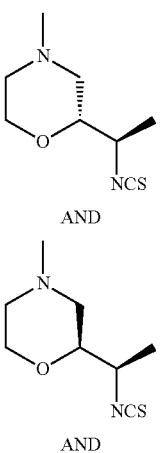<br>AND |

TABLE 15-continued

| Example Reagents | Structure, Name and Data |
|---|---|
| | 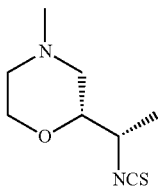 AND 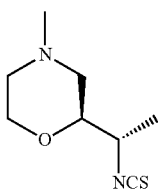<br>(R)-2-((R)-1-isothiocyanatoethyl)-4-methylmorpholine and (S)-2-((R)-1-isothiocyanatoethyl)-4-methylmorpholine and (R)-2-((S)-1-isothiocyanatoethyl)-4-methylmorpholine and (S)-2-((S)-1-isothiocyanatoethyl)-4-methylmorpholine.<br>LCMS-ESI (pos.) m/z: 187.2 (M + H)$^+$. |

Example 142.2. Preparation of 2-(1-isothiocyanatoethyl)-1,4-dioxane

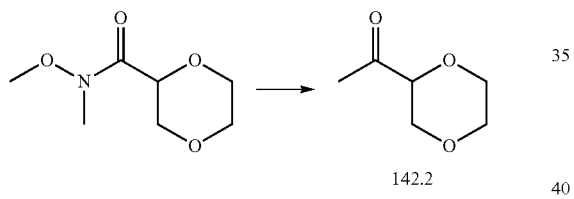

142.2

1-(1,4-Dioxan-2-yl)ethan-1-one, Example 142.2

A solution of N-methoxy-N-methyl-1,4-dioxane-2-carboxamide (1.8 g, 10.27 mmol) in THF (34.2 ml) was cooled to −78° C. and methylmagnesium chloride (3.0 M solution in THF, 6.85 mL, 20.55 mmol) was added dropwise. The reaction mixture was allowed to warm to RT overnight after which LCMS indicated complete consumption of the starting material. The mixture was poured into an aqueous solution of NH$_4$Cl and extracted with DCM, dried over Na$_2$SO$_4$ and concentrated in vacuo to yield 1-(1,4-dioxan-2-yl)ethan-1-one (1.3 g, 9.99 mmol, 97% yield) which was carried forward without further purification. LCMS-ESI (pos.) m/z: 131.2 (M+H)$^+$.

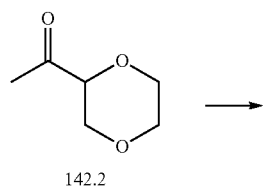

142.2

-continued

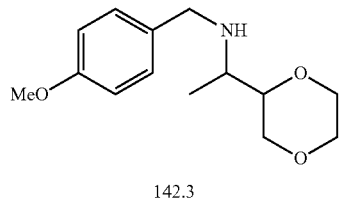

142.3

1-(1,4-Dioxan-2-yl)-N-(4-methoxybenzyl)ethan-1-amine, Example 142.3

To a solution of 1-(1,4-dioxan-2-yl)ethan-1-one (1.3 g, 9.99 mmol) in 1,1-dichloroethane (33.3 ml) was added (4-methoxyphenyl)methanamine (1.566 mL, 11.99 mmol) followed by 4A molecular sieves (10 g) and AcOH (1.14 mL, 19.98 mmol). The reaction mixture was stirred at RT for 1 h after which LCMS indicated complete consumption of the starting material. To the mixture was added sodium triacetoxyborohydride (2.96 g, 13.98 mmol) and the reaction was stirred at RT overnight after which LCMS indicated conversion to product. The mixture was quenched with addition of MeOH followed by NaHCO$_3$. The organics were extracted with DCM, dried over Na$_2$SO$_4$ and concentrated in vacuo. The mixture was purified by silica gel chromatography (0-100%) EtOAc:EtOH 3:1 in heptanes to yield 1-(1,4-dioxan-2-yl)-N-(4-methoxybenzyl)ethan-1-amine (1.5 g, 5.97 mmol, 59.7% yield). LCMS-ESI (pos.) m/z: 252.2 (M+H)$^+$.

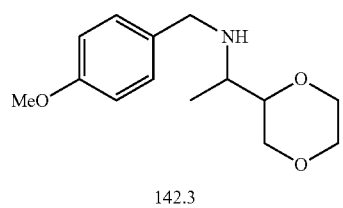

142.3

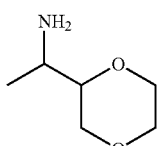

142.4

1-(1,4-Dioxan-2-yl)ethan-1-amine, Example 142.4

To a solution of 1-(1,4-dioxan-2-yl)-N-(4-methoxybenzyl)ethan-1-amine (1.5 g, 5.97 mmol) in MeOH (29.8 mL) was added palladium 10 wt. % on activated carbon (0.053 mL, 5.97 mmol). The reaction was evacuated and backfilled with H$_2$ (30 psi) 5 times. The flask was sealed and stirred at RT for 12 h after which LCMS indicated complete conversion to product. The mixture was filtered over Celite® brand filter aid and concentrated in vacuo to yield 1-(1,4-dioxan-2-yl)ethan-1-amine (0.75 g, 5.72 mmol, 96% yield) which was carried forward without further purification. LCMS-ESI (pos.) m/z: 132.2 (M+H)$^+$.

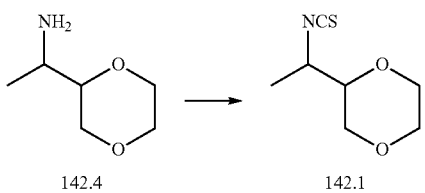

142.4 → 142.1

2-(1-Isothiocyanatoethyl)-1,4-dioxane, Example 142.1

To a flask containing 1-(1,4-dioxan-2-yl)ethan-1-amine (0.75 g, 5.72 mmol) in anhydrous DCM (28.6 mL) was added N,N-diisoproylethylamine (1.997 ml, 11.44 mmol) at 0° C. Upon complete addition of Hunig's base, 1,1"-thiocarbonyldi-2(1H)-pyridone (1.461 g, 6.29 mmol) was added carefully in portions to the homogeneous solution. Upon complete addition of Hunig's base, 1,1"-thiocarbonyldi-2(1H)-pyridone (1.461 g, 6.29 mmol) was added. The light orange homogeneous solution was then allowed to warm to 23° C. and monitored with TLC and LC-MS. After 2 h, the reaction was complete by LCMS. The mixture was concentrated and purified by silica gel chromatography (0-100%) EtOAc:EtOH 3:1 in heptanes to yield 2-(1-isothiocyanatoethyl)-1,4-dioxane (0.67 g, 3.87 mmol, 68% yield). LCMS-ESI (pos.) m/z: 153.2 (M+H)$^+$.

Example 148.0. Preparation of (1R,2S)-1-(5-chloropyrimidin-2-yl)-N-(4-(cyclopropyl-2,2,3,3-d4)-5-(6-methoxypyridin-2-yl)-4H-1,2,4-triazol-3-yl)-1-methoxypropane-2-sulfonamide 148.1

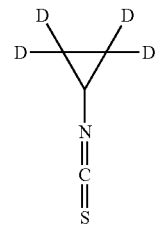

1-Isothiocyanatocyclopropane-2,2,3,3-d4, Example 148.1

A solution of cyclopropan-2,2,3,3-d4-1-amine (commercially available from Enamine, 1.00 g, 16.36 mmol) and N,N-diisopropylethylamine (2.86 ml, 16.36 mmol) in DCM (5 mL) was added slowly to a solution of O,O-di(pyridin-2-yl) carbonothiolate (commercially available from Alpha Aesar, 3.99 g, 17.17 mmol) in DCM (10 mL). After stirring for 1 h, the reaction mixture was purified directly by silica gel column chromatography (0-100% EtOAc/heptane) yielding 1-isothiocyanatocyclopropane-2,2,3,3-d4 (0.465 g, 4.51 mmol, 28% yield) as a clear oil. $^1$H NMR (500 MHz, CD$_3$CN) δ 3.00 (s, 1H).

148.2

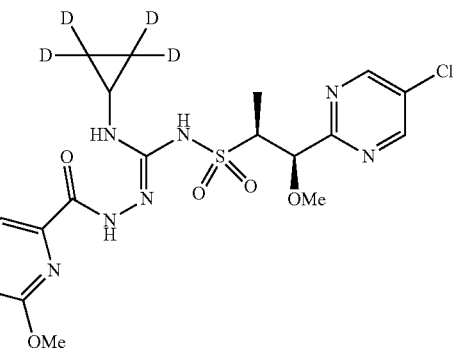

(1R,2S)-1-(5-Chloropyrimidin-2-yl)-N-((E)-N-(cyclopropyl-2,2,3,3-d4)-N'-(6-methoxypicolinoyl)carbamohydrazonoyl)-1-methoxypropane-2-sulfonamide, Example 148.2

A solution of Example 29.3 (0.644 g, 2.423 mmol), Example 148.1 (0.250 g, 2.423 mmol), and cesium carbonate (0.789 g, 2.423 mmol) in 5 mL ACN was allowed to stir at room temperature for 1 h. 6-Methoxypicolinohydrazide (commercially available from Milestone Pharmtech, 0.446 g, 2.67 mmol) was added followed by silver nitrate (0.823 g, 4.85 mmol). After stirring for 1 h, the reaction mixture was purified directly by silica gel column chromatography (0-97% EtOAc/heptane, 3% MeOH) yielding Example 148.2 (1.066 g, 2.124 mmol, 88% yield) with minor impurities. LCMS-ESI (pos.) m/z: 502.2 (M+H)$^+$.

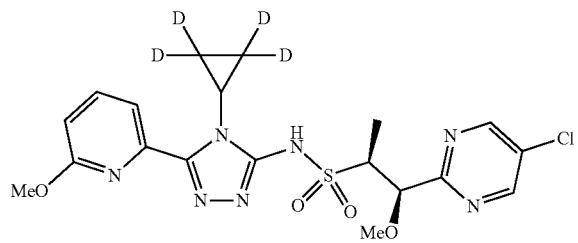

148.0

(1R,2S)-1-(5-Chloropyrimidin-2-yl)-N-(4-(cyclopropyl-2,2,3,3-d4)-5-(6-methoxypyridin-2-yl)-4H-1,2,4-triazol-3-yl)-1-methoxypropane-2-sulfonamide, Example 148.0

A solution of Example 148.2 (1.06 g, 2.11 mmol) in IPA (10 mL) was treated with sodium hydroxide (1.0 M, 2.75 ml, 2.75 mmol) and was heated at reflux for 4 h. The reaction mixture was then poured into a saturated aqueous NH$_4$Cl solution and extracted with DCM. The combined organic layers were dried over MgSO$_4$ and concentrated in vacuo. Purification of the residue by silica gel column chromatography (0-100% EtOAc/heptane) gave Example 148.0 (0.375 g, 0.775 mmol, 36.7% yield) as a white solid. $^1$H NMR (500 MHz, CD$_3$CN) δ 1.38 (d, J=7.01 Hz, 3H) 3.17 (s, 3H) 3.58 (dd, J=6.88, 4.67 Hz, 1H) 3.96 (s, 1H) 4.92 (d, J=4.67 Hz, 1H) 6.93 (d, J=8.43 Hz, 1H) 7.42 (d, J=7.27 Hz, 1H) 7.80 (t, J=7.85 Hz, 1H) 8.77 (s, 1H) 11.12 (br s, 1H). LCMS-ESI (pos.) m/z: 484.2 (M+H)$^+$.

Example 149.0. Preparation of (1R,2S)-1-(5-chloropyrimidin-2-yl)-N-(4-cyclopropyl-5-(5-methylpyridin-3-yl)-4H-1,2,4-triazol-3-yl)-1-methoxypropane-2-sulfonamide

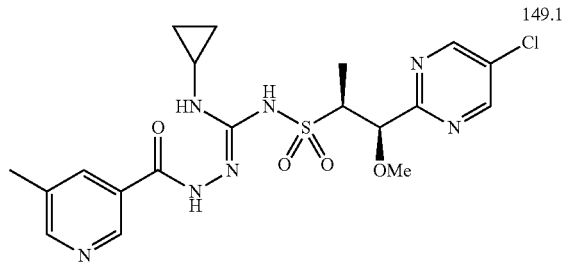 [SMILES: CO[C@H](c1ncc(Cl)cn1)[C@H](C)S(=O)(=O)N/C(=N/NC(=O)c1cncc(C)c1)NC1CC1]

149.1

(1R,2S)-1-(5-chloropyrimidin-2-yl)-N-((E)-N-cyclopropyl-N'-(5-methylnicotinoyl)carbamohydrazonoyl)-1-methoxypropane-2-sulfonamide, Example 149.1

A solution of Example 29.3 (0.644 g, 2.42 mmol, cyclopropyl isothiocyanate (commercially available from Alpha Aesar, 0.093 ml, 1.009 mmol) and cesium carbonate (0.329 g, 1.01 mmol) in 5 mL ACN was allowed to stir at room temperature for 1 h. 5-Methylnicotinohydrazide (0.168 g, 1.11 mmol) was added followed by silver nitrate (0.343 g, 2.017 mmol). After stirring for 1 h, the reaction mixture was purified directly by silica gel column chromatography (0-97% EtOAc/heptane, 3% MeOH) yielding Example 149.1 (0.430 g, 0.89 mmol, 88% yield). LCMS-ESI (pos.) m/z: 482.2 (M+H)$^+$.

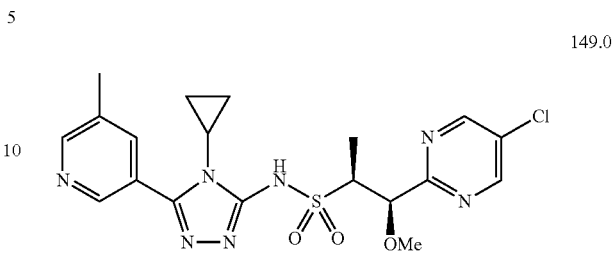

149.0

(1R,2S)-1-(5-Chloropyrimidin-2-yl)-N-(4-cyclopropyl-5-(5-methylpyridin-3-yl)-4H-1,2,4-triazol-3-yl)-1-methoxypropane-2-sulfonamide, Example 149.0

A solution of Example 149.1 (0.430 g, 0.89 mmol) in 3 mL IPA was treated with sodium hydroxide (1.0 M, 16 ml, 1.16 mmol), and the mixture was heated at reflux for 4 h. The reaction mixture was then poured into a saturated aqueous NH$_4$Cl solution and extracted with DCM. The combined organic layers were dried over MgSO$_4$ and concentrated. Purification of the residue by silica gel column chromatography (0-100% EtOAc/heptane) gave Example 149.0 (0.087 g, 0.188 mmol, 21.02% yield). $^1$H NMR (500 MHz, CD$_3$CN) δ 0.57-0.68 (m, 1H) 0.74-0.81 (m, 1H) 0.90-1.05 (m, 2H) 1.37 (d, J=7.01 Hz, 3H) 2.41 (s, 3H) 3.07 (dt, J=7.14, 3.44 Hz, 1H) 3.19 (s, 3H) 3.57 (dd, J=7.01, 4.41 Hz, 1H) 4.95 (d, J=4.41 Hz, 1H) 7.92 (s, 1H) 8.59 (d, J=1.43 Hz, 1H) 8.73 (d, J=1.82 Hz, 1H) 8.77 (s, 1H) 11.17 (br s, 1H). LCMS-ESI (pos.) m/z: 464.2 (M+H)$^+$.

Example 150.0. Preparation of (1R,2S)-1-(5-chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide and (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide

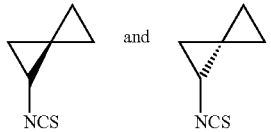

150.01

(R)-1-Isothiocyanatospiro[2.2]pentane and (S)-1-isothiocyanatospiro[2.2]pentane, Example 150.01

A solution of spiro[2.2]pentan-1-amine hydrochloride (commercially available from Enamine, 2.00 g, 16.72 mmol) and N,N-diisopropylethylamine (2.92 ml, 16.72 mmol) in DCM (5 mL) was added slowly to a solution of O,O-di(pyridin-2-yl) carbonothioate (commercially available from Alpha Aesar, 4.08 g, 17.56 mmol) in DCM (10 mL). After stirring for 1 h, the reaction mixture was purified directly by silica gel column chromatography (0-100% EtOAc/heptane) yielding 1-isothiocyanatospiro[2.2]pentane (1.13 g, 9.03 mmol, 54.0% yield) as a clear oil. ¹H NMR (500 MHz, CD₃CN) δ 0.87-1.08 (m, 4H) 1.30-1.41 (m, 2H) 3.21 (dd, J=6.68, 3.05 Hz, 1H).

150.1

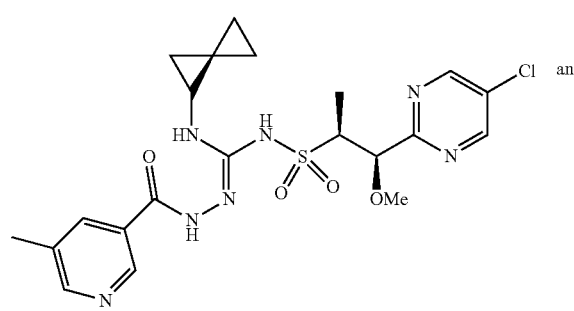

(1R,2S)-1-(5-Chloropyrimidin-2-yl)-1-methoxy-N-((E)-N'-(5-methylnicotinoyl)-N—((R)-spiro[2.2]pentan-1-yl)carbamohydrazonoyl)propane-2-sulfonamide and (1R,2S)-1-(5-chloropyrimidin-2-yl)-1-methoxy-N-((E)-N'-(5-methylnicotinoyl)-N—((S)-spiro[2.2]pentan-1-yl)carbamohydrazonoyl)propane-2-sulfonamide, Example 150.1

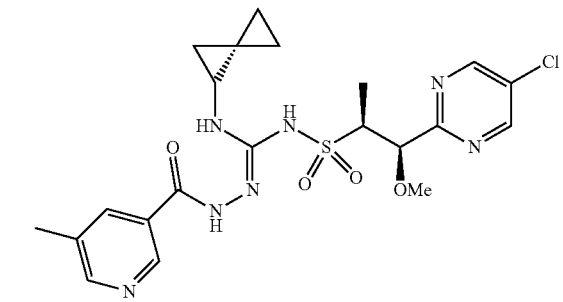

A solution of Example 29.3 (0.212 g, 0.80 mmol), Example 150.01 (0.100 g, 0.799 mmol), and cesium carbonate (0.260 g, 0.80 mmol) in ACN (5 mL) was allowed to stir at room temperature for 1 h. 5-Methylnicotinohydrazide (0.133 g, 0.879 mmol) was added followed by silver nitrate (0.271 g, 1.598 mmol). After stirring for 1 h, the reaction mixture was purified directly by silica gel column chromatography (0-97% EtOAc/heptane, 3% MeOH) yielding Example 150.1 (0.300 g, 0.59 mmol, 74% yield) with minor impurities. LCMS-ESI (pos.) m/z: 508.2 (M+H)⁺.

150.0

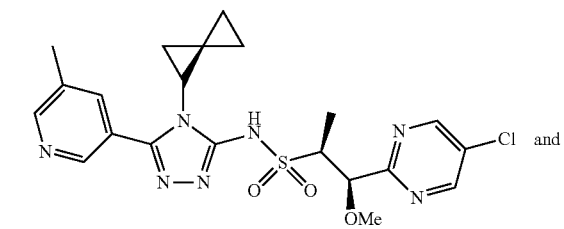

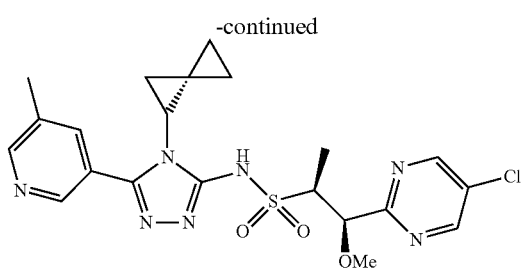

(1R,2S)-1-(5-Chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide and (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide, Example 150

A solution of Example 150.0 (0.300 g, 0.591 mmol) in IPA (3 mL) was treated with sodium hydroxide (1.0M, 0.77 ml, 0.77 mmol). The mixture was then heated at reflux for 4 h. The reaction mixture was poured into a saturated aqueous NH₄Cl solution and extracted with DCM. The combined organic layers were dried over MgSO₄ and concentrated. Purification of the residue by silica gel column chromatography (0-100% EtOAc/heptane) gave Example 150.0 (0.182 g, 0.37 mmol, 63% yield) as a white solid. ¹H NMR (500 MHz, CD₃CN) δ 0.32-0.39 (m, 1H) 0.62 (br d, J=3.76 Hz, 2H) 0.70-0.86 (m, 2H) 1.15 (dd, J=5.77, 3.70 Hz, 1H) 1.37 (dd, J=11.87, 7.07 Hz, 3H) 1.41-1.51 (m, 1H) 2.40 (s, 3H) 3.14-3.26 (d, 3H) 3.46-3.52 (m, 1H) 3.62 (dd, J=7.01, 5.06 Hz, 1H) 4.89 (d, J=5.06 Hz, 1H) 4.98 (d, J=3.89 Hz, 1H) 7.87 (d, J=2.21 Hz, 1H) 8.58 (s, 1H) 8.68 (s, 1H) 8.77 (d, J=2.34 Hz, 2H) 11.11-11.25 (m, 1H). LCMS-ESI (pos.) m/z: 490.0 (M+H)⁺.

Example 151.0. Preparation of (1R,2S)-1-(5-chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide or (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide 151.0

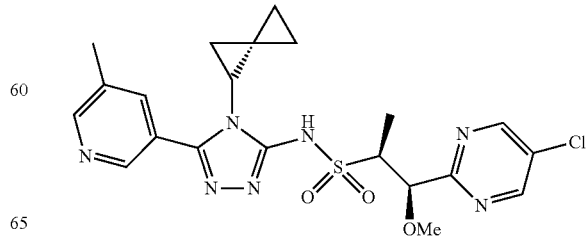

(1R,2S)-1-(5-Chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide or (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide, Example 151.0

Example 150.0 was separated by SFC chromatography (peak assignment determined by SFC: Chiralpak AD-H analytical column, 50% MeOH.) yielding Example 151.0 as peak 1. $^1$H NMR (500 MHz, CD$_3$CN) δ 0.33-0.39 (m, 1H) 0.64 (br d, J=4.28 Hz, 2H) 0.72-0.81 (m, 2H) 0.91 (s, 1H) 1.28-1.42 (m, 3H) 1.51 (s, 1H) 2.42 (s, 3H) 3.16 (s, 3H) 3.48-3.58 (m, 1H) 3.62 (m, 1H) 5.00 (d, J=3.89 Hz, 1H) 7.89 (s, 1H) 8.60 (s, 1H) 8.70 (s, 1H) 8.79 (s, 1H). LCMS-ESI (pos.) m/z: 490.0 (M+H)$^+$.

Example 152.0. Preparation of (1R,2S)-1-(5-chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide or (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide

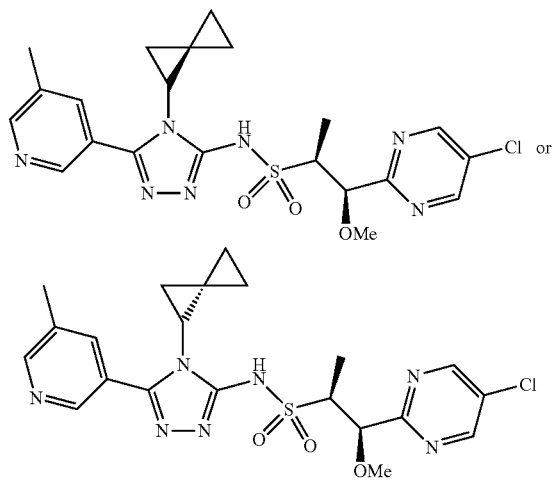

152.0

(1R,2S)-1-(5-Chloropyrimidin-2-yl)-1-methoxy-N-(5-(5-methylpyridin-3-yl)-4-((R)-spiro[2.2]pentan-1-yl)-4H-1,2,4-triazol-3-yl)propane-2-sulfonamide or (1R,2S)-1-(5-chloropyrimidin-2-yl)-1-methoxy-N-(5-(5-methylpyridin-3-yl)-4-((S)-spiro[2.2]pentan-1-yl)-4H-1,2,4-triazol-3-yl)propane-2-sulfonamide, Example 152.0

Further elution under the conditions described in Example 151.0 delivered Example 152.0 as peak 2. $^1$H NMR (500 MHz, CD$_3$CN) δ 0.33-0.39 (m, 1H) 0.53-0.64 (m, 2H) 0.73-0.84 (m, 2H) 1.38 (d, J=7.01 Hz, 3H) 1.44 (s, 1H) 2.40 (s, 3H) 3.26 (s, 3H) 3.47 (dd, J=7.07, 3.57 Hz, 1H) 3.59-3.66 (m, 1H) 4.89 (d, J=5.06 Hz, 1H) 7.86 (s, 1H) 8.58 (s, 1H) 8.68 (s, 1H) 8.78 (s, 1H). LCMS-ESI (pos.) m/z: 490.0 (M+H)$^+$.

Example 155.0. Preparation of (1R,2S)-1-(5-chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide and (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide

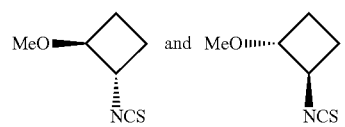

155.1

(1S,2S)-1-Isothiocyanato-2-methoxycyclobutane and (1R,2R)-1-isothiocyanato-2-methoxycyclobutane, Example 155.1

A solution of trans-2-methoxycyclobutan-1-amine hydrochloride (commercially available from Enamine, 1.00 g, 7.27 mmol) and N,N-diisopropylethylamine (1.27 ml, 7.27 mmol) in DCM (5 mL) was added slowly to a solution of 1-(2-oxopyridine-1-carbothioyl)pyridin-2-one (commercially available from Alpha Aesar, 1.77 ml, 7.63 mmol) in DCM (10 mL). After stirring for 1 h, the reaction mixture was purified directly by silica gel column chromatography (0-100% EtOAc/heptane) yielded Example 155.1 as a clear oil. $^1$H NMR (500 MHz, CD$_3$CN) δ 1.48-1.61 (m, 1H) 1.64-1.75 (m, 1H) 2.06-2.23 (m, 2H) 3.30 (s, 3H) 3.80-3.96 (m, 2H).

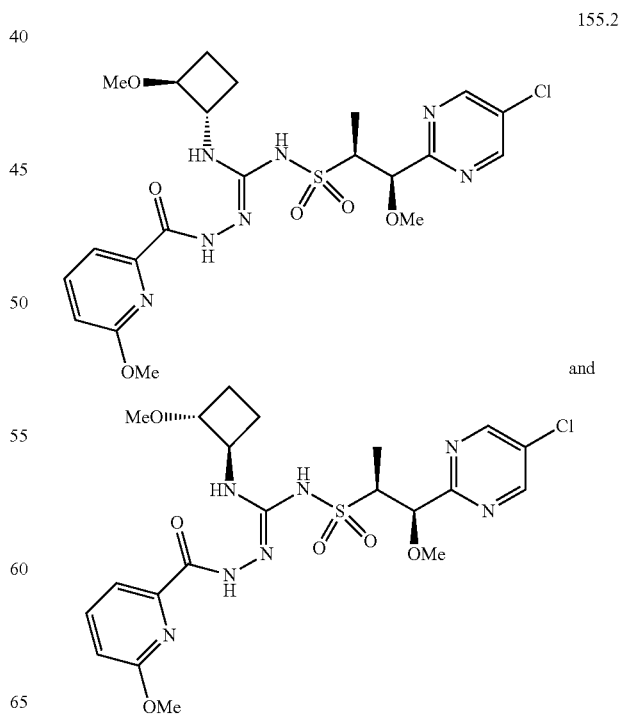

155.2

(1R,2S)-1-(5-Chloropyrimidin-2-yl)-1-methoxy-N-((E)-N-((1R,2R)-2-methoxycyclobutyl)-N'-(6-methoxypicolinoyl)carbamohydrazonoyl)propane-2-sulfonamide and (1R,2S)-1-(5-chloropyrimidin-2-yl)-1-methoxy-N-((E)-N-((1S,2S)-2-methoxycyclobutyl)-N'-(6-methoxypicolinoyl)carbamohydrazonoyl)propane-2-sulfonamide, Example 155.2

A solution of Example 29.3 (0.186 g, 0.70 mmol), Example 155.1 (0.100 g, 0.70 mmol), and cesium carbonate (0.228 g, 0.70 mmol) in ACN (5 mL) was allowed to stir at room temperature for 1 h. 6-Methoxypicolinohydrazide (0.128 g, 0.768 mmol) was added followed by silver nitrate (0.237 g, 1.40 mmol). After stirring for 1 h, the reaction mixture was purified directly by silica gel column chromatography (0-97% EtOAc/heptane, 3% MeOH) yielding Example 155.2 (0.294 g, 0.542 mmol, 78% yield) with minor impurities. LCMS-ESI (pos.) m/z: 542.2 (M+H)$^+$.

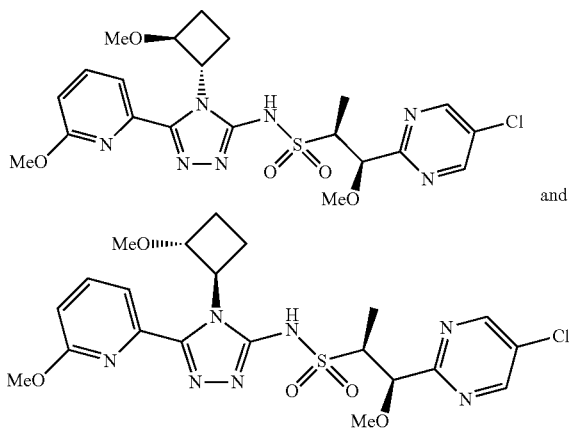

155.0 and (1R,2S)-1-(5-Chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide and (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide, Example 155.0

A solution of Example 155.2 (0.294 g, 0.542 mmol) in IPA (3 L) treated with sodium hydroxide (1.0M, 0.705 ml, 0.705 mmol). The mixture was then heated at reflux for 4 h. The reaction mixture was poured into saturated aqueous NH$_4$Cl solution and extracted with DCM. The organics were combined, dried over MgSO$_4$ and concentrated in vacuo. Purification of the residue by silica gel column chromatography (0-100% EtOAc/heptane) gave Example 155.0 (0.165 g, 0.315 mmol, 58.1% yield) as a white solid. $^1$H NMR (500 MHz, CD$_3$CN) 1.39 (t, J=7.33 Hz, 3H) 1.49-1.59 (m, 1H) 2.16-2.26 (m, 1H) 2.57-2.68 (m, 1H) 3.16-3.26 (m, 6H) 3.57 (ddt, J=11.58, 4.57, 2.30, 2.30 Hz, 1H) 4.00 (d, J=1.56 Hz, 3H) 4.99 (dd, J=9.41, 4.09 Hz, 1H) 5.07 (q, J=7.78 Hz, 1H) 5.55-5.68 (m, 1H) 6.96 (d, J=8.31 Hz, 1H) 7.50 (d, J=7.40 Hz, 1H) 7.81 (dd, J=8.30, 7.40 Hz, 1H) 8.77 (d, J=1.56 Hz, 1H) 11.29 (br s, 1H). LCMS-ESI (pos.) m/z: 524.2 (M+H)$^+$.

Example 161. Preparation of (1R,2S)-1-(5-chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide or (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide

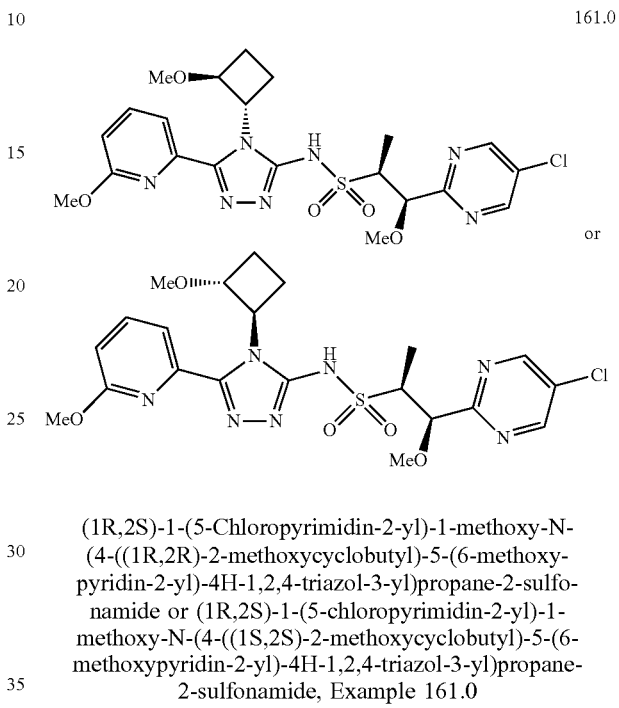

161.0 or (1R,2S)-1-(5-Chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide or (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide, Example 161.0

Example 155.0 (0.074 g, 0.151 mmol) was separated by SFC chromatography (peak assignment determined by SFC: Chiralpak AD-H analytical column, 50% IPA.) yielding Example 161.0 as peak 1. $^1$H NMR (500 MHz, CD$_3$CN) δ 1.40 (d, J=7.01 Hz, 3H) 1.56 (br dd, J=9.60, 8.30 Hz, 1H) 1.99-2.06 (m, 1H) 2.65 (quin, J=10.09 Hz, 1H) 3.23 (d, J=5.71 Hz, 6H) 3.60 (dd, J=7.01, 4.15 Hz, 1H) 4.02 (s, 3H) 5.00 (d, J=4.02 Hz, 1H) 5.09 (q, J=7.53 Hz, 1H) 5.56-5.67 (m, 1H) 6.98 (d, J=8.43 Hz, 1H) 7.52 (d, J=7.40 Hz, 1H) 7.83 (dd, J=8.30, 7.40 Hz, 1H) 8.79 (s, 2H). LCMS-ESI (pos.) m/z: 0.524.2 (M+H)$^+$.

Example 162.0. Preparation of (1R,2S)-1-(5-chloropyrimidin-2-yl)-1-methoxy-N-(4-((1R,2R)-2-methoxycyclobutyl)-5-(6-methoxypyridin-2-yl)-4H-1,2,4-triazol-3-yl)propane-2-sulfonamide or (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide

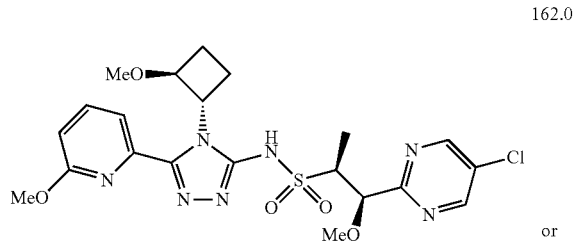

162.0 or

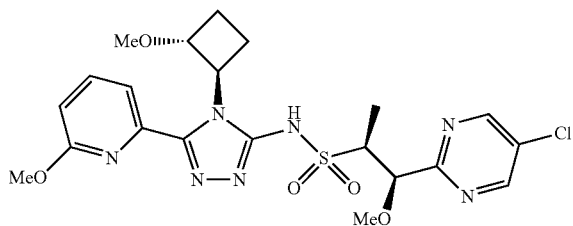

(1R,2S)-1-(5-Chloropyrimidin-2-yl)-1-methoxy-N-(4-((1R,2R)-2-methoxycyclobutyl)-5-(6-methoxy-pyridin-2-yl)-4H-1,2,4-triazol-3-yl)propane-2-sulfonamide or (1R,2S)-1-(5-chloropyrimidin-2-yl)-1-methoxy-N-(4-((1S,2S)-2-methoxycyclobutyl)-5-(6-methoxypyridin-2-yl)-4H-1,2,4-triazol-3-yl)propane-2-sulfonamide, Example 162.0

Further elution under the conditions described in Example 161.0 delivered Example 162.0 as peak 2. $^1$H NMR (500 MHz, CD$_3$CN) δ 1.40 (d, J=7.01 Hz, 3H) 1.49-1.60 (m, 1H) 2.16-2.25 (m, 1H) 2.62 (s, 1H) 3.20 (s, 1H) 3.24 (s, 6H) 3.51-3.64 (m, 1H) 4.01 (s, 3H) 5.00 (d, J=4.15 Hz, 1H) 5.07 (br d, J=7.79 Hz, 1H) 5.57-5.68 (m, 1H) 6.96 (d, J=8.44 Hz, 1H) 7.50 (d, J=7.40 Hz, 1H) 7.82 (br d, J=0.91 Hz, 1H) 8.77 (s, 2H) 11.22-11.31 (m, 1H). LCMS-ESI (pos.) m/z: 524.2 (M+H)$^+$.

Example 156.0. Preparation of (1R,2S)-1-(5-chloro-pyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide and (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide

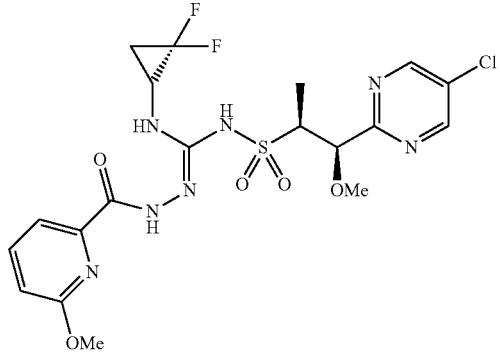

(1R,2S)-1-(5-Chloropyrimidin-2-yl)-N-((E)-N—((S)-2,2-difluorocyclopropyl)-N'-(6-methoxypicolinoyl)carbamohydrazonoyl)-1-methoxypropane-2-sulfonamide and (1R,2S)-1-(5-chloropyrimidin-2-yl)-N-((E)-N—((R)-2,2-difluorocyclopropyl)-N'-(6-methoxypicolinoyl)carbamohydrazonoyl)-1-methoxypropane-2-sulfonamide, Example 156.1

A solution of Example 29.3 (1.090 g, 4.10 mmol), O,O-di(pyridin-2-yl) carbonothioate (commercially available from Alpha Aesar, 1.00 g, 4.31 mmol), 2,2-difluorocyclopropan-1-amine hydrochloride (commercially available from Manchester Organics, 0.531 g, 4.10 mmol), and potassium phosphate (4.35 g, 20.50 mmol) in 15 mL ACN was allowed to stir at room temperature for 2 h. 6-Methoxypicolinohydrazide (0.823 g, 4.92 mmol) was added followed by silver nitrate (1.393 g, 8.20 mmol). After stirring for 10 minutes, the reaction mixture was purified directly by silica gel column chromatography (0-97% EtOAc/heptane, 3% MeOH) yielding Example 156.1 (1.203 g, 2.25 mmol, 55% yield) with minor impurities. LCMS-ESI (pos.) m/z: 534.2 (M+H)$^+$.

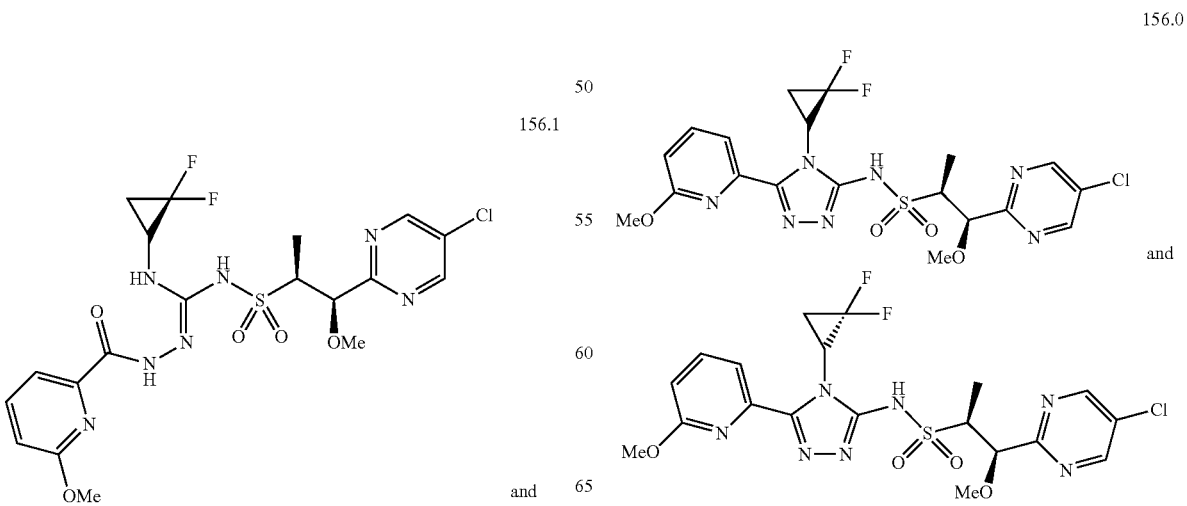

(1R,2S)-1-(5-Chloropyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide and (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide, Example 156.0

A microwave vial charged with Example 156.1 (1.203 g, 2.25 mmol) and HCl (4.0 M in dioxane, 2.82 ml, 11.27 mmol) was heated to 120° C. for 20 minutes in a Biotage Initiator microwave reactor. The reaction mixture was then poured into water and was extracted with DCM. The organic layers were combined and concentrated in vacuo. Purification by silica gel column chromatography gave Example 156.0 (0.250 g, 0.485 mmol, 21.51% yield). $^1$H NMR (500 MHz, CD$_3$CN) δ 1.29-1.42 (m, 3H) 2.17-2.29 (m, 1H) 3.06-3.24 (d, 3H) 3.44-3.55 (m, 1H) 3.64-3.77 (m, 1H) 3.97 (s, 3H) 3.99-4.11 (m, 1H) 4.90-5.04 (m, 1H) 6.96 (d, J=8.30 Hz, 1H) 7.51 (s, 1H) 7.82 (d, J=1.04 Hz, 1H) 8.77 (d, J=2.34 Hz, 2H) 11.16-11.38 (m, 1H). LCMS-ESI (pos.) m/z: 516.0 (M+H)$^+$.

Example 167.0. Preparation of (1R,2S)-1-(5-chloropyrimidin-2-yl)-N-(4-((S)-2,2-difluorocyclopropyl)-5-(6-methoxypyridin-2-yl)-4H-1,2,4-triazol-3-yl)-1-methoxypyane-2-sulfonamide or (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide

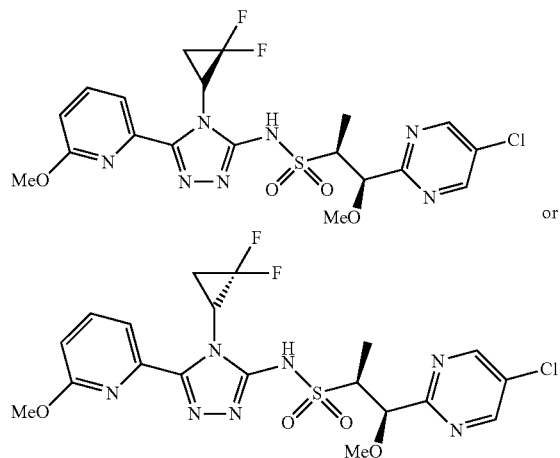

167.0

(1R,2S)-1-(5-Chloropyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide, Example 167.0

Example 156.0 was separated by SFC chromatography (peak assignment determined by SFC: Chiralpak IC, 40% MeOH.) yielding Example 167.0 as peak 1. $^1$H NMR (500 MHz, CD$_3$CN) δ 1.38 (d, J=7.01 Hz, 3H) 1.98-2.09 (m, 1H) 2.14-2.25 (m, 1H) 3.24 (s, 3H) 3.63 (dd, J=7.01, 4.67 Hz, 1H) 3.97 (s, 4H) 4.90 (d, J=4.54 Hz, 1H) 6.95 (d, J=8.44 Hz, 1H) 7.50 (d, J=7.27 Hz, 1H) 7.82 (dd, J=8.30, 7.40 Hz, 1H) 8.77 (s, 2H) 11.06-11.22 (m, 1H). LCMS-ESI (pos.) m/z: 516.0 (M+H)$^+$.

Example 168.0. Preparation of (1R,2S)-1-(5-chloropyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide

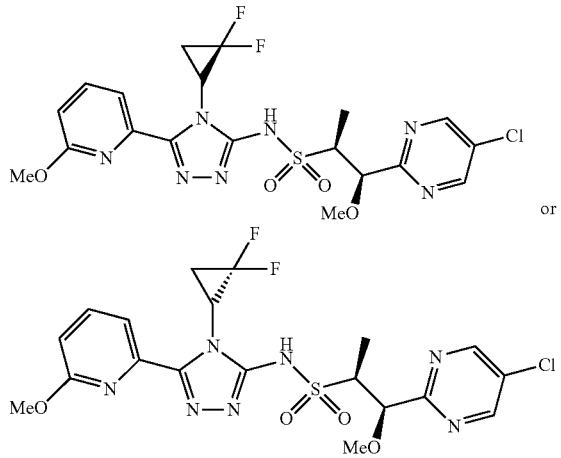

168.0

(1R,2S)-1-(5-Chloropyrimidin-2-yl)-N-(4-((S)-2,2-difluorocyclopropyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((R)-2,2-difluorocyclopropyl)-5-(6-methoxypyridin-2-yl)-4H-1,2,4-triazol-3-yl)-1-methoxypropane-2-sulfonamide, Example 168.0

Further elution using the condition described in Example 167.0 delivered Example 168.0 as peak 2. $^1$H NMR (500 MHz, CD$_3$CN) δ 1.34 (d, J=7.01 Hz, 3H) 2.16-2.30 (m, 2H) 3.06 (s, 3H) 3.48 (dd, J=7.07, 3.18 Hz, 1H) 3.97 (s, 3H) 4.02-4.13 (m, 1H) 5.04 (d, J=3.24 Hz, 1H) 6.96 (d, J=8.17 Hz, 1H) 7.52 (d, J=7.27 Hz, 1H) 7.82 (dd, J=8.24, 7.46 Hz, 1H) 8.77 (s, 2H) 11.33 (br s, 1H). LCMS-ESI (pos.) m/z: 516.0 (M+H)$^+$.

Example 163.0. Preparation of (1R,2S)-1-(5-chloropyrimidin-2-yl)-N-(4-(dispiro[2.0.24.13]heptan-7-yl)-5-(6-methoxypyridin-2-yl)-4H-1,2,4-triazol-3-yl)-1-methoxypropane-2-sulfonamide

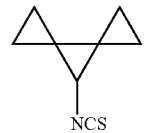

163.1

7-Isothiocyanatodispiro[2.0.2⁴.1³]heptane, Example 163.1

A solution of dispiro[2.0.2⁴.1³]heptan-7-amine hydrochloride (commercially available from Enamine, 1.000 g, 6.87 mmol) and N,N-diisopropylethylamine (1.199 ml, 6.87 mmol) in DCM (5 mL) was added slowly to a solution of O,O-di(pyridin-2-yl) carbonothioate (commercially available from Alpha Aesar, 1.675 g, 7.21 mmol) in DCM (10 mL). After stirring for 1 h, the reaction mixture was purified directly by silica gel column chromatography (0-100% EtOAc/heptane) yielding Example 163.1 (0.265 g, 1.75 mmol, 26% yield) as a clear oil. $^1$H NMR (500 MHz, CD$_3$CN) δ 0.80-0.90 (m, 4H) 1.02-1.15 (m, 4H) 2.13 (s, 1H).

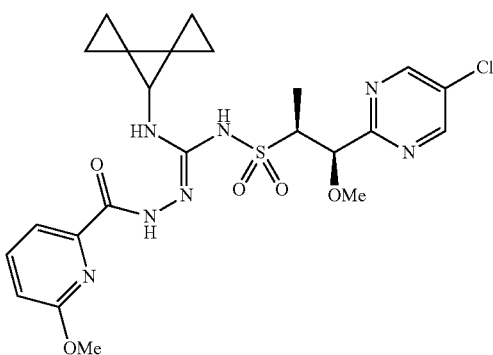

163.2

(1R,2S)-1-(5-Chloropyrimidin-2-yl)-N-((E)-N-(dispiro[2.0.2⁴.1³]heptan-7-yl)-N'-(6-methoxypicolinoyl)carbamohydrazonoyl)-1-methoxypropane-2-sulfonamide, Example 163.2

A solution of Example 29.3 (0.351 g, 1.32 mmol), Example 163.1 (0.200 g, 1.32 mmol), and potassium phosphate (1.123 g, 5.29 mmol) in 5 mL ACN was allowed to stir at room temperature for 1 h. 6-Methoxypicolinohydrazide (0.221 g, 1.323 mmol) was added followed by silver nitrate (0.449 g, 2.65 mmol). After stirring for 1 h, the reaction mixture was purified directly by silica gel column chromatography (0-97% EtOAc/heptane, 3% MeOH) yielding Example 163.2 (0.649 g, 1.180 mmol, 89% yield) with minor impurities. LCMS-ESI (pos.) m/z: 550.2 (M+H)$^+$.

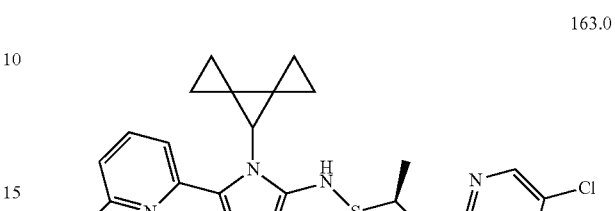

163.0

(1R,2S)-1-(5-Chloropyrimidin-2-yl)-N-(4-(dispiro[2.0.2⁴.1³]heptan-7-yl)-5-(6-methoxypyridin-2-yl)-4H-1,2,4-triazol-3-yl)-1-methoxypropane-2-sulfonamide, Example 163

A suspension of Example 163.2 (0.649 g, 1.180 mmol) in water (3 mL) was treated with sodium hydroxide (1.0M, 1.53 mL, 1.53 mmol). The mixture was then heated to 80° C. for 3 h. The reaction mixture was then poured into saturated aqueous NH$_4$Cl solution and was extracted with DCM. The organic layers were combined, dried over MgSO$_4$, and concentrated in vacuo. Purification of the residue by silica gel column chromatography (0-100% EtOAc/heptane) gave Example 163.0 (0.050 g, 0.094 mmol, 7.97% yield) as a white solid. $^1$H NMR (500 MHz, CD$_3$CN) δ 0.34-0.48 (m, 3H) 0.64 (ddt, J=12.81, 8.56, 4.43, 4.43 Hz, 2H) 0.74-0.85 (m, 3H) 1.40 (d, J=7.01 Hz, 3H) 3.21 (s, 3H) 3.56-3.66 (m, 1H) 3.87 (s, 1H) 3.96 (s, 3H) 4.82 (d, J=5.45 Hz, 1H) 6.95 (d, J=8.30 Hz, 1H) 7.40 (d, J=7.27 Hz, 1H) 7.81 (t, J=7.91 Hz, 1H) 8.76 (s, 2H) 10.98-11.12 (m, 1H). LCMS-ESI (pos.) m/z: 532.2 (M+H)$^+$.

The compounds set forth in the following table were synthesized following the procedure in Example 151.0 using the known starting material as described.

TABLE 16

| Example | Reagents | Structure, Name and Data |
|---|---|---|
| 153.0 | (2S,3R)-3-(5-chloropyrimidin-2-yl)butane-2-sulfonamide (Example 32.0), 6-methoxypicolinohydrazide (commercially available from Milestone PharmTech), and 1-isothiocyanatospiro[2.2]pentane (Example 150.01). | | and

| Example | Reagents | Structure, Name and Data |
|---|---|---|
| | | (2S,3R)-3-(5-chloro-2-pyrimidinyl)-N-(5-(6-methoxy-2-pyridinyl)-4-((1R)-spiro[2.2]pentan-1-yl)-4H-1,2,4-triazol-3-yl)-2-butanesulfonamide and (2S,3R)-3-(5-chloro-2-pyrimidinyl)-N-(5-(6-methoxy-2-pyridinyl)-4-((1S)-spiro[2.2]pentan-1-yl)-4H-1,2,4-triazol-3-yl)-2-butanesulfonamide. $^1$H NMR (500 MHz, CD$_3$CN) δ 0.26 (dq, J = 9.10, 4.45 Hz, 1 H) 0.58 (dt, J = 8.66, 4.56 Hz, 1 H) 0.62-0.69 (m, 1 H) 0.69-0.76 (m, 1 H) 1.33 (br d, J = 4.16 Hz, 1 H) 1.36-1.42 (m, 3 H) 1.42-1.46 (m, 1 H) 3.59 (dt, J = 7.36, 3.91 Hz, 1 H) 3.68-3.82 (m, 2 H) 3.97 (s, 3 H) 6.95 (d, J = 8.30 Hz, 1 H) 7.43 (dd, J = 7.33, 1.36 Hz, 1 H) 7.70-7.88 (m, 1 H) 8.70 (s, 1 H) 11.03-11.15 (m, 1 H). LCMS-ESI (pos.) m/z: 490.2 (M + H)$^+$. |
| 154.0 | (1R,2S)-1-methoxy-1-(5-methoxypyrimidin-2-yl)propane-2-sulfonamide (Example 29.8), 6-methoxypicolinohydrazide (commercially available from Milestone PhamTech), and 1-isothiocyanatospiro[2.2]pentane (Example 150.01). | 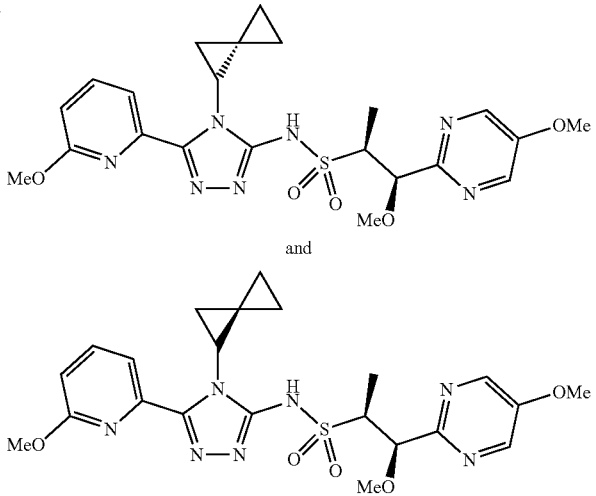 (1R,2S)-1-methoxy-N-(5-(6-methoxypyridin-2-yl)-4-((R)-spiro[2.2]pentan-1-yl)-4H-1,2,4-triazol-3-yl)-1-(5-methoxypyrimidin-2-yl)propane-2-sulfonamide and (1R,2S)-1-methoxy-N-(5-(6-methoxypyridin-2-yl)-4((S)-spiro[2.2]pentan-1-yl)-4H-1,2,4-triazol-3-yl)-1-(5-methoxypyrimidin-2-yl)propane-2-sulfonamide. $^1$H NMR (500 MHz, CD$_3$CN) δ 0.08-0.24 (m, 1 H) 0.52-0.66 (m, 2 H) 0.68-0.76 (m, 3 H) 1.31-1.36 (m, 1 3 H) 1.38--1.61 (m, 2 H) 3.13-3.26 (m, 3 H) 3.31-3.52 (m, 1 H) 3.59-3.73 (m, 1 H) 3.89-3.93 (m, 1 3 H) 3.93-3.96 (m, 3 H) 4.82-4.98 (m, 1H) 6.93 (d, J = 8.43 Hz, 1 H) 7.34-7.46 (m, 1 H) 7.80 (t, J = 7.85 Hz, 1 H) 8.10-8.22 (m, 1 H) 10.89-11.06 (m, 1 H), LCMS-ESI (pos.) m/z: 502.2 (M + H)$^+$. |

TABLE 16-continued

| Example | Reagents | Structure, Name and Data |
|---|---|---|
| 157.0 | (2S,3R)-3-(5-chloropyrimidin-2-yl)butane-2-sulfonamide (Example 32.0), 6-methoxypicolinohydrazide (commercially available from Milestone PharmTech), and 1-isothiocyanatospiro[2.2]pentane (Example 150.01). Peak 1 assignment determined by SFC: Chiralpak IC, 45% MeOH. | 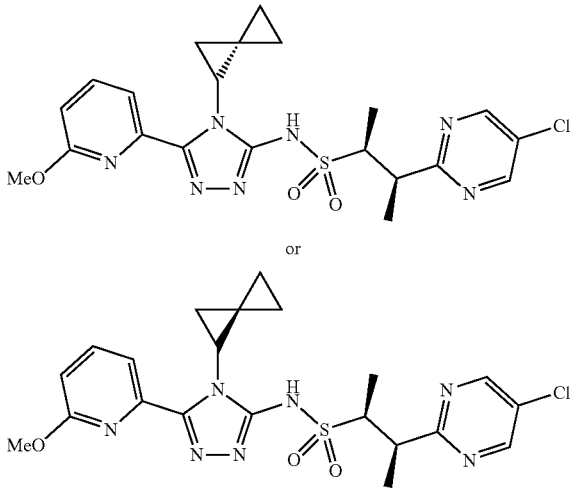<br><br>or<br><br>(2S,3R)-3-(5-chloro-2-pyrimidinyl)-N-(5-(6-methoxy-2-pyridinyl)-4((1R)-spiro[2.2]pentan-1-yl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-spiro[2.2]pentan-1-yl)-4H-1,2,4-triazol-3-yl)-2-butanesulfonamide.<br>$^1$H NMR (500 MHz, CD$_3$CN) δ 0.26 (dt, J = 9.37, 4.85 Hz, 1 H) 0.54-0.61 (m, 1 H) 0.63-0.69 (m, 1 H) 0.72 (dd, J = 8.50, 4.74 Hz, 1 H) 1.40 (dd, J = 8.37, 7.07 Hz, 3 H) 1.44 (t, J = 6.55 Hz, 1 H) 3.59 (dd, J = 7.14, 3.63 Hz, 1 H) 3.68-3.83 (m, 2H) 3.97 (s, 3 H) 6.92-6.98 (m, 1H) 7.43 (dd, J = 7.27, 0.65 Hz, 1 H) 7.82 (dd, J = 8.37, 7.33 Hz, 1 H) 8.70 (s, 2 H) 10.99-11.08 (m, 1 H). LCMS-ESI (pos.) m/z: 490.2 (M + H)$^+$. |
| 158.0 | (2S,3R)-3-(5-chloropyrimidin-2-yl)butane-2-sulfonamide (Example 32.0), 6-methoxypicolinohydrazide (commercially available from Milestone PharmTech), and 1-isothiocyanatospiro[2.2]pentane (Example 150.01). Peak 2 assignment determined by SFC: Chiralpak IC, 45% MeOH. | 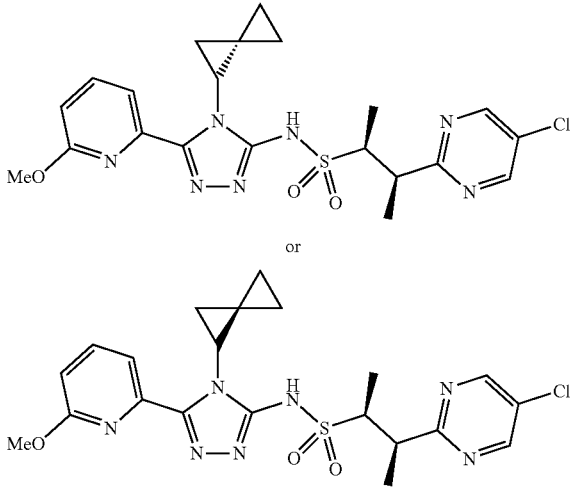<br><br>or<br><br>(2S,3R)-3-(5-chloro-2-pyrimidinyl)-N-(5-(6-methoxy-2-pyridinyl)-4-((1R)-spiro[2.2]pentan-1-yl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-spiro[2.2]pentan-1-yl)-4H-1,2,4-triazol-3-yl)-2-butanesulfonamide.<br>$^1$H NMR (500 MHz, CD$_3$CN) δ 0.27 (dt, J = 9.05, 4.75 Hz, 1 H) 0.58 (dt, J = 9.34, 4.80 Hz, 1 H) 0.63-0.69 (m, 1 H) 0.70-0.76 (m, 1 H) 1.40 (dd, J = 10.77, 7.01 Hz, 3 H) 1.45 (t, J = 6.62 Hz, 1 H) 3.60 (dd, J = 7.07, 3.83 Hz, 1 H) 3.67-3.81 (m, 2 H) 3.97 (s, 3 H) 6.95 (d, J = 8.43 Hz, 1 H) 7.43 (d, |

TABLE 16-continued

| Example | Reagents | Structure, Name and Data |
|---|---|---|
| | | J = 7.27 Hz, 1 H) 7.79-7.86 (m, 1 H) 8.70 (s, 2 H) 10.97-11.08 (m, 1 H). . LCMS-ESI (pos.) m/z: 490.2 (M + H)+. |
| 159.0 | (1R,2S)-1-methoxy-1-(5-methoxypyrimidin-2-yl)propane-2-sulfonamide (Example 29.8), 6-methoxypicolinohydrazide (commercially available from Milestone PharmTech), and 1-isothiocyanatospiro[2.2]pentane (Example 150.01). Peak 1 assignment determined by SFC: Chiralpak IC, 55% MeOH. | (1R,2S)-1-methoxy-1-(5-methoxypyrazin-2-yl)-N-(5-(6-methoxypyridin-2-yl)-4-((S)-spiro[2.2]pentan-1-yl)-4H-1,2,4-triazol-3-yl)propane-2-sulfonamide or (1R,2S)-1-methoxy-1-(5-methoxypyrazin-2-yl)-N-(5-(6-methoxypyridin-2-yl)-4-((R)-spiro[2.2]pentan-1-yl)-4H-1,2,4-triazol-3-yl)propane-2-sulfonamide. <br> 1H NMR (500 MHz, CD3CN) δ 0.21 (dt, J = 9.18, 4.69 Hz, 1 H) 0.52-0.59 (m, 1 H) 0.60-0.67 (m, 1 H) 0.68-0.74 (m, 1 H) 1.34(d, J = 7.14 Hz, 3 H) 1.39 (dd, J = 5.90, 3.70 Hz, 1 H) 1.46 (s, 1 H) 3.26 (s, 3 H) 3.44-3.53 (m, 1 H) 3.63 (dd, J = 7.01, 3.50 Hz, 1 H) 3.91 (s, 3 H) 3.95 (s, 3 H) 4.86 (d, J = 4.15 Hz, 1 H) 6.93 (d, J = 8.31 Hz, 1 H) 7.41 (d, J = 7.14 Hz, 1 H) 7.80 (dd, J = 8.30, 7.40 Hz, 1 H) 8.13-8.21 (m, 2 H) 11.04-11.12 (m, 1 H). LCMS-ESI (pos.) m/z: 502.2 (M + H)+. |
| 160.0 | (1R,2S)-1-methoxy-1-(5-methoxypyrimidin-2-yl)propane-2-sulfonamide (Example 29.8), 6-methoxypicolinohydrazide (commercially available from Milestone PharmTech), and 1-isothiocyanatospiro[2.2]pentane (Example 150.01). Peak 2 assignment determined by SFC: Chiralpak IC, 55% MeOH | (1R,2S)-1-methoxy-1-(5-methoxypyrazin-2-yl)-N-(5-(6-methoxypyridin-2-yl)-4-((S)-spiro[2.2]pentan-1-yl)-4H-1,2,4-triazol-3-yl)propane-2-sulfonamide or (1R,2S)-1-methoxy-1-(5-methoxypyrazin-2-yl)-N-(5-(6-methoxypyridin-2-yl)-4-((R)-spiro[2.2]pentan-1-yl)-4H-1,2,4-triazol-3-y)propane-2-sulfonamide. |

TABLE 16-continued

| Example Reagents | Structure, Name and Data |
|---|---|
| | $^1$H NMR (500 MHz, CD$_3$CN) δ 0.14 (br s, 1 H) 0.55-0.68 (m, 2 H) 0.74 (br d, J = 4.16 Hz, 1 H) 1.32-1.37 (m, 3 H) 1.47-1.55 (m, 1 H) 1.60 (br d, J = 3.76 Hz, 1 H) 3.16 (s, 3 H) 3.37 (qd, J = 7.03, 3.44 Hz, 1 H) 3.72 (dd, J = 7.01, 3.63 Hz, 1 H) 3.93 (s, 3 H) 3.97 (s, 3 H) 4.97 (d, J = 3.12 Hz, 1 H) 6.95 (d, J = 8.43 Hz, 1 H) 7.44 (d, J = 7.27 Hz, 1 H) 7.82 (t, J = 7.85 Hz, 1 H) 8.14 (s, 1 H) 8.22 (d, J = 1.17 Hz, 1 H) 11.15-11.27 (m, 1 H). LCMS-ESI (pos.) m/z: 502.2 (M + H)$^+$. |

Example 164.0. Preparation of (1S,2S)—N-(4-(cyclopropyl-2,2,3,3-d4)-5-(6-methoxypyridin-2-yl)-4H-1,2,4-triazol-3-yl)-1-isopropoxy-1-(5-methylpyrimidin-2-yl)propane-2-sulfonamide

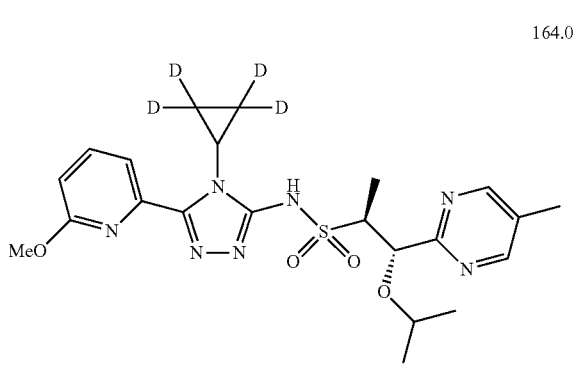 [SMILES: [2H]C1([2H])C(n2c(NS(=O)(=O)[C@@H](C)[C@@H](OC(C)C)c3ncc(C)cn3)nnc2-c2cccc(OC)n2)C1([2H])[2H]]

164.0

(1S,2S)—N-(4-(Cyclopropyl-2,2,3,3-d4)-5-(6-methoxypyridin-2-yl)-4H-1,2,4-triazol-3-yl)-1-isopropoxy-1-(5-methylpyrimidin-2-yl)propane-2-sulfonamide, Example 164.0

Example 164.0 was prepared in a similar fashion to Example 148.0 using Example 31.0 instead of Example 29.3. $^1$H NMR (500 MHz, CD$_3$CN) δ 0.77 (d, J=6.10 Hz, 3H) 1.01 (d, J=5.97 Hz, 3H) 1.35 (d, J=7.14 Hz, 3H) 2.30 (s, 3H) 3.21 (s, 1H) 3.36-3.46 (m, 1H) 3.65 (dd, J=7.07, 5.52 Hz, 1H) 3.95 (s, 3H) 4.85 (d, J=5.32 Hz, 1H) 6.93 (d, J=8.44 Hz, 1H) 7.44 (d, J=7.14 Hz, 1H) 7.80 (dd, J=8.24, 7.46 Hz, 1H) 8.62 (s, 2H) 11.76-11.98 (m, 1H) m/z: 492.2 (M+H)$^+$.

Example 169.0. Preparation (1R,2S)-1-(5-chloropyrimidin-2-yl)-N-(4-((1R,2S)-2-fluorocyclopropyl)-5-(6-methoxypyridin-2-yl)-4H-1,2,4-triazol-3-yl)-1-methoxypropane-2-sulfonamide

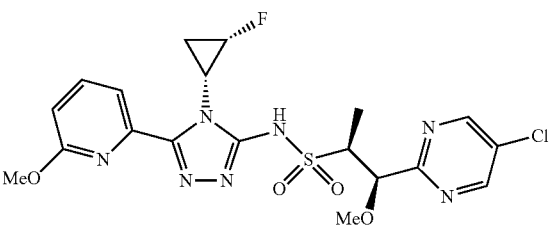

169.0

(1R,2S)-1-(5-Chloropyrimidin-2-yl)-N-(4-((1R,2S)-2-fluorocyclopropyl)-5-(6-methoxypyridin-2-yl)-4H-1,2,4-triazol-3-yl)-1-methoxypropane-2-sulfonamide, Example 169.0

Example 169.0 was prepared in a similar fashion to Example 156.0 using (1R,2S)-2-fluorocyclopropanamine 4-methylbenzenesulfonate (commercially available from Pharmablock) instead of 2,2-difluorocyclopropan-1-amine hydrochloride. $^1$H NMR (500 MHz, CD$_3$CN) δ 1.35 (d, J=7.14 Hz, 3H) 1.50-1.61 (m, 1H) 1.67-1.83 (m, 1H) 3.05 (s, 3H) 3.31-3.38 (m, 1H) 3.48 (dd, J=7.14, 3.37 Hz, 1H) 3.96 (s, 3H) 4.01-4.10 (m, 1H) 4.62-4.78 (m, 1H) 5.04 (d, J=3.25 Hz, 1H) 6.94 (d, J=8.43 Hz, 1H) 7.49 (d, J=7.39 Hz, 1H) 7.80 (t, J=7.85 Hz, 1H) 8.73-8.82 (m, 3H). m/z: 498.2 (M+H)$^+$.

The compounds in the following table were synthesized following the procedure in Example 1.0 using the known starting material as described.

TABLE 17

| Example | Reagents | Structure, Name and Data |
|---|---|---|
| 170.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 1-(isothiocyanatomethyl)-4-methoxybenzene (commercially available from Frontier Scientific Services Inc.). | 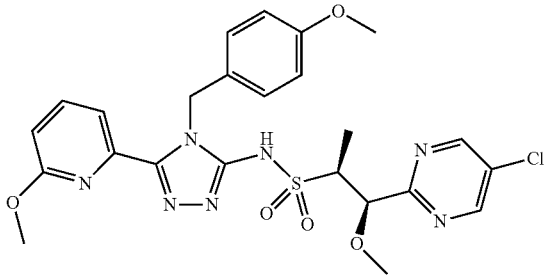 [SMILES: COc1ccc(Cn2c(NS(=O)(=O)[C@@H](C)[C@H](OC)c3ncc(Cl)cn3)nnc2-c2cccc(OC)n2)cc1]<br>(1R,2S)-1-(5-chloropyrimidin-2-yl)-1-methoxy-N-(4-(4-methoxybenzyl)-5-(6-methoxypyridin-2- |

TABLE 17-continued

| Example | Reagents | Structure, Name and Data |
|---|---|---|
| | | yl)-4H-1,2,4-triazol-3-yl)propane-2-sulfonamide.<br>$^1$H NMR (500 MHz, CDCl$_3$) δ 10.99 (br s, 1H), 8.71 (s, 2H), 7.71 (t, J = 7.81 Hz, 1H), 7.61 (d, J = 7.27 Hz, 1H), 7.14-7.19 (m, J = 8.56 Hz, 2H), 6.89 (d, J = 8.30 Hz, 1H), 6.71-6.78 (m, J = 8.69 Hz, 2H), 5.62-5.69 (m, 2H), 4.82 (d, J = 5.19 Hz, 1H), 3.83 (s, 3H), 3.73-3.77 (m, 1H), 3.73 (s, 3H), 3.27-3.38 (m, 3H), 1.33 (d, J = 7.01 Hz, 3H).<br>LCMS ESI (pos.) m/z: 560.0 (M + H)$^+$. |
| 171.0 | (1S,2S)-1-(5-fluoropyrimidin-2-yl)-1-isopropoxypropane-2-sulfonamide (Example 171.1), 6-methoxypicolinohydrazide (commercially available from Sigma Aldrich), and 2-isothiocyanato-1,3-dimethoxypropane (Example 71.0). | 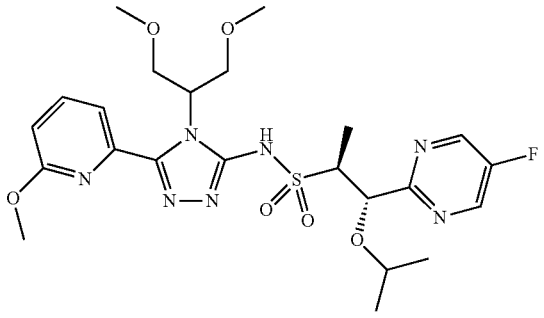 [SMILES: COCC(COC)n1c(NS(=O)(=O)[C@@H](C)[C@@H](OC(C)C)c2ncc(F)cn2)nnc1-c1cccc(OC)n1]<br>(1S,2S)-N-(4-(1,3-dimethoxy-2-propanyl)-5-(6-methoxy-2-pyridinyl)-4H-1,2,4-triazol-3-yl)-1-(5-fluoro-2-pyrimidinyl)-1-(2-propanyloxy)-2-propanesulfonamide.<br>$^1$H NMR (500 MHz, CDCl$_3$) δ 11.93 (br s, 1 H) 8.67 (s, 2 H) 7.72 (dd, J = 8.17, 7.53 Hz, 1 H) 7.54 (d, J = 7.27 Hz, 1 H) 6.89 (d, J = 8.30 Hz, 1 H) 5.72 (quin, J = 6.91 Hz, 1 H) 4.98 (d, J = 4.15 Hz, 1 H) 4.26 (t, J = 8.95 Hz, 1 H) 4.16 (dd, J = 9.67, 7.46 Hz, 1 H) 3.99 (s, 3 H) 3.82-3.89 (m, 2 H) 3.79 (dd, J = 9.73, 5.84 Hz, 1 H) 3.57 (m, 1 H) 3.31 (s, 3 H) 3.29 (s, 3 H) 1.57 (d, J = 7.14 Hz, 3 H) 1.13 (d, J = 5.97 Hz, 3 H) 0.97 (d, J = 6.23 Hz, 3 H).<br>LCMS ESI (pos.) m/z: 554.2 (M + H)$^+$. |
| 172.0 | (1S,2S)-1-isopropoxy-1-(5-methoxypyrimidin-2-yl)propane-2-sulfonamide (Example 172.1), 6-methoxypicolinohydrazide (commercially available from Sigma Aldrich), and 2-isothiocyanato-1,3-dimethoxypropane (Example 71.0). | 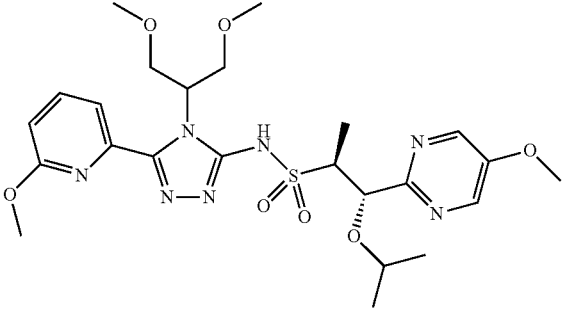 [SMILES: COCC(COC)n1c(NS(=O)(=O)[C@@H](C)[C@@H](OC(C)C)c2ncc(OC)cn2)nnc1-c1cccc(OC)n1]<br>(1S,2S)-N-(4-(1,3-dimethoxy-2-propanyl)-5-(6-methoxy-2-pyridinyl)-4H-1,2,4-triazol-3-yl)-1-(5-methoxy-2-pyrimidinyl)-1-(2-propanyloxy)-2-propanesulfonamide.<br>$^1$H NMR (500 MHz, CDCl$_3$) δ 12.61 (br s, 1 H) 8.48 (s, 2 H) 7.71 (t, J = 7.85 Hz, 1 H) 7.55 (d, J = 7.40 Hz, 1 H) 6.88 (d, J = 8.30 Hz, 1 H) 5.71 (quin, J = 6.91 Hz, 1 H) 4.93 (d, J = 3.89 Hz, 1 H) 4.27 (t, J = 8.95 Hz, 1 H) 4.17 (dd, J = 9.67, 7.33 Hz, 1 H) 3.99 (s, 3 H) 3.95 (s, 3 H) 3.87 (dd, J = 9.73, 6.49 Hz, 1 H) 3.75-3.83 (m, 2 H) 3.55 (quin, J = 6.10 Hz, 1 H) 3.31 (s, 3 H) 3.29 (s, 3 H) 1.58 (d, J = 7.14 Hz, 3 H) 1.11 (d, J = 5.97 Hz, 3 H) 0.95 (d, J = 6.23 Hz, 3 H). LCMS ESI (pos.) m/z: 566.2 (M + H)$^+$. |

TABLE 17-continued

| Example | Reagents | Structure, Name and Data |
|---|---|---|
| 173.0 | (1S,2S)-1-(5-chloropyrimidin-2-yl)-1-isopropoxypropane-2-sulfonamide (Example 31.01), 6-methoxypicolinohydrazide (commercially available from Sigma Aldrich), and 2-isothiocyanato-1,3-dimethoxypropane (Example 71.0). | 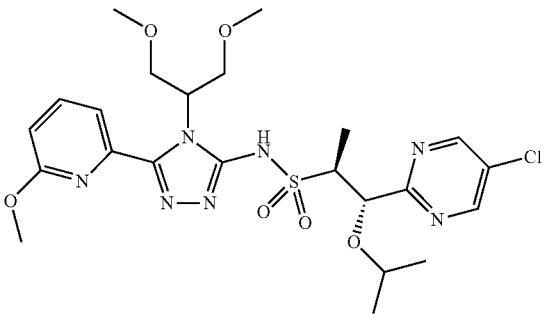 [SMILES: COCC(COC)n1c(NS(=O)(=O)[C@@H](C)[C@@H](OC(C)C)c2ncc(Cl)cn2)nnc1-c1cccc(OC)n1]<br>(1S,2S)-N-(4-(1,3-dimethoxy-2-propanyl)-5-(6-methoxy-2-pyridinyl)-4H-1,2,4-triazol-3-yl)-1-(5-fluoro-2-pyrimidinyl)-1-(2-propanyloxy)-2-propanesulfonamide.<br>$^1$H NMR (500 MHz, CDCl$_3$) δ 11.93 (br s, 1 H) 8.75 (s, 2 H) 7.71 (dd, J = 8.17, 7.53 Hz, 1 H) 7.54 (d, J = 7.27 Hz, 1 H) 6.88 (d, J = 8.43 Hz, 1 H) 5.72 (quin, J = 6.91 Hz, 1 H) 4.93 (d, J = 4.02 Hz, 1 H) 4.25 (t, J = 8.95 Hz, 1 H) 4.15 (dd, J = 9.67, 7.46 Hz, 1 H) 3.99 (s, 3 H) 3.81-3.89 (m, 2 H) 3.78 (dd, J = 9.86, 5.84 Hz, 1 H) 3.57 (spt, J = 6.08 Hz, 1 H) 3.30 (s, 3 H) 3.28 (s, 3 H) 1.57 (d, J = 7.14 Hz, 3 H) 1.12 (d, J = 6.10 Hz, 3 H) 0.96 (d, J = 6.10 Hz, 3 H). LCMS ESI (pos.) m/z: 570.0 (M + H)$^+$. |
| 174.0 | (2S,3R)-3-(5-chloropyrimidin-2-yl)butane-2-sulfonamide (Example 27.4), 6-methoxypicolinohydrazide (commercially available from Sigma Aldrich), and (S)-2-isothiocyanato-1-methoxypropane (Example 28.10). | 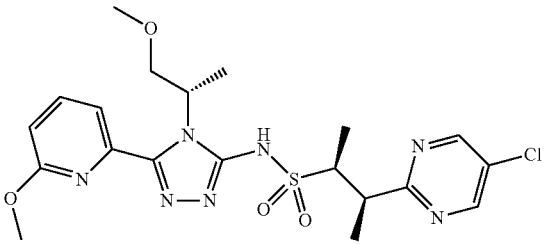 [SMILES: COC[C@H](C)n1c(NS(=O)(=O)[C@@H](C)[C@H](C)c2ncc(Cl)cn2)nnc1-c1cccc(OC)n1]<br>(2S,3R)-3-(5-chloro-2-pyrimidinyl)-N-(4-((2S)-1-methoxy-2-propanyl)-5-(6-methoxy-2-pyridinyl)-4H-1,2,4-triazol-3-yl)-2-butanesulfonamide.<br>$^1$H NMR (400 MHz, CDCl$_3$) δ 11.09 (s, 1 H) 8.65 (s, 2 H) 7.73 (t, J = 7.88 Hz, 1 H) 7.53 (d, J = 7.26 Hz, 1 H) 6.89 (d, J = 8.40 Hz, 1 H) 5.35-5.50 (m, 1 H) 4.24 (t, J = 9.28 Hz, 1 H) 3.96 (s, 3 H) 3.87-3.94 (m, 1 H) 3.82 (quin, J = 6.92 Hz, 1 H) 3.57 (dd, J = 9.64, 5.70 Hz, 1 H) 3.24 (s, 3 H) 1.64 (d, J = 7.05 Hz, 3 H) 1.48 (d, J = 3.63 Hz, 3 H) 1.46 (d, J = 3.73 Hz, 3 H). LCMS ESI (pos.) m/z: 496.0 (M + H)$^+$. |
| 175.0 | (2S,3R)-3-(5-chloropyrimidin-2-yl)butane-2-sulfonamide (Example 27.4), picolinohydrazide (commercially available from Sigma Aldrich) and (S)-2-isothiocyanato-1-methoxypropane (Example 28.10). | 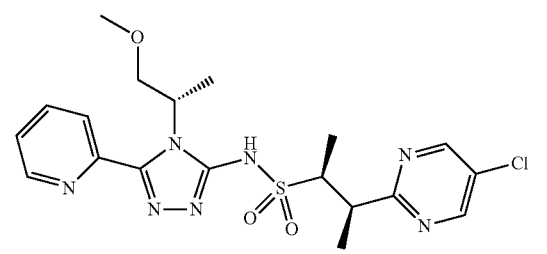 [SMILES: COC[C@H](C)n1c(NS(=O)(=O)[C@@H](C)[C@H](C)c2ncc(Cl)cn2)nnc1-c1ccccn1]<br>(2S,3R)-3-(5-chloro-2-pyrimidinyl)-N-(4-((2S)-1-methoxy-2-propanyl)-5-(2-pyridinyl)-4H-1,2,4-triazol-3-yl)-2-butanesulfonamide.<br>$^1$H MR (600 MHz, DMSO-d$_6$) δ 13.19 (s, 1 H) 8.87 (s, 2 H) 8.74 (br d, J = 4.28 Hz, 1 H) 8.02 (td, J = 7.75, 1.32 Hz, 1 H) 7.88-7.96 (m, 1 H) 7.56-7.63 (m, 1 H) 5.29-5.44 (m, 1 H) 4.05 (br t, J = 9.77 Hz, 1 H) 3.65-3.80 (m, 2 H) 3.44 (dd, J = 10.04, 5.22 Hz, 1 H) 3.06 (s, 3 H) 1.45 (d, |

TABLE 17-continued

| Example | Reagents | Structure, Name and Data |
|---|---|---|
| | | J = 7.01 Hz, 3 H) 1.36 (d, J = 7.08 Hz, 3 H) 1.27 (d, J = 6.93 Hz, 3 H). LCMS ESI (pos.) m/z: 466.0 (M + H)⁺. |
| 176.0 | (2S,3R)-3-(5-chloropyrimidin-2-yl)butane-2-sulfonamide (Example 27.4), 5-methylnicotinohydrazide (commercially available from Bellen), and (S)-2-isothiocyanato-1-methoxypropane (Example 28.10). | (2S,3R)-3-(5-chloro-2-pyrimidinyl)-N-(4-((2S)-1-methoxy-2-propanyl)-5-(5-methyl-3-pyridinyl)-4H-1,2,4-triazol-3-yl)-2-butanesulfonamide.<br>¹H NMR (600 MHz, DMSO-d₆) δ 12.45-13.84 (m, 1 H) 8.88 (s, 2 H) 8.61 (s, 1 H) 8.56 (d, J = 1.40 Hz, 1 H) 7.83 (s, 1 H) 4.16-4.28 (m, 1 H) 4.02 (br t, J = 9.77 Hz, 1 H) 3.77 (td, J = 6.91, 3.23 Hz, 2 H) 3.44 (m, 1 H) 3.13 (s, 3 H) 2.54 (s, 2 H) 2.38 (s, 3 H) 1.40 (d, J = 7.01 Hz, 3 H) 1.36 (d, J = 7.01 Hz, 3 H) 1.25 (br d, J = 6.70 Hz, 3 H). LCMS ESI (pos.) m/z: 480.0 (M + H)⁺. |
| 177.0 | (1S,2S)-1-(5-chloropyrimidin-2-yl)-1-isopropoxypropane-2-sulfonamide (Example 31.01), 6-methoxypicolinohydrazide (commercially available from Sigma Aldrich), and isonicotinohydrazide (commercially available from Sigma-Aldrich Inc.). | (1S,2S)-1-(5-chloro-2-pyrimidinyl)-N-(5-(6-methoxy-2-pyridinyl)-4-(2-propanyl)-4H-1,2,4-triazol-3-yl)-1-(2-propanyloxy)-2-propanesulfonamide.<br>¹H NMR (600 MHz, DMSO-d₆) δ 12.85 (s, 1 H) 8.95 (s, 2 H) 7.91 (dd, J = 8.37, 7.36 Hz, 1 H) 7.45-7.51 (m, 1 H) 7.03 (d, J = 8.41 Hz, 1 H) 5.12 (spt, J = 6.86 Hz, 1 H) 4.94 (d, J = 6.62 Hz, 1 H) 3.91 (s, 3 H) 3.59 (quin, J = 6.99 Hz, 1 H) 3.41 (spt, J = 6.10 Hz, 1 H) 3.32 (s, 10 H) 1.53 (d, J = 2.65 Hz, 3 H) 1.52 (d, J = 2.65 Hz, 3 H) 1.16 (d, J = 7.08 Hz, 3 H) 1.03 (d, J = 6.07 Hz, 3 H) 0.81 (d, J = 6.15 Hz, 3 H). LCMS ESI (pos.) m/z: 510.2 (M + H)⁺. |
| 178.0 | (1S,2S)-1-(5-chloropyrimidin-2-yl)-1-isopropoxypropane-2-sulfonamide (Example 31.01), 6-methoxypicolinohydrazide (commercially available from Sigma Aldrich), and (R)-2-isothiocyanato-1-methoxypropane (Example 28.9). | (1S,2S)-1-(5-chloro-2-pyrimidinyl)-N-(4-((2R)-1-methoxy-2-propanyl)-5-(6-methoxy-2-pyridinyl)-4H-1,2,4-triazol-3-yl)-1-(2-propanyloxy)-2-propanesulfonamide.<br>¹H NMR (600 MHz, DMSO-d₆) δ 12.92 (s, 1 H |

| Example | Reagents | Structure, Name and Data |
|---|---|---|
| | | 8.96 (s, 2 H) 7.91 (dd, J = 8.37, 7.36 Hz, 1 H) 7.45-7.53 (m, 1 H) 7.03 (dd, J = 8.37, 0.66 Hz, 1 H) 5.23-5.34 (m, 1 H) 4.93 (d, J = 6.93 Hz, 1 H) 4.09-4.17 (m, 1 H) 3.90 (s, 3 H) 3.57 (quin, J = 7.05 Hz, 1 H) 3.48 (dd, J = 9.81, 5.37 Hz, 1 H) 3.41 (dt, J = 12.20, 6.08 Hz, 1 H) 3.12 (s, 3 H) 1.54 (d, J = 7.01 Hz, 3 H) 1.13 (d, J = 7.08 Hz, 3 H) 1.03 (d, J = 6.07 Hz, 3 H) 0.82 (d, J = 6.15 Hz, 3 H). LCMS ESI (pos.) m/z: 540.2 (M + H)+. |
| 179.0 | (1S,2S)-1-(5-chloropyrimidin-2-yl)-1-isopropoxypropane-2-sulfonamide (Example 31.01), 6-methoxypicolinohydrazide (commercially available from Sigma Aldrich), and (S)-2-isothiocyanato-1-methoxypropane (Example 28.10). | 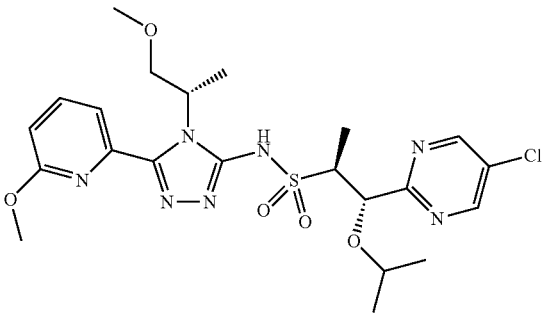 [SMILES: COC[C@H](C)n1c(NS(=O)(=O)[C@@H](C)[C@@H](OC(C)C)c2ncc(Cl)cn2)nnc1-c1cccc(OC)n1] (1S,2S)-1-(5-chloro-2-pyrimidinyl)-N-(4-((2S)-1-methoxy-2-propanyl)-5-(6-methoxy-2-pyridinyl)-4H-1,2,4-triazol-3-yl)-1-(2-propanyloxy)-2-propanesulfonamide. <br> 1H NMR (600 MHz, DMSO-d6) δ 12.90 (s, 1 H) 8.95 (s, 2 H) 7.91 (dd, J = 8.29, 7.43 Hz, 1 H) 7.50 (d, J = 6.93 Hz, 1 H) 7.03 (d, J = 8.17 Hz, 1 H) 5.26 (dq, J = 14.20, 6.92 Hz, 1 H) 4.95 (d, J = 6.46 Hz, 1 H) 4.08 (br t, J = 9.54 Hz, 1 H) 3.91 (s, 3 H) 3.60 (quin, J = 6.93 Hz, 1 H) 3.42-3.53 (m, 2 H) 3.32 (s, 9 H) 3.11 (s, 3 H) 1.52 (d, J = 7.01 Hz, 3 H) 1.18 (d, J = 7.08 Hz, 4 H) 1.05 (d, J = 5.99 Hz, 3 H) 0.84 (d, J = 6.15 Hz, 3 H). LCMS ESI (pos.) m/z: 540.2 (M + H)+. |
| 180.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (1s,3s)-1-isothiocyanato-3-methoxycyclobutane (Example 180.1). | 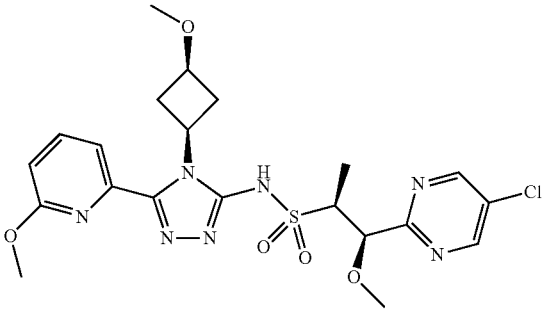 [SMILES: COc1cccc(-c2nnc(NS(=O)(=O)[C@@H](C)[C@H](OC)c3ncc(Cl)cn3)n2[C@H]2C[C@@H](OC)C2)n1] (1R,2S)-1-(5-chloro-2-pyrimidinyl)-1-methoxy-N-(4-(cis-3-methoxycyclobutyl)-5-(6-methoxy-2-pyridinyl)-4H-1,2,4-triazol-3-yl)-2-propanesulfonamide. <br> 1H NMR (600 MHz, DMSO-d6) δ 12.58 (br s, 1 H) 8.92 (s, 2 H) 7.90 (dd, J = 8.33, 7.32 Hz, 1 H) 7.47 (dd, J = 7.28, 0.74 Hz, 1 H) 7.02 (d, J = 8.33 Hz, 1 H) 4.87-4.98 (m, 2 H) 3.94 (s, 3 H) 3.59-3.68 (m, 2 H) 3.17 (s, 3 H) 3.12 (s, 3 H) 2.88-2.97 (m, 2 H) 2.42-2.49 (m, 2 H) 1.38 (d, J = 7.01 Hz, 3 H). LCMS ESI (pos.) m/z: 524.2 (M + H)+. |

TABLE 17-continued

| Example | Reagents | Structure, Name and Data |
|---|---|---|
| 181.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (1r,3r)-1-isothiocyanato-3-methoxycyclobutane (Example 181.1). | 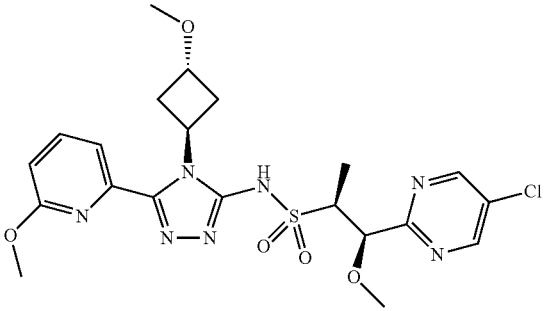 [SMILES: COc1cccc(-c2nnc(NS(=O)(=O)[C@@H](C)[C@H](OC)c3ncc(Cl)cn3)n2[C@H]2C[C@H](OC)C2)n1]<br>(1R,2S)-1-(5-chloro-2-pyrimidinyl)-1-methoxy-N-(4-(trans-3-methoxycyclobutyl)-5-(6-methoxy-2-pyridinyl)-4H-1,2,4-triazol-3-yl)-2-propanesulfonamide.<br>$^1$H NMR (600 MHz, DMSO-$d_6$) δ 13.01 (br s, 1 H) 8.93 (s, 2 H) 7.90 (dd, J = 8.33, 7.47 Hz, 1 H) 7.48-7.54 (m, 1 H) 7.03 (d, J = 8.33 Hz, 1 H) 5.75 (quin, J = 8.62 Hz, 1 H) 4.92 (d, J = 4.52 Hz, 1 H) 4.03 (br t, J = 6.62 Hz, 1 H) 3.94 (s, 3 H) 3.57-3.67 (m, 1 H) 3.11-3.21 (m, 8 H) 2.19-2.30 (m, 2 H) 1.35 (d, J = 7.01 Hz, 3 H). LCMS ESI (pos.) m/z: 524.2 (M + H)$^+$. |
| 182.0 | (1R,2S)-1-(5-chloropyrimidin-2-yl)-1-methoxypropane-2-sulfonamide (Example 29.3), 6-methoxypicolinohydrazide (commercially available from Sigma Aldrich), and isothiocyanatocyclobutane (commercially available from Enamine). | 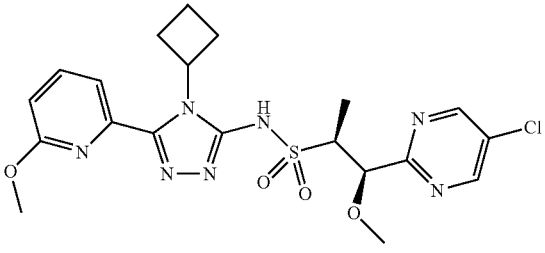 [SMILES: COc1cccc(-c2nnc(NS(=O)(=O)[C@@H](C)[C@H](OC)c3ncc(Cl)cn3)n2C2CCC2)n1]<br>(1R,2S)-1-(5-chloro-2-pyrimidinyl)-N-(4-cyclobutyl-5-(6-methoxy-2-pyridinyl)-4H-1,2,4-triazol-3-yl)-1-methoxy-2-propanesulfonamide.<br>$^1$H NMR (600 MHz, DMSO-$d_6$) δ 13.06 (br s, 1 H) 8.92 (s, 1 H) 7.89 (dd, J = 8.21, 7.51 Hz, 1 H) 7.47 (dd, J = 7.28, 0.66 Hz, 1 H) 7.01 (d, J = 8.41 Hz, 1 H) 5.36 (quin, J = 8.89 Hz, 1 H) 4.89 (d, J = 4.90 Hz, 1 H) 3.95 (s, 3 H) 3.68 (br s, 1 H) 3.32 (br s, 11 H) 3.17 (s, 3 H) 2.99 (quin, J = 10.08 Hz, 2 H) 2.12 (td, J = 7.34, 3.00 Hz, 2 H) 1.61-1.79 (m, 2 H) 1.36 (d, J = 7.01 Hz, 3 H). LCMS ESI (pos.) m/z: 494.2 (M + H)$^+$. |
| 183.0 | (1R,2S)-1-(5-chloropyrimidin-2-yl)-1-methoxypropane-2-sulfonamide (Example 29.3), 6-methoxypicolinohydrazide (commercially available from Sigma Aldrich), and isothiocyanatocyclopentane (commercially available from Enamine). | 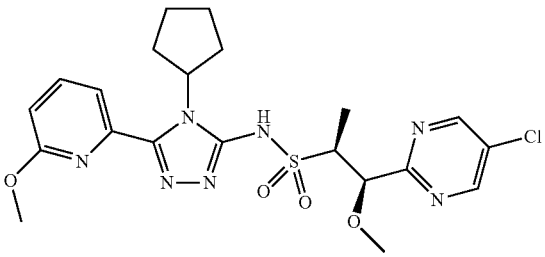 [SMILES: COc1cccc(-c2nnc(NS(=O)(=O)[C@@H](C)[C@H](OC)c3ncc(Cl)cn3)n2C2CCCC2)n1]<br>(1R,2S)-1-(5-chloro-2-pyrimidinyl)-N-(4-cyclopentyl-5-(6-methoxy-2-pyridinyl)-4H-1,2,4-triazol-3-yl)-1-methoxy-2-propanesulfonamide.<br>$^1$H NMR (600 MHz, DMSO-$d_6$) δ 13.14 (br s, 1 H) 8.94 (s, 2 H) 7.90 (dd, J = 8.33, 7.40 Hz, 1 H) |

TABLE 17-continued

| Example | Reagents | Structure, Name and Data |
|---|---|---|
| | | 7.51 (dd, J = 7.32, 0.70 Hz, 1 H) 7.02 (d, J = 8.33 Hz, 1 H) 5.37 (quin, J = 8.80 Hz, 1 H) 4.93 (d, J = 4.20 Hz, 1 H) 3.91 (s, 3 H) 3.56 (br dd, J = 6.38, 4.52 Hz, 1 H) 3.14 (s, 3 H) 2.25-2.37 (m, 2 H) 1.76-1.97 (m, 4 H) 1.47-1.62 (m, 2 H) 1.30 (d, J = 7.01 Hz, 3 H). LCMS ESI (pos.) m/z: 508.2 (M + H)+. |
| 184.0 | (1R,2S)-1-(5-chloropyrimidin-2-yl)-1-methoxypropane-2-sulfonamide (Example 29.3), 6-methoxypicolinohydrazide (commercially available from Sigma Aldrich), and isothiocyanatocyclohexane (commercially available from Enamine). | 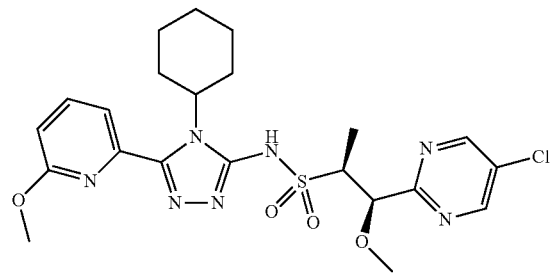 [SMILES: COc1cccc(-c2nnc(NS(=O)(=O)[C@@H](C)[C@H](OC)c3ncc(Cl)cn3)n2C2CCCCC2)n1]<br>(1R,2S)-1-(5-chloro-2-pyrimidinyl)-N-(4-cyclohexyl-5-(6-methoxy-2-pyridinyl)-4H-1,2,4-triazol-3-yl)-1-methoxy-2-propanesulfonamide.<br>$^1$H NMR (600 MHz, DMSO-d$_6$) δ 13.09 (br s, 1 H) 8.94 (s, 2 H) 7.90 (dd, J = 8.33, 7.40 Hz, 1 H) 7.50 (dd, J = 7.32, 0.70 Hz, 1 H) 7.03 (d, J = 8.41 Hz, 1 H) 4.93 (d, J = 4.36 Hz, 1 H) 4.76-4.86 (m, 1 H) 3.93 (s, 3 H) 3.56 (br dd, J = 6.31, 4.75 Hz, 1 H) 3.16 (s, 3 H) 2.34-2.48 (m, 2 H) 1.79 (br t, J = 11.44 Hz, 4 H) 1.61 (br d, J = 12.53 Hz, 1H) 1.32 (d, J = 7.01 Hz, 3 H) 1.18-1.29 (m, 2 H) 1.05-1.17 (m, 1 H). LCMS ESI (pos.) m/z: 522.2 (M + H)+. |
| 185.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (1R,2r,3S)-2-isothiocyanato-1,3-dimethoxycyclohexane (Example 1.3). | 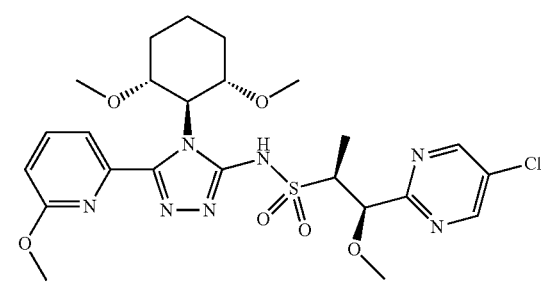 [SMILES: COc1cccc(-c2nnc(NS(=O)(=O)[C@@H](C)[C@H](OC)c3ncc(Cl)cn3)n2[C@@H]2[C@@H](OC)CCC[C@H]2OC)n1]<br>(1R,2S)-1-(5-chloro-2-pyrimidinyl)-N-(4-((1r,2R,6 S)-2,6-dimethoxycyclohexyl)-5-(6-methoxy-2-pyridinyl)-4H-1,2,4-triazol-3-yl)-1-methoxy-2-propanesulfonamide.<br>$^1$H NMR (600 MHz, DMSO-d$_6$) δ 13.09 (br s, 1 H) 8.97 (s, 2 H) 7.85 (t, J = 7.86 Hz, 1 H) 7.60 (dd, J = 7.43, 0.66 Hz, 1 H) 6.96 (br d, J = 8.10 Hz, 1 H) 5.56 (t, J = 10.24 Hz, 1 H) 5.01 (d, J = 3.97 Hz, 1 H) 4.33 (td, J = 10.69, 4.55 Hz, 1 H) 4.22-4.30 (m, 1 H) 3.92 (s, 3 H) 3.47-3.64 (m, 1 H) 3.23 (s, 3 H) 3.16 (s, 3 H) 3.15 (s, 3 H) 2.23 (br d, J = 12.30 Hz, 2 H) 1.73-1.81 (m, 1 H) 1.33 (d, J = 6.93 Hz, 3 H) 1.16-1.25 (m, 1 H) 0.98-1.08 (m, 2 H). LCMS ESI (pos.) m/z: 582.2 (M + H)+. |

The compounds in the following table were synthesized following the procedure in Example 31.0 using the known starting material as described.

TABLE 18

| Example | Reagents | Structure, Name and Data |
|---|---|---|
| 171.1 | 2-chloro-5-fluoro-pyrimidine (commercially available from Sigma Aldrich). | 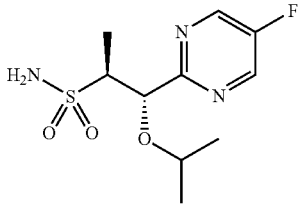 [SMILES: CC(C)O[C@@H](c1ncc(F)cn1)[C@H](C)S(N)(=O)=O]<br>(1S,2S)-1-(5-fluoropyrimidin-2-yl)-1-isopropoxypropane-2-sulfonamide.<br>$^1$H NMR (500 MHz, DMSO-$d_6$) δ 8.89-9.00 (m, 2 H) 6.38-6.52 (m, 2 H) 4.69-4.85 (m, 1 H) 3.44-3.59 (m, 2 H) 3.26-3.35 (m, 1 H) 1.09-1.19 (m, 3 H) 0.95-1.04 (m, 3 H) 0.86-0.94 (m, 3 H). LCMS-ESI (pos.) m/z: 278.2 (M + H)$^+$. |
| 172.1 | 2-chloro-5-methoxy-pyrimidine (commercially available from Sigma Aldrich). | 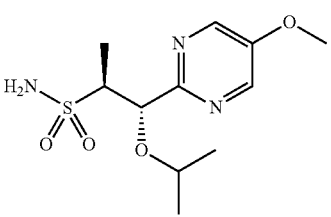 [SMILES: COc1cnc([C@H](OC(C)C)[C@H](C)S(N)(=O)=O)nc1]<br>(1S,2S)-1-isopropoxy-1-(5-methoxypyrimidin-2-yl)propane-2-sulfonamide.<br>LCMS ESI (pos.) m/z: 290.2 (M + H)$^+$. |

The compounds set forth in the following table were synthesized following the procedure in Example 28.0 using the known starting material as described.

TABLE 19

| Example | Reagents | Structure, Name and Data |
|---|---|---|
| 180.1 | (1s,3s)-3-methoxycyclobutan-1-amine hydrochloride (commercially available from Enamine) and Hunig's base (commercially available from Sigma-Aldrich). | <br>(1s,3s)-1-isothiocyanato-3-methoxycyclobutane.<br>$^1$H NMR (400 MHz, CDCl$_3$) δ 0.83-0.91 (m, 1 H) 1.20-1.33 (m, 2 H) 2.16-2.25 (m, 2 H) 2.74-2.83 (m, 2 H) 3.57-3.75 (m, 2 H). |
| 181.1 | (1r,3r)-3-methoxycyclobutan-1-amine hydrochloride (commercially available from Enamine) and Hunig's base (commercially available from Sigma-Aldrich) | 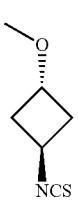<br>(1r,3r)-1-isothiocyanato-3-methoxycyclobutane.<br>$^1$H NMR (400 MHz, |

TABLE 19-continued

| Example | Reagents | Structure, Name and Data |
|---|---|---|
| | | CDCl$_3$) δ 0.83-0.92 (m, 1 H) 1.20-1.33 (m, 2 H) 2.36-2.52 (m, 4 H) 4.08-4.15 (m, 1 H) 4.20-4.28 (m, 1 H). |

Preparation of (R)-Cyclopropyl(3-methylisoxazol-4-yl)methanamine hydrochloride and (S)-Cyclopropyl (3-methylisoxazol-4-yl)methanamine hydrochloride, Example 227.1

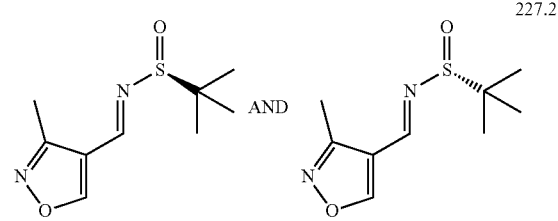

(R)-2-Methyl-N-((3-methylisoxazol-4-yl)methylene) propane-2-sulfinamide and (S)-2-methyl-N-((3-methylisoxazol-4-yl)methylene)propane-2-sulfinamide, Example 227.2

A 100 mL round bottom flask with a magnetic stir bar was charged with 3-methyl-1,2-oxazole-4-carbaldehyde (1.0 g, 9.00 mmol, commercially available from Enamine), 2-methyl-2-propanesulfinamide (1.20 g, 9.90 mmol, commercially available from AK Scientific), cupric(ii) sulfate (5.75 g, 36.0 mmol, commercially available from Sigma Aldrich), and 1,2-dichloroethane (36.0 ml). The reaction was stirred at 75° C. for 18 h. The solids were filtered away and the solution was concentrated in vacuo. The product thus obtained was purified by Biotage on a Biotage pre-packed silica gel column (50 g), 0-40% EtOAc in heptane to give 2-methyl-N-((3-methylisoxazol-4-yl)methylene)propane-2-sulfinamide as a white solid (1.60 g). $^1$H NMR (500 MHz, DMSO-d$_6$) δ 9.53 (s, 1H) 8.58 (s, 1H) 2.45 (s, 3H) 1.16 (s, 9H). LCMS-ESI (pos.) m/z: 215.2 (M+H)$^+$.

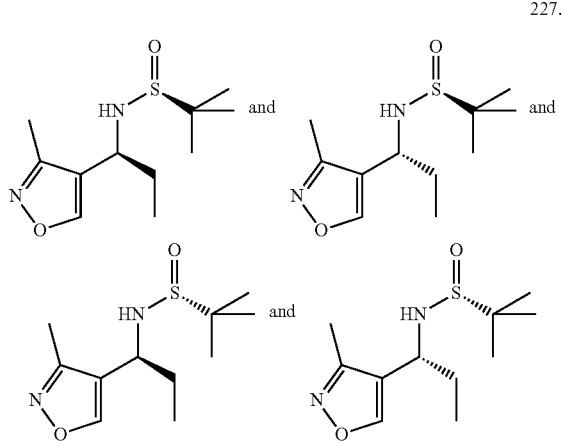

(S)-2-Methyl-N—((S)-1-(3-methylisoxazol-4-yl) propyl)propane-2-sulfinamide and (S)-2-methyl-N—((R)-1-(3-methylisoxazol-4-yl)propyl)propane-2-sulfinamide and (R)-2-methyl-N—((S)-1-(3-methylisoxazol-4-yl)propyl)propane-2-sulfinamide and (R)-2-methyl-N—((S)-1-(3-methylisoxazol-4-yl)propyl)propane-2-sulfinamide, Example 227.3

A 50 mL round bottom flask with a magnetic stir bar was charged with 2-methyl-N-((3-methylisoxazol-4-yl)methylene)propane-2-sulfinamide (500 mg, 2.33 mmol) and DCM (7.8 mL). The solution was stirred at −78° C. for 5 minutes followed by drop-wise addition of ethylmagnesium bromide solution (1.6 mL, 4.67 mmol, 3.0M in diethyl ether). The reaction was stirred for 1 h and then allowed to warm to RT over 1 h. The mixture was diluted with DCM and quenched by drop-wise addition of saturated ammonium chloride solution. The layers were separated and the aqueous layer was washed 2× with DCM. The combined organic layers were filtered through a phase-separation filter and concentrated in vacuo to give a yellow oil. The yellow oil thus obtained was purified by Biotage on a Biotage pre-packed silica gel column (25 g), 5-75% 3:1 EtOAc/EtOH in heptane to give 2-methyl-N-(1-(3-methylisoxazol-4-yl)propyl)propane-2-sulfinamide (438 mg) as a mixture of diastereomers. LCMS-ESI (pos.) m/z: 245.2 (M+H)$^+$.

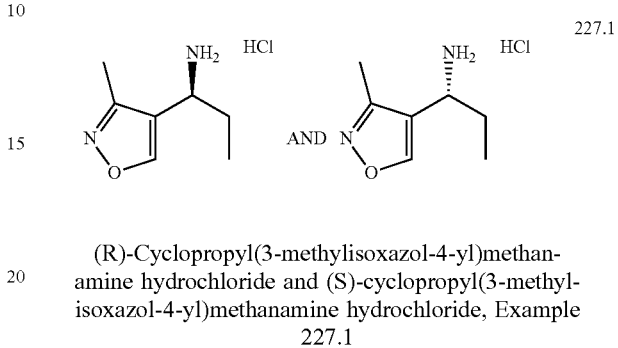

(R)-Cyclopropyl(3-methylisoxazol-4-yl)methanamine hydrochloride and (S)-cyclopropyl(3-methylisoxazol-4-yl)methanamine hydrochloride, Example 227.1

A 20 mL vial with a stir bar was charged with 2-methyl-N-(1-(3-methylisoxazol-4-yl)propyl)propane-2-sulfinamide (438 mg, 1.79 mmol) and then with hydrogen chloride (4.0 M in dioxane, 1.8 mL, 7.17 mmol) and DCM (7170 µL). The reaction was then stirred at room temperature for 18 h. The reaction mixture was then concentrated in vacuo to give a yellow oil. The oil was taken up in DCM and the pH was adjusted to 10 with sodium hydroxide. The layers were separated and the organic layer was washed with water twice. The layers were separated, and the organic layer was filtered through a phase separation column and concentrated in vacuo to give a yellow gum. The material thus obtained was dissolved in DCM and HCl (4.0 M in dioxane, 0.45 mL) was added. The solution was concentrated in vacuo to give cyclopropyl(3-methylisoxazol-4-yl)methanamine hydrochloride as a yellow solid (159 mg). $^1$H NMR (500 MHz, DMSO-d6) δ 8.97 (s, 1H) 8.54 (br s, 3H) 4.03-4.13 (m, 1H) 2.22-2.36 (m, 3H) 1.81-2.01 (m, 2H) 0.84 (t, J=7.40 Hz, 3H). LCMS-ESI (pos.) m/z: 141.2 (M+H)$^+$.

The compounds in the following table were synthesized following the procedure in Example 227.1 using known starting materials described.

TABLE 20

| Example | Reagents | Structure, Name, and Data |
|---|---|---|
| 228.1 | 3-methylisoxazole-4-carbaldehyde (commercially available from Enamine), 2-methyl-2-propanesulfinamide (commercially available from AK Scientific), cyclopropylmagnesium bromide (commercially available from Sigma Aldrich), and HCl (4.0 M in dioxaone, commercially available from Sigma Aldrich). | (R)-cyclopropyl(3-methylisoxazol-4-yl)methanamine hydrochloride and (S)-cyclopropyl(3-methylisoxazol-4-yl)methanamine hydrochloride. $^1$H NMR (500 MHz, DMSO-d$_6$) δ 9.01 (s, 1 H) 8.52 (br s, 3 H) 3.58-3.63 (m, 1 H) 2.30 (s, 3 H) 1.33-1.42 (m, 1 H) 0.62-0.69 (m, 1 H) 0.49-0.59 (m, 2 H) 0.31-0.41 (m, 1 H). LCMS-ESI (pos.) m/z: 136.2 (M − NH$_2$)$^+$. |

The compounds set forth in the following table were synthesized following the procedure in Example 28.0 using the known starting material as described.

TABLE 21

| Example | Reagents | Structure, Name and Data |
|---|---|---|
| 28.12 | isoxazol-4-ylmethanamine (commercially available from Enamine) | 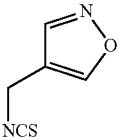<br>4-(isothiocyanatomethyl)isoxazole.<br>$^1$H NMR (500 MHz, CDCl$_3$) δ 8.50 (s, 1 H) 8.34 (s, 1 H) 4.65 (s, 2 H) 4.12 (q, J = 7.01 Hz, 1 H) 2.05 (s, 2 H) 1.26 (t, J = 7.14 Hz, 2 H). |
| 28.13 | (3-methylisoxazol-5-yl)methanamine (commercially available from Enamine) | 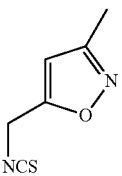<br>5-(isothiocyanatomethyl)-3-methylisoxazole.<br>$^1$H NMR (500 MHz, CDCl$_3$) δ 6.18 (s, 1 H) 4.72-4.81 (m, 2 H) 2.27-2.46 (m, 3 H). |
| 28.14 | (3-ethyl-5-methylisoxazol-4-yl)methanamine (commercially available from Enamine) | 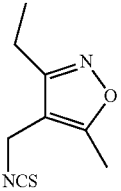<br>3-ethyl-4-(isothiocyanatomethyl)-5-methylisoxazole.<br>$^1$H NMR (500 MHz, CDCl$_3$) δ 4.43-4.59 (m, 2 H) 2.70 (q, J = 7.61 Hz, 2 H) 2.33-2.51 (m, 3 H) 1.33 (t, J = 7.53 Hz, 3 H) |
| 28.15 | (3-ethylisoxazol-5-yl)methanamine (commercially available from Enamine) | 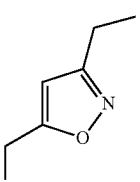<br>3-ethyl-5-(isothiocyanatomethyl)isoxazole.<br>$^1$H NMR (500 MHz, CDCl$_3$) δ 6.20 (s, 1 H) 4.78 (s, 2 H) 2.71 (q, J = 7.53 Hz, 2 H) 1.29 (t, J = 7.53 Hz, 3 H). |
| 28.16 | (3-methoxyisoxazol-5-yl)methanamine (commercially available from Enamine) | 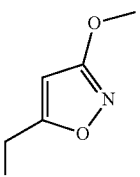<br>5-(isothiocyanatomethyl)-3-methoxyisoxazole.<br>$^1$H NMR (500 MHz, CDCl$_3$) δ 5.98 (s, 1 H) 4.69 (d, J = 0.78 Hz, 2 H) 3.98-4.00 (m, 3 H). |

TABLE 21-continued

| Example | Reagents | Structure, Name and Data |
|---|---|---|
| 28.17 | 1-(isoxazol-5-yl)ethan-1-amine (commercially available from Enamine). | 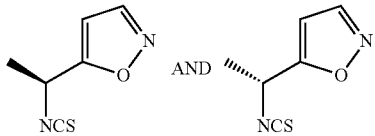<br>(R)-5-(1-isothiocyanatoethyl)isoxazole and (S)-5-(1-isothiocyanatoethyl)isoxazole.<br>$^1$H NMR (500 MHz, CDCl$_3$) δ 8.22-8.25 (m, 1 H) 6.29-6.32 (m, 1 H) 5.10 (q, J = 6.75 Hz, 1 H) 1.78 (d, J = 6.75 Hz, 4 H). |
| 28.18 | (3-(trifluoromethyl)isoxazol-5-yl)methanamine | 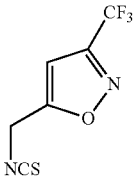<br>5-(isothiocyanatomethyl)-3-(trifluoromethyl)isoxazole.<br>$^1$H NMR (500 MHz, CDCl$_3$) δ 6.62 (s, 1 H) 4.90-4.92 (m, 2 H). |
| 28.19 | 1-(3,5-dimethylisoxazol-4-yl)propan-1-amine (commercially available from Enamine) | 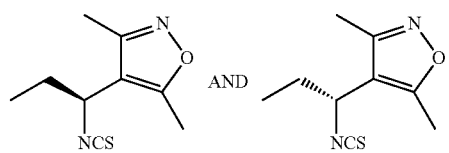<br>(R)-4-(1-isothiocyanatopropyl)-3,5-dimethylisoxazole and (S)-4-(1-isothiocyanatopropyl)-3,5-dimethylisoxazole.<br>$^1$H NMR (500 MHz, CDCl$_3$) δ 4.57 (dd, J = 7.91, 6.62 Hz, 1 H) 2.39 (s, 3H) 2.31 (s, 3 H) 1.99-2.08 (m, 1 H) 1.80-1.90 (m, 1 H) 1.02 (t, J = 7.40 Hz, 3 H). |
| 28.20 | 1-(1-methyl-1H-1,2,4-triazol-3-yl)ethan-1-amine (commercially available from Enamine) | 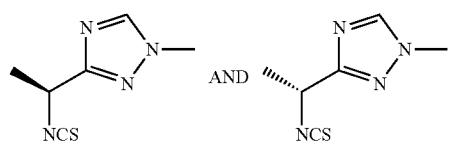<br>(R)-3-(1-isothiocyanatoethyl)-1-methyl-1H-1,2,4-triazole and (S)-3-(1-isothiocyanatoethyl)-1-methyl-1H-1,2,4-triazole.<br>$^1$H NMR (500 MHz, DMSO-d$_6$) δ 8.48 (s, 1 H) 5.26 (q, J = 6.83 Hz, 1 H) 3.86 (s, 3 H) 1.63 (d, J = 6.75 Hz, 3 H). |
| 28.21 | 1-(3-methyl-1,2,4-oxadiazol-5-yl)ethan-1-amine (commercially available from Enamine). | 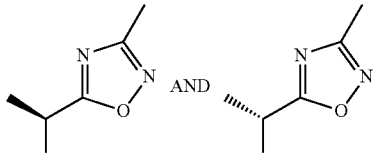<br>(R)-5-(1-isothiocyanatoethyl)-3-methyl-1,2,4-oxadiazole and (S)-5-(1-isothiocyanatoethyl)-3-methyl-1,2,4-oxadiazole.<br>$^1$H NMR (500 MHz, DMSO-d$_6$) δ 5.71 (q, J = 7.01 Hz, 1 H) 2.32-2.45 (m, 3 H) 1.72 (d, J = 7.01 Hz, 3 H). |

TABLE 21-continued

| Example | Reagents | Structure, Name and Data |
|---|---|---|
| 28.22 | 1-(5-methyloxazol-2-yl)ethan-1-amine (commercially available from Enamine) | 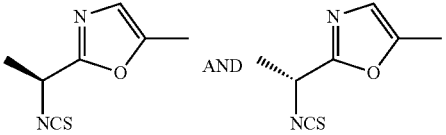<br>(S)-2-(1-isothiocyanatoethyl)-5-methyloxazole and (R)-2-(1-isothiocyanatoethyl)-5-methyloxazole.<br>$^1$H NMR (500 MHz, DMSO-$d_6$) δ 7.94 (s, 1 H) 5.53-5.63 (m, 1 H) 3.88 (s, 3 H) 1.68 (d, J = 6.75 Hz, 3 H). |
| 28.23 | 1-(5-methyl-1,2,4-oxadiazol-3-yl)ethan-1-amine (commercially available from Enamine). | 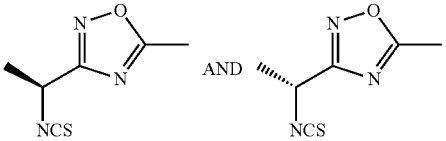<br>(S)-3-(1-isothiocyanatoethyl)-5-methyl-1,2,4-oxadiazole and (R)-3-(1-isothiocyanatoethyl)-5-methyl-1,2,4-oxadiazole.<br>$^1$H NMR (500 MHz, DMSO-$d_6$) δ 5.48 (q, J = 6.75 Hz, 1 H) 2.61-2.67 (m, 3 H) 1.65 (d, J = 6.75 Hz, 3 H). |
| 28.24 | 1-(1-methyl-1H-1,2,4-triazol-5-yl)ethan-1-amine (commercially available from Enamine) | 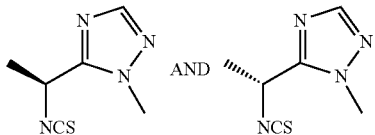<br>(S)-5-(1-isothiocyanatoethyl)-1-methyl-1H-1,2,4-triazole and (R)-5-(1-isothiocyanatoethyl)-1-methyl-1H-1,2,4-triazole.<br>$^1$H NMR (500 MHz, DMSO-$d_6$) δ 6.87 (s, 1 H) 5.41 (q, J = 6.75 Hz, 1 H) 2.31 (d, J = 1.30 Hz, 3H) 1.65 (d, J = 6.75 Hz, 3 H). |
| 28.25 | isoxazol-5-ylmethanamine hydrochloride (commercially available from J&W Pharmalab Inc.). | 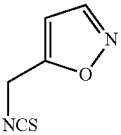<br>5-(isothiocyanatomethyl)isoxazole.<br>$^1$H NMR (500 MHz, CDCl$_3$) δ 8.27 (d, J = 1.56 Hz, 1 H) 6.36 (s, 1 H) 4.79-4.91 (m, 2 H). |
| 28.26 | cyclopropyl(3-methylisoxazol-4-yl)methanamine hydrochloride (Example 228.1). | 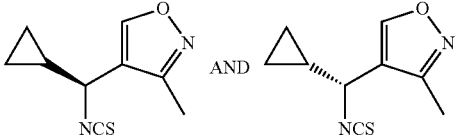<br>(R)-4-(cyclopropyl(isothiocyanato)methyl)-3-methylisoxazole and (S)-4-(cyclopropyl(isothiocyanato)methyl)-3-methylisoxazole.<br>$^1$H NMR (500 MHz, DMSO-$d_6$) δ 8.98 (s, 1 H) 4.59 (d, J = 8.82 Hz, 1 H) 2.30 (s, 3 H) 1.43-1.65 (m, 1 H) 0.35-0.78 (m, 4 H). |
| 28.27 | ethyl(3-methylisoxazol-4-yl)methanamine hydrochloride (Example 227.1). | 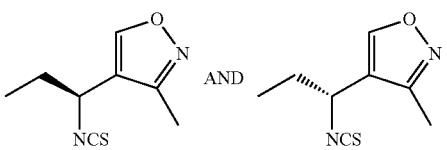<br>(R)-4-(1-isothiocyanatopropyl)-3-methylisoxazole and (S)-4-(1-isothiocyanatopropyl)-3-methylisoxazole.<br>$^1$H NMR (500 MHz, DMSO-$d_6$) δ 8.94 (s, 1 H) 5.08 |

TABLE 21-continued

| Example | Reagents | Structure, Name and Data |
|---------|----------|--------------------------|
|         |          | (dd, J = 7.91, 5.84 Hz, 1 H) 2.29 (s, 3 H) 1.89-2.02 (m, 2 H) 0.98 (t, J = 7.27 Hz, 3 H). |

The compounds in the following table were synthesized following the procedure in Example 1.0 using the known starting material as described.

TABLE 22

| Example | Reagents | Structure, Name, and Data |
|---------|----------|---------------------------|
| 186.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 4-(isothiocyanatomethyl)isoxazole (Example 28.12). | 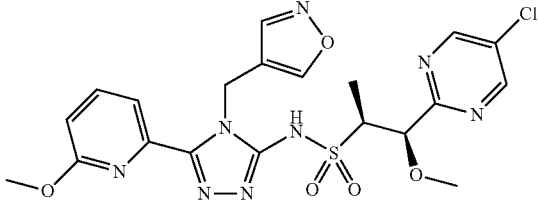 [SMILES: COc1cccc(-c2nnc(NS(=O)(=O)[C@@H](C)[C@H](OC)c3ncc(Cl)cn3)n2Cc2cnoc2)n1]<br>(1R,2S)-1-(5-chloropyrimidin-2-yl)-N-(4-(isoxazol-4-ylmethyl)-5-(6-methoxypyridin-2-yl)-4H-1,2,4-triazol-3-yl)-1-methoxypropane-2-sulfonamide.<br>$^1$H NMR (600 MHz, DMSO-d$_6$) δ 8.81 (s, 1 H), 8.59 (s, 1 H), 8.41 (s, 1 H), 7.72-7.76 (m, 1 H), 7.59-7.64 (m, 1 H), 6.75 (dd, J = 8.10, 0.62 Hz, 1 H), 5.11-5.46 (m, 2 H), 4.78 (d, J = 5.29 Hz, 1 H), 4.17-4.30 (m, 1 H), 3.79 (s, 3 H), 3.19 (s, 3 H), 2.54 (s, 5 H), 1.25 (d, J = 7.16 Hz, 3 H). LCMS-ESI (pos.) m/z: 521.1 (M + H)+. |
| 187.0 | (2S,3R)-3-(5-chloropyrimidin-2-yl)butane-2-sulfonamide (Example 27.4), 6-methoxypicolinohydrazide (commercially available from Sigma Aldrich), and 4-(isothiocyanatomethyl)isoxazole (Example 28.12). | 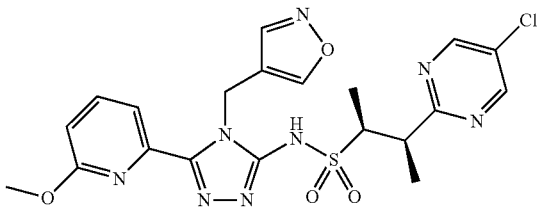 [SMILES: COc1cccc(-c2nnc(NS(=O)(=O)[C@@H](C)[C@H](C)c3ncc(Cl)cn3)n2Cc2cnoc2)n1]<br>(2S,3R)-3-(5-chloropyrimidin-2-yl)-N-(4-(isoxazol-4-ylmethyl)-5-(6-methoxypyridin-2-yl)-4H-1,2,4-triazol-3-yl)butane-2-sulfonamide.<br>$^1$H NMR (600 MHz, DMSO-d$_6$) δ 8.80 (s, 2 H), 8.62 (s, 1 H), 8.44 (s, 1 H), 7.69-7.80 (m, 1 H), 7.61 (dd, J = 7.47, 0.62 Hz, 1 H), 6.75 (dd, J = 8.10, 0.62 Hz, 1 H), 5.26-5.50 (m, 2 H), 4.23 (ddd, J = 7.01, 3.89, 1.56 Hz, 1 H), 3.71-3.83 (m, 4 H), 1.34 (d, J = 7.16 Hz, 3 H), 1.14 (d, J = 7.16 Hz, 3 H). LCMS-ESI (pos.) m/z: 505.1 (M + H)+. |
| 188.0 | (2S,3R)-3-(5-methylpyrazin-2-yl)butane-2-sulfonamide (Example 27.2), 6-methoxypicolinohydrazide (commercially available from Sigma Aldrich), and 4-(isothiocyanatomethyl)isoxazole (Example 28.12). | 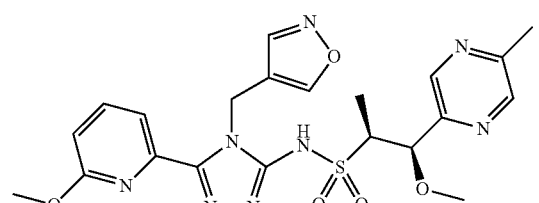<br>(1R,2S)-N-(4-(isoxazol-4-ylmethyl)-5-(6-methoxypyridin-2-yl)-4H-1,2,4-triazol-3-yl)-1-methoxy-1-(5-methylpyrazin-2-yl)propane-2-sulfonamide.<br>$^1$H NMR (600 MHz, DMSO-d$_6$) δ 8.60 (s, 1 H), 8.36-8.46 (m, 3 H), 7.75 (dd, J = 8.25, 7.63 Hz, 1 H), 7.63 (dd, J = 7.47, 0.62 Hz, 1 H), 6.76 (dd, J = 8.10, 0.62 Hz, 1 H), 5.17-5.44 (m, 2 H), 4.81 (d, J = 4.36 Hz, 1 H), 4.09 (ddd, J = 6.77, 4.44, 1.87 |

TABLE 22-continued

| Example | Reagents | Structure, Name, and Data |
|---|---|---|
| | | Hz, 1 H), 3.79 (s, 3 H), 3.23 (s, 3 H), 2.42 (s, 3 H), 1.16 (d, J = 7.16 Hz, 3 H). LCMS-ESI (pos.) m/z: 501.2 (M + H)+. |
| 189.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 4-(isothiocyanatomethyl)isoxazole (Example 28.13). | (1R,2S)-1-(5-chloropyrimidin-2-yl)-1-methoxy-N-(5-(6-methoxypyridin-2-yl)-4-((3-methylisoxazol-5-yl)methyl)-4H-1,2,4-triazol-3-yl)propane-2-sulfonamide.<br>$^1$H NMR (600 MHz, DMSO-d$_6$) δ 8.92 (s, 1 H), 7.89 (t, J = 7.94 Hz, 1 H), 7.68 (d, J = 7.16 Hz, 1 H), 6.99 (d, J = 8.10 Hz, 1 H), 6.19 (s, 1 H), 5.55-5.72 (m, 2 H), 4.79 (d, J = 4.67 Hz, 1 H), 3.69 (s, 3 H), 3.56 (dd, J = 7.01, 4.83 Hz, 1 H), 3.13 (s, 3 H), 2.13 (s, 3 H), 1.24 (d, J = 6.85 Hz, 3 H). LCMS-ESI (pos.) m/z: 535.0 (M + H)+. |
| 190.0 | (2S,3R)-3-(5-chloropyrimidin-2-yl)butane-2-sulfonamide (Example 27.4), 6-methoxypicolinohydrazide (commercially available from Sigma Aldrich), and 4-(isothiocyanatomethyl)isoxazole (Example 28.13). | (2S,3R)-3-(5-chloropyrimidin-2-yl)-N-(5-(6-methoxypyridin-2-yl)-4-((3-methylisoxazol-5-yl)methyl)-4H-1,2,4-triazol-3-yl)butane-2-sulfonamide.<br>$^1$H NMR (600 MHz, DMSO-d$_6$) δ 13.39 (br s, 1 H), 8.83 (s, 2 H), 7.89 (dd, J = 8.25, 7.63 Hz, 1 H), 7.68 (dd, J = 7.47, 0.62 Hz, 1 H), 6.99 (d, J = 8.41 Hz, 1 H), 6.17 (s, 1 H), 5.51-5.69 (m, 2 H), 3.61-3.73 (m, 5 H), 2.11 (s, 3 H), 1.27 (d, J = 7.16 Hz, 3 H), 1.19-1.24 (m, 3 H). LCMS-ESI (pos.) m/z: 519.0 (M + H)+. |
| 191.0 | (2S,3R)-3-(5-methylpyrazin-2-yl)butane-2-sulfonamide (Example 27.2), 6-methoxypicolinohydrazide (commercially available from Sigma Aldrich), and 4-(isothiocyanatomethyl)isoxazole (Example 28.13). | (1R,2S)-1-methoxy-N-(5-(6-methoxypyridin-2-yl)-4-((3-methylisoxazol-5-yl)methyl)-4H-1,2,4-triazol-3-yl)-1-(5-methylpyrazin-2-yl)propane-2-sulfonamide.<br>$^1$H NMR (600 MHz, DMSO-d$_6$) δ 13.45 (br s, 1 H), 8.42-8.53 (m, 2H), 7.90 (dd, J = 8.41, 7.47 Hz, 1 H), 7.69 (dd, J = 7.47, 0.62 Hz, 1 H), 6.99 (dd, J = 8.41, 0.62 Hz, 1 H), 6.19 (s, 1 H), 5.65 (s, 2 H), 4.84 (d, J = 3.74 Hz, 1 H), 4.09 (q, J = 5.29 Hz, 1 H), 3.69 (s, 3 H), 3.39-3.45 (m, 1 H), 3.14-3.19 (m, 6 H), 2.46 (s, 3 H), 2.11 (s, 3 H), 1.15 (d, J = 6.85 Hz, 3 H). LCMS-ESI (pos.) m/z: 515.2 (M + H)+. |

TABLE 22-continued

| Example | Reagents | Structure, Name, and Data |
|---|---|---|
| 192.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (3-ethyl-5-methylisoxazol-4-yl)methanamine (Example 28.14). | 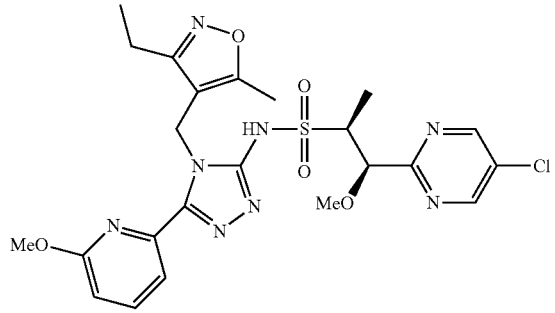 [SMILES: CCc1noc(C)c1Cn1c(NS(=O)(=O)[C@@H](C)[C@H](OC)c2ncc(Cl)cn2)nnc1-c1cccc(OC)n1]<br>(1R,2S)-1-(5-chloro-2-pyrimidinyl)-N-(4-((3-ethyl-5-methyl-1,2-oxazol-4-yl)methyl)-5-(6-methoxy-2-pyridinyl)-4H-1,2,4-triazol-3-yl)-1-methoxy-2-propanesulfonamide.<br>$^1$H NMR (600 MHz, DMSO-d$_6$) δ 13.30 (br s, 1 H), 8.92 (s, 2 H), 7.94 (t, J = 7.78 Hz, 1 H), 7.62 (d, J = 7.34 Hz, 1 H), 7.06 (d, J = 8.41 Hz, 1 H), 5.35 (d, J = 15.57 Hz, 1 H), 5.25 (d, J = 15.88 Hz, 1 H), 4.71 (d, J = 4.98 Hz, 1 H), 3.83 (s, 3 H), 3.46-3.61 (m, 1 H), 3.17 (d, J = 4.67 Hz, 1 H), 3.04-3.13 (m, 3 H), 2.36 (q, J = 7.47 Hz, 2 H), 2.18 (s, 3 H), 1.19 (d, J = 7.16 Hz, 3 H), 0.96 (t, J = 7.47 Hz, 3 H). LCMS-ESI (pos.) m/z: 563.0 (M + H)$^+$. |
| 193.0 | (2S,3R)-3-(5-chloropyrimidin-2-yl)butane-2-sulfonamide (Example 27.4), 6-methoxypicolinohydrazide (commercially available from Sigma Aldrich), and (3-ethyl-5-methylisoxazol-4-yl)methanamine (Example 28.14). | 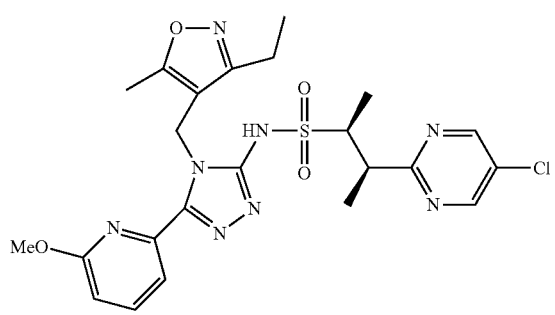 [SMILES: CCc1noc(C)c1Cn1c(NS(=O)(=O)[C@@H](C)[C@H](C)c2ncc(Cl)cn2)nnc1-c1cccc(OC)n1]<br>(2S,3R)-3-(5-chloro-2-pyrimidinyl)-N-(4-((3-ethyl-5-methyl-1,2-oxazol-4-yl)methyl)-5-(6-methoxy-2-pyridinyl)-4H-1,2,4-triazol-3-yl)-2-butanesulfonamide.<br>$^1$H NMR (600 MHz, DMSO-d$_6$) δ 13.29 (s, 1 H), 8.82 (s, 2 H), 7.94 (t, J = 7.84 Hz, 1 H), 7.62 (d, J = 7.34 Hz, 1 H), 7.05 (d, J = 8.41 Hz, 1 H), 5.22-5.31 (m, 2 H), 3.82 (s, 3 H), 3.65-3.72 (m, 1 H), 3.48-3.54 (m, 1 H), 3.17 (d, J = 3.74 Hz, 1 H), 2.34 (q, J = 7.47 Hz, 2 H), 2.16 (s, 3 H), 1.25 (d, J = 7.16 Hz, 3 H), 1.16 (d, J = 7.16 Hz, 3 H), 0.94 (t, J = 7.47 Hz, 3 H). LCMS-ESI (pos.) m/z: 547.0 (M + H)$^+$. |
| 194.0 | (2S,3R)-3-(5-methylpyrazin-2-yl)butane-2-sulfonamide (Example 27.2), 6-methoxypicolinohydrazide (commercially available from Sigma Aldrich), and (3-ethyl-5-methylisoxazol-4-yl)methanamine (Example 28.14). | 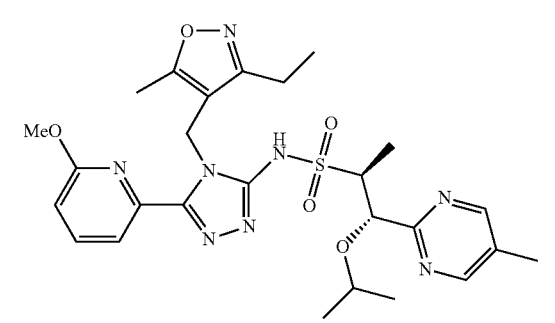 [SMILES: CCc1noc(C)c1Cn1c(NS(=O)(=O)[C@@H](C)[C@@H](OC(C)C)c2ncc(C)cn2)nnc1-c1cccc(OC)n1]<br>(1S,2S)-N-(4-((3-ethyl-5-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide. |

| Example | Reagents | Structure, Name, and Data |
|---|---|---|
| | | $^1$H NMR (600 MHz, DMSO-d$_6$) δ 13.29 (s, 1 H), 8.66 (s, 2 H), 7.94 (dd, J = 8.41, 7.47 Hz, 1 H), 7.60 (d, J = 7.49 Hz, 1 H), 7.06 (d, J = 8.41 Hz, 1 H), 5.40 (d, J = 15.57 Hz, 1 H), 5.29 (d, J = 15.57 Hz, 1 H), 4.78 (d, J = 6.85 Hz, 1 H), 3.83 (s, 3 H), 3.57 (quin, J = 7.08 Hz, 1 H), 3.17 (d, J = 5.29 Hz, 1 H), 2.35 (q, J = 7.58 Hz, 3 H), 2.26 (s, 3 H), 2.20 (s, 3 H), 0.92-1.02 (m, 11 H), 0.75 (d, J = 6.23 Hz, 4 H). LCMS-ESI (pos.) m/z: 571.2 (M + H)$^+$. |
| 195.0 | (2S,3R)-3-(5-methylpyrazin-2-yl)butane-2-sulfonamide (Example 27.2), 6-methoxypicolinohydrazide (commercially available from Sigma Aldrich), and (3-ethyl-5-methylisoxazol-4-yl)methanamine (Example 28.14). | 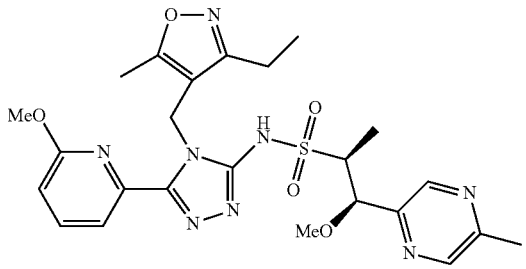 [SMILES: CCc1noc(C)c1Cn1c(NS(=O)(=O)[C@@H](C)[C@H](OC)c2cnc(C)cn2)nnc1-c1cccc(OC)n1]<br>(1R,2S)-N-(4-((3-ethyl-5-methylisoxazol-4-yl)methyl)-5-(6-methoxypyridin-2-yl)-4H-1,2,4-triazol-3-yl)-1-methoxy-1-(5-methylpyrazin-2-yl)propane-2-sulfonamide.<br>$^1$H NMR (600 MHz, DMSO-d$_6$) δ 13.33 (s, 1 H), 8.48 (s, 1 H), 8.45 (s, 1 H), 7.94 (dd, J = 8.41, 7.47 Hz, 1 H), 7.63 (d, J = 7.59 Hz, 1 H), 7.06 (d, J = 8.41 Hz, 1 H), 5.28-5.36 (m, 2 H), 4.78 (d, J = 3.74 Hz, 1 H), 3.83 (s, 3 H), 3.14-3.18 (m, 5 H), 2.46-2.49 (m, 3 H), 2.36 (q, J = 7.47 Hz, 2 H), 2.18 (s, 3 H), 1.11 (d, J = 6.85 Hz, 3 H), 0.96 (t, J = 7.47 Hz, 3 H). LCMS-ESI (pos.) m/z: 543.2 (M + H)$^+$. |
| 196.0 | (2S,3R)-3-(5-chloropyrimidin-2-yl)butane-2-sulfonamide (Example 27.4), 6-methoxypicolinohydrazide (commercially available from Sigma Aldrich), and 3-ethyl-5-(isothiocyanatomethyl)isoxazole (Example 28.15). | 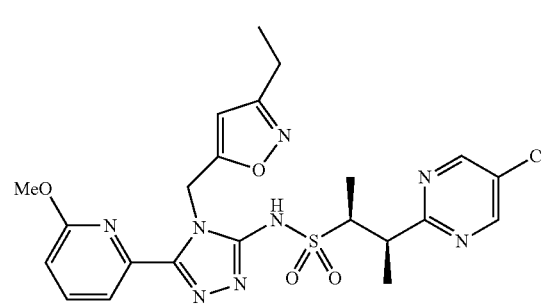<br>(2S,3R)-3-(5-chloropyrimidin-2-yl)-N-(4-((3-ethylisoxazol-5-yl)methyl)-5-(6-methoxypyridin-2-yl)-4H-1,2,4-triazol-3-yl)butane-2-sulfonamide.<br>$^1$H NMR (600 MHz, DMSO-d$_6$) δ 13.38 (s, 1 H), 8.83 (s, 2 H), 7.90 (dd, J = 8.25, 7.63 Hz, 1 H), 7.65-7.69 (m, 1 H), 6.99 (d, J = 8.41 Hz, 1 H), 6.24 (s, 1 H), 5.50-5.67 (m, 2 H), 3.54-3.73 (m, 6 H), 2.51-2.54 (m, 1 H), 2.47-2.49 (m, 1 H), 1.26 (d, J = 7.16 Hz, 3 H), 1.19 (d, J = 6.85 Hz, 3 H), 1.05 (t, J = 7.63 Hz, 3 H). LCMS-ESI (pos.) m/z: 533.1 (M + H)$^+$. |

TABLE 22-continued

| Example | Reagents | Structure, Name, and Data |
|---|---|---|
| 197.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 5-(isothiocyanatomethyl)-3-methoxyisoxazole (Example 28.16). | 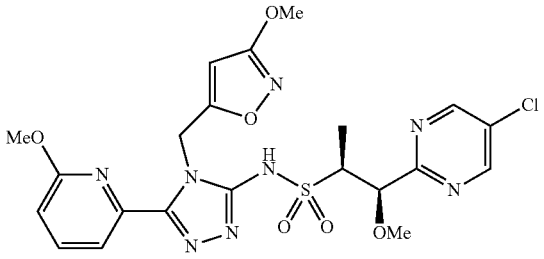 [SMILES: COc1cc(Cn2c(NS(=O)(=O)[C@@H](C)[C@H](OC)c3ncc(Cl)cn3)nnc2-c2cccc(OC)n2)on1]<br>(1R,2S)-1-(5-chloro-2-pyrimidinyl)-1-methoxy-N-(4-((3-methoxy-1,2-oxazol-5-yl)methyl)-5-(6-methoxy-2-pyridinyl)-4H-1,2,4-triazol-3-yl)-2-propanesulfonamide.<br>$^1$H NMR (600 MHz, DMSO-d$_6$) δ 13.41 (s, 1 H), 8.92 (s, 1 H), 7.89 (t, J = 7.94 Hz, 1 H), 7.68 (d, J = 7.46 Hz, 1 H), 6.99 (d, J = 8.10 Hz, 1 H), 6.13 (s, 1 H), 5.61 (d, J = 16.82 Hz, 1 H), 5.54 (d, J = 16.82 Hz, 1 H), 4.81 (d, J = 4.67 Hz, 1 H), 3.81 (s, 3 H), 3.73 (s, 3 H), 3.49-3.60 (m, 1 H), 3.17 (s, 1 H), 3.13 (s, 3 H), 1.25 (d, J = 6.85 Hz, 3 H). LCMS-ESI (pos.) m/z: 551.0 (M + H)$^+$. |
| 198.0 | (2S,3R)-3-(5-chloropyrimidin-2-yl)butane-2-sulfonamide (Example 27.4), 6-methoxypicolinohydrazide (commercially available from Sigma Aldrich), and 5-(isothiocyanatomethyl)-3-methoxyisoxazole (Example 28.16). | 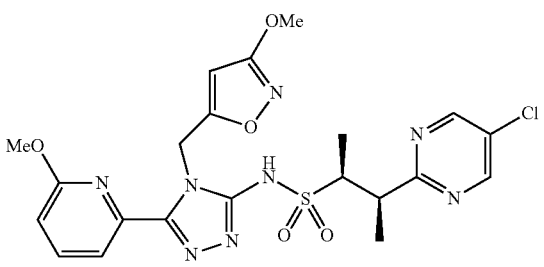 [SMILES: COc1cc(Cn2c(NS(=O)(=O)[C@@H](C)[C@H](C)c3ncc(Cl)cn3)nnc2-c2cccc(OC)n2)on1]<br>(2S,3R)-3-(5-chloro-2-pyrimidinyl)-N-(4-((3-methoxy-1,2-oxazol-5-yl)methyl)-5-(6-methoxy-2-pyridinyl)-4H-1,2,4-triazol-3-yl)-2-butanesulfonamide.<br>$^1$H NMR (600 MHz, DMSO-d6) δ 1.19-1.30 (m, 6 H) 3.17 (s, 1 H) 3.58-3.67 (m, 1 H) 3.68-3.74 (m, 4 H) 3.79 (s, 3 H) 5.50 (d, J = 17.20 Hz, 1 H) 5.58 (d, J = 17.21 Hz, 1 H) 6.11 (s, 1 H) 6.99 (d, J = 8.33 Hz, 1 H) 7.67 (d, J = 7.40 Hz, 1 H) 7.90 (t, J = 7.90 Hz, 1 H) 8.83 (s, 1 H) 13.37 (s, 1 H). LCMS-ESI (pos.) m/z: 535.2 (M + H)$^+$. |
| 199.0 | (2S,3R)-3-(5-methylpyrazin-2-yl)butane-2-sulfonamide (Example 27.2), 6-methoxypicolinohydrazide (commercially available from Sigma Aldrich), and 5-(isothiocyanatomethyl)-3-methoxyisoxazole (Example 28.16). | 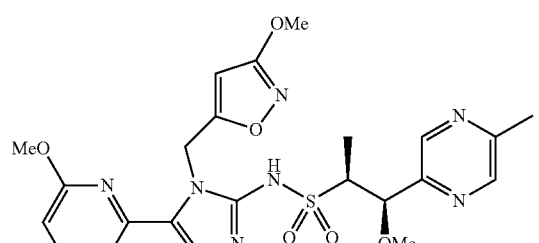<br>(1R,2S)-1-methoxy-N-(4-((3-methoxy-1,2-oxazol-5-yl)methyl)-5-(6-methoxy-2-pyridinyl)-4H-1,2,4-triazol-3-yl)-1-(5-methyl-2-pyrazinyl)-2-propanesulfonamide.<br>$^1$H NMR (600 MHz, DMSO-d$_6$) δ 13.43 (s, 1 H), 8.49 (s, 1 H), 8.45 (s, 1 H), 7.90 (dd, J = 8.25, 7.63 Hz, 1 H), 7.68 (d, J = 7.54 Hz, 1 H), 7.00 (d, J = 8.10 Hz, 1 H), 6.14 (s, 1 H), 5.55-5.63 (m, 2 H), 4.85 (d, J = 3.43 Hz, 1 H), 4.09 (br d, J = 4.67 Hz, 1 H), 3.78-3.84 (m, 3 H), 3.72 (s, 3 H), 3.38-3.45 (m, 1 H), 3.17 (s, 3 H), 2.46 (s, 3 H), 1.16 (d, J = 7.16 Hz, 3 H). LCMS-ESI (pos.) m/z: 531.2 (M + H)$^+$. |

TABLE 22-continued

| Example | Reagents | Structure, Name, and Data |
|---|---|---|
| 200.0 | (2S,3R)-3-(5-methylpyrazin-2-yl)butane-2-sulfonamide (Example 27.2), 6-methoxypicolinohydrazide (commercially available from Sigma Aldrich), and (R)-1-(isoxazol-5-yl)ethan-1-amine and (S)-1-(isoxazol-5-yl)ethan-1-amine (Example 28.17). | 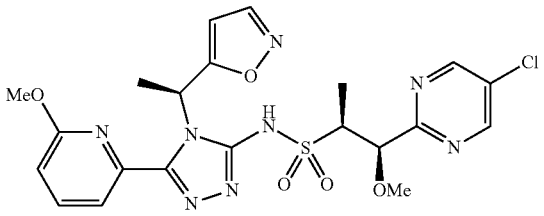 [SMILES: COc1cccc(-c2nnc(NS(=O)(=O)[C@@H](C)[C@H](OC)c3ncc(Cl)cn3)n2[C@@H](C)c2ccno2)n1]<br>and<br>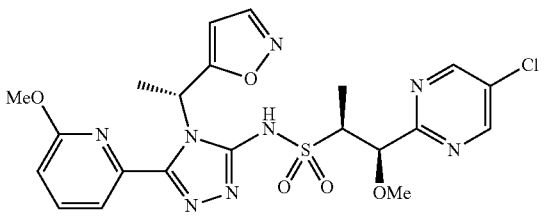 [SMILES: COc1cccc(-c2nnc(NS(=O)(=O)[C@@H](C)[C@H](OC)c3ncc(Cl)cn3)n2[C@H](C)c2ccno2)n1]<br>(1R,2S)-1-(5-chloro-2-pyrimidinyl)-1-methoxy-N-(5-(6-methoxy-2-pyridinyl)-4-((1R)-1-(1,2-oxazol-5-yl)ethyl)-4H-1,2,4-triazol-3-yl)-2-propanesulfonamide and (1R,2S)-1-(5-chloro-2-pyrimidinyl)-1-methoxy-N-(5-(6-methoxy-2-pyridinyl)-4-((1S)-1-(1,2-oxazol-5-yl)ethyl)-4H-1,2,4-triazol-3-yl)-2-propanesulfonamide.<br>LCMS-ESI (pos.) m/z: 535.1 (M + H)$^+$. |
| 201.0 | (2S,3R)-3-(5-chloropyrimidin-2-yl)butane-2-sulfonamide (Example 27.4), 6-methoxypicolinohydrazide (commercially available from Sigma Aldrich), and (R)-1-(isoxazol-5-yl)ethan-1-amine and (S)-1-(isoxazol-5-yl)ethan-1-amine (Example 28.17). | 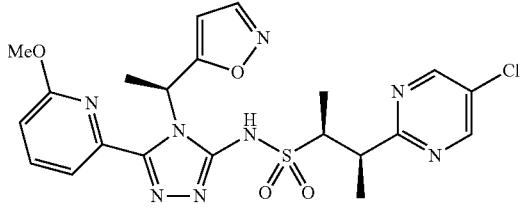 [SMILES: COc1cccc(-c2nnc(NS(=O)(=O)[C@@H](C)[C@H](C)c3ncc(Cl)cn3)n2[C@@H](C)c2ccno2)n1]<br>and<br>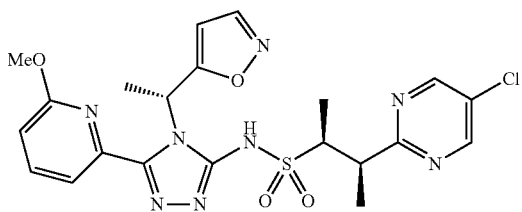 [SMILES: COc1cccc(-c2nnc(NS(=O)(=O)[C@@H](C)[C@H](C)c3ncc(Cl)cn3)n2[C@H](C)c2ccno2)n1]<br>(2S,3R)-3-(5-chloro-2-pyrimidinyl)-N-(5-(6-methoxy-2-pyridinyl)-4-((1R)-1-(1,2-oxazol-5-yl)ethyl)-4H-1,2,4-triazol-3-yl)-2-butanesulfonamide and (2S,3R)-3-(5-chloro-2-pyrimidinyl)-N-(5-(6-methoxy-2-pyridinyl)-4-((1S)-1-(1,2-oxazol-5-yl)ethyl)-4H-1,2,4-triazol-3-yl)-2-butanesulfonamide.<br>LCMS-ESI (pos.) m/z: 519.1 (M + H)$^+$. |

TABLE 22-continued

| Example | Reagents | Structure, Name, and Data |
|---|---|---|
| 202.0 | (2S,3R)-3-(5-methylpyrazin-2-yl)butane-2-sulfonamide (Example 27.2), 6-methoxypicolinohydrazide (commercially available from Sigma Aldrich), and (R)-1-(isoxazol-5-yl)ethan-1-amine and (S)-1-(isoxazol-5-yl)ethan-1-amine (Example 28.17). | 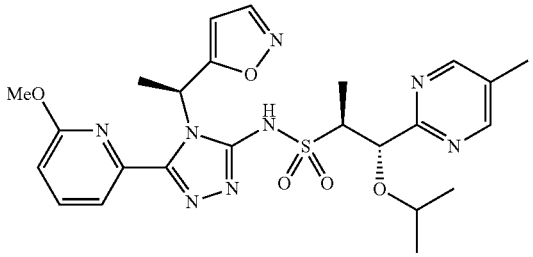 [SMILES: COc1cccc(-c2nnc(NS(=O)(=O)[C@@H](C)[C@@H](OC(C)C)c3ncc(C)cn3)n2[C@@H](C)c2ccno2)n1]<br>and<br>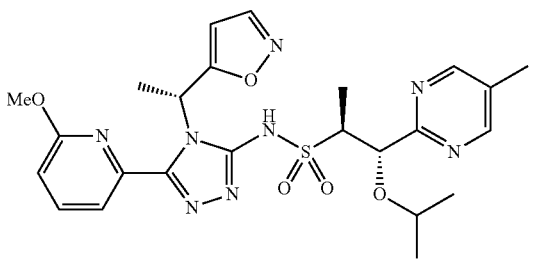 [SMILES: COc1cccc(-c2nnc(NS(=O)(=O)[C@@H](C)[C@@H](OC(C)C)c3ncc(C)cn3)n2[C@H](C)c2ccno2)n1]<br>2-((1S,2S)-2-(((5-(6-methoxy-2-pyridinyl)-4-((1R)-1-(1,2-oxazol-5-yl)ethyl)-4H-1,2,4-triazol-3-yl)methyl)sulfonyl)-1-(2-propanyloxy)propyl)-5-methylpyrimidine and 2-((1S,2S)-2-(((5-(6-methoxy-2-pyridinyl)-4-((1S)-1-(1,2-oxazol-5-yl)ethyl)-4H-1,2,4-triazol-3-yl)methyl)sulfonyl)-1-(2-propanyloxy)propyl)-5-methyl)pyrimidine. LCMS-ESI (pos.) m/z: 542.2 (M + H)+. |
| 203.0 | (2S,3R)-3-(5-methylpyrazin-2-yl)butane-2-sulfonamide (Example 27.2), 6-methoxypicolinohydrazide (commercially available from Sigma Aldrich), and 5-(isothiocyanatomethyl)-3-(trifluoromethyl)isoxazole (Example 28.18). | 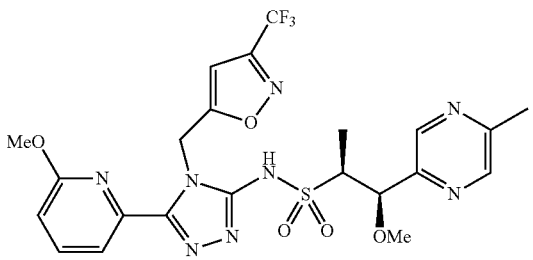 [SMILES: COc1cccc(-c2nnc(NS(=O)(=O)[C@@H](C)[C@H](OC)c3cnc(C)cn3)n2Cc2cc(C(F)(F)F)no2)n1]<br>(1R,2S)-1-methoxy-N-(5-(6-methoxy-2-pyridinyl)-4-((3-(trifluoromethyl)-1,2-oxazol-5-yl)methyl)-4H-1,2,4-triazol-3-yl)-1-(5-methyl-2-pyrazinyl)-2-propanesulfonamide.<br>¹H NMR (600 MHz, DMSO-d₆) δ 13.46 (s, 1 H), 8.49 (s, 1 H), 8.40 (d, J = 1.25 Hz, 1 H), 7.91 (dd, J = 8.41, 7.47 Hz, 1 H), 7.70 (d, J = 7.46 Hz, 1 H), 7.21 (s, 1 H), 7.01 (d, J = 8.10 Hz, 1 H), 5.81-5.89 (m, 1 H), 5.72-5.79 (m, 1 H), 4.85 (d, J = 3.11 Hz, 1 H), 3.62 (s, 3 H), 3.34-3.38 (m, 1 H), 3.13 (s, 3 H), 2.46-2.48 (m, 3 H), 1.07 (d, J = 7.16 Hz, 3 H). LCMS-ESI (pos.) m/z: 569.2 (M + H)+. |

TABLE 22-continued

| Example | Reagents | Structure, Name, and Data |
|---|---|---|
| 204.0 | (2S,3R)-3-(5-chloropyrimidin-2-yl)butane-2-sulfonamide (Example 27.4), 6-methoxypicolinohydrazide (commercially available from Sigma Aldrich), and 5-(isothiocyanatomethyl)-3-(trifluoromethyl)isoxazole (Example 28.18). | 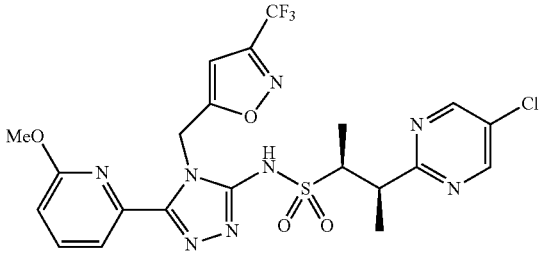<br>(2S,3R)-3-(5-chloro-2-pyrimidinyl)-N-(5-(6-methoxy-2-pyridinyl)-4-((3-(trifluoromethyl)-1,2-oxazol-5-yl)methyl)-4H-1,2,4-triazol-3-yl)-2-butanesulfonamide.<br>$^1$H NMR (600 MHz, DMSO-d$_6$) δ 13.40 (s, 1 H), 8.83 (s, 2 H), 7.91 (dd, J = 8.10, 7.47 Hz, 1 H), 7.69 (d, J = 7.41 Hz, 1 H), 7.21 (s, 1 H), 7.00 (d, J = 8.41 Hz, 1 H), 5.70-5.81 (m, 2 H), 3.56-3.68 (m, 5 H), 1.24 (d, J = 7.16 Hz, 3 H), 1.17 (d, J = 7.16 Hz, 3 H). LCMS-ESI (pos.) m/z: 573.1 (M + H)$^+$. |
| 205.0 | (1R,2S)-1-(5-chloropyrimidin-2-yl)-1-methoxypropane-2-sulfonamide (Example 29.3), 6-methoxypicolinohydrazide (commercially available from Sigma Aldrich), and 5-(isothiocyanatomethyl)-3-(trifluoromethyl)isoxazole (Example 28.18). | 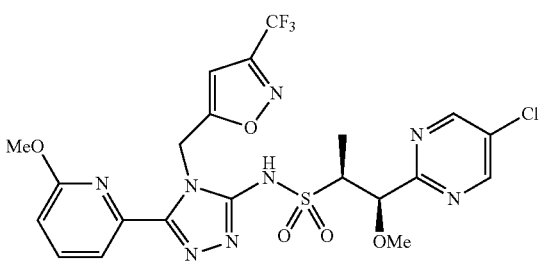 [SMILES: COc1cccc(-c2nnc(NS(=O)(=O)[C@@H](C)[C@H](OC)c3ncc(Cl)cn3)n2Cc2cc(C(F)(F)F)no2)n1]<br>(1R,2S)-1-(5-chloro-2-pyrimidinyl)-1-methoxy-N-(5-(6-methoxy-2-pyridinyl)-4-((3-(trifluoromethyl)-1,2-oxazol-5-yl)methyl)-4H-1,2,4-triazol-3-yl)-2-propanesulfonamide.<br>$^1$H NMR (600 MHz, DMSO-d$_6$) δ 13.44 (s, 1 H), 8.92 (s, 2 H), 7.91 (dd, J = 8.41, 7.47 Hz, 1 H), 7.69 (d, J = 7.49 Hz, 1 H), 7.21 (s, 1 H), 7.00 (d, J = 8.41 Hz, 1 H), 5.74-5.82 (m, 2 H), 4.78 (d, J = 4.67 Hz, 1 H), 3.62 (s, 3 H), 3.47-3.55 (m, 1 H), 3.11 (s, 3 H), 1.19 (d, J = 6.85 Hz, 3 H). LCMS-ESI (pos.) m/z: 589.1 (M + H)$^+$. |
| 206.0 | (2S,3R)-3-(5-methylpyrazin-2-yl)butane-2-sulfonamide (Example 27.2), 6-methoxypicolinohydrazide (commercially available from Sigma Aldrich), and 5-(isothiocyanatomethyl)isoxazole (Example 28.25). | 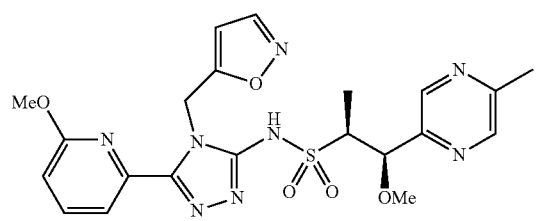 [SMILES: COc1cccc(-c2nnc(NS(=O)(=O)[C@@H](C)[C@H](OC)c3cnc(C)cn3)n2Cc2ccno2)n1]<br>(1R,2S)-1-methoxy-N-(5-(6-methoxy-2-pyridinyl)-4-(1,2-oxazol-5-ylmethyl)-4H-1,2,4-triazol-3-yl)-1-(5-methyl-2-pyrazinyl)-2-propanesulfonamide.<br>$^1$H NMR (500 MHz, DMSO-d$_6$) δ 13.46 (br s, 1 H), 8.50 (s, 2 H), 8.45 (s, 1 H), 7.89 (t, J = 7.79 Hz, 1 H), 7.68 (d, J = 7.53 Hz, 1 H), 6.99 (br d, J = 8.30 Hz, 1 H), 6.35 (br s, 1 H), 5.70 (s, 2 H), 4.85 (d, J = 3.11 Hz, 1 H), 3.65 (s, 3 H), 3.41 (br s, 1 H), 3.15 (s, 3 H), 2.45-2.48 (m, 3 H), 1.14 (d, J = 7.01 Hz, 3 H). LCMS-ESI (pos.) m/z: 501.2 (M + H)$^+$. |

TABLE 22-continued

| Example | Reagents | Structure, Name, and Data |
|---|---|---|
| 207.0 | (2S,3R)-3-(5-chloropyrimidin-2-yl)butane-2-sulfonamide (Example 27.4), 6-methoxypicolinohydrazide (commercially available from Sigma Aldrich), and 5-(isothiocyanatomethyl)isoxazole (Example 28.25). | (2S,3R)-3-(5-chloro-2-pyrimidinyl)-N-(5-(6-methoxy-2-pyridinyl)-4-(1,2-oxazol-5-ylmethyl)-4H-1,2,4-triazol-3-yl)-2-butanesulfonamide.<br>$^1$H NMR (500 Hz, DMSO-d$_6$) δ 13.40 (s, 1 H), 8.84 (s, 2 H), 8.48 (d, J = 1.82 Hz, 1 H), 7.90 (dd, J = 8.30, 7.53 Hz, 1 H), 7.68 (d, J = 7.27 Hz, 1 H), 6.99 (d, J = 8.30 Hz, 1 H), 6.34 (s, 1 H), 5.70 (d, J = 16.87 Hz, 1 H), 5.61 (d, J = 16.87 Hz, 1 H), 3.59-3.71 (m, 5 H), 1.16-1.30 (m, 6 H).<br>LCMS-ESI (pos.) m/z: 505.2 (M + H)$^+$. |
| 208.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). | AND<br>(1R,2S)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide and (1R,2S)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide.<br>LCMS-ESI (pos.) m/z: 557.2 (M + H)$^+$. |
| 209.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). | AND |

TABLE 22-continued

| Example | Reagents | Structure, Name, and Data |
|---|---|---|
| | | 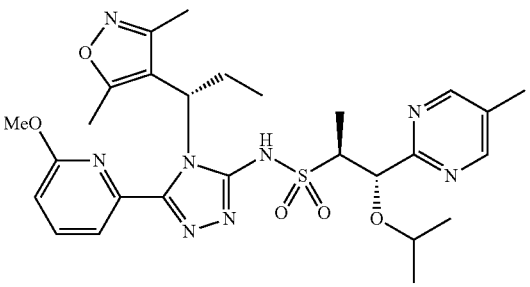 [SMILES: CC[C@@H](c1c(C)noc1C)n1c(NS(=O)(=O)[C@@H](C)[C@@H](OC(C)C)c2ncc(C)cn2)nnc1-c1cccc(OC)n1](1S,2S)-N-(4-((1R)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide and (1S,2S)-N-(4-((1S)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide. LCMS-ESI (pos.) m/z: 585.3 (M + H)+. |
| 210.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). | 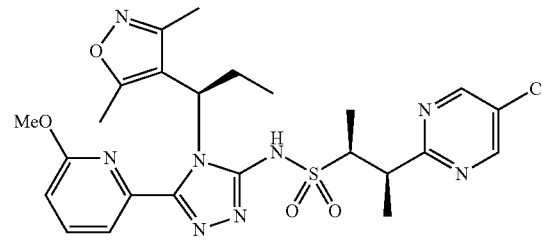AND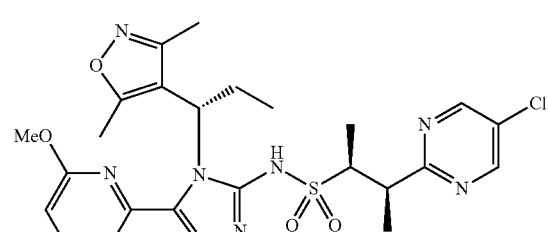(2S,3R)-3-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-2-butanesulfonamide and (2S,3R)-3-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-2-butanesulfonamide. LCMS-ESI (pos.) m/z: 561.2 (M + H)+. |
| 211.0 | (1R,2S)-1-(5-chloropyrimidin-2-yl)-1-methoxypropane-2-sulfonamide (Example 29.3), and 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). | 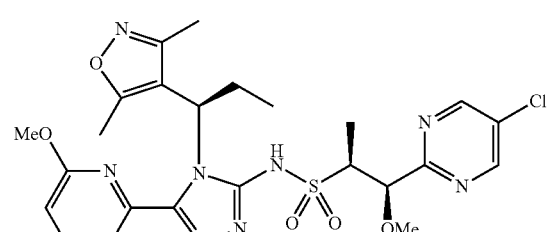AND |

TABLE 22-continued

| Example | Reagents | Structure, Name, and Data |
|---|---|---|
| | | 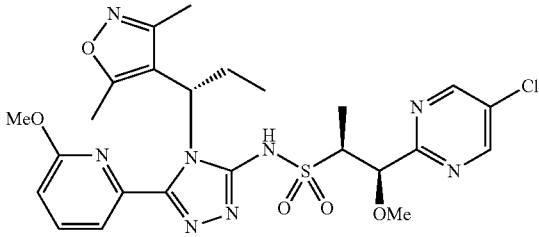 [SMILES: CC[C@@H](c1c(C)noc1C)n1c(NS(=O)(=O)[C@@H](C)[C@H](OC)c2ncc(Cl)cn2)nnc1-c1cccc(OC)n1]<br>(1R,2S)-1-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide and (1R,2S)-1-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide.<br>LCMS-ESI (pos.) m/z: 577.2 (M + H)⁺. |
| 212.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17).<br>The title compound was the first to elute from a Chiralpak IC column, SFC with 40% MeOH. | 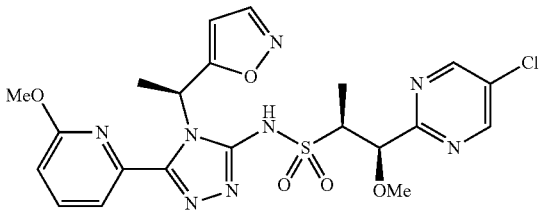 [SMILES: COc1cccc(-c2nnc(NS(=O)(=O)[C@@H](C)[C@H](OC)c3ncc(Cl)cn3)n2[C@@H](C)c2ccno2)n1]<br>OR<br>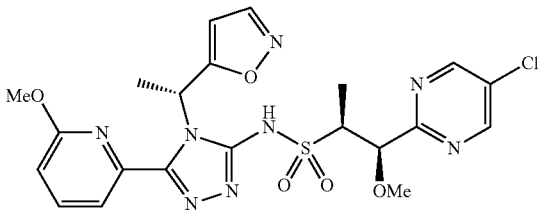 [SMILES: COc1cccc(-c2nnc(NS(=O)(=O)[C@@H](C)[C@H](OC)c3ncc(Cl)cn3)n2[C@H](C)c2ccno2)n1]<br>(1R,2S)-1-(5-chloro-2-pyrimidinyl)-1-methoxy-N-(5-(6-methoxy-2-pyridinyl)-4-((1S)-1-(1,2-oxazol-5-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1R)-1-(1,2-oxazol-5-yl)ethyl)-4H-1,2,4-triazol-3-yl)-2-propanesulfonamide.<br>¹H NMR (500 MHz, DMSO-d₆) δ 13.23 (s, 1 H) 8.94 (s, 2 H) 8.48 (d, J = 1.56 Hz, 1 H) 7.90 (t, J = 7.91 Hz, 1 H) 7.56 (d, J = 7.27 Hz, 1 H) 7.01 (d, J = 8.56 Hz, 1 H) 6.61 (q, J = 6.49 Hz, 1 H) 6.50 (s, 1 H) 4.71 (d, J = 4.41 Hz, 1 H) 3.78 (s, 3 H) 3.34-3.42 (m, 1 H) 3.15 (s, 3 H) 1.97 (d, J = 7.01 Hz, 3 H) 1.11 (d, J = 7.01 Hz, 3 H). LCMS-ESI (pos.) m/z: 535.2 (M + H)⁺. |

TABLE 22-continued

| Example | Reagents | Structure, Name, and Data |
|---|---|---|
| 213.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17). The title compound was the second to elute from Chiralpak IC column, SFC with 40% MeOH. | 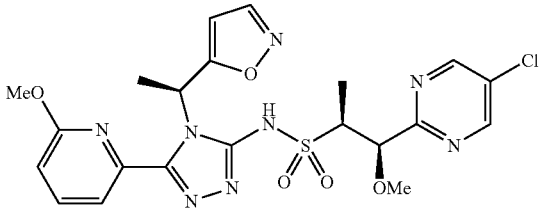 [SMILES: COc1cccc(-c2nnc(NS(=O)(=O)[C@@H](C)[C@H](OC)c3ncc(Cl)cn3)n2[C@@H](C)c2ccno2)n1]<br>OR<br>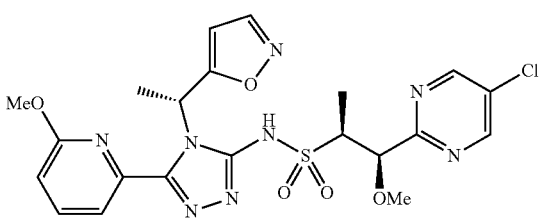 [SMILES: COc1cccc(-c2nnc(NS(=O)(=O)[C@@H](C)[C@H](OC)c3ncc(Cl)cn3)n2[C@H](C)c2ccno2)n1]<br>(1R,2S)-1-(5-chloro-2-pyrimidinyl)-1-methoxy-N-(5-(6-methoxy-2-pyridinyl)-4-((1R)-1-(1,2-oxazol-5-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1,2-oxazol-5-yl)ethyl)-4H-1,2,4-triazol-3-yl)-2-propanesulfonamide.<br>¹H NMR (500 MHz, DMSO-d₆) δ 13.28 (s, 1 H) 8.94 (s, 2 H) 8.50 (s, 1 H) 7.90 (t, J = 7.91 Hz, 1 H) 7.57 (d, J = 7.53 Hz, 1 H) 7.01 (d, J = 8.30 Hz, 1 H) 6.62 (q, J = 6.57 Hz, 1 H) 6.51 (s, 1 H) 4.73 (d, J = 4.67 Hz, 1 H) 3.79 (s, 3 H) 3.35-3.45 (m, 1 H) 3.15 (s, 3 H) 1.99 (d, J = 7.01 Hz, 3 H) 1.14 (d, J = 7.01 Hz, 3 H). LCMS-ESI (pos.) m/z: 535.2 (M + H)⁺. |
| 214.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17). The title compound was the first to elute from Chiralpak IC column, SFC with 45% MeOH. | 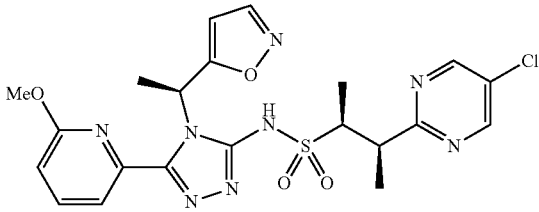 [SMILES: COc1cccc(-c2nnc(NS(=O)(=O)[C@@H](C)[C@H](C)c3ncc(Cl)cn3)n2[C@@H](C)c2ccno2)n1]<br>OR<br>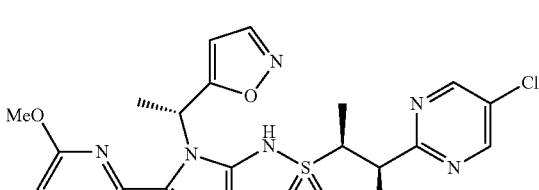<br>(2S,3R)-3-(5-chloro-2-pyrimidinyl)-N-(5-(6-methoxy-2-pyridinyl)-4-((1S)-1-(1,2-oxazol-5-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1R)-1-(1,2-oxazol-5-yl)ethyl)-4H-1,2,4-triazol-3-yl)-2-butanesulfonamide.<br>¹H NMR (500 MHz, DMSO-d₆) δ 13.22 (s, 1 H) 8.86 (s, 2 H) 8.47 (d, J = 1.82 Hz, 1 H) 7.91 (t, J = 7.91 Hz, 1 H) 7.59 (d, J = 7.27 Hz, 1 H) 7.02 (d, J = 8.30 Hz, 1 H) 6.65 (q, J = 7.01 Hz, 1 H) 6.51 (s, 1 H) 3.79 (s, 3 H) 3.45-3.55 (m, 2 H) 1.95 (d, |

TABLE 22-continued

| Example | Reagents | Structure, Name, and Data |
|---|---|---|
| | | J = 7.01 Hz, 3 H) 1.24 (d, J = 6.75 Hz, 3 H) 1.07 (d, J = 6.75 Hz, 3 H). LCMS-ESI (pos.) m/z: 519.2 (M + H)+. |
| 215.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17). The title compound was the second to elute from Chiralpak IC column, SFC with 45% MeOH. | (2S,3R)-3-(5-chloro-2-pyrimidinyl)-N-(5-(6-methoxy-2-pyridinyl)-4-((1R)-1-(1,2-oxazol-5-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(1,2-oxazol-5-yl)ethyl)-4H-1,2,4-triazol-3-yl)-2-butanesulfonamide. <br> 1H NMR (500 MHz, DMSO-d6) δ 13.25 (s, 1 H) 8.86 (s, 2 H) 8.48 (d, J = 1.82 Hz, 1 H) 7.91 (t, J = 7.91 Hz, 1 H) 7.58 (d, J = 7.27 Hz, 1 H) 7.02 (d, J = 8.56 Hz, 1 H) 6.65 (q, J = 6.83 Hz, 1 H) 6.50 (s, 1 H) 3.79 (s, 3 H) 3.47-3.64 (m, 2 H) 1.97 (d, J = 7.01 Hz, 3 H) 1.24 (d, J = 7.01 Hz, 3 H) 1.05 (d, J = 6.75 Hz, 3 H). LCMS-ESI (pos.) m/z: 519.2 (M + H)+. |
| 216.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17). The title compound was the first to elute from Chiralpak AS-H column, SFC with 15% MeOH. | (1S,2S)-N-(5-(6-methoxy-2-pyridinyl)-4-((1S)-1-(1,2-oxazol-5-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1R)-1-(1,2-oxazol-5-yl)ethyl)-4H-1,2,4-triazol-3-yl)-1-(5-methyl-2- |

TABLE 22-continued

| Example | Reagents | Structure, Name, and Data |
|---|---|---|
| | | pyrimidinyl)-1-(2-propanyloxy)-2-propanesulfonamide.<br>$^1$H NMR (500 MHz, DMSO-$d_6$) δ 13.21 (s, 1 H) 8.67 (s, 2 H) 8.50 (d, J = 1.82 Hz, 1 H) 7.90 (t, J = 7.81 Hz, 1 H) 7.56 (d, J = 7.27 Hz, 1 H) 7.01 (d, J = 8.30 Hz, 1 H) 6.60 (q, J = 7.01 Hz, 1 H) 6.52 (s, 1 H) 4.75 (d, J = 7.01 Hz, 1 H) 3.79 (s, 3 H) 3.42 (quin, J = 7.14 Hz, 1 H) 2.53-2.74 (m, 1 H) 2.27 (s, 3 H) 2.00 (d, J = 7.01 Hz, 3 H) 0.99 (d, J = 5.97 Hz, 3 H) 0.92 (d, J = 7.01 Hz, 3 H) 0.76 (d, J = 5.97 Hz, 3 H). LCMS-ESI (pos.) m/z: 543.2 (M + H)$^+$. |
| 217.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)isoxazole and (S)-5-(1-isothiocyanatoethyl)isoxazole (Example 28.17).<br>The title compound was the second to elute from Chiralpak AS-H column, SFC with 15% MeOH. | 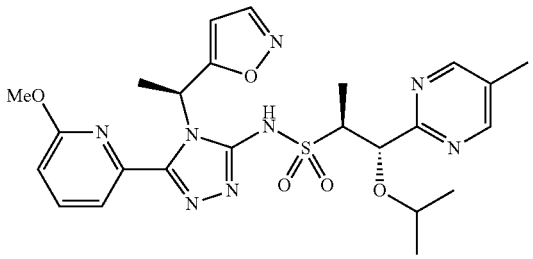 [SMILES: COc1cccc(-c2nnc(NS(=O)(=O)[C@@H](C)[C@@H](OC(C)C)c3ncc(C)cn3)n2[C@@H](C)c2ccno2)n1]<br>OR<br>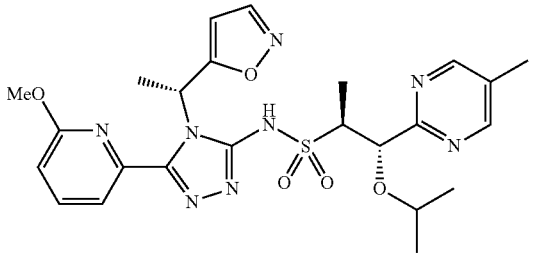 [SMILES: COc1cccc(-c2nnc(NS(=O)(=O)[C@@H](C)[C@@H](OC(C)C)c3ncc(C)cn3)n2[C@H](C)c2ccno2)n1]<br>(1S,2S)-N-(5-(6-methoxy-2-pyridinyl)-4-((1R)-1-(1,2-oxazol-5-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(1,2-oxazol-5-yl)ethyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 13.24 (s, 1 H) 8.68 (s, 2 H) 8.46 (d, J = 1.56 Hz, 1 H) 7.89 (t, J = 7.82 Hz, 1 H) 7.53 (d, J = 7.53 Hz, 1 H) 6.99 (d, J = 8.30 Hz, 1 H) 6.49-6.58 (m, 2 H) 4.77 (d, J = 7.53 Hz, 1 H) 3.77 (s, 3 H) 3.35-3.48 (m, 2 H) 2.27 (s, 3 H) 1.98 (d, J = 7.01 Hz, 3 H) 1.03 (d, J = 5.97 Hz, 3 H) 0.91 (d, J = 7.01 Hz, 3 H) 0.76 (d, J = 5.97 Hz, 3 H). LCMS-ESI (pos.) m/z: 543.2 (M + H)$^+$. |
| 218.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19).<br>The title compound was the first to elute from a Regis Whelk-O s,s column, SFC with 30% MeOH. | 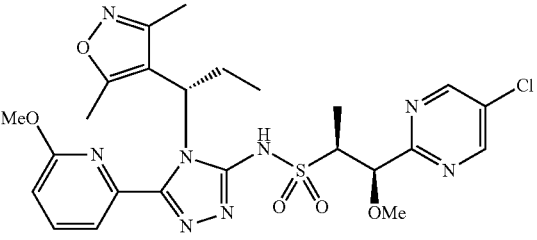 [SMILES: CC[C@@H](c1c(C)noc1C)n1c(NS(=O)(=O)[C@@H](C)[C@H](OC)c2ncc(Cl)cn2)nnc1-c1cccc(OC)n1]<br>OR |

| Example | Reagents | Structure, Name, and Data |
|---|---|---|
| | | 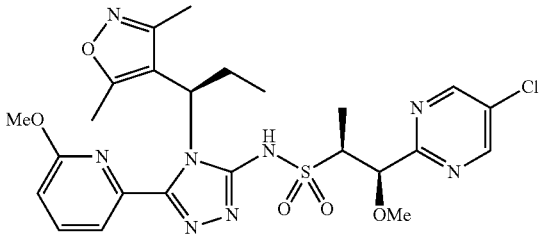 [SMILES: CC[C@H](c1c(C)noc1C)n1c(NS(=O)(=O)[C@@H](C)[C@H](OC)c2ncc(Cl)cn2)nnc1-c1cccc(OC)n1]<br>(1R,2S)-1-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide or (1R,2S)-1-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide.<br>$^1$H NMR (500 MHz, DMSO-d$_6$) δ 13.19 (s, 1 H), 8.92 (s, 2 H), 7.94 (t, J = 7.91 Hz, 1 H), 7.63 (d, J = 7.27 Hz, 1 H), 7.08 (d, J = 8.56 Hz, 1 H), 6.47 (br t, J = 7.91 Hz, 1 H), 4.79 (d, J = 3.37 Hz, 1 H), 3.92 (s, 3 H), 3.34-3.39 (m, 1 H), 3.12 (s, 3 H), 2.53-2.64 (m, 1 H), 2.31-2.43 (m, 4 H), 1.96 (s, 3 H), 0.99 (d, J = 7.01 Hz, 3 H), 0.90 (t, J = 7.40 Hz, 3 H). LCMS-ESI (pos.) m/z: 577.2 (M + H)+. |
| 219.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the first to elute from a Regis Whelk-O s,s column, SFC with 30% MeOH. | 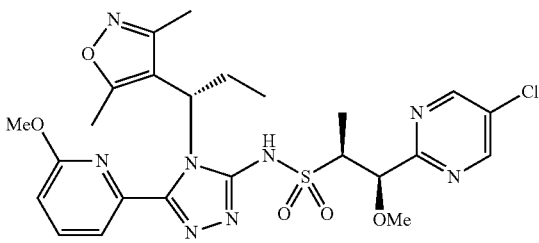 [SMILES: CC[C@@H](c1c(C)noc1C)n1c(NS(=O)(=O)[C@@H](C)[C@H](OC)c2ncc(Cl)cn2)nnc1-c1cccc(OC)n1]<br>OR<br>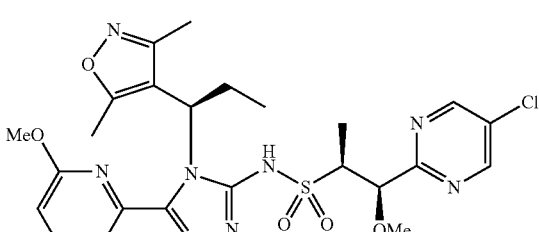<br>(1R,2S)-1-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide or (1R,2S)-1-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-2-propanesulfonamide.<br>$^1$H NMR (500 MHz, DMSO-d$_6$) δ 13.21 (s, 1 H), 8.96 (s, 2 H), 7.95 (dd, J = 8.30, 7.53 Hz, 1 H), 7.63 (d, J = 7.27 Hz, 1 H), 7.08 (d, J = 8.30 Hz, 1 H), 6.43 (t, J = 7.72 Hz, 1 H), 4.95 (d, J = 3.37 Hz, 1 H), 3.93 (s, 3 H), 3.44 (qd, J = 7.01, 3.37 Hz, 1 H), 3.10 (s, 3 H), 2.52-2.68 (m, 1 H), 2.28-2.45 (m, 4 H), 1.91 (s, 3 H), 1.20 (d, J = 7.01 Hz, 3 H), 0.96 (t, J = 7.27 Hz, 3 H). LCMS-ESI (pos.) m/z: 577.2 (M + H)$^+$. |

TABLE 22-continued

| Example | Reagents | Structure, Name, and Data |
|---|---|---|
| 220.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the first to elute from a Regis Whelk-O s,s column, SFC with 30% MeOH. | 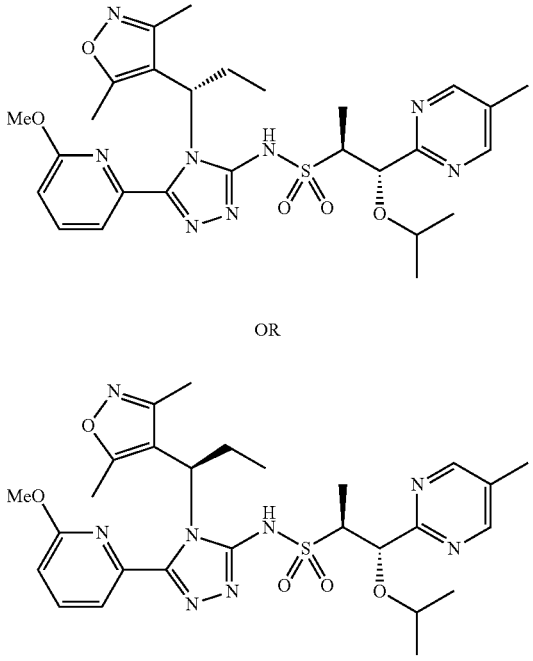<br><br>OR<br><br><br><br>(1S,2S)-N-(4-((1S)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide or (1S,2S)-N-(4-((1R)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-d$_6$) δ 13.25 (s, 1 H), 8.70 (s, 2 H), 7.95 (t, J = 7.87 Hz, 1 H), 7.62 (d, J = 7.53 Hz, 1 H), 7.08 (d, J = 8.30 Hz, 1 H), 6.40 (t, J = 8.04 Hz, 1 H), 4.77 (d, J = 5.97 Hz, 1 H), 3.93 (s, 3 H), 3.42-3.56 (m, 1 H), 3.26-3.31 (m, 1 H), 2.52-2.66 (m, 1 H), 2.35-2.44 (m, 4 H), 2.25-2.31 (m, 3 H), 1.94 (s, 3 H), 0.99 (d, J = 7.27 Hz, 3 H), 0.94 (t, J = 7.40 Hz, 3 H), 0.90 (d, J = 6.23 Hz, 3 H), 0.74 (d, J = 6.23 Hz, 3 H). LCMS-ESI (pos.) m/z: 585.2 (M + H)$^+$. |
| 221.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the second to elute from a Regis Whelk-O s,s column, SFC with 30% MeOH. | 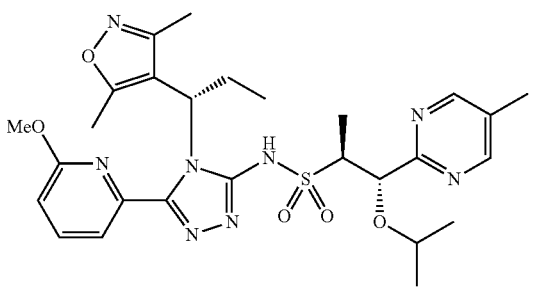 [SMILES: CC[C@@H](c1c(C)noc1C)n1c(NS(=O)(=O)[C@@H](C)[C@@H](OC(C)C)c2ncc(C)cn2)nnc1-c1cccc(OC)n1]<br><br>OR |

TABLE 22-continued

| Example | Reagents | Structure, Name, and Data |
|---|---|---|
| | | 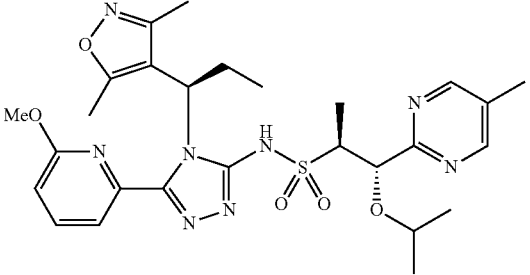 [SMILES: CC[C@H](c1c(C)noc1C)n1c(NS(=O)(=O)[C@@H](C)[C@@H](OC(C)C)c2ncc(C)cn2)nnc1-c1cccc(OC)n1]
(1S,2S)-N-(4-((1R)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide or (1S,2S)-N-(4-((1S)-1-(3,5-dimethyl-1,2-oxazol-4-yl)propyl)-5-(6-methoxy-2-pyridinyl)-4H-1,2,4-triazol-3-yl)-1-(5-methyl-2-pyrimidinyl)-1-(2-propanyloxy)-2-propanesulfonamide.
$^1$H NMR (500 MHz, DMSO-$d_6$) δ 13.23 (s, 1 H), 8.67 (s, 2 H), 7.87-8.02 (m, 1 H), 7.60 (d, J = 7.27 Hz, 1 H), 7.08 (d, J = 8.30 Hz, 1 H), 6.34 (br t, J = 7.91 Hz, 1 H), 4.82 (d, J = 5.97 Hz, 1 H), 3.93 (s, 3 H), 3.52 (quin, J = 6.81 Hz, 1 H), 3.39 (dt, J = 12.07, 5.90 Hz, 1 H), 2.60-2.71 (m, 1 H), 2.37-2.44 (m, 1 H), 2.36 (s, 3 H), 2.28 (s, 3 H), 1.90 (s, 3 H), 1.10 (d, J = 7.27 Hz, 3 H), 0.90-1.06 (m, 6 H), 0.79 (d, J = 5.97 Hz, 3 H). LCMS-ESI (pos.) m/z: 585.2 (M + H)$^+$. |
| 222.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the first to elute from a Regis Whelk-O s,s column, SFC with 30% MeOH. | 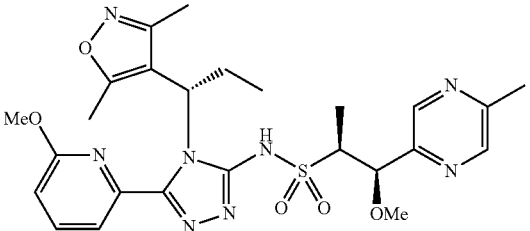 [SMILES: CC[C@@H](c1c(C)noc1C)n1c(NS(=O)(=O)[C@@H](C)[C@H](OC)c2cnc(C)cn2)nnc1-c1cccc(OC)n1]
OR
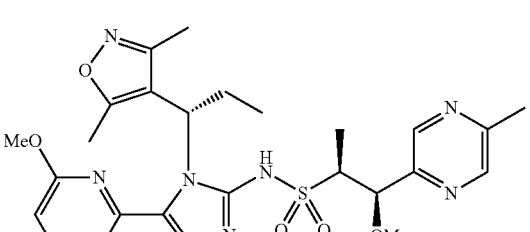
(1R,2S)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide or (1R,2S)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide.
$^1$H NMR (500 MHz, DMSO-$d_6$) δ 13.24 (s, 1 H), 8.49 (s, 1 H), 8.39 (s, 1 H), 7.95 (t, J = 7.79 Hz, 1 H), 7.64 (d, J = 7.27 Hz, 1 H), 7.08 (d, J = 8.30 Hz, 1 H), 6.48 (t, J = 7.79 Hz, 1 H), 4.74 (d, J = 2.34 Hz, 1 H), 3.92 (s, 3 H), 3.18-3.25 (m, 4 H), 2.53-2.64 (m, 1 H), 2.48-2.49 (m, 3 H), 2.29-2.44 (m, 4 H), 1.93-2.01 (m, 3 H), 0.86-0.98 (m, 6 H). LCMS-ESI (pos.) m/z: 557.2 (M + H)$^+$. |

TABLE 22-continued

| Example | Reagents | Structure, Name, and Data |
|---|---|---|
| 223.0 | (2S,3R)-3-(5-methylpyrazin-2-yl)butane-2-sulfonamide (Example 27.2), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the second to elute from a Regis Whelk-O s,s column, SFC with 30% MeOH. | 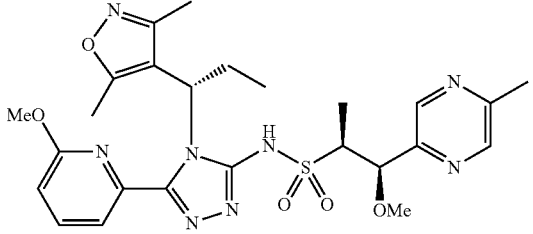 [SMILES: CC[C@@H](c1c(C)noc1C)n1c(NS(=O)(=O)[C@@H](C)[C@H](OC)c2cnc(C)cn2)nnc1-c1cccc(OC)n1]<br>OR<br>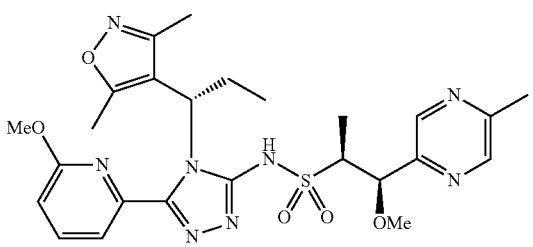 [SMILES: CC[C@@H](c1c(C)noc1C)n1c(NS(=O)(=O)[C@@H](C)[C@H](OC)c2cnc(C)cn2)nnc1-c1cccc(OC)n1]<br>(1R,2S)-N-(4-((1R)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide or (1R,2S)-N-(4-((1S)-1-(3,5-dimethyl-1,2-oxazol-4-yl)propyl)-5-(6-methoxy-2-pyridinyl)-4H-1,2,4-triazol-3-yl)-1-methoxy-1-(5-methyl-2-pyrazinyl)-2-propanesulfonamide.<br>$^1$H NMR (500 MHz, DMSO-$d_6$) δ 13.25 (s, 1 H), 8.53 (s, 1 H), 8.47 (s, 1 H), 7.95 (t, J = 7.91 Hz, 1 H), 7.63 (d, J = 7.27 Hz, 1 H), 7.08 (d, J = 8.30 Hz, 1 H), 6.42 (t, J = 8.04 Hz, 1 H), 4.97 (d, J = 2.60 Hz, 1 H), 3.93 (s, 3 H), 3.28-3.33 (m, 4 H), 3.15 (s, 3 H), 2.60-2.71 (m, 1 H), 2.31-2.43 (m, 4 H), 1.91 (s, 3 H), 1.14 (d, J = 7.01 Hz, 3 H), 0.96 (t, J = 7.27 Hz, 3 H). LCMS-ESI (pos.) m/z: 557.2 (M + H)$^+$. |
| 224.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the first to elute from Chiralpak AD-H analytical column, SFC with 30% MeOH. | 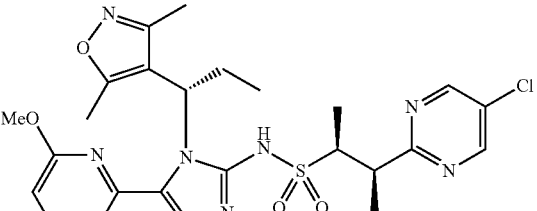<br>OR<br>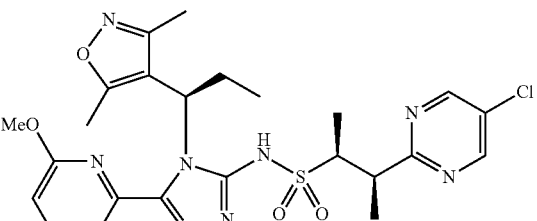<br>(2S,3R)-3-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-2-butanesulfonamide or (2S,3R)-3-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-2-butanesulfonamide. |

| Example | Reagents | Structure, Name, and Data |
|---|---|---|
| | | ¹H NMR (500 MHz, DMSO-d₆) δ 13.24 (s, 1 H), 8.84 (s, 2 H), 7.95 (t, J = 7.94 Hz, 1 H), 7.64 (d, J = 7.27 Hz, 1 H), 7.08 (d, J = 8.30 Hz, 1 H), 6.44 (t, J = 8.04 Hz, 1 H), 3.92 (s, 3 H), 3.52-3.62 (m, 1 H), 3.35-3.43 (m, 1 H), 2.53-2.65 (m, 1 H), 2.31-2.39 (m, 4 H), 1.92 (s, 3 H), 1.26 (d, J = 7.01 Hz, 3 H), 1.06 (d, J = 7.01 Hz, 3 H), 0.90 (t, J = 7.40 Hz, 3 H). LCMS-ESI (pos.) m/z: 561.2 (M + H)⁺. |
| 225.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3,5-dimethylisoxazole and (S)-4-(1-isothiocyanatopropyl)-3,5-dimethylisoxazole (Example 28.19). The title compound was the second to elute from Chiralpak AD-H analytical column, SFC with 30% MeOH. | OR<br><br>(2S,3R)-3-(5-chloro-2-pyrimidinyl)-N-(4-((1R)-1-(3,5-dimethyl-1,2-oxazol-4-yl)propyl)-5-(6-methoxy-2-pyridinyl)-4H-1,2,4-triazol-3-yl)-2-butanesulfonamide or (2S,3R)-3-(5-chloro-2-pyrimidinyl)-N-(4-((1S)-1-(3,5-dimethyl-1,2-oxazol-4-yl)propyl)-5-(6-methoxy-2-pyridinyl)-4H-1,2,4-triazol-3-yl)-2-butanesulfonamide.<br>¹H NMR (500 MHz, DMSO-d₆) δ 13.23 (s, 1 H) 8.86 (s, 2 H) 7.94 (t, J = 7.81 Hz, 1 H) 7.61 (d, J = 7.27 Hz, 1 H) 7.08 (d, J = 8.56 Hz, 1 H) 6.38 (t, J = 7.91 Hz, 1 H) 3.91 (s, 3 H) 3.60-3.69 (m, 2 H) 2.52-2.60 (m, 1 H) 2.29-2.42 (m, 4 H) 1.91 (s, 3 H) 1.30 (d, J = 7.01 Hz, 3 H) 1.09 (d, J = 6.75 Hz, 3 H) 0.89 (t, J = 7.27 Hz, 3 H). LCMS-ESI (pos.) m/z: 561.2 (M + H)⁺. |
| 226.0 | (2S,3R)-3-(5-methylpyrazin-2-yl)butane-2-sulfonamide (Example 27.2), 6-methoxypicolinohydrazide (commercially available from Sigma Aldrich), and (R)-4-(cyclopropyl(isothiocyanato)methyl)-3-methylisoxazole and (S)-4-(cyclopropyl(isothiocyanato)methyl)-3-methylisoxazole (Example 28.26). | AND |

US 10,689,367 B2

TABLE 22-continued

| Example | Reagents | Structure, Name, and Data |
|---|---|---|
| | | (1S,2S)-N-(4-((R)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide and (1S,2S)-N-(4-((S)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide.<br>LCMS-ESI (pos.) m/z: 583.2 (M + H)+. |
| 227.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3-methylisoxazole and (S)-4-(1-isothiocyanatopropyl)-3-methylisoxazole (Example 28.27). | AND<br><br>(2S,3R)-3-(5-chloro-2-pyrimidinyl)-N-(5-(6-methoxy-2-pyridinyl)-4-((1R)-1-(3-methyl-1,2-oxazol-4-yl)propyl)-4H-1,2,4-triazol-3-yl)-2-butanesulfonamide and (2S,3R)-3-(5-chloro-2-pyrimidinyl)-N-(5-(6-methoxy-2-pyridinyl)-4-((1S)-1-(3-methyl-1,2-oxazol-4-yl)propyl)-4H-1,2,4-triazol-3-yl)-2-butanesulfonamide.<br>LCMS-ESI (pos.) m/z: 547.2 (M + H)+. |
| 228.0 | (2S,3R)-3-(5-chloropyrimidin-2-yl)butane-2-sulfonamide (Example 27.4), 6-methoxypicolinohydrazide (commercially available from Sigma Aldrich), and (R)-4-(cyclopropyl(isothiocyanato)methyl)-3-methylisoxazole and (S)-4-(cyclopropyl(isothiocyanato)methyl)-3-methylisoxazole (Example 28.26). | AND |

TABLE 22-continued

| Example | Reagents | Structure, Name, and Data |
|---|---|---|
| | | 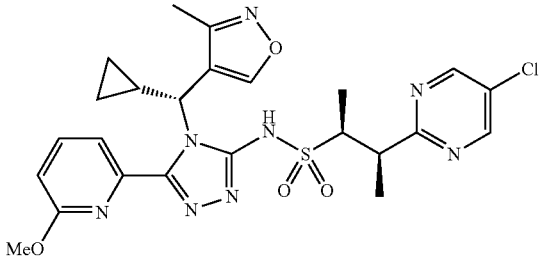 [SMILES: COc1cccc(-c2nnc(NS(=O)(=O)[C@@H](C)[C@H](C)c3ncc(Cl)cn3)n2[C@@H](c2conc2C)C2CC2)n1]<br>(2S,3R)-3-(5-chloro-2-pyrimidinyl)-N-(4-((S)-cyclopropyl(3-methyl-1,2-oxazol-4-yl)methyl)-5-(6-methoxy-2-pyridinyl)-4H-1,2,4-triazol-3-yl)-2-butanesulfonamide and (2S,3R)-3-(5-chloro-2-pyrimidinyl)-N-(4-((R)-cyclopropyl(3-methyl-1,2-oxazol-4-yl)methyl)-5-(6-methoxy-2-pyridinyl)-4H-1,2,4-triazol-3-yl)-2-butanesulfonamide.<br>LCMS-ESI (pos.) m/z: 559.2 (M + H)+. |
| 229.0 | (2S,3R)-3-(5-chloropyrimidin-2-yl)butane-2-sulfonamide (Example 27.4), 6-methoxypicolinohydrazide (commercially available from Sigma Aldrich), and (R)-4-(cyclopropyl(isothiocyanato)methyl)-3-methylisoxazole and (S)-4-(cyclopropyl(isothiocyanato)methyl)-3-methylisoxazole (Example 28.26). The title compound was the first to elute from Chiralpak AD-H, SFC with 35% MeOH. | 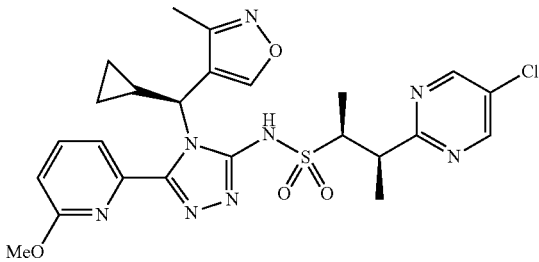 [SMILES: COc1cccc(-c2nnc(NS(=O)(=O)[C@@H](C)[C@H](C)c3ncc(Cl)cn3)n2[C@H](c2conc2C)C2CC2)n1]<br>OR<br>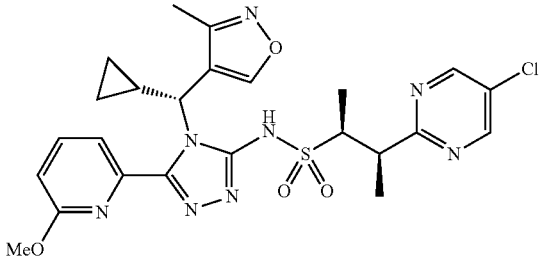 [SMILES: COc1cccc(-c2nnc(NS(=O)(=O)[C@@H](C)[C@H](C)c3ncc(Cl)cn3)n2[C@@H](c2conc2C)C2CC2)n1]<br>(2S,3R)-3-(5-chloro-2-pyrimidinyl)-N-(4-((S)-cyclopropyl(3-methyl-1,2-oxazol-4-yl)methyl)-5-(6-methoxy-2-pyridinyl)-4H-1,2,4-triazol-3-yl)-2-butanesulfonamide or (2S,3R)-3-(5-chloro-2-pyrimidinyl)-N-(4-((R)-cyclopropyl(3-methyl-1,2-oxazol-4-yl)methyl)-5-(6-methoxy-2-pyridinyl)-4H-1,2,4-triazol-3-yl)-2-butanesulfonamide.<br>$^1$H NMR (500 MHz, DMSO-$d_6$) δ 13.20 (s, 1 H) 8.93 (br s, 1 H) 8.84 (s, 2 H) 7.90 (t, J = 7.91 Hz, 1 H) 7.56 (br s, 1 H) 7.04 (d, J = 8.30 Hz, 1 H) 5.55 (br s, 1 H) 3.78 (s, 3 H) 3.47-3.64 (m, 1 H) 3.33-3.43 (m, 1 H) 2.24-2.35 (m, 1 H) 1.87 (s, 3 H) 1.24 (d, J = 7.27 Hz, 4 H) 1.11 (d, J = 7.01 Hz, 3 H) 0.77-0.87 (m, 1 H) 0.46-0.60 (m, 3 H).<br>LCMS-ESI (pos.) m/z: 559.2 (M + H)+. |

TABLE 22-continued

| Example | Reagents | Structure, Name, and Data |
|---|---|---|
| 230.0 | (2S,3R)-3-(5-methylpyrazin-2-yl)butane-2-sulfonamide (Example 27.2), 6-methoxypicolinohydrazide (commercially available from Sigma Aldrich), and (R)-4-(cyclopropyl(isothiocyanato)methyl)-3-methylisoxazole and (S)-4-(cyclopropyl(isothiocyanato)methyl)-3-methylisoxazole (Example 28.26). The title compound was the first to elute from Regis Whelk-O s,s, SFC with 30% MeOH. | 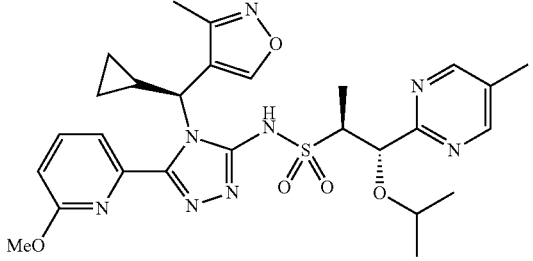 [SMILES: COc1cccc(-c2nnc(NS(=O)(=O)[C@@H](C)[C@@H](OC(C)C)c3ncc(C)cn3)n2[C@H](c2conc2C)C2CC2)n1]<br>OR<br>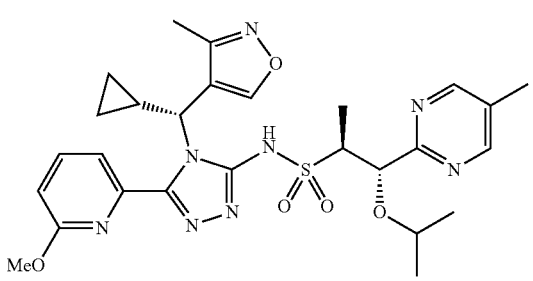 [SMILES: COc1cccc(-c2nnc(NS(=O)(=O)[C@@H](C)[C@@H](OC(C)C)c3ncc(C)cn3)n2[C@@H](c2conc2C)C2CC2)n1]<br>(1S,2S)-N-(4-((S)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide or (1S,2S)-N-(4-((R)-cyclopropyl(3-methyl-1,2-oxazol-4-yl)methyl)-5-(6-methoxy-2-pyridinyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 13.26 (s, 1 H) 8.95 (br s, 1 H) 8.67 (s, 2 H) 7.89 (t, J = 7.91 Hz, 1 H) 7.50 (br s, 1 H) 7.03 (d, J = 8.30 Hz, 1 H) 5.44 (br s, 1 H) 4.81 (d, J = 6.49 Hz, 1 H) 3.80 (s, 3 H) 3.51 (quin, J = 6.88 Hz, 1 H) 3.34-3.40 (m, 1 H) 2.33-2.46 (m, 1 H) 2.25-2.31 (m, 3 H) 1.88 (s, 3 H) 1.48 (br d, J = 18.94 Hz, 1 H) 1.23 (br s, 2 H) 0.95-1.06 (m, 6 H) 0.79 (d, J = 5.97 Hz, 4 H) 0.47-0.64 (m, 3 H). LCMS-ESI (pos.) m/z: 583.2 (M + H)$^+$. |
| 231.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3-methylisoxazole and (S)-4-(1-isothiocyanatopropyl)-3-methylisoxazole (Example 28.27). The title compound was the first to elute from Regis Whelk-O s,s, SFC with 35% IPA. | 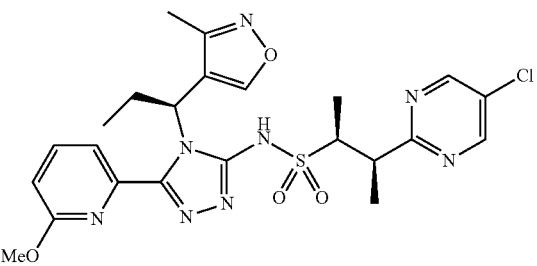 [SMILES: CC[C@@H](c1conc1C)n1c(NS(=O)(=O)[C@@H](C)[C@H](C)c2ncc(Cl)cn2)nnc1-c1cccc(OC)n1]<br>OR<br>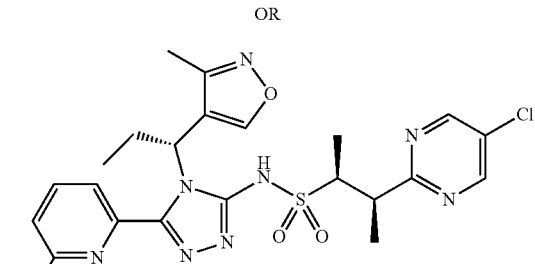<br>(2S,3R)-3-(5-chloro-2-pyrimidinyl)-N-(5-(6-methoxy-2-pyridinyl)-4-((1S)-1-(3-methyl-1,2- |

TABLE 22-continued

| Example | Reagents | Structure, Name, and Data |
|---|---|---|
| | | oxazol-4-yl)propyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1R)-1-(3-methyl-1,2-oxazol-4-yl)propyl)-4H-1,2,4-triazol-3-yl)-2-butanesulfonamide. $^1$H NMR (500 MHz, DMSO-$d_6$) δ 13.17 (s, 1 H) 8.85 (s, 3 H) 7.91 (t, J = 7.79 Hz, 1 H) 7.53 (d, J = 7.27 Hz, 1 H) 7.05 (d, J = 8.56 Hz, 1 H) 6.23 (br s, 1 H) 3.86 (s, 3 H) 3.51-3.61 (m, 1 H) 3.34-3.46 (m, 1 H) 2.53-2.64 (m, 1 H) 2.26 (dt, J = 13.82, 6.71 Hz, 1 H) 1.89 (s, 3 H) 1.26 (d, J = 7.27 Hz, 3 H) 1.12 (d, J = 7.01 Hz, 3 H) 0.88 (t, J = 7.27 Hz, 3 H). LCMS-ESI (pos.) m/z: 547.2 (M + H)$^+$. |
| 232.0 | (2S,3R)-3-(5-chloropyrimidin-2-yl)butane-2-sulfonamide (Example 27.4), 6-methoxypicolinohydrazide (commercially available from Sigma Aldrich), and (R)-4-(1-isothiocyanatopropyl)-3-methylisoxazole and (S)-4-(1-isothiocyanatopropyl)-3-methylisoxazole (Example 28.27). The title compound was the second to elute from Regis Whelk-O s,s, SFC with 35% IPA. | 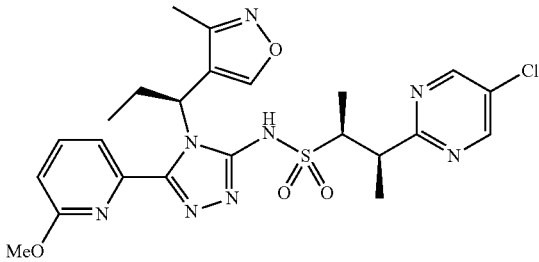 [SMILES: CC[C@@H](c1conc1C)n1c(NS(=O)(=O)[C@@H](C)[C@H](C)c2ncc(Cl)cn2)nnc1-c1cccc(OC)n1]<br>OR<br>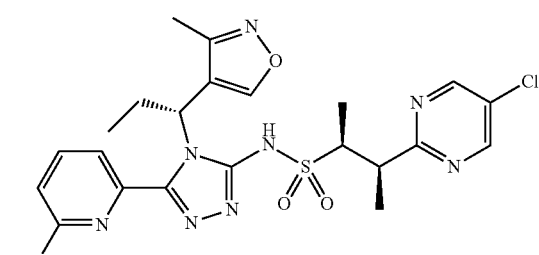<br>(2S,3R)-3-(5-chloro-2-pyrimidinyl)-N-(5-(6-methoxy-2-pyridinyl)-4-((1R)-1-(3-methyl-1,2-oxazol-4-yl)propyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(3-methyl-1,2-oxazol-4-yl)propyl)-4H-1,2,4-triazol-3-yl)-2-butanesulfonamide. $^1$H NMR (500 MHz, DMSO-$d_6$) δ 13.23 (s, 1 H) 8.86 (s, 2 H) 8.80 (s, 1 H) 7.91 (t, J = 7.79 Hz, 1 H) 7.50 (d, J = 7.27 Hz, 1 H) 7.05 (d, J = 8.56 Hz, 1 H) 6.18 (br s, 1 H) 3.85 (s, 3 H) 3.56-3.66 (m, 2 H) 2.52-2.62 (m, 1 H) 2.24 (dquin, J = 13.88, 6.97, 6.97, 6.97, 6.97 Hz, 1 H) 1.86 (s, 3 H) 1.29 (d, J = 6.75 Hz, 3 H) 1.13 (d, J = 6.75 Hz, 3 H) 0.88 (t, J = 7.27 Hz, 3 H). LCMS-ESI (pos.) m/z: 547.2 (M + H)$^+$. |
| 233.0 | (2S,3R)-3-(5-methylpyrazin-2-yl)butane-2-sulfonamide (Example 27.2), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the first to elute from Chiralpak IC, SFC with 50% MeOH. | 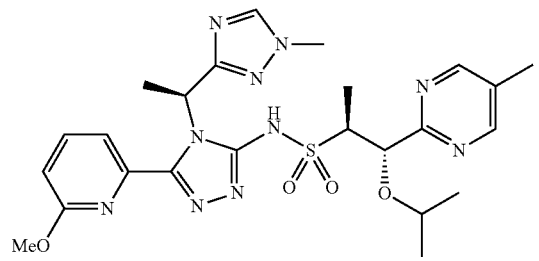 [SMILES: COc1cccc(-c2nnc(NS(=O)(=O)[C@@H](C)[C@@H](OC(C)C)c3ncc(C)cn3)n2[C@@H](C)c2ncn(C)n2)n1]<br>OR |

TABLE 22-continued

| Example | Reagents | Structure, Name, and Data |
|---|---|---|
|  |  | 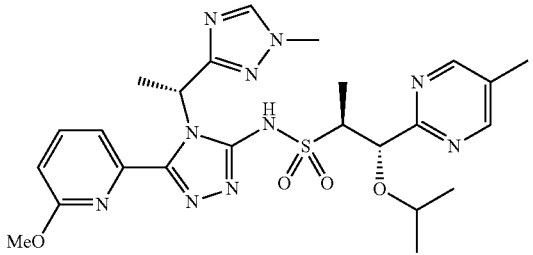 [SMILES: COc1cccc(-c2nnc(NS(=O)(=O)[C@@H](C)[C@@H](OC(C)C)c3ncc(C)cn3)n2[C@H](C)c2ncn(C)n2)n1]<br>(1S,2S)-N-(5-(6-methoxy-2-pyridinyl)-4-((1S)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1R)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 13.07 (br s, 1 H) 8.66 (s, 2 H) 8.24 (s, 1 H) 7.83 (t, J = 7.91 Hz, 1 H) 7.44 (br d, J = 7.27 Hz, 1 H) 6.92 (br d, J = 8.30 Hz, 1 H) 6.16-6.26 (m, 1 H) 4.67 (br d, J = 7.53 Hz, 1 H) 3.78 (s, 3 H) 3.71 (s, 3 H) 3.34-3.51 (m, 2 H) 2.27 (s, 3 H) 2.00 (br d, J = 7.01 Hz, 3 H) 1.03 (br d, J = 5.97 Hz, 3 H) 0.75-0.87 (m, 6 H). LCMS-ESI (pos.) m/z: 557.2 (M + H)$^+$. |
| 234.0 | (2S,3R)-3-(5-methylpyrazin-2-yl)butane-2-sulfonamide (Example 27.2), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the second to elute from Chiralpak IC, SFC with 50% MeOH. | 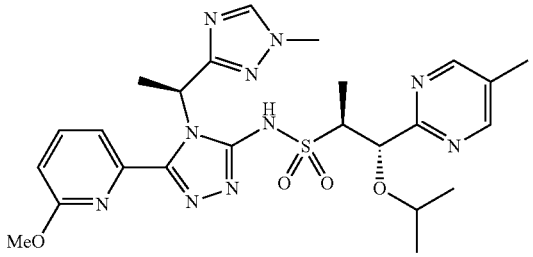 [SMILES: COc1cccc(-c2nnc(NS(=O)(=O)[C@@H](C)[C@@H](OC(C)C)c3ncc(C)cn3)n2[C@@H](C)c2ncn(C)n2)n1]<br>OR<br>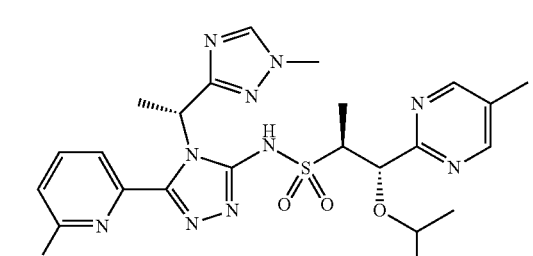<br>(1S,2S)-N-(5-(6-methoxy-2-pyridinyl)-4-((1R)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(1-methyl-1H-1,2,4-triazol-3-yl)ethyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-$d_6$) δ 13.06 (br s, 1 H) 8.65 (s, 2 H) 8.27 (s, 1 H) 7.84 (t, J = 7.79 Hz, 1 H) 7.46 (d, J = 7.27 Hz, 1 H) 6.93 (d, J = 8.30 Hz, 1 H) 6.24 (q, J = 6.92 Hz, 1 H) 4.67 (d, J = 7.27 Hz, 1 H) 3.78 (s, 3 H) 3.70-3.76 (m, 3 H) 3.33-3.42 (m, 2 H) 2.26 (s, 3 H) 1.99 (d, J = 7.01 Hz, 3 H) 1.00 (d, J = 5.97 Hz, 3 H) 0.91 (d, J = 7.01 Hz, 3 H) 0.79 (d, J = 5.97 Hz, 3 H). LCMS-ESI (pos.) m/z: 557.2 (M + H)$^+$. |

TABLE 22-continued

| Example | Reagents | Structure, Name, and Data |
|---|---|---|
| 235.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the first to elute from Lux Cellulose-2 analytical column SFC with 45% MeOH. | 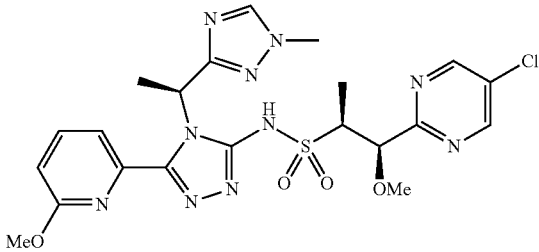 [SMILES: COc1cccc(-c2nnc(NS(=O)(=O)[C@@H](C)[C@H](OC)c3ncc(Cl)cn3)n2[C@@H](C)c2ncn(C)n2)n1]<br>OR<br>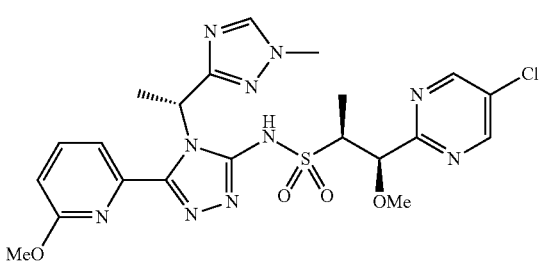 [SMILES: COc1cccc(-c2nnc(NS(=O)(=O)[C@@H](C)[C@H](OC)c3ncc(Cl)cn3)n2[C@H](C)c2ncn(C)n2)n1]<br>(1R,2S)-1-(5-chloro-2-pyrimidinyl)-1-methoxy-N-(5-(6-methoxy-2-pyridinyl)-4-((1S)-1-(1-methyl-1H-1,2,4-triazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1R)-1-(1-methyl-1H-1,2,4-triazol-3-yl)ethyl)-4H-1,2,4-triazol-3-yl)-2-propanesulfonamide.<br>$^1$H NMR (500 MHz, DMSO-d$_6$) δ 13.14 (br s, 1 H) 8.94 (s, 2 H) 8.25 (s, 1 H) 7.80-7.90 (m, 1 H) 7.46 (d, J = 7.27 Hz, 1 H) 6.93 (d, J = 8.56 Hz, 1 H) 6.26 (br d, J = 6.75 Hz, 1 H) 4.69 (d, J = 4.67 Hz, 1 H) 3.79 (s, 3 H) 3.70 (s, 3 H) 3.34-3.43 (m, 1 H) 3.16 (s, 3 H) 1.97 (d, J = 7.01 Hz, 3 H) 1.12 (d, J = 6.75 Hz, 3 H). LCMS-ESI (pos.) m/z: 549.2 (M + H)$^+$. |
| 236.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the second to elute from Lux Cellulose-2 analytical column SFC with 45% MeOH. | 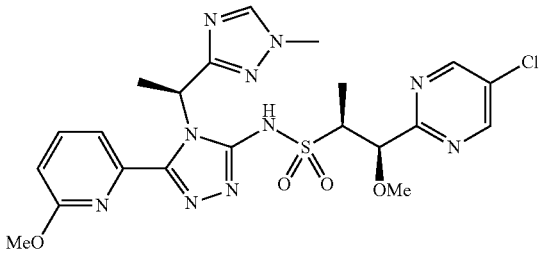 [SMILES: COc1cccc(-c2nnc(NS(=O)(=O)[C@@H](C)[C@H](OC)c3ncc(Cl)cn3)n2[C@@H](C)c2ncn(C)n2)n1]<br>OR<br>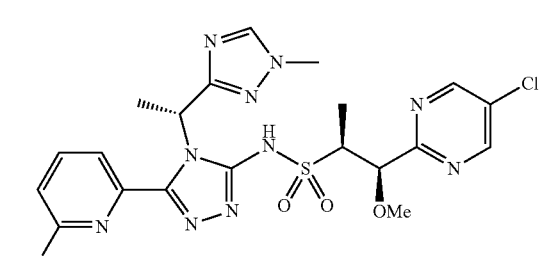<br>(1R,2S)-1-(5-chloro-2-pyrimidinyl)-1-methoxy-N-(5-(6-methoxy-2-pyridinyl)-4-((1R)-1-(1-methyl-1H-1,2,4-triazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1-methyl-1H- |

| Example | Reagents | Structure, Name, and Data |
|---|---|---|
| | | 1,2,4-triazol-3-yl)ethyl)-4H-1,2,4-triazol-3-yl)-2-propanesulfonamide.<br>$^1$H NMR (500 MHz, DMSO-d$_6$) δ 13.14 (s, 1 H) 8.93 (s, 2 H) 8.27 (s, 1 H) 7.86 (t, J = 7.79 Hz, 1 H) 7.51 (d, J = 7.27 Hz, 1 H) 6.95 (d, J = 8.30 Hz, 1 H) 6.33 (q, J = 6.57 Hz, 1 H) 4.69 (d, J = 4.93 Hz, 1 H) 3.80 (s, 3 H) 3.71 (s, 3 H) 3.33-3.40 (m, 1 H) 3.17 (s, 3 H) 2.00 (d, J = 7.01 Hz, 3 H) 1.08 (d, J = 7.01 Hz, 3 H). LCMS-ESI (pos.) m/z: 549.2 (M + H)$^+$. |
| 237.0 | (2S,3R)-3-(5-chloropyrimidin-2-yl)butane-2-sulfonamide (Example 27.4), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the first to elute from Chiralpak AD-H, SFC with 35% MeOH. | 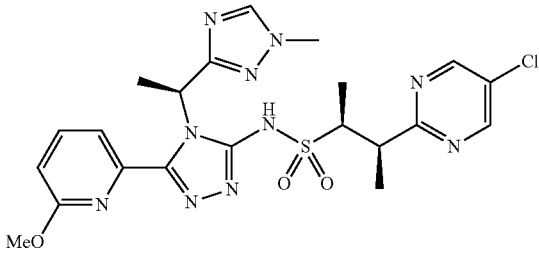 [SMILES: COc1cccc(-c2nnc(NS(=O)(=O)[C@@H](C)[C@H](C)c3ncc(Cl)cn3)n2[C@@H](C)c2ncn(C)n2)n1]<br>OR<br>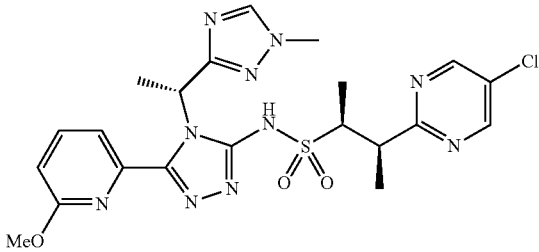 [SMILES: COc1cccc(-c2nnc(NS(=O)(=O)[C@@H](C)[C@H](C)c3ncc(Cl)cn3)n2[C@H](C)c2ncn(C)n2)n1]<br>(2S,3R)-3-(5-chloro-2-pyrimidinyl)-N-(5-(6-methoxy-2-pyridinyl)-4-((1S)-1-(1-methyl-1H-1,2,4-triazol-3-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1R)-1-(1-methyl-1H-1,2,4-triazol-3-yl)ethyl)-4H-1,2,4-triazol-3-yl)-2-butanesulfonamide.<br>$^1$H NMR (500 MHz, DMSO-d$_6$) δ 13.09 (br s, 1 H) 8.86 (s, 2 H) 8.24 (s, 1 H) 7.84 (t, J = 7.79 Hz, 1 H) 7.51 (d, J = 7.53 Hz, 1 H) 6.93 (br d, J = 8.30 Hz, 1 H) 6.34 (br d, J = 6.49 Hz, 1 H) 3.79 (s, 3 H) 3.70 (s, 3 H) 3.51-3.62 (m, 1 H) 3.42-3.51 (m, 1 H) 1.96 (d, J = 7.01 Hz, 3 H) 1.23 (d, J = 7.27 Hz, 3 H) 1.05 (d, J = 6.75 Hz, 3 H). LCMS-ESI (pos.) m/z: 533.2 (M + H)$^+$. |
| 238.0 | (2S,3R)-3-(5-chloropyrimidin-2-yl)butane-2-sulfonamide (Example 27.4), 6-methoxypicolinohydrazide (commercially available from Sigma Aldrich), and (R)-3-(1-isothiocyanatoethyl)-1-methyl-1H-1,2,4-triazole and (S)-3-(1-isothiocyanatoethyl)-1-methyl-1H-1,2,4-triazole (Example 28.20). The title compound was the second to elute from Chiralpak AD-H, SFC with 35% MeOH. | 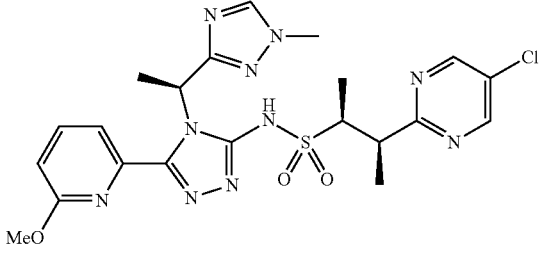 [SMILES: COc1cccc(-c2nnc(NS(=O)(=O)[C@@H](C)[C@H](C)c3ncc(Cl)cn3)n2[C@@H](C)c2ncn(C)n2)n1]<br>OR |

| Example | Reagents | Structure, Name, and Data |
|---|---|---|
| | | 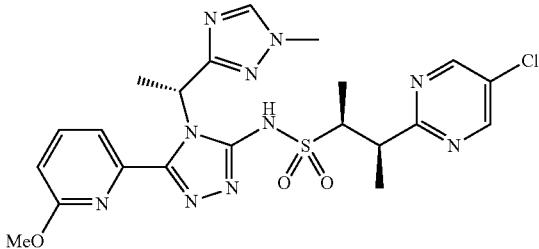 [SMILES: COc1cccc(-c2nnc(NS(=O)(=O)[C@@H](C)[C@H](C)c3ncc(Cl)cn3)n2[C@H](C)c2ncn(C)n2)n1]
(2S,3R)-3-(5-chloro-2-pyrimidinyl)-N-(5-(6-methoxy-2-pyridinyl)-4-((1R)-1-(1-methyl-1H-1,2,4-triazol-3-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(1-methyl-1H-1,2,4-triazol-3-yl)ethyl)-4H-1,2,4-triazol-3-yl)-2-butanesulfonamide.
$^1$H NMR (500 MHz, DMSO-d6) δ 13.09 (br s, 1 H) 8.86 (s, 2 H) 8.27 (s, 1 H) 7.86 (t, J = 7.91 Hz, 1 H) 7.53 (d, J = 7.27 Hz, 1 H) 6.95 (br d, J = 8.30 Hz, 1 H) 6.37 (br d, J = 7.01 Hz, 1 H) 3.78-3.85 (m, 3 H) 3.71 (s, 3 H) 3.50-3.60 (m, 1 H) 3.45 (br s, 1 H) 1.98 (d, J = 7.01 Hz, 3 H) 1.22 (d, J = 7.01 Hz, 3 H) 0.98 (d, J = 6.75 Hz, 3 H). LCMS-ESI (pos.) m/z: 533.2 (M + H)$^+$. |
| 239.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)-3-methyl-1,2,4-oxadiazole and (S)-5-(1-isothiocyanatoethyl)-3-methyl-1,2,4-oxadiazole (Example 28.21).
The title compound was the first to elute from Chiralpak AD-H, SFC with 15% EtOH. | 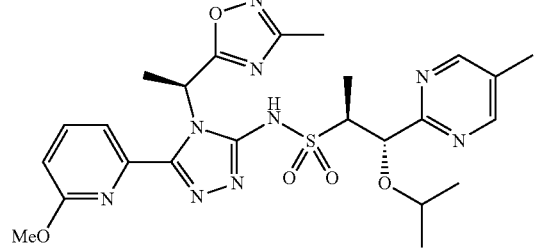
OR
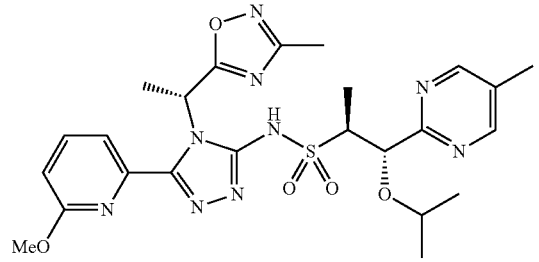 [SMILES: COc1cccc(-c2nnc(NS(=O)(=O)[C@@H](C)[C@@H](OC(C)C)c3ncc(C)cn3)n2[C@H](C)c2nc(C)no2)n1]
(1S,2S)-N-(5-(6-methoxy-2-pyridinyl)-4-((1S)-1-(3-methyl-1,2,4-oxadiazol-5-yl)ethyl)-4H-1,2,4-triazol-3-yl)-1-(5-methyl-2-pyrimidinyl)-1-(2-propanyloxy)-2-propanesulfonamide.
$^1$H NMR (500 MHz, DMSO-d6) δ 13.29 (td, J = 4.35, 2.47 Hz, 1 H) 8.64 (s, 2 H) 7.84 (br d, J = 7.27 Hz, 1 H) 7.63 (d, J = 7.53 Hz, 1 H) 6.54-6.98 (m, 2 H) 4.77 (br d, J = 4.93 Hz, 1 H) 3.76 (br s, 3 H) 3.41 (br dd, J = 2.85, 1.82 Hz, 1 H) 2.27 (m, 6 H) 2.00 (br d, J = 6.75 Hz, 3 H) 1.02 (d, J = 5.97 Hz, 3 H) 0.92 (d, J = 7.01 Hz, 3 H) 0.79 (d, J = 6.23 Hz, 3 H). LCMS-ESI (pos.) m/z: 558.2 (M + H)$^+$. |

TABLE 22-continued

| Example | Reagents | Structure, Name, and Data |
|---|---|---|
| 240.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)-3-methyl-1,2,4-oxadiazole and (S)-5-(1-isothiocyanatoethyl)-3-methyl-1,2,4-oxadiazole (Example 28.21). The title compound was the second to elute from Chiralpak AD-H, SFC with 15% EtOH. | 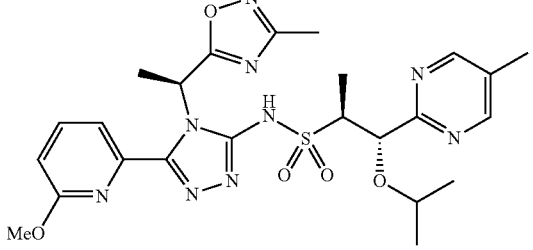<br>OR<br>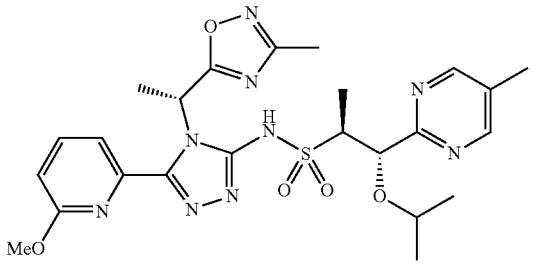 [SMILES: COc1cccc(-c2nnc(NS(=O)(=O)[C@@H](C)[C@@H](OC(C)C)c3ncc(C)cn3)n2[C@H](C)c2nc(C)no2)n1]<br>(1S,2S)-N-(5-(6-methoxy-2-pyridinyl)-4-((1S)-1-(3-methyl-1,2,4-oxadiazol-5-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1R)-1-(3-methyl-1,2,4-oxadiazol-5-yl)ethyl)-4H-1,2,4-triazol-3-yl)-1-(5-methyl-2-pyrimidinyl)-1-(2-propanyloxy)-2-propanesulfonamide.<br>$^1$H NMR (500 MHz, DMSO-d$_6$) δ 13.35 (br s, 1 H) 8.66 (s, 2 H) 7.90 (t, J = 7.91 Hz, 1 H) 7.62 (d, J = 7.53 Hz, 1 H) 6.99 (br d, J = 8.30 Hz, 1 H) 6.71 (br d, J = 6.49 Hz, 1 H) 4.72 (d, J = 7.53 Hz, 1 H) 3.81 (s, 3 H) 3.35-3.49 (m, 2 H) 2.23-2.32 (m, 6 H) 2.01 (d, J = 7.01 Hz, 3 H) 1.03 (d, J = 6.23 Hz, 3 H) 0.89 (d, J = 7.27 Hz, 3 H) 0.79 (d, J = 6.23 Hz, 3 H). LCMS-ESI (pos.) m/z: 558.2 (M + H)$^+$. |
| 241.0 | (2S,3R)-3-(5-methylpyrazin-2-yl)butane-2-sulfonamide (Example 27.2), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the first to elute from a Phenomenex Lux Cellulose-2 column, SFC with 45% MeOH. | 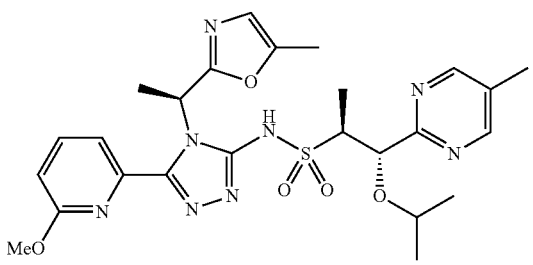 [SMILES: COc1cccc(-c2nnc(NS(=O)(=O)[C@@H](C)[C@@H](OC(C)C)c3ncc(C)cn3)n2[C@@H](C)c2ncc(C)o2)n1]<br>OR<br>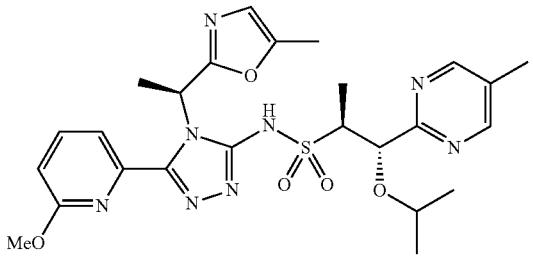 [SMILES: COc1cccc(-c2nnc(NS(=O)(=O)[C@@H](C)[C@@H](OC(C)C)c3ncc(C)cn3)n2[C@@H](C)c2ncc(C)o2)n1]<br>(1S,2S)-N-(5-(6-methoxy-2-pyridinyl)-4-((1S)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide or (1S,2S)- |

TABLE 22-continued

| Example | Reagents | Structure, Name, and Data |
|---|---|---|
| | | N-(5-(6-methoxy-2-pyridinyl)-4-((1R)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide. <br> $^1$H NMR (500 MHz, DMSO-d$_6$) δ 12.93-13.38 (m, 1 H) 8.65 (s, 2 H) 7.84 (br t, J = 7.14 Hz, 1 H) 7.51 (d, J = 7.27 Hz, 1 H) 6.92 (br d, J = 2.60 Hz, 1 H) 6.67 (s, 1 H) 6.27 (br d, J = 1.56 Hz, 1 H) 4.79 (br d, J = 7.01 Hz, 1 H) 3.80 (s, 3 H) 3.36-3.61 (m, 2 H) 2.26 (s, 3 H) 2.14 (s, 3 H) 1.97 (d, J = 7.01 Hz, 3 H) 1.01 (d, J = 5.97 Hz, 3 H) 0.93-0.99 (m, 3 H) 0.79 (d, J = 5.97 Hz, 3 H). LCMS-ESI (pos.) m/z: 557.2 (M + H)$^+$. |
| 242.0 | (2S,3R)-3-(5-methylpyrazin-2-yl)butane-2-sulfonamide (Example 27.2), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the second to elute from Phenomenex Lux Cellulose-2 column, SFC with 45% MeOH. | OR <br><br> (1S,2S)-N-(5-(6-methoxy-2-pyridinyl)-4-((1S)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(5-methyl-1,3-oxazol-2-yl)ethyl)-4H-1,2,4-triazol-3-yl)-1-(5-methyl-2-pyrimidinyl)-1-(2-propanyloxy)-2-propanesulfonamide. <br> $^1$H NMR (500 MHz, DMSO-d$_6$) δ 13.24 (s, 1 H) 8.66 (s, 2 H) 7.85 (t, J = 7.91 Hz, 1 H) 7.49 (d, J = 7.27 Hz, 1 H) 6.94 (d, J = 8.30 Hz, 1 H) 6.65 (s, 1 H) 6.23 (q, J = 6.66 Hz, 1 H) 4.77 (d, J = 7.79 Hz, 1 H) 3.82 (s, 3 H) 3.35-3.47 (m, 2 H) 2.27 (s, 3 H) 2.13 (s, 3 H) 1.97 (d, J = 7.01 Hz, 3 H) 1.02 (d, J = 5.97 Hz, 3 H) 0.92 (d, J = 7.27 Hz, 3 H) 0.77 (d, J = 5.97 Hz, 3 H). LCMS-ESI (pos.) m/z: 557.2 (M + H)$^+$. |
| 243.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-3-(1-isothiocyanatoethyl)-5-methyl-1,2,4-oxadiazole and (S)-3-(1-isothiocyanatoethyl)-5-methyl-1,2,4-oxadiazole (Example 28.23). The title compound was the first to elute from a Chiralpak IC analytical column, SFC with 40% MeOH. | OR |

TABLE 22-continued

| Example | Reagents | Structure, Name, and Data |
|---|---|---|
| | | 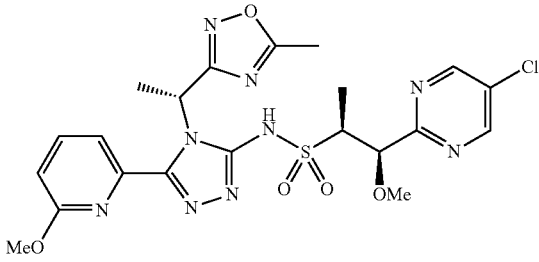 [SMILES: COc1cccc(-c2nnc(NS(=O)(=O)[C@@H](C)[C@H](OC)c3ncc(Cl)cn3)n2[C@H](C)c2noc(C)n2)n1]<br>(1R,2S)-1-(5-chloro-2-pyrimidinyl)-1-methoxy-N-(5-(6-methoxy-2-pyridinyl)-4-((1S)-1-(5-methyl-1,2,4-oxadiazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1R)-1-(5-methyl-1,2,4-oxadiazol-3-yl)ethyl)-4H-1,2,4-triazol-3-yl)-2-propanesulfonamide.<br>$^1$H NMR (500 MHz, DMSO-$d_6$) δ 13.26 (br s, 1 H) 8.86-8.95 (m, 2 H) 7.88 (br t, J = 7.79 Hz, 1 H) 7.60 (d, J = 7.27 Hz, 1 H) 6.96 (br s, 1 H) 6.59 (br s, 1 H) 4.73 (d, J = 4.93 Hz, 1 H) 3.81 (s, 3 H) 3.36-3.61 (m, 1 H) 3.17 (s, 3 H) 2.46-2.48 (m, 3 H) 1.99 (br d, J = 7.01 Hz, 3 H) 1.09 (d, J = 7.01 Hz, 3 H). LCMS-ESI (pos.) m/z: 550.2 (M + H)$^+$. |
| 244.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-3-(1-isothiocyanatoethyl)-5-methyl-1,2,4-oxadiazole and (S)-3-(1-isothiocyanatoethyl)-5-methyl-1,2,4-oxadiazole (Example 28.23).<br>The title compound was the second to elute from Chiralpak IC analytical column, SFC with 40% MeOH | 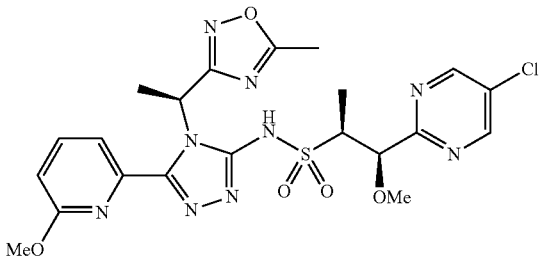 [SMILES: COc1cccc(-c2nnc(NS(=O)(=O)[C@@H](C)[C@H](OC)c3ncc(Cl)cn3)n2[C@@H](C)c2noc(C)n2)n1]<br>OR<br>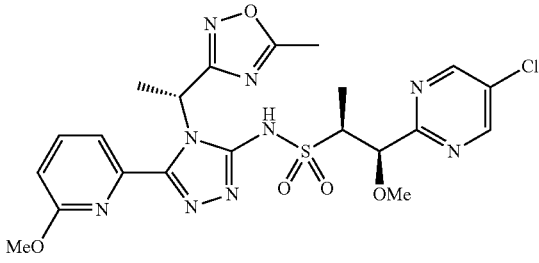 [SMILES: COc1cccc(-c2nnc(NS(=O)(=O)[C@@H](C)[C@H](OC)c3ncc(Cl)cn3)n2[C@H](C)c2noc(C)n2)n1]<br>(1R,2S)-1-(5-chloro-2-pyrimidinyl)-1-methoxy-N-(5-(6-methoxy-2-pyridinyl)-4-((1R)-1-(5-methyl-1,2,4-oxadiazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(5-methyl-1,2,4-oxadiazol-3-yl)ethyl)-4H-1,2,4-triazol-3-yl)-2-propanesulfonamide.<br>$^1$H NMR (500 MHz, DMSO-$d_6$) δ 13.25 (br s, 1 H) 8.93 (s, 2 H) 7.77-7.96 (m, 1 H) 7.58 (d, J = 7.53 Hz, 1 H) 6.94 (br s, 1 H) 6.54 (br s, 1 H) 4.65 (br d, J = 4.41 Hz, 1 H) 3.79 (br s, 3 H) 3.34-3.56 (m, 1 H) 3.17 (s, 3 H) 2.46-2.49 (m, 3 H) 1.96 (br d, J = 6.75 Hz, 3 H) 1.14 (br d, J = 7.01 Hz, 3 H). LCMS-ESI (pos.) m/z: 550.2 (M + H)$^+$. |

TABLE 22-continued

| Example | Reagents | Structure, Name, and Data |
|---|---|---|
| 245.0 | (2S,3R)-3-(5-chloropyrimidin-2-yl)butane-2-sulfonamide (Example 27.4), 6-methoxypicolinohydrazide (commercially available from Sigma Aldrich), and (R)-3-(1-isothiocyanatoethyl)-5-methyl-1,2,4-oxadiazole and (S)-3-(1-isothiocyanatoethyl)-5-methyl-1,2,4-oxadiazole (Example 28.23). The title compound was the second to elute from Chiralpak IC analytical column, SFC with 45% MeOH. | 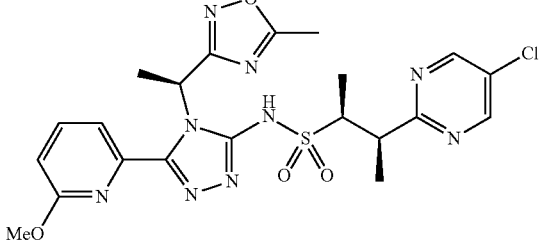<br>OR<br>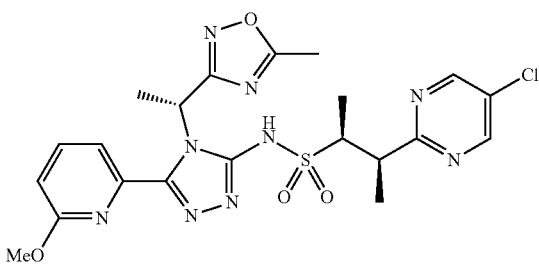 [SMILES: COc1cccc(-c2nnc(NS(=O)(=O)[C@@H](C)[C@H](C)c3ncc(Cl)cn3)n2[C@H](C)c2noc(C)n2)n1]<br>(2S,3R)-3-(5-chloro-2-pyrimidinyl)-N-(5-(6-methoxy-2-pyridinyl)-4-((1R)-1-(5-methyl-1,2,4-oxadiazol-3-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(5-methyl-1,2,4-oxadiazol-3-yl)ethyl)-4H-1,2,4-triazol-3-yl)-2-butanesulfonamide.<br>$^1$H NMR (500 MHz, DMSO-d$_6$) δ 13.25 (s, 1 H) 8.86 (s, 2 H) 7.91 (t, J = 7.92 Hz, 1 H) 7.61 (d, J = 7.53 Hz, 1 H) 7.02 (d, J = 8.16 Hz, 1 H) 6.64 (q, J = 6.75 Hz, 1 H) 3.83 (s, 3 H) 3.51-3.68 (m, 1 H) 3.34-3.50 (m, 1 H) 2.47-2.49 (m, 3 H) 1.98 (d, J = 7.01 Hz, 3 H) 1.24 (d, J = 7.01 Hz, 3 H) 1.02 (d, J = 7.01 Hz, 3 H). LCMS-ESI (pos.) m/z: 534.2 (M + H)$^+$. |
| 246.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)-3-methyl-1,2,4-oxadiazole and (S)-5-(1-isothiocyanatoethyl)-3-methyl-1,2,4-oxadiazole (Example 28.21). The title compound was the first to elute from Chiralpak IC, SFC with 45% MeOH. | 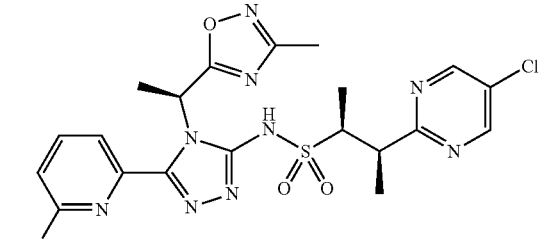<br>OR<br>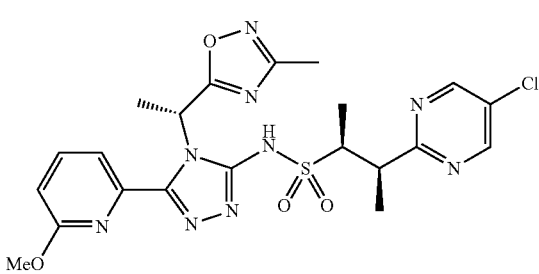 [SMILES: COc1cccc(-c2nnc(NS(=O)(=O)[C@@H](C)[C@H](C)c3ncc(Cl)cn3)n2[C@H](C)c2nc(C)no2)n1]<br>(2S,3R)-3-(5-chloro-2-pyrimidinyl)-N-(5-(6-methoxy-2-pyridinyl)-4-((1R)-1-(5-methyl-1,2,4-oxadiazol-3-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(5-methyl-1,2,4-oxadiazol-3-yl)ethyl)- |

TABLE 22-continued

| Example | Reagents | Structure, Name, and Data |
|---|---|---|
| | | 4H-1,2,4-triazol-3-yl)-2-butanesulfonamide. $^1$H NMR (500 MHz, DMSO-d$_6$) δ 13.34 (s, 1 H) 8.86 (s, 2 H) 7.92 (t, J = 7.91 Hz, 1 H) 7.64 (d, J = 7.53 Hz, 1 H) 7.02 (d, J = 8.30 Hz, 1 H) 6.79-6.90 (m, 1 H) 3.40-3.55 (m, 2 H) 3.32 (s, 3 H) 2.25 (s, 3 H) 1.98 (d, J = 7.01 Hz, 3 H) 1.25 (d, J = 6.75 Hz, 3 H) 1.08 (d, J = 6.75 Hz, 3 H). LCMS-ESI (pos.) m/z: 534.2 (M + H)$^+$. |
| 247.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)-3-methyl-1,2,4-oxadiazole and (S)-5-(1-isothiocyanatoethyl)-3-methyl-1,2,4-oxadiazole (Example 28.21). The title compound was the second to elute from Chiralpak IC, SFC with 45% MeOH. | 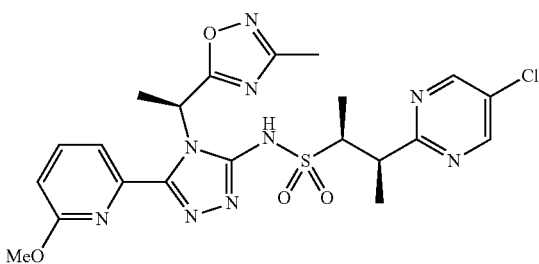 [SMILES: COc1cccc(-c2nnc(NS(=O)(=O)[C@@H](C)[C@H](C)c3ncc(Cl)cn3)n2[C@@H](C)c2nc(C)no2)n1]  OR  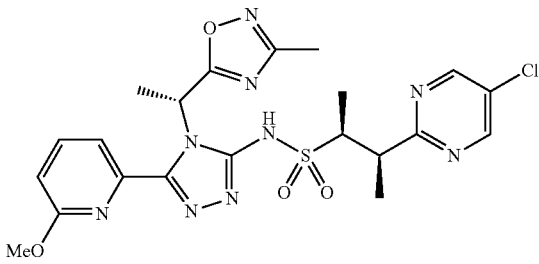 [SMILES: COc1cccc(-c2nnc(NS(=O)(=O)[C@@H](C)[C@H](C)c3ncc(Cl)cn3)n2[C@H](C)c2nc(C)no2)n1]  (2S,3R)-3-(5-chloro-2-pyrimidinyl)-N-(5-(6-methoxy-2-pyridinyl)-4-((1R)-1-(3-methyl-1,2,4-oxadiazol-5-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(3-methyl-1,2,4-oxadiazol-5-yl)ethyl)-4H-1,2,4-triazol-3-yl)-2-butanesulfonamide. $^1$H NMR (500 MHz, DMSO-d$_6$) δ 13.37 (s, 1 H) 8.86 (s, 2 H) 7.92 (t, J = 7.91 Hz, 1 H) 7.63 (d, J = 7.27 Hz, 1 H) 7.02 (d, J = 8.30 Hz, 1 H) 6.84 (q, J = 6.66 Hz, 1 H) 3.84 (s, 3 H) 3.44-3.59 (m, 2 H) 2.25 (s, 3 H) 2.01 (d, J = 7.01 Hz, 3 H) 1.24 (d, J = 6.75 Hz, 3 H) 1.05 (d, J = 6.75 Hz, 3 H). LCMS-ESI (pos.) m/z: 534.2 (M + H)$^+$. |
| 248.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the first to elute from Chiralpak AD-H, SFC with 25% MeOH. | 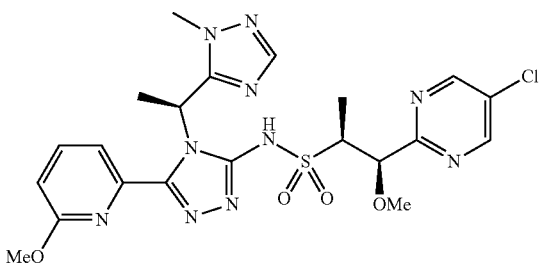 [SMILES: COc1cccc(-c2nnc(NS(=O)(=O)[C@@H](C)[C@H](OC)c3ncc(Cl)cn3)n2[C@@H](C)c2ncnn2C)n1]  OR |

TABLE 22-continued

| Example | Reagents | Structure, Name, and Data |
|---|---|---|
| | | (1R,2S)-1-(5-chloro-2-pyrimidinyl)-1-methoxy-N-(5-(6-methoxy-2-pyridinyl)-4-((1S)-1-(1-methyl-1H-1,2,4-triazol-5-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1R)-1-(1-methyl-1H-1,2,4-triazol-5-yl)ethyl)-4H-1,2,4-triazol-3-yl)-2-propanesulfonamide.<br>$^1$H NMR (500 MHz, DMSO-d$_6$) δ 13.17 (br s, 1 H) 8.92 (s, 2 H) 7.87 (br t, J = 7.79 Hz, 1 H) 7.72 (s, 1 H) 7.48 (br d, J = 7.27 Hz, 1 H) 6.99 (br d, J = 7.78 Hz, 1 H) 6.54 (br s, 1 H) 4.56 (br d, J = 3.63 Hz, 1 H) 3.86 (s, 3 H) 3.58 (br s, 3 H) 3.53 (br s, 1 H) 3.15 (s, 3 H) 1.94 (d, J = 6.75 Hz, 3 H) 1.06 (br d, J = 6.75 Hz, 3 H). LCMS-ESI (pos.) m/z: 549.2 (M + H)$^+$. |
| 249.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the second to elute from Chiralpak AD-H, SFC with 25% MeOH. | OR<br><br>(1R,2S)-1-(5-chloro-2-pyrimidinyl)-1-methoxy-N-(5-(6-methoxy-2-pyridinyl)-4-((1R)-1-(1-methyl-1H-1,2,4-triazol-5-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1-methyl-1H-1,2,4-triazol-5-yl)ethyl)-4H-1,2,4-triazol-3-yl)-2-propanesulfonamide.<br>$^1$H NMR (500 MHz, DMSO-d6) δ 13.30 (br s, 1 H) 8.94 (s, 2 H) 7.85 (br t, J = 7.91 Hz, 1 H) 7.70 (s, 1 H) 7.46 (d, J = 7.27 Hz, 1 H) 6.97 (br d, J = 8.56 Hz, 1 H) 6.42-6.55 (m, 1 H) 4.82 (d, J = 4.67 Hz, 1 H) 3.86 (s, 3 H) 3.54 (s, 3 H) 3.45 (br s, 1 H) 3.18 (s, 3 H) 1.97 (d, J = 6.75 Hz, 3 H) 1.15 (d, J = 7.01 Hz, 3 H). LCMS-ESI (pos.) m/z: 549.2 (M + H)$^+$. |

TABLE 22-continued

| Example | Reagents | Structure, Name, and Data |
|---|---|---|
| 250.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the first to elute from Chiralpak AD-H, SFC with 25% MeOH. | 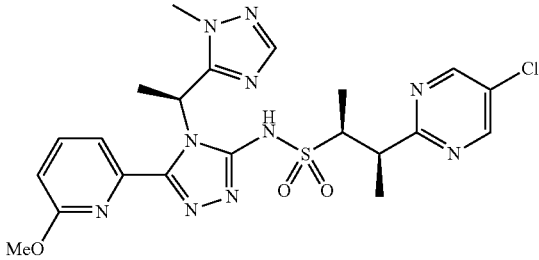<br>OR<br>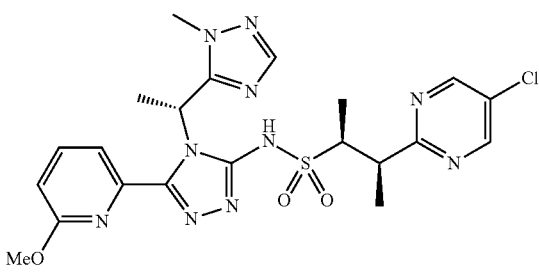<br>(1R,2S)-1-(5-chloro-2-pyrimidinyl)-1-methoxy-N-(5-(6-methoxy-2-pyridinyl)-4-((1R)-1-(1-methyl-1H-1,2,4-triazol-5-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1-methyl-1H-1,2,4-triazol-5-yl)ethyl)-4H-1,2,4-triazol-3-yl)-2-propanesulfonamide.<br>$^1$H NMR (500 MHz, DMSO-d$_6$) δ 13.19-13.26 (m, 1 H) 8.93-8.96 (m, 2 H) 7.88-7.94 (m, 1 H) 7.54-7.57 (m, 1 H) 7.00-7.07 (m, 1 H) 5.75 (s, 1 H) 4.93-5.12 (m, 2 H) 4.54 (br d, J = 10.12 Hz, 1 H) 3.79-3.91 (m, 4 H) 3.48-3.60 (m, 2 H) 3.15 (s, 3 H) 2.91 (br t, J = 12.20 Hz, 1 H) 2.51-2.55 (m, 1 H) 1.90-2.05 (m, 5 H) 1.77-1.87 (m, 1 H) 1.47 (br d, J = 12.72 Hz, 1 H) 1.26-1.37 (m, 4 H). LCMS-ESI (pos.) m/z: 549.2 (M + H)$^+$. |
| 251.0 | (2S,3R)-3-(5-chloropyrimidin-2-yl)butane-2-sulfonamide (Example 27.4), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the second to elute from Chiralpak AD-H, SFC with 25% MeOH. | 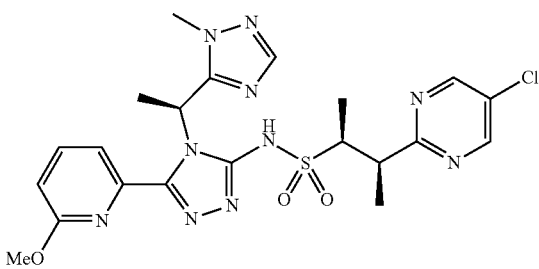 [SMILES: COc1cccc(-c2nnc(NS(=O)(=O)[C@@H](C)[C@H](C)c3ncc(Cl)cn3)n2[C@@H](C)c2ncnn2C)n1]<br>OR<br>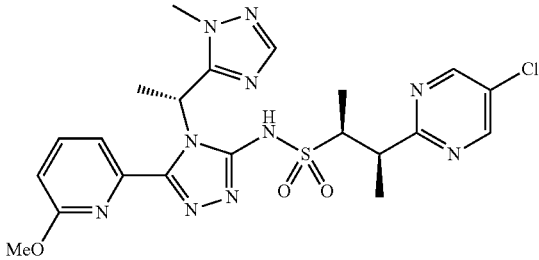 [SMILES: COc1cccc(-c2nnc(NS(=O)(=O)[C@@H](C)[C@H](C)c3ncc(Cl)cn3)n2[C@H](C)c2ncnn2C)n1]<br>(2S,3R)-3-(5-chloro-2-pyrimidinyl)-N-(5-(6-methoxy-2-pyridinyl)-4-((1R)-1-(1-methyl-1H-1,2,4-triazol-5-yl)ethyl)-4H-1,2,4-triazol-3-yl)-2- |

TABLE 22-continued

| Example | Reagents | Structure, Name, and Data |
|---|---|---|
| | | butanesulfonamide or (2S,3R)-3-(5-chloro-2-pyrimidinyl)-N-(5-(6-methoxy-2-pyridinyl)-4-((1S)-1-(1-methyl-1H-1,2,4-triazol-5-yl)ethyl)-4H-1,2,4-triazol-3-yl)-2-butanesulfonamide.<br>$^1$H NMR (500 MHz, DMSO-d$_6$) δ 13.30 (s, 1 H) 8.86 (s, 2 H) 7.87 (t, J = 7.91 Hz, 1 H) 7.70 (s, 1 H) 7.49 (d, J = 7.27 Hz, 1 H) 7.00 (d, J = 8.56 Hz, 1 H) 6.53 (q, J = 6.92 Hz, 1 H) 3.86 (s, 3 H) 3.55-3.65 (m, 1 H) 3.51 (s, 4 H) 1.95 (d, J = 7.01 Hz, 3 H) 1.26 (d, J = 7.01 Hz, 3 H) 1.06 (d, J = 7.01 Hz, N NH 3 H). LCMS-ESI (pos.) m/z: 549.2 (M + H)$^+$. |
| 252.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the first to elute from Chiralpak AD-H, SFC with 25% MeOH. | 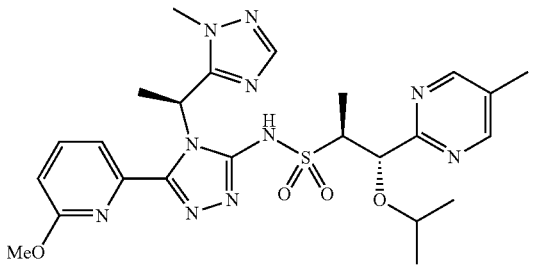 [SMILES: COc1cccc(-c2nnc(NS(=O)(=O)[C@@H](C)[C@@H](OC(C)C)c3ncc(C)cn3)n2[C@@H](C)c2ncnn2C)n1]<br>OR<br>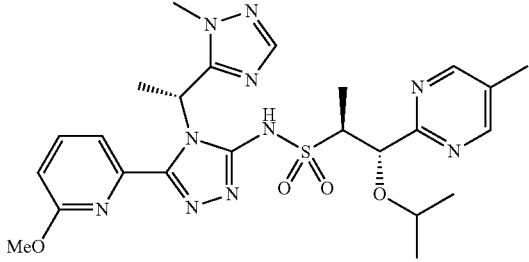 [SMILES: COc1cccc(-c2nnc(NS(=O)(=O)[C@@H](C)[C@@H](OC(C)C)c3ncc(C)cn3)n2[C@H](C)c2ncnn2C)n1]<br>(2S,3R)-3-(5-chloro-2-pyrimidinyl)-N-(5-(6-methoxy-2-pyridinyl)-4-((1R)-1-(1-methyl-1H-1,2,4-triazol-5-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1S)-1-(1-methyl-1H-1,2,4-triazol-5-yl)ethyl)-4H-1,2,4-triazol-3-yl)-2-butanesulfonamide.<br>$^1$H NMR (500 MHz, DMSO-d$_6$) δ 8.66 (s, 2 H) 7.77-7.90 (m, 2 H) 7.61-7.75 (m, 1 H) 7.43 (d, J = 7.27 Hz, 1 H) 6.94 (br d, J = 8.30 Hz, 1 H) 6.36-6.46 (m, 1 H) 4.80 (d, J = 7.27 Hz, 1 H) 3.80-3.99 (m, 5 H) 3.48-3.61 (m, 4 H) 3.39 (dt, J = 11.94, 5.97 Hz, 1 H) 2.23-2.30 (m, 4 H) 1.96 (d, J = 7.01 Hz, 3 H) 1.35-1.52 (m, 1 H) 1.08-1.14 (m, 1 H) 0.87-1.05 (m, 8 H) 0.79 (d, J = 6.23 Hz, 3 H). LCMS-ESI (pos.) m/z: 557.2 (M + H)$^+$. |
| 253.0 | (2S,3R)-3-(5-methylpyrazin-2-yl)butane-2-sulfonamide (Example 27.2), 6-methoxypicolinohydrazide (commercially available from Sigma Aldrich), and (R)-5-(1-isothiocyanatoethyl)-1-methyl-1H-1,2,4-triazole and (S)-5-(1-isothiocyanatoethyl)-1-methyl-1H-1,2,4-triazole (Example 28.24). The title compound was the second to elute from Chiralpak AD-H, SFC with 15% MeOH. | 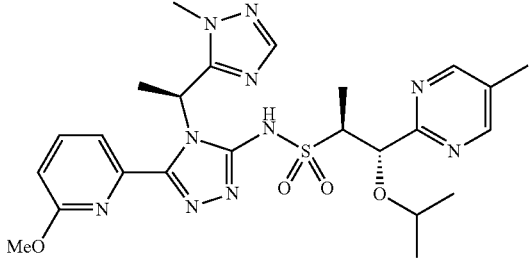 [SMILES: COc1cccc(-c2nnc(NS(=O)(=O)[C@@H](C)[C@@H](OC(C)C)c3ncc(C)cn3)n2[C@@H](C)c2ncnn2C)n1]<br>OR |

TABLE 22-continued

| Example | Reagents | Structure, Name, and Data |
|---|---|---|
| | | 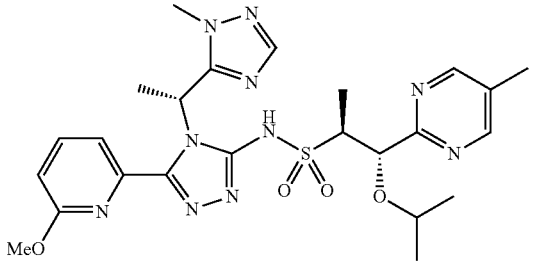 [SMILES: COc1cccc(-c2nnc(NS(=O)(=O)[C@@H](C)[C@@H](OC(C)C)c3ncc(C)cn3)n2[C@H](C)c2ncnn2C)n1]
(1S,2S)-N-(5-(6-methoxy-2-pyridinyl)-4-((1R)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propanesulfonamide.
$^1$H NMR (500 MHz, DMSO-$d_6$) δ 13.25 (br s, 1 H) 8.66 (s, 2 H) 7.81 (t, J = 7.89 Hz, 1 H) 7.66 (s, 1 H) 7.39 (d, J = 7.27 Hz, 1 H) 6.89-6.99 (m, 1 H) 6.29-6.39 (m, 1 H) 4.79 (d, J = 7.53 Hz, 1 H) 3.81-3.90 (m, 3 H) 3.53 (s, 3 H) 3.43 (dt, J = 11.94, 5.97 Hz, 1 H) 2.26 (s, 3 H) 1.96 (d, J = 6.75 Hz, 3 H) 1.04 (d, J = 5.97 Hz, 3 H) 0.93 (d, J = 7.01 Hz, 3 H) 0.79 (d, J = 5.97 Hz, 3 H). LCMS-ESI (pos.) m/z: 557.2 (M + H)$^+$. |
| 254.0 | (2S,3R)-3-(5-methylpyrazin-2-yl)butane-2-sulfonamide (Example 27.2), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the first to elute from Chiralpak IC, SFC with 40% MeOH. | 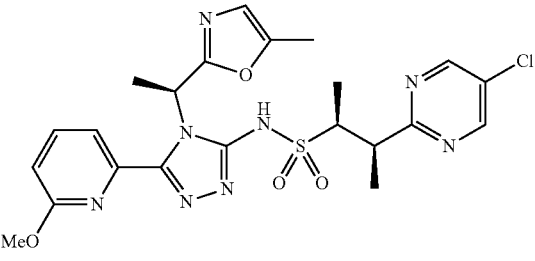 [SMILES: COc1cccc(-c2nnc(NS(=O)(=O)[C@@H](C)[C@H](C)c3ncc(Cl)cn3)n2[C@@H](C)c2ncc(C)o2)n1]
OR
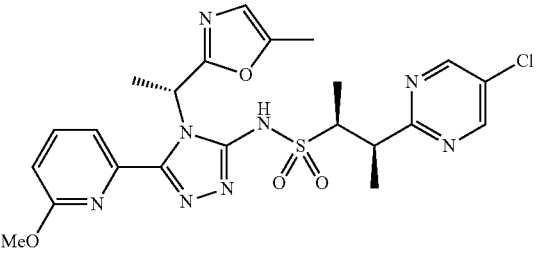 [SMILES: COc1cccc(-c2nnc(NS(=O)(=O)[C@@H](C)[C@H](C)c3ncc(Cl)cn3)n2[C@H](C)c2ncc(C)o2)n1]
(1S,2S)-N-(5-(6-methoxy-2-pyridinyl)-4-((1R)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(1-methyl-1H-1,2,4-triazol-5-yl)ethyl)-4H-1,2,4-triazol-3-yl)-1-(5-methyl-2-pyrimidinyl)-1-(2-propanyloxy)-2-propanesulfonamide.
$^1$H NMR (500 MHz, DMSO-$d_6$) δ 13.21 (br s, 1 H) 8.66 (s, 2 H) 7.89 (br t, J = 7.66 Hz, 1 H) 7.58 (d, J = 7.53 Hz, 1 H) 6.99 (br d, J = 8.04 Hz, 1 H) 6.47-6.58 (m, 1 H) 4.67 (br d, J = 7.53 Hz, 1 H) 3.81 (s, 3 H) 3.43 (dt, J = 12.07, 6.16 Hz, 1 H) 3.34-3.38 (m, 1 H) 2.27 (s, 3 H) 1.99 (d, J = 7.01 Hz, 3 H) 1.04 (d, J = 5.97 Hz, 3 H) 0.87 (d, J = 7.01 Hz, 3 H) 0.80 (d, J = 6.23 Hz, 3 H). LCMS-ESI (pos.) m/z: 558.2 (M + H)$^+$. |

TABLE 22-continued

| Example | Reagents | Structure, Name, and Data |
|---|---|---|
| 255.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the first to elute from Phenomenex Lux Cellulose-2 column, SFC with 40% MeOH. | 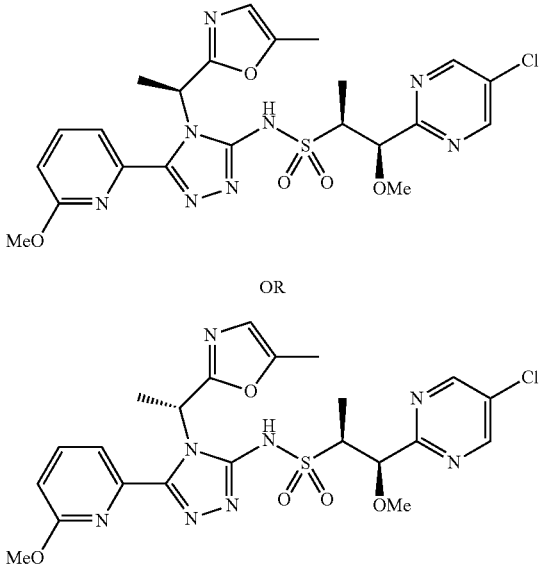<br>OR<br><br>(1R,2S)-1-(5-chloro-2-pyrimidinyl)-1-methoxy-N-(5-(6-methoxy-2-pyridinyl)-4-((1S)-1-(5-methyl-1,3-oxazol-2-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1R)-1-(5-methyl-1,3-oxazol-2-yl)ethyl)-4H-1,2,4-triazol-3-yl)-2-propanesulfonamide.<br>$^1$H NMR (500 MHz, DMSO-d6) δ 13.25 (br s, 1 H) 8.94 (s, 2 H) 7.87 (t, J = 7.79 Hz, 1 H) 7.54 (d, J = 7.27 Hz, 1 H) 6.97 (br d, J = 8.30 Hz, 1 H) 6.67 (s, 1 H) 6.38 (br d, J = 6.49 Hz, 1 H) 4.76 (d, J = 4.41 Hz, 1 H) 3.82 (s, 3 H) 3.34-3.52 (m, 1 H) 3.11-3.19 (m, 3 H) 2.15 (s, 3 H) 1.96 (d, J = 7.01 Hz, 3 H) 1.12 (d, J = 7.01 Hz, 3 H). LCMS-ESI (pos.) m/z: 549.2 (M + H)$^+$. |
| 256.0 | (1R,2S)-1-(5-chloropyrimidin-2-yl)-1-methoxypropane-2-sulfonamide (Example 29.3), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the second to elute from Phenomenex Lux Cellulose-2 column, SFC with 40% MeOH. | 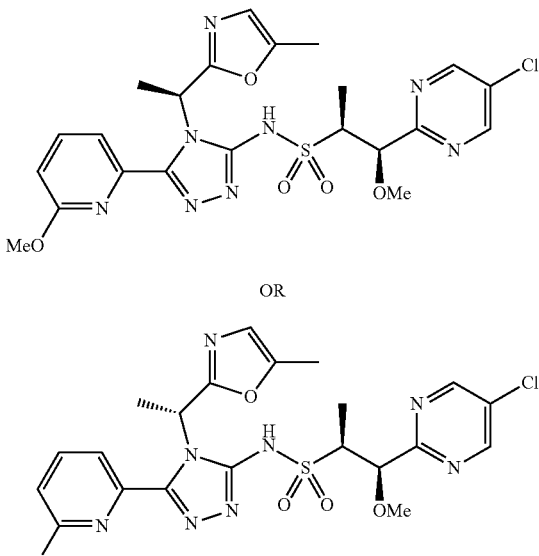<br>OR<br><br>(1R,2S)-1-(5-chloro-2-pyrimidinyl)-1-methoxy-N-(5-(6-methoxy-2-pyridinyl)-4-((1S)-1-(5-methyl-1,3-oxazol-2-yl)ethyl)-4H-1,2,4-triazol-3-yl)-2-propanesulfonamide or (1R,2S)-1-(5-chloro-2-pyrimidinyl)-1-methoxy-N-(5-(6- |

TABLE 22-continued

| Example | Reagents | Structure, Name, and Data |
|---|---|---|
| | | methoxy-2-pyridinyl)-4-((1R)-1-(5-methyl-1,3-oxazol-2-yl)ethyl)-4H-1,2,4-triazol-3-yl)-2-propanesulfonamide.<br>$^1$H NMR (500 MHz, DMSO-d$_6$) δ 13.28 (br s, 1 H) 8.93 (s, 2 H) 7.87 (br t, J = 7.27 Hz, 1 H) 7.54 (br d, J = 7.01 Hz, 1 H) 6.95 (br d, J = 7.01 Hz, 1 H) 6.68 (br s, 1 H) 6.36 (br s, 1 H) 4.75 (br d, J = 4.67 Hz, 1 H) 3.82 (s, 3 H) 3.46 (br s, 1 H) 3.17 (s, 3 H) 2.14 (s, 3 H) 1.97 (br d, J = 6.75 Hz, 3 H) 1.16 (br d, J = 6.75 Hz, 3 H). LCMS-ESI (pos.) m/z: 549.2 (M + H)$^+$. |
| 257.0 | (2S,3R)-3-(5-chloropyrimidin-2-yl)butane-2-sulfonamide (Example 27.4), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the second to elute from a Phenomenex Lux Cellulose-2 column, SFC with 40% MeOH. | (2S,3R)-3-(5-chloro-2-pyrimidinyl)-N-(5-(6-methoxy-2-pyridinyl)-4-((1S)-1-(5-methyl-1,3-oxazol-2-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1R)-1-(5-methyl-1,3-oxazol-2-yl)ethyl)-4H-1,2,4-triazol-3-yl)-2-butanesulfonamide.<br>$^1$H NMR (500 MHz, DMSO-d$_6$) δ 13.21 (br s, 1 H) 8.86 (s, 2 H) 7.89 (t, J = 7.79 Hz, 1 H) 7.57 (d, J = 7.27 Hz, 1 H) 6.98 (d, J = 8.30 Hz, 1 H) 6.68 (s, 1 H) 6.45 (br d, J = 6.49 Hz, 1 H) 3.81-3.91 (m, 3 H) 3.54 (br s, 1 H) 3.42-3.51 (m, 1 H) 2.14 (s, 3 H) 1.93 (d, J = 7.01 Hz, 3 H) 1.25 (d, J = 7.01 Hz, 3 H) 1.10 (d, J = 6.75 Hz, 3 H). LCMS-ESI (pos.) m/z: 533.2 (M + H)$^+$. |
| 258.0 | (2S,3R)-3-(5-chloropyrimidin-2-yl)butane-2-sulfonamide (Example 27.4), 6-methoxypicolinohydrazide (commercially available from Sigma Aldrich), and (R)-2-(1-isothiocyanatoethyl)-5-methyloxazole and (S)-2-(1-isothiocyanatoethyl)-5-methyloxazole (Example 28.22). The title compound was the second to elute from a Phenomenex Lux Cellulose-2 column, SFC with 40% MeOH. | |

TABLE 22-continued

| Example | Reagents | Structure, Name, and Data |
|---------|----------|---------------------------|
| | | 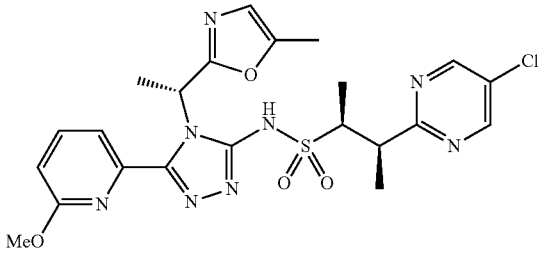 [SMILES: COc1cccc(-c2nnc(NS(=O)(=O)[C@@H](C)[C@H](C)c3ncc(Cl)cn3)n2[C@H](C)c2ncc(C)o2)n1]
(2S,3R)-3-(5-chloro-2-pyrimidinyl)-N-(5-(6-methoxy-2-pyridinyl)-4-((1S)-1-(5-methyl-1,3-oxazol-2-yl)ethyl)-4H-1,2,4-triazol-3-yl)-2-butanesulfonamide or (2S,3R)-3-(5-chloro-2-pyrimidinyl)-N-(5-(6-methoxy-2-pyridinyl)-4-((1R)-1-(5-methyl-1,3-oxazol-2-yl)ethyl)-4H-1,2,4-triazol-3-yl)-2-butanesulfonamide.
$^1$H NMR (500 MHz, DMSO-d$_6$) δ 13.26 (s, 1 H) 8.86 (s, 2 H) 7.89 (t, J = 7.79 Hz, 1 H) 7.56 (d, J = 7.53 Hz, 1 H) 6.98 (d, J = 8.30 Hz, 1 H) 6.68 (s, 1 H) 6.44 (br d, J = 7.01 Hz, 1 H) 3.80-3.88 (m, 3 H) 3.45-3.62 (m, 2 H) 2.15 (s, 3 H) 1.95 (d, J = 6.75 Hz, 3 H) 1.25 (d, J = 7.01 Hz, 3 H) 1.08 (d, J = 7.01 Hz, 3 H). LCMS-ESI (pos.) m/z: 533.2 (M + H)$^+$. |
| 259.0 | (2S,3R)-3-(5-methylpyrazin-2-yl)butane-2-sulfonamide (Example 27.2), 6-methoxypicolinohydrazide (commercially available from Sigma Aldrich), and (R)-3-(1-isothiocyanatoethyl)-5-methyl-1,2,4-oxadiazole and (S)-3-(1-isothiocyanatoethyl)-5-methyl-1,2,4-oxadiazole (Example 28.23).
The title compound was the first to elute from a Chiralpak IC, SFC with 40% MeOH. | 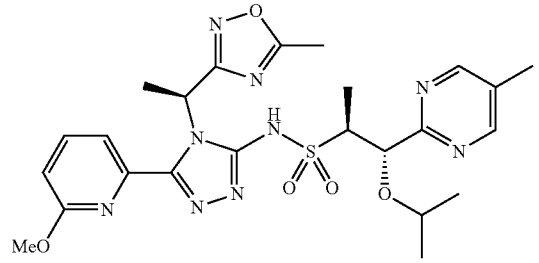 [SMILES: COc1cccc(-c2nnc(NS(=O)(=O)[C@@H](C)[C@@H](OC(C)C)c3ncc(C)cn3)n2[C@@H](C)c2noc(C)n2)n1]

OR

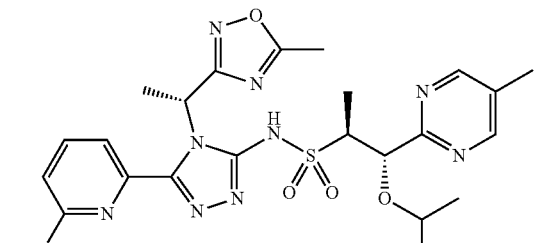

(1S,2S)-N-(5-(6-methoxy-2-pyridinyl)-4-((1R)-1-(5-methyl-1,2,4-oxadiazol-3-yl)ethyl)-4H-1,2,4-triazol-3-yl)-1-(5-methyl-2-pyrimidinyl)-1-(2-propanyloxy)-2-propanesulfonamide or (1S,2S)-N-(5-(6-methoxy-2-pyridinyl)-4-((1S)-1-(5-methyl-1,2,4-oxadiazol-3-yl)ethyl)-4H-1,2,4-triazol-3-yl)-1-(5-methyl-2-pyrimidinyl)-1-(2-propanyloxy)-2-propanesulfonamide.
$^1$H NMR (500 MHz, DMSO-d$_6$) δ 13.19 (br s, 1 H) 8.66 (s, 2 H) 7.90 (br t, J = 7.66 Hz, 1 H) 7.59 (d, J = 7.27 Hz, 1 H) 7.00 (br d, J = 8.04 Hz, 1 H) 6.59 (br d, J = 4.93 Hz, 1 H) 4.68 (br d, J = 6.75 Hz, 1 H) 3.80 (s, 3 H) 3.39 (br s, 1 H) 2.52-2.54 (m, 3 H) 2.27 (s, 3 H) 2.00 (br d, J = 6.75 Hz, 3 H) 1.00 (d, J = 6.23 Hz, 3 H) 0.90 (d, J = 7.01 Hz, 3 H) 0.77 (d, J = 6.23 Hz, 3 H). LCMS-ESI (pos.) m/z: 558.2 (M + H)$^+$. |

TABLE 22-continued

| Example | Reagents | Structure, Name, and Data |
|---|---|---|
| 260.0 | (2S,3R)-3-(5-chloropyrimidin-2-yl)butane-2-sulfonamide (Example 27.4), 1-isothiocyanato-1-methylcyclobutane (commercially available from Enamine), and 6-methoxypicolinohydrazide (commercially available from Milestone PharmTech USA Inc.). | 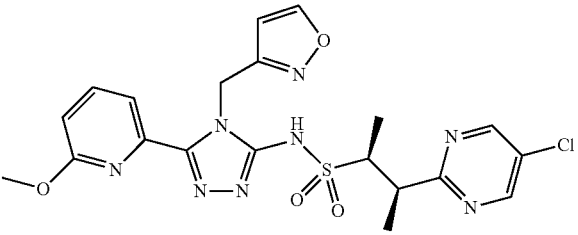 [SMILES: COc1cccc(-c2nnc(NS(=O)(=O)[C@@H](C)[C@H](C)c3ncc(Cl)cn3)n2Cc2ccon2)n1]<br>(2S,3R)-3-(5-chloropyrimidin-2-yl)-N-(4-(isoxazol-3-ylmethyl)-5-(6-methoxypyridin-2-yl)-4H-1,2,4-triazol-3-yl)butane-2-sulfonamide.<br>$^1$H NMR (400 MHz, DMSO-d$_6$) δ 13.53-13.01 (m, 1H), 8.85-8.79 (m, 3H), 7.85 (t, J = 7.9 Hz, 1H), 7.68-7.64 (m, 1H), 6.91 (d, J = 8.3 Hz, 1H), 6.50 (s, 1H), 5.74-5.47 (m, 2H), 3.83-3.73 (m, 1H), 3.69 (s, 3H), 3.67-3.61 (m, 1H), 1.26 (d, J = 7.3 Hz, 3H), 1.18 (d, J = 6.8 Hz, 3H). LCMS ESI (pos.) m/z: 505.0 (M + H)$^+$. |
| 261.0 | (1S,2S)-1-isopropoxy-1-(5-methylpyrimidin-2-yl)propane-2-sulfonamide (Example 31.0), 1-isothiocyanato-1-methylcyclobutane (commercially available from Enamine), and 6-methoxypicolinohydrazide (commercially available from Milestone PharmTech USA Inc.). | 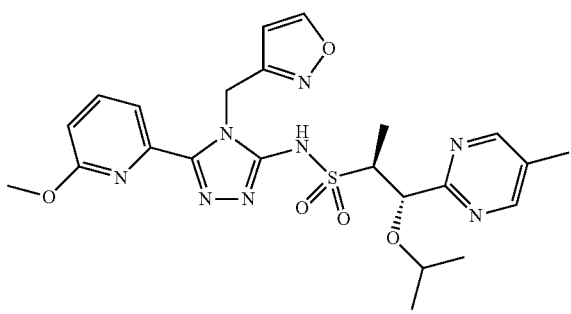<br>(1S,2S)-1-isopropoxy-N-(4-(isoxazol-3-ylmethyl)-5-(6-methoxypyridin-2-yl)-4H-1,2,4-triazol-3-yl)-1-(5-methylpyrimidin-2-yl)propane-2-sulfonamide.<br>$^1$H NMR (400 MHz, DMSO-d$_6$) δ 13.33 (br s, 1H), 8.86 (d, J = 1.7 Hz, 1H), 8.66 (s, 2H), 7.87 (t, J = 7.9 Hz, 1H), 7.66 (d, J = 7.5 Hz, 1H), 6.96 (d, J = 8.3 Hz, 1H), 6.61 (d, J = 1.7 Hz, 1H), 5.73-5.63 (m, 2H), 4.80 (d, J = 7.5 Hz, 1H), 3.75-3.67 (m, 3H), 3.57 (quin, J = 7.1 Hz, 1H), 3.37-3.29 (m, 1H), 2.26 (s, 3H), 1.01 (d, J = 7.0 Hz, 3H), 1.00-0.96 (m, 3H), 0.73 (d, J = 6.0 Hz, 3H). LCMS ESI (pos.) m/z: 529.0 (M + H)$^+$. |
| 262.0 | (1R,2S)-1-(5-chloropyrimidin-2-yl)-1-methoxypropane-2-sulfonamide (Example 29.3, 1-isothiocyanato-1-methylcyclobutane (commercially available from Enamine), and 5-methylnicotinic acid hydrazide (commercially available from Bellen). | 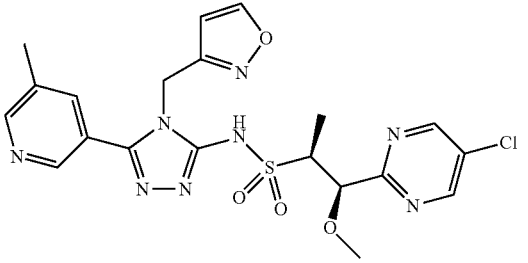 [SMILES: CO[C@H](c1ncc(Cl)cn1)[C@H](C)S(=O)(=O)Nc1nnc(-c2cncc(C)c2)n1Cc1ccon1]<br>(1R,2S)-1-(5-chloropyrimidin-2-yl)-N-(4-(isoxazol-3-ylmethyl)-5-(5-methylpyridin-3-yl)-4H-1,2,4-triazol-3-yl)-1-methoxypropane-2-sulfonamide.<br>$^1$H NMR (400 MHz, DMSO-d$_6$) δ = 13.35 (br s, 1H), 9.00-8.93 (m, 2H), 8.92-8.89 (m, 1H), 8.60 (br d, J = 6.0 Hz, 2H), 7.89 (s, 1H), 6.60 (s, 1H), 5.21-5.07 (m, 2H), 4.82 (d, J = 4.6 Hz, 1H), 3.56 (br s, 1H), 3.15 (s, 3H), 2.35 (s, 3H), 1.23 (d, J = 6.8 Hz, 3H). LCMS ESI (pos.) m/z: 505.0 (M + H)$^+$. |

Example 263.0. Preparation of (1R,2S)—N-(4-(bicyclo[1.1.1]pentan-1-yl)-5-(6-methoxy-2-pyridinyl)-4H-1,2,4-triazol-3-yl)-1-(5-chloro-2-pyrimidinyl)-1-methoxy-2-propanesulfonamide

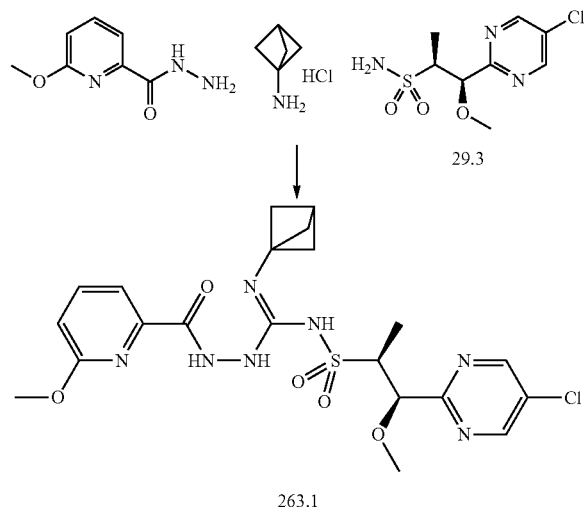

(Z)—N'-(Bicyclo[1.1.1]pentan-1-yl)-N-(((1R,2S)-1-(5-chloropyrimidin-2-yl)-1-methoxypropan-2-yl)sulfonyl)-2-(6-methoxypicolinoyl)hydrazinecarboximidamide, Example 263.1

To a vial containing Example 29.3 (140 mg, 0.53 mmol) was added DCM (2 mL). After 10 minutes, cesium carbonate (267 mg, 0.82 mmol) was added carefully in portions. The cloudy mixture was stirred at 23° C. and 1,1''-thiocarbonyldi-2(1H)-pyridone (153 mg, 0.66 mmol) was added carefully in portions. After 1 h, a solution of bicyclo[1.1.1]pentan-1-amine hydrochloride (commercially available from Pharmablock, 94 mg, 0.79 mmol) in DCM (0.5 mL) and diisopropylethylamine (0.15 mL, 0.86 mmol) was carefully added dropwise. After 18 h, 6-methoxypicolinohydrazide (commercially available from Milestone PharmTech USA Inc., 105 mg, 0.63 mmol) and then silver nitrate (192 mg, 1.13 mmol) were added carefully in portions. After 19 h, the mixture was filtered directly onto a silica gel column and purified (20-45% 3:1 EtOAc:EtOH in heptane). Fractions containing product were combined and then concentrated in vacuo to afford Example 263.1 (127 mg, 0.24 mmol, 46% yield) as a white foam that was used without further purification. LCMS ESI (pos.) m/z: 524.0 (M+H)+.

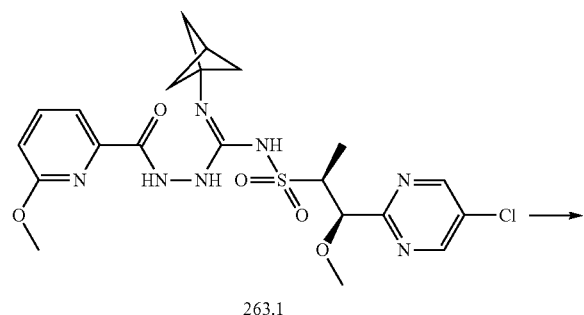

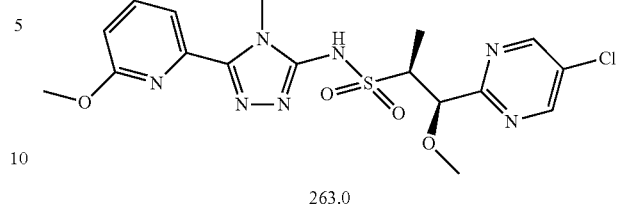

(1R,2S)—N-(4-(Bicyclo[1.1.1]pentan-1-yl)-5-(6-methoxypyridin-2-yl)-4H-1,2,4-triazol-3-yl)-1-(5-chloropyrimidin-2-yl)-1-methoxypropane-2-sulfonamide, Example 263.0

To a vial containing Example 263.1 (127 mg, 0.24 mmol) in IPA (0.7 mL) and water (0.3 mL) was added sodium hydroxide, (1.0 M, 0.32 mL, 0.32 mmol) carefully and dropwise to the reaction mixture. The mixture was heated on a preheated stir plate at 80° C. After 20 h, the reaction was cooled to room temperature and then diluted with water. The pH was carefully adjusted with dropwise addition of aqueous citric acid (1 N) solution to a pH~7. The reaction mixture was extracted three times with DCM. The organic layers were combined and then dried over anhydrous magnesium sulfate. After filtration and concentration in vacuo, the residue was loaded onto a silica gel column (15-45% 3:1 EtOAc:EtOH in heptane). Fractions containing product were combined and then concentrated in vacuo to afford a colorless film that was dissolved with DMSO and water and then filtered through a 0.45 syringe tip filter. The homogeneous solution was purified by preparative HPLC: 50u Silica Gel 19×100 mm+XSelect CSH Prep C18 10 u ODB 19×100 mm, A: Water 0.1% formic acid B: ACN 0.1% formic acid, Gradient: 25% (2 min), 25-70% (12 min), Flow Rate: 40 mL/min, monitored @ 215 nm. Fractions containing product were collected and then concentrated in vacuo to afford Example 263.0 (65 mg, 0.13 mmol, 53% yield) as a white solid. $^1$H NMR (400 MHz, CD$_2$Cl$_2$) δ 10.94 (br s, 1H), 8.73 (s, 2H), 7.73 (t, J=7.8 Hz, 1H), 7.21 (d, J=7.3 Hz, 1H), 6.93 (d, J=8.5 Hz, 1H), 4.99 (d, J=4.4 Hz, 1H), 3.97 (s, 3H), 3.69-3.61 (m, 1H), 3.29 (s, 3H), 2.47 (s, 1H), 2.29-2.22 (m, 6H), 1.40 (d, J=7.0 Hz, 3H). LCMS ESI (pos.) m/z: 506.0 (M+H)+.

Example 264.0. Preparation of (1R,2S)-1-(5-chloro-2-pyrimidinyl)-1-methoxy-N-(5-(6-methoxy-2-pyridinyl)-4-((1R)-1-(1,2-oxazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1,2-oxazol-3-yl)ethyl)-4H-1,2,4-triazol-3-yl)-2-propanesulfonamide

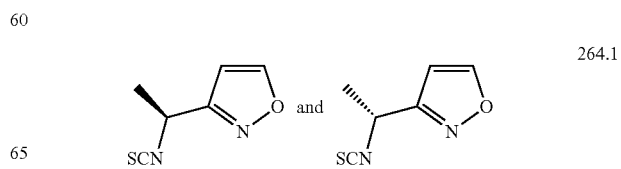

(S)-3-(1-Isothiocyanatoethyl)isoxazole and (R)-3-(1-isothiocyanatoethyl)isoxazole, Example 264.1

To a flask containing 1-(isoxazol-3-yl)ethanamine hydrochloride (commercially available from Enamine, 1.30 g, 8.8 mmol) in anhydrous DCM (35 mL) was added diisopropylethylamine (1.9 mL, 10.9 mmol) carefully and dropwise at 0° C. Upon complete addition, 1,1''-thiocarbonyldi-2(1H)-pyridone (2.124 g, 9.15 mmol) was added carefully in portions. The light orange homogeneous solution was allowed to warm to 23° C. After 30 minutes, the reaction was concentrated in vacuo and then loaded onto a silica gel column (5-20% EtOAc in heptane). Fractions containing desired product were combined and then concentrated in vacuo to afford Example 264.1 (1.02 g, 6.6 mmol, 76% yield) as a colorless liquid that used without further purification. $^1$H NMR (500 MHz, DMSO-$d_6$) δ=8.97 (d, J=1.6 Hz, 1H), 6.77 (d, J=1.6 Hz, 1H), 5.45 (q, J=6.7 Hz, 1H), 1.66 (d, J=6.7 Hz, 3H).

The compounds set forth in the following table were synthesized following the procedure in Example 264.1 using the known starting material as described.

TABLE 23

| Example | Reagents | Structure, Name, Data |
|---|---|---|
| 264.2 | isoxazol-5-ylmethanamine hydrochloride (commercially available from J&W Pharmlab). | 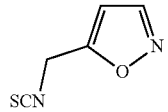<br>5-(isothiocyanatomethyl)isoxazole.<br>$^1$H NMR (400 MHz, CD$_2$Cl$_2$) δ 8.26 (d, J = 1.7 Hz, 1H), 6.35 (td, J = 0.8, 1.7 Hz, 1H), 4.85-4.83 (m, 2H).<br>LCMS ESI (pos.) m/z: 141.0 (M + H)$^+$. |
| 264.3 | (tetrahydrofuran-3-yl)methanamine hydrochloride. (commercially available from Enamine). | 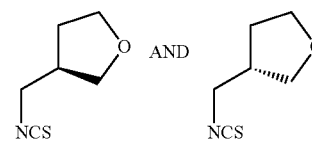<br>(R)-3-(isothiocyanatomethyl)tetrahydrofuran and (S)-3-(isothiocyanatomethyl)tetrahydrofuran.<br>LCMS ESI (pos.) m/z: 144.2 (M + H)$^+$. |
| 264.4 | (5,5-dimethyltetrahydrofuran-2-yl)methanamine hydrochloride (commercially available from Enamine). | 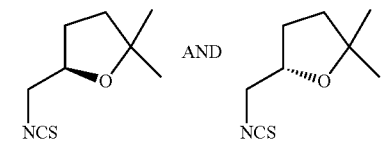<br>(R)-5-(isothiocyanatomethyl)-2,2-dimethyltetrahydrofuran and (S)-5-(isothiocyanatomethyl)-2,2-dimethyltetrahydrofuran.<br>LCMS ESI (pos.) m/z: 172.3 (M + H)$^+$. |
| 264.5 | (3-ethyl-1,2-oxazol-5-yl)methanamine (commercially available from Enamine). | 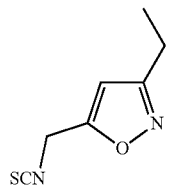<br>3-ethyl-5-(isothiocyanatomethyl)isoxazole.<br>LCMS ESI (pos.) m/z: 169.1 (M + H)$^+$. |
| 264.6 | 1-(1,2,3-thiadiazol-4-yl)ethan-1-amine (commercially available from Enamine). | 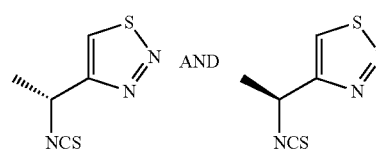<br>(R)-4-(1-isothiocyanatoethyl)-1,2,3-thiadiazole and (S)-4-(1-isothiocyanatoethyl)-1,2,3-thiadiazole.<br>$^1$H NMR (500 MHz, CD$_2$Cl$_2$) δ = 8.56 (s, 1H), 5.57 (q, J = 6.7 Hz, 1H), 1.90 (d, J = 6.7 Hz, 3H). |

TABLE 23-continued

| Example | Reagents | Structure, Name, Data |
|---|---|---|
| 264.7 | 1-(1-methyl-1H-pyrazol-4-yl)ethan-1-amine (commercially available from Enamine). | 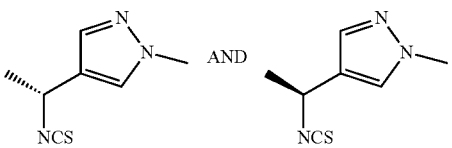<br>(R)-4-(1-isothiocyanatoethyl)-1-methyl-1H-pyrazole and (S)-4-(1-isothiocyanatoethyl)-1-methyl-1H-pyrazole. LCMS ESI (pos.) m/z: 168.0 (M + H)⁺. |
| 264.8 | (tetrahydro-2H-pyran-4-yl)methanamine (commercially available from Combi-Blocks). | 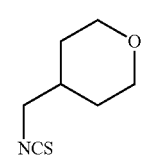<br>4-(isothiocyanatomethyl)tetrahydro-2H-pyran. LCMS-ESI (pos.) m/z: 158.3 (M + H)⁺. |
| 264.9 | 1-(1,4-dioxan-2-yl)methanamine (commercially available from Enamine). | 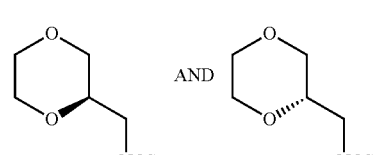<br>(R)-2-(isothiocyanatomethyl)-1,4-dioxane and (S)-2-(isothiocyanatomethyl)-1,4-dioxane. LCMS-ESI (pos.) m/z: 160.2 (M + H)⁺. |
| 264.10 | (6-methyloxan-2-yl)methanamine (commercially available from Enamine). | 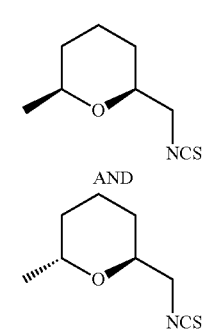<br>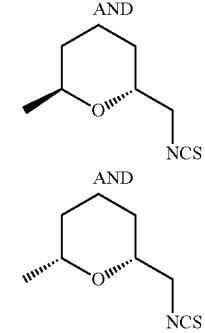<br>(2S,6S)-2-(isothiocyanatomethyl)-6-methyltetrahydro-2H-pyran and (2R,6R)-2-(isothiocyanatomethyl)-6-methyltetrahydro-2H-pyran and (2S,6R)-2-(isothiocyanatomethyl)-6-methyltetrahydro-2H-pyran and (2R,6S)-2-(isothiocyanatomethyl)-6-methyltetrahydro-2H-pyran. LCMS-ESI (pos.) m/z: 172.2 (M + H)⁺. |

TABLE 23-continued

| Example | Reagents | Structure, Name, Data |
|---|---|---|
| 264.11 | 1-(dimethyl-1,2-oxazol-4-yl)ethan-1-amine (commercially available from Enamine) | 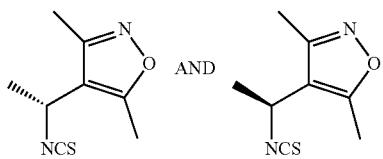<br>(R)-4-(1-isothiocyanatoethyl)-3,5-dimethylisoxazole and (S)-4-(1-isothiocyanatoethyl)-3,5-dimethylisoxazole.<br>LCMS-ESI (pos.) m/z: 183.2 (M + H)$^+$. |
| 264.12 | 3-(aminomethyl)tetrahydropyran (commercially available from Enamine) | 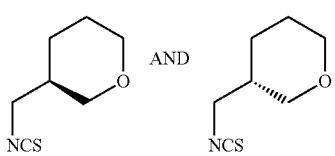<br>(R)-3-(isothiocyanatomethyl)tetrahydro-2H-pyran and (S)-3-(isothiocyanatomethyl)tetrahydro-2H-pyran.<br>LCMS-ESI (pos.) m/z: 158.2 (M + H)$^+$. |
| 264.13 | 1-(tetrahydro-2H-pyran-2-yl)ethanamine (commercially available from Enamine). | 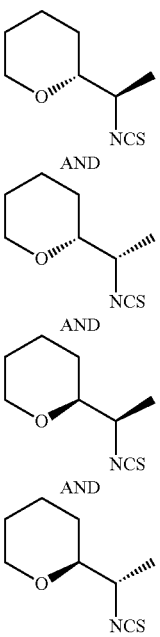<br>(R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran.<br>LCMS-ESI (pos.) m/z: 172.4 (M + H)$^+$. |
| 264.14 | 1-(oxan-2-yl)propan-1-amine (commercially available from Enamine). | 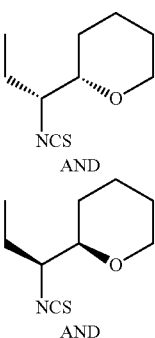 |

TABLE 23-continued

| Example | Reagents | Structure, Name, Data |
|---|---|---|
| | | 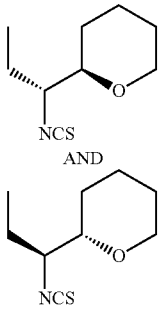
(R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran. LCMS-ESI (pos.) m/z: 186.0 (M + H)+. |

The compounds in the following table were synthesized following the procedure in Example 1.0 using the known starting material as described.

TABLE 24

| Example | Reagents | Structure, Name, Data |
|---|---|---|
| 264.0 | (1R,2S)-1-(5-chloropyrimidin-2-yl)-1-methoxypropane-2-sulfonamide (Example 29.3), (S)-3-(1-isothiocyanatoethyl)isoxazole and (R)-3-(1-isothiocyanatoethyl)isoxazole (Example 264.1, and 6-methoxypicolinohydrazide (commercially available from Milestone PharmTech USA Inc.). The racemic mixture was purified using the following preparative SFC method: Column: OZ-H (2 × 25 cm) + OJ-H (2 × 15 cm), Mobile Phase: 55:45 (A:B) A: Liquid CO₂, B: MeOH, Flow Rate: 80 mL/min, 294 nm, 100 bar inlet pressure to deliver peak 1. | 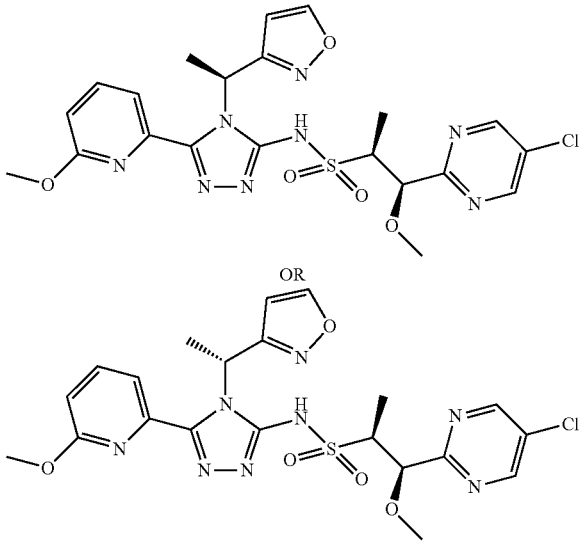
(1R,2S)-1-(5-chloro-2-pyrimidinyl)-1-methoxy-N-(5-(6-methoxy-2-pyridinyl)-4-((1R)-1-(1,2-oxazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1,2-oxazol-3-yl)ethyl)-4H-1,2,4-triazol-3-yl)-2-propanesulfonamide.
¹H NMR (400 MHz, DMSO-d₆) δ 13.21 (s, 1H), 8.93 (s, 2H), 8.82 (s, 1H), 7.88 (t, J = 7.9 Hz, 1H), 7.56 (d, J = 7.5 Hz, 1H), 6.98 (d, J = 8.3 Hz, 1H), 6.59 (s, 1H), 6.56-6.47 (m, 1H), 4.74 (d, J = 4.4 Hz, 1H), 3.74 (s, 3H), 3.47-3.35 (m, 1H), 3.15 (s, 3H), 1.96 (d, J = 6.8 Hz, 3H), 1.13 (d, J = 6.8 Hz, 3H). LCMS ESI (pos.) m/z: 535.0 (M + H)+. |

TABLE 24-continued

| Example | Reagents | Structure, Name, Data |
|---|---|---|
| 265.0 | (1R,2S)-1-(5-chloropyrimidin-2-yl)-1-methoxypropane-2-sulfonamide (Example 29.3), (S)-3-(1-isothiocyanatoethyl)isoxazole and (R)-3-(1-isothiocyanatoethyl)isoxazole (Example 264.1), and 6-methoxypicolinohydrazide (commercially available from Milestone PharmTech USA Inc.). The racemic mixture was purified using the following preparative SFC method: Column: OZ-H (2 × 25 cm) + OJ-H (2 × 15 cm), Mobile Phase: 55:45 (A:B) A: Liquid $CO_2$, B: MeOH, Flow Rate: 80 mL/min, 294 nm, 100 bar inlet pressure to deliver peak 2. | 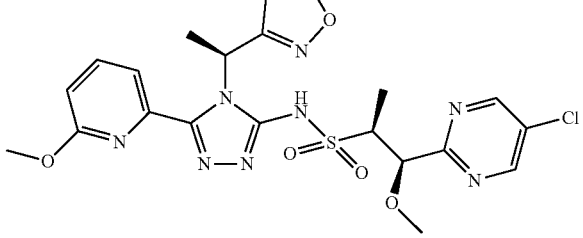<br>OR<br>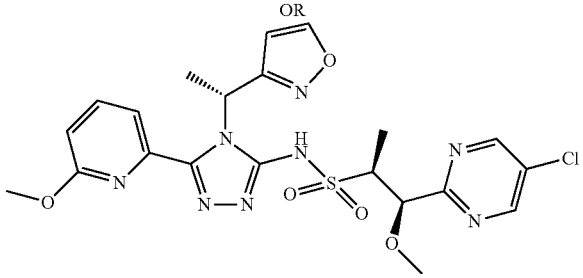<br>(1R,2S)-1-(5-chloro-2-pyrimidinyl)-1-methoxy-N-(5-(6-methoxy-2-pyridinyl)-4-((1R)-1-(1,2-oxazol-3-yl)ethyl)-4H-1,2,4-triazol-3-yl)-2-propanesulfonamide or (1R,2S)-1-(5-chloro-2-pyrimidinyl)-1-methoxy-N-(5-(6-methoxy-2-pyridinyl)-4-((1S)-1-(1,2-oxazol-3-yl)ethyl)-4H-1,2,4-triazol-3-yl)-2-propanesulfonamide.<br>$^1$H NMR (400 MHz, DMSO-$d_6$) δ 13.24 (br s, 1H), 8.93 (s, 2H), 8.85 (s, 1H), 7.89 (t, J = 7.9 Hz, 1H), 7.56 (d, J = 7.5 Hz, 1H), 6.99 (d, J = 8.3 Hz, 1H), 6.60 (s, 1H), 6.59-6.51 (m, 1H), 4.76 (d, J = 4.8 Hz, 1H), 3.75 (s, 3H), 3.47-3.35 (m, 1H), 3.15 (s, 3H), 1.97 (d, J = 7.0 Hz, 3H), 1.14 (d, J = 6.8 Hz, 3H). LCMS ESI ESI (pos.) m/z: 535.0 (M + H)$^+$. |
| 266.0 | (1R,2S)-1-(5-chloropyrimidin-2-yl)-1-methoxypropane-2-sulfonamide (Example 29.3), 5-(isothiocyanatomethyl)isoxazole, (Example 264.2), and 6-methoxypicolinohydrazide (commercially available from Milestone PharmTech USA Inc.). | 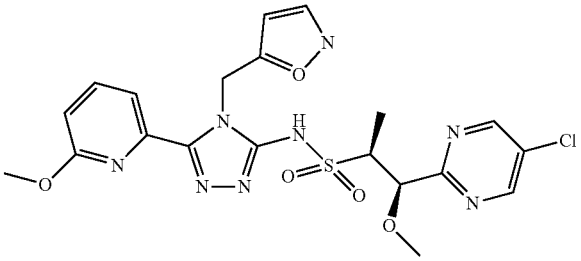<br>(1R,2S)-1-(5-chloropyrimidin-2-yl)-N-(4-(isoxazol-5-ylmethyl)-5-(6-methoxypyridin-2-yl)-4H-1,2,4-triazol-3-yl)-1-methoxypropane-2-sulfonamide.<br>$^1$H NMR (400 MHz, $CD_2Cl_2$) δ 8.73-8.70 (m, 2H), 8.16 (d, J = 1.7 Hz, 1H), 7.76-7.69 (m, 2H), 6.89 (dd, J = 1.1, 8.0 Hz, 1H), 6.25-6.21 (m, 1H), 5.90 (s, 2H), 4.91 (d, J = 4.6 Hz, 1H), 3.81 (s, 3H), 3.70-3.63 (m, 1H), 3.24 (s, 3H), 1.32 (d, J = 7.0 Hz, 3H). LCMS ESI (pos.) m/z: 521.0 (M + H)$^+$. |
| 267.0 | (2S,3R)-3-(5-chloropyrimidin-2-yl)butane-2-sulfonamide (Example 27.4), (S)-3-(1-isothiocyanatoethyl)isoxazole and (R)-3-(1-isothiocyanatoethyl)isoxazole (Example 264.1), and 6-methoxypicolinohydrazide (commercially available from Milestone PharmTech USA Inc.). The racemic mixture was purified using the following preparative SFC | 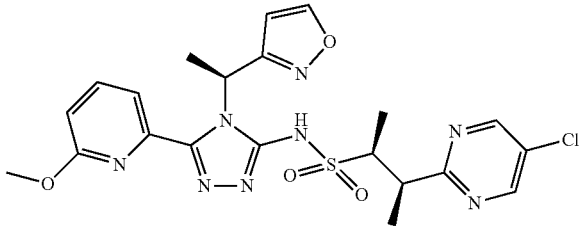 [SMILES: COc1cccc(-c2nnc(NS(=O)(=O)[C@@H](C)[C@H](C)c3ncc(Cl)cn3)n2[C@@H](C)c2ccon2)n1]<br>OR |

TABLE 24-continued

| Example | Reagents | Structure, Name, Data |
|---|---|---|
| | method: Column: AD-H (2 × 25 cm), Mobile Phase: 60:40 (A:B) A: Liquid CO₂, B: MeOH, Flow Rate: 80 mL/min, 217 nm, 100 bar inlet pressure to deliver peak 1. | 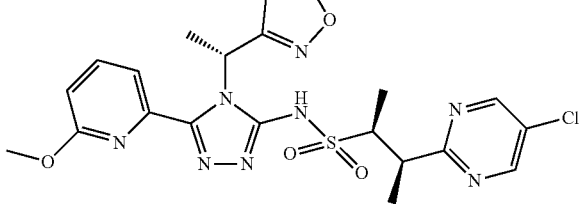<br>(2S,3R)-3-(5-chloropyrimidin-2-yl)-N-(4-((R)-1-(isoxazol-3-yl)ethyl)-5-(6-methoxypyridin-2-yl)-4H-1,2,4-triazol-3-yl)butane-2-sulfonamide or (2S,3R)-3-(5-chloropyrimidin-2-yl)-N-(4-((S)-1-(isoxazol-3-yl)ethyl)-5-(6-methoxypyridin-2-yl)-4H-1,2,4-triazol-3-yl)butane-2-sulfonamide.<br>¹H NMR (500 MHz, DMSO-d₆) δ 13.20 (br s, 1H), 8.90-8.78 (m, 3H), 7.90 (t, J = 7.8 Hz, 1H), 7.58 (d, J = 7.5 Hz, 1H), 6.99 (d, J = 8.3 Hz, 1H), 6.64-6.53 (m, 2H), 3.75 (s, 3H), 3.61-3.47 (m, 2H), 1.94 (br d, J = 7.0 Hz, 3H), 1.24 (br d, J = 6.5 Hz, 3H), 1.13-1.06 m, 3H). LCMS ESI (pos.) m/z: 519.0 (M + H)⁺. |
| 268.0 | (2S,3R)-3-(5-chloropyrimidin-2-yl)butane-2-sulfonamide (Example 27.4), (S)-3-(1-isothiocyanatoethyl)isoxazole and (R)-3-(1-isothiocyanatoethyl)isoxazole (Example 264.1), and 6-methoxypicolinohydrazide (commercially available from Milestone PharmTech USA Inc.). The racemic mixture was purified using the following preparative SFC method: Column: AD-H (2 × 25 cm), Mobile Phase: 60:40 (A:B) A: Liquid CO₂, B: MeOH, Flow Rate: 80 mL/min, 217 nm, 100 bar inlet pressure to deliver peak 2. | 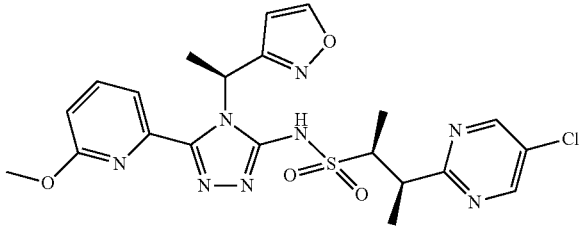 [SMILES: COc1cccc(-c2nnc(NS(=O)(=O)[C@@H](C)[C@H](C)c3ncc(Cl)cn3)n2[C@@H](C)c2ccon2)n1]<br>OR<br>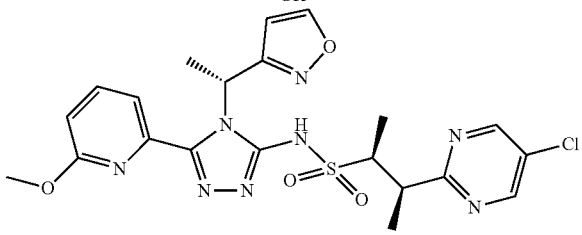<br>(2S,3R)-3-(5-chloropyrimidin-2-yl)-N-(4-((R)-1-(isoxazol-3-yl)ethyl)-5-(6-methoxypyridin-2-yl)-4H-1,2,4-triazol-3-yl)butane-2-sulfonamide or (2S,3R)-3-(5-chloropyrimidin-2-yl)-N-(4-((S)-1-(isoxazol-3-yl)ethyl)-5-(6-methoxypyridin-2-yl)-4H-1,2,4-triazol-3-yl)butane-2-sulfonamide.<br>¹H NMR (500 MHz, DMSO-d₆) δ 13.22 (s, 1H), 8.86-8.82 (m, 3H), 7.90 (t, J = 7.8 Hz, 1H), 7.58 (d, J = 7.3 Hz, 1H), 6.99 (d, J = 8.6 Hz, 1H), 6.62-6.55 (m, 2H), 3.76 (s, 3H), 3.62-3.56 (m, 1H), 3.55-3.49 (m, 1H), 1.96 (d, J = 7.0 Hz, 3H), 1.23 (d, J = 7.0 Hz, 3H), 1.04 (d, J = 7.0 Hz, 3H). LCMS ESI (pos.) m/z: 519.0 (M + H)⁺. |
| 269.0 | (1S,2S)-1-isopropoxy-1-(5-methylpyrimidin-2-yl)propane-2-sulfonamide (Example 31.0), (S)-3-(1-isothiocyanatoethyl)isoxazole and (R)-3-(1-isothiocyanatoethyl)isoxazole, (Example 264.1), and 6-methoxypicolinohydrazide (commercially available from Milestone PharmTech USA Inc.). The racemic mixture was purified using the following preparative SFC method: Column: IC (2 × 25 cm), Mobile Phase: 55:45 (A:B) A: Liquid CO₂, B: EtOH, Flow Rate: | 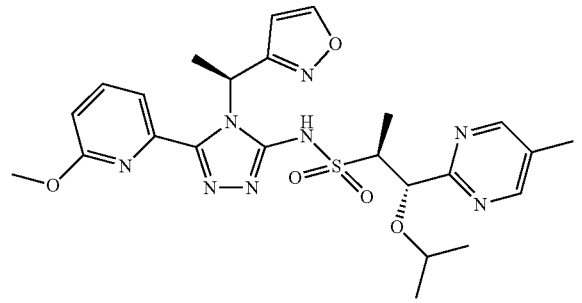<br>OR |

| Example | Reagents | Structure, Name, Data |
|---|---|---|
| | 80 mL/min, 220 nm, 100 bar inlet pressure to deliver peak 1. | 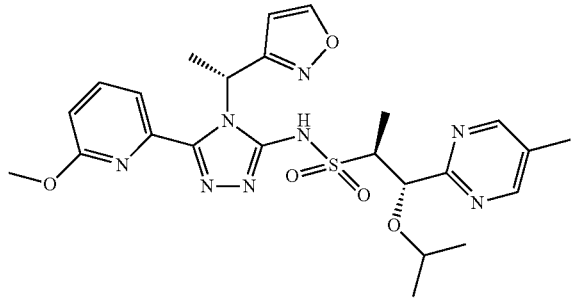<br><br>(1S,2S)-1-isopropoxy-N-(4-((R)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide or (1S,2S)-1-isopropoxy-N-(4-((S)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide.<br>$^1$H NMR (500 MHz, DMSO-d$_6$) δ 13.20 (br s, 1H), 8.82 (d, J = 1.3 Hz, 1H), 8.67 (s, 2H), 7.88 (t, J = 7.9 Hz, 1H), 7.54 (d, J = 7.5 Hz, 1H), 6.97 (d, J = 8.3 Hz, 1H), 6.63 (s, 1H), 6.46 (q, J = 6.9 Hz, 1H), 4.77 (d, J = 7.5 Hz, 1H), 3.74 (s, 3H), 3.51-3.42 (m, 1H), 3.41-3.35 (m, 1H), 2.27 (s, 3H), 1.96 (d, J = 7.0 Hz, 3H), 1.03 (d, J = 6.0 Hz, 3H), 0.94 (d, J = 7.0 Hz, 3H), 0.76 (d, J = 6.2 Hz, 3H). LCMS ESI (pos.) m/z: 543.2 (M + H)$^+$. |
| 270.0 | (1S,2S)-1-isopropoxy-1-(5-methylpyrimidin-2-yl)propane-2-sulfonamide (Example 31.0), (S)-3-(1-isothiocyanatoethyl)isoxazole and (R)-3-(1-isothiocyanatoethyl)isoxazole (Example 264.1), and 6-methoxypicolinohydrazide (commercially available from Milestone PharmTech USA Inc.). The racemic mixture was purified using the following preparative SFC method: Column: IC (2 × 25 cm), Mobile Phase: 55:45 (A:B) A: Liquid CO$_2$, B: EtOH, Flow Rate: 80 mL/min, 220 nm, 100 bar inlet pressure to deliver peak 2. | 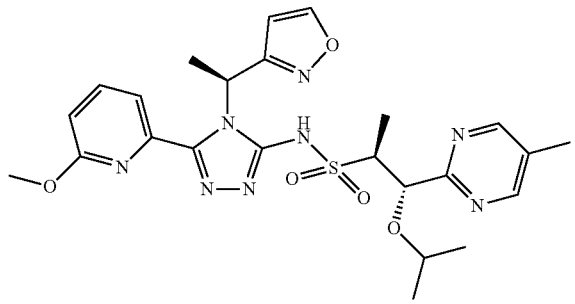<br><br>(1S,2S)-1-isopropoxy-N-(4-((R)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide or (1S,2S)-1-isopropoxy-N-(4-((S)-1-(isoxazol-3-yl)ethyl)-5-(6-methoxypyridin-2-yl)-4H-1,2,4-triazol-3-yl)-1-(5-methylpyrimidin-2-yl)propane-2-sulfonamide.<br>$^1$H NMR (400 MHz, CD$_2$Cl$_2$) δ 12.83 (br s, 1H), 8.63 (s, 2H), 8.36 (d, J = 1.7 Hz, 1H), 7.73 (dd, J = 7.6, 8.2 Hz, 1H), 7.57 (d, J = 7.5 Hz, 1H), 6.87 (d, J = 8.3 Hz, 1H), 6.73 (q, J = 7.1 Hz, 1H), 6.51 (d, J = 1.5 Hz, 1H), 4.78 (d, J = 3.7 Hz, 1H), 3.85 (s, 3H), 3.67-3.59 (m, 1H), 3.49-3.41 (m, 1H), 2.34 (s, 3H), 2.06 (d, J = 7.0 Hz, 3H), 1.33 (d, J = 7.0 Hz, 3H), 1.02 (d, J = 6.0 Hz, 3H), 0.89 (d, J = 6.2 Hz, 3H). LCMS ESI (pos.) m/z: 543.2 (M + H)$^+$. |

TABLE 24-continued

| Example | Reagents | Structure, Name, Data |
|---|---|---|
| 271.0 | (1R,2S)-1-(5-chloropyrimidin-2-yl)-1-methoxypropane-2-sulfonamide (Example 29.3), 3-(isothiocyanatomethyl)-5-methylisoxazole (commercially available from Enamine), and 6-methoxypicolinohydrazide (commercially available from Milestone PharmTech USA Inc.). | 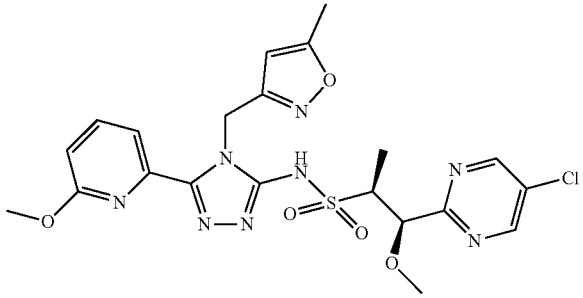 [SMILES: COc1cccc(-c2nnc(NS(=O)(=O)[C@@H](C)[C@H](OC)c3ncc(Cl)cn3)n2Cc2cc(C)on2)n1]<br>(1R,2S)-1-(5-chloropyrimidin-2-yl)-1-methoxy-N-(5-(6-methoxypyridin-2-yl)-4-((5-methylisoxazol-3-yl)methyl)-4H-1,2,4-triazol-3-yl)propane-2-sulfonamide.<br>$^1$H NMR (500 MHz, DMSO-d$_6$) δ 13.38 (br s, 1H), 8.91 (s, 2H), 7.89-7.85 (m, 1H), 7.66 (d, J = 7.0 Hz, 1H), 6.96 (d, J = 8.3 Hz, 1H), 6.17 (s, 1H), 5.66 (d, J = 16.6 Hz, 1H), 5.48 (d, J = 16.3 Hz, 1H), 4.76 (d, J = 5.2 Hz, 1H), 3.74 (s, 3H), 3.63-3.56 (m, 1H), 3.13 (s, 3H), 2.31 (s, 3H), 1.25 (d, J = 7.0 Hz, 3H).<br>LCMS ESI (pos.) m/z: 535.2 (M + H)$^+$. |
| 272.0 | (2S,3R)-3-(5-chloropyrimidin-2-yl)butane-2-sulfonamide (Example 27.4), 3-(isothiocyanatomethyl)-5-methylisoxazole (commercially available from Enamine), and 6-methoxypicolinohydrazide (commercially available from Milestone PharmTech USA Inc.). | 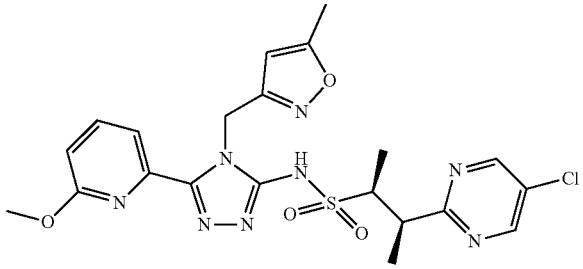 [SMILES: COc1cccc(-c2nnc(NS(=O)(=O)[C@@H](C)[C@H](C)c3ncc(Cl)cn3)n2Cc2cc(C)on2)n1]<br>(2S,3R)-3-(5-chloropyrimidin-2-yl)-N-(5-(6-methoxypyridin-2-yl)-4-((5-methylisoxazol-3-yl)methyl)-4H-1,2,4-triazol-3-yl)butane-2-sulfonamide.<br>$^1$H NMR (500 MHz, DMSO-d$_6$) δ 13.34 (s, 1H), 8.82 (s, 2H), 7.87 (t, J = 7.9 Hz, 1H), 7.66 (d, J = 7.5 Hz, 1H), 6.96 (d, J = 8.3 Hz, 1H), 6.15 (s, 1H), 5.60 (d, J = 16.3 Hz, 1H), 5.51-5.45 (m, 1H), 3.73 (s, 3H), 3.72-3.68 (m, 1H), 3.64-3.59 (m, 1H), 2.30 (s, 3H), 1.28-1.24 (m, 3H), 1.23-1.18 (m, 3H).<br>LCMS ESI (pos.) m/z: 519.2 (M + H)$^+$. |
| 273.0 | (1S,2S)-1-isopropoxy-1-(5-methylpyrimidin-2-yl)propane-2-sulfonamide (Example 31.0), (R)-2-((R)-1-isothiocyanatoethyl)tetrahydrofuran and (R)-2-((S)-1-isothiocyanatoethyl)tetrahydrofuran and (S)-2-((S)-1-isothiocyanatoethyl)tetrahydrofuran and (S)-2-((R)-1-isothiocyanatoethyl)tetrahydrofuran, (commercially available from Enamine), and 6-methoxypicolinohydrazide (commercially available from | 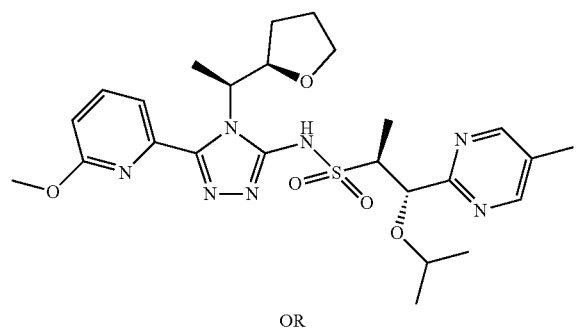<br>OR |

TABLE 24-continued

| Example | Reagents | Structure, Name, Data |
|---|---|---|
| | Milestone PharmTech USA Inc.). The racemic mixture was purified using the following preparative SFC method: Column AD-H (2 × 25 cm) + AD-H (2 × 15 cm), Mobile Phase: 80:20 (A:B) A: Liquid CO$_2$, B: IPA, Flow Rate: 70 mL/min, 295 nm, 100 bar inlet pressure to deliver peak 1. | 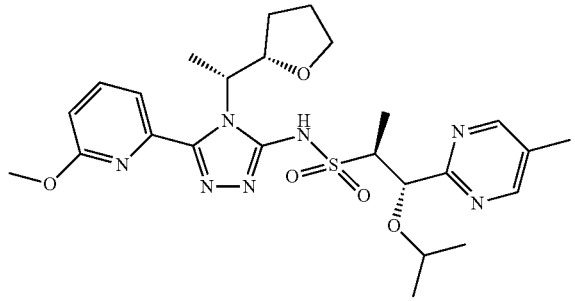<br>OR<br>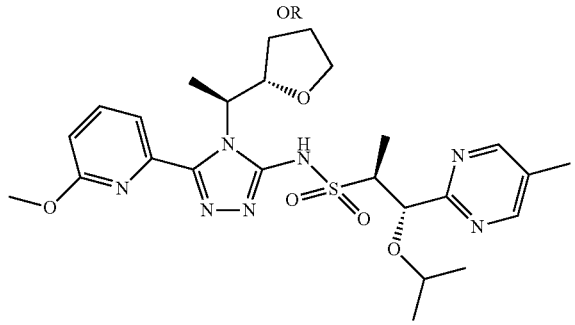<br>OR<br>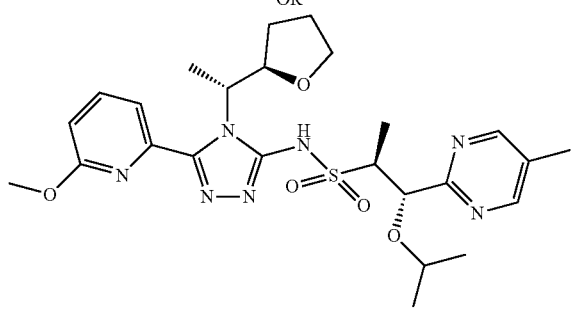<br>(1S,2S)-1-isopropoxy-N-(5-(6-methoxypyridin-2-yl)-4-((R)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((R)-tetrahydrofuran-2-yl)ethyl)-4H-1,2,4-triazol-3-yl)-1-(5-methylpyrimidin-2-yl)propane-2-sulfonamide.<br>$^1$H-NMR (500 MHz, CD$_2$Cl$_2$) δ = 12.93-12.39 (m, 1H), 8.63 (s, 2H), 7.74 (dd, J = 7.3, 8.3 Hz, 1H), 7.51 (d, J = 7.3 Hz, 1H), 6.90 (d, J = 8.3 Hz, 1H), 5.05 (br s, 1H), 4.84 (d, J = 3.6 Hz, 1H), 4.79 (td, J = 6.9, 9.3 Hz, 1H), 3.95 (s, 3H), 3.82-3.74 (m, 2H), 3.73-3.67 (m, 1H), 3.51 (td, J = 6.1, 12.2 Hz, 1H), 2.34 (s, 3H), 1.97-1.90 (m, 1H), 1.89-1.78 (m, 2H), 1.71-1.57 (m, 4H), 1.55 (d, J = 7.0 Hz, 3H), 1.06 (d, J = 6.0 Hz, 3H), 0.88 (d, J = 6.2 Hz, 3H). LCMS ESI (pos.) m/z: 546.2 (M + H)$^+$. |

TABLE 24-continued

| Example | Reagents | Structure, Name, Data |
|---|---|---|
| 274.0 | (1S,2S)-1-isopropoxy-1-(5-methylpyrimidin-2-yl)propane-2-sulfonamide (Example 31.0), (R)-2-((R)-1-isothiocyanatoethyl)tetrahydrofuran and (R)-2-((S)-1-isothiocyanatoethyl)tetrahydrofuran and (S)-2-((S)-1-isothiocyanatoethyl)tetrahydrofuran and (S)-2-((R)-1-isothiocyanatoethyl)tetrahydrofuran, (commercially available from Enamine), and 6-methoxypicolinohydrazide (commercially available from Milestone PharmTech USA Inc.). The racemic mixture was purified using the following preparative SFC method: Column AD-H (2 × 25 cm) + AD-H (2 × 15 cm), Mobile Phase: 80:20 (A:B) A: Liquid $CO_2$, B: IPA, Flow Rate: 70 mL/min, 295 nm, 100 bar inlet pressure to deliver peak 2. | 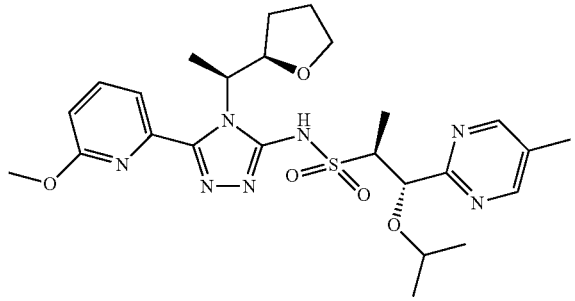<br>OR<br>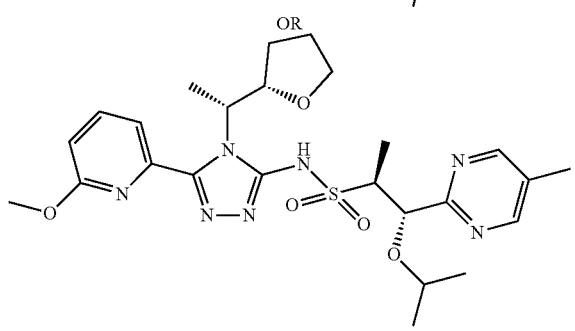<br>OR<br>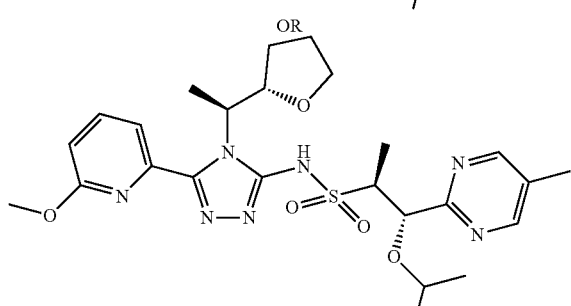<br>OR<br>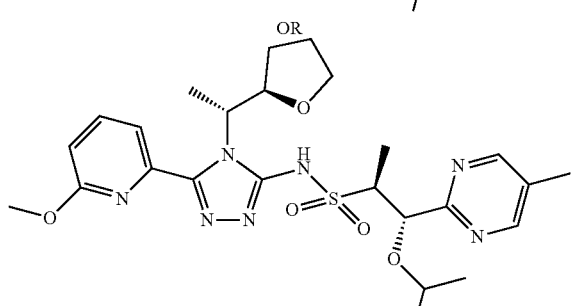<br>(1S,2S)-1-isopropoxy-N-(5-(6-methoxypyridin-2-yl)-4-((R)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((R)-tetrahydrofuran-2-yl)ethyl)-4H-1,2,4-triazol-3-yl)-1-(5-methylpyrimidin-2-yl)propane-2-sulfonamide.<br>$^1$H NMR (500 MHz, $CD_2Cl_2$) δ 12.62-12.17 (m, 1H), 8.62 (s, 2H), 7.74 (dd, J = 7.5, 8.3 Hz, 1H), 7.53 (d, J = 7.3 Hz, 1H), 6.88 (d, J = 8.3 Hz, 1H), 5.08 (br s, 1H), 4.85 (d, J = 3.9 Hz, 1H), 4.83-4.68 (m, 1H), |

TABLE 24-continued

| Example | Reagents | Structure, Name, Data |
|---|---|---|
| | | 3.95 (s, 3H), 3.69 (dq, J = 4.0, 7.0 Hz, 1H), 3.62 (dt, J = 5.6, 8.0 Hz, 1H), 3.55-3.48 (m, 2H), 2.33 (s, 3H), 2.13-2.03 (m, 1H), 1.91-1.79 (m, 2H), 1.65 (d, J = 7.0 Hz, 3H), 1.50 (d, J = 7.0 Hz, 3H), 1.49-1.43 (m, 1H), 1.06 (d, J = 6.0 Hz, 3H), 0.89 (d, J = 6.0 Hz, 3H). LCMS ESI (pos.) m/z: 546.2 (M + H)+. |
| 275.0 | (1S,2S)-1-isopropoxy-1-(5-methylpyrimidin-2-yl)propane-2-sulfonamide (Example 31.0), (R)-2-((R)-1-isothiocyanatoethyl)tetrahydrofuran and (R)-2-((S)-1-isothiocyanatoethyl)tetrahydrofuran and (S)-2-((S)-1-isothiocyanatoethyl)tetrahydrofuran and (S)-2-((R)-1-isothiocyanatoethyl)tetrahydrofuran, (commercially available from Enamine), and 6-methoxypicolinohydrazide (commercially available from Milestone PharmTech USA Inc.). The racemic mixture was purified using the following preparative SFC method: Column AD-H (2 × 25 cm) + AD-H (2 × 15 cm), Mobile Phase: 80:20 (A:B) A: Liquid CO2, B: IPA, Flow Rate: 70 mL/min, 295 nm, 100 bar inlet pressure to deliver peak 3. | 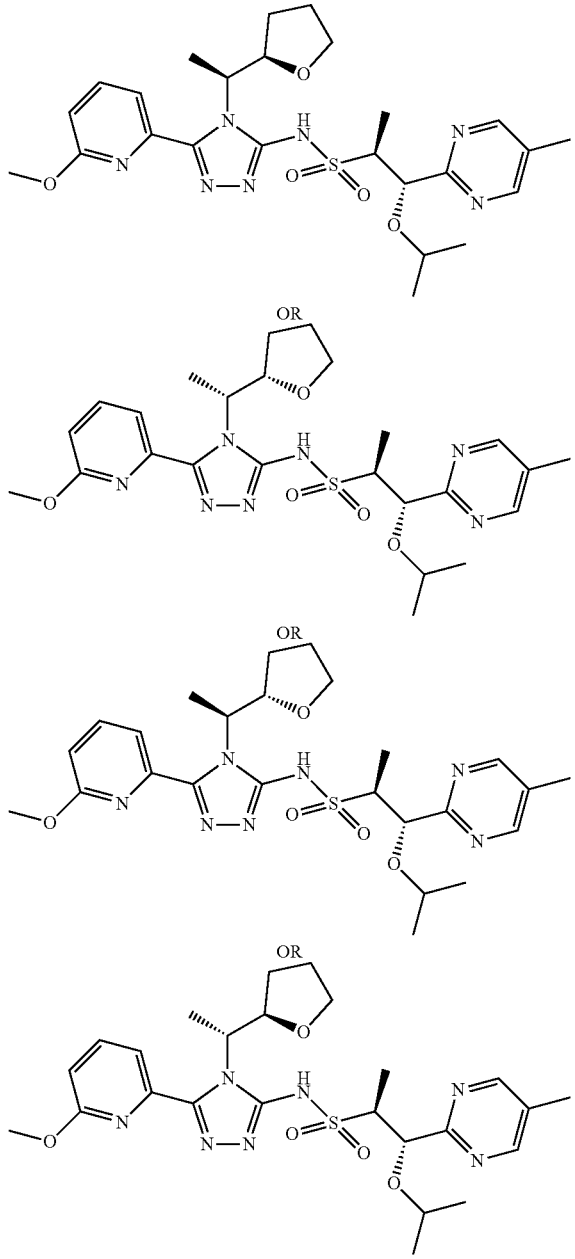 (1S,2S)-1-isopropoxy-N-(5-(6-methoxypyridin-2-yl)-4-((R)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6- |

TABLE 24-continued

| Example | Reagents | Structure, Name, Data |
|---|---|---|
| | | methoxypyridin-2-yl)-4-((S)-1-((R)-tetrahydrofuran-2-yl)ethyl)-4H-1,2,4-triazol-3-yl)-1-(5-methylpyrimidin-2-yl)propane-2-sulfonamide. <br> $^1$H NMR (500 MHz, CD$_2$Cl$_2$) δ 12.98-12.51 (m, 1H), 8.64 (s, 2H), 7.74 (dd, J = 7.5, 8.3 Hz, 1H), 7.51 (d, J = 7.3 Hz, 1H), 6.91-6.88 (m, 1H), 5.11 (br s, 1H), 4.86 (d, J = 4.2 Hz, 1H), 4.85-4.76 (m, 1H), 3.95 (s, 3H), 3.80 (t, J = 7.0 Hz, 2H), 3.70 (dq, J = 4.0, 7.0 Hz, 1H), 3.50 (td, J = 6.1, 12.2 Hz, 1H), 2.34 (s, 3H), 2.09-1.98 (m, 1H), 1.92-1.77 (m, 2H), 1.66 (d, J = 6.7 Hz, 3H), 1.60-1.53 (m, 1H), 1.51 (d, J = 7.0 Hz, 3H), 1.08 (d, J = 6.0 Hz, 3H), 0.93 (d, J = 6.2 Hz, 3H). LCMS ESI (pos.) m/z: 546.2 (M + H)$^+$. |
| 276.0 | (1S,2S)-1-isopropoxy-1-(5-methylpyrimidin-2-yl)propane-2-sulfonamide (Example 31.0), (R)-2-((R-1-isothiocyanatoethyl)tetrahydrofuran and (R)-2-((S)-1-isothiocyanatoethyl)tetrahydrofuran and (S)-2-((S)-1-isothiocyanatoethyl)tetrahydrofuran and (S)-2-((R)-1-isothiocyanatoethyl)tetrahydrofuran, (commercially available from Enamine), and 6-methoxypicolinohydrazide (commercially available from Milestone PharmTech USA Inc.). The racemic mixture was purified using the following preparative SFC method: Column AD-H (2 × 25 cm) + AD-H (2 × 15 cm), Mobile Phase: 80:20 (A:B) A: Liquid CO$_2$, B: IPA, Flow Rate: 70 mL/min, 295 nm, 100 bar inlet pressure to deliver peak 4. | 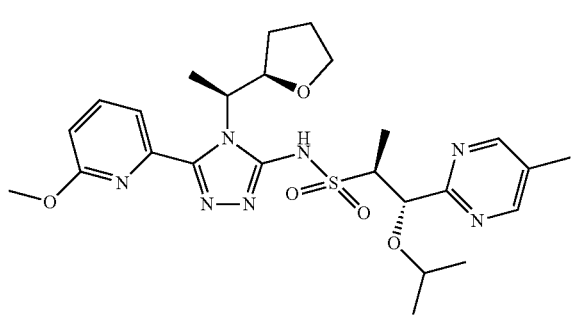 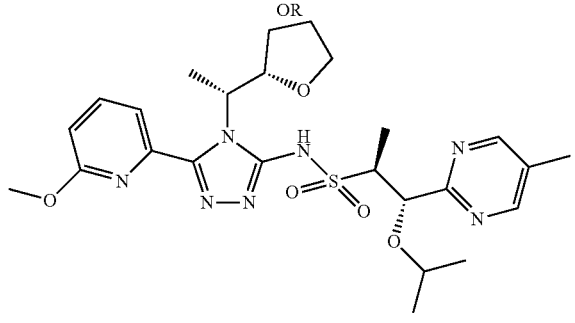 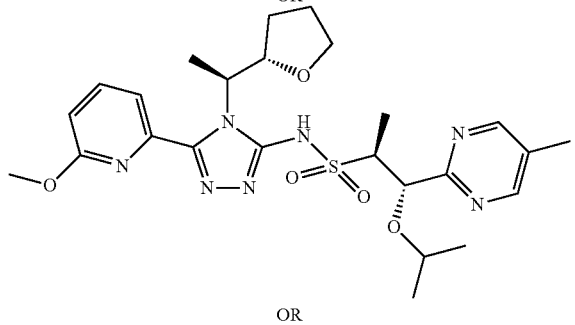 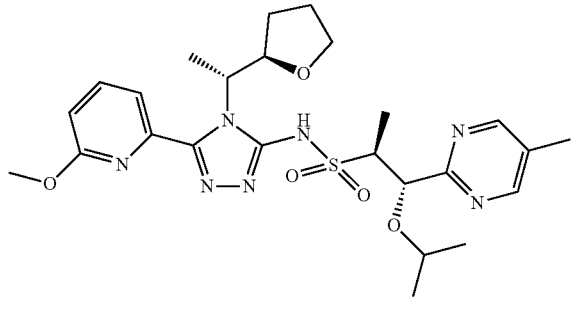 (1S,2S)-1-isopropoxy-N-(5-(6-methoxypyridin-2-yl)-4-((R)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6- |

TABLE 24-continued

| Example | Reagents | Structure, Name, Data |
|---|---|---|
| | | methoxypyridin-2-yl)-4-((R)-1-((R)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydrofuran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((R)-tetrahydrofuran-2-yl)ethyl)-4H-1,2,4-triazol-3-yl)-1-(5-methylpyrimidin-2-yl)propane-2-sulfonamide. $^1$H NMR (500 MHz, CD$_2$Cl$_2$) δ = 12.26 (br s, 1H), 8.62 (s, 2H), 7.73 (dd, J = 7.5, 8.3 Hz, 1H), 7.52 (d, J = 7.3 Hz, 1H), 6.87 (d, J = 8.3 Hz, 1H), 5.10 (br s, 1H), 4.86 (d, J = 4.7 Hz, 1H), 4.84-4.66 (m, 1H), 3.94 (s, 3H), 3.69 (dq, J = 4.8, 7.0 Hz, 1H), 3.64-3.59 (m, 1H), 3.55 (q, J = 7.3 Hz, 1H), 3.48 (spt, J = 6.1 Hz, 1H), 2.33 (s, 3H), 2.11-2.04 (m, 1H), 1.92-1.77 (m, 2H), 1.65 (d, J = 7.0 Hz, 3H), 1.49-1.41 (m, 4H), 1.06 (d, J = 6.0 Hz, 3H), 0.93 (d, J = 6.0 Hz, 3H). LCMS ESI (pos.) m/z: 546.2 (M + H)$^+$. |
| 277.0 | (1S,2S)-1-isopropoxy-1-(5-methylpyrimidin-2-yl)propane-2-sulfonamide (Example 31.0), (R)-2-(isothiocyanatomethyl)tetrahydrofuran and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified using the following preparative SFC method: Column Regis Whelk-O s,s (2 × 25 cm) + Regis Whelk-O s,s (2 × 15 cm) + Regis Whelk-O s,s (2 × 15 cm), Mobile Phase: 55:45 (A:B) A: Liquid CO$_2$, B: IPA, Flow Rate: 50 mL/min, 215 nm, 100 bar inlet pressure to deliver peak 1. | 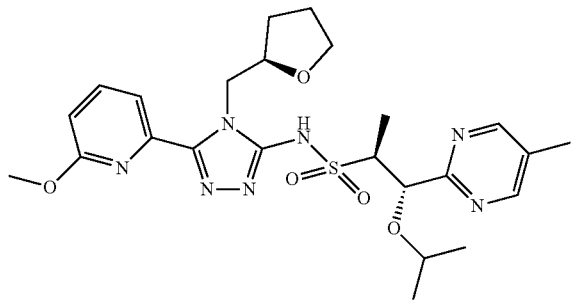<br><br>OR<br><br>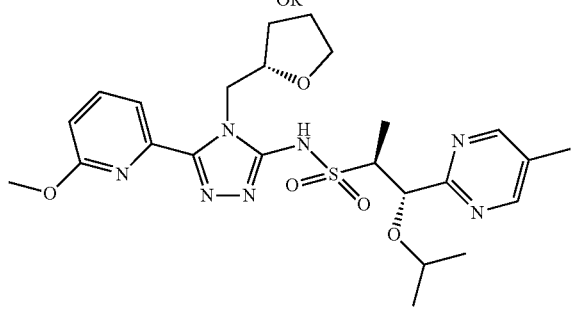<br><br>(1S,2S)-1-isopropoxy-N-(5-(6-methoxypyridin-2-yl)-4-(((R)-tetrahydrofuran-2-yl)methyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-(((S)-tetrahydrofuran-2-yl)methyl)-4H-1,2,4-triazol-3-yl)-1-(5-methylpyrimidin-2-yl)propane-2-sulfonamide. $^1$H NMR (500 MHz, CD$_2$Cl$_2$) δ = 12.57 (br s, 1H), 8.63 (s, 2H), 7.73 (dd, J = 7.3, 8.3 Hz, 1H), 7.64-7.61 (m, 1H), 6.87 (dd, J = 0.8, 8.3 Hz, 1H), 4.86 (d, J = 4.4 Hz, 1H), 4.60 (dd, J = 7.5, 13.5 Hz, 1H), 4.46 (dd, J = 4.9, 13.5 Hz, 1H), 4.27-4.20 (m, 1H), 3.96 (s, 3H), 3.75-3.67 (m, 1H), 3.58 (t, J = 6.9 Hz, 2H), 3.52-3.47 (m, 1H), 2.33 (s, 3H), 1.98-1.92 (m, 1H), 1.91-1.78 (m, 2H), 1.74-1.67 (m, 1H), 1.48 (d, J = 7.0 Hz, 3H), 1.05 (d, J = 6.0 Hz, 3H), 0.90 (d, J = 6.2 Hz, 3H). LCMS ESI (pos.) m/z: 532.3 (M + H)$^+$. |

TABLE 24-continued

| Example | Reagents | Structure, Name, Data |
|---|---|---|
| 278.0 | (1S,2S)-1-isopropoxy-1-(5-methylpyrimidin-2-yl)propane-2-sulfonamide (Example 31.0), (R)-2-(isothiocyanatomethyl)tetrahydrofuran and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified using the following preparative SFC method: Column Regis Whelk-O s,s (2 × 25 cm) + Regis Whelk-O s,s (2 × 15 cm) + Regis Whelk-O s,s (2 × 15 cm), Mobile Phase: 55:45 (A:B) A: Liquid CO$_2$, B: IPA, Flow Rate: 50 mL/min, 215 nm, 100 bar inlet pressure to deliver peak 2. | 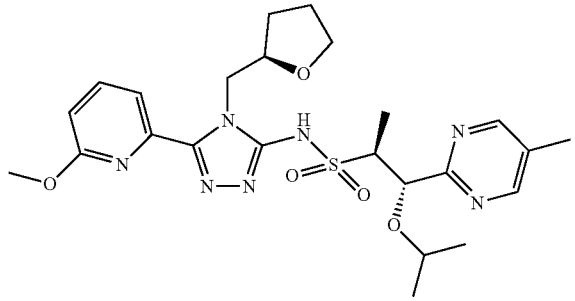<br>OR<br>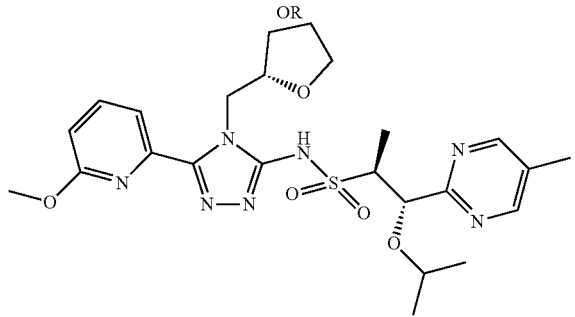<br>(1S,2S)-1-isopropoxy-N-(5-(6-methoxypyridin-2-yl)-4-(((R)-tetrahydrofuran-2-yl)methyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-(((S)-tetrahydrofuran-2-yl)methyl)-4H-1,2,4-triazol-3-yl)-1-(5-methylpyrimidin-2-yl)propane-2-sulfonamide.<br>$^1$H NMR (500 MHz, CD$_2$Cl$_2$) δ 12.75 (br s, 1H), 8.64 (s, 2H), 7.73 (dd, J = 7.5, 8.3 Hz, 1H), 7.64-7.62 (m, 1H), 6.86 (dd, J = 0.8, 8.3 Hz, 1H), 4.86 (d, J = 3.9 Hz, 1H), 4.77-4.70 (m, 1H), 4.32-4.25 (m, 2H), 3.97 (s, 3H), 3.71 (dq, J = 3.9, 7.1 Hz, 1H), 3.57 (t, J = 6.2 Hz, 2H), 3.54-3.47 (m, 1H), 2.34 (s, 3H), 1.98-1.88 (m, 2H), 1.87-1.78 (m, 2H), 1.53 (d, J = 7.0 Hz, 3H), 1.04 (d, J = 6.0 Hz, 3H), 0.90 (d, J = 6.2 Hz, 3H). LCMS ESI (pos.) m/z: 532.3 (M + H)$^+$. |
| 279.0 | (1R,2S)-1-(5-chloropyrimidin-2-yl)-1-methoxypropane-2-sulfonamide (Example 29.3), (R)-2-(isothiocyanatomethyl)tetrahydrofuran and and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified using the following preparative SFC method: Column IC (2 × 25 cm), Mobile Phase: 50:50 (A:B) A: Liquid CO$_2$, B: MeOH, Flow Rate: 80 mL/min, 219 nm, 100 bar inlet pressure to deliver peak 1. | 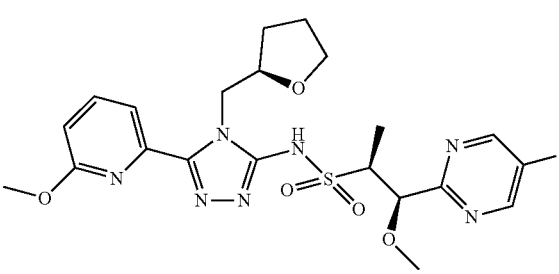<br>OR<br>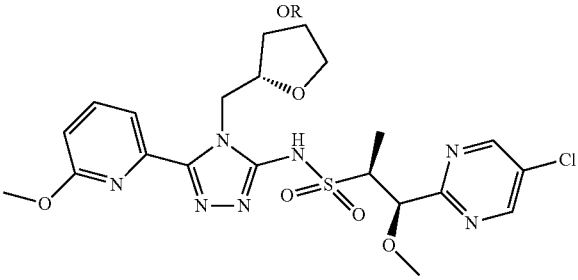<br>(1R,2S)-1-(5-chloropyrimidin-2-yl)-1-methoxy-N-(5-(6-methoxypyridin-2-yl)-4-(((R)-tetrahydrofuran-2-yl)methyl)-4H-1,2,4-triazol-3-yl)propane-2-sulfonamide or (1R,2S)-1-(5-chloropyrimidin-2-yl)- |

TABLE 24-continued

| Example | Reagents | Structure, Name, Data |
|---|---|---|
| | | 1-methoxy-N-(5-(6-methoxypyridin-2-yl)-4-(((S)-tetrahydrofuran-2-yl)methyl)-4H-1,2,4-triazol-3-yl)propane-2-sulfonamide. <br> $^1$H NMR (500 MHz, CD$_2$Cl$_2$) δ 11.47-10.58 (m, 1H), 8.72 (s, 2H), 7.73 (dd, J = 7.5, 8.3 Hz, 1H), 7.63 (dd, J = 0.8, 7.5 Hz, 1H), 6.88 (dd, J = 0.8, 8.3 Hz, 1H), 4.94 (d, J = 4.9 Hz, 1H), 4.65 (dd, J = 8.6, 13.5 Hz, 1H), 4.35 (dd, J = 4.7, 13.5 Hz, 1H), 4.29-4.23 (m, 1H), 3.96 (s, 3H), 3.71 (dq, J = 4.9, 7.0 Hz, 1H), 3.59-3.51 (m, 2H), 3.28 (s, 3H), 2.00-1.93 (m, 1H), 1.89-1.80 (m, 2H), 1.71-1.64 (m, 1H), 1.40 (d, J = 7.0 Hz, 3H). LCMS ESI (pos.) m/z: 524.2 (M + H)$^+$. |
| 280.0 | (1R,2S)-1-(5-chloropyrimidin-2-yl)-1-methoxypropane-2-sulfonamide (Example 29.3), (R)-2-(isothiocyanatomethyl)tetrahydrofuran and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified using the following preparative SFC method: Column IC (2 × 25 cm), Mobile Phase: 50:50 (A:B) A: Liquid CO$_2$, B: MeOH, Flow Rate: 80 mL/min, 219 nm, 100 bar inlet pressure to deliver peak 2. | 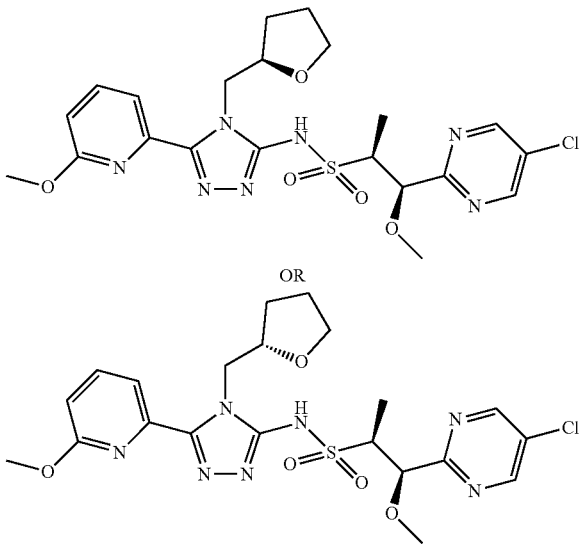 <br> OR <br> 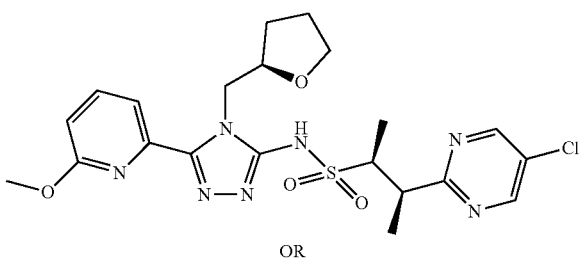 <br><br> (1R,2S)-1-(5-chloropyrimidin-2-yl)-1-methoxy-N-(5-(6-methoxypyridin-2-yl)-4-(((R)-tetrahydrofuran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydrofuran-2-yl)methyl)-4H-1,2,4-triazol-3-yl)propane-2-sulfonamide. <br> $^1$H NMR (500 MHz, CD$_2$Cl$_2$) δ 11.14 (br s, 1H), 8.72 (s, 2H), 7.76-7.71 (m, 1H), 7.62 (d, J = 7.3 Hz, 1H), 6.88 (d, J = 8.3 Hz, 1H), 5.01 (d, J = 4.2 Hz, 1H), 4.66 (dd, J = 8.6, 13.5 Hz, 1H), 4.36 (dd, J = 4.7, 13.5 Hz, 1H), 4.31-4.24 (m, 1H), 3.96 (s, 3H), 3.68 (dq, J = 4.4, 7.0 Hz, 1H), 3.58-3.50 (m, 2H), 3.25 (s, 3H), 2.00-1.94 (m, 1H), 1.90-1.81 (m, 2H), 1.72-1.65 (m, 1H), 1.38 (d, J = 7.0 Hz, 3H). LCMS ESI (pos.) m/z: 524.2 (M + H)$^+$. |
| 281.0 | (2S,3R)-3-(5-chloropyrimidin-2-yl)butane-2-sulfonamide (Example 27.4), (R)-2-(isothiocyanatomethyl)tetrahydrofuran and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified | <br> OR |

TABLE 24-continued

| Example | Reagents | Structure, Name, Data |
|---------|----------|------------------------|
| | using the following preparative SFC method: Column IC (2 × 25 cm), Mobile Phase: 50:50 (A:B) A: Liquid $CO_2$, B: MeOH, Flow Rate: 80 mL/min, 217 nm, 100 bar inlet pressure to deliver peak 1. | 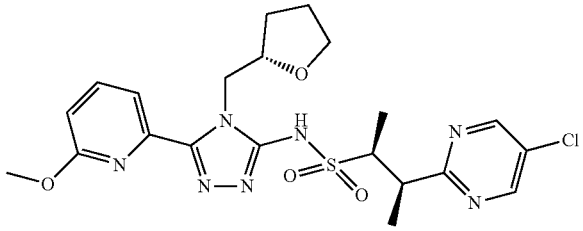 [SMILES: COc1cccc(-c2nnc(NS(=O)(=O)[C@@H](C)[C@H](C)c3ncc(Cl)cn3)n2C[C@@H]2CCCO2)n1]<br>(2S,3R)-3-(5-chloropyrimidin-2-yl)-N-(5-(6-methoxypyridin-2-yl)-4-(((R)-tetrahydrofuran-2-yl)methyl)-4H-1,2,4-triazol-3-yl)butane-2-sulfonamide or (2S,3R)-3-(5-chloropyrimidin-2-yl)-N-(5-(6-methoxypyridin-2-yl)-4-(((S)-tetrahydrofuran-2-yl)methyl)-4H-1,2,4-triazol-3-yl)butane-2-sulfonamide.<br>$^1$H NMR (500 MHz, $CD_2Cl_2$) δ = 11.04 (br s, 1H), 8.64 (s, 2H), 7.76-7.70 (m, 1H), 7.66-7.61 (m, 1H), 6.88 (d, J = 7.8 Hz, 1H), 4.56 (dd, J = 8.3, 13.5 Hz, 1H), 4.35 (dd, J = 4.5, 13.6 Hz, 1H), 4.24-4.19 (m, 1H), 3.95 (s, 3H), 3.85 (quin, J = 6.9 Hz, 1H), 3.74 (quin, J = 6.9 Hz, 1H), 3.57 (t, J = 6.7 Hz, 2H), 1.98-1.91 (m, 1H), 1.89-1.78 (m, 2H), 1.69-1.63 (m, 1H), 1.48-1.38 (m, 6H). LCMS ESI (pos.) m/z: 508.1 $(M + H)^+$. |
| 282.0 | (2S,3R)-3-(5-chloropyrimidin-2-yl)butane-2-sulfonamide (Example 27.4), (R)-2-(isothiocyanatomethyl)tetrahydrofuran and (S)-2-(isothiocyanatomethyl)tetrahydrofuran (commercially available from Alfa Aesar), and 6-methoxypicolinohydrazide (commercially available from Milestone PharmTech USA Inc.). The racemic mixture was purified using the following preparative SFC method: Column IC (2 × 25 cm), Mobile Phase: 50:50 (A:B) A: Liquid $CO_2$, B: MeOH, Flow Rate: 80 mL/min, 217 nm, 100 bar inlet pressure to deliver peak 2. | 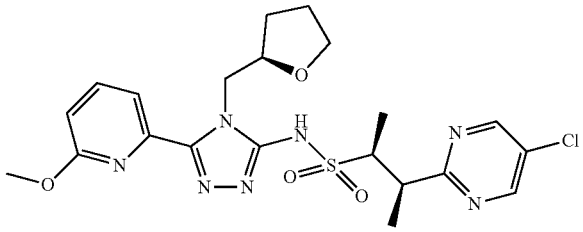 [SMILES: COc1cccc(-c2nnc(NS(=O)(=O)[C@@H](C)[C@H](C)c3ncc(Cl)cn3)n2C[C@H]2CCCO2)n1]<br>(2S,3R)-3-(5-chloropyrimidin-2-yl)-N-(5-(6-methoxypyridin-2-yl)-4-(((R)-tetrahydrofuran-2-yl)methyl)-4H-1,2,4-triazol-3-yl)butane-2-sulfonamide or (2S,3R)-3-(5-chloropyrimidin-2-yl)-N-(5-(6-methoxypyridin-2-yl)-4-(((S)-tetrahydrofuran-2-yl)methyl)-4H-1,2,4-triazol-3-yl)butane-2-sulfonamide.<br>$^1$H NMR (500 MHz, $CD_2Cl_2$) δ 11.06 (br s, 1H), 8.64 (s, 2H), 7.75-7.71 (m, 1H), 7.63 (d, J = 7.3 Hz, 1H), 6.88 (d, J = 8.3 Hz, 1H), 4.60 (dd, J = 8.3, 13.5 Hz, 1H), 4.31 (dd, J = 4.7, 13.5 Hz, 1H), 4.23-4.17 (m, 1H), 3.96 (s, 3H), 3.85 (quin, J = 6.8 Hz, 1H), 3.78-3.73 (m, 1H), 3.57-3.53 (m, 2H), 1.98-1.91 (m, 1H), 1.89-1.79 (m, 2H), 1.68-1.62 (m, 1H), 1.48-1.38 (m, 6H). LCMS ESI (pos.) m/z: 508.2 $(M + H)^+$. |

TABLE 24-continued

| Example | Reagents | Structure, Name, Data |
|---|---|---|
| 283.0 | (1R,2S)-1-(5-chloropyrimidin-2-yl)-1-methoxypropane-2-sulfonamide (Example 29.3), 2-(2-isothiocyanatoethyl)pyridine, (commercially available from Enamine), and 6-methoxypicolinohydrazide (commercially available from Milestone PharmTech USA Inc.). | 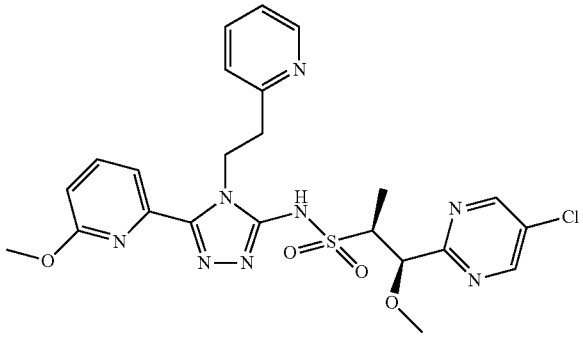 [SMILES: COc1cccc(-c2nnc(NS(=O)(=O)[C@@H](C)[C@H](OC)c3ncc(Cl)cn3)n2CCc2ccccn2)n1]<br>(1R,2S)-1-(5-chloropyrimidin-2-yl)-1-methoxy-N-(5-(6-methoxypyridin-2-yl)-4-(2-(pyridin-2-yl)ethyl)-4H-1,2,4-triazol-3-yl)propane-2-sulfonamide.<br>$^1$H NMR (500 MHz, DMSO-d$_6$) δ 13.22 (br s, 1H), 8.91 (s, 2H), 8.34 (dd, J = 0.8, 4.9 Hz, 1H), 7.82 (dd, J = 7.4, 8.2 Hz, 1H), 7.61 (dt, J = 1.8, 7.7 Hz, 1H), 7.47 (d, J = 7.5 Hz, 1H), 7.16-7.11 (m, 2H), 6.95 (d, J = 8.0 Hz, 1H), 4.89 (d, J = 4.7 Hz, 1H), 4.72-4.65 (m, 1H), 4.64-4.57 (m, 1H), 3.84 (s, 3H), 3.62-3.57 (m, 1H), 3.17-3.12 (m, 5H), 1.33 (d, J = 7.0 Hz, 3H). LCMS ESI (pos.) m/z: 545.2 (M + H)$^+$. |
| 284.0 | (1R,2S)-1-(5-chloropyrimidin-2-yl)-1-methoxypropane-2-sulfonamide (Example 29.3), 3-(2-isothiocyanatoethyl)pyridine, (commercially available from Enamine), and 6-methoxypicolinohydrazide (commercially available from Milestone PharmTech USA Inc.). | 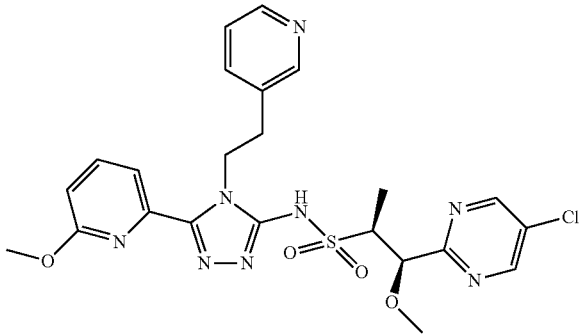 [SMILES: COc1cccc(-c2nnc(NS(=O)(=O)[C@@H](C)[C@H](OC)c3ncc(Cl)cn3)n2CCc2cccnc2)n1]<br>(1R,2S)-1-(5-chloropyrimidin-2-yl)-1-methoxy-N-(5-(6-methoxypyridin-2-yl)-4-(2-(pyridin-3-yl)ethyl)-4H-1,2,4-triazol-3-yl)propane-2-sulfonamide.<br>$^1$H NMR (500 MHz, DMSO-d$_6$) δ 13.25 (br s, 1H), 8.92 (s, 2H), 8.31 (dd, J = 1.6, 4.7 Hz, 1H), 8.23 (d, J = 2.1 Hz, 1H), 7.81 (dd, J = 7.5, 8.3 Hz, 1H), 7.46 (td, J = 1.8, 7.8 Hz, 1H), 7.39 (d, J = 6.7 Hz, 1H), 7.16 (dd, J = 4.7, 7.5 Hz, 1H), 6.96 (d, J = 8.0 Hz, 1H), 4.91 (d, J = 4.4 Hz, 1H), 4.62-4.52 (m, 2H), 3.88 (s, 3H), 3.61-3.54 (m, 1H), 3.15 (s, 3H), 3.14-3.00 (m, 2H), 1.32 (d, J = 7.0 Hz, 3H). LCMS ESI (pos.) m/z: 545.2 (M + H)$^+$. |
| 285.0 | (1R,2S)-1-(5-chloropyrimidin-2-yl)-1-methoxypropane-2-sulfonamide (Example 29.3), (R)-3-(isothiocyanatomethyl)tetrahydrofuran and (S)-3-(isothiocyanatomethyl)tetrahydrofuran (Example 264.3), and 6-methoxypicolinohydrazide (commercially available from Milestone PharmTech USA Inc.). The racemic mixture was purified using the following preparative SFC method: Column OZ-H (2 × 15 | 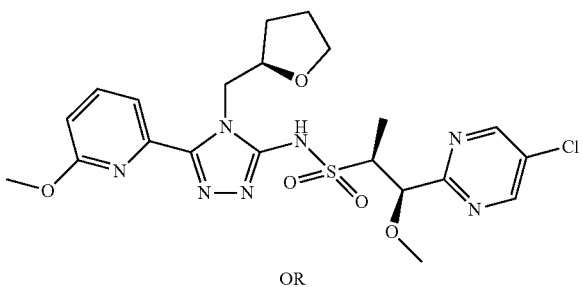<br>OR |

| Example | Reagents | Structure, Name, Data |
|---|---|---|
| | cm), Mobile Phase: 50:50 (A:B) A: Liquid CO₂, B: MeOH, Flow Rate: 100 mL/min, 220 nm, 100 bar inlet pressure to deliver peak 1. | 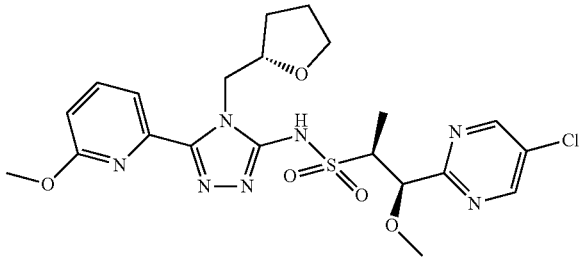 [SMILES: COc1cccc(-c2nnc(NS(=O)(=O)[C@@H](C)[C@H](OC)c3ncc(Cl)cn3)n2C[C@@H]2CCCO2)n1]<br>(1R,2S)-1-(5-chloropyrimidin-2-yl)-1-methoxy-N-(5-(6-methoxypyridin-2-yl)-4-(((R)-tetrahydrofuran-3-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydrofuran-3-yl)methyl)-4H-1,2,4-triazol-3-yl)propane-2-sulfonamide.<br>¹H NMR (500 MHz, DMSO-d₆) δ 13.27 (br s, 1H), 8.91 (s, 2H), 7.90 (t, J = 7.8 Hz, 1H), 7.66 (d, J = 7.3 Hz, 1H), 7.02 (d, J = 8.3 Hz, 1H), 4.88 (d, J = 4.9 Hz, 1H), 4.35 (dd, J = 7.5, 13.5 Hz, 1H), 4.23 (dd, J = 8.0, 13.5 Hz, 1H), 3.94-3.90 (m, 3H), 3.74-3.68 (m, 1H), 3.63-3.57 (m, 1H), 3.57-3.52 (m, 2H), 3.51-3.47 (m, 1H), 3.17-3.12 (m, 3H), 2.75-2.66 (m, 1H), 1.86-1.78 (m, 1H), 1.61-1.53 (m, 1H), 1.36-1.30 (m, 3H). LCMS ESI (pos.) m/z: 524.2 (M + H)⁺. |
| 286.0 | (1R,2S)-1-(5-chloropyrimidin-2-yl)-1-methoxypropane-2-sulfonamide, (Example 29.3), (R)-3-(isothiocyanatomethyl)tetrahydrofuran and (S)-3-(isothiocyanatomethyl)tetrahydrofuran (Example 264.3), and 6-methoxypicolinohydrazide (commercially available from Milestone PharmTech USA Inc.). The racemic mixture was purified using the following preparative SFC method: Column OZ-H (2 × 15 cm), Mobile Phase: 50:50 (A:B) A: Liquid CO₂, B: MeOH, Flow Rate: 100 mL/min, 220 nm, 100 bar inlet pressure to deliver peak 2. | 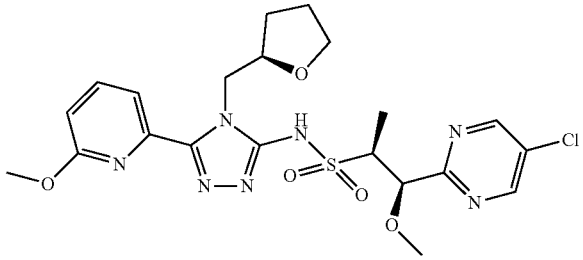 [SMILES: COc1cccc(-c2nnc(NS(=O)(=O)[C@@H](C)[C@H](OC)c3ncc(Cl)cn3)n2C[C@H]2CCCO2)n1]<br>OR<br>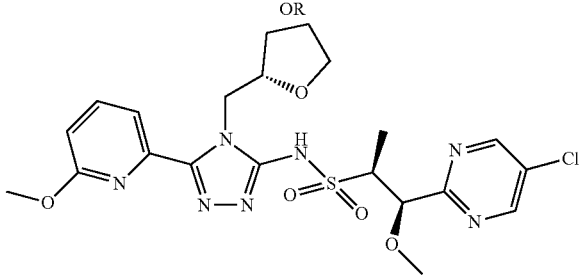<br>(1R,2S)-1-(5-chloropyrimidin-2-yl)-1-methoxy-N-(5-(6-methoxypyridin-2-yl)-4-(((R)-tetrahydrofuran-3-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydrofuran-3-yl)methyl)-4H-1,2,4-triazol-3-yl)propane-2-sulfonamide.<br>¹H NMR (500 MHz, DMSO-d₆) δ 13.27 (s, 1H), 8.91 (s, 2H), 7.90 (t, J = 7.9 Hz, 1H), 7.66 (d, J = 7.5 Hz, 1H), 7.02 (d, J = 8.3 Hz, 1H), 4.88 (d, J = 4.7 Hz, 1H), 4.36-4.31 (m, 1H), 4.29-4.23 (m, 1H), 3.92 (s, 3H), 3.70 (dt, J = 5.8, 8.0 Hz, 1H), 3.63-3.58 (m, 1H), 3.58-3.52 (m, 2H), 3.49-3.45 (m, 1H), 3.14 (s, 3H), 2.76-2.66 (m, 1H), 1.86-1.79 (m, 1H), 1.58 (qd, J = 6.5, 12.9 Hz, 1H), 1.33 (d, J = 7.0 Hz, 3H). LCMS ESI (pos.) m/z: 524.2 (M + H)⁺. |

TABLE 24-continued

| Example | Reagents | Structure, Name, Data |
|---|---|---|
| 287.0 | (1R,2S)-1-(5-chloropyrimidin-2-yl)-1-methoxypropane-2-sulfonamide (Example 29.3), (R)-2-(isothiocyanatomethyl)tetrahydro-2H-pyran and (S)-2-(isothiocyanatomethyl)tetrahydro-2H-pyran (commercially available from Enamine), and 6-methoxypicolinohydrazide (commercially available from Milestone PharmTech USA Inc.). The racemic mixture was purified using the following preparative SFC method: Column OZ-H (2 × 15 cm), Mobile Phase: 50:50 (A:B) A: Liquid CO$_2$, B: MeOH, Flow Rate: 100 mL/min, 220 nm, 100 bar inlet pressure to deliver peak 1. | 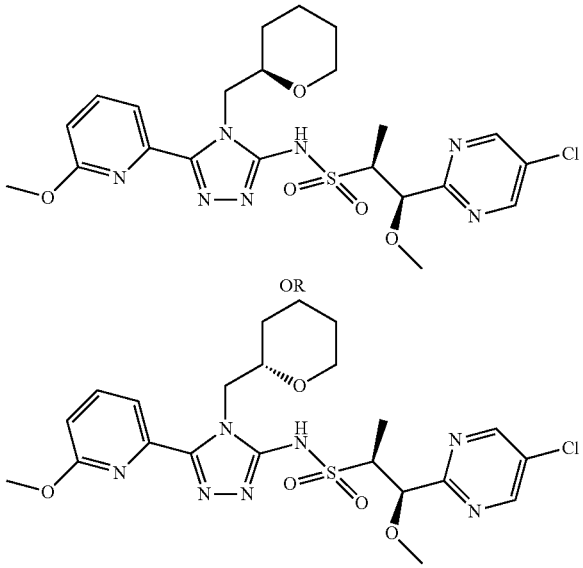<br>OR<br><br>(1R,2S)-1-(5-chloropyrimidin-2-yl)-1-methoxy-N-(5-(6-methoxypyridin-2-yl)-4-(((R)-tetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydro-2H-pyran-2-yl)methyl)-4H-1,2,4-triazol-3-yl)propane-2-sulfonamide.<br>$^1$H NMR (500 MHz, DMSO-d$_6$) δ 13.22 (s, 1H), 8.91 (s, 2H), 7.88 (t, J = 7.9 Hz, 1H), 7.62 (d, J = 7.5 Hz, 1H), 7.00 (d, J = 8.3 Hz, 1H), 4.83 (d, J = 4.9 Hz, 1H), 4.61 (dd, J = 7.9, 13.6 Hz, 1H), 4.03 (dd, J = 5.2, 13.5 Hz, 1H), 3.94 (s, 3H), 3.67-3.57 (m, 3H), 3.17-3.11 (m, 4H), 1.70 (br s, 1H), 1.47 (br d, J = 12.2 Hz, 1H), 1.38-1.31 (m, 6H), 1.21-1.12 (m, 1H).<br>LCMS ESI (pos.) m/z: 538.1 (M + H)$^+$. |
| 288.0 | (1R,2S)-1-(5-chloropyrimidin-2-yl)-1-methoxypropane-2-sulfonamide (Example 29.3), (R)-2-(isothiocyanatomethyl)tetrahydro-2H-pyran and (S)-2-(isothiocyanatomethyl)tetrahydro-2H-pyran (commercially available from Enamine), and 6-methoxypicolinohydrazide (commercially available from Milestone PharmTech USA Inc.). The racemic mixture was purified using the following preparative SFC method: Column OZ-H (2 × 15 cm), Mobile Phase: 50:50 (A:B) A: Liquid CO$_2$, B: MeOH, Flow Rate: 100 mL/min, 220 nm, 100 bar inlet pressure to deliver peak 2. | 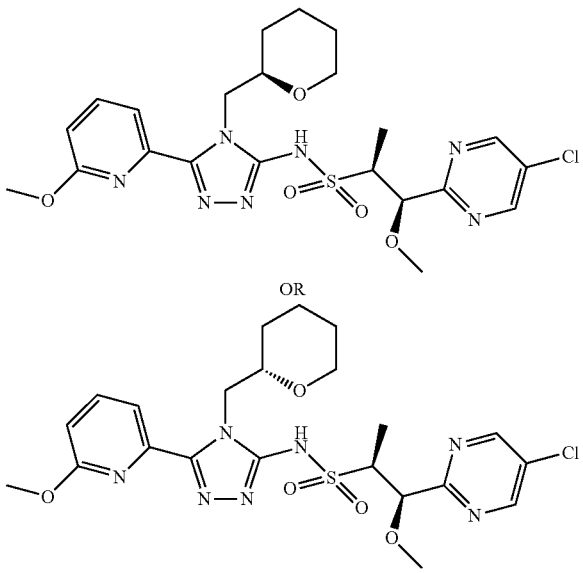<br>OR<br><br>(1R,2S)-1-(5-chloropyrimidin-2-yl)-1-methoxy-N-(5-(6-methoxypyridin-2-yl)-4-(((R)-tetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydro-2H-pyran-2-yl)methyl)-4H-1,2,4-triazol- |

TABLE 24-continued

| Example | Reagents | Structure, Name, Data |
|---|---|---|
| | | 3-yl)propane-2-sulfonamide.<br>¹H NMR (500 MHz, DMSO-d₆) δ 13.19 (br s, 1H), 8.92 (s, 2H), 7.88 (t, J = 7.9 Hz, 1H), 7.61 (d, J = 7.3 Hz, 1H), 6.99 (d, J = 8.6 Hz, 1H), 4.90 (d, J = 4.7 Hz, 1H), 4.52 (br dd, J = 8.6, 13.5 Hz, 1H), 4.17 (br dd, J = 4.4, 13.8 Hz, 1H), 3.94 (s, 3H), 3.69-3.54 (m, 3H), 3.14 (s, 4H), 1.76-1.66 (m, 1H), 1.51 (br d, J = 12.5 Hz, 1H), 1.39-1.28 (m, 6H), 1.21-1.11 (m, 1H). LCMS ESI (pos.) m/z: 538.3 (M + H)⁺. |
| 289.0 | (1R,2S)-1-(5-chloropyrimidin-2-yl)-1-methoxypropane-2-sulfonamide (Example 29.3), (R)-5-(isothiocyanatomethyl)-2,2-dimethyltetrahydrofuran and (S)-5-(isothiocyanatomethyl)-2,2-dimethyltetrahydrofuran (Example 264.4), and 6-methoxypicolinohydrazide (commercially available from Milestone PharmTech USA Inc.). The racemic mixture was purified using the following preparative SFC method: Column IC (2 × 25 cm), Mobile Phase: 60:40 (A:B) A: Liquid CO₂, B: MeOH, Flow Rate: 100 mL/min, 220 nm, 100 bar inlet pressure to deliver peak 1. | 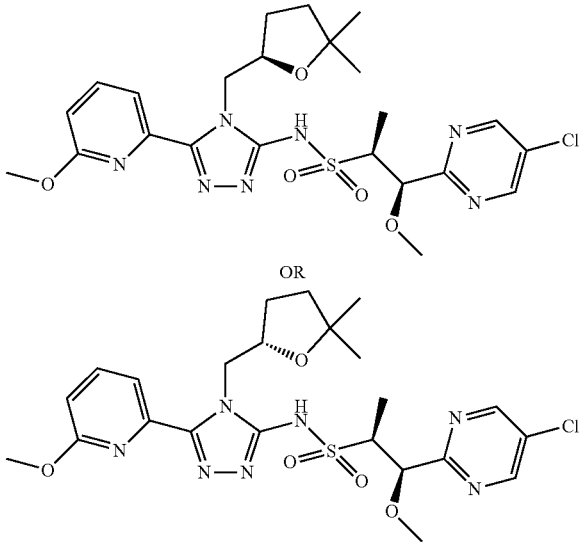<br><br>OR<br><br>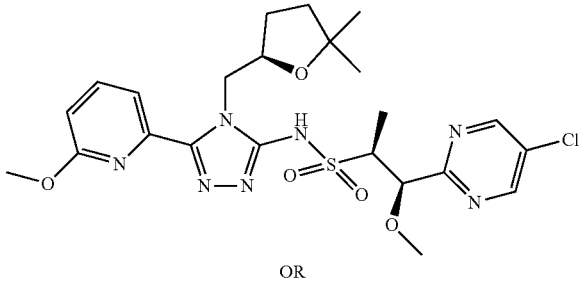<br><br>(1R,2S)-1-(5-chloropyrimidin-2-yl)-N-(4-(((R)-5,5-dimethyltetrahydrofuran-2-yl)methyl)-5-(6-methoxy)yridin-2-yl)-4H-1,2,4-triazol-3-yl)-1-methoxypropane-2-sulfonamide or (1R,2S)-1-(5-chloropyrimidin-2-yl)-N-(4-(((S)-5,5-dimethyltetrahydrofuran-2-yl)methyl)-5-(6-methoxypyridin-2-yl)-4H-1,2,4-triazol-3-yl)-1-methoxypropane-2-sulfonamide.<br>¹H NMR (500 MHz, DMSO-d₆) δ 13.23 (br s, 1H), 8.90 (s, 2H), 7.88 (t, J = 7.9 Hz, 1H), 7.56 (d, J = 7.5 Hz, 1H), 6.99 (d, J = 8.3 Hz, 1H), 4.80 (d, J = 5.4 Hz, 1H), 4.61 (dd, J = 7.9, 13.4 Hz, 1H), 4.14 (quin, J = 6.5 Hz, 1H), 3.98 (dd, J = 5.1, 13.4 Hz, 1H), 3.96-3.93 (m, 3H), 3.66 (quin, J = 6.5 Hz, 1H), 3.15 (s, 3H), 2.01-1.94 (m, 1H), 1.74-1.65 (m, 1H), 1.65-1.58 (m, 1H), 1.56-1.49 (m, 1H), 1.34 (d, J = 7.0 Hz, 3H), 0.95 (s, 3H), 0.73 (s, 3H). LCMS ESI (pos.) m/z: 552.2 (M + H)⁺. |
| 290.0 | (1R,2S)-1-(5-chloropyrimidin-2-yl)-1-methoxypropane-2-sulfonamide (Example 29.3), (R)-5-(isothiocyanatomethyl)-2,2-dimethyltetrahydrofuran and (S)-5-(isothiocyanatomethyl)-2,2-dimethyltetrahydrofuran (Example 264.4), and 6-methoxypicolinohydrazide (commercially available from Milestone PharmTech USA Inc.). The racemic mixture was purified using the following preparative SFC | <br><br>OR |

TABLE 24-continued

| Example | Reagents | Structure, Name, Data |
|---|---|---|
| | method: Column IC (2 × 25 cm), Mobile Phase: 60:40 (A:B) A: Liquid CO₂, B: MeOH, Flow Rate: 100 mL/min, 220 nm, 100 bar inlet pressure to deliver peak 2. | 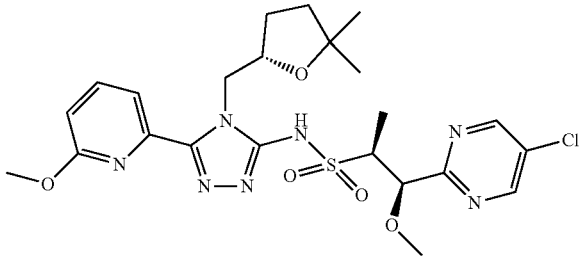 [SMILES: COc1cccc(-c2nnc(NS(=O)(=O)[C@@H](C)[C@H](OC)c3ncc(Cl)cn3)n2C[C@@H]2CCC(C)(C)O2)n1]<br>(1R,2S)-1-(5-chloropyrimidin-2-yl)-N-(4-(((R)-5,5-dimethyltetrahydrofuran-2-yl)methyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-(((S)-5,5-dimethyltetrahydrofuran-2-yl)methyl)-5-(6-methoxypyridin-2-yl)-4H-1,2,4-triazol-3-yl)-1-methoxypropane-2-sulfonamide.<br>¹H NMR (500 MHz, DMSO-d₆) δ = 13.19 (br s, 1H), 8.92 (s, 2H), 7.88 (t, J = 7.9 Hz, 1H), 7.56 (d, J = 7.3 Hz, 1H), 6.99 (d, J = 8.3 Hz, 1H), 4.88 (d, J = 4.9 Hz, 1H), 4.51-4.45 (m, 1H), 4.20-4.14 (m, 2H), 3.93 (s, 3H), 3.63-3.56 (m, 1H), 3.15 (s, 3H), 2.00-1.92 (m, 1H), 1.74-1.67 (m, 1H), 1.64-1.59 (m, 1H), 1.57-1.50 (m, 1H), 1.32 (d, J = 7.0 Hz, 3H), 0.97 (s, 3H), 0.80 (s, 3H). LCMS ESI (pos.) m/z: 552.2 (M + H)⁺. |
| 291.0 | (2S,3R)-3-(5-methylpyrimidin-2-yl)butane-2-sulfonamide (Example 27.0), 1-isothiocyanato-1-methylcyclobutane (commercially available from Enamine), and 6-methoxypicolinohydrazide (commercially available from Milestone PharmTech USA Inc.). | 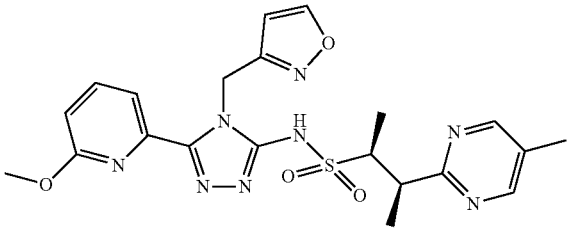<br>(2S,3R)-N-(4-(isoxazol-3-ylmethyl)-5-(6-methoxypyridin-2-yl)-4H-1,2,4-triazol-3-yl)-3-(5-methylpyrimidin-2-yl)butane-2-sulfonamide.<br>¹H NMR (400 MHz, DMSO-d₆) δ 13.33 (br s, 1H), 8.82 (d, J = 1.7 Hz, 1H), 8.54 (s, 2H), 7.89-7.84 (m, 1H), 7.67 (d, J = 7.5 Hz, 1H), 6.95 (d, J = 8.3 Hz, 1H), 6.53 (d, J = 1.5 Hz, 1H), 5.67-5.48 (m, 2H), 3.79-3.71 (m, 1H), 3.68 (s, 3H), 3.66-3.59 (m, 1H), 2.18 (s, 3H), 1.24 (d, J = 7.3 Hz, 3H), 1.16 (d, J = 7.0 Hz, 3H). LCMS ESI (pos.) m/z: 485.2 (M + H)⁺. |
| 295.0 | (2S,3R)-3-(5-chloropyrimidin-2-yl)butane-2-sulfonamide (Example 27.4), (R)-4-(1-isothiocyanatoethyl)-1,2,3-thiadiazole and (S)-4-(1-isothiocyanatoethyl)-1,2,3-thiadiazole (Example 264), and 6-methoxypicolinohydrazide (commercially available from Milestone PharmTech USA Inc.). The racemic mixture was purified using the following preparative SFC method: Column: AD-H (2 × 25 cm), Mobile Phase: 60:40 (A:B) A: Liquid CO₂, B: MeOH, Flow Rate: 80 mL/min, 217 nm, 100 bar inlet pressure to deliver peak 1. | 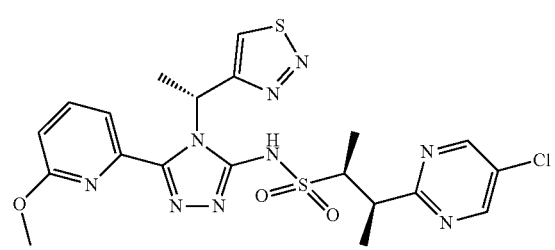 [SMILES: COc1cccc(-c2nnc(NS(=O)(=O)[C@@H](C)[C@H](C)c3ncc(Cl)cn3)n2[C@H](C)c2csnn2)n1]<br>OR<br>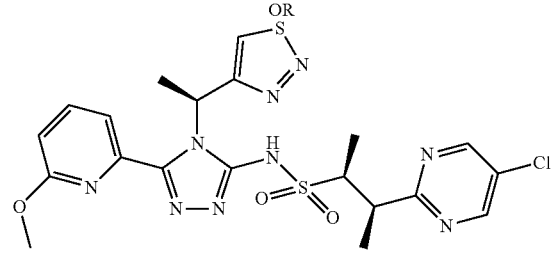 |

TABLE 24-continued

| Example | Reagents | Structure, Name, Data |
|---|---|---|
| | | (2S,3R)-N-(4-((R)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((S)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide. <br> $^1$H NMR (500 MHz, DMSO-d$_6$) δ 9.10 (s, 1H), 8.85 (s, 2H), 7.86 (t, J = 7.9 Hz, 1H), 7.55 (d, J = 7.3 Hz, 1H), 6.96-6.88 (m, 2H), 3.72 (s, 3H), 3.57 (br s, 1H), 3.51-3.43 (m, 1H), 2.11 (d, J = 7.0 Hz, 3H), 1.22 (d, J = 7.3 Hz, 3H), 1.02-0.96 (m, 3H). LCMS-ESI (pos.) m/z: 536.2 (M + H)$^+$. |
| 296.0 | (2S,3R)-3-(5-chloropyrimidin-2-yl)butane-2-sulfonamide (Example 27.4), (R)-4-(1-isothiocyanatoethyl)-1,2,3-thiadiazole and (S)-4-(1-isothiocyanatoethyl)-1,2,3-thiadiazole (Example 264.6), and 6-methoxypicolinohydrazide (commercially available from Milestone PharmTech USA The racemic mixture was purified using the following preparative SFC method: Column: AD-H (2 × 25 cm), Mobile Phase: 60:40 (A:B) A: Liquid CO$_2$, B: MeOH, Flow Rate: 80 mL/min, 217 nm, 100 bar inlet pressure to deliver peak 2. | 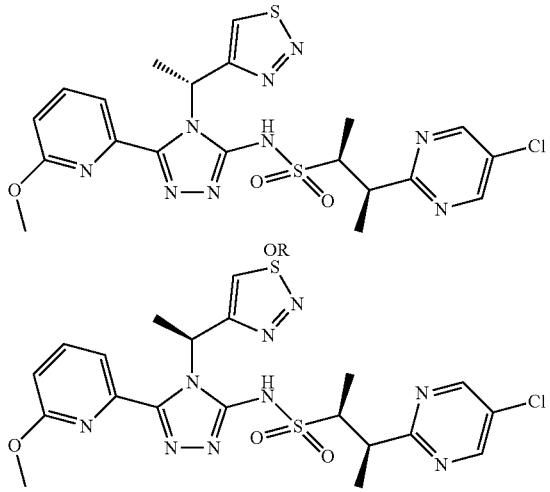 <br> (2S,3R)-N-(4-((R)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide or (2S,3R)-N-(4-((S)-1-(1,2,3-thiadiazol-4-yl)ethyl)-5-(6-methoxypyridin-2-yl)-4H-1,2,4-triazol-3-yl)-3-(5-chloropyrimidin-2-yl)butane-2-sulfonamide. <br> $^1$H NMR (500 MHz, DMSO-d$_6$) δ 13.17 (br s, 1H), 9.15 (s, 1H), 8.85 (s, 2H), 7.89 (dd, J = 7.5, 8.3 Hz, 1H), 7.57 (d, J = 7.3 Hz, 1H), 6.99 (d, J = 8.3 Hz, 1H), 6.93-6.86 (m, 1H), 3.75 (s, 3H), 3.50-3.41 (m, 2H), 2.13 (d, J = 7.0 Hz, 3H), 1.19 (d, J = 6.7 Hz, 3H), 0.94 (d, J = 6.7 Hz, 3H). LCMS-ESI (pos.) m/z: 536.2 (M + H)$^+$. |
| 297.0 | (2S,3R)-3-(5-chloropyrimidin-2-yl)butane-2-sulfonamide (Example 27.4), (R)-4-(1-isothiocyanatoethyl)-1-methyl-1H-pyrazole and (S)-4-(1-isothiocyanatoethyl)-1-methyl-1H-pyrazole (Example 264.7), and 6-methoxypicolinohydrazide (commercially available from Milestone PharmTech USA Inc.). The racemic mixture was purified using the following preparative SFC method: Column: AD-H (2 × 25 cm), Mobile Phase: 65:35 (A:B) A: Liquid CO$_2$, B: MeOH, Flow Rate: 80 mL/min, 219 nm, 100 bar inlet pressure to deliver peak 1. | 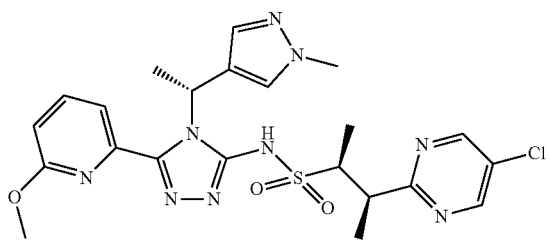 [SMILES: COc1cccc(-c2nnc(NS(=O)(=O)[C@@H](C)[C@H](C)c3ncc(Cl)cn3)n2[C@H](C)c2cnn(C)c2)n1] <br> (2S,3R)-3-(5-chloropyrimidin-2-yl)-N-(5-(6-methoxypyridin-2-yl)-4-((R)-1-(1-methyl-1H-pyrazol-4-yl)ethyl)-4H-1,2,4-triazol-3-yl)butane-2- |

TABLE 24-continued

| Example | Reagents | Structure, Name, Data |
|---|---|---|
| | | sulfonamide or (2S,3R)-3-(5-chloropyrimidin-2-yl)-N-(5-(6-methoxypyridin-2-yl)-4-((S)-1-(1-methyl-1H-pyrazol-4-yl)ethyl)-4H-1,2,4-triazol-3-yl)butane-2-sulfonamide.<br>$^1$H NMR (500 MHz, DMSO-d$_6$) δ 13.01 (br s, 1H), 8.85 (s, 2H), 7.92-7.86 (m, 1H), 7.60 (s, 1H), 7.48 (d, J = 7.3 Hz, 1H), 7.29 (s, 1H), 7.01 (d, J = 8.3 Hz, 1H), 6.32 (q, J = 7.0 Hz, 1H), 3.82 (s, 3H), 3.67 (s, 3H), 3.60-3.54 (m, 1H), 3.53-3.47 (m, 1H), 1.83 (d, J = 7.3 Hz, 3H), 1.26 (d, J = 7.0 Hz, 3H), 1.08 (d, J = 7.0 Hz, 3H). LCMS-ESI (pos.) m/z: 532.2 (M + H)$^+$. |
| 298.0 | (2S,3R)-3-(5-chloropyrimidin-2-yl)butane-2-sulfonamide (Example 27.4), (R)-4-(1-isothiocyanatoethyl)-1-methyl-1H-pyrazole and (S)-4-(1-isothiocyanatoethyl)-1-methyl-1H-pyrazole (Example 264.7), and 6-methoxypicolinohydrazide (commercially available from Milestone PharmTech USA Inc.). The racemic mixture was purified using the following preparative SFC method: Column: AD-H (2 × 25 cm), Mobile Phase: 65:35 (A:B) A: Liquid CO$_2$, B: MeOH, Flow Rate: 80 mL/min, 219 nm, 100 bar inlet pressure to deliver peak 2. | 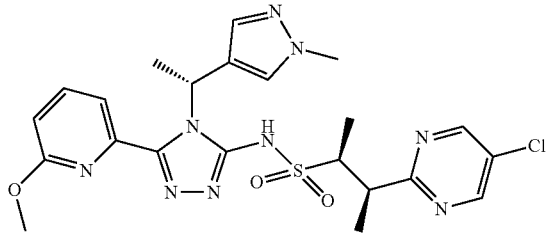 [SMILES: COc1cccc(-c2nnc(NS(=O)(=O)[C@@H](C)[C@H](C)c3ncc(Cl)cn3)n2[C@H](C)c2cnn(C)c2)n1]<br>OR<br>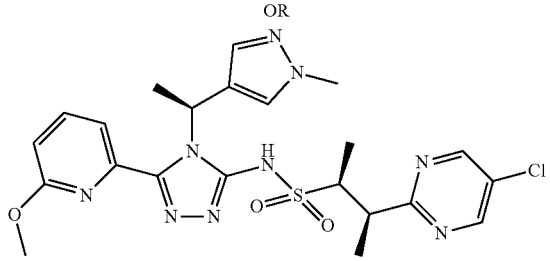<br>(2S,3R)-3-(5-chloropyrimidin-2-yl)-N-(5-(6-methoxypyridin-2-yl)-4-((R)-1-(1-methyl-1H-pyrazol-4-yl)ethyl)-4H-1,2,4-triazol-3-yl)butane-2-sulfonamide or (2S,3R)-3-(5-chloropyrimidin-2-yl)-N-(5-(6-methoxypyridin-2-yl)-4-((S)-1-(1-methyl-1H-pyrazol-4-yl)ethyl)-4H-1,2,4-triazol-3-yl)butane-2-sulfonamide.<br>$^1$H NMR (500 MHz, DMSO-d$_6$) δ 13.40-12.70 (m, 1H), 8.88-8.84 (m, 2H), 7.91-7.85 (m, 1H), 7.57 (s, 1H), 7.47 (d, J = 7.3 Hz, 1H), 7.28 (s, 1H), 7.00 (d, J = 8.3 Hz, 1H), 6.30 (q, J = 6.8 Hz, 1H), 3.83-3.79 (m, 3H), 3.68 (s, 3H), 3.64-3.54 (m, 2H), 1.84 (d, J = 7.0 Hz, 3H), 1.26 (d, J = 7.0 Hz, 3H), 1.08 (d, J = 6.7 Hz, 3H). LCMS-ESI (pos.) m/z: 532.2 (M + H)$^+$. |
| 299.0 | (1R,2S)-1-(5-chloropyrimidin-2-yl)-1-methoxypropane-2-sulfonamide (Example 29.3), (R)-2-(isothiocyanatomethyl)tetrahydro-2H-pyran and (S)-2-(isothiocyanatomethyl)tetrahydro-2H-pyran (commercially available from Enamine), and 5-methylnicotinic acid hydrazide (commercially available from Bellen). | 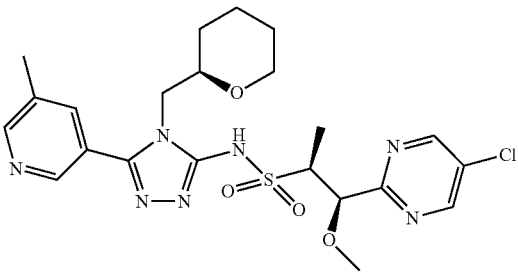 [SMILES: CO[C@H](c1ncc(Cl)cn1)[C@H](C)S(=O)(=O)Nc1nnc(-c2cncc(C)c2)n1C[C@H]1CCCCO1]<br>AND |

TABLE 24-continued

| Example | Reagents | Structure, Name, Data |
|---|---|---|
| | | 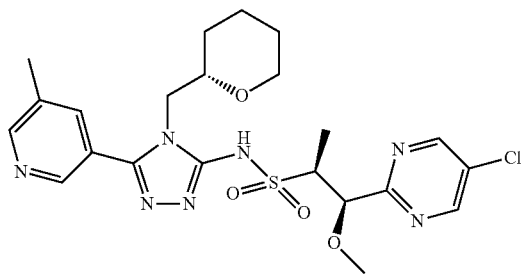 [SMILES: CO[C@H](c1ncc(Cl)cn1)[C@H](C)S(=O)(=O)Nc1nnc(-c2cncc(C)c2)n1C[C@@H]1CCCCO1]
(1R,2S)-1-(5-chloropyrimidin-2-yl)-1-methoxy-N-(5-(5-methylpyridin-3-yl)-4-(((R)-tetrahydro-2H-pyran-2-yl)methyl)-4H-1,2,4-triazol-3-yl)propane-2-sulfonamide and (1R,2S)-1-(5-chloropyrimidin-2-yl)-1-methoxy-N-(5-(5-methylpyridin-3-yl)-4-(((S)-tetrahydro-2H-pyran-2-yl)methyl)-4H-1,2,4-triazol-3-yl)propane-2-sulfonamide.
$^1$H NMR (400 MHz, CD$_2$Cl$_2$) δ 11.35 (br s, 1H), 8.85-8.77 (m, 1H), 8.72 (s, 2H), 8.60 (s, 1H), 8.00-7.96 (m, 1H), 5.06-4.97 (m, 1H), 3.97-3.82 (m, 3H), 3.77-3.61 (m, 2H), 3.44-3.31 (m, 1H), 3.26 (d, J = 4.4 Hz, 3H), 2.41 (s, 3H), 1.91-1.82 (m, 1H), 1.67 (br d, J = 12.6 Hz, 1H), 1.57-1.46 (m, 3H), 1.38 (dd, J = 3.7, 7.0 Hz, 3H), 1.27-1.18 (m, 1H). LCMS-ESI (pos.) m/z: 522.2 (M + H)$^+$. |
| 300.0 | (1S,2S)-1-isopropoxy-1-(5-methylpyrimidin-2-yl)propane-2-sulfonamide (Example 31.0), (R)-2-(isothiocyanatomethyl)tetrahydro-2H-pyran and (S)-2-(isothiocyanatomethyl)tetrahydro-2H-pyran (commercially available from Enamine), and 6-methoxypicolinohydrazide (commercially available from Milestone PharmTech USA Inc.). The racemic mixture was purified using the following preparative SFC method: Column: AS-H (2 × 25 cm), Mobile Phase: 75:25 (A:B) A: Liquid CO$_2$, B: IPA, Flow Rate: 70 mL/min, 220 nm, 100 bar inlet pressure to deliver peak 1. | 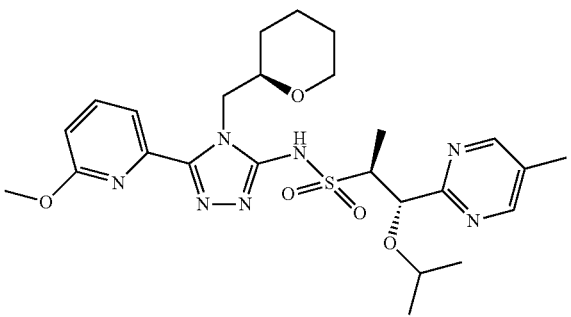
OR
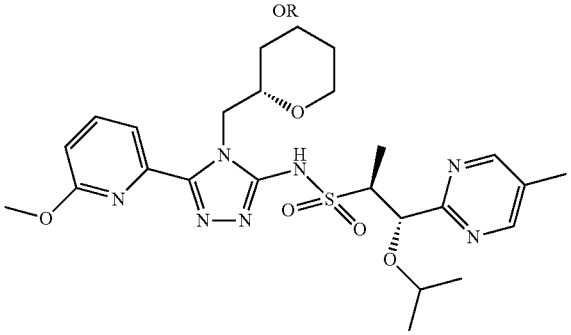
(1S,2S)-1-isopropoxy-N-(5-(6-methoxypyridin-2-yl)-4-(((R)-tetrahydro-2H-pyran-2-yl)methyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-(((S)-tetrahydro-2H-pyran-2-yl)methyl)-4H-1,2,4-triazol-3-yl)-1-(5-methylpyrimidin-2-yl)propane-2-sulfonamide.
$^1$H NMR (400 MHz, DMSO-d$_6$) δ 13.14 (s, 1H), 8.65 (s, 2H), 7.88 (t, J = 7.9 Hz, 1H), 7.60 (d, J = 7.5 Hz, 1H), 7.00 (d, J = 8.3 Hz, 1H), 4.83 (br d, J = 7.5 Hz, 1H), 4.63 (br dd, J = 7.9, 13.5 Hz, 1H), 4.15 (br dd, J = 4.8, 13.5 Hz, 1H), 3.92 (s, 3H), 3.72-3.55 (m, 3H), 3.40-3.32 (m, 1H), 3.22-3.10 (m, 1H), 2.26 (s, 3H), 1.73 (br s, 1H), 1.56 (br d, J = 12.4 Hz, 1H), 1.40-1.14 (m, 4H), 1.05 (br d, J = 7.0 Hz, 3H), 1.00 (br d, J = 6.0 Hz, 3H), 0.78-0.71 (m, 3H). LCMS-ESI (pos.) m/z: 546.2 (M + H)$^+$. |

TABLE 24-continued

| Example | Reagents | Structure, Name, Data |
|---|---|---|
| 301.0 | (1S,2S)-1-isopropoxy-1-(5-methylpyrimidin-2-yl)propane-2-sulfonamide (Example 31.0), (R)-2-(isothiocyanatomethyl)tetrahydro-2H-pyran and (S)-2-(isothiocyanatomethyl)tetrahydro-2H-pyran (commercially available from Enamine), and 6-methoxypicolinohydrazide (commercially available from Milestone PharmTech USA Inc.). The racemic mixture was purified using the following preparative SFC method: Column: AS-H (2 × 25 cm), Mobile Phase: 75:25 (A:B) A: Liquid $CO_2$, B: IPA, Flow Rate: 70 mL/min, 220 nm, 100 bar inlet pressure to deliver peak 2. | 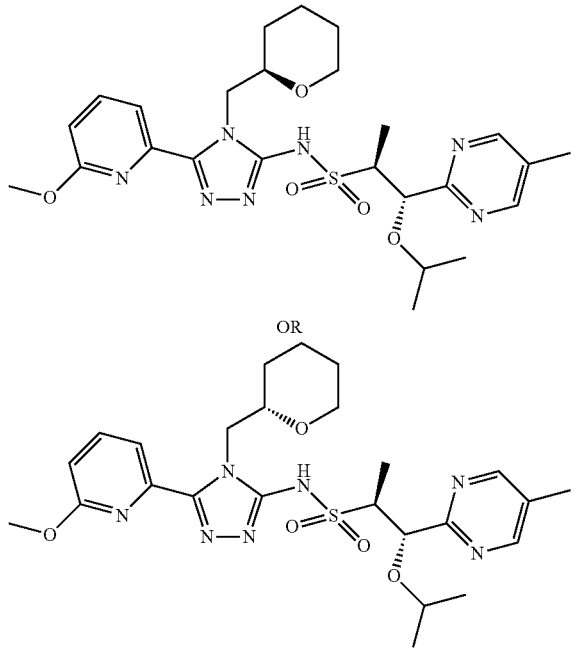 OR 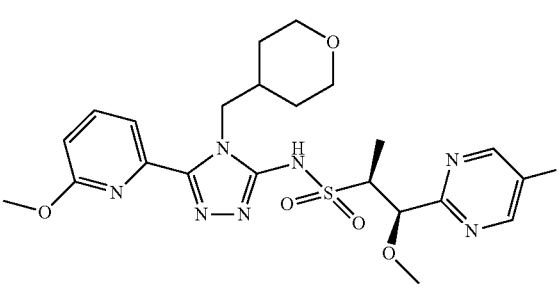<br>(1S,2S)-1-isopropoxy-N-(5-(6-methoxypyridin-2-yl)-4-(((R)-tetrahydro-2H-pyran-2-yl)methyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-(((S)-tetrahydro-2H-pyran-2-yl)methyl)-4H-1,2,4-triazol-3-yl)-1-(5-methylpyrimidin-2-yl)propane-2-sulfonamide.<br>$^1$H NMR (400 MHz, DMSO-$d_6$) δ 13.17 (s, 1H), 8.67 (s, 2H), 7.89 (t, J = 7.9 Hz, 1H), 7.61 (d, J = 7.5 Hz, 1H), 7.00 (d, J = 8.5 Hz, 1H), 4.84 (br d, J = 7.0 Hz, 1H), 4.63 (br dd, J = 8.1, 13.5 Hz, 1H), 4.19 (br dd, J = 4.8, 13.5 Hz, 1H), 3.92 (s, 3H), 3.71 (br d, J = 11.0 Hz, 1H), 3.66-3.53 (m, 2H), 3.52-3.32 (m, 2H), 3.22-3.12 (m, 1H), 2.27 (s, 3H), 1.72 (br s, 1H), 1.53 (br d, J = 12.2 Hz, 1H), 1.38 (br s, 3H), 1.20 (br d, J = 14.7 Hz, 1H), 1.07 (d, J = 7.0 Hz, 3H), 0.99 (d, J = 6.0 Hz, 3H), 0.77 (d, J = 6.2 Hz, 3H). LCMS-ESI (pos.) m/z: 546.2 (M + H)$^+$. |
| 302.0 | (1R,2S)-1-(5-chloropyrimidin-2-yl)-1-methoxypropane-2-sulfonamide (Example 29.3), 4-(isothiocyanatomethyl)tetrahydro-2H-pyran (Example 264.8), and 6-methoxypicolinohydrazide (commercially available from Milestone PharmTech USA Inc.). | (1R,2S)-1-(5-chloropyrimidin-2-yl)-1-methoxy-N-(5-(6-methoxypyridin-2-yl)-4-((tetrahydro-2H-pyran-4-yl)methyl)-4H-1,2,4-triazol-3-yl)propane-2-sulfonamide.<br>$^1$H NMR (400 MHz, DMSO-$d_6$) δ 13.27 (s, 1H), 8.92 (s, 2H), 7.90 (t, J = 8.0 Hz, 1H), 7.65 (d, J = 7.5 Hz, 1H), 7.02 (d, J = 8.5 Hz, 1H), 4.86 (d, J = 4.8 Hz, 1H), 4.26 (br dd, J = 7.4, 13.4 Hz, 1H), 4.18-4.08 (m, 1H), 3.94 (s, 3H), 3.79-3.72 (m, 2H), 3.65-3.57 (m, 1H), 3.18-3.10 (m, 5H), 2.13-2.00 (m, 1H), 1.41-1.30 (m, 5H), 1.26-1.13 (m, 2H). LCMS-ESI (pos.) m/z: 538.2 (M + H)$^+$. |

TABLE 24-continued

| Example | Reagents | Structure, Name, Data |
|---|---|---|
| 303.0 | (1R,S5)-1-(5-chloropyrimidin-2-yl)-1-methoxypropane-2-sulfonamide (Example 29.3), (R)-2-(isothiocyanatomethyl)-1,4-dioxane and (S)-2-(isothiocyanatomethyl)-1,4-dioxane (Example 264.9), and 6-methoxypicolinohydrazide (commercially available from Milestone PharmTech USA Inc.). The racemic mixture was purified using the following preparative SFC method: Column: IC (2 × 15 cm), Mobile Phase: 55:45 (A:B) A: Liquid $CO_2$, B: MeOH, Flow Rate: 100 mL/min, 218 nm, 100 bar inlet pressure to deliver peak 1. | 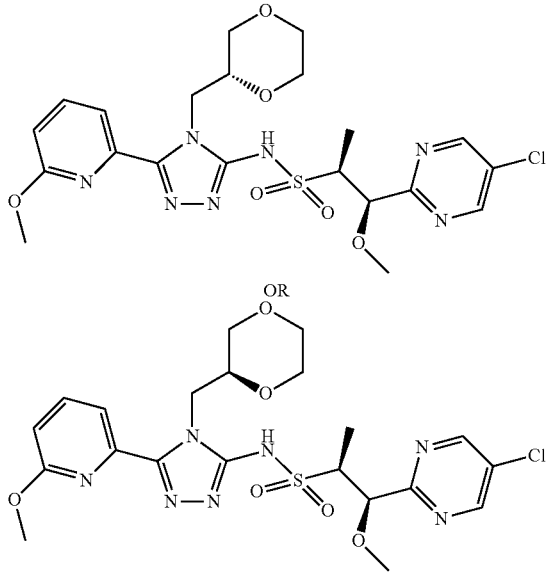<br>(1R,2S)-N-(4-(((R)-1,4-dioxan-2-yl)methyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-(((S)-1,4-dioxan-2-yl)methyl)-5-(6-methoxypyridin-2-yl)-4H-1,2,4-triazol-3-yl)-1-(5-chloropyrimidin-2-yl)-1-methoxypropane-2-sulfonamide.<br>$^1$H NMR (500 MHz, DMSO-$d_6$) δ 13.25 (s, 1H), 8.93 (s, 2H), 7.89 (t, J = 7.9 Hz, 1H), 7.62 (d, J = 7.5 Hz, 1H), 7.01 (d, J = 8.3 Hz, 1H), 4.93 (d, J = 4.4 Hz, 1H), 4.58 (dd, J = 8.0, 13.8 Hz, 1H), 4.16 (dd, J = 4.9, 14.0 Hz, 1H), 3.95 (s, 3H), 3.91-3.86 (m, 1H), 3.70 (br d, J = 10.4 Hz, 1H), 3.62-3.53 (m, 3H), 3.43-3.36 (m, 2H), 3.29-3.24 (m, 1H), 3.13 (s, 3H), 1.32 (d, J = 7.0 Hz, 3H). LCMS-ESI pos.) m/z: 540.2 (M + H)$^+$. |
| 304.0 | (1R,2S)-1-(5-chloropyrimidin-2-yl)-1-methoxypropane-2-sulfonamide (Example 29.3), (R)-2-(isothiocyanatomethyl)-1,4-dioxane and (S)-2-(isothiocyanatomethyl)-1,4-dioxane (Example 264.9), and 6-methoxypicolinohydrazide (commercially available from Milestone PharmTech USA Inc.). The racemic mixture was purified using the following preparative SFC method: Column: IC (2 × 15 cm), Mobile Phase: 55:45 (A:B) A: Liquid $CO_2$, B: MeOH, Flow Rate: 100 mL/min, 218 nm, 100 bar inlet pressure to deliver peak 2. | 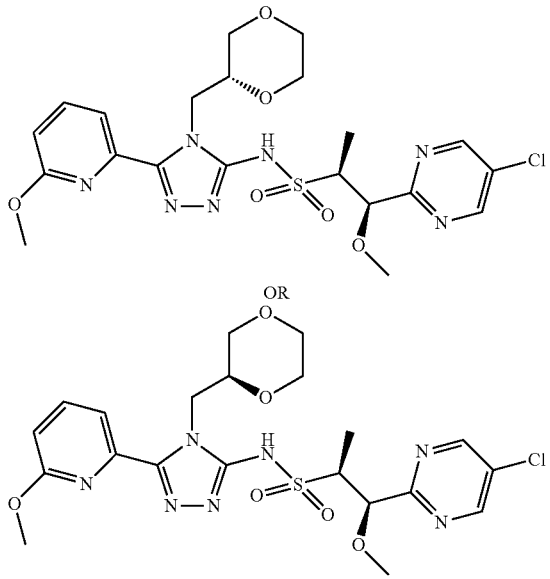<br>(1R,2S)-N-(4-(((R)-1,4-dioxan-2-yl)methyl)-5-(6-methoxypyridin-2-yl)-4H-1,2,4-triazol-3-yl)-1-(5-chloropyrimidin-2-yl)-1-methoxypropane-2-sulfonamide or (1R,2S)-N-(4-(((S)-1,4-dioxan-2- |

TABLE 24-continued

| Example | Reagents | Structure, Name, Data |
|---|---|---|
| | | yl)methyl)-5-(6-methoxypyridin-2-yl)-4H-1,2,4-triazol-3-yl)-1-(5-chloropyrimidin-2-yl)-1-methoxypropane-2-sulfonamide.<br>$^{1}$H NMR (500 MHz, DMSO-$d_{6}$) δ 13.27 (s, 1H), 8.91 (s, 2H), 7.89 (t, J = 7.9 Hz, 1H), 7.63 (d, J = 7.5 Hz, 1H), 7.01 (d, J = 8.3 Hz, 1H), 4.85 (d, J = 4.9 Hz, 1H), 4.65 (dd, J = 7.5, 13.8 Hz, 1H), 4.05 (dd, J = 5.4, 13.8 Hz, 1H), 3.95 (s, 3H), 3.89 (q, J = 6.2 Hz, 1H), 3.69-3.54 (m, 4H), 3.43-3.35 (m, 2H), 3.31-3.25 (m, 1H), 3.17 (s, 3H), 1.33 (d, J = 7.0 Hz, 3H). LCMS-ESI pos.) m/z: 540.2 (M + H)$^{+}$. |
| 305.0 | (1R,2S)-1-(5-chloropyrimidin-2-yl)-1-methoxypropane-2-sulfonamide (Example 29.3), (2S,6S)-2-(isothiocyanatomethyl)-6-methyltetrahydro-2H-pyran and (2R,6R)-2-(isothiocyanatomethyl)-6-methyltetrahydro-2H-pyran and (2S,6R)-2-(isothiocyanatomethyl)-6-methyltetrahydro-2H-pyran and (2R,6S)-2-(isothiocyanatomethyl)-6-methyltetrahydro-2H-pyran (Example 264.10), and 6-methoxypicolinohydrazide (commercially available from Milestone PharmTech USA Inc.). The racemic mixture was purified using the following preparative SFC method: Column: Phenomenex CEL 2 (2 ×15 cm) + Phenomenex CEL 2 (2 × 15 cm), Mobile Phase: 60:40 (A:B) A: Liquid CO$_{2}$, B: MeOH, Flow Rate: 80 mL/min, 215 nm, 100 bar inlet pressure to deliver Fraction 1. Fraction 1 was purified using the following preparative SFC method: Column: Column: AD-H (2 × 25 cm) + AD-H (2 × 15 cm), Mobile Phase: 65:35 (A:B) A: Liquid CO$_{2}$, B: MeOH, Flow Rate: 60 mL/min, 215 nm, 100 bar inlet pressure to deliver peak 1. | 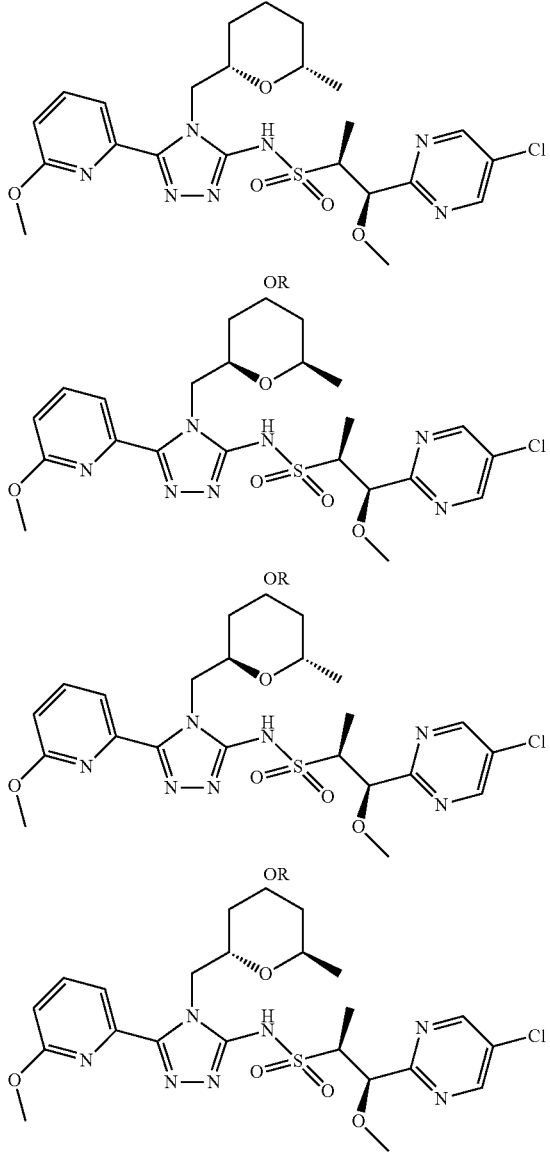<br><br>(1R,2S)-1-(5-chloropyrimidin-2-yl)-1-methoxy-N-(5-(6-methoxypyridin-2-yl)-4-(((2R,6R)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2R,6S)-6- |

TABLE 24-continued

| Example | Reagents | Structure, Name, Data |
|---|---|---|
| | | methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6R)-6-methyltetrahydro-2H-pyran-2-yl)methyl)-4H-1,2,4-triazol-3-yl)propane-2-sulfonamide.<br>$^1$H NMR (500 MHz, CD$_2$Cl$_2$) δ 11.05 (s, 1H), 8.72 (s, 2H), 7.70 (t, J = 7.9 Hz, 1H), 7.56 (d, J = 7.3 Hz, 1H), 6.86 (d, J = 8.3 Hz, 1H), 4.95 (d, J = 4.4 Hz, 1H), 4.77 (dd, J = 8.0, 13.5 Hz, 1H), 4.25 (dd, J = 4.7, 13.5 Hz, 1H), 3.98 (s, 3H), 3.72-3.62 (m, 2H), 3.26 (s, 3H), 3.23-3.16 (m, 1H), 1.79-1.73 (m, 1H), 1.59-1.53 (m, 1H), 1.47-1.38 (m, 5H), 1.20-1.13 (m, 1H), 1.05-0.96 (m, 1H), 0.80 (d, J = 6.0 Hz, 3H). LCMS-ESI (pos.) m/z: 552.2 (M + H)$^+$. |
| 306.0 | (1R,2S)-1-(5-chloropyrimidin-2-yl)-1-methoxypropane-2-sulfonamide (Example 29.3), (2S,6S)-2-(isothiocyanatomethyl)-6-methyltetrahydro-2H-pyran and (2R,6R)-2-(isothiocyanatomethyl)-6-methyltetrahydro-2H-pyran and (2S,6R)-2-(isothiocyanatomethyl)-6-methyltetrahydro-2H-pyran and (2R,6S)-2-(isothiocyanatomethyl)-6-methyltetrahydro-2H-pyran (Example 264.10), and 6-methoxypicolinohydrazide (commercially available from Milestone PharmTech USA Inc.). The racemic mixture was purified using the following preparative SFC method: Column: Phenomenex CEL 2 (2 × 15 cm) + Phenomenex CEL 2 (2 × 15 cm), Mobile Phase: 60:40 (A:B) A: Liquid CO$_2$, B: MeOH, Flow Rate: 80 mL/min, 215 nm, 100 bar inlet pressure to deliver Fraction 1. Fraction 1 was purified using the following preparative SFC method: Column: Column: AD-H (2 × 25 cm) + AD-H (2 × 15 cm), Mobile Phase: 65:35 (A:B) A: Liquid CO$_2$, B: MeOH, Flow Rate: 60 mL/min, 215 nm, 100 bar inlet pressure to deliver peak 2. | 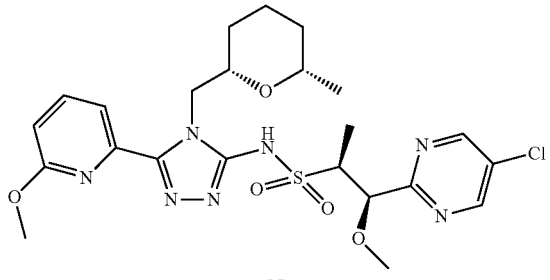 [SMILES: COc1cccc(-c2nnc(NS(=O)(=O)[C@@H](C)[C@H](OC)c3ncc(Cl)cn3)n2C[C@@H]2CCC[C@H](C)O2)n1]<br>OR<br>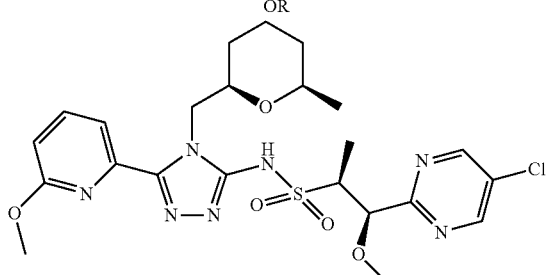<br>OR<br>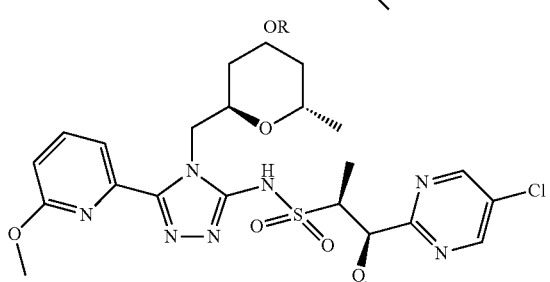<br>OR<br>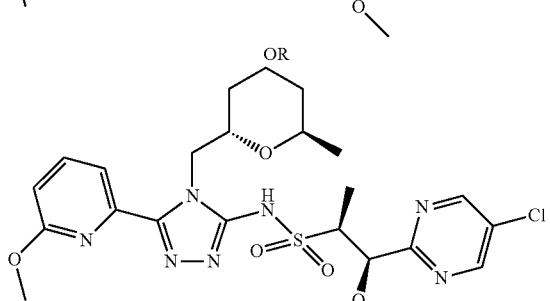<br>(1R,2S)-1-(5-chloropyrimidin-2-yl)-1-methoxy-N-(5-(6-methoxypyridin-2-yl)-4-(((2R,6R)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6S)-6- |

TABLE 24-continued

| Example | Reagents | Structure, Name, Data |
|---|---|---|
| | | methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2R,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6R)-6-methyltetrahydro-2H-pyran-2-yl)methyl)-4H-1,2,4-triazol-3-yl)propane-2-sulfonamide.<br>$^1$H NMR (500 MHz, CD$_2$Cl$_2$) δ 11.01 (s, 1H), 8.73 (s, 2H), 7.73 (t, J = 7.9 Hz, 1H), 7.61 (d, J = 7.3 Hz, 1H), 6.89 (d, J = 8.3 Hz, 1H), 4.94 (d, J = 4.7 Hz, 1H), 4.88 (dd, J = 8.8, 13.5 Hz, 1H), 4.29 (dd, J = 4.9, 13.5 Hz, 1H), 4.09-4.03 (m, 1H), 3.98 (s, 3H), 3.73-3.61 (m, 2H), 3.29 (s, 3H), 1.65-1.59 (m, 3H), 1.58-1.53 (m, 1H), 1.45-1.38 (m, 4H), 1.22-1.16 (m, 1H), 0.88 (d, J = 6.5 Hz, 3H). LCMS-ESI (pos.) m/z: 552.2 (M + H)$^+$. |
| 307.0 | (1R,2S)-1-(5-chloropyrimidin-2-yl)-1-methoxypropane-2-sulfonamide (Example 29.3), (2S,6S)-2-(isothiocyanatomethyl)-6-methyltetrahydro-2H-pyran and (2R,6R)-2-(isothiocyanatomethyl)-6-methyltetrahydro-2H-pyran and (2S,6R)-2-(isothiocyanatomethyl)-6-methyltetrahydro-2H-pyran and (2R,6S)-2-(isothiocyanatomethyl)-6-methyltetrahydro-2H-pyran (Example 264.10), and 6-methoxypicolinohydrazide (commercially available from Milestone PharmTech USA Inc.). The racemic mixture was purified using the following preparative SFC method: Column: Phenomenex CEL 2 (2 × 15 cm) + Phenomenex CEL 2 (2 × 15 cm), Mobile Phase: 60:40 (A:B) A: Liquid CO$_2$, B: MeOH, Flow Rate: 80 mL/min, 215 nm, 100 bar inlet pressure to deliver Fraction 2. | 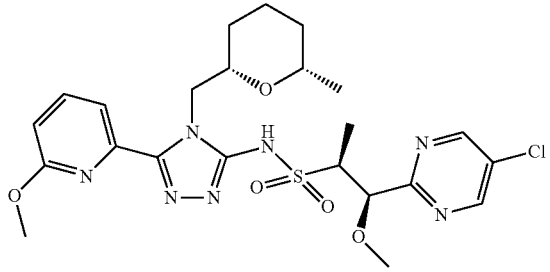 [SMILES: COc1cccc(-c2nnc(NS(=O)(=O)[C@@H](C)[C@H](OC)c3ncc(Cl)cn3)n2C[C@@H]2CCC[C@H](C)O2)n1]<br>OR<br>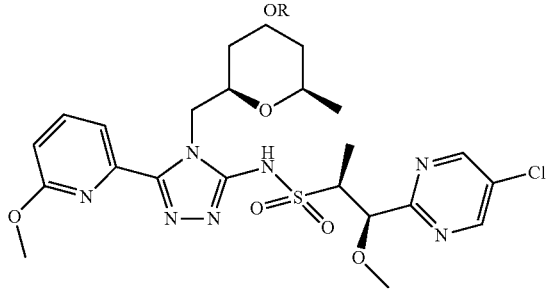<br>OR<br>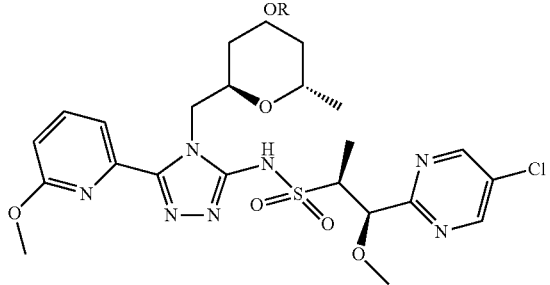<br>OR<br>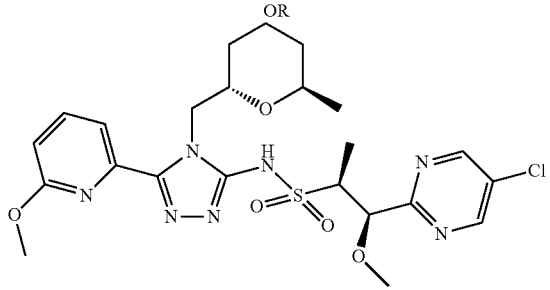<br>(1R,2S)-1-(5-chloropyrimidin-2-yl)-1-methoxy-N-(5-(6-methoxypyridin-2-yl)-4-(((2R,6R)-6-methyltetrahydro-2H-pyran-2-yl)methyl)-4H-1,2,4- |

TABLE 24-continued

| Example | Reagents | Structure, Name, Data |
|---|---|---|
| | | triazol-3-yl)propane-2-sulfonamide or (1R,2S)-1-(5-chloropyrimidin-2-yl)-1-methoxy-N-(5-(6-methoxypyridin-2-yl)-4-(((2S,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2R,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6R)-6-methyltetrahydro-2H-pyran-2-yl)methyl)-4H-1,2,4-triazol-3-yl)propane-2-sulfonamide. $^1$H NMR (500 MHz, CD$_2$Cl$_2$) δ 11.05 (s, 1H), 8.72 (s, 2H), 7.70 (t, J = 7.8 Hz, 1H), 7.56 (d, J = 7.3 Hz, 1H), 6.86 (d, J = 8.3 Hz, 1H), 4.98 (d, J = 4.7 Hz, 1H), 4.75 (dd, J = 8.4, 13.6 Hz, 1H), 4.26 (dd, J = 4.4, 13.5 Hz, 1H), 3.98 (s, 3H), 3.72-3.64 (m, 2H), 3.26 (s, 3H), 3.24-3.19 (m, 1H), 1.81-1.74 (m, 1H), 1.58-1.53 (m, 1H), 1.49-1.37 (m, 5H), 1.19-1.11 (m, 1H), 1.06-0.97 (m, 1H), 0.80 (d, J = 6.2 Hz, 3H). LCMS-ESI (pos.) m/z: 552.2 (M + H)$^+$. |
| 308.0 | (1R,2S)-1-(5-chloropyrimidin-2-yl)-1-methoxypropane-2-sulfonamide (Example 29.3), (2S,6S)-2-(isothiocyanatomethyl)-6-methyltetrahydro-2H-pyran and (2R,6R)-2-(isothiocyanatomethyl)-6-methyltetrahydro-2H-pyran and (2S,6R)-2-(isothiocyanatomethyl)-6-methyltetrahydro-2H-pyran and (2R,6S)-2-(isothiocyanatomethyl)-6-methyltetrahydro-2H-pyran (Example 264.10), and 6-methoxypicolinohydrazide (commercially available from Milestone PharmTech USA Inc.). The racemic mixture was purified using the following preparative SFC method: Column: Phenomenex CEL 2 (2 × 15 cm) + Phenomenex CEL 2 (2 × 15 cm), Mobile Phase: 60:40 (A:B) A: Liquid CO$_2$, B: MeOH, Flow Rate: 80 mL/min, 215 nm, 100 bar inlet pressure to deliver Fraction 3. Fraction 3 mixture was purified using the following preparative SFC method: Column: Phenomenex CEL 2 (2 × 15 cm) + Phenomenex CEL 2 (2 × 15 cm), Mobile Phase: 60:40 (A:B) A: Liquid CO$_2$, B: MeOH, Flow Rate: 80 mL/min, 215 nm, 100 bar inlet pressure to deliver peak 4. | 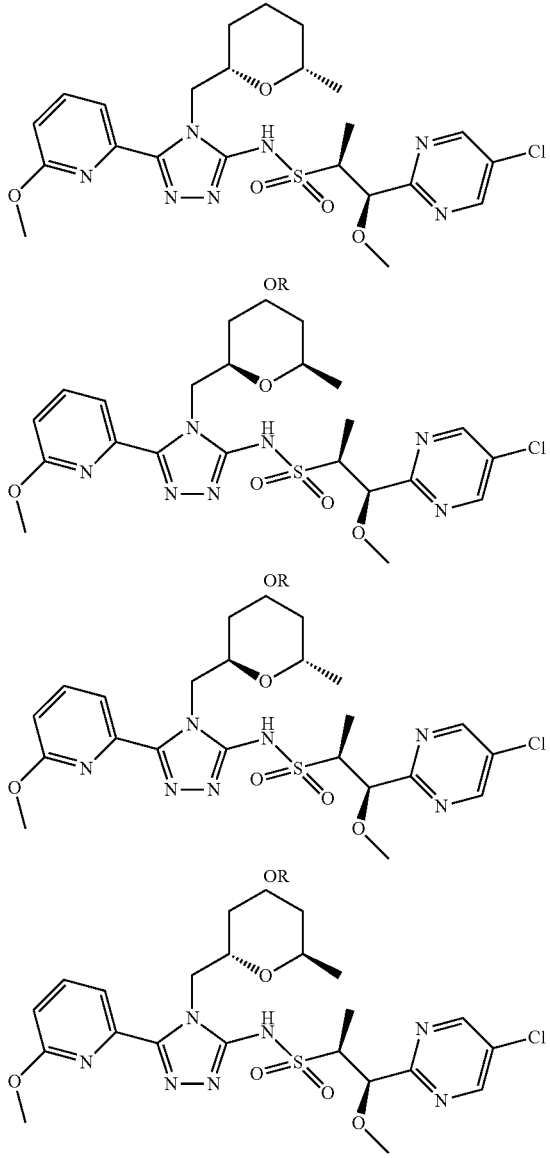 |

TABLE 24-continued

| Example | Reagents | Structure, Name, Data |
|---|---|---|
| | | (1R,2S)-1-(5-chloropyrimidin-2-yl)-1-methoxy-N-(5-(6-methoxypyridin-2-yl)-4-(((2R,6R)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2R,6S)-6-methyltetrahydro-2H-pyran-2-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((2S,6R)-6-methyltetrahydro-2H-pyran-2-yl)methyl)-4H-1,2,4-triazol-3-yl)propane-2-sulfonamide.<br>$^1$H NMR (500 MHz, CD$_2$Cl$_2$) δ 11.05 (br s, 1H), 8.73 (s, 2H), 7.73 (t, J = 7.8 Hz, 1H), 7.60 (d, J = 7.3 Hz, 1H), 6.89 (d, J = 8.3 Hz, 1H), 4.99 (d, J = 4.2 Hz, 1H), 4.96-4.87 (m, 1H), 4.29 (dd, J = 4.5, 13.6 Hz, 1H), 4.14-4.07 (m, 1H), 3.98 (s, 3H), 3.72-3.64 (m, 1H), 3.62-3.55 (m, 1H), 3.25 (s, 3H), 1.71-1.57 (m, 4H), 1.48-1.42 (m, 1H), 1.37 (d, J = 7.0 Hz, 3H), 1.21-1.15 (m, 1H), 0.85 (d, J = 6.2 Hz, 3H). LCMS-ESI (pos.) m/z: 552.2 (M + H)$^+$. |
| 309.0 | (1R,2S)-1-(5-chloropyrimidin-2-yl)-1-methoxypropane-2-sulfonamide (Example 29.3), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column AD-H (2 × 25 cm), Mobile Phase: 75:25 (A:B) A: Liquid CO$_2$, B: MeOH, Flow Rate: 80 mL/min, 218 nm, 100 bar inlet pressure to deliver peak 1. | (1R,2S)-1-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)-1-methoxypropane-2-sulfonamide.<br>$^1$H NMR (500 MHz, DMSO-d$_6$) δ 13.12 (s, 1H), 8.92 (s, 2H), 7.94 (t, J = 7.9 Hz, 1H), 7.58 (d, J = 7.3 Hz, 1H), 7.06 (d, J = 8.3 Hz, 1H), 6.41 (q, J = 7.0 Hz, 1H), 4.76 (d, J = 3.6 Hz, 1H), 3.92 (s, 3H), 3.40-3.33 (m, 1H), 3.12 (s, 3H), 2.34 (s, 3H), 1.96-1.89 (m, 6H), 0.98 (d, J = 7.0 Hz, 3H). LCMS-ESI (pos.) m/z: 563.2 (M + H)$^+$. |

TABLE 24-continued

| Example | Reagents | Structure, Name, Data |
|---|---|---|
| 310.0 | (1R,2S)-1-(5-chloropyrimidin-2-yl)-1-methoxypropane-2-sulfonamide (Example 29.3), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column AD-H (2 × 25 cm), Mobile Phase: 75:25 (A:B) A: Liquid $CO_2$, B: MeOH, Flow Rate: 80 mL/min, 218 nm, 100 bar inlet pressure to deliver peak 2. | 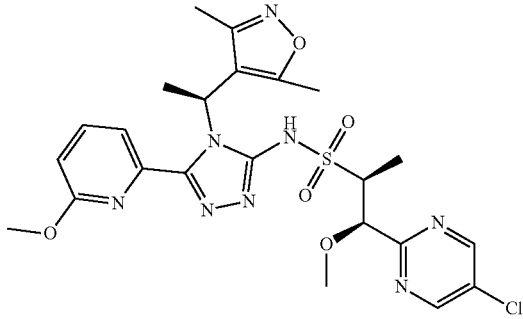 [SMILES: COc1cccc(-c2nnc(NS(=O)(=O)[C@@H](C)[C@H](OC)c3ncc(Cl)cn3)n2[C@@H](C)c2c(C)noc2C)n1]<br>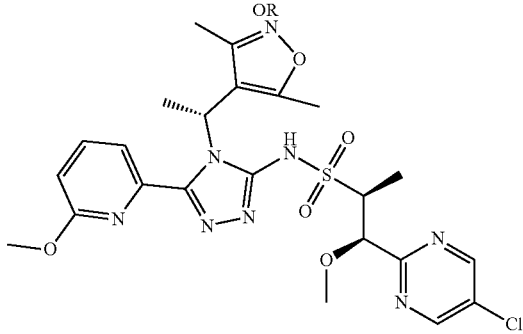<br>(1R,2S)-1-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)-1-methoxypropane-2-sulfonamide.<br>$^1$H NMR (500 MHz, DMSO-$d_6$) δ 13.19 (s, 1H), 8.94 (s, 2H), 7.97-7.91 (m, 1H), 7.58 (d, J = 7.3 Hz, 1H), 7.06 (d, J = 8.3 Hz, 1H), 6.37 (q, J = 7.0 Hz, 1H), 4.84 (d, J = 4.2 Hz, 1H), 3.92 (s, 3H), 3.55-3.44 (m, 1H), 3.10 (s, 3H), 2.36 (s, 3H), 1.93 (d, J = 7.0 Hz, 3H), 1.87 (s, 3H), 1.19 (d, J = 7.0 Hz, 3H). LCMS-ESI (pos.) m/z: 563.2 (M + H)$^+$. |
| 311.0 | (1R,2S)-1-(5-chloropyrimidin-2-yl)-1-methoxypropane-2-sulfonamide (Example 29.3), (R)-3-(isothiocyanatomethyl)tetrahydro-2H-pyran and (S)-3-(isothiocyanatomethyl)tetrahydro-2H-pyran (Example 264.12), and 6-methoxypicolinohydrazide (commercially available from Milestone PharmTech USA Inc.). The racemic mixture was purified using the following preparative SFC method: Column: IC (2 × 15 cm), Mobile Phase: 50:50 (A:B) A: Liquid $CO_2$, B: MeOH, Flow Rate: 80 mL/min, 219 nm, 100 bar inlet pressure to deliver peak 1. | 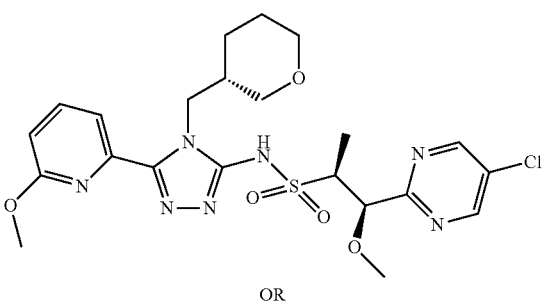<br>OR<br>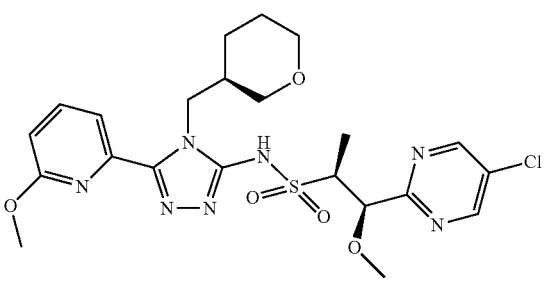 [SMILES: COc1cccc(-c2nnc(NS(=O)(=O)[C@@H](C)[C@H](OC)c3ncc(Cl)cn3)n2C[C@H]2CCCOC2)n1]<br>(1R,2S)-1-(5-chloropyrimidin-2-yl)-1-methoxy-N-(5-(6-methoxypyridin-2-yl)-4-(((R)-tetrahydro-2H- |

TABLE 24-continued

| Example | Reagents | Structure, Name, Data |
|---|---|---|
| | | pyran-3-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydro-2H-pyran-3-yl)methyl)-4H-1,2,4-triazol-3-yl)propane-2-sulfonamide.<br>$^1$H NMR (500 MHz, CD$_2$Cl$_2$) δ 11.73-10.71 (m, 1H), 8.72 (s, 2H), 7.77-7.70 (m, 1H), 7.65 (br d, J = 7.3 Hz, 1H), 6.91 (br d, J = 8.3 Hz, 1H), 5.00 (br d, J = 3.9 Hz, 1H), 4.37 (br d, J = 7.5 Hz, 2H), 3.98 (s, 3H), 3.76-3.67 (m, 3H), 3.34 (br t, J = 10.1 Hz, 1H), 3.27 (s, 3H), 3.20 (br t, J = 10.3 Hz, 1H), 2.13 (br s, 1H), 1.74-1.66 (m, 1H), 1.58 (br d, J = 13.2 Hz, 1H), 1.51-1.45 (m, 1H), 1.40 (br d, J = 7.0 Hz, 3H), 1.33-1.26 (m, 1H). LCMS-ESI (pos.) m/z: 538.2 (M + H)$^+$. |
| 312.0 | (1R,2S)-1-(5-chloropyrimidin-2-yl)-1-methoxypropane-2-sulfonamide (Example 29.3), (R)-3-(isothiocyanatomethyl)tetrahydro-2H-pyran and (S)-3-(isothiocyanatomethyl)tetrahydro-2H-pyran (Example 264.12), and 6-methoxypicolinohydrazide (commercially available from Milestone PharmTech USA Inc.). The racemic mixture was purified using the following preparative SFC method: Column: IC (2 × 15 cm), Mobile Phase: 50:50 (A:B) A: Liquid CO$_2$, B: MeOH, Flow Rate: 80 mL/min, 219 nm, 100 bar inlet pressure to deliver peak 2. | 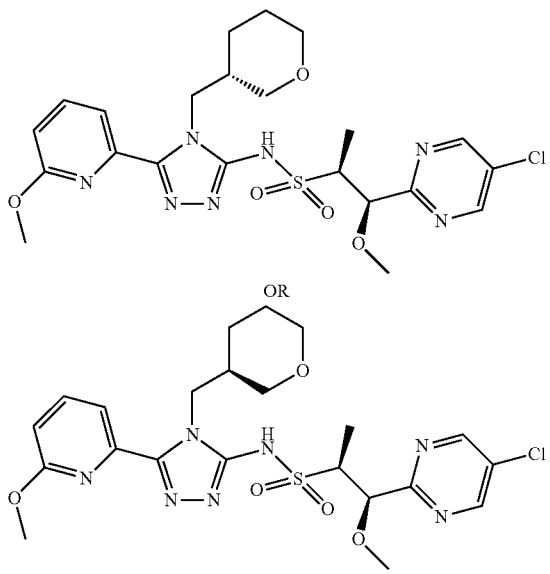<br>OR<br><br>(1R,2S)-1-(5-chloropyrimidin-2-yl)-1-methoxy-N-(5-(6-methoxypyridin-2-yl)-4-(((R)-tetrahydro-2H-pyran-3-yl)methyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-(((S)-tetrahydro-2H-pyran-3-yl)methyl)-4H-1,2,4-triazol-3-yl)propane-2-sulfonamide.<br>$^1$H NMR (500 MHz, CD$_2$Cl$_2$) δ 12.27-9.94 (m, 1H), 8.72-8.69 (m, 1H), 7.77-7.71 (m, 1H), 7.65 (d, J = 7.5 Hz, 1H), 6.90 (d, J = 8.3 Hz, 1H), 4.99 (d, J = 4.4 Hz, 1H), 4.38 (d, J = 7.8 Hz, 2H), 3.98 (s, 3H), 3.76-3.71 (m, 1H), 3.70-3.65 (m, 2H), 3.34 (dt, J = 2.6, 10.9 Hz, 1H), 3.28 (s, 3H), 3.20 (dd, J = 9.6, 11.2 Hz, 1H), 2.20-2.11 (m, 1H), 1.75-1.67 (m, 1H), 1.57 (td, J = 3.6, 13.4 Hz, 1H), 1.50-1.43 (m, 1H), 1.40 (d, J = 7.0 Hz, 3H), 1.33-1.24 (m, 1H). LCMS-ESI (pos.) m/z: 538.2 (M + H)$^+$. |
| 313.0 | (2S,3R)-3-(5-chloropyrimidin-2-yl)butane-2-sulfonamide (Example 27.4), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column AD-H (2 × 25 cm), Mobile Phase: 70:30 (A:B) A: Liquid CO$_2$, B: MeOH, Flow Rate: | 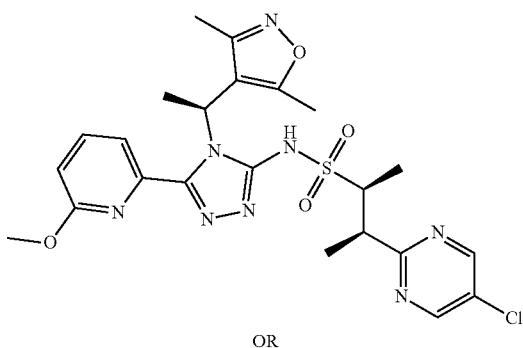<br>OR |

TABLE 24-continued

| Example | Reagents | Structure, Name, Data |
|---|---|---|
|  | 80 mL/min, 218 nm, 100 bar inlet pressure to deliver peak 1. | 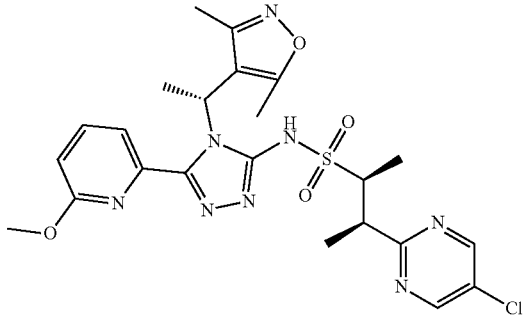 [SMILES: COc1cccc(-c2nnc(NS(=O)(=O)[C@@H](C)[C@H](C)c3ncc(Cl)cn3)n2[C@H](C)c2c(C)noc2C)n1]<br>(2S,3R)-3-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)butane-2-sulfonamide or (2S,3R)-3-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)butane-2-sulfonamide.<br>$^1$H NMR (500 MHz, DMSO-$d_6$) δ 13.17 (s, 1H), 8.84 (s, 2H), 7.97-7.91 (m, 1H), 7.60 (d, J = 7.3 Hz, 1H), 7.06 (d, J = 8.3 Hz, 1H), 6.40 (q, J = 7.2 Hz, 1H), 3.92 (s, 3H), 3.61-3.50 (m, 1H), 3.38-3.33 (m, 1H), 2.33 (s, 3H), 1.93 (d, J = 7.3 Hz, 3H), 1.88 (s, 3H), 1.24 (d, J = 7.0 Hz, 3H), 1.04 (d, J = 7.0 Hz, 3H). LCMS-ESI (pos.) m/z: 547.2 (M + H)$^+$. |
| 314.0 | (2S,3R)-3-(5-chloropyrimidin-2-yl)butane-2-sulfonamide (Example 27.4), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column AD-H (2 × 25 cm), Mobile Phase: 70:30 (A:B) A: Liquid CO$_2$, B: MeOH, Flow Rate: 80 mL/min, 218 nm, 100 bar inlet pressure to deliver peak 2. | 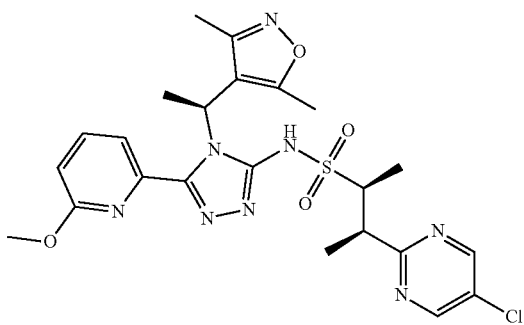 [SMILES: COc1cccc(-c2nnc(NS(=O)(=O)[C@@H](C)[C@H](C)c3ncc(Cl)cn3)n2[C@@H](C)c2c(C)noc2C)n1]<br>(2S,3R)-3-(5-chloropyrimidin-2-yl)-N-(4-((R)-1-(3,5-dimethylisoxazol-4-yl)ethyl)-5-(6-methoxypyridin-2-yl)-4H-1,2,4-triazol-3-yl)butane-2-sulfonamide or (2S,3R)-3-(5-chloropyrimidin-2-yl)-N-(4-((S)-1-(3,5-dimethylisoxazol-4-yl)ethyl)-5-(6-methoxypyridin-2-yl)-4H-1,2,4-triazol-3-yl)butane-2-sulfonamide.<br>$^1$H NMR (500 MHz, DMSO-$d_6$) δ 13.18 (s, 1H), 8.85 (s, 2H), 7.93 (t, J = 7.9 Hz, 1H), 7.57 (d, J = 7.3 Hz, 1H), 7.06 (d, J = 8.3 Hz, 1H), 6.35 (q, J = 7.2 Hz, 1H), 3.91 (s, 3H), 3.70-3.64 (m, 1H), 3.62-3.56 (m, 1H), 2.35 (s, 3H), 1.89 (d, J = 7.0 Hz, 3H), 1.87-1.85 (m, 3H), 1.28 (d, J = 7.0 Hz, 3H), 1.07 (d, J = 7.0 Hz, 3H). LCMS-ESI (pos.) m/z: 547.2 (M + H)$^+$. |

TABLE 24-continued

| Example | Reagents | Structure, Name, Data |
|---|---|---|
| 315.0 | (1S,2S)-1-isopropoxy-1-(5-methylpyrimidin-2-yl)propane-2-sulfonamide (Example 31.0), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column Regis Whelk-O s,s (2 × 15 cm) + Regis Whelk-O s,s (2 × 15 cm), Mobile Phase: 65:35 (A:B) A: Liquid $CO_2$, B: MeOH, Flow Rate: 80 mL/min, 218 nm, 100 bar inlet pressure to deliver peak 1. | 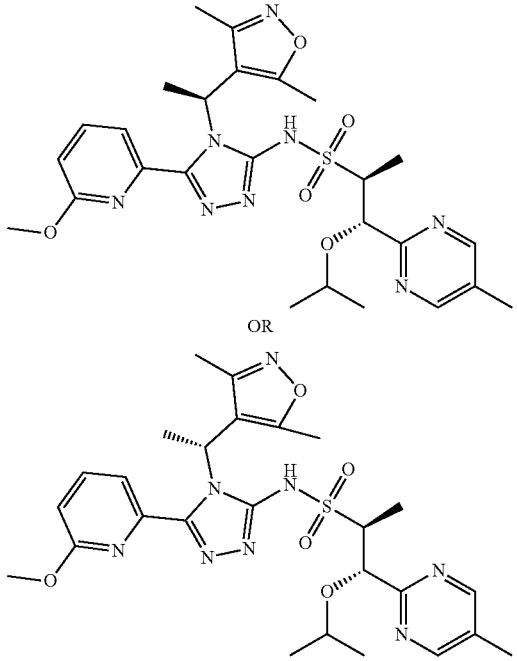 OR <br><br>(1S,2S)-N-(4-((R)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide or (1S,2S)-N-(4-((S)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide.<br><br>$^1$H NMR (500 MHz, DMSO-$d_6$) δ 12.98-11.78 (m, 1H), 8.68 (s, 2H), 7.95-7.90 (m, 1H), 7.57 (d, J = 7.3 Hz, 1H), 7.04 (d, J = 8.3 Hz, 1H), 6.40 (q, J = 7.3 Hz, 1H), 4.78 (d, J = 6.7 Hz, 1H), 3.91 (s, 3H), 3.56 (quin, J = 6.8 Hz, 1H), 3.31-3.27 (m, 1H), 2.37 (s, 3H), 2.28 (s, 3H), 1.96 (d, J = 7.3 Hz, 3H), 1.90 (s, 3H), 0.94 (d, J = 7.3 Hz, 3H), 0.91 (d, J = 6.0 Hz, 3H), 0.73 (d, J = 6.2 Hz, 3H). LCMS-ESI (pos.) m/z: 571.2 (M + H)$^+$. |
| 316.0 | (1S,2S)-1-isopropoxy-1-(5-methylpyrimidin-2-yl)propane-2-sulfonamide (Example 31.0), (R)-4-(1-isothiocyanatoethyl)-3,5-dimethylisoxazole and (S)-4-(1-isothiocyanatoethyl)-3,5-dimethylisoxazole (Example 264.11), and 6-methoxypicolinohydrazide (commercially available from Milestone PharmTech USA Inc.). The racemic mixture was purified using the following preparative SFC method: Column Regis Whelk-O s,s (2 × 15 cm) + Regis Whelk-O s,s (2 × 15 cm), Mobile Phase: 65:35 | 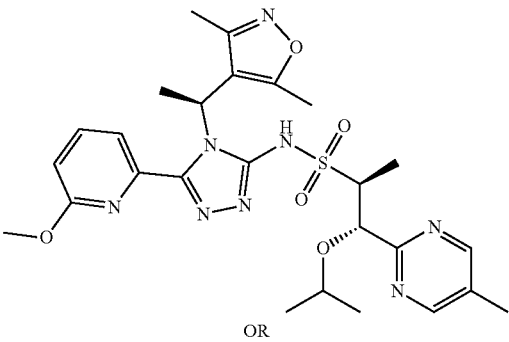 OR |

TABLE 24-continued

| Example | Reagents | Structure, Name, Data |
|---|---|---|
| | (A:B) A: Liquid $CO_2$, B: MeOH, Flow Rate: 80 mL/min, 218 nm, 100 bar inlet pressure to deliver peak 2. | 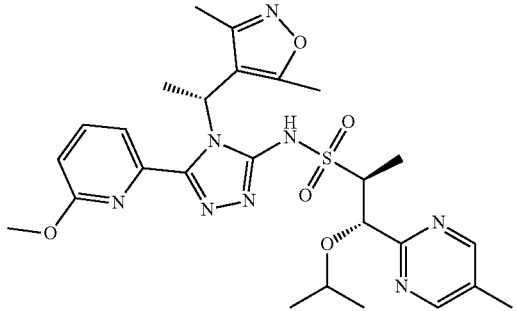<br>(1S,2S)-N-(4-((R)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide or (1S,2S)-N-(4-((S)-1-(3,5-dimethylisoxazol-4-yl)ethyl)-5-(6-methoxypyridin-2-yl)-4H-1,2,4-triazol-3-yl)-1-isopropoxy-1-(5-methylpyrimidin-2-yl)propane-2-sulfonamide.<br>$^1$H NMR (500 MHz, DMSO-$d_6$) δ 13.51-12.60 (m, 1H), 8.65 (s, 2H), 7.96-7.89 (m, 1H), 7.55 (d, J = 7.0 Hz, 1H), 7.05 (d, J = 8.3 Hz, 1H), 6.32 (q, J = 7.0 Hz, 1H), 4.83 (d, J = 6.2 Hz, 1H), 3.91 (s, 3H), 3.61-3.53 (m, 1H), 3.41 (m, 1H), 2.37-2.33 (m, 3H), 2.29-2.25 (m, 3H), 1.95 (d, J = 7.3 Hz, 3H), 1.87 (s, 3H), 1.07-0.99 (m, 6H), 0.79 (d, J = 6.2 Hz, 3H). LCMS-ESI (pos.) m/z: 571.2 (M + H)$^+$. |
| 317.0 | (1R,2S)-1-(5-chloropyrimidin-2-yl)-1-methoxypropane-2-sulfonamide (Example 29.3), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: AD-H (2 × 25 cm), Mobile Phase: 75:25 (A:B) A: Liquid $CO_2$, B: MeOH, Flow Rate: 80 mL/min, 229 nm, 100 bar inlet pressure to deliver peak 1. | 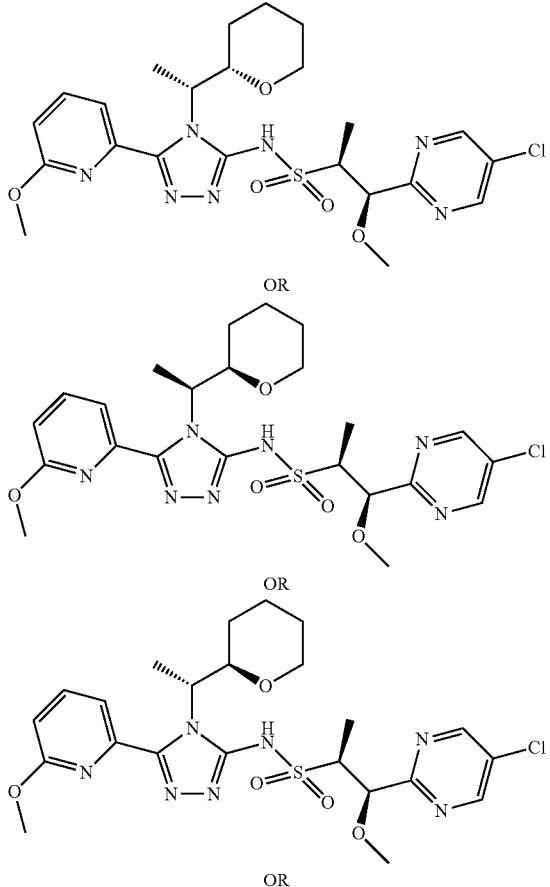<br>OR |

TABLE 24-continued

| Example | Reagents | Structure, Name, Data |
|---|---|---|

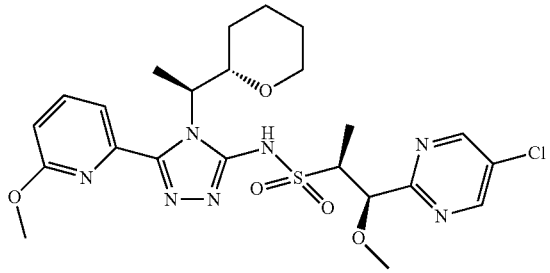 [SMILES: COc1cccc(-c2nnc(NS(=O)(=O)[C@@H](C)[C@H](OC)c3ncc(Cl)cn3)n2[C@@H](C)[C@@H]2CCCCO2)n1]

(1R,2S)-1-(5-chloropyrimidin-2-yl)-1-methoxy-N-(5-(6-methoxypyridin-2-yl)-4-((S)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((S)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-tetrahydro-2H-pyran-2-yl)ethyl)-4H-1,2,4-triazol-3-yl)propane-2-sulfonamide.

$^1$H NMR (400 MHz, CD$_2$Cl$_2$) δ 8.73 (s, 2H), 7.74 (dd, J = 7.4, 8.4 Hz, 1H), 7.50 (d, J = 7.3 Hz, 1H), 6.91 (d, J = 8.3 Hz, 1H), 5.17 (br dd, J = 7.0, 9.1 Hz, 1H), 4.99 (d, J = 4.4 Hz, 1H), 4.19-4.12 (m, 1H), 3.98 (s, 3H), 3.96-3.91 (m, 1H), 3.67 (dq, J = 4.6, 7.0 Hz, 1H), 3.44 (dt, J = 3.3, 10.9 Hz, 1H), 3.32 (s, 3H), 1.83-1.74 (m, 1H), 1.63 (d, J = 6.8 Hz, 3H), 1.51-1.45 (m, 3H), 1.40 (d, J = 7.0 Hz, 4H), 1.28-1.20 (m, 1H).

LCMS-ESI (pos.) m/z: 552.2 (M + H)$^+$.

| 318.0 | (1R,2S)-1-(5-chloropyrimidin-2-yl)-1-methoxypropane-2-sulfonamide (Example 29.3), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.).<br><br>The racemic mixture was purified using the following preparative SFC method: Column: AD-H (2 × 25 cm), Mobile Phase: 75:25 (A:B) A: Liquid CO$_2$, B: MeOH, Flow Rate: 80 mL/min, 229 nm, 100 bar inlet pressure to deliver peak 2. | 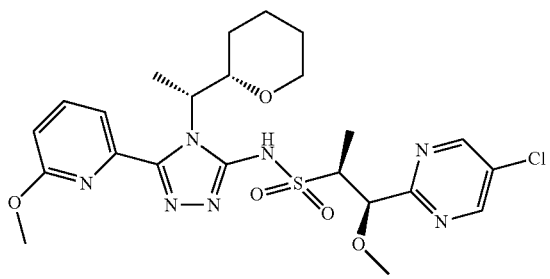 [SMILES: COc1cccc(-c2nnc(NS(=O)(=O)[C@@H](C)[C@H](OC)c3ncc(Cl)cn3)n2[C@H](C)[C@@H]2CCCCO2)n1]<br>OR<br>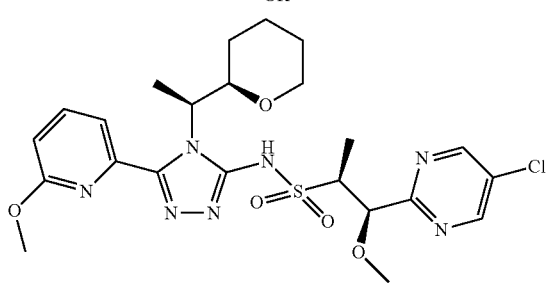<br>OR |

TABLE 24-continued

| Example | Reagents | Structure, Name, Data |
|---------|----------|----------------------|

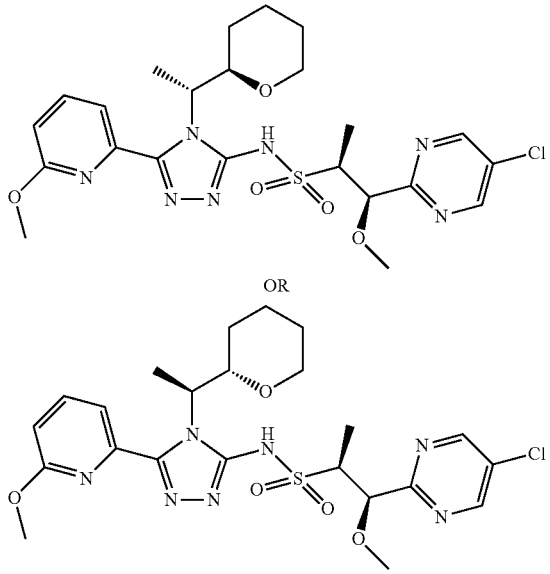

OR (1R,2S)-1-(5-chloropyrimidin-2-yl)-1-methoxy-N-(5-(6-methoxypyridin-2-yl)-4-((S)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((S)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-tetrahydro-2H-pyran-2-yl)ethyl)-4H-1,2,4-triazol-3-yl)propane-2-sulfonamide.

$^1$H NMR (400 MHz, CD$_2$Cl$_2$) δ 8.74 (s, 2H), 7.73 (dd, J = 7.6, 8.2 Hz, 1H), 7.49 (d, J = 7.3 Hz, 1H), 6.91 (d, J = 8.3 Hz, 1H), 5.21-5.12 (m, 1H), 5.01 (d, J = 4.1 Hz, 1H), 4.19-4.12 (m, 1H), 3.98 (s, 3H), 3.93 (br d, J = 11.0 Hz, 1H), 3.64 (dq, J = 4.4, 6.9 Hz, 1H), 3.47 (dt, J = 2.8, 11.1 Hz, 1H), 3.30 (s, 3H), 1.75 (br d, J = 10.0 Hz, 1H), 1.66 (d, J = 6.8 Hz, 2H), 1.49-1.42 (m, 3H), 1.42-1.38 (m, 4H), 1.23-1.15 (m, 1H). LCMS-ESI (pos.) m/z: 552.2 (M + H)$^+$.

| 319.0 | (1R,2S)-1-(5-chloropyrimidin-2-yl)-1-methoxypropane-2-sulfonamide (Example 29.3), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified | 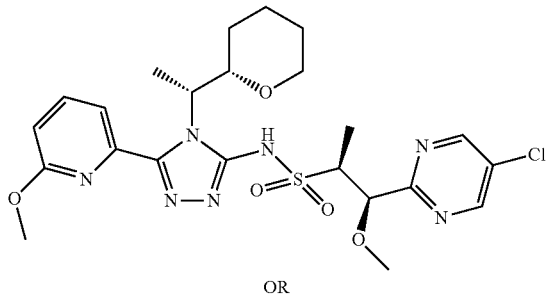<br><br>OR |

TABLE 24-continued

| Example | Reagents | Structure, Name, Data |
|---|---|---|
| | using the following preparative SFC method: Column: AD-H (2 × 25 cm) + AD-H (2 × 25 cm), Mobile Phase: 55:45 (A:B) A: Liquid $CO_2$, B: IPA, Flow Rate: 40 mL/min, 215 nm, 100 bar inlet pressure to deliver peak 1. | 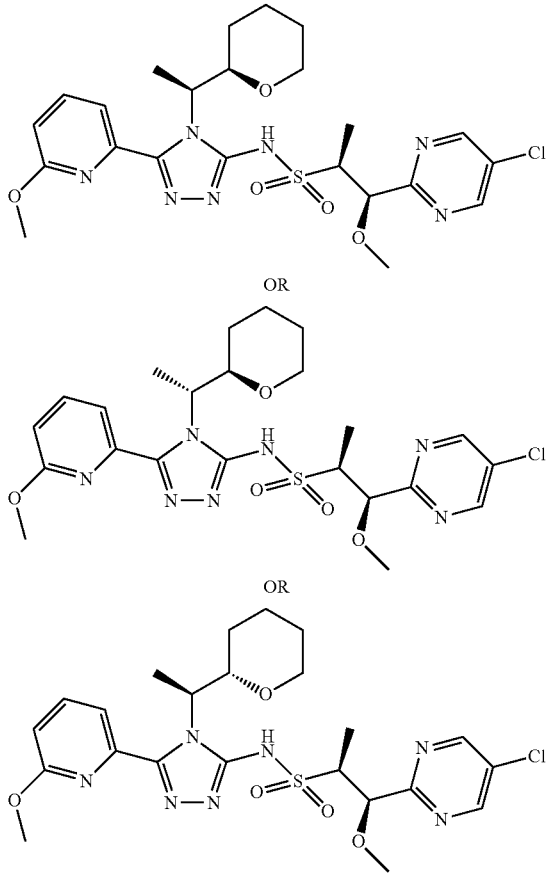<br><br>(1R,2S)-1-(5-chloropyrimidin-2-yl)-1-methoxy-N-(5-(6-methoxypyridin-2-yl)-4-((S)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((S)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-tetrahydro-2H-pyran-2-yl)ethyl)-4H-1,2,4-triazol-3-yl)propane-2-sulfonamide.<br>$^1$H NMR (400 MHz, $CD_2Cl_2$) δ 11.06 (br s, 1H), 8.73 (s, 2H), 7.73 (dd, J = 7.3, 8.3 Hz, 1H), 7.51 (d, J = 7.5 Hz, 1H), 6.91-6.87 (m, 1H), 5.18 (br s, 1H), 5.01 (d, J = 4.1 Hz, 1H), 4.24 (br s, 1H), 3.96 (s, 3H), 3.74-3.68 (m, 1H), 3.68-3.61 (m, 1H), 3.34-3.23 (m, 4H), 1.87-1.77 (m, 2H), 1.64 (d, J = 7.0 Hz, 3H), 1.58-1.47 (m, 1H), 1.44-1.37 (m, 5H), 1.16-1.05 (m, 1H). LCMS-ESI (pos.) m/z: 552.2 (M + H)$^+$. |

TABLE 24-continued

| Example | Reagents | Structure, Name, Data |
|---|---|---|
| 320.0 | (1R,2S)-1-(5-chloropyrimidin-2-yl)-1-methoxypropane-2-sulfonamide (Example 29.3), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: AD-H (2 × 25 cm) + AD-H (2 × 25 cm), Mobile Phase: 55:45 (A:B) A: Liquid $CO_2$, B: IPA, Flow Rate: 40 mL/min, 215 nm, 100 bar inlet pressure to deliver peak 2. | (1R,2S)-1-(5-chloropyrimidin-2-yl)-1-methoxy-N-(5-(6-methoxypyridin-2-yl)-4-((S)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((S)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-((R)-tetrahydro-2H-pyran-2-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-((S)-tetrahydro-2H-pyran-2-yl)ethyl)-4H-1,2,4-triazol-3-yl)propane-2-sulfonamide. <br> $^1$H NMR (400 MHz, $CD_2Cl_2$) δ 11.29-10.83 (m, 1H), 8.74 (s, 2H), 7.73 (dd, J = 7.5, 8.3 Hz, 1H), 7.50 (d, J = 7.3 Hz, 1H), 6.91-6.87 (m, 1H), 5.27-5.06 (m, 1H), 5.00 (d, J = 4.6 Hz, 1H), 4.34-4.05 (m, 1H), 3.95 (s, 3H), 3.78-3.71 (m, 1H), 3.70-3.64 (m, 1H), 3.39-3.21 (m, 4H), 1.85-1.75 (m, 2H), 1.61 (d, J = 7.0 Hz, 3H), 1.56-1.45 (m, 1H), 1.44-1.38 |

TABLE 24-continued

| Example | Reagents | Structure, Name, Data |
|---------|----------|----------------------|

(m, 5H), 1.18-1.08 (m, 1H). LCMS-ESI (pos.) m/z: 552.2 (M + H)+.

321.0    (1S,2S)-1-isopropoxy-1-(5-methylpyrimidin-2-yl)propane-2-sulfonamide (Example 31.0), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: Lux Cellulose-2 (2 × 15 cm) + Lux Cellulose-2 (2 × 15 cm), Mobile Phase: 65:35 (A:B) A: Liquid CO$_2$, B: MeOH, Flow Rate: 70 mL/min, 215 nm, 100 bar inlet pressure to deliver peak 1.

OR

OR

OR (1S,2S)-1-isopropoxy-N-(5-(6-methoxypyridin-2-yl)-4-((S)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((S)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-

TABLE 24-continued

| Example | Reagents | Structure, Name, Data |
|---|---|---|
| | | 4-((S)-1-((S)-tetrahydro-2H-pyran-2-yl)ethyl)-4H-1,2,4-triazol-3-yl)-1-(5-methylpyrimidin-2-yl)propane-2-sulfonamide.<br>$^1$H NMR (400 MHz, CD$_2$Cl$_2$) δ 8.63 (s, 2H), 7.73 (dd, J = 7.5, 8.3 Hz, 1H), 7.49 (d, J = 7.3 Hz, 1H), 6.89 (d, J = 8.1 Hz, 1H), 5.13-5.03 (m, 1H), 4.85 (d, J = 3.7 Hz, 1H), 4.21-4.14 (m, 1H), 3.99 (s, 3H), 3.95-3.88 (m, 1H), 3.69 (dq, J = 3.9, 7.0 Hz, 1H), 3.55-3.44 (m, 2H), 2.33 (s, 3H), 1.79-1.71 (m, 1H), 1.62 (d, J = 6.8 Hz, 3H), 1.53 (d, J = 7.0 Hz, 3H), 1.51-1.40 (m, 4H), 1.25-1.17 (m, 1H), 1.06 (d, J = 6.0 Hz, 3H), 0.88 (d, J = 6.2 Hz, 3H). LCMS-ESI (pos.) m/z: 560.2 (M + H)$^+$. |
| 322.0 | (1S,2S)-1-isopropoxy-1-(5-methylpyrimidin-2-yl)propane-2-sulfonamide (Example 31.0), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: Lux Cellulose-2 (2 × 15 cm) + Lux Cellulose-2 (2 × 15 cm), Mobile Phase: 65:35 (A:B) A: Liquid CO$_2$, B: MeOH, Flow Rate: 70 mL/min, 215 nm, 100 bar inlet pressure to deliver peak 2. Peak 2 was purified using the following preparative SFC method: Column: Regis Whelk-O s,s (2 × 15 cm), Mobile Phase: 80:20 (A:B) A: Liquid CO$_2$, B: MeOH, Flow Rate: 80 mL/min, 215 nm 100 bar inlet pressure to deliver peak 2. | 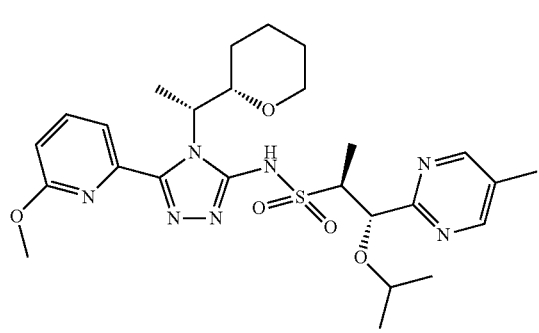 [SMILES: COc1cccc(-c2nnc(NS(=O)(=O)[C@@H](C)[C@@H](OC(C)C)c3ncc(C)cn3)n2[C@H](C)[C@@H]2CCCCO2)n1]<br>OR<br>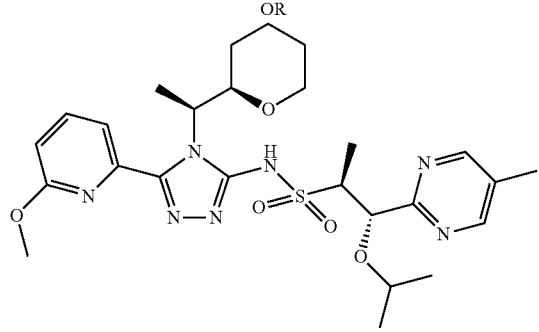<br>OR<br>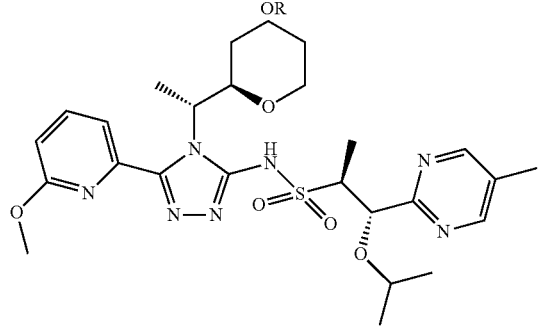<br>OR<br>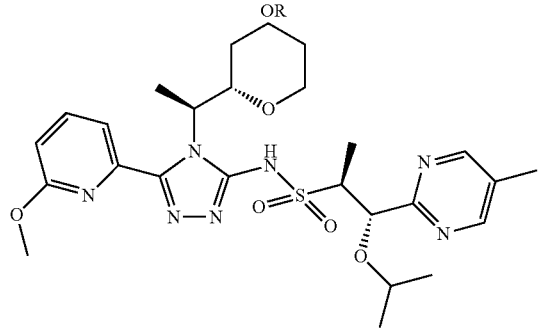<br>(1S,2S)-1-isopropoxy-N-(5-(6-methoxypyridin-2-yl)-4-((S)-1-((R)-tetrahydro-2H-pyran-2-yl)ethyl)-4H- |

| Example | Reagents | Structure, Name, Data |
|---|---|---|
| | | 1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((S)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydro-2H-pyran-2-yl)ethyl)-4H-1,2,4-triazol-3-yl)-1-(5-methylpyrimidin-2-yl)propane-2-sulfonamide.<br>$^1$H NMR (400 MHz, CD$_2$Cl$_2$) δ 8.62 (s, 2H), 7.73 (t, J = 7.9 Hz, 1H), 7.51 (d, J = 7.5 Hz, 1H), 6.88 (d, J = 8.3 Hz, 1H), 5.11 (br s, 1H), 4.85 (d, J = 4.4 Hz, 1H), 4.31-4.12 (m, 1H), 3.96 (s, 3H), 3.75-3.66 (m, 2H), 3.51 (td, J = 6.0, 12.2 Hz, 1H), 3.25 (br s, 1H), 2.33 (s, 3H), 1.86-1.74 (m, 2H), 1.62 (d, J = 7.0 Hz, 3H), 1.58-1.47 (m, 4H), 1.46-1.36 (m, 2H), 1.18-1.08 (m, 1H), 1.06 (d, J = 6.0 Hz, 3H), 0.88 (d, J = 6.2 Hz, 3H). LCMS-ESI (pos.) m/z: 560.2 (M + H)$^+$. |
| 323.0 | (1S,2S)-1-isopropoxy-1-(5-methylpyrimidin-2-yl)propane-2-sulfonamide (Example 31.0), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: Lux Cellulose-2 (2 × 15 cm) + Lux Cellulose-2 (2 × 15 cm), Mobile Phase: 65:35 (A:B) A: Liquid CO$_2$, B: MeOH, Flow Rate: 70 mL/min, 215 nm, 100 bar inlet pressure to deliver peak 3. Peak 3 was purified using the following preparative SFC method: Column: Regis Whelk-O s,s (2 × 15 cm), Mobile Phase: 80:20 (A:B) A: Liquid CO$_2$, B: MeOH, Flow Rate: 80 mL/min, 215 nm 100 bar inlet pressure to deliver peak 3. | 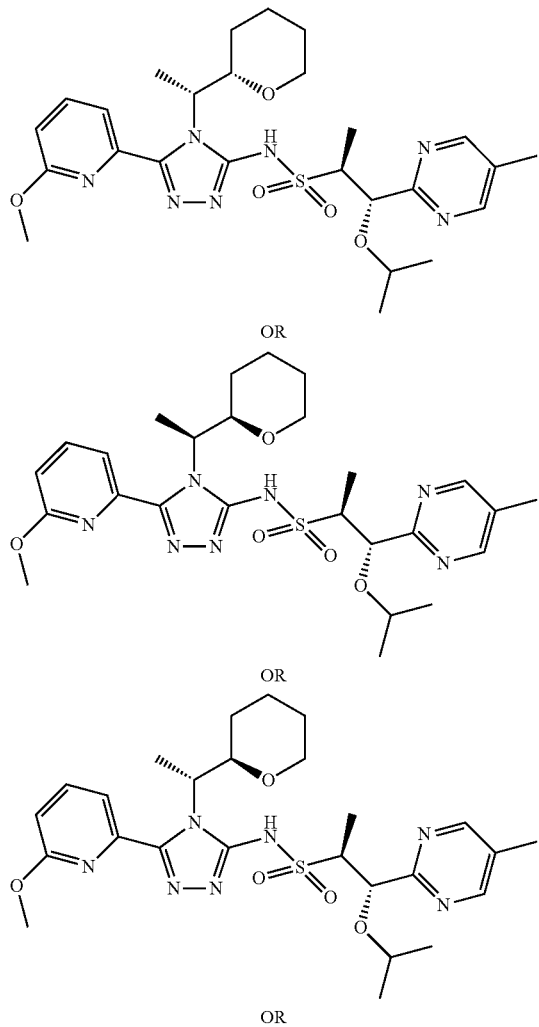 |

| Example | Reagents | Structure, Name, Data |
|---|---|---|
| | | 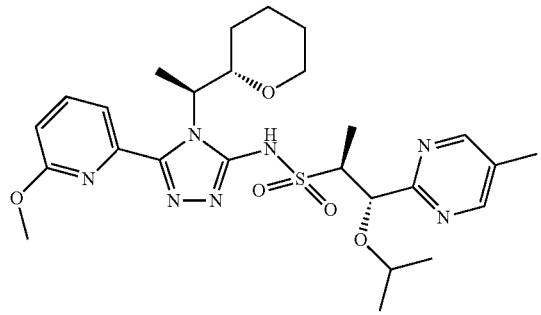 [SMILES: COc1cccc(-c2nnc(NS(=O)(=O)[C@@H](C)[C@@H](OC(C)C)c3ncc(C)cn3)n2[C@@H](C)[C@@H]2CCCCO2)n1] (1S,2S)-1-isopropoxy-N-(5-(6-methoxypyridin-2-yl)-4-((S)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((S)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydro-2H-pyran-2-yl)ethyl)-4H-1,2,4-triazol-3-yl)-1-(5-methylpyrimidin-2-yl)propane-2-sulfonamide. <br> $^1$H NMR (400 MHz, CD$_2$Cl$_2$) δ 8.65 (s, 2H), 7.73 (dd, J = 7.3, 8.3 Hz, 1H), 7.49 (d, J = 6.8 Hz, 1H), 6.89 (d, J = 7.9 Hz, 1H), 5.15-5.07 (m, 1H), 4.83 (d, J = 3.3 Hz, 1H), 4.24-4.17 (m, 1H), 3.99 (s, 3H), 3.97-3.91 (m, 1H), 3.70 (dq, J = 3.5, 7.0 Hz, 1H), 3.54-3.44 (m, 2H), 2.35 (s, 3H), 1.83 (br d, J = 12.2 Hz, 1H), 1.71 (br d, J = 12.0 Hz, 1H), 1.62 (d, J = 6.8 Hz, 3H), 1.58 (d, J = 7.0 Hz, 3H), 1.56-1.45 (m, 3H), 1.28-1.18 (m, 1H), 1.04 (d, J = 6.0 Hz, 3H), 0.93 (d, J = 6.2 Hz, 3H). LCMS-ESI (pos.) m/z: 560.2 (M + H)$^+$. |
| 324.0 | (1S,2S)-1-isopropoxy-1-(5-methylpyrimidin-2-yl)propane-2-sulfonamide (Example 31.0), (R)-2-((R)-1-isothiocyanatoethyl)tetrahydro-2H-pyran and (S)-2-((S)-1-isothiocyanatoethyl)tetrahydro-2H-pyran and (R)-2-((S)-1-isothiocyanatoethyl)tetrahydro-2H-pyran and (S)-2-((R)-1-isothiocyanatoethyl)tetrahydro-2H-pyran (Example 264.13), and 6-methoxypicolinohydrazide (commercially available from Milestone PharmTech USA Inc.). The racemic mixture was purified using the following preparative SFC method: Column: Lux Cellulose-2 (2 × 15 cm) + Lux Cellulose-2 (2 × 15 cm), Mobile Phase: 65:35 (A:B) A: Liquid CO$_2$, B: MeOH, Flow Rate: 70 mL/min, 215 nm, 100 bar inlet pressure to deliver peak 4. | 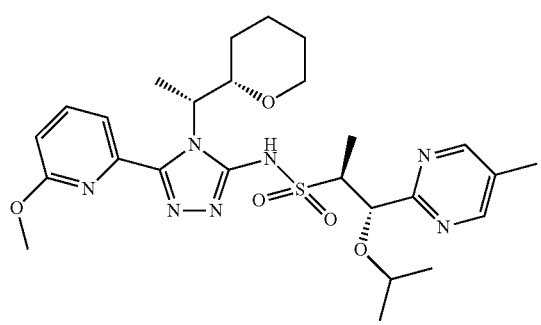 [SMILES: COc1cccc(-c2nnc(NS(=O)(=O)[C@@H](C)[C@@H](OC(C)C)c3ncc(C)cn3)n2[C@H](C)[C@@H]2CCCCO2)n1] OR 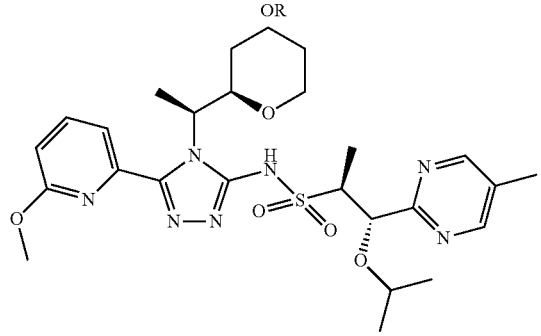 OR |

TABLE 24-continued

| Example | Reagents | Structure, Name, Data |
|---|---|---|
| | | 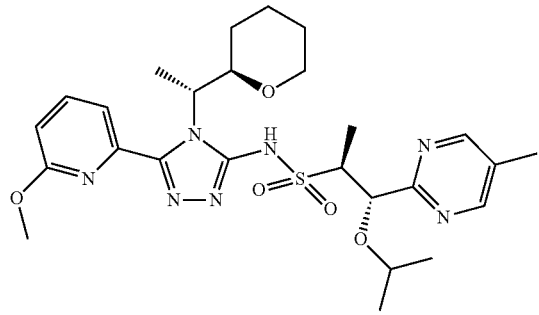 [SMILES: COc1cccc(-c2nnc(NS(=O)(=O)[C@@H](C)[C@@H](OC(C)C)c3ncc(C)cn3)n2[C@H](C)[C@H]2CCCCO2)n1] OR (1S,2S)-1-isopropoxy-N-(5-(6-methoxypyridin-2-yl)-4-((S)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((S)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((R)-1-((R)-tetrahydro-2H-pyran-2-yl)ethyl)-4H-1,2,4-triazol-3-yl)-1-(5-methylpyrimidin-2-yl)propane-2-sulfonamide or (1S,2S)-1-isopropoxy-N-(5-(6-methoxypyridin-2-yl)-4-((S)-1-((S)-tetrahydro-2H-pyran-2-yl)ethyl)-4H-1,2,4-triazol-3-yl)-1-(5-methylpyrimidin-2-yl)propane-2-sulfonamide.
$^1$H NMR (400 MHz, CD$_2$Cl$_2$) δ 8.63 (s, 2H), 7.75-7.70 (m, 1H), 7.51 (d, J = 7.3 Hz, 1H), 6.87 (d, J = 8.3 Hz, 1H), 5.16 (br s, 1H), 4.87 (d, J = 4.1 Hz, 1H), 4.27 (br s, 1H), 3.96-3.94 (m, 3H), 3.83-3.75 (m, 1H), 3.70 (dq, J = 4.1, 7.0 Hz, 1H), 3.52 (td, J = 6.1, 12.1 Hz, 1H), 3.43-3.17 (m, 1H), 2.33 (s, 3H), 1.88-1.76 (m, 2H), 1.61 (d, J = 7.0 Hz, 3H), 1.58-1.48 (m, 4H), 1.48-1.41 (m, 2H), 1.18-1.10 (m, 1H), 1.07 (d, J = 6.0 Hz, 3H), 0.93 (d, J = 6.0 Hz, 2H). LCMS-ESI (pos.) m/z: 560.2 (M + H)$^+$. |
| 325.0 | (1R,2S)-1-(5-chloropyrimidin-2-yl)-1-methoxypropane-2-sulfonamide (Example 29.3), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). | 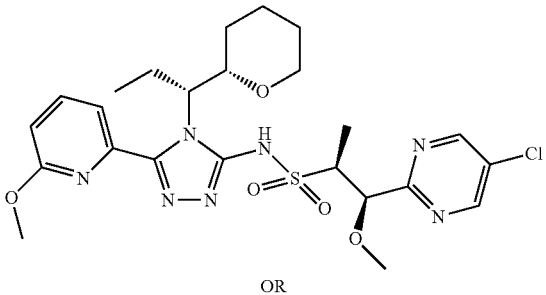 OR |

TABLE 24-continued

| Example | Reagents | Structure, Name, Data |
|---|---|---|
| | The racemic mixture was purified using the following preparative SFC method: Column: IC (2 × 25 cm), Mobile Phase: 60:40 (A:B) A: Liquid CO₂, B: MeOH, Flow Rate: 80 mL/min, 235 nm, 100 bar inlet pressure to deliver fraction 1. Fraction 1 was purified using the following preparative SFC method: Column: AD-H (2 × 25 cm) + AD-H (2 × 25 cm), Mobile Phase: 60:40 (A:B) A: Liquid CO₂, B: IPA, Flow Rate: 40 mL/min, 235 nm, 100 bar inlet pressure to deliver peak 1. | (1R,2S)-1-methoxy-N-(5-(6-methoxy-2-pyridinyl)-4-((1R)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1R)-1-((2R)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2R)-tetrahydro-2H-pyran-2-yl)propyl)-4H-1,2,4-triazol-3-yl)-1-(5-methyl-2-pyrimidinyl)-2-propanesulfonamide.<br>¹H NMR (400 MHz, CD₂Cl₂) δ 8.74 (s, 2H), 7.73 (dd, J = 7.5, 8.3 Hz, 1H), 7.51 (br d, J = 7.3 Hz, 1H), 6.91 (d, J = 8.3 Hz, 1H), 5.30-5.11 (m, 1H), 4.99 (d, J = 4.4 Hz, 1H), 4.11 (br t, J = 8.8 Hz, 1H), 4.00 (s, 3H), 3.96-3.90 (m, 1H), 3.69-3.61 (m, 1H), 3.52-3.40 (m, 1H), 3.33 (s, 3H), 2.43 (br s, 1H), 2.00 (dqd, J = 3.9, 7.5, 14.5 Hz, 1H), 1.84-1.70 (m, 1H), 1.48-1.27 (m, 8H), 0.79 (t, J = 7.5 Hz, 3H). LCMS-ESI (pos.) m/z: 566.2 (M + H)⁺. |

TABLE 24-continued

| Example | Reagents | Structure, Name, Data |
|---|---|---|
| 326.0 | (1R,2S)-1-(5-chloropyrimidin-2-yl)-1-methoxypropane-2-sulfonamide (Example 29.3), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: IC (2 × 25 cm), Mobile Phase: 60:40 (A:B) A: Liquid CO$_2$, B: MeOH, Flow Rate: 80 mL/min, 235 nm, 100 bar inlet pressure to deliver fraction 1. Fraction 1 was purified using the following preparative SFC method: Column: AD-H (2 × 25 cm) + AD-H (2 × 25 cm), Mobile Phase: 60:40 (A:B) A: Liquid CO$_2$, B: IPA, Flow Rate: 40 mL/min, 235 nm, 100 bar inlet pressure to deliver peak 2. | 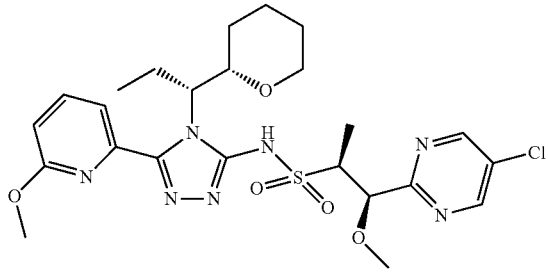 [SMILES: CC[C@H]([C@@H]1CCCCO1)n1c(NS(=O)(=O)[C@@H](C)[C@H](OC)c2ncc(Cl)cn2)nnc1-c1cccc(OC)n1]  OR  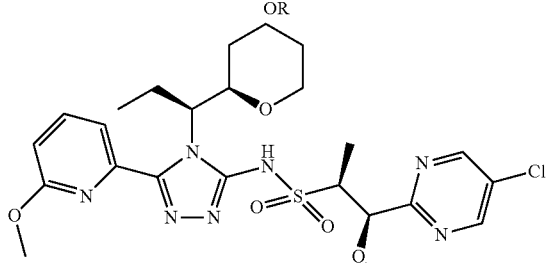  OR  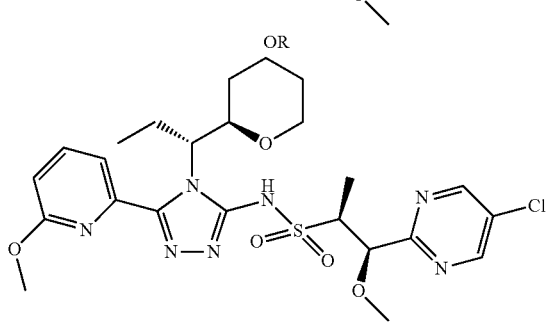  OR  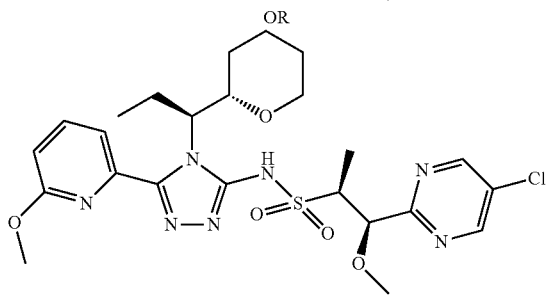  (1R,2S)-1-methoxy-N-(5-(6-methoxy-2-pyridinyl)-4-((1R)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1R)-1-((2R)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2R)-tetrahydro-2H-pyran-2-yl)propyl)-4H-1,2,4-triazol-3-yl)-1-(5-methyl-2-pyrimidinyl)-2-propanesulfonamide. $^1$H NMR (400 MHz, CD$_2$Cl$_2$) δ 8.73 (s, 2H), 7.73 (dd, J = 7.5, 8.3 Hz, 1H), 7.51 (br d, J = 7.3 Hz, 1H), 6.93-6.89 (m, 1H), 5.28-5.07 (m, 1H), 4.98 (d, J = 4.4 Hz, 1H), 4.12 (br t, J = 9.4 Hz, 1H), 4.01 (s, 3H), 3.93 (br d, J = 11.0 Hz, 1H), 3.65 (dq, J = 4.4, 7.0 Hz, 1H), 3.45 (br t, J = 9.6 Hz, 1H), 3.32 (s, 3H), 2.53-2.35 (m, 1H), 1.99 (ddd, J = 3.8, 7.5, 14.4 Hz, 1H), 1.79 (br d, |

TABLE 24-continued

| Example | Reagents | Structure, Name, Data |
|---|---|---|
| | | J = 1.7 Hz, 1H), 1.56-1.38 (m, 8H), 0.74 (t, J = 7.5 Hz, 3H). LCMS-ESI (pos.) m/z: 566.2 (M + H)⁺. |
| 327.0 | (1R,2S)-1-(5-chloropyrimidin-2-yl)-1-methoxypropane-2-sulfonamide (Example 29.3), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: IC (2 × 25 cm), Mobile Phase: 60:40 (A:B) A: Liquid CO₂, B: MeOH, Flow Rate: 80 mL/min, 235 nm, 100 bar inlet pressure to deliver fraction 2. Fraction 2 was purified using the following preparative SFC method: Column: AD-H (2 × 25 cm) + AD-H (2 × 25 cm), Mobile Phase: 60:40 (A:B) A: Liquid CO₂, B: IPA, Flow Rate: 40 mL/min, 235 nm, 100 bar inlet pressure to deliver peak 3. | 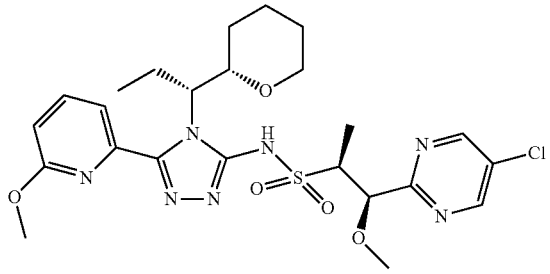 [SMILES: CC[C@H]([C@@H]1CCCCO1)n1c(NS(=O)(=O)[C@@H](C)[C@H](OC)c2ncc(Cl)cn2)nnc1-c1cccc(OC)n1]<br>OR<br>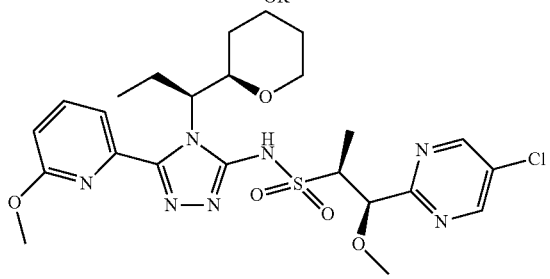<br>OR<br>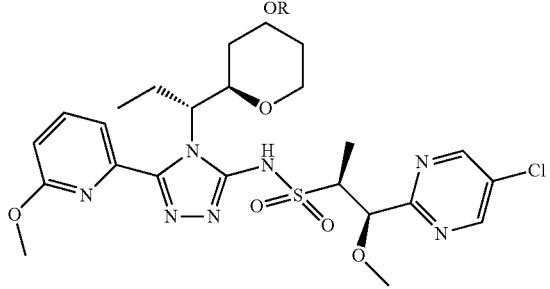<br>OR<br>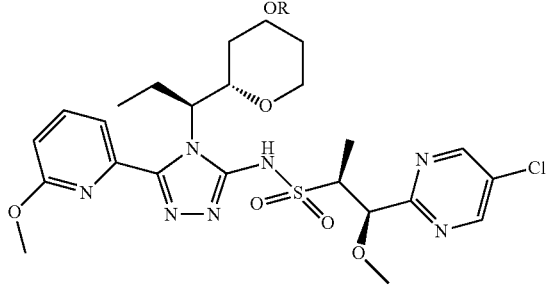<br>(1R,2S)-1-methoxy-N-(5-(6-methoxy-2-pyridinyl)-4-((1R)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1R)-1-((2R)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2R)-tetrahydro-2H-pyran-2-yl)propyl)-4H-1,2,4-triazol-3-yl)-1-(5-methyl-2-pyrimidinyl)-2-propanesulfonamide.<br>¹H NMR (400 MHz, CD₂Cl₂) δ 8.74 (s, 2H), 7.72 (t, J = 7.9 Hz, 1H), 7.55 (d, J = 7.5 Hz, 1H), 6.88 (d, J = 8.3 Hz, 1H), 5.39-5.32 (m, 1H), 5.00 (d, J = 4.1 Hz, 1H), 4.22 (br t, J = 9.8 Hz, 1H), 3.97(s, 3H), 3.71 (br d, J = 11.2 Hz, 1H), 3.69-3.64 (m, 1H), 3.38-3.32(m, |

US 10,689,367 B2

481 482

TABLE 24-continued

| Example | Reagents | Structure, Name, Data |
|---|---|---|
| | | 1H), 3.30 (s, 2H), 2.57-2.42 (m, 1H), 1.87-1.78 (m, 2H), 1.74-1.67 (m, 1H), 1.60-1.50 (m, 1H), 1.43-1.35 (m, 5H), 1.19-1.10 (m, 1H), 0.98 (t, J = 7.4 Hz, 3H). LCMS-ESI (pos.) m/z: 566.2 (M + H)$^+$. |
| 328.0 | (1R,2S)-1-(5-chloropyrimidin-2-yl)-1-methoxypropane-2-sulfonamide (Example 29.3), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: IC (2 × 25 cm), Mobile Phase: 60:40 (A:B) A: Liquid CO$_2$, B: MeOH, Flow Rate: 80 mL/min, 235 nm, 100 bar inlet pressure to deliver fraction 2. Fraction 2 was purified using the following preparative SFC method: Column: AD-H (2 × 25 cm) + AD-H (2 × 25 cm), Mobile Phase: 60:40 (A:B) A: Liquid CO$_2$, B: IPA, Flow Rate: 40 mL/min, 235 nm, 100 bar inlet pressure to deliver peak 4. | 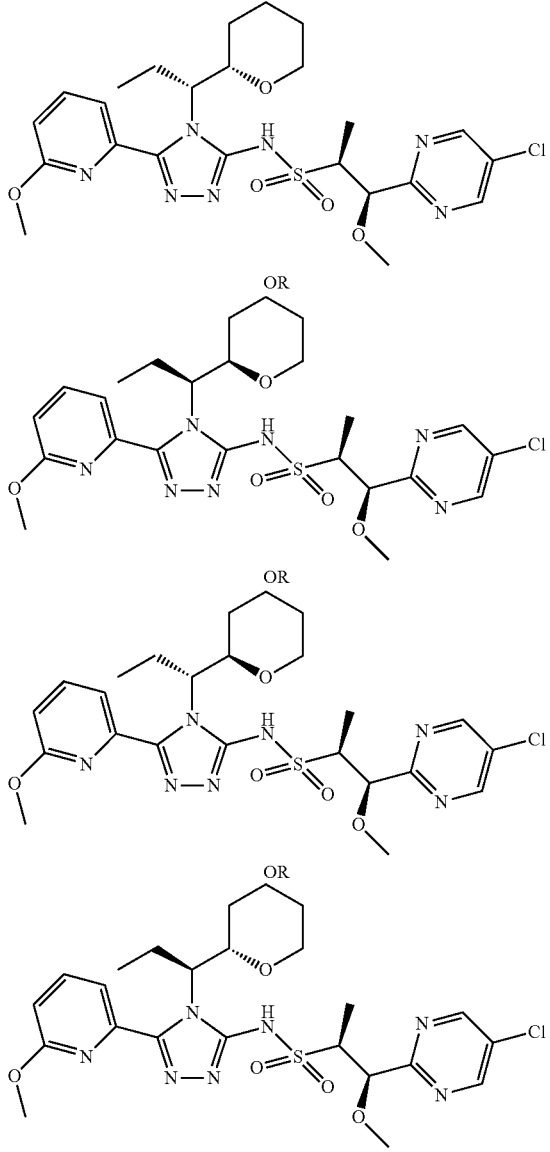 |

(1R,2S)-1-methoxy-N-(5-(6-methoxy-2-pyridinyl)-4-((1R)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1R)-1-((2R)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2S)-tetrahydro-2H-pyran-2-yl)propyl)-4H-1,2,4-triazol-3-yl)-1-(5-methyl-2-pyrimidinyl)-2-propanesulfonamide or (1R,2S)-1-methoxy-N-(5-(6-methoxy-2-pyridinyl)-4-((1S)-1-((2R)-tetrahydro-2H-pyran-2-yl)propyl)-4H-1,2,4-triazol-3-yl)-1-(5-methyl-2-pyrimidinyl)-2-propanesulfonamide.
$^1$H NMR (400 MHz, CD$_2$Cl$_2$) δ 8.74 (s, 2H), 7.72 (t, J = 7.9 Hz, 1H), 7.54 (d, J = 7.3 Hz, 1H), 6.88 (d, J = 8.3

TABLE 24-continued

| Example | Reagents | Structure, Name, Data |
|---|---|---|
| | | Hz, 1H), 5.39-5.32 (m, 1H), 4.99 (d, J = 4.6 Hz, 1H), 4.21 (br t, J = 10.0 Hz, 1H), 3.97 (s, 3H), 3.80-3.72 (m, 1H), 3.69-3.62 (m, 1H), 3.40-3.33 (m, 1H), 3.32-3.28 (m, 3H), 2.55-2.40 (m, 1H), 1.88-1.77 (m, 2H), 1.73-1.67 (m, 1H), 1.55-1.48 (m, 1H), 1.47-1.37 (m, 5H), 1.18-1.08 (m, 1H), 0.93 (t, J = 7.4 Hz, 3H). LCMS-ESI (pos.) m/z: 566.2 (M + H)$^+$. |
| 329.0 | (1R,2S)-1-Methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver fraction 1. Fraction 1 was purified using the following preparative SFC method: Column: IC (3 × 15 cm) + IC (3 × 15 cm), Mobile Phase: 55:45 (A:B) A: Liquid CO$_2$, B: MeOH, Flow Rate: 80 mL/min, 296 nm, 100 bar inlet pressure to deliver peak 1. | OR<br><br>OR<br><br>OR<br><br>(1R,2S)-1-methoxy-N-(5-(6-methoxypyridin-2-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((S)-tetrahydro- |

| Example | Reagents | Structure, Name, Data |
|---|---|---|
| | | 2H-pyran-2-yl)propyl)-4H-1,2,4-triazol-3-yl)-1-(5-methylpyrimidin-2-yl)propane-2-sulfonamide. <br> $^1$H NMR (400 MHz, CD$_2$Cl$_2$) δ 8.59 (s, 2H), 7.73 (t, J = 7.9 Hz, 1H), 7.51 (br d, J = 7.3 Hz, 1H), 6.90 (d, J = 8.3 Hz, 1H), 5.19 (br s, 1H), 4.96 (d, J = 4.1 Hz, 1H), 4.12 (br t, J = 9.0 Hz, 1H), 4.00 (s, 3H), 3.96-3.88 (m, 1H), 3.71-3.58 (m, 1H), 3.47 (br t, J = 10.3 Hz, 1H), 3.30 (s, 3H), 2.62-2.35 (m, 1H), 2.31 (s, 3H), 2.06-1.93 (m, 1H), 1.84-1.72 (m, 1H), 1.52-1.31 (m, 8H), 0.79 (t, J = 7.5 Hz, 3H). LCMS-ESI (pos.) m/z: 546.2 (M + H)$^+$. |
| 330.0 | (1R,2S)-1-Methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver fraction 1. Fraction 1 was purified using the following preparative SFC method: Column: IC (3 × 15 cm) + IC (3 × 15 cm), Mobile Phase: 55:45 (A:B) A: Liquid CO$_2$, B: MeOH, Flow Rate: 80 mL/min, 296 nm, 100 bar inlet pressure to deliver peak 2. | 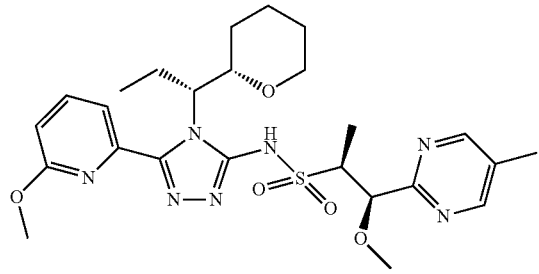 [SMILES: CC[C@H]([C@@H]1CCCCO1)n1c(NS(=O)(=O)[C@@H](C)[C@H](OC)c2ncc(C)cn2)nnc1-c1cccc(OC)n1] <br> OR <br> 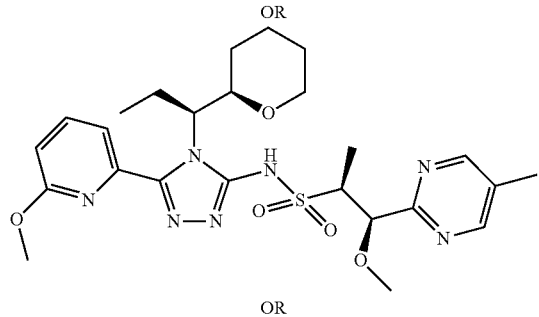 <br> OR <br> 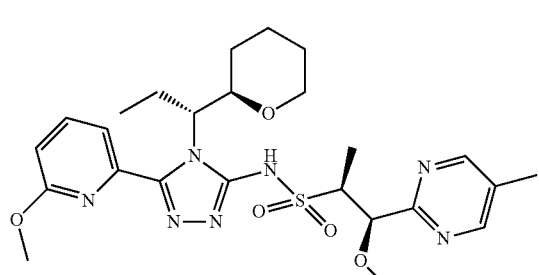 <br> OR <br> 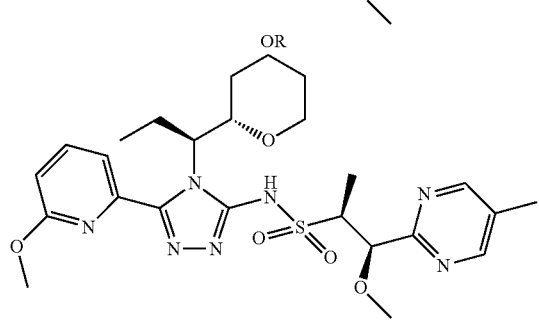 <br> (1R,2S)-1-methoxy-N-(5-(6-methoxypyridin-2-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((R)-tetrahydro-2H-pyran-2-yl)propyl)-4H- |

TABLE 24-continued

| Example | Reagents | Structure, Name, Data |
|---|---|---|
| | | 1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide. $^1$H NMR (400 MHz, CD$_2$Cl$_2$) δ 8.59 (s, 2H), 7.72 (t, J = 7.8 Hz, 1H), 7.55 (d, J = 7.3 Hz, 1H), 6.88 (d, J = 8.3 Hz, 1H), 5.38-5.32 (m, 1H), 4.98 (d, J = 3.7 Hz, 1H), 4.23 (br t, J = 10.0 Hz, 1H), 3.97 (s, 3H), 3.73-3.60 (m, 2H), 3.38-3.31 (m, 1H), 3.31-3.26 (m, 3H), 2.58-2.43 (m, 1H), 2.31 (s, 3H), 1.89-1.77 (m, 2H), 1.74-1.65 (m, 1H), 1.61-1.50 (m, 1H), 1.44-1.35 (m, 5H), 1.18-1.07 (m, 1H), 0.99 (t, J = 7.4 Hz, 3H). LCMS-ESI (pos.) m/z: 546.2 (M + H)$^+$. |
| 331.0 | (1R,2S)-1-Methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver fraction 2. Fraction 2 was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver peak 3. | OR<br><br>OR<br><br>OR<br><br>(1R,2S)-1-methoxy-N-(5-(6-methoxypyridin-2-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((S)-1-((S)-tetrahydro-2H-pyran-2-yl)propyl)-4H-1,2,4-triazol-3-yl)-1-(5- |

TABLE 24-continued

| Example | Reagents | Structure, Name, Data |
|---|---|---|
| | | methylpyrimidin-2-yl)propane-2-sulfonamide or (1R,2S)-1-methoxy-N-(5-(6-methoxypyridin-2-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide.<br>$^1$H NMR (400 MHz, CD$_2$Cl$_2$) δ 8.59 (s, 2H), 7.73 (dd, J = 7.4, 8.4 Hz, 1H), 7.51 (br d, J = 7.3 Hz, 1H), 6.90 (d, J = 8.3 Hz, 1H), 5.31-5.04 (m, 1H), 4.95 (d, J = 4.1 Hz, 1H), 4.13 (br t, J = 9.4 Hz, 1H), 4.01 (s, 3H), 3.93 (br d, J = 11.2 Hz, 1H), 3.65 (dq, J = 4.3, 7.0 Hz, 1H), 3.51-3.38 (m, 1H), 3.29 (s, 3H), 2.54-2.33 (m, 1H), 2.31 (s, 3H), 1.98 (ddd, J = 3.7, 7.6, 14.4 Hz, 1H), 1.86-1.76 (m, 1H), 1.62-1.55 (m, 1H), 1.52-1.41 (m, 4H), 1.38 (d, J = 7.0 Hz, 3H), 0.73 (t, J = 7.5 Hz, 3H). LCMS-ESI (pos.) m/z: 546.2 (M + H)$^+$. |
| 332.0 | (1R,2S)-1-Methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 6-methoxypicolinohydrazide (commercially available from Milestone PharmTech USA Inc.). The racemic mixture was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver fraction 3. Fraction 3 was purified using the following preparative SFC method: Column: Column: AD-H (2 × 25 cm), Mobile Phase: 65:35 (A:B) A: Liquid CO$_2$, B: IPA, Flow Rate: 80 mL/min, 296 nm, 100 bar inlet pressure to deliver peak 4. | 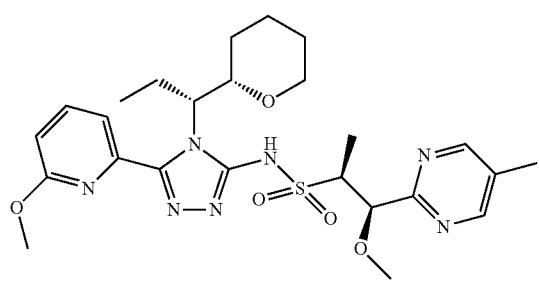 [SMILES: CC[C@H]([C@@H]1CCCCO1)n1c(NS(=O)(=O)[C@@H](C)[C@H](OC)c2ncc(C)cn2)nnc1-c1cccc(OC)n1]<br>OR<br>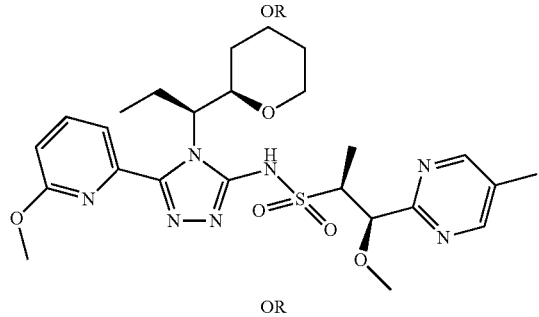<br>OR<br>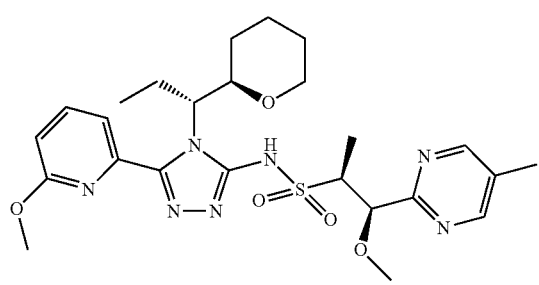 [SMILES: CC[C@H]([C@H]1CCCCO1)n1c(NS(=O)(=O)[C@@H](C)[C@H](OC)c2ncc(C)cn2)nnc1-c1cccc(OC)n1]<br>OR<br>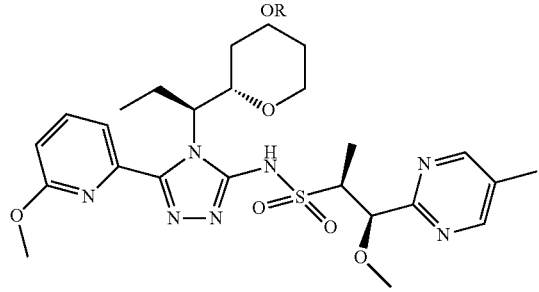<br>(1R,2S)-1-methoxy-N-(5-(6-methoxypyridin-2-yl)-4-((S)-1-((R)-tetrahydro-2H-pyran-2-yl)propyl)-4H- |

TABLE 24-continued

| Example | Reagents | Structure, Name, Data |
|---|---|---|
| | | 1,2,4-triazol-3-yl)-1-(5-methylpyrimidin-2-yl)propane-2-sulfonamide or (1R,2S)-1-methoxy-N-(5-(6-methoxypyridin-2-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(6-methoxypyridin-2-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide. <br> $^1$H NMR (400 MHz, CD$_2$Cl$_2$) δ 8.59 (s, 2H), 7.72 (t, J = 7.9 Hz, 1H), 7.59-7.30 (m, 1H), 6.88 (br d, J = 8.3 Hz, 1H), 5.40-5.32 (m, 1H), 4.97 (d, J = 4.1 Hz, 1H), 4.53-4.18 (m, 1H), 3.97 (s, 3H), 3.75 (br d, J = 11.0 Hz, 1H), 3.69-3.62 (m, 1H), 3.45-3.33 (m, 1H), 3.29 (s, 3H), 2.58-2.43 (m, 1H), 2.31 (s, 3H), 1.81 (br t, J = 13.1 Hz, 2H), 1.72-1.63 (m, 1H), 1.59-1.47 (m, 1H), 1.46-1.36 (m, 5H), 1.16-1.06 (m, 1H), 0.98-0.88 (m, 3H). LCMS-ESI (pos.) m/z: 546.2 (M + H)$^+$. |
| 333.0 | (1R,2S)-1-methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 5-methylnicotinic acid hydrazide (commercially available from Bellen). <br> The racemic mixture was purified using the following preparative SFC method: Column: AD-H (2 × 15 cm), Mobile Phase: 50:50 (A:B) A: Liquid CO$_2$, B: IPA, Flow Rate: 80 mL/min, 216 nm, 100 bar inlet pressure to deliver fraction 1. Fraction 1 was purified using the following preparative SFC method: Column: Lux Cellulose (2 × 15 cm), Mobile Phase: 50:50 (A:B) A: Liquid CO$_2$, B: MeOH, Flow Rate: 80 mL/min, 216 nm, 100 bar inlet pressure to deliver peak 2. | 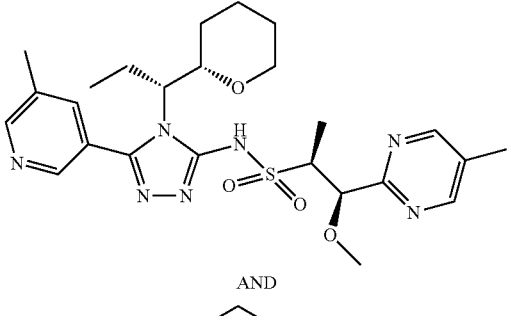 <br> AND <br> 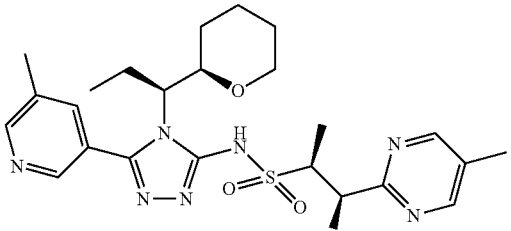 <br> OR <br> 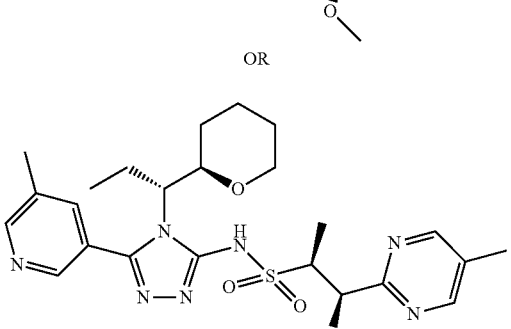 <br> AND |

TABLE 24-continued

| Example | Reagents | Structure, Name, Data |
|---|---|---|
| | | 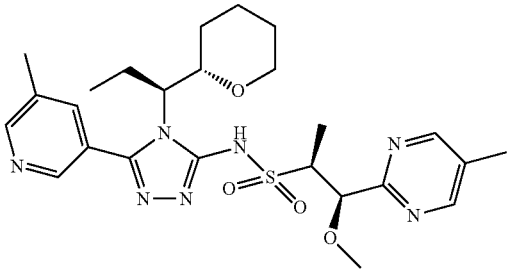 [SMILES: CC[C@@H]([C@@H]1CCCCO1)n1c(NS(=O)(=O)[C@@H](C)[C@H](OC)c2ncc(C)cn2)nnc1-c1cncc(C)c1]<br>(1R,2S)-1-methoxy-N-(5-(5-methylpyridin-3-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide and (1R,2S)-1-methoxy-N-(5-(5-methylpyridin-3-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(5-methylpyridin-3-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide and (1R,2S)-1-methoxy-N-(5-(5-methylpyridin-3-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide.<br>$^1$H NMR (400 MHz, CD$_2$Cl$_2$) δ 11.55-11.14 (m, 1H), 8.72-8.52 (m, 4H), 7.89-7.62 (m, 1H), 5.02-4.93 (m, 1H), 4.33-3.94 (m, 1H), 3.93-3.86 (m, 1H), 3.80-3.58 (m, 2H), 3.4-3.40 (m, 1H), 3.30 (s, 3H), 2.59-2.37 (m, 4H), 2.31 (s, 3H), 2.08-1.66 (m, 4H), 1.62-1.50 (m, 2H), 1.41-1.33 (m, 3H), 0.89-0.70 (m, 3H). LCMS-ESI (pos.) m/z: 530.2 (M + H)$^+$. |
| 334.0 | (1R,2S)-1-methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 5-methylnicotinic acid hydrazide (commercially available from Bellen).<br>The racemic mixture was purified using the following preparative SFC method: Column: Column: AD-H (2 × 15 cm), Mobile Phase: 50:50 (A:B) A: Liquid CO$_2$, B: IPA, Flow Rate: 80 mL/min, 216 nm, 100 bar inlet pressure to deliver fraction 2. Fraction 2 was purified using the following preparative SFC method: Column: Chromega Chiral CC4 (2 × 25 cm), Mobile Phase: 50:50 (A:B) A: Liquid CO$_2$, B: MeOH, Flow Rate: 80 mL/min, 216 nm, 100 bar inlet pressure to deliver peak 3. | 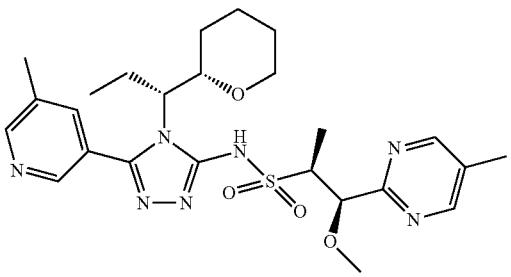 [SMILES: CC[C@H]([C@@H]1CCCCO1)n1c(NS(=O)(=O)[C@@H](C)[C@H](OC)c2ncc(C)cn2)nnc1-c1cncc(C)c1]<br>OR<br>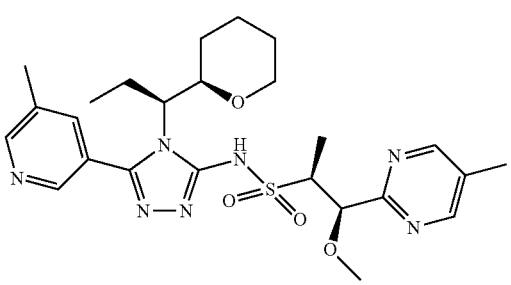 [SMILES: CC[C@@H]([C@H]1CCCCO1)n1c(NS(=O)(=O)[C@@H](C)[C@H](OC)c2ncc(C)cn2)nnc1-c1cncc(C)c1]<br>OR |

TABLE 24-continued

| Example | Reagents | Structure, Name, Data |
|---|---|---|
| | | 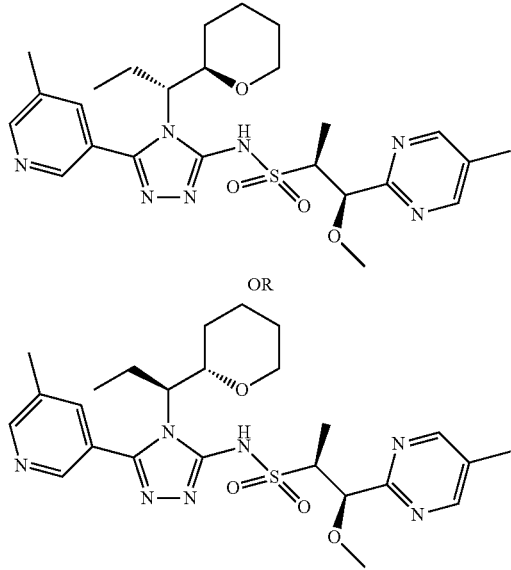 |

(1R,2S)-1-methoxy-N-(5-(5-methylpyridin-3-yl)-4-
((S)-1-((S)-tetrahydro-2H-pyran-2-yl)propyl)-4H-
1,2,4-triazol-3-yl)-1-(5-methylpyrimidin-2-
yl)propane-2-sulfonamide and (1R,2S)-1-methoxy-
N-(5-(5-methylpyridin-3-yl)-4-((R)-1-((R)-
tetrahydro-2H-pyran-2-yl)propyl)-4H-1,2,4-triazol-
3-yl)-1-(5-methylpyrimidin-2-yl)propane-2-
sulfonamide or (1R,2S)-1-methoxy-N-(5-(5-
methylpyridin-3-yl)-4-((S)-1-((R)-tetrahydro-2H-
pyran-2-yl)propyl)-4H-1,2,4-triazol-3-yl)-1-(5-
methylpyrimidin-2-yl)propane-2-sulfonamide and
(1R,2S)-1-methoxy-N-(5-(5-methylpyridin-3-yl)-4-
((R)-1-((S)-tetrahydro-2H-pyran-2-yl)propyl)-4H-
1,2,4-triazol-3-yl)-1-(5-methylpyrimidin-2-
yl)propane-2-sulfonamide.

$^1$H NMR (400 MHz, CD$_2$Cl$_2$) δ 11.32 (br s, 1H), 8.63-
8.55 (m, 4H), 7.67 (s, 1H), 4.96 (d, J = 4.1 Hz, 1H),
4.20-3.88 (m, 2H), 3.82-3.57 (m, 2H), 3.48-3.36
(m, 1H), 3.30 (s, 3H), 2.63-2.35 (m, 4H), 2.31 (s,
3H), 2.02-1.91 (m, 1H), 1.89-1.81 (m, 1H), 1.75-
1.64 (m, 2H), 1.64-1.58 (m, 1H), 1.55-1.50 (m,
1H), 1.38 (d, J = 7.0 Hz, 3H), 1.24-1.07 (m, 1H),
0.80 (t, J = 7.5 Hz, 3H). LCMS-ESI (pos.) m/z: 530.2
(M + H)$^+$.

| 335.0 | (1R,2S)-1-methoxy-1-(5-methylpyrimidin-2-yl)propane-2-sulfonamide (Example 29.0), (R)-2-((S)-1-isothiocyanatopropyl)tetrahydro-2H-pyran and (S)-2-((S)-1-isothiocyanatopropyl)tetrahydro-2H-pyran and (R)-2-((R)-1-isothiocyanatopropyl)tetrahydro-2H-pyran and (S)-2-((R)-1-isothiocyanatopropyl)tetrahydro-2H-pyran (Example 264.14), and 5-methylnicotinic acid hydrazide (commercially available from | 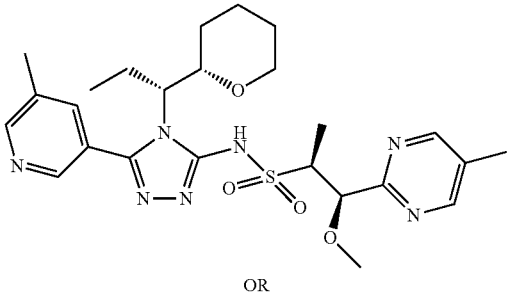 |

TABLE 24-continued

| Example | Reagents | Structure, Name, Data |
|---|---|---|
| | Bellen). The racemic mixture was purified using the following preparative SFC method: Column: Column: AD-H (2 × 15 cm), Mobile Phase: 50:50 (A:B) A: Liquid $CO_2$, B: IPA, Flow Rate: 80 mL/min, 216 nm, 100 bar inlet pressure to deliver fraction 2. Fraction 2 was purified using the following preparative SFC method: Column: Chromega Chiral CC4 (2 × 25 cm), Mobile Phase: 50:50 (A:B) A: Liquid $CO_2$, B: MeOH, Flow Rate: 80 mL/min, 216 nm, 100 bar inlet pressure to deliver peak 4. | OR OR (1R,2S)-1-methoxy-N-(5-(5-methylpyridin-3-yl)-4-((S)-1-((S)-tetrahydro-2H-pyran-2-yl)propyl)-4H-1,2,4-triazol-3-yl)-1-(5-methylpyrimidin-2-yl)propane-2-sulfonamide and (1R,2S)-1-methoxy-N-(5-(5-methylpyridin-3-yl)-4-((R)-1-((R)-tetrahydro-2H-pyran-2-yl)propyl)-4H-1,2,4-triazol-3-yl)-1-(5-methylpyrimidin-2-yl)propane-2-sulfonamide or (1R,2S)-1-methoxy-N-(5-(5-methylpyridin-3-yl)-4-((S)-1-((R)-tetrahydro-2H-pyran-2-yl)propyl)-4H-1,2,4-triazol-3-yl)-1-(5-methylpyrimidin-2-yl)propane-2-sulfonamide and (1R,2S)-1-methoxy-N-(5-(5-methylpyridin-3-yl)-4-((R)-1-((S)-tetrahydro-2H-pyran-2-yl)propyl)-4H-1,2,4-triazol-3-yl)-1-(5-methylpyrimidin-2-yl)propane-2-sulfonamide. $^1$H NMR (400 MHz, $CD_2Cl_2$) δ 11.29 (br s, 1H), 8.85-8.48 (m, 4H), 7.89-7.56 (m, 1H), 4.98 (d, J = 3.9 Hz, 1H), 4.52-4.25 (m, 1H), 4.01-3.78 (m, 1H), 3.75-3.60 (m, 2H), 3.55-3.38 (m, 1H), 3.28 (s, 3H), 2.57-2.40 (m, 4H), 2.31 (s, 3H), 1.94-1.83 (m, 1H), 1.82-1.74 (m, 1H), 1.73-1.64 (m, 2H), 1.62-1.56 (m, 1H), 1.39 (d, J = 7.0 Hz, 3H), 1.18-1.05 (m, 1H), 0.90-0.62 (m, 3H). LCMS-ESI (pos.) m/z: 530.2 (M + H)$^+$. |

Example 292.0. Preparation of (1R,2S)-1-(5-chloro-pyrimidin-2-yl)-N-(4-((3-ethylisoxazol-5-yl)methyl)-5-(6-methoxypyridin-2-yl)-4H-1,2,4-triazol-3-yl)-1-methoxypropane-2-sulfonamide

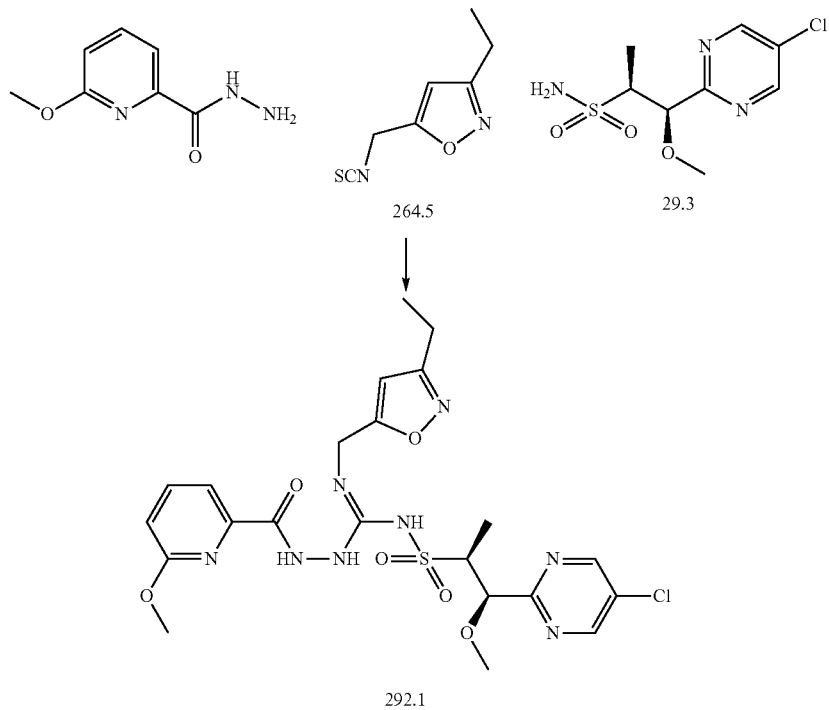

(Z)—N-(((1R,2S)-1-(5-Chloropyrimidin-2-yl)-1-methoxypropan-2-yl)sulfonyl)-N'-((3-ethylisoxazol-5-yl)methyl)-2-(6-methoxypicolinoyl)hydrazinecarboximidamide, Example 292.1

To a vial containing Example 29.3 (201 mg, 0.76 mmol) was added ACN (3 mL). After 10 mins, Example 264.5 (130 mg, 0.77 mmol) was added carefully and dropwise. The mixture was cooled in an ice-bath and then cesium carbonate (322 mg, 0.99 mmol) was added carefully in portions to the homogeneous solution. Upon complete addition of cesium carbonate, the mixture was allowed to warm to 23° C. After 17 h, the mixture was cooled in an ice-water bath. After 20 mins, 6-methoxypicolinohydrazide (commercially available from Milestone PharmTech USA Inc, 127 mg, 0.76 mmol) and then silver nitrate (257 mg, 1.51 mmol) were carefully added in portions. The mixture was allowed to warm to 23° C. After 25 additional mins, the mixture was filtered directly onto a silica gel column and purified (30-70% 3:1 EtOAc:EtOH in heptane.) Fractions containing product were combined and then concentrated in vacuo to afford Example 292.1 (310 mg, 0.55 mmol, 72% yield) as a colorless film that was used without further purification. LCMS ESI (pos.) m/z: 567.2 (M+H)$^+$.

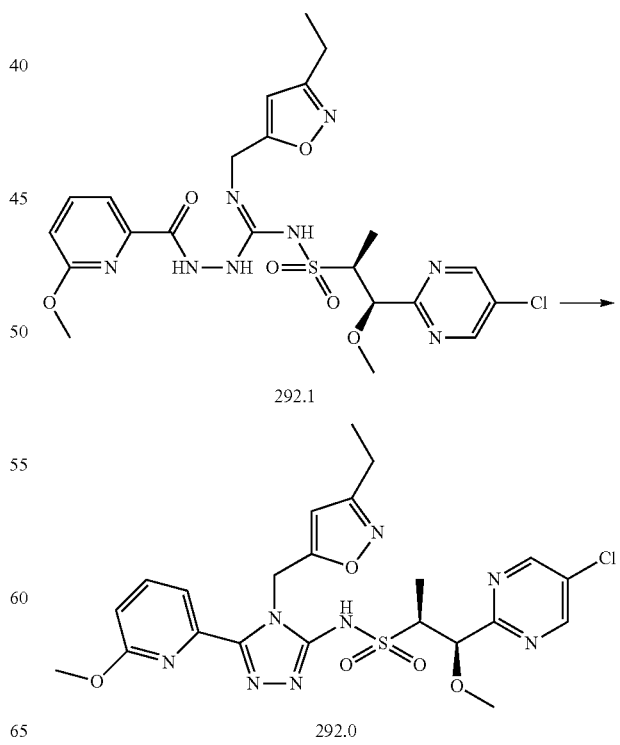

(1R,2S)-1-(5-Chloropyrimidin-2-yl)-N-(4-((3-ethyl-isoxazol-5-yl)methyl)-5-(6-methoxypyridin-2-yl)-4H-1,2,4-triazol-3-yl)-1-methoxypropane-2-sulfonamide, Example 292.0

To a vial containing Example 292.1 (310 mg, 0.55 mmol) in 1,4-dioxane (2.2 mL) was added methane sulfonic acid (0.15 mL, 2.31 mmol) carefully and dropwise to the reaction mixture. Upon complete addition of methanesulfonic acid, the mixture was heated on a preheated stir plate at 75° C. After 18 h, the reaction was cooled to RT and then diluted with water. The pH was carefully adjusted with dropwise addition of a saturated aqueous sodium bicarbonate solution to pH~7. The reaction mixture was extracted three times with DCM. The organic layers were pooled and then dried over anhydrous magnesium sulfate. After filtration and concentration in vacuo, the residue was loaded onto a silica gel column (20-55% 3:1 EtOAc:EtOH in heptane). Fractions containing product were combined and then concentrated in vacuo to afford a light yellow film that was dissolved with DMSO and water and then filtered through a 0.45 g syringe tip filter. The solution was purified by preparative HPLC: 50u Silica Gel 19×100 mm+XSelect CSH Prep C18 10u ODB 19×100 mm, A: water 0.1% formic acid B: ACN 0.1% formic acid, Gradient: 25% (2 min), 25-70% (12 min), Flow Rate: 40 mL/min, monitored at 215 nm. Fractions containing product were collected and then concentrated in vacuo to afford Example 292.0 (25 mg, 0.05 mmol, 8% yield) as a white solid. $^1$H NMR (500 MHz, CD$_2$Cl$_2$) δ=8.71 (s, 2H), 7.76-7.71 (m, 1H), 7.70-7.68 (m, 1H), 6.89 (d, J=8.0 Hz, 1H), 6.08 (s, 1H), 5.85-5.77 (m, 2H), 4.92 (d, J=4.4 Hz, 1H), 3.82 (s, 3H), 3.70-3.64 (m, 1H), 3.25 (s, 3H), 2.61-2.56 (m, 2H), 1.31 (d, J=6.7 Hz, 3H), 1.17 (t, J=7.7 Hz, 3H). LCMS ESI (pos.) m/z: 549.2 (M+H)$^+$.

The compounds set forth in the following table were synthesized following the procedure in Example 1.0 using the known starting material as described.

TABLE 25

| Example | Reagents | Structure, Name, Data |
|---|---|---|
| 293.0 | (1R,2S)-1-(5-chloropyrimidin-2-yl)-1-methoxypropane-2-sulfonamide (Example 29.3), 3-ethyl-5-(isothiocyanatomethyl)isoxazole (Example 264.5), and 5-methylnicotinic acid hydrazide (commercially available from Bellen). | 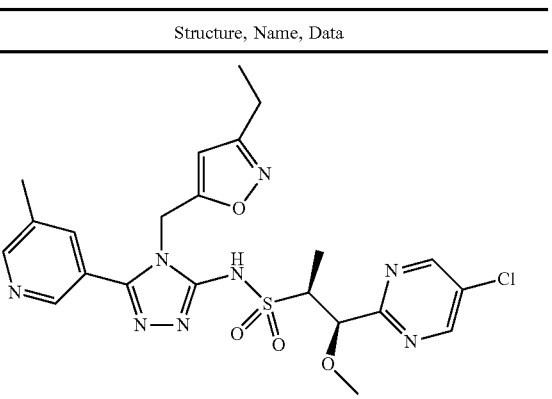<br>(1R,2S)-1-(5-chloropyrimidin-2-yl)-N-(4-((3-ethylisoxazol-5-yl)methyl)-5-(5-methylpyridin-3-yl)-4H-1,2,4-triazol-3-yl)-1-methoxypropane-2-sulfonamide.<br>$^1$H NMR (400 MHz, CD$_2$Cl$_2$) δ 8.74-8.70 (m, 2H), 8.64 (dd, J = 1.8, 4.9 Hz, 2H), 7.75 (s, 1H), 6.28 (s, 1H), 5.14-5.05 (m, 2H), 4.92 (d, J = 4.4 Hz, 1H), 3.70-3.63 (m, 1H), 3.26 (s, 3H), 2.67-2.62 (m, 2H), 2.42 (s, 3H), 1.31 (d, J = 7.0 Hz, 3H), 1.24-1.20 (m, 3H). LCMS ESI (pos.) m/z: 533.2 (M + H)$^+$. |
| 294.0 | (1S,2S)-1-isopropoxy-1-(5-methylpyrimidin-2-yl)propane-2-sulfonamide (Example 31.0), (3-ethyl-5-(isothiocyanatomethyl)isoxazole (Example 264.5), and 6-methoxypicolinohydrazide (commercially available from Milestone PharmTech USA Inc.). | 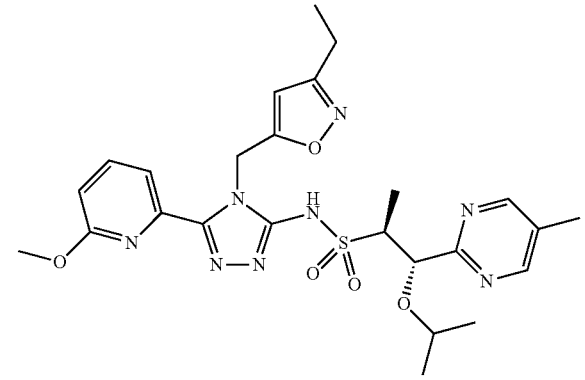<br>(1S,2S)-N-(4-((3-ethylisoxazol-5-yl)methyl)-5-(6-methoxypyridin-2-yl)-4H-1,2,4-triazol-3-yl)-1-isopropoxy-1-(5-methylpyrimidin-2-yl)propane-2-sulfonamide.<br>$^1$H NMR (500 MHz, CD$_2$Cl$_2$) δ 8.65 (s, 2H), 7.75-7.69 (m, 2H), 6.87 (d, J = 7.8 Hz, 1H), 6.12 (s, 1H), 5.99 (d, J = 16.1 Hz, 1H), 5.65 (d, J = 16.1 Hz, 1H), 4.84 (d, |

TABLE 25-continued

| Example | Reagents | Structure, Name, Data |
|---|---|---|
| | | J = 3.9 Hz, 1H), 3.84 (s, 3H), 3.71 (dq, J = 3.9, 7.0 Hz, 1H), 3.47 (spt, J = 6.1 Hz, 1H), 2.61 (q, J = 7.5 Hz, 2H), 2.34 (s, 3H), 1.48 (d, J = 7.0 Hz, 3H), 1.19 (t, J = 7.5 Hz, 3H), 1.01 (d, J = 6.2 Hz, 3H), 0.84 (d, J = 6.2 Hz, 3H). LCMS-ESI (pos.) m/z: 557.2 (M + H)⁺. |
| 336.0 | (1R,2S)-1-(5-chloropyrimidin-2-yl)-1-methoxypropane-2-sulfonamide (Example 29.3), (R)-5-(1-isothiocyanatoethyl)pyrimidine and (S)-5-(1-isothiocyanatoethyl)pyrimidine (Example 336.1), and 6-methoxypicolinohydrazide (commercially available from Sigma Aldrich). The mixture was purified using the following preparative SFC method: Column: Chiralpak IC, Mobile Phase: 50:50 (A:B) A: Liquid CO₂, B: MeOH. This was peak 1. | 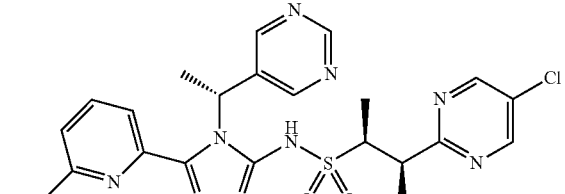 or 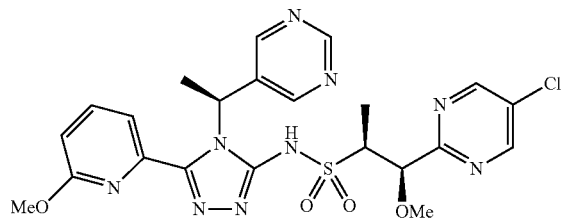 [SMILES: COc1cccc(-c2nnc(NS(=O)(=O)[C@@H](C)[C@H](OC)c3ncc(Cl)cn3)n2[C@@H](C)c2cncnc2)n1] (1R,2S)-1-(5-chloropyrimidin-2-yl)-1-methoxy-N-(5-(6-methoxypyridin-2-yl)-4-((R)-1-(pyrimidin-5-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(pyrimidin-5-yl)ethyl)-4H-1,2,4-triazol-3-yl)propane-2-sulfonamide. ¹H NMR (500 MHz, CD₃OD) δ 9.05 (s, 1 H), 8.94 (s, 2 H), 8.80 (s, 2 H), 7.87 (t, J = 7.91 Hz, 1 H), 7.65 (d, J = 7.40 Hz, 1 H), 6.99 (d, J = 8.30 Hz, 1 H), 6.81 (q, J = 7.09 Hz, 1 H), 4.67 (d, J = 4.28 Hz, 1 H), 3.81 (s, 3 H), 3.37-3.50 (m, 1 H), 3.23 (s, 3 H), 2.09 (d, J = 7.01 Hz, 3 H), 1.05 (d, J = 7.01 Hz, 3 H). LCMS-ESI (pos): 546.0 (M + H)⁺. |
| 337.0 | (1R,2S)-1-(5-chloropyrimidin-2-yl)-1-methoxypropane-2-sulfonamide (Example 29.3), (R)-5-(1-isothiocyanatoethyl)pyrimidine and (S)-5-(1-isothiocyanatoethyl)pyrimidine (Example 336.1), and 6-methoxypicolinohydrazide (commercially available from Sigma Aldrich). The mixture was purified using the following preparative SFC method: Column: Chiralpak IC, Mobile Phase: 50:50 (A:B) A: Liquid CO₂, B: MeOH. This was peak 2 | 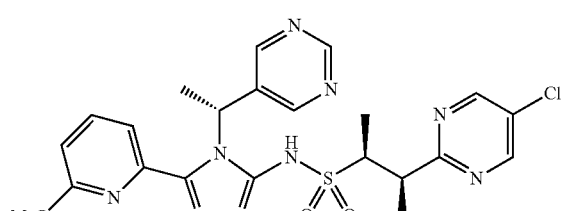 or 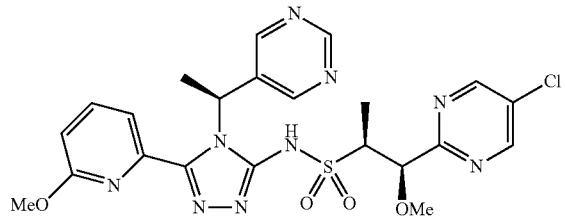 [SMILES: COc1cccc(-c2nnc(NS(=O)(=O)[C@@H](C)[C@H](OC)c3ncc(Cl)cn3)n2[C@@H](C)c2cncnc2)n1] (1R,2S)-1-(5-chloropyrimidin-2-yl)-1-methoxy-N-(5-(6-methoxypyridin-2-yl)-4-((R)-1-(pyrimidin-5-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(pyrimidin-5-yl)ethyl)-4H-1,2,4-triazol-3-yl)propane-2-sulfonamide. ¹H NMR (500 MHz, CD₃OD) δ 9.06 (s, 1 H), 8.91 (s, |

| Example | Reagents | Structure, Name, Data |
|---|---|---|
| | | 2 H), 8.82 (s, 2 H), 7.85 (t, J = 7.85 Hz, 1 H), 7.61 (d, J = 7.27 Hz, 1 H), 6.96 (d, J = 8.30 Hz, 1 H), 6.77 (q, J = 6.83 Hz, 1 H), 4.78 (d, J = 4.28 Hz, 1 H), 3.78 (s, 3 H), 3.44-3.52 (m, 1 H), 3.25 (s, 3 H), 2.10 (d, J = 7.01 Hz, 3 H), 1.17 (d, J = 7.01 Hz, 3 H). LCMS-ESI (pos): 546.0 (M + H)+. |
| 338.0 | (1R,2S)-1-(5-chloropyrimidin-2-yl)-1-methoxypropane-2-sulfonamide (Example 29.3), (R)-4-(1-isothiocyanatoethyl)-1-methyl-1H-pyrazole and (S)-4-(1-isothiocyanatoethyl)-1-methyl-1H-pyrazole (Example 338.1), and 6-methoxypicolinohydrazide (commercially available from Sigma Aldrich). The mixture was purified using the following preparative SFC method: Column: Chiralpak IF, Mobile Phase: 50:50 (A:B) A: Liquid CO$_2$, B: MeOH. This was peak 1 | 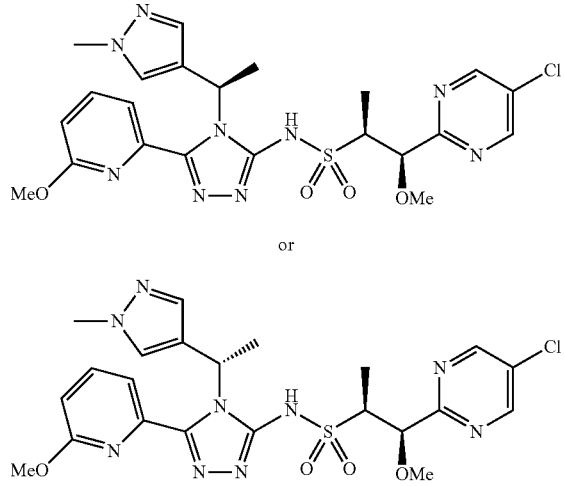

or (1R,2S)-1-(5-chloropyrimidin-2-yl)-1-methoxy-N-(5-(6-methoxypyridin-2-yl)-4-((R)-1-(1-methyl-1H-pyrazol-4-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(1-methyl-1H-pyrazol-4-yl)ethyl)-4H-1,2,4-triazol-3-yl)propane-2-sulfonamide.
$^1$H NMR (500 MHz, CDCl$_3$) δ 10.92-11.25 (br s, 1 H), 8.77 (s, 2 H), 8.06 (s, 1 H), 7.79 (t, J = 7.85 Hz, 1 H), 7.72 (s, 1 H), 7.57 (d, J = 7.40 Hz, 1 H), 6.96 (d, J = 8.30 Hz, 1 H), 6.77 (d, J = 6.36 Hz, 1 H), 4.98 (d, J = 4.15 Hz, 1 H), 4.15 (s, 3 H), 3.96 (s, 3 H), 3.70 (dd, J = 7.01, 4.15 Hz, 1 H), 3.35 (s, 4 H), 2.02-2.08 (d, 3 H), 1.34 (d, J = 7.01 Hz, 3 H). LCMS-ESI (pos): 548.2 (M + H)+. |
| 339.0 | (1R,2S)-1-(5-chloropyrimidin-2-yl)-1-methoxypropane-2-sulfonamide (Example 29.3), (R)-4-(1-isothiocyanatoethyl)-1-methyl-1H-pyrazole and (S)-4-(1-isothiocyanatoethyl)-1-methyl-1H-pyrazole (Example 338.1), and 6-methoxypicolinohydrazide (commercially available from Sigma Aldrich). The mixture was purified using the following preparative SFC method: Column: Chiralpak IF, Mobile Phase: 50:50 (A:B) A: Liquid CO$_2$, B: MeOH. This was peak 2 | 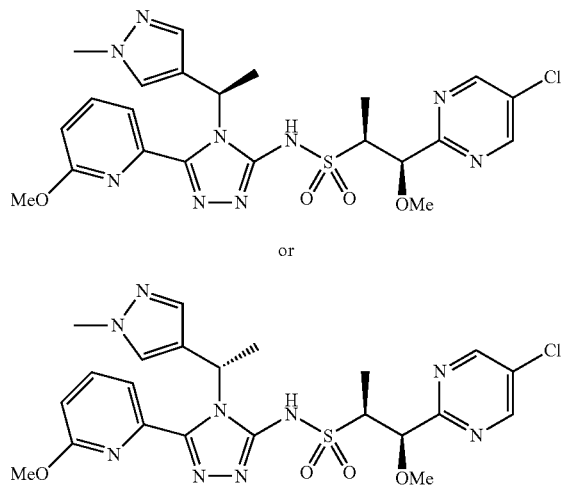

or (1R,2S)-1-(5-chloropyrimidin-2-yl)-1-methoxy-N-(5-(6-methoxypyridin-2-yl)-4-((R)-1-(1-methyl-1H-pyrazol-4-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(1-methyl-1H-pyrazol-4-yl)ethyl)-4H-1,2,4-triazol-3-yl)propane-2-sulfonamide. |

| Example | Reagents | Structure, Name, Data |
|---|---|---|
| | | ¹H NMR (500 MHz, CDCl₃) δ 10.99 (br s, 1 H), 8.75 (s, 2 H), 7.76 (dd, J = 8.17, 7.53 Hz, 1 H), 7.66 (s, 1 H), 7.44-7.60 (m, 2 H), 6.94 (d, J = 8.43 Hz, 1 H), 6.65 (q, J = 6.83 Hz, 1 H), 4.88 (d, J = 4.93 Hz, 1 H), 3.96 (s, 3 H), 3.94 (s, 3 H), 3.65-3.73 (m, 1 H), 3.37 (s, 3 H), 2.02 (d, J = 7.14 Hz, 3 H), 1.26 (d, J = 7.01 Hz, 3 H). LCMS-ESI (pos): 548.2 (M + H)⁺. |
| 340.0 | (1R,2S)-1-(5-chloropyrimidin-2-yl)-1-methoxypropane-2-sulfonamide (Example 29.3), (R)-1,3-difluoro-5-(1-isothiocyanatoethyl)benzene or (S)-1,3-difluoro-5-(1-isothiocyanatoethyl)benzene (Example 340.1), and 6-methoxypicolinohydrazide (commercially available from Sigma Aldrich). The mixture was purified using the following preparative SFC method: Column: Chiralpak AD-H, Mobile Phase: 75:25 (A:B) A: Liquid CO₂, B: MeOH. This was peak 1 | 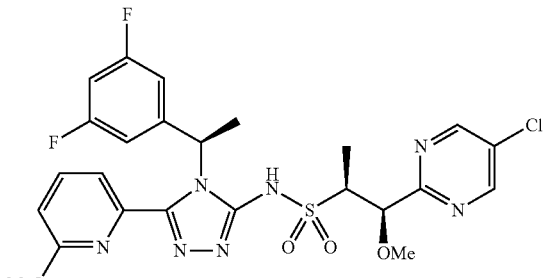<br>or<br>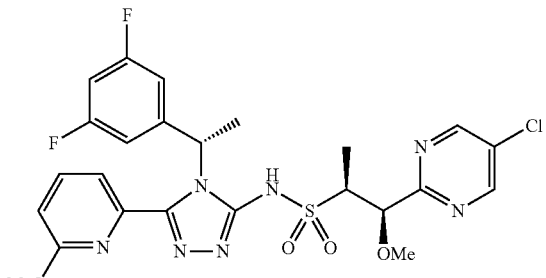<br>(1R,2S)-1-(5-chloropyrimidin-2-yl)-N-(4-((R)-1-(3,5-difluorophenyl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-difluorophenyl)ethyl)-5-(6-methoxypyridin-2-yl)-4H-1,2,4-triazol-3-yl)-1-methoxypropane-2-sulfonamide.<br>¹H NMR (500 MHz, CDCl₃) δ 8.69 (s, 2 H), 7.69-7.81 (m, 2 H), 7.57 (d, J = 7.40 Hz, 1 H), 6.96 (br d, J = 6.62 Hz, 2 H), 6.91 (d, J = 8.30 Hz, 2 H), 6.57-6.71 (m, 2 H), 4.63 (d, J = 5.06 Hz, 1 H), 3.79 (s, 3 H), 3.49-3.61 (m, 1 H), 3.30 (s, 3 H), 2.00 (d, J = 7.01 Hz, 3 H), 1.14 (d, J = 7.01 Hz, 3 H). ¹⁹F NMR (471 MHz, CDCl₃) δ −110.70 (s, 1 F). LCMS-ESI (pos): 580.2 (M + H)⁺. |

TABLE 25-continued

| Example | Reagents | Structure, Name, Data |
|---|---|---|
| 341.0 | (1R,2S)-1-(5-chloropyrimidin-2-yl)-1-methoxypropane-2-sulfonamide (Example 29.3), (R)-1,3-difluoro-5-(1-isothiocyanatoethyl)benzene or (S)-1,3-difluoro-5-(1-isothiocyanatoethyl)benzene (Example 340.1), and 6-methoxypicolinohydrazide (commercially available from Sigma Aldrich). The mixture was purified using the following preparative SFC method: Column: Chiralpak AD-H, Mobile Phase: 75:25 (A:B) A: Liquid $CO_2$, B: MeOH. This was peak 2 | 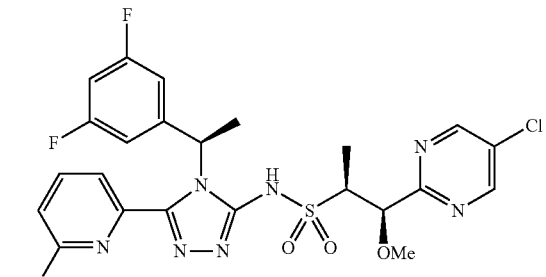 or 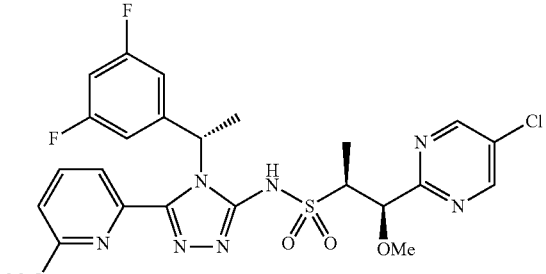 (1R,2S)-1-(5-chloropyrimidin-2-yl)-N-(4-((R)-1-(3,5-difluorophenyl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-difluorophenyl)ethyl)-5-(6-methoxypyridin-2-yl)-4H-1,2,4-triazol-3-yl)-1-methoxypropane-2-sulfonamide. $^1$H NMR (500 MHz, $CDCl_3$) δ 8.72 (s, 2 H), 7.74 (t, J = 7.91 Hz, 1 H), 7.55 (d, J = 7.27 Hz, 1 H), 6.87-6.98 (m, 3 H), 6.54-6.72 (m, 2 H), 4.71 (d, J = 5.06 Hz, 1 H), 3.78 (s, 3 H), 3.55-3.65 (m, 1 H), 3.30 (s, 3 H), 2.02 (d, J = 7.14 Hz, 3 H), 1.24 (d, J = 7.01 Hz, 3 H). $^{19}$F NMR (471 MHz, $CDCl_3$) δ −110.48 (s, 1 F) LCMS-ESI (pos): 580.2 (M + H)$^+$. |
| 342.0 | (1R,2S)-1-(5-chloropyrimidin-2-yl)-1-methoxypropane-2-sulfonamide (Example 29.3), (R)-1,3-difluoro-5-(1-isothiocyanatopropyl)benzene and (S)-1,3-difluoro-5-(1-isothiocyanatopropyl)benzene (Example 342.1), and 6-methoxypicolinohydrazide (commercially available from Sigma Aldrich). The mixture was purified using the following preparative SFC method: Column: Chiralpak AD-H, Mobile Phase: 80:20 (A:B) A: Liquid $CO_2$, B: MeOH. This was peak 1 | 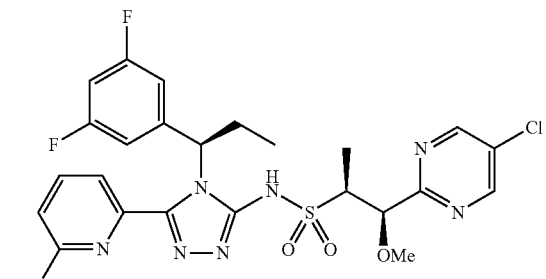 or 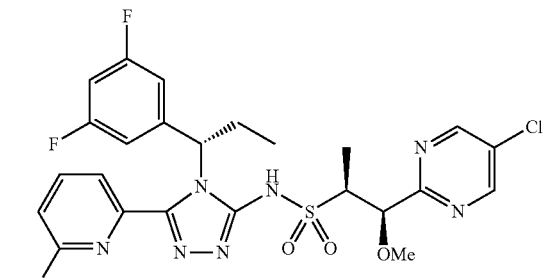 |

| Example | Reagents | Structure, Name, Data |
|---|---|---|
| | | (1R,2S)-1-(5-chloropyrimidin-2-yl)-N-(4-((R)-1-(3,5-difluorophenyl)propyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-difluorophenyl)propyl)-5-(6-methoxypyridin-2-yl)-4H-1,2,4-triazol-3-yl)-1-methoxypropane-2-sulfonamide.<br>$^1$H NMR (500 MHz, CDCl$_3$) δ 8.69 (s, 2 H), 7.76 (t, J = 7.91 Hz, 1 H), 7.59 (d, J = 7.40 Hz, 1 H), 7.08 (br d, J = 6.36 Hz, 2 H), 6.93 (d, J = 8.43 Hz, 1 H), 6.63-6.76 (m, 1 H), 6.49 (br dd, J = 10.12, 5.71 Hz, 1 H), 4.65 (d, J = 5.19 Hz, 1 H), 3.83 (s, 3 H), 3.54-3.64 (m, 1 H), 3.32 (s, 3 H), 2.74-2.89 (m, 1 H), 2.29 (dt, J = 13.88, 6.68 Hz, 1 H), 1.15 (d, J = 6.88 Hz, 3 H), 0.91 (t, J = 7.33 Hz, 3 H). $^{19}$F NMR (471 MHz, CDCl$_3$) δ −110.78 (s, 1 F). LCMS-ESI (pos): 594.2 (M + H). |
| 343.0 | (1R,2S)-1-(5-chloropyrimidin-2-yl)-1-methoxypropane-2-sulfonamide (Example 29.3), (R)-1,3-difluoro-5-(1-isothiocyanatopropyl)benzene and (S)-1,3-difluoro-5-(1-isothiocyanatopropyl)benzene (Example 342.1), and 6-methoxypicolinohydrazide (commercially available from Sigma Aldrich).<br>The mixture was purified using the following preparative SFC method: Column: Chiralpak AD-H, Mobile Phase: 80:20 (A:B) A: Liquid CO$_2$, B: MeOH.<br>This was peak 2 | 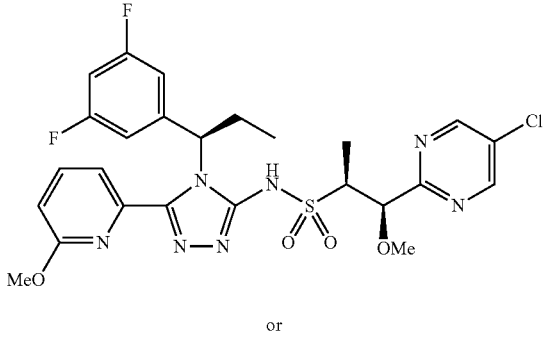<br>or<br>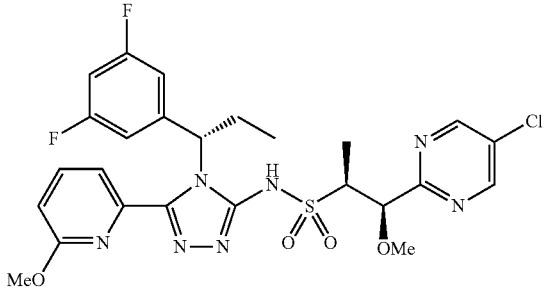 [SMILES: CC[C@@H](c1cc(F)cc(F)c1)n1c(NS(=O)(=O)[C@@H](C)[C@H](OC)c2ncc(Cl)cn2)nnc1-c1cccc(OC)n1]<br>(1R,2S)-1-(5-chloropyrimidin-2-yl)-N-(4-((R)-1-(3,5-difluorophenyl)propyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(3,5-difluorophenyl)propyl)-5-(6-methoxypyridin-2-yl)-4H-1,2,4-triazol-3-yl)-1-methoxypropane-2-sulfonamide.<br>$^1$H NMR (500 MHz, CDCl$_3$) δ 8.71 (s, 2 H), 7.74 (t, J = 7.85 Hz, 1 H), 7.56 (d, J = 7.27 Hz, 1 H), 7.05 (br d, J = 6.49 Hz, 2 H), 6.92 (d, J = 8.43 Hz, 1 H), 6.68 (br t, J = 8.69 Hz, 1 H), 6.45 (dd, J = 9.86, 5.97 Hz, 1 H), 4.72 (d, J = 4.93 Hz, 1 H), 3.81 (s, 3 H), 3.54-3.70 (m, 1 H), 3.30 (s, 3 H), 2.80 (ddd, J = 13.92, 9.57, 7.53 Hz, 1 H), 2.31 (dt, J = 13.85, 6.76 Hz, 1 H), 1.26 (d, J = 6.88 Hz, 4 H), 0.94 (t, J = 7.33 Hz, 3 H). $^{19}$F NMR (471 MHz, CDCl$_3$) δ −110.56 (s, 1 F). LCMS-ESI (pos): 594.2 (M + H)$^+$. |

| Example | Reagents | Structure, Name, Data |
|---|---|---|
| 344.0 | (1R,2S)-1-(5-chloropyrimidin-2-yl)-1-methoxypropane-2-sulfonamide (Example 29.3), (R)-4-(1-isothiocyanatoethyl)thiazole and (S)-4-(1-isothiocyanatoethyl)thiazole (Example 344.1), and 6-methoxypicolinohydrazide (commercially available from Sigma Aldrich). The mixture was purified using the following preparative SFC method: Column: Lux Cellulose-2, Mobile Phase: 55:45 (A:B) A: Liquid CO$_2$, B: MeOH. This was peak 1 | 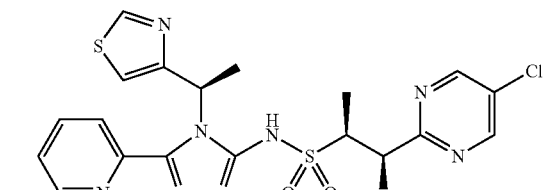<br>or<br>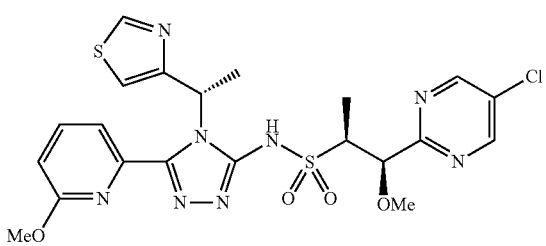 [SMILES: COc1cccc(-c2nnc(NS(=O)(=O)[C@@H](C)[C@H](OC)c3ncc(Cl)cn3)n2[C@@H](C)c2cscn2)n1]<br>(1R,2S)-1-(5-chloropyrimidin-2-yl)-1-methoxy-N-(5-(6-methoxypyridin-2-yl)-4-((S)-1-(thiazol-4-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((R)-1-(thiazol-4-yl)ethyl)-4H-1,2,4-triazol-3-yl)propane-2-sulfonamide.<br>$^1$H NMR (500 MHz, CDCl$_3$) δ 8.72 (s, 2 H), 8.66 (d, J = 1.69 Hz, 1 H), 7.70 (t, J = 7.91 Hz, 1 H), 7.56 (d, J = 7.27 Hz, 1 H), 7.36 (s, 1 H), 6.85 (d, J = 8.30 Hz, 1 H), 6.73 (q, J = 7.01 Hz, 1 H), 4.82 (d, J = 5.19 Hz, 1 H), 3.85 (s, 3 H), 3.50-3.63 (m, 1 H), 3.35 (s, 3 H), 2.15 (d, J = 7.01 Hz, 3 H), 1.16 (d, J = 7.01 Hz, 3 H). LCMS-ESI (pos): 551.0 (M + H)$^+$. |
| 345.0 | (1R,2S)-1-(5-chloropyrimidin-2-yl)-1-methoxypropane-2-sulfonamide (Example 29.3), (R)-4-(1-isothiocyanatoethyl)thiazole and (S)-4-(1-isothiocyanatoethyl)thiazole (Example 344.1), and 6-methoxypicolinohydrazide (commercially available from Sigma Aldrich).<br>The mixture was purified using the following preparative SFC method: Column: Lux Cellulose-2, Mobile Phase: 55:45 (A:B) A: Liquid CO$_2$, B: MeOH. This was peak 2 | 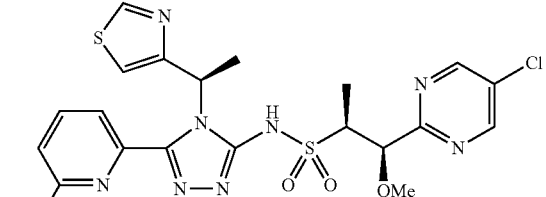<br>or<br>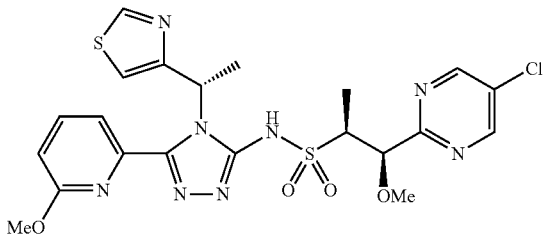 [SMILES: COc1cccc(-c2nnc(NS(=O)(=O)[C@@H](C)[C@H](OC)c3ncc(Cl)cn3)n2[C@@H](C)c2cscn2)n1]<br>(1R,2S)-1-(5-chloropyrimidin-2-yl)-1-methoxy-N-(5-(6-methoxypyridin-2-yl)-4-((S)-1-(thiazol-4-yl)ethyl)-4H-1,2,4-triazol-3-yl)propane-2-sulfonamide or (1R,2 S)-1-(5-chloropyrimidin-2-yl)-1-methoxy-N-(5-(6-methoxypyridin-2-yl)-4-((R)-1-(thiazol-4-yl)ethyl)-4H-1,2,4-triazol-3-yl)propane-2-sulfonamide.<br>$^1$H NMR (500 MHz, CDCl$_3$) δ 11.07 (br s, 1 H), 8.72 (s, 2 H), 8.66 (d, J = 1.56 Hz, 1 H), 7.70 (t, J = 7.91 Hz, 1 H), 7.56 (d, J = 7.27 Hz, 1 H), 7.40 (s, 1 H), 6.85 (d, |

TABLE 25-continued

| Example | Reagents | Structure, Name, Data |
|---|---|---|
| | | J = 8.30 Hz, 1 H), 6.73 (q, J = 6.96 Hz, 1 H), 4.79 (d, J = 4.93 Hz, 1 H), 3.86 (s, 3 H), 3.52-3.66 (m, 1 H), 3.33 (s, 3 H), 2.17 (d, J = 7.14 Hz, 3 H), 1.25 (d, J = 6.88 Hz, 3 H). LCMS-ESI (pos): 551.0 (M + H)+. |
| 346.0 | (1R,2S)-1-(5-chloropyrimidin-2-yl)-1-methoxypropane-2-sulfonamide (Example 29.3), (R)-5-(1-isothiocyanatoethyl)thiazole and 5-(1-isothiocyanatoethyl)thiazole (Example 346.1), and 6-methoxypicolinohydrazide (commercially available from Sigma Aldrich). The mixture was purified using the following preparative SFC method: Column: Phenomenex Lux Cellulose-2, Mobile Phase: 50:50 (A:B) A: Liquid CO2, B: MeOH. This was peak 1 | 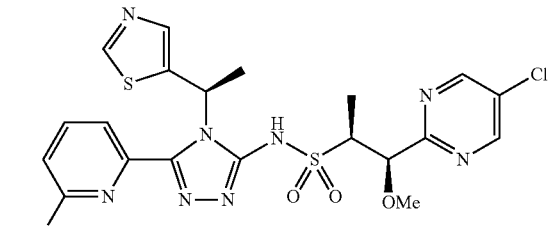<br>or<br>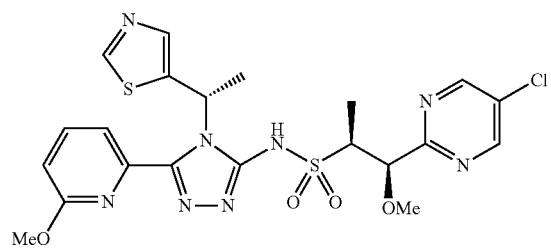 [SMILES: COc1cccc(-c2nnc(NS(=O)(=O)[C@@H](C)[C@H](OC)c3ncc(Cl)cn3)n2[C@@H](C)c2cncs2)n1]<br>(1R,2S)-1-(5-chloropyrimidin-2-yl)-1-methoxy-N-(5-(6-methoxypyridin-2-yl)-4-((R)-1-(thiazol-5-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(thiazol-5-yl)ethyl)-4H-1,2,4-triazol-3-yl)propane-2-sulfonamide.<br>1H NMR (500 MHz, CDCl3) δ 11.20 (br s, 1 H), 8.64-8.84 (m, 3 H), 7.85 (s, 1 H), 7.74 (t, J = 7.85 Hz, 1 H), 7.57 (d, J = 7.27 Hz, 1 H), 7.06 (d, J = 6.75 Hz, 1 H), 6.92 (d, J = 8.30 Hz, 1 H), 4.84 (br d, J = 4.54 Hz, 1 H), 3.89 (s, 3 H), 3.61-3.68 (m, 1 H), 3.36 (s, 3 H), 2.15 (d, J = 7.01 Hz, 3 H), 1.21 (d, J = 6.88 Hz, 3 H). LCMS-ESI (pos): 551.0 (M + H)+. |
| 347.0 | (1R,2S)-1-(5-chloropyrimidin-2-yl)-1-methoxypropane-2-sulfonamide (Example 29.3), (R)-5-(1-isothiocyanatoethyl)thiazole and (S)-5-(1-isothiocyanatoethyl)thiazole (Example 346.1), and 6-methoxypicolinohydrazide (commercially available from Sigma Aldrich). The mixture was purified using the following preparative SFC method: Column: Phenomenex Lux Cellulose-2, Mobile Phase: 50:50 (A:B) A: Liquid CO2, B: MeOH. This was peak 2 | 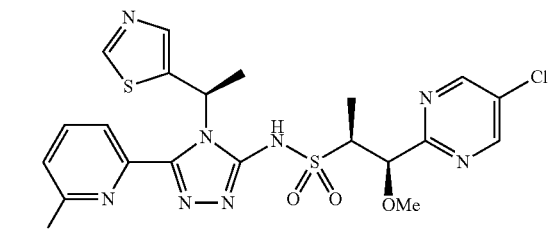<br>or<br>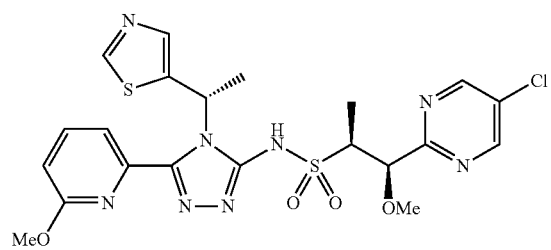 [SMILES: COc1cccc(-c2nnc(NS(=O)(=O)[C@@H](C)[C@H](OC)c3ncc(Cl)cn3)n2[C@@H](C)c2cncs2)n1]<br>(1R,2S)-1-(5-chloropyrimidin-2-yl)-1-methoxy-N-(5-(6-methoxypyridin-2-yl)-4-((R)-1-(thiazol-5-yl)ethyl)-4H-1,2,4-triazol-3-yl)propane-2-sulfonamide or (1R,2S)-1-(5-chloropyrimidin-2-yl)- |

TABLE 25-continued

| Example | Reagents | Structure, Name, Data |
|---|---|---|
| | | 1-methoxy-N-(5-(6-methoxypyridin-2-yl)-4-((S)-1-(thiazol-5-yl)ethyl)-4H-1,2,4-triazol-3-yl)propane-2-sulfonamide.<br>$^1$H NMR (500 MHz, CDCl$_3$) δ 11.03-11.43 (m, 1 H), 8.67-8.77 (m, 3 H), 7.85 (s, 1 H), 7.74 (t, J = 7.91 Hz, 1 H), 7.56 (d, J = 7.27 Hz, 1 H), 7.07 (q, J = 6.88 Hz, 1 H), 6.92 (d, J = 8.30 Hz, 1 H), 4.85 (d, J = 4.80 Hz, 1 H), 3.90 (s, 3 H), 3.61-3.72 (m, 1 H), 3.33 (s, 3 H), 2.16 (d, J = 7.01 Hz, 3 H), 1.34 (d, J = 7.01 Hz, 3 H). LCMS-ESI (pos): 551.0 (M + H)$^+$. |
| 348.0 | (1R,2S)-1-(5-chloropyrimidin-2-yl)-1-methoxypropane-2-sulfonamide (Example 29.3), (R)-3-fluoro-5-(1-isothiocyanatoethyl)pyridine and (S)-3-fluoro-5-(1-isothiocyanatoethyl)pyridine. (Example 348.1), and 6-methoxypicolinohydrazide (commercially available from Sigma Aldrich).<br>The mixture was purified using the following preparative SFC method: Column: ChromegaChiral CC4, Mobile Phase: 70:30 (A:B) A: Liquid CO$_2$, B: MeOH.<br>This was peak 1 | 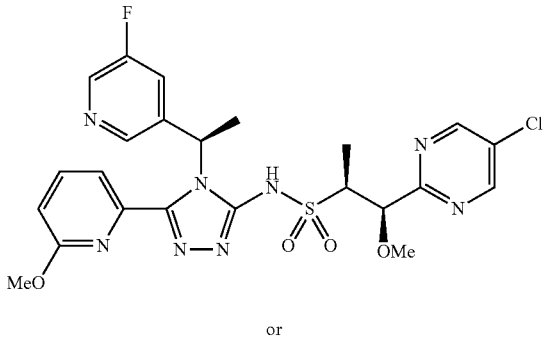<br>or<br>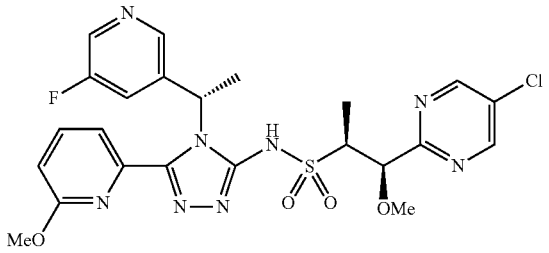 [SMILES: COc1cccc(-c2nnc(NS(=O)(=O)[C@@H](C)[C@H](OC)c3ncc(Cl)cn3)n2[C@@H](C)c2cncc(F)c2)n1]<br>(1R,2S)-1-(5-chloropyrimidin-2-yl)-N-(4-((R)-1-(5-fluoropyridin-3-yl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(5-fluoropyridin-3-yl)ethyl)-5-(6-methoxypyridin-2-yl)-4H-1,2,4-triazol-3-yl)-1-methoxypropane-2-sulfonamide.<br>$^1$H NMR (500 MHz, CDCl$_3$) δ 10.69-11.72 (m, 1 H), 8.70 (s, 2 H), 8.53-8.53 (m, 1 H), 8.36 (br d, J = 1.56 Hz, 1 H), 7.76 (dd, J = 8.24, 7.46 Hz, 1 H), 7.57-7.65 (m, 2 H), 6.93 (d, J = 8.43 Hz, 1 H), 6.81 (q, J = 7.09 Hz, 1 H), 4.68 (d, J = 4.80 Hz, 1 H), 3.81 (s, 3 H), 3.49-3.61 (m, 1 H), 3.31 (s, 3 H), 2.07 (d, J = 7.14 Hz, 3 H), 1.10 (d, J = 7.01 Hz, 3 H). $^{19}$F NMR (471 MHz, CDCl$_3$) δ −127.84 (s, 1 F). LCMS-ESI (pos): 563.2 (M + H)$^+$. |

TABLE 25-continued

| Example | Reagents | Structure, Name, Data |
|---|---|---|
| 349.0 | (1R,2S)-1-(5-chloropyrimidin-2-yl)-1-methoxypropane-2-sulfonamide (Example 29.3), (R)-3-fluoro-5-(1-isothiocyanatoethyl)pyridine and (S)-3-fluoro-5-(1-isothiocyanatoethyl)pyridine. (Example 348.1), and 6-methoxypicolinohydrazide (commercially available from Sigma Aldrich). The mixture was purified using the following preparative SFC method: Column: ChromegaChiral CC4, Mobile Phase: 70:30 (A:B) A: Liquid CO$_2$, B: MeOH. This was peak 2 | 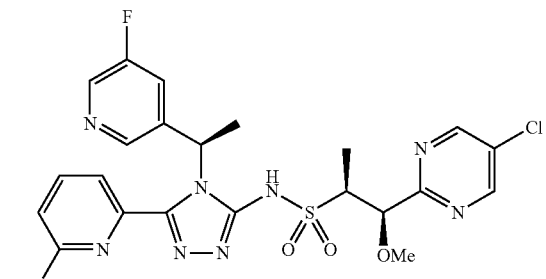<br>or<br>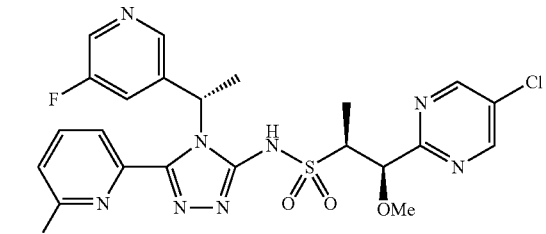<br>(1R,2S)-1-(5-chloropyrimidin-2-yl)-N-(4-((R)-1-(5-fluoropyridin-3-yl)ethyl)-5-(6-methoxypyridin-2-yl)-4H-1,2,4-triazol-3-yl)-1-methoxypropane-2-sulfonamide or (1R,2S)-1-(5-chloropyrimidin-2-yl)-N-(4-((S)-1-(5-fluoropyridin-3-yl)ethyl)-5-(6-methoxypyridin-2-yl)-4H-1,2,4-triazol-3-yl)-1-methoxypropane-2-sulfonamide.<br>$^1$H NMR (500 MHz, CDCl$_3$) δ 10.96-11.65 (m, 1 H), 8.72 (s, 2 H), 8.48 (s, 1 H), 8.37 (d, J = 2.08 Hz, 1 H), 7.75 (dd, J = 8.30, 7.53 Hz, 1 H), 7.51-7.66 (m, 2 H), 6.92 (d, J = 8.30 Hz, 1 H), 6.77 (q, J = 7.09 Hz, 1 H), 4.73 (d, J = 4.93 Hz, 1 H), 3.79 (s, 3 H), 3.53-3.62 (m, 1 H), 3.30 (s, 3 H), 2.09 (d, J = 7.14 Hz, 3 H), 1.24 (d, J = 7.01 Hz, 3 H). $^{19}$F NMR (471 MHz, CDCl$_3$) δ −127.57 (s, 1 F). LCMS-ESI (pos.) m/z: 563.2 (M + H)$^+$. |
| 350.0 | (1R,2S)-1-(5-chloropyrimidin-2-yl)-1-methoxypropane-2-sulfonamide (Example 29.3), (R)-3-(1-isothiocyanatoethyl)pyridine and (S)-3-(1-isothiocyanatoethyl)pyridine (Example 350.1), and 6-methoxypicolinohydrazide (commercially available from Sigma Aldrich). The mixture was purified using the following preparative SFC method: Column: ChromegaChiral CC4, Mobile Phase: 50:50 (A:B) A: Liquid CO$_2$, B: MeOH. This was peak 1 | 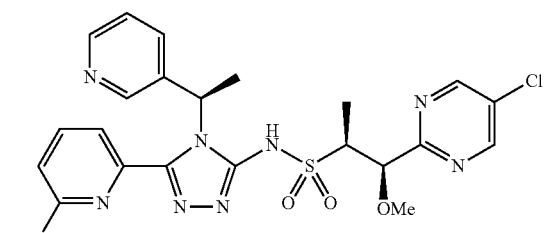<br>or<br>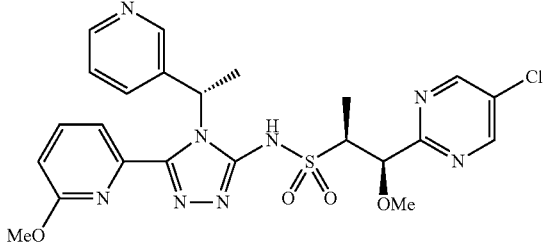 [SMILES: COc1cccc(-c2nnc(NS(=O)(=O)[C@@H](C)[C@H](OC)c3ncc(Cl)cn3)n2[C@@H](C)c2cccnc2)n1]<br>(1R,2S)-1-(5-chloropyrimidin-2-yl)-1-methoxy-N-(5-(6-methoxypyridin-2-yl)-4-((R)-1-(pyridin-3-yl)ethyl)-4H-1,2,4-triazol-3-yl)propane-2-sulfonamide or (1R,2S)-1-(5-chloropyrimidin-2-yl)- |

TABLE 25-continued

| Example | Reagents | Structure, Name, Data |
|---------|----------|----------------------|
| | | 1-methoxy-N-(5-(6-methoxypyridin-2-yl)-4-((S)-1-(pyridin-3-yl)ethyl)-4H-1,2,4-triazol-3-yl)propane-2-sulfonamide.<br>$^1$H NMR (500 MHz, CDCl$_3$) δ 10.98-11.74 (m, 1 H), 8.38-8.75 (m, 4 H), 7.76-7.85 (m, 1 H), 7.72 (t, J = 7.85 Hz, 1 H), 7.55 (d, J = 7.40 Hz, 1 H), 7.20-7.31 (m, 1 H), 6.89 (d, J = 8.30 Hz, 1 H), 6.74 (q, J = 6.96 Hz, 1 H), 4.68 (d, J = 5.06 Hz, 1 H), 3.78 (s, 3 H), 3.46-3.56 (m, 1 H), 3.29 (s, 3 H), 2.06 (d, J = 7.14 Hz, 3 H), 1.05 (d, J = 6.88 Hz, 3 H). LCMS-ESI (pos.) m/z: 545.2 (M + H)$^+$. |
| 351.0 | (1R,2S)-1-(5-chloropyrimidin-2-yl)-1-methoxypropane-2-sulfonamide (Example 29.3), (R)-3-(1-isothiocyanatoethyl)pyridine and (S)-3-(1-isothiocyanatoethyl)pyridine (Example 350.1), and 6-methoxypicolinohydrazide (commercially available from Sigma Aldrich).<br>The mixture was purified using the following preparative SFC method: Column: ChromegaChiral CC4, Mobile Phase: 50:50 (A:B) A: Liquid CO$_2$, B: MeOH.<br>This was peak 2. | 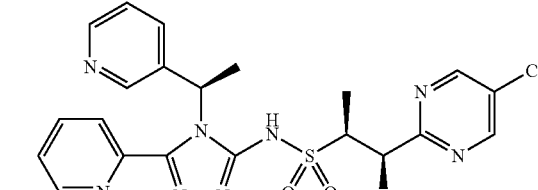<br>or<br>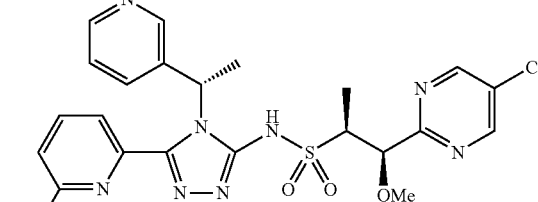<br>(1R,2S)-1-(5-chloropyrimidin-2-yl)-1-methoxy-N-(5-(6-methoxypyridin-2-yl)-4-((R)-1-(pyridin-3-yl)ethyl)-4H-1,2,4-triazol-3-yl)propane-2-sulfonamide or (1R,2S)-1-(5-chloropyrimidin-2-yl)-1-methoxy-N-(5-(6-methoxypyridin-2-yl)-4-((S)-1-(pyridin-3-yl)ethyl)-4H-1,2,4-triazol-3-yl)propane-2-sulfonamide.<br>$^1$H NMR (500 MHz, CDCl$_3$) δ 11.14-11.69 (bs, 1 H), 8.70 (s, 2 H), 8.41-8.66 (m, 2 H), 7.83 (br d, J = 7.66 Hz, 1 H), 7.72 (t, J = 7.85 Hz, 1 H), 7.53 (d, J = 7.27 Hz, 1 H), 7.21-7.29 (m, 1 H), 6.89 (d, J = 8.30 Hz, 1 H), 6.71 (q, J = 6.62 Hz, 1 H), 4.76 (d, J = 4.80 Hz, 1 H), 3.78 (s, 3 H), 3.51-3.62 (m, 1 H), 3.29 (s, 3 H), 2.09 (d, J = 7.01 Hz, 3 H), 1.21 (d, J = 7.01 Hz, 3 H). LCMS-ESI (pos.) m/z: 545.2 (M + H)$^+$. |

The compounds set forth in the following table were synthesized following the procedure in Example 71.0 using the known starting material as described.

TABLE 26

| Example | Reagents | Structure, Name and Data |
|---------|----------|--------------------------|
| 336.1 | 1-(pyrimidin-5-yl)ethanamine (commercially available from Enamine) | 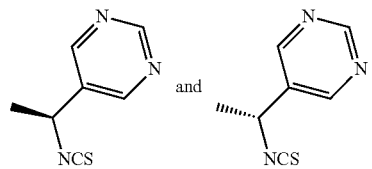<br>(R)-5-(1-isothiocyanatoethyl)pyrimidine and (S)-5-(1-isothiocyanatoethyl)pyrimidine.<br>$^1$H NMR (500 MHz, CDCl$_3$) δ 9.22 (s, 1 H), 8.77 (s, 2 H), 5.04 (q, J = 6.75 Hz, 1 H), 1.77 (d, J = 6.88 Hz, 3 H). |

TABLE 26-continued

| Example | Reagents | Structure, Name and Data |
|---|---|---|
| 338.1 | 1-(1-methyl-1H-pyrazol-4-yl)ethanamine (commercially available from Enamine) | 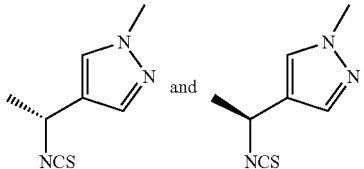<br>(R)-4-(1-isothiocyanatoethyl)-1-methyl-1H-pyrazole and (S)-4-(1-isothiocyanatoethyl)-1-methyl-1H-pyrazole.<br>LCMS-ESI (pos.) m/z: 168.2 (M + H)$^+$. |
| 340.1 | 1-(3,5-difluorophenyl)ethanamine (commercially available from Enamine) | 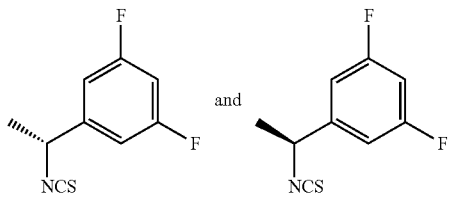<br>(R)-1,3-difluoro-5-(1-isothiocyanatoethyl)benzene or (S)-1,3-difluoro-5-(1-isothiocyanatoethyl)benzene.<br>LCMS-ESI (pos.) m/z: 200.0 (M + H)$^+$. |
| 342.1 | 1-(3,5-difluorophenyl)propan-1-amine (commercially available from Enamine). | 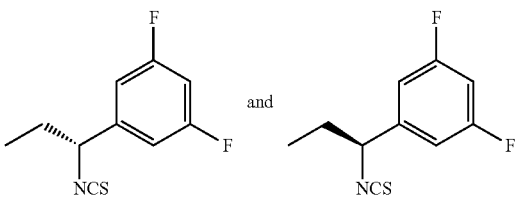<br>(R)-1,3-difluoro-5-(1-isothiocyanatopropyl)benzene and (S)-1,3-difluoro-5-(1-isothiocyanatopropyl)benzene.<br>LCMS-ESI (pos.) m/z: 214.0 (M + H)$^+$. |
| 344.1 | 1-(thiazol-4-yl)ethanamine (commercially available from Enamine) | 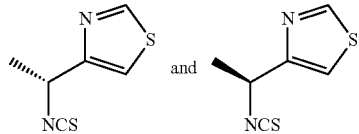<br>(R)-4-(1-isothiocyanatoethyl)thiazole and (S)-4-(1-isothiocyanatoethyl)thiazole.<br>LCMS-ESI (pos.) m/z: 171.2 (M + H)$^+$. |
| 346.1 | 1-(thiazol-5-yl)ethanamine (commercially available from Enamine) | 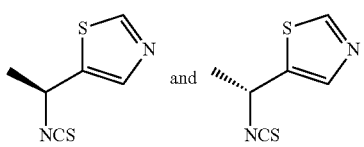<br>(R)-5-(1-isothiocyanatoethyl)thiazole and (S)-5-(1-isothiocyanatoethyl)thiazole.<br>LCMS-ESI (pos.) m/z: 171.2 (M + H)$^+$. |
| 348.1 | 1-(5-fluoropyridin-3-yl)ethanamine (commercially available from Enamine) | 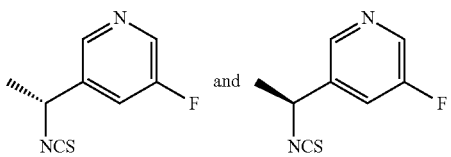<br>(R)-3-fluoro-5-(1-isothiocyanatoethyl)pyridine and (S)-3-fluoro-5-(1-isothiocyanatoethyl)pyridine.<br>LCMS-ESI (pos.) m/z: 183.2 (M + H)$^+$. |

TABLE 26-continued

| Example | Reagents | Structure, Name and Data |
|---------|----------|--------------------------|
| 350.1 | 1-(pyridin-3-yl)ethanamine (commercially available from Enamine) | 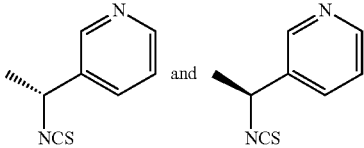<br>(R)-3-(1-isothiocyanatoethyl)pyridine and (S)-3-(1-isothiocyanatoethyl)pyridine.<br>LCMS-ESI (pos.) m/z: 165.2 (M + H)+. |

Biological Activity

[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in 9 µL assay buffer [20 mM HEPES, pH 7.5, 5 mM MgCl$_2$, 100 mM NaCl and 0.1% (w/v) BSA], 1 µL of diluted test compound (starting with 0.75 mM, 2-fold serial dilution with DMSO, total 22 points), 10 µL of 18 µM GDP (final concentration of 3 µM GDP), 20 µL of 0.25 µg/mL membrane protein expressing human APJ receptor captured with WGA PS beads (final concentration of 5 µg per well), and 20 µL of 0.3 nM [$^{35}$S]GTPγS (final concentration is 0.1 nM [$^{35}$S]GTPγS)(Perkin Elmer Life and Analytical Sciences, Waltham USA). One column of the plate was 1 µL of DMSO as background and another column of the plate was 1 µL of 180 µM Pyr-Apelin-13 which was used as control at a final concentration of 3 µM. Incubation was at RT for 90 min and the microplate was read using a ViewLux™ ultra HTS Microplate Imager (PerkinElmer, Inc.). All the results presented are means of several independent experiments and analyzed by non-linear regression methods using the commercially available program Prism (GraphPad, San Diego, Calif.) providing the EC$_{50}$ values detailed in Table 27.

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several h. A balloon was inserted into the left ventricle (LV) to measure dP/dt$_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects (Table 28). APJ agonists of the present invention showed improvement in cardiac contractility and relaxation when perfused into the heart as described above.

Evidence for Improvement in Cardiac Contractility In Vivo in Heart Failure Rat Model Based on the ex vivo findings in isolated heart assay, APJ agonists may be dosed in vivo to investigate the translation of cardiac contractility in in vivo settings. Male Lewis rats (Charles River, USA) at 2-3 months of age are used for the study. Heart failure is induced by permanent ligation of the left descending coronary artery which results in injury to the heart with an ejection fraction of <35%. APJ agonists are administered dose dependently acutely for a period of 30 min. Administration of example compounds will be found to lead to an increase in cardiac contractility as measured by dP/dt$_{max}$ (derivative of left ventricular pressure) (Table 28).

The following table includes biological activity data obtained using the procedures and assays set forth above for the Example compounds described herein.

TABLE 27

Biological Activity Information for Example Compounds.

| Example(s) | Activity hAPJ SPA EC$_{50}$ IP (µM) |
|------------|--------------------------------------|
| 1.0 | 0.68 |
| 2.0 | >4.2 |
| 3.0 | 0.0028 |
| 4.0 | 0.00016 |
| 5.0 | 0.050 |
| 6.0 | 0.00030 |
| 7.0 | 0.24 |
| 8.0 | 0.019 |
| 9.0 | 0.14 |
| 10.0 | 0.00032 |
| 11.0 | 0.0064 |
| 12.0 | 0.12 |
| 13.0 | 0.080 |
| 14.0 | 0.0064 |
| 15.0 | 0.030 |
| 16.0 | 0.044 |
| 17.0 | 0.38 |
| 18.0 | 0.25 |
| 19.0 | 0.026 |
| 20.0 | 0.11 |
| 21.0 | 0.43 |
| 22.0 | 0.0032 |
| 23.0 | 0.015 |
| 24.0 | 0.00066 |
| 25.0 | 0.000080 |
| 26.0 | 0.012 |
| 42.0 | 0.017 |
| 43.0 | 0.0037 |
| 44.0 | 0.0049 |
| 45.0 | 0.060 |
| 46.0 | 0.00033 |
| 47.0 | 0.0053 |
| 48.0 | 0.0013 |
| 49.0 | 0.00088 |
| 50.0 | 0.00046 |

TABLE 27-continued

Biological Activity Information for Example Compounds.

| Example(s) | Activity hAPJ SPA EC$_{50}$ IP (μM) |
|---|---|
| 51.0 | 0.0018 |
| 52.0 | 0.016 |
| 53.0 | 0.030 |
| 54.0 | 0.00050 |
| 55.0 | 0.00040 |
| 56.0 | 0.0019 |
| 57.0 | 0.211 |
| 58.0 | 0.042 |
| 59.0 | 0.028 |
| 60.0 | 0.0012 |
| 61.0 | 0.00089 |
| 62.0 | 0.027 |
| 63.0 | 0.020 |
| 64.0 | 0.00016 |
| 65.0 | 0.024 |
| 66.0 | 0.038 |
| 67.0 | 0.024 |
| 68.0 | 0.0028 |
| 69.0 | 0.00089 |
| 70.0 | 0.00060 |
| 73.0 | 0.0030 |
| 74.0 | 0.031 |
| 75.0 | 0.0030 |
| 76.0 | 0.0033 |
| 77.0 | 0.135 |
| 78.0 | Prophetic |
| 79.0 | Prophetic |
| 80.0 | Prophetic |
| 81.0 | Prophetic |
| 82.0 | Prophetic |
| 83.0 | Prophetic |
| 84.0 | Prophetic |
| 85.0 | Prophetic |
| 86.0 | 0.057 |
| 87.0 | 0.17 |
| 88.0 | 1.9 |
| 89.0 | 0.00076 |
| 90.0 | 0.0062 |
| 91.0 | 0.038 |
| 92.0 | 0.0012 |
| 93.0 | 0.0023 |
| 94.0 | 1.0 |
| 95.0 | 0.026 |
| 97.0 | 0.011 |
| 98.0 | 0.0062 |
| 99.0 | 0.0042 |
| 100.0 | 0.0064 |
| 101.0 | 0.0089 |
| 102.0 | 0.020 |
| 103.0 | 0.015 |
| 104.0 | 0.00039 |
| 105.0 | 0.0028 |
| 106.0 | 0.00038 |
| 107.0 | 0.00042 |
| 108.0 | 0.0059 |
| 109.0 | 0.0096 |
| 110.0 | 0.11 |
| 111.0 | 0.027 |
| 112.0 | 0.0033 |
| 113.0 | 0.0018 |
| 114.0 | 0.054 |
| 118.0 | 0.031 |
| 119.0 | 0.028 |
| 120.0 | 0.024 |
| 121.0 | 0.021 |
| 122.0 | 0.056 |
| 123.0 | 0.0056 |
| 124.0 | 0.024 |
| 125.0 | 0.090 |
| 126.0 | 0.038 |
| 127.0 | 0.048 |
| 128.0 | 0.055 |
| 129.0 | 0.066 |
| 130.0 | 0.35 |
| 131.0 | 0.025 |
| 132.0 | 0.15 |
| 134.0 | 0.17 |
| 135.0 | 1.9 |
| 136.0 | 0.057 |
| 137.0 | 0.022 |
| 138.0 | 0.011 |
| 139.0 | 0.011 |
| 140.0 | 0.042 |
| 141.0 | 0.016 |
| 142.0 | 0.011 |
| 143.0 | 0.0098 |
| 144.0 | 0.014 |
| 145.0 | 0.019 |
| 146.0 | 0.0015 |
| 147.0 | 0.0049 |
| 148.0 | 0.0068 |
| 149.0 | 0.036 |
| 150.0 | 0.10 |
| 151.0 | 0.051 |
| 152.0 | 1.14 |
| 153.0 | 0.055 |
| 154.0 | 0.20 |
| 155.0 | 0.0031 |
| 156.0 | 0.037 |
| 157.0 | 0.33 |
| 158.0 | 0.020 |
| 159.0 | 0.55 |
| 160.0 | 0.090 |
| 161.0 | 0.0022 |
| 162.0 | 0.0028 |
| 163.0 | 0.052 |
| 164.0 | 0.011 |
| 167.0 | 0.088 |
| 168.0 | 0.018 |
| 169.0 | 0.020 |
| 170.0 | 0.00076 |
| 171.0 | 0.00037 |
| 172.0 | 0.0014 |
| 173.0 | 0.00013 |
| 174.0 | 0.0033 |
| 175.0 | 0.030 |
| 176.0 | 0.11 |
| 177.0 | 0.0089 |
| 178.0 | 0.00032 |
| 179.0 | 0.00064 |
| 180.0 | 0.074 |
| 181.0 | 0.19 |
| 182.0 | 0.025 |
| 183.0 | 0.0048 |
| 184.0 | 0.0073 |
| 185.0 | 0.0072 |
| 186.0 | 0.098 |
| 187.0 | 0.65 |
| 188.0 | 1.4 |
| 189.0 | 0.018 |
| 190.0 | 0.026 |
| 191.0 | 0.39 |
| 192.0 | 0.26 |
| 193.0 | 0.43 |
| 194.0 | 0.056 |
| 195.0 | 0.65 |
| 196.0 | 0.0048 |
| 197.0 | 0.012 |
| 198.0 | 0.024 |
| 199.0 | 0.22 |
| 200.0 | 0.00087 |
| 201.0 | 0.0035 |
| 202.0 | 0.0027 |
| 203.0 | 0.056 |
| 204.0 | 0.021 |
| 205.0 | 0.0045 |
| 206.0 | 0.21 |
| 207.0 | 0.030 |
| 208.0 | 0.042 |
| 209.0 | 0.014 |

TABLE 27-continued

Biological Activity Information for Example Compounds.

| Example(s) | Activity hAPJ SPA EC$_{50}$ IP (µM) |
|---|---|
| 210.0 | 0.0053 |
| 211.0 | 0.0018 |
| 212.0 | 0.00085 |
| 213.0 | 0.00066 |
| 214.0 | 0.0029 |
| 215.0 | 0.0020 |
| 216.0 | 0.0022 |
| 217.0 | 0.0053 |
| 218.0 | 0.0037 |
| 219.0 | 0.0018 |
| 220.0 | 0.055 |
| 221.0 | 0.014 |
| 222.0 | 0.058 |
| 223.0 | 0.032 |
| 224.0 | 0.013 |
| 225.0 | 0.0051 |
| 226.0 | 0.00088 |
| 227.0 | 0.0045 |
| 228.0 | 0.00088 |
| 229.0 | 0.0012 |
| 230.0 | 0.00050 |
| 231.0 | 0.021 |
| 232.0 | 0.0015 |
| 233.0 | 0.010 |
| 234.0 | 0.084 |
| 235.0 | 0.10 |
| 236.0 | 0.0072 |
| 237.0 | 0.13 |
| 238.0 | 0.0062 |
| 239.0 | 0.0026 |
| 240.0 | 0.0020 |
| 241.0 | 0.0074 |
| 242.0 | 0.013 |
| 243.0 | 0.0037 |
| 244.0 | 0.0082 |
| 245.0 | 0.0070 |
| 246.0 | 0.0034 |
| 247.0 | 0.0053 |
| 248.0 | 0.27 |
| 249.0 | 0.0030 |
| 250.0 | 0.37 |
| 251.0 | 0.0017 |
| 252.0 | 0.079 |
| 253.0 | 0.032 |
| 254.0 | 0.015 |
| 255.0 | 0.0075 |
| 256.0 | 0.00048 |
| 257.0 | 0.016 |
| 258.0 | 0.00088 |
| 259.0 | 0.0087 |
| 260.0 | 0.0051 |
| 261.0 | 0.0052 |
| 262.0 | 0.20 |
| 263.0 | 0.049 |
| 264.0 | 0.0029 |
| 265.0 | 0.00092 |
| 266.0 | 0.0096 |
| 267.0 | 0.0042 |
| 268.0 | 0.0027 |
| 269.0 | 0.017 |
| 270.0 | 0.0051 |
| 271.0 | 0.0054 |
| 272.0 | 0.012 |
| 273.0 | 0.023 |
| 274.0 | 0.0022 |
| 275.0 | 0.018 |
| 276.0 | 0.0013 |
| 277.0 | 0.014 |
| 278.0 | 0.016 |
| 279.0 | 0.075 |
| 280.0 | 0.021 |
| 281.0 | 0.11 |
| 282.0 | 0.054 |
| 283.0 | 0.069 |
| 284.0 | 0.12 |
| 285.0 | 0.065 |
| 286.0 | 0.055 |
| 287.0 | 0.0059 |
| 288.0 | 0.0033 |
| 289.0 | 0.082 |
| 290.0 | 0.015 |
| 291.0 | 0.035 |
| 292.0 | 0.0024 |
| 293.0 | 0.20 |
| 294.0 | 0.0054 |
| 295.0 | 0.0064 |
| 296.0 | 0.0018 |
| 297.0 | 0.0043 |
| 298.0 | 0.0015 |
| 299.0 | 0.12 |
| 300.0 | 0.014 |
| 301.0 | 0.0044 |
| 302.0 | 0.053 |
| 303.0 | 0.027 |
| 304.0 | 0.020 |
| 305.0 | 0.0040 |
| 306.0 | 0.035 |
| 307.0 | 0.0088 |
| 308.0 | 0.0019 |
| 309.0 | 0.0092 |
| 310.0 | 0.0074 |
| 311.0 | 0.033 |
| 312.0 | 0.013 |
| 313.0 | 0.021 |
| 314.0 | 0.033 |
| 315.0 | 0.057 |
| 316.0 | 0.021 |
| 317.0 | 0.00071 |
| 318.0 | 0.0024 |
| 319.0 | 0.00044 |
| 320.0 | 0.00024 |
| 321.0 | 0.012 |
| 322.0 | 0.0012 |
| 323.0 | 0.00066 |
| 324.0 | 0.00035 |
| 325.0 | 0.00033 |
| 326.0 | 0.00014 |
| 327.0 | 0.00011 |
| 328.0 | 0.000064 |
| 329.0 | 0.0014 |
| 330.0 | 0.00023 |
| 331.0 | 0.00060 |
| 332.0 | 0.00012 |
| 333.0 | 0.0077 |
| 334.0 | 0.029 |
| 335.0 | 0.014 |
| 336.0 | 0.015 |
| 337.0 | 0.0014 |
| 338.0 | 0.00056 |
| 339.0 | 0.0031 |
| 340.0 | 0.00018 |
| 341.0 | 0.00013 |
| 342.0 | 0.000050 |
| 343.0 | 0.00010 |
| 344.0 | 0.0071 |
| 345.0 | 0.0011 |
| 346.0 | 0.0044 |
| 347.0 | 0.00048 |
| 348.0 | 0.00134 |
| 349.0 | 0.00043 |
| 350.0 | 0.00784 |
| 351.0 | 0.00036 |

The following table includes data obtained using the procedures and assays set forth above for the Example compounds described herein.

TABLE 28

Contractile Effects of Examples Observed in ex vivo
(Isolated Heart Assay) and in vivo (MI Rat Model).

| Example(s) | Isolated Heart Assay | | MI Rat Model |
|---|---|---|---|
| | $dP/dt_{max}$ (%) | $dP/dt_{min}$ (%) | $dP/dt_{max}$ (%) |
| 8 | 4.21 | −1.57 | nd* |
| 52 | 18.7 | 20.2 | nd* |
| 61 | 9.06 | 8.48 | nd* |

*nd is not determined

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun., 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15k/well in a 96 well plate overnight. The next day, the culture medium was replaced with medium containing no serum for 4 hours. The compound AngII at a range of concentrations (1 pM-10 µM) with or without different concentrations of APJ agonists were diluted in stimulation buffer and added to the cell plate. The plate was sealed and incubated for 1 hour. This was followed by addition of IP-d2 conjugate followed by europium cryptate antibody conjugate into the wells. The plate was sealed, followed with incubation for 2 hours at RT. Time-resolved fluorescence resonance energy (TR-FRET) at 620 nm and 665 nm was measured after 2 hours with an Envision reader. The signal ratios and delta F were calculated and the amount of IP1 produced was inversely proportional to the TR-FRET ratio, 665/620 nm.

Results

Figure 2:
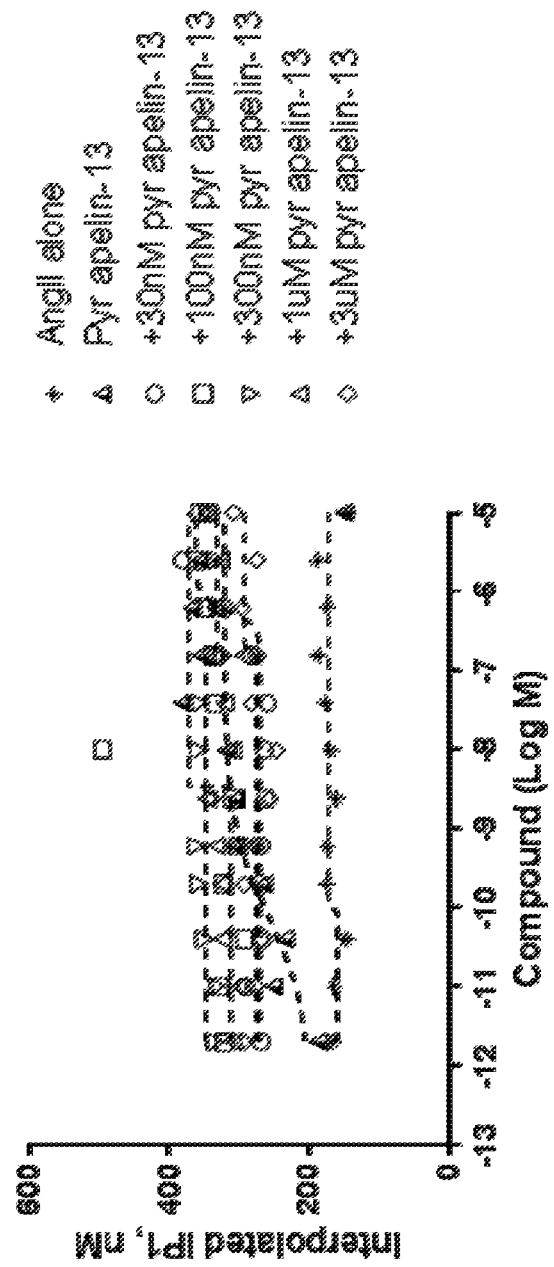
FIG. 2 is a graph plotting different concentrations of angiotensin (AngIII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.
Figure 3:
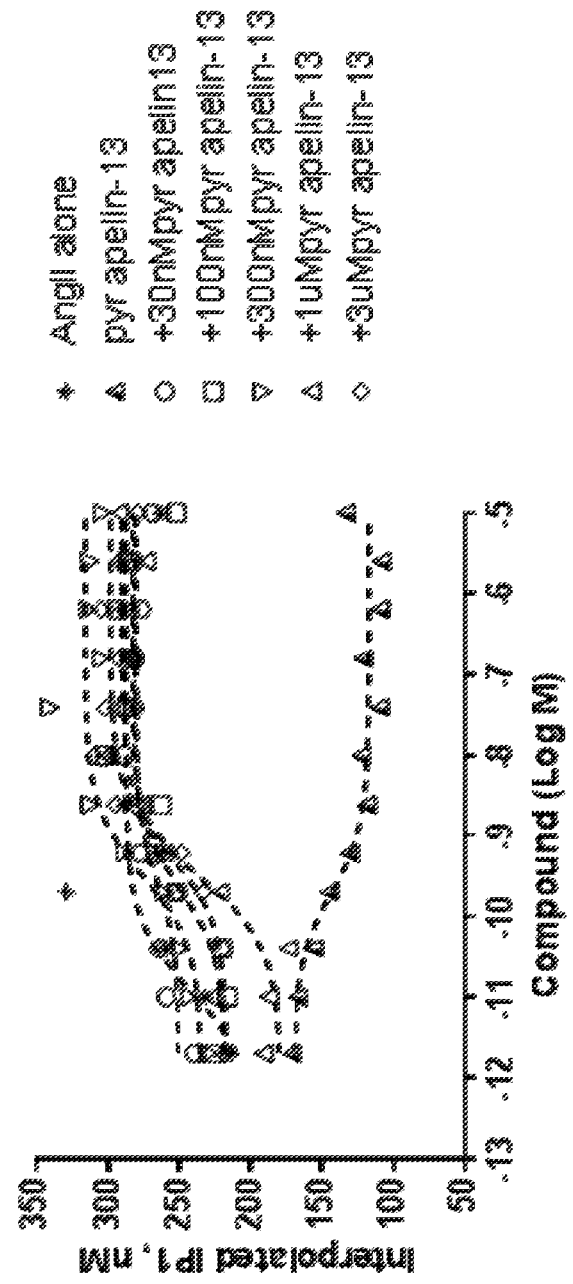
FIG. 3 is a graph plotting different concentrations of angiotensin (AngIII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 1). However, this effect of cooperativity was not observed in either APJ or AT1R recombinant stable cell lines indicating that there is functional cross-talk between the two receptors through physical interaction or with downstream effectors (FIG. 2 and FIG. 3). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound of Formula I or Formula II:

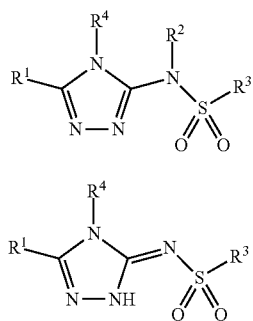

or a pharmaceutically acceptable salt thereof, a tautomer thereof, a pharmaceutically acceptable salt of the tautomer, a stereoisomer of any of the foregoing, or a mixture thereof,
wherein:
$R^1$ is a pyridyl group that is unsubstituted or is substituted with 1, 2, or 3 $R^{1a}$ substituents;
$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$NH$_2$, —S(=O)$_2$NH($C_1$-$C_6$ alkyl), or —S(=O)$_2$N($C_1$-$C_6$ alkyl)$_2$;
$R^2$ is selected from —H, or $C_1$-$C_4$ alkyl or is absent in the compounds of Formula II;
$R^3$ is selected from an unsubstituted $C_1$-$C_{10}$ alkyl, a $C_1$-$C_{10}$ alkyl substituted with 1, 2, or 3 $R^{3a}$ substituents, a group of formula —(CR$^{3b}$R$^{3c}$)-Q, a group of formula NH—(CR$^{3b}$R$^{3c}$)-Q, a group of formula —(CR$^{3b}$R$^{3c}$)—C(=O)-Q, a group of formula —(CR$^{3d}$R$^{3e}$)—(CR$^{3f}$R$^{3g}$)-Q, a group of formula —(CR$^{3b}$=CR$^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;
$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —NH$_2$, —NH($C_1$-$C_6$ alkyl), or —N($C_1$-$C_6$ alkyl)$_2$;
$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;
$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;
$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), or —N($C_1$-$C_6$ alkyl)$_2$;
$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —NH$_2$, —NH($C_1$-$C_6$ alkyl), —N($C_1$-$C_6$ alkyl)$_2$, or oxo;
Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;
$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl $R^4$ group is unsubstituted or is substituted with 1, 2, 3, or 4 $R^{4a}$ substituents, wherein the $C_5$-$C_{10}$ polycyclic cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl $R^{4a}$ group is unsubstituted or is substituted with 1 or 2 $R^{4aa}$ substituents, and further wherein two $R^{4a}$ substituents on the same carbon atom of the $C_3$-$C_8$ cycloalkyl $R^4$ group may join together with the carbon atom to which they are attached to form a 3 to 6-membered heterocyclyl group containing 1 or 2 heteroatoms selected from N, O, or S which is unsubstituted or is substituted with 1 or 2 $R^{4aa}$ substituents;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^{4c}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

2. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

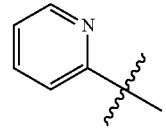 [SMILES: *c1ccccn1]

wherein the pyridyl is unsubstituted or is substituted with 1 or 2 $R^{1a}$ substituents, and the symbol ⌇, when drawn across a bond, indicates the point of attachment to the rest of the molecule.

3. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

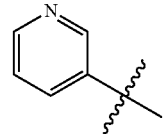 [SMILES: *c1cccnc1]

wherein the pyridyl is unsubstituted or is substituted with 1 or 2 $R^{1a}$ substituents, and the symbol ⌇, when drawn across a bond, indicates the point of attachment to the rest of the molecule.

4. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a pyridyl having the formula

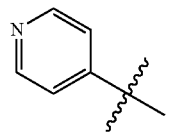 [SMILES: *c1ccncc1]

wherein the pyridyl is unsubstituted or is substituted with 1 or 2 $R^{1a}$ substituents, and the symbol ⌇, when drawn across a bond, indicates the point of attachment to the rest of the molecule.

5. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^{1a}$ in each instance is independently selected from —$C_1$-$C_6$ alkyl, —O—($C_1$-$C_6$ alkyl), or —O—($C_1$-$C_6$ alkyl)-O—($C_1$-$C_6$ alkyl).

6. The compound of claim 1 or the pharmaceutically acceptable salt thereof, the stereoisomer of any of the foregoing, or the mixture thereof, wherein $R^1$ is selected from

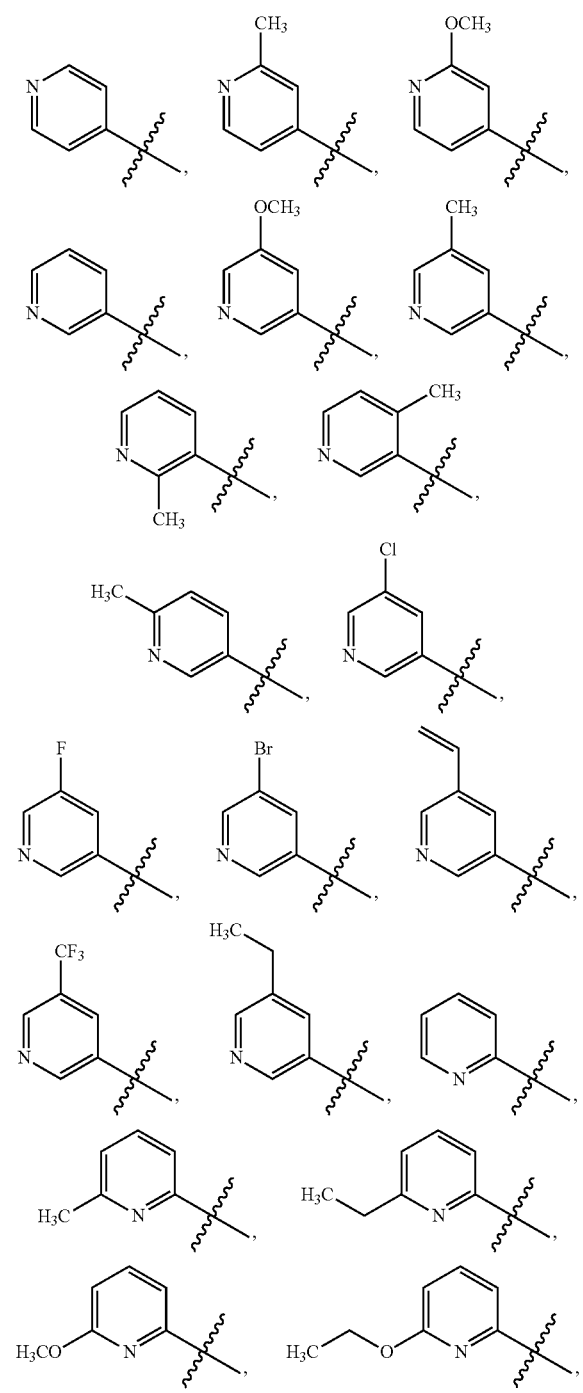

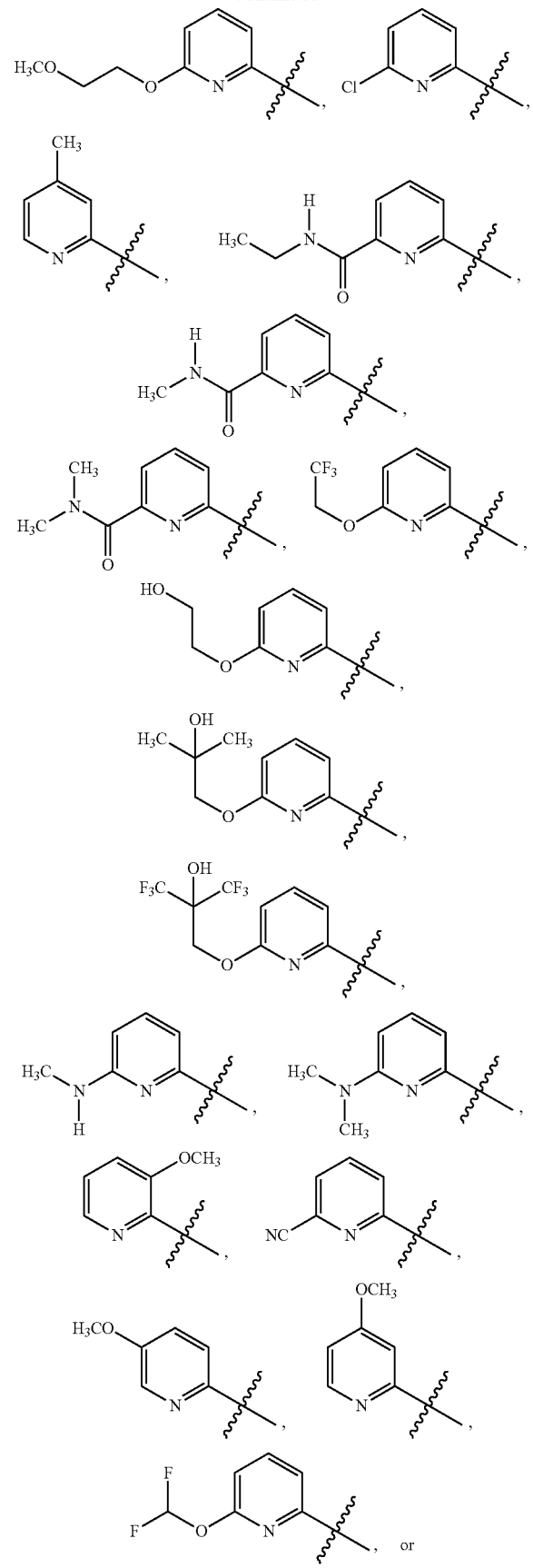

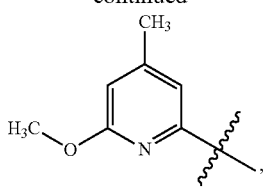

wherein the symbol ⌇, when drawn across a bond, indicates the point of attachment to the rest of the molecule.

7. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is selected from —H or —CH$_3$.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H.

9. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic $C_3$-$C_8$ cycloalkyl group and is unsubstituted or is substituted with 1, 2, or 3 $R^{4a}$ substituents.

10. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a $C_5$-$C_{10}$ polycyclic cycloalkyl $R^4$ group and is unsubstituted or is substituted with 1 or 2 $R^{4b}$ substituents.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a straight or branched chain $C_1$-$C_6$ alkyl $R^4$ group and is unsubstituted or is substituted with 1, 2, or 3 $R^{4c}$ substituents.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is selected from

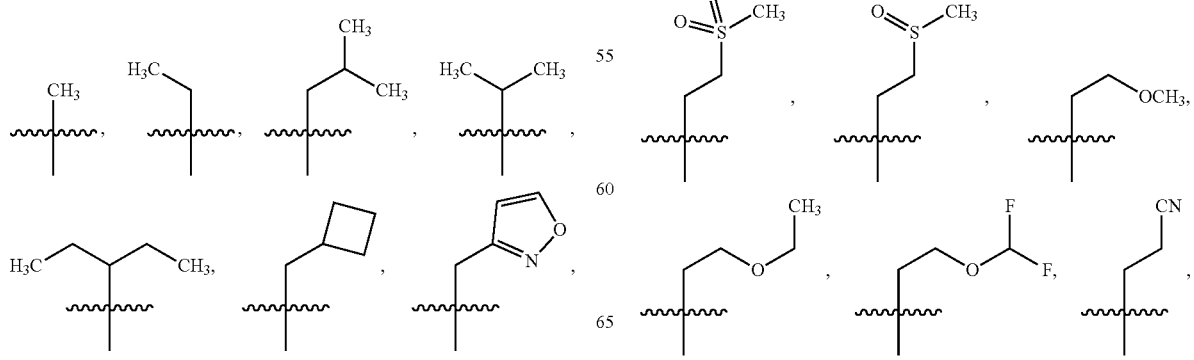

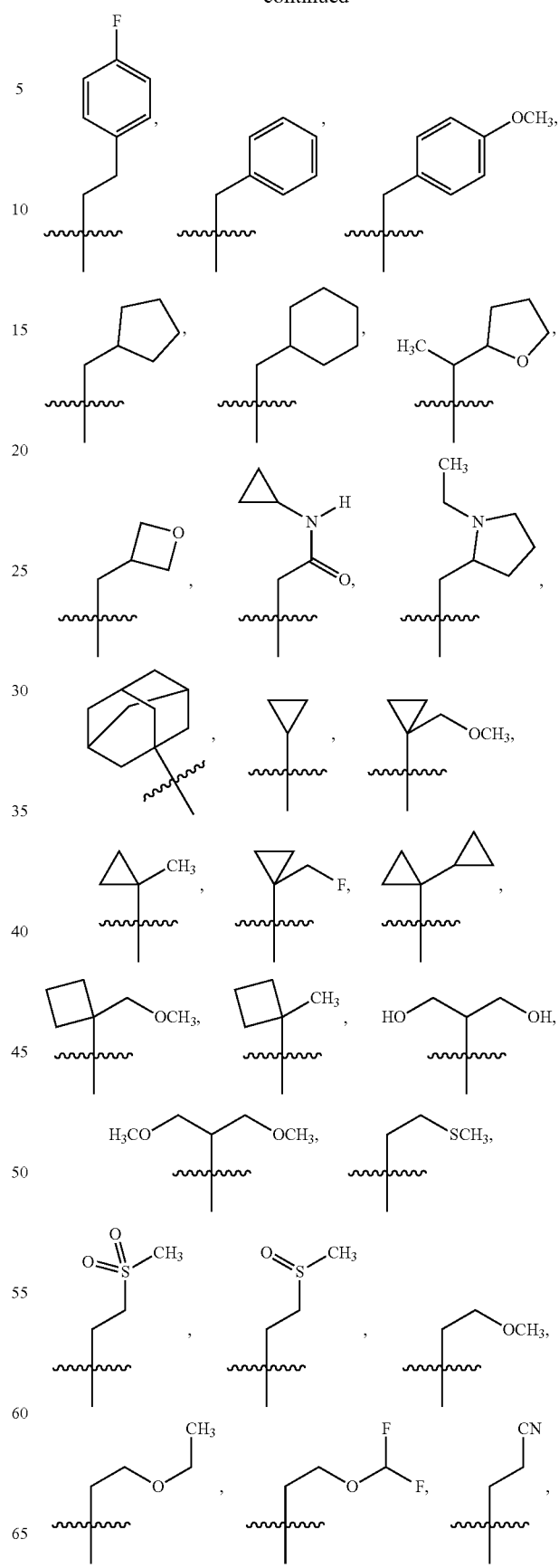

541
-continued

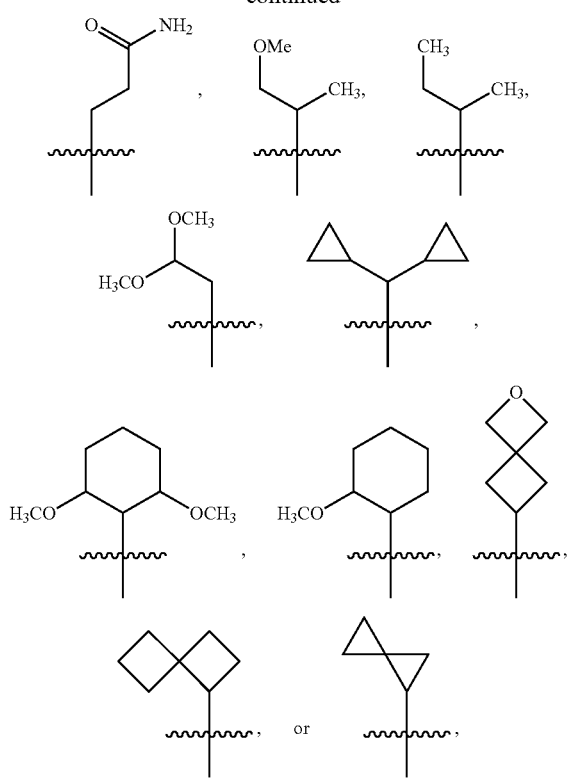

wherein the symbol ∿, when drawn across a bond, indicates the point of attachment to the rest of the molecule.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is selected from

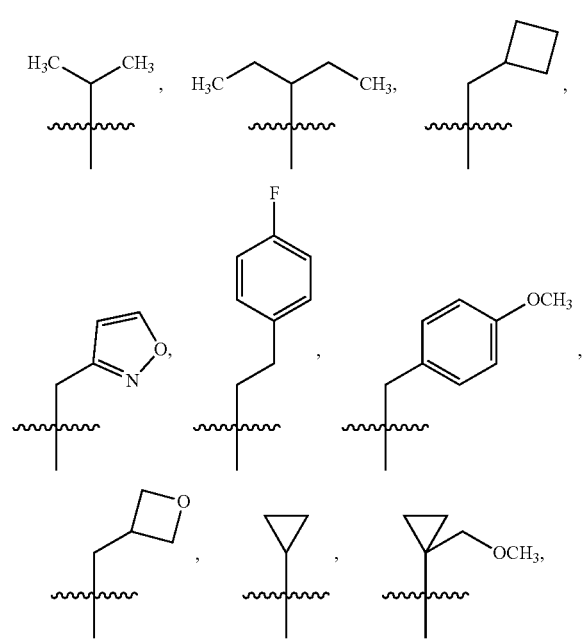

542
-continued

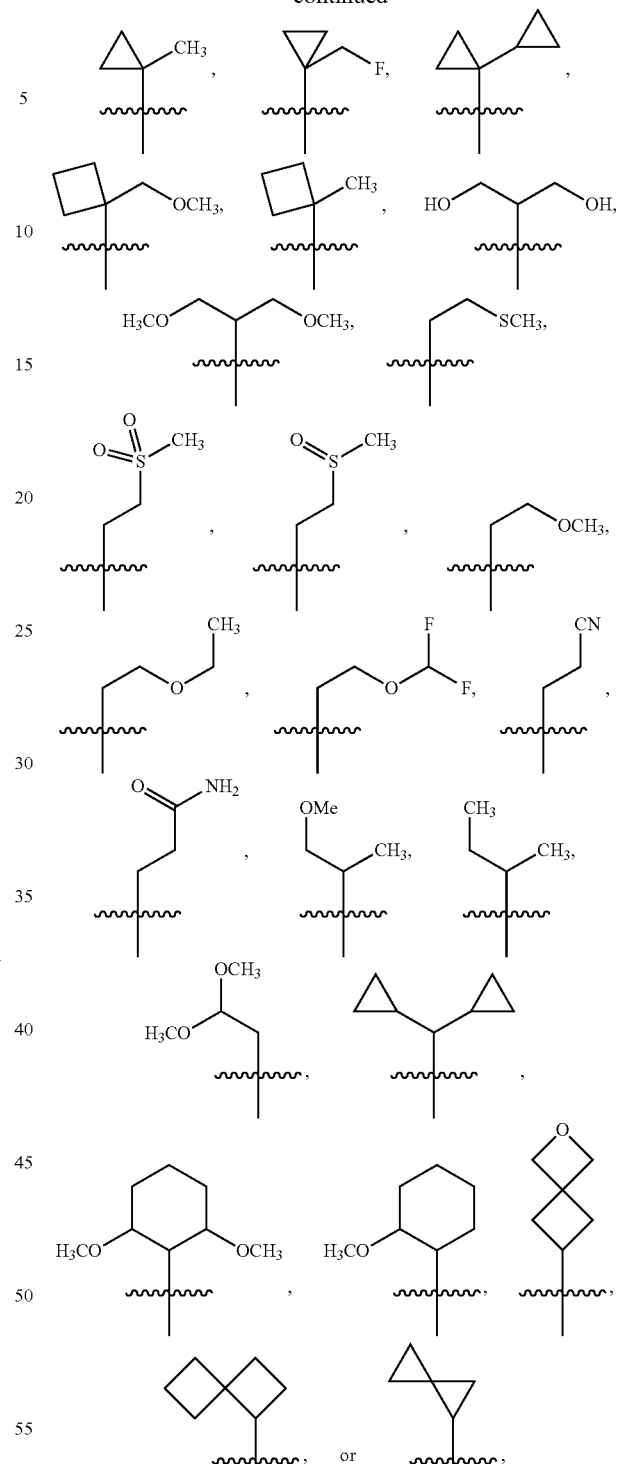

wherein the symbol ∿, when drawn across a bond, indicates the point of attachment to the rest of the molecule.

14. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

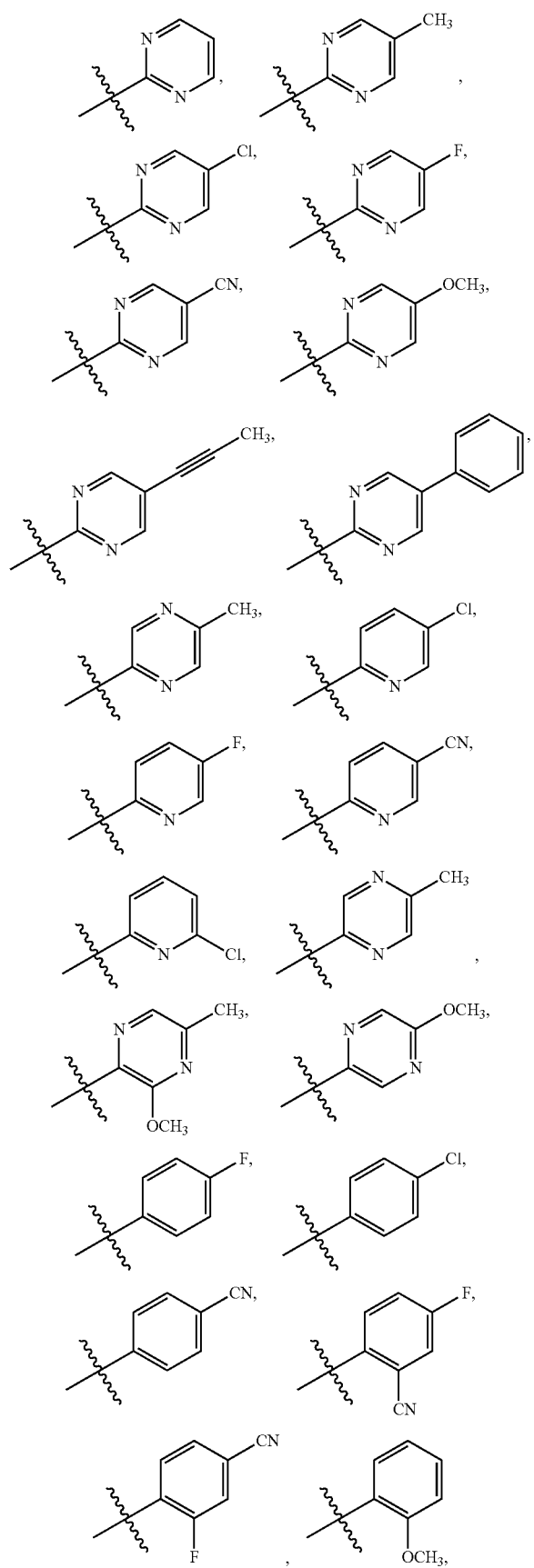

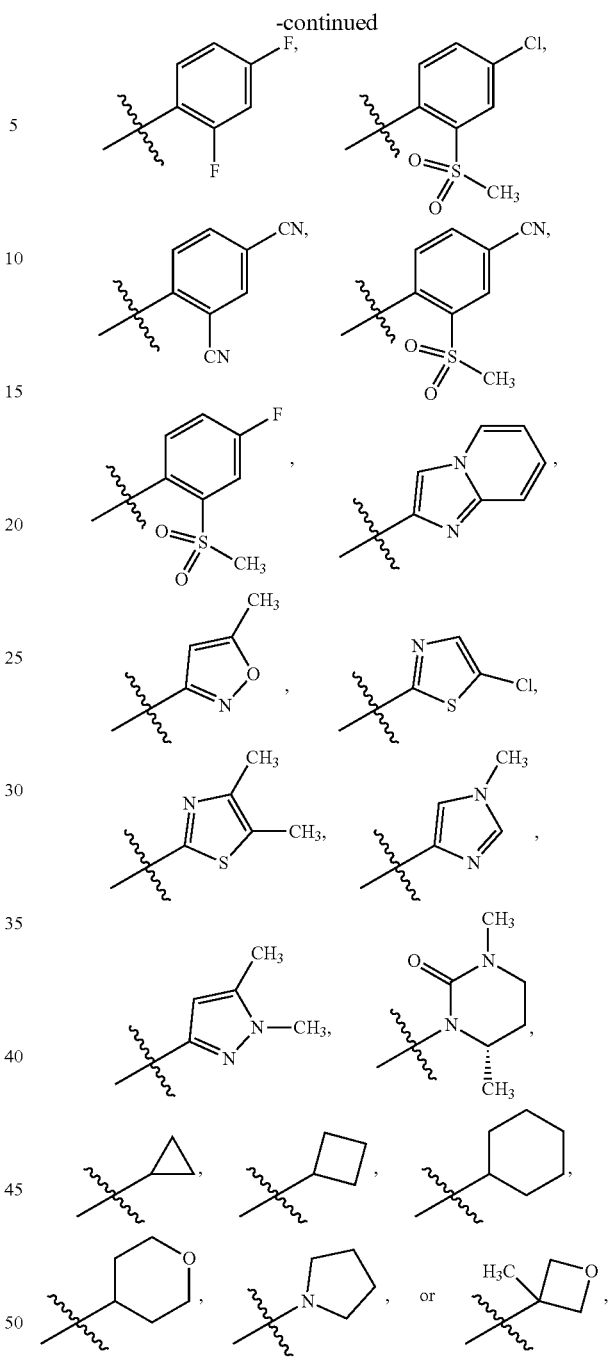

wherein the symbol ~, when drawn across a bond, indicates the point of attachment to the rest of the molecule.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

16. The compound of claim 15 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl, pyrazinyl, or pyridyl group and Q is unsubstituted or is substituted with 1 or 2 $R^Q$ substituents.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 Rah substituents.

18. The compound of claim 17 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula

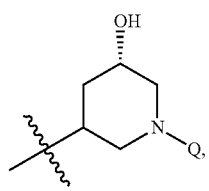

wherein the symbol ∼∼∼, when drawn across a bond, indicates the point of attachment to the rest of the molecule.

19. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

20. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ has the formula

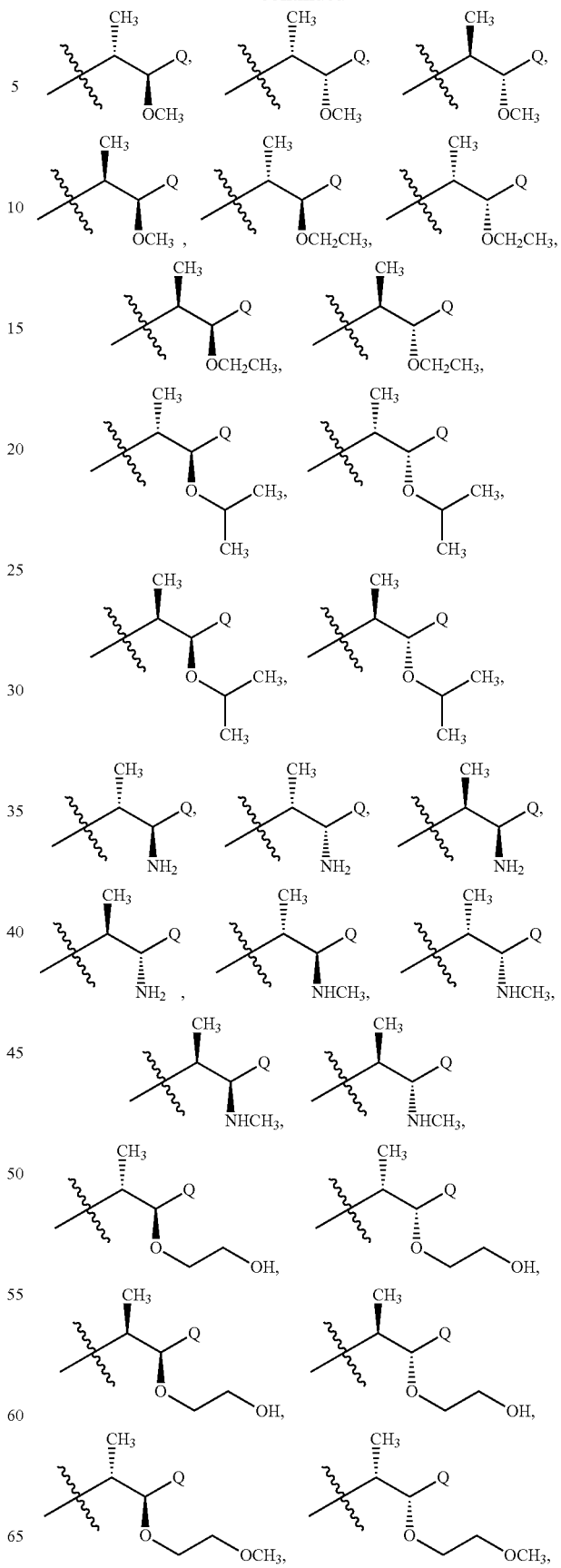

-continued

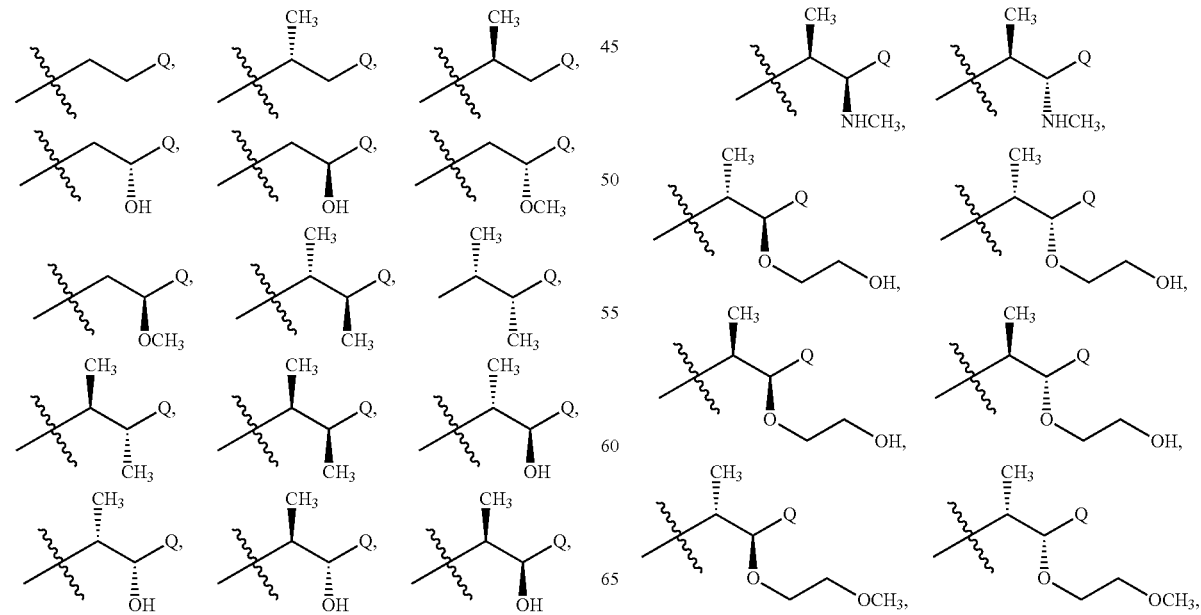

-continued

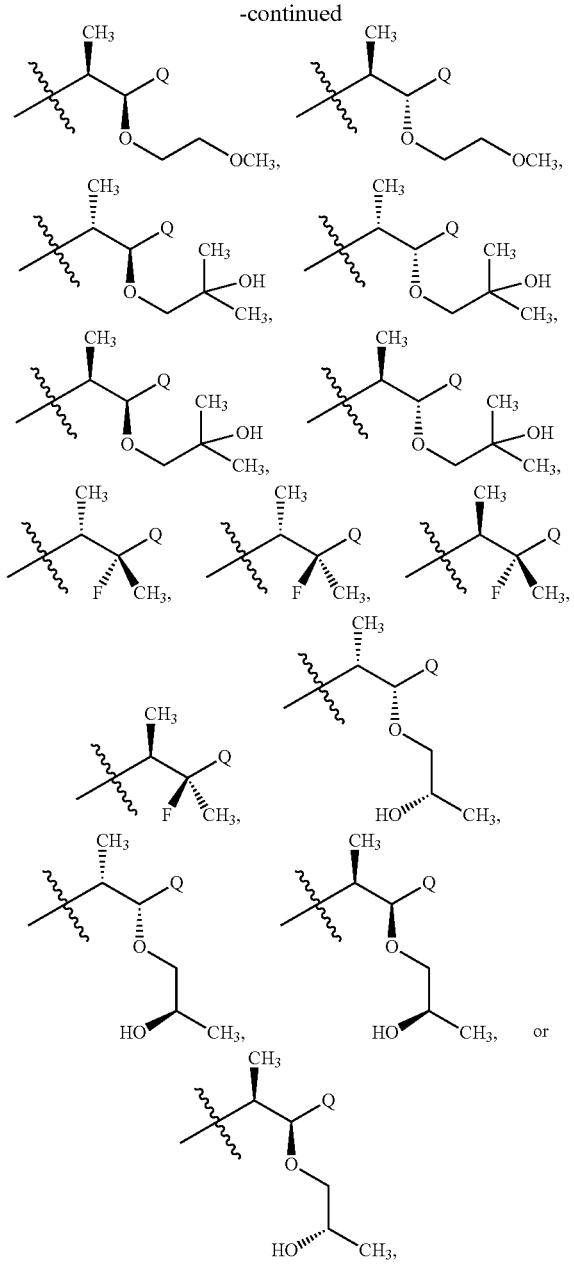

wherein the symbol ⁓, when drawn across a bond, indicates the point of attachment to the rest of the molecule.

21. The compound of claim 1, wherein the compound has the formula IA

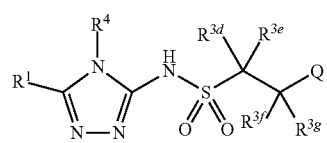

or is the pharmaceutically acceptable salt thereof, the tautomer thereof, the pharmaceutically acceptable salt of the tautomer, the stereoisomer of any of the foregoing, or the mixture thereof, wherein:
$R^1$ is as defined in claim 1;
$R^{3d}$ and $R^{3e}$ are independently selected from —H or —$C_1$-$C_3$ alkyl;
$R^{3f}$ and $R^{3g}$ are independently selected from —H, —$C_1$-$C_6$ alkyl, or —O—($C_1$-$C_6$ alkyl);
$R^4$ is as defined in claim 1;
Q is a monocyclic heteroaryl group with 6 ring members containing 1 or 2 N heteroatoms, wherein the monocyclic heteroaryl Q groups are unsubstituted or are substituted with 1 or 2 $R^Q$ substituent; and
$R^Q$ is independently selected from —F, —Br, —CN, —O—$C_1$-$C_6$ alkyl or —$C_1$-$C_6$ alkyl.

22. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

23. A pharmaceutical composition, comprising the compound of claim 1 or the pharmaceutically acceptable salt thereof and at least one pharmaceutically acceptable excipient.

24. The pharmaceutical composition of claim 22, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

25. A method of treating a cardiovascular condition, the method comprising: administering to a subject an effective amount of the compound of claim 1 or the pharmaceutically acceptable salt thereof, the stereoisomer of any of the foregoing, or the mixture thereof.

26. The method of claim 25, wherein the cardiovascular condition is heart failure.

27. The method of claim 25, wherein the cardiovascular condition is heart failure with reduced ejection fraction.

28. The method of claim 25, wherein the cardiovascular condition is heart failure with preserved ejection fraction.

29. The method of claim 25, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

30. A compound of Formula V, a salt thereof, a tautomer thereof, or a salt of the tautomer:

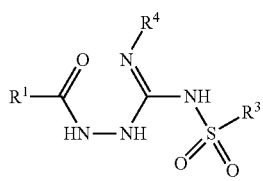

wherein:
$R^1$ is a pyridyl group that is unsubstituted or is substituted with 1, 2, or 3 $R^{1a}$ substituents;
$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ haloalkyl)-OH, —($C_1$-$C_6$ perhaloalkyl)-OH, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —S(=O)$_2$ $NH_2$, —S(=O)$_2$NH($C_1$-$C_6$ alkyl), or —S(=O)$_2$N($C_1$-$C_6$ alkyl)$_2$;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —NH—($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3b}$=$CR^{3c}$)-Q, or a group of formula -(heterocyclyl)-Q, wherein the heterocyclyl of the -(heterocyclyl)-Q has 5 to 7 ring members of which 1, 2, or 3 are heteroatoms selected from N, O, or S and is unsubstituted or is substituted with 1, 2, or 3 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, or oxo;

Q is a monocyclic or bicyclic $C_6$-$C_{10}$ aryl group, a monocyclic or bicyclic heteroaryl group with 5 to 10 ring members containing 1, 2, or 3 heteroatoms selected from N, O, or S, a $C_3$-$C_8$ cycloalkyl group, or a 3 to 7 membered heterocyclyl group containing 1, 2, or 3 heteroatoms selected from N, O, or S, wherein the $C_6$-$C_{10}$ aryl group, the heteroaryl group, the cycloalkyl group, and the heterocyclyl group are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), phenyl, or a heteroaryl group, and the Q heterocyclyl group may be substituted with 1 oxo $R^Q$ substituent;

$R^4$ is selected from a monocyclic $C_3$-$C_8$ cycloalkyl group, a $C_5$-$C_{10}$ polycyclic cycloalkyl group, or a straight or branched chain $C_1$-$C_6$ alkyl group, wherein the $C_3$-$C_8$ cycloalkyl $R^4$ group group is unsubstituted or is substituted with 1, 2, 3, or 4 $R^{4a}$ substituents, wherein the $C_5$-$C_{10}$ polycyclic cycloalkyl $R^4$ group is unsubstituted or is substituted with 1, 2, 3, or 4 $R^{4b}$ substituents, and further wherein the straight or branched chain $C_1$-$C_6$ alkyl $R^4$ group is unsubstituted or is substituted with 1, 2, or 3 $R^{4c}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or a 3 to 6 membered cycloalkyl group, wherein the 3 to 6 membered cycloalkyl $R^{4a}$ group is unsubstituted or is substituted with 1 or 2 $R^{4aa}$ substituents, and further wherein two $R^{4a}$ substituents on the same carbon atom of the $C_3$-$C_8$ cycloalkyl $R^4$ group may join together with the carbon atom to which they are attached to form a 3 to 6-membered heterocyclyl group containing 1 or 2 heteroatoms selected from N, O, or S which is unsubstituted or is substituted with 1 or 2 $R^{4aa}$ substituents;

$R^{4b}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, oxo, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^{4c}$ in each instance is selected from —F, —Cl, —Br, —I, —CN, —OH, oxo, —O—($C_1$-$C_6$ alkyl), —O—($C_1$-$C_6$ haloalkyl), —O—($C_1$-$C_6$ perhaloalkyl), —S—($C_1$-$C_6$ alkyl), —S—($C_1$-$C_6$ haloalkyl), —S—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)NH($C_3$-$C_6$ cycloalkyl), —C(=O)N($C_1$-$C_6$ alkyl)($C_3$-$C_6$ cycloalkyl), —C(=O)N($C_3$-$C_6$ cycloalkyl)$_2$, —S(=O)—($C_1$-$C_6$ alkyl), —S(=O)$_2$—($C_1$-$C_6$ alkyl), a 3 to 6 membered cycloalkyl group, a 3 to 6 membered heterocyclyl group containing 1 or 2 heteroatoms selected from N, O, or S, a phenyl group, or a 5 or 6 membered heteroaryl ring containing 1, 2, or 3 heteroatoms selected from N, O, or S, wherein the a 3 to 6 membered cycloalkyl $R^{4c}$ group, the 3 to 6 membered heterocyclyl $R^{4c}$ group, the phenyl $R^{4c}$ group, or the a 5 or 6 membered heteroaryl $R^{4c}$ ring are unsubstituted or are substituted with 1 or 2 $R^{4aa}$ substituents; and further wherein the 3 to 6 membered cycloalkyl $R^{4c}$ group and the 3 to 6 membered heterocyclyl $R^{4c}$ group may optionally be additionally substituted with an oxo substituent; and $R^{4aa}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$.

* * * * *